(12) United States Patent
Muchero et al.

(10) Patent No.: US 12,203,927 B2
(45) Date of Patent: Jan. 21, 2025

(54) METHODS FOR IMMUNOREGULATION BY MODULATING PLASMINOGEN-APPLE-NEMATODE (PAN) DOMAIN-CONTAINING PROTEINS

(71) Applicant: UT-Battelle, LLC, Oak Ridge, TN (US)

(72) Inventors: Wellington Muchero, Oak Ridge, TN (US); Carly M. Shanks, New York, NY (US); Debjani Pal, Knoxville, TN (US); Kuntal De, Knoxville, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 670 days.

(21) Appl. No.: 17/012,139

(22) Filed: Sep. 4, 2020

(65) Prior Publication Data
US 2021/0072228 A1 Mar. 11, 2021

Related U.S. Application Data

(60) Provisional application No. 62/896,605, filed on Sep. 6, 2019.

(51) Int. Cl.
| | | |
|---|---|---|
| *G01N 33/50* | (2006.01) | |
| *A61P 15/08* | (2006.01) | |
| *A61P 35/00* | (2006.01) | |
| *C12N 9/22* | (2006.01) | |
| *C12N 15/11* | (2006.01) | |
| *C12N 15/113* | (2010.01) | |
| *C12N 15/82* | (2006.01) | |
| *G01N 33/68* | (2006.01) | |

(52) U.S. Cl.
CPC .......... *G01N 33/5041* (2013.01); *A61P 15/08* (2018.01); *A61P 35/00* (2018.01); *C12N 9/22* (2013.01); *C12N 15/11* (2013.01); *C12N 15/113* (2013.01); *C12N 15/8279* (2013.01); *G01N 33/6818* (2013.01); *C12N 2310/11* (2013.01); *C12N 2310/20* (2017.05); *G01N 2500/00* (2013.01)

(58) Field of Classification Search
None
See application file for complete search history.

(56) References Cited

U.S. PATENT DOCUMENTS

| | | | |
|---|---|---|---|
| 7,265,204 B2* | 9/2007 | Hresko ................ | C07K 14/705 435/7.1 |
| 10,738,322 B2 | 8/2020 | Kaloshian et al. | |
| 2003/0104505 A1 | 6/2003 | Robison | |
| 2010/0055099 A1 | 3/2010 | Filvaroff et al. | |
| 2017/0305985 A1 | 10/2017 | Cochran et al. | |
| 2018/0119168 A1 | 5/2018 | Kaloshian et al. | |

FOREIGN PATENT DOCUMENTS

| | | |
|---|---|---|
| WO | 01/32874 A2 | 5/2001 |
| WO | 2004/070015 A2 | 8/2004 |

OTHER PUBLICATIONS

Yang Y. et al., "Genome-Wide Analysis of Lectin Receptor-Like Kinases in Populus", BMC Genomics 17(1):699 (Sep. 1, 2016).
International Search Report and Written Opinion dated Feb. 5, 2021 received in International Application No. PCT/US20/49303.
"Invitation to Pay Additional Fees" dated Nov. 24, 2020, received in a corresponding foreign application, namely International Application No. PCT/US20/49303.
Armstrong, P. B., "Role of α2-macroglobulin in the immune responses of invertebrates", Invertebrate Survival Journal, 7(2), 165-180 (2010).
Baglia, F. A. et al. "A Binding Site for the Kringle II Domain of Prothrombin in the Apple 1 Domain of Factor XI." Journal of Biological Chemistry 275.41: 31954-31962 (Oct. 13, 2000).
Berbee, M. L., "The phylogeny of plant and animal pathogens in the Ascomycot", Physiological and Molecular Plant Pathology, 59(4), 165-187 (2001).
Bertschinger, H. J. et al., "Porcine zona pellucida vaccine immunocontraception of African elephant (*Loxodonta africana*) cows: A review of 22 years of research", Bothalia-African Biodiversity & Conservation, 48 (2), 1-8 (2018).
Bhattacharya, S. et al., "Bacterial Plasminogen Receptors Utilize Host Plasminogen System for Effective Invasion and Dissemination", BioMed Research International, vol. 2012, Article ID 482096, 19 pgs.(2012).
Brogden, K. A. et al., "Antimicrobial peptides in animals and their role in host defences", International Journal of Antimicrobial Agents 22.5: 465-478 (2003).
Champer, J. et al., "Cheating evolution: engineering gene drives to manipulate the fate of wild populations", Nature Reviews Genetics, 17(3), 146 (Mar. 2016).
Diamond, G. et al., "Tracheal antimicrobial peptide, a cysteine-rich peptide from mammalian tracheal mucosa: peptide isolation and cloning of a cDNA", Proceedings of the National Academy of Sciences, 88(9), 3952-3956 (May 1991).
Etxebeste, O. et al., "GmcA is a putative glucose-methanol-choline oxidoreductase required for the induction of asexual development in Aspergillus nidulans", PLoS One, 7(7), e40292 (Jul. 2012).
Frick, I. M. et al., "The contact system—a novel branch of innate immunity generating antibacterial peptides", The EMBO Journal, 25(23), 5569-5578 (2006).
Ghosh, A. K. et al., "Surface-expressed enolases of Plasmodium and other pathogens", Memorias do Instituto Oswaldo Cruz, 106 (Suppl. 1), 85-90 (2011).

(Continued)

*Primary Examiner* — Brent T Page
(74) *Attorney, Agent, or Firm* — Scully, Scott, Murphy & Presser, P.C.

(57) ABSTRACT

The present disclosure based on the inventors' recognition that PAN domain containing proteins play important immune regulating functions. Disclosed herein are methods for modulating immune responses in plants and animals, improving in vitro fertilization efficiency, and inhibiting human cell division and cellular migration in cancer cells. Also disclosed herein are genetically modified plants that are resistant to pathogenic infections.

2 Claims, 27 Drawing Sheets
(25 of 27 Drawing Sheet(s) Filed in Color)
Specification includes a Sequence Listing.

(56) References Cited

OTHER PUBLICATIONS

Gong, H. et al., "A novel PAN/apple domain-containing protein from Toxoplasma gondii: characterization and receptor identification", PLoS One, 7(1), e30169 (Jan. 2012).

Grünwald, N. J. et al., "Emergence of the sudden oak death pathogen Phytophthora ramorum", Trends in microbiology, 20(3), 131-138 (Mar. 2012).

Herwald, H. et al., "Mapping of the Discontinuous Kininogen Binding Site of Prekallikrein: A Distal Binding Segment is Located in the Heavy Chain Domain A4", Journal of Biological Chemistry, 271(22), 13061-13067 (May 31, 1996).

Ho, D. H. et al., "A binding site for heparin in the apple 3 domain of factor XI", Journal of Biological Chemistry, 273(26), 16382-16390 (Jun. 26, 1998).

Holdich, D. M., et al., "A review of the ever increasing threat to European crayfish from non-indigenous crayfish species", Knowledge and management of aquatic ecosystems, 11, pp. 394-395, (2009).

Huizinga, E. G. et al., "The structure of leech anti-platelet protein, an inhibitor of haemostasis", Acta Crystallographica Section D: Biological Crystallography, D57(8), 1071-1078 (2001).

Jones II, D. S. et al., "Engineering hepatocyte growth factor fragments with high stability and activity as Met receptor agonists and antagonists", Proceedings of the National Academy of Sciences, 108(32), 13035-13040 (Aug. 9, 2011).

Kereszt, A. et al., "Impact of plant peptides on symbiotic nodule development and functioning", Frontiers in Plant Science, 9 (Jul. 17, 2018).

Kirsch, R. et al., "Host plant shifts affect a major defense enzyme in Chrysomela lapponica", Proceedings of the National Academy of Sciences, 108(12), 4897-4901 (Mar. 22, 2011).

Kliukova, M. et al., "NCR Peptides—Plant Effectors Governing Terminal Differentiation of Nodule Bacteria into the Symbiotic Form", Agricultural Biology, vol. 52, No. 5, 869-877 (2017).

Krem, M. M. et al., "Evolution of enzyme cascades from embryonic development to blood coagulation", Trends in biochemical sciences, 27(2), 67-74 (Feb. 2, 2002).

Labbé, J. et al., "Mediation of plant-mycorrhizal interaction by a lectin receptor-like kinase", Nature Plants, 5(7), 676 (Jul. 2019).

Lähteenmäki, K. et al., "Bacterial plasminogen activators and receptors", FEMS microbiology reviews, 25(5), 531-552 (2001).

Lietha, D. et al., "Crystal structures of NK1-heparin complexes reveal the basis for NK1 activity and enable engineering of potent agonists of the MET receptor", The EMBO Journal, 20(20), 5543-5555 (2001).

Long, A. T. et al., "Contact system revisited: an interface between inflammation, coagulation, and innate immunity", Journal of Thrombosis and Haemostasis, 14(3), 427-437 (2016).

Loof, T. G. et al., "The role of coagulation/fibrinolysis during *Streptococcus pyogenes* infection", Frontiers in cellular and infection microbiology, 4, 128 (Sep. 11, 2014).

Mahajan, T. et al., "Embryogenesis: A comprehensive review", Journal of Entomology and Zoology Studies, 6(1): 1151-1153 (2018).

Marshall, E. et al., "Cysteine-rich peptides (CRPs) mediate diverse aspects of cell-cell communication in plant reproduction and development", Journal of experimental botany, 62(5), 1677-1686 (2011).

Mattsson, E. et al., "*Staphylococcus aureus* induces release of bradykinin in human plasma", Infection and mmunity, 69(6), 3877-3882 (Jun. 2001).

Mcmullen, B. A. et al., "Location of the disulfide bonds in human plasma prekallikrein: the presence of four novel apple domains in the amino-terminal portion of the molecule", Biochemistry, 30(8), 2050-2056 (1991).

Mcpherson, B. A. et al., "Attraction of ambrosia and bark beetles to coast live oaks infected by Phytophthora ramorum", Agricultural and Forest Entomology, 10(4), 315-321 (2008).

Monné, M. et al., "Tracking down the ZP domain: from the mammalian zona pellucida to the molluscan vitelline envelope", Seminars in Reproductive Medicine, vol. 24, No. 4, pp. 204-216 (2006).

Muchero, W. et al., "Association mapping, transcriptomics, and transient expression identify candidate genes mediating plant-pathogen interactions in a tree", Proceedings of the National Academy of Sciences, 115(45):11573-11578 (Nov. 6, 2018).

Naithani, S. et al., "Structural modules for receptor dimerization in the S-locus receptor kinase extracellular domain. Proceedings of the National Academy of Sciences", 104(29), 12211-12216 (Jul. 17, 2007).

Papaccio, F. et al., "HGF/MET and the Immune System: Relevance for Cancer Immunotherapy", International Journal of Molecular Sciences, 19(11), 3595, pp. 1-13 (2018).

Penrith, M. L. et al., "Review of African swine fever: transmission, spread and control", Journal of the South African Veterinary Association, 80(2), 58-62 (2009).

Rahfeld, P. et al., "Independently recruited oxidases from the glucose-methanol-choline oxidoreductase family enabled chemical defences in leaf beetle larvae (subtribe Chrysomelina) to evolve", Proceedings of the Royal Society B: Biological Sciences, 281(1788), 20140842 (2014).

Raoult, D. et al., "Redefining Viruses: Lessons from Mimivirus", Nature Reviews Microbiology, 6(4), pp. 315-319 (Apr. 2008).

Silverstein, K. A. et al., "Small cysteine-rich peptides resembling antimicrobial peptides have been under-predicted in plants", The Plant Journal, 51(2), 262-280 (2007).

Srinivasan, P. et al., "Disrupting malaria parasite AMA1-RON2 interaction with a small molecule prevents erythrocyte invasion", Nature Communications, 4, 2261, pp. 1-9 (2013).

Summerell, B.A., "Resolving Fusarium: Current Status of the Genus", Annual Review of Phytopathology, 57, pp. 323-339 and v-vii (2019).

Takasaki, T. et al., "The S receptor kinase determines self-incompatibility in *Brassica* stigma", Nature, 403 (6772), pp. 913-916 (Feb. 24, 2000).

Tordai, H. et al., "The PAN module: the N-terminal domains of plasminogen and hepatocyte growth factor are homologous with the apple domains of the prekallikrein family and with a novel domain found in numerous nematode proteins", FEBS letters, 461(1-2), 63-67 (1999).

Tyler, J. S. et al., "The C-terminus of Toxoplasma RON2 provides the crucial link between AMA1 and the host-associated invasion complex", PLoS pathogens, 7(2), e1001282 (Feb. 2011).

Ventura, T. et al., " Redefining metamorphosis in spiny lobsters: molecular analysis of the phyllosoma to puerulus transition in Sagmariasus verreauxi", Scientific Reports, 5, 13537, pp. 1-14 (2015).

Wang, G. et al., "Low-density lipoprotein receptor-related protein-1 facilitates heme scavenging after intracerebral hemorrhage in mice", Journal of Cerebral Blood Flow & Metabolism, 37(4), 1299-1310 (2017).

Yap, N. V. et al., "The evolution of the scavenger receptor cysteine-rich domain of the class A scavenger receptors", Frontiers in Immunology, vol. 6, article 342, pp. 1-9 (Jul. 6, 2015).

Zhou, H. et al., "The solution structure of the N-terminal domain of hepatocyte growth factor reveals a potential heparin-binding site", Structure, 6(1), 109-116 (1998).

Fernandes, et al., "Zona Pellucida Domain Proteins Remodel the Apical Compartment for Localized Cell Shape Changes", Cell Press, Jan. 19, 2010, Developmental Cell 18, Elsevier, Inc., pp. 64-76, Supplemental Information, pp. 77-82.

Liu P-L et al., "Duplication and Diversification of Lectin Receptor-Like Kinases (LecRLK) Genes in Soybean", Scientific Reports 8(1): DOI: 10.1038/s41598-018-24266-6 (Apr. 12, 2018).

Ma N. et al., "Genome-Wide Identification of Lectin Receptor Kinases in Pear: Functional Characterization of the L-Type LecRLK Gene PbLRK138", Gene 661:11-21 (Mar. 27, 2018).

Naithani S. et al., "Structural Modules for Receptor Dimerization in the S-Locus Receptor Kinase Extracellular Domain", PNAS 104(29):12211-12216 (Jul. 17, 2007).

(56) References Cited

OTHER PUBLICATIONS

European Supplementary Partial Search Report dated Oct. 2, 2023 received in European Application No. 20 86 0537.8.

\* cited by examiner

A

B

G

H

A

B

# METHODS FOR IMMUNOREGULATION BY MODULATING PLASMINOGEN-APPLE-NEMATODE (PAN) DOMAIN-CONTAINING PROTEINS

CROSS REFERENCE TO RELATED APPLICATION

This application claims the benefit of priority from U.S. Provisional Application No. 62/896,605, filed Sep. 6, 2019, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in an ASCII text file, named as 38529Seglist_ST25.txt of 49 KB, created on Sep. 1, 2020, and submitted to the United States Patent and Trademark Office via EFS-Web, is incorporated herein by reference.

BACKGROUND

Immunoregulation (e.g. immunosuppression) is an essential phenomenon governing fertilization during sexual reproduction, cell growth and proliferation as well as recruitment of beneficial symbionts. However, the same phenomenon predisposes host organisms to uncontrolled cell growth and infection by parasites, pathogens, and viruses. Consequently, understanding the molecular basis of immunoregulation (e.g., immunosuppression or immunostimulation) has broad implications.

The Plasminogen-Apple-Nematode (PAN) domain (IPR003609) was first characterized by Tordai et al., (*FEBS Letters*, 461(1-2), 63-67, (1999)) in which they noted that the domain was shared by the plasminogen/hepatocyte growth factor protein family, the prekallikrein/coagulation factor XI protein family and nematode proteins. The domain possesses the characteristic 6-cysteine residues in its core that are highly conserved. These cysteine residues coordinate three disulfide bridges to form a hair-pin loop structure.

Plasma kallikrein (EC 3.4.21.34) and coagulation factor XI (EC 3.4.21.27) are two related plasma serine proteases activated by factor XIIA and which share the same domain topology: an N-terminal region that contains four tandem repeats of about 90 amino acids and a C-terminal catalytic domain. The 90 amino-acid repeated domain contains 6 conserved cysteines. Three disulfide bonds link the first and sixth, second and fifth, and third and fourth cysteines. The domain can be drawn in the shape of an apple and has been accordingly called the "apple domain".

The apple domains of plasma prekallikrein are known to mediate its binding to high molecular weight kininogen, the apple domains of factor XI bind to factor XIIa, platelets, kininogen, factor IX and heparin.

The apple domains display some sequence similarity with the N domain of plasminogen/hepatocyte growth factor (HGF) and to some nematode and protozoan proteins. They all belong to the same domain superfamily that have been called the PAN module. The N domain of hepatocyte growth factor binds to the c-Met receptor and to the heparin molecule. The structure of the PAN module of HGF has been solved. It contains a characteristic hairpin-loop structure stabilised by two disulfide bridges, Cys-1 and 6 are not conserved in HGF PAN modules.

Apart from the cysteines, there are a number of other conserved positions in the apple domain. The PAN domain is thought to mediate protein-protein or carbohydrate-protein interactions and facilitate receptor dimerization.

Immunoregulation has been well recorded in plants. Plasma membrane bound pattern recognition receptors (PRR) are integral part of surveillance system against pathogens. Among the PRR which has a receptor kinase domain are known as receptor kinases. These receptor kinases are further classified into specific sub-types including Lectin-rich receptor kinases (L-type RLKs). L-type RLKs are well known for their role in triggering plant defense responses upon pathogen invasion. In contrast, it has been shown that a different class of receptor kinases, the PAN domain-containing D-mannose lectin binding domain receptor-like protein kinases (G-type RLKs), function to suppress defense response in plants. G-type RLKs were shown to function as negative regulators of defense signaling during pathogenesis by the fungal pathogen *Sphaerulina musiva*, parasitism of *Arabidopsis* by nematodes, and conversion of *Arabidopsis* into a host of the fungal symbiont *Laccaria bicolor*. Moreover, PAN domain carrying S-locus kinases, reported to mediate self-incompatibility during pollination, fall under the same class of G-LecRLKs. However, the specific role of the PAN domain in all these processes has not been fully described.

In animal systems, PAN domain proteins function in cell growth and proliferation. One example is the Hepatocyte growth factor (HGF) which has a similar domain structure with N terminal PAN domain, multiple kringle domain and a serine protease domain. HGF consists of characteristic heterodimer connected by a disulfide bond. HGF acts as an important paracrine mediator of growth, invasion and angiogenesis in several cancers. All biological impacts of HGF are triggered by stimulating its cell surface receptor. Both high and low affinity receptors have been identified for HGF. The high affinity receptor c-MET proto-oncogene is a receptor tyrosine kinase that is turned on by HGF ligand binding leading to a series of phosphorylation events including STAT3 phosphorylation, eventually turning on the HGF/c-MET signaling cascade. Hyperactivation of HGF/c-MET for instance, has been reported in lung cancer, colorectal cancer, glioblastoma, acute myeloid lymphoma among others with higher mortality rate. Recent evidence suggests that HGF can confer significant resistance to targeted cancer drugs including multiple kinase inhibitors interfering with current anti-cancer effort.

However, HGF/c-MET signaling is a key step for embryogenesis and tissue regeneration in the adult life which suggests a strict regulatory mechanism is important to determine the fate of the cells from a healthy one to tumorigenic. Recently, HGF/MET pathway emerged as a key target for anti-cancer therapy, although the major problem associated with small molecule inhibitors of MET and anti HGF-antibodies is that most of them are unstable and expensive. Although the interaction between MET and HGF were well studied, it was not clear which amino acids in α-chain of HGF serve as the binding region for cMET receptor.

SUMMARY OF THE DISCLOSURE

In one aspect the disclosure is directed to a method for screening for an immunoregulatory protein comprising assessing the sequence of a candidate protein, and determining that the candidate protein is an immunoregulatory protein when at least one Plasminogen Apple Nematode (PAN) domain is found in the sequence.

In some embodiments, the PAN domain has a consensus sequence as shown in SEQ ID NO: 23.

Another aspect of the disclosure is directed to a method for screening for a therapeutic compound targeting a PAN domain in a protein, comprising contacting the protein comprising the PAN domain with a candidate therapeutic compound, and assessing whether the compound binds to the PAN domain.

In some embodiments, the PAN domain-containing protein is selected from proteins listed in List 1.

Another aspect of the disclosure is directed to a method for screening for a MET signaling inhibitor, comprising expressing a c-MET receptor on the surface of a cell; incubating the cell with Hepatocyte Growth Factor (HGF) in the presence of a candidate inhibitor of PAN domain interactions; and determining that the candidate inhibitor is an inhibitor of c-MET signaling if the interaction with c-MET and HGF is inhibited.

In some embodiments, the candidate inhibitor of PAN domain interactions is a peptide comprising a consensus sequence as shown in SEQ ID NO: 23. In some embodiments, the candidate inhibitor of PAN domain interactions is a small molecule.

Another aspect of the disclosure is directed to a method for enhancing immune response to a pathogen in a plant comprising inactivating a gene encoding a PAN domain-containing protein in the plant. In some embodiments, the inactivating is achieved by introducing a non-silent mutation in the gene at a position encoding a conserved cysteine residue of the PAN domain. In some embodiments, the PAN domain-containing protein is selected from plant G-type receptor-like protein kinases. In some embodiments, the conserved cysteine residue is selected from a residue equivalent to a cysteine at position 1, 32, 36, 40, 42, or 57 of SEQ ID NO: 25.

In some embodiments, the non-silent mutation is a non-conservative mutation. In some embodiments, the nonconservative mutation is a cysteine to alanine mutation.

In some embodiments, the inactivating of the gene encoding a PAN domain-containing protein is achieved by introducing an exogenous nucleic acid inhibitor of the gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the selected gene is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the gene encoding a PAN domain containing protein.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the gene encoding a PAN domain containing protein gene, and a third nucleic acid comprising a template for homologous recombination.

In some embodiments, the pathogen is selected from a bacterium, a virus or a fungus.

Another aspect of the disclosure I directed to a genetically engineered plant, wherein an endogenous gene encoding a PAN domain-containing protein has been inactivated as a result of a genetic modification.

In some embodiments, the inactivating is achieved by introducing a non-silent mutation in the gene at a residue encoding a conserved cysteine residue of the PAN domain.

In some embodiments, the PAN domain-containing protein is selected from G-type receptor-like protein kinases. In some embodiments, the conserved cysteine residue is selected from a residue equivalent to a cysteine at position 1, 32, 36, 40, 42, or 57 of SEQ ID NO: 25.

In some embodiments, the non-silent mutation is a non-conservative mutation. In some embodiments, the nonconservative mutation is a cysteine to alanine mutation.

Another aspect of the disclosure is directed to a method for preventing cell division of a human cell comprising inactivating a gene encoding a PAN domain containing protein in the human cell. In some embodiments, the inactivating is achieved by introducing a non-silent mutation in the gene at a residue encoding a conserved cysteine residue of the PAN domain.

In some embodiments, the PAN domain containing protein gene is Hepatocyte Growth Factor (HGF).

In some embodiments, the conserved cysteine residue is selected from a residue equivalent to a cysteine at position 34, 38, 48, or 60 of SEQ ID NO: 32.

In some embodiments, the non-silent mutation is a non-conservative mutation. In some embodiments, the nonconservative mutation is a cysteine to alanine mutation.

In some embodiments, the inactivating of the gene encoding a PAN domain-containing protein is achieved by introducing an exogenous nucleic acid inhibitor of the gene to the cancer cell.

In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the gene encoding a PAN domain-containing protein is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the cancer cell a first nucleic acid encoding a Cas9 nuclease, and a second nucleic acid comprising a guide RNA (gRNA), wherein said gRNA is specific to the gene encoding a PAN domain containing protein.

In some embodiments, the CRISPR-mediated genome editing comprises introducing into the cancer cell a first nucleic acid encoding a Cas9 nuclease, a second nucleic acid comprising a guide RNA (gRNA), wherein said gRNA is specific to the gene encoding a PAN domain containing protein, and a third nucleic acid comprising a template for homologous recombination.

Another aspect of the disclosure is directed to a method for improving in vitro fertilization (IVF) efficiency in a non-human subject suffering from infertility comprising determining the sequence of a gene that encodes a PAN domain-containing protein, and obtaining an ovum or a sperm from the subject when a mutation is found in a conserved cysteine of the PAN domain of the PAN domain-containing protein, correcting the mutation in the PAN domain-containing protein in the ovum or the sperm.

In some embodiments, the PAN domain-containing protein gene is a Zona Pellicuda(ZP) protein.

In some embodiments, wherein the conserved cysteine residue is selected from a residue equivalent to a cysteine residue in SEQ ID NO: 23.

In some embodiments, the correcting of the PAN domain is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the gene encoding a PAN domain-containing protein, and a third nucleic acid comprising a template for homologous recombination that corrects the mutated residue to cysteine.

In some embodiments, the ovum or the sperm is from a domesticated animal.

Another aspect of the disclosure is directed to a method for preventing pregnancy or implantation of a fetus in a non-human subject comprising inactivating a gene encoding a PAN domain-containing protein in an ovum or a sperm.

In some embodiments, the inactivating is achieved by introducing a non-silent mutation in the gene at a residue encoding a conserved cysteine residue of the PAN domain.

In some embodiments, the PAN domain containing protein gene is a Zona Pellicuda protein.

In some embodiments, the conserved cysteine residue is selected from a residue equivalent to a cysteine a cysteine residue in SEQ ID NO: 23.

In some embodiments, the non-silent mutation is a non-conservative mutation. In some embodiments, the nonconservative mutation is a cysteine to alanine mutation.

In some embodiments, the inactivating of the gene encoding a PAN domain-containing protein is achieved by introducing an exogenous nucleic acid inhibitor of the gene to the ovum or the sperm. In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the gene encoding a PAN domain-containing protein is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the gene encoding a PAN domain-containing protein.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the selected gene, and a third nucleic acid comprising a template for homologous recombination.

In some embodiments, the ovum or the sperm is from a domesticated animal.

Another aspect of the disclosure is directed to a method for screening for an oncoprotein protein in a mammalian cell comprising assessing the sequence of a candidate protein, and determining that the candidate protein is an oncoprotein when at least one Plasminogen Apple Nematode (PAN) domain is found in the sequence.

In some embodiments, the PAN domain has a consensus sequence as shown in SEQ ID NO: 23.

Another aspect of the disclosure is directed to a method for inactivating a PAN domain-containing protein comprising introducing a non-silent mutation in the protein at a residue encoding a conserved cysteine residue of the PAN domain.

In some embodiments, the PAN domain-containing protein is selected from proteins listed in List 1.

In some embodiments, the conserved cysteine residue is selected from a residue equivalent to a cysteine residue in SEQ ID NO: 23.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
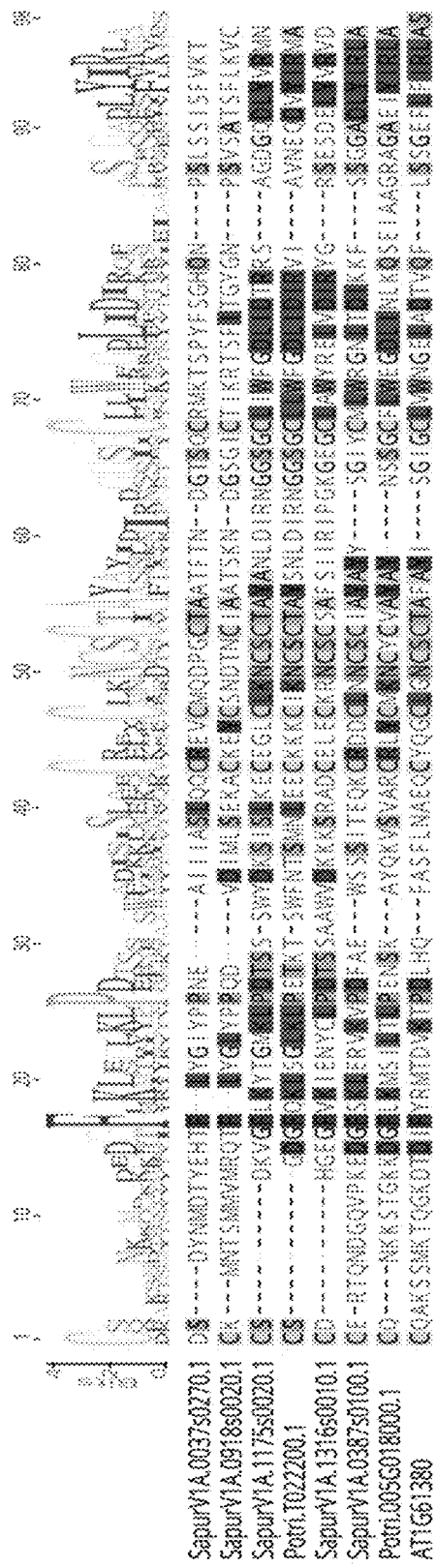
FIG. 1. Amino acid conservation within different G-LecRK PAN domains and naturally occurring variation in non-immunosuppressive Salix orthologs SapurV1A.0037s0270.1 and SapurV1A.0918s0020. The aligned PAN domains are the following: SapurV1A.0387s0100.1 (SEQ ID NO: 24), SapurV1A.1175s0020.1 (SEQ ID NO: 25), SapurV1A.0037s0270.1 (SEQ ID NO: 26), SapurV1A.1316s0010.1 (SEQ ID NO: 27), SapurV1A.0918s0020.1 (SEQ ID NO: 28), AT1G61380 (SEQ ID NO: 29), Potri.005G018000.1 (SEQ ID NO: 30), Potri.T022200.1 (SEQ ID NO: 31).

FIG. 2. Domain architecture of PAN domain proteins in *Anopheles gambiae* and *Diaphorina citri*.

FIG. 3. Proportion of protein domains co-occurring with the PAN domain in *Fusarium oxysporum* species complex.

FIGS. 4A-4B. Proportion of protein domain co-occurring with the PAN domain in oomycetes *Aphanomyces astaci* and *Phytophthora ramorum*.

FIGS. 5A-5B. Tandem expansion of G-LecRKs (orange blocks) on chromosome 4 and 9 of *Oryza sativa* compared to the syntenic region in the *Oryza punctata* genome.

FIGS. 6A-6K. Protein domain co-occurring with the PAN domain across organismal categories. (A) Alveolata, (B) Amoebozoa, (C) Archea, (D) Bacteria, (E) Cryptophyta; (F) Euglenozoa, (G) Haptophyceae, (H) Meta Genomics, (I) Opisthokonka, (J) Stramenoplies, (K) Viridplantae.

FIG. 7. Domain composition of PAN domain-containing proteins in viruses.

FIG. 8. Amino acid conservation within the PAN domain in different human proteins. NM_000601.5 represents HGF. Arrows show the four conserved Cysteine (C) and one conserved Asparagine (N). PAN domains used in the alignment are from the following proteins: NM_000601.5 (SEQ ID NO: 32); NP_001258662.1 (SEQ ID NO: 33); XP_016861955.1 (SEQ ID NO: 34); XP_016861956.1 (SEQ ID NO: 35); NP_066278.3 (SEQ ID NO: 36); XP_016861952.1 (SEQ ID NO: 37); XP_011532040.1 (SEQ ID NO: 38); XP_016861957.1 (SEQ ID NO: 39); XP_016861954.1 (SEQ ID NO: 40); XP_016861953.1 (SEQ ID NO: 41); XP_016861949.1 (SEQ ID NO: 42); XP_016861950.1 (SEQ ID NO: 43); XP_016861951.1 (SEQ ID NO: 44); XP_006713229.1 (SEQ ID NO: 45); XP_011532034.1 (SEQ ID NO: 46).

CRISPR/Cas system is a method based on the bacterial type II CRISPR (clustered regularly interspaced short palindromic repeats)/Cas (CRISPR-associated) immune system. The CRISPR/Cas system allows targeted cleavage of genomic DNA guided by a customizable small noncoding RNA, resulting in gene modifications by both non-homologous end joining (NHEJ) and homology-directed repair (HDR) mechanisms. Belhaj et al. (*Plant Methods,* 2013, 9:39) summarizes and discusses applications of the CRISPR/Cas technology in plants and is incorporated herein in its entirety.

In a specific embodiment genome editing is achieved by CRISPR (Clustered regularly-interspaced short palindromic repeats)/Cas technology. CRISPR-Cas and similar gene targeting systems are well known in the art with reagents and protocols readily available. Exemplary genome editing protocols are described in Jennifer Doudna, and Prashant *Mali,* "CRISPR-Cas: *A Laboratory Manual*" (2016) (CSHL Press, ISBN: 978-1-621821-30-4) and Ran, F. Ann, et al. (*Nature Protocols* (2013), 8 (11): 2281-2308).

In a specific embodiment, CRISPR-mediated gene repair comprises introducing said plant a first nucleic acid encoding a wild type Cas9 nuclease, a second nucleic acid comprising a guide RNA (gRNA) specific for targeting the mutated genomic region and a third nucleic acid comprising a homologous repair template (aka. Homology Directed Repair—HDR template) of said RLP1, RLP2, L-type lecRLK genes with said deleterious mutation. In this embodiment, the specific guide RNA targets the Cas9 nuclease to the mutated genomic region and the Cas9 nuclease introduces a double strand break in the targeted DNA region. In the presence of the homology template which contains a substantially functional copy of the mutated genomic region (with the deleterious mutation corrected), DNA repair mechanism favors Homology Directed Repair (HDR) and the mutation in the targeted gene is corrected.

The Plasminogen Apple Nematode (PAN) Domain

The PAN domain (Pfam ID: PF00024; InterPro ID: IPR003609; PROSITE ID: PDOC00376) contains 4 to 6 conserved cysteine residues. The conserved residues are involved in the formation of disulfide bond links between the first and sixth, second and fifth, third and fourth cysteines to form a hairpin-loop structure. Cysteine residues 1 and 6 are not conserved in some PAN domain containing proteins such as the Hepatocyte Growth Factor (HGF). As used herein, a PAN domain has the following consensus sequence: C-x(3)-[LIVMFY]-x(5)-[LIVMFY]-x(3)-[DENQ]-[LIVMFY]-x(10)-C-x(3)-C-T-x(4)-C-x-[LIVMFY]-F-x-[FY]-x(13-14)-C-x-[LIVMFY]-[RK]-x-[ST]-x(14-15)-S-G-x-[ST]-[LIVMFY]-x(2)-C(SEQ ID NO: 23). In some embodiments, the consensus sequence has the sequence as shown in any one of SEQ ID NO: 50-52. The skilled artisan can determine whether a protein comprises a PAN domain by searching the amino acid sequence of the protein using the consensus PAN domain sequence as a query sequence and any sequence alignment software.

The inventors of the instant disclosure have curated >28,000 proteins across eukaryotes, archaea, bacteria and viruses carrying the PAN domain. See List 1. After classifying 2,496 organisms representing 959 genera, into 13 categories (Alveolata, Archea, Amoebazoa, Bacteria, Cryptophyta, Euglenozoa, Haptophyceae, Opisthokonta, Rhizaria, Rhodophyta, Stramenopilles, Viridplantae, and Viruses) the inventors observed that proteins carrying the PAN domain have been implicated in modulation of immune responses across divergent organisms (e.g., from plants to animals, from viruses to bacteria and fungi), suggesting that the domain may have been co-opted to serve the same immunosuppressive function under different biological circumstances.

Methods for Screening for an Immunoregulatory Protein

The inventors of the instant disclosure have discovered that proteins that contain at least one PAN domain are involved in immunoregulation. In some embodiments, a PAN domain-containing protein functions as an immunosuppressor.

One aspect of the disclosure is directed to a method for screening for an immune regulating protein comprising assessing the sequence of a candidate protein, and determining that the candidate protein is an immune regulating protein when at least one Plasminogen Apple Nematode (PAN) domain is found in the sequence.

It has been found by the present inventors that a PAN domain is present in proteins having an immunoregulatory function. For example, a GO-enrichment analysis by the present inventors using >28,000 PAN domain-containing proteins listed in List 1 revealed 39 GO-terms that were enriched at $p<0.05$. These included terms like cell recognition ($p<1E-30$), cell communication ($p<1E-30$), proteolysis ($p<1E-30$), pollen-pistil interaction ($p<1E-30$), reproduction ($p<1E-30$), response to stimulus ($p<1E-30$) and response to stress ($p<1E-30$). These processes are consistent with roles in modulation of immune responses.

In some embodiments, the PAN domain has a consensus sequence as shown in SEQ ID NO: 23.

In some embodiments, the candidate protein is selected from a plant protein, an animal protein, a bacterial protein, a viral protein and a fungal protein. In some embodiments, the animal is a domesticated animal (cow, sheep, cat, dog, goat, etc) or a human.

In some embodiments, at least four conserved cysteine residues in the PAN domain of the immunoregulatory protein. In some embodiments, the at least four conserved cysteine residues comprise cysteines corresponding to the second cysteine to the fifth cysteine of SEQ ID NO: 23. In some embodiments, all six cysteine residues that correspond to the six cysteine residues of SEQ ID NO: 23 are conserved in the protein.

Methods for Screening for a Therapeutic Compound Targeting a PAN Domain

Another aspect of the disclosure is directed to a method for screening for a therapeutic compound targeting a PAN domain in a protein, comprising contacting the protein comprising the PAN domain with a candidate therapeutic compound, and assessing whether the compound binds to the PAN domain.

In some embodiments, the candidate compound is a small molecule compound.

In some embodiments, the candidate compound binds to the PAN domain with a KD of $10^{-7}$ M, $10^{-8}$ M, $10^{-9}$ M, $10^{-10}$ M, $10^{-11}$ M, $10^{-12}$ M or less.

In some embodiments, the binding affinity of the candidate compound is measured by a competitive binding assay.

In some embodiments, the PAN-domain containing protein is selected from the proteins listed in List 1.

In some embodiments, the PAN domain in the PAN domain containing protein has a consensus sequence as shown in SEQ ID NO: 23.

In some embodiments, the protein is selected from a plant protein, an animal protein, a bacterial protein, a viral protein and a fungal protein.

In some embodiments, a compound, which is identified as binding to the PAN domain, inhibits the immunoregulatory function of the PAN domain-containing protein. For example, hepatocyte growth factor (HGF), a PAN domain-containing protein, is an immunoregulator that acts through its interaction with the cMET receptor. The inventors of the instant disclosure have found that the PAN domain in HGF is critical for its interaction with cMET receptor and its role in immunoregulation.

Methods for Screening for a MET Signaling Inhibitor

A different aspect of the disclosure is directed to a method for screening for a MET signaling inhibitor, comprising expressing a c-MET receptor on the surface of a cell; incubating the cell with Hepatocyte Growth Factor (HGF) in the presence of a candidate inhibitor of PAN domain interactions; and determining that the candidate inhibitor is an inhibitor of c-MET signaling if the interaction with c-MET and HGF is inhibited.

In some embodiments, the candidate inhibitor of PAN domain interactions is a competitive inhibitor of PAN domain binding. In some embodiments, the candidate inhibitor of PAN domain interactions is an allosteric inhibitor of PAN domain binding.

In some embodiments, the candidate inhibitor of PAN domain interactions is a peptide comprising a consensus sequence as shown in SEQ ID NO: 23.

In some embodiments, the inhibitor candidate is a small molecule compound.

In some embodiments, the inhibitor candidate binds to the PAN domain with a KD of $10^{-7}$ M, $10^{-8}$ M, $10^{-9}$ M, $10^{-10}$ M, $10^{-1}$ M, $10^{-1}$ M or less.

In some embodiments, the cell is a mammalian cell.

Methods for Enhancing Immune Response to Pathogens in Plants

It has been found in accordance with this disclosure that PAN domain-containing proteins in plants have the function of suppressing the plant immune response to foreign entities. While in some instances the foreign entity is a symbiont beneficial to the plant, in other instances the foreign entity is a pathogen.

Another aspect of the disclosure is directed to a method for enhancing immune response or resistance to a pathogen in a plant comprising inactivating a gene encoding a PAN domain-containing protein in the plant.

In some embodiments, the inactivating is achieved by introducing a non-silent mutation in the gene at a residue encoding a conserved cysteine residue of the PAN domain.

In some embodiments, the PAN domain containing protein gene is selected from a plant G-type receptor-like protein kinase gene. In some embodiments, a G-type receptor-like protein kinase gene has a nucleotide sequence that is homologous to SEQ ID NO: 47. In some embodiments, a G-type receptor-like protein kinase gene has a nucleotide sequence that is at least 70%, 73% 75%, 78%, 80%, 83%, 85%, 88%, 90%, 93%, 95% or 99%, or more identical to SEQ ID NO: 47. In some embodiments, a G-type receptor-like protein kinase gene encodes a protein that has an amino acid sequence that is homologous to SEQ ID NO: 48. In some embodiments, a G-type receptor-like protein kinase gene encodes a protein that has an amino acid sequence that is at least 70%, 73% 75%, 78%, 80%, 83%, 85%, 88%, 90%, 93%, 95% or 99%, or more identical to SEQ ID NO: 48.

In some embodiments, the conserved cysteine residue is selected from a residue equivalent to a cysteine at position 1, 32, 36, 40, 42, or 57 of SEQ ID NO: 25.

In some embodiments, the non-silent mutation is a nonconservative mutation.

In some embodiments, the nonconservative mutation is a cysteine to alanine mutation.

In some embodiments, the inactivating of the gene encoding a PAN domain containing protein is achieved by introducing an exogenous nucleic acid inhibitor of the gene to the plant.

In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the selected gene is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the gene encoding a PAN domain containing protein.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the gene encoding a PAN domain containing protein, and a third nucleic acid comprising a template for homologous recombination.

In some embodiments, the pathogen is selected from a bacterium, a virus or a fungus.

In some embodiments, the pathogen is a necrotropic fungus selected from the group consisting of *Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillae-junceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaer-* ulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosae-pigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea subsp. myriadea, Sphaerulina myrtillina, Sphaerulina naumovii, Sphaerulina nephromiaria, Sphaerulina oleifolia, Sphaerulina orae-maris, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen. Pharcidiella, Sphaerulina subgen, Sphaerulina, Sphaerulina subglacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae, and Sphaerulina zizyphi.

Genetically-Engineered Plants Resistant to Pathogens and Parasites

Another aspect of the disclosure is directed to a genetically engineered plant, wherein an endogenous gene encoding a PAN domain-containing protein in the plant has been inactivated as a result of a genetic modification.

In some embodiments, the inactivation is achieved by introducing a non-silent mutation in the gene at a residue encoding a conserved cysteine residue of the PAN domain.

In some embodiments, the gene encoding a PAN domain-containing protein is selected from a plant G-type receptor-like protein kinase gene. In some embodiments, a G-type receptor-like protein kinase gene has a nucleotide sequence that is homologous to SEQ ID NO: 47. In some embodiments, a G-type receptor-like protein kinase gene has a nucleotide sequence that is at least 70%, 73% 75%, 78%, 80%, 83%, 85%, 88%, 90%, 93%, 95% or 99%, or more identical to SEQ ID NO: 47. In some embodiments, a G-type receptor-like protein kinase gene encodes a protein that has an amino acid sequence that is homologous to SEQ ID NO: 48. In some embodiments, a G-type receptor-like protein kinase gene encodes a protein that has an amino acid sequence that is at least 70%, 73% 75%, 78%, 80%, 83%, 85%, 88%, 90%, 93%, 95% or 99%, or more identical to SEQ ID NO: 48.

In some embodiments, the conserved cysteine residue is selected from a residue equivalent to a cysteine at position 1, 32, 36, 40, 42, or 57 of SEQ ID NO: 25.

In some embodiments, the non-silent mutation is a nonconservative mutation.

In some embodiments, the nonconservative mutation is a cysteine to alanine mutation.

In some embodiments, the pathogen is selected from a bacterium, a virus or a fungus.

In some embodiments, the pathogen is a necrotropic fungus selected from the group consisting of Sphaerulina abeliceae, Sphaerulina aceris, Sphaerulina acetabulum, Sphaerulina acori, Sphaerulina aechmeae, Sphaerulina affinis, Sphaerulina albispiculata, Sphaerulina alni, Sphaerulina amelanchier, Sphaerulina amicta, Sphaerulina amphilomatis, Sphaerulina amygdali, Sphaerulina anemones, Sphaerulina annae, Sphaerulina antarctica, Sphaerulina arctica, Sphaerulina arthoniae, Sphaerulina assurgens, Sphaerulina aucubae, Sphaerulina azaleae, Sphaerulina baccarum, Sphaerulina bambusicola, Sphaerulina berberidis, Sphaerulina betulae, Sphaerulina blyttii, Sphaerulina bonariana, Sphaerulina boudieriana, Sphaerulina bryophila, Sphaerulina callista, Sphaerulina camelliae, Sphaerulina camelliae, Sphaerulina carestiae, Sphaerulina caricae, Sphaerulina caricis, Sphaerulina ceanothi, Sphaerulina centellae, Sphaerulina cercidis, Sphaerulina cetraricola, Sphaerulina cetrariicola, Sphaerulina chlorococca, Sphaerulina cibotii, Sphaerulina citri, Sphaerulina codiicola, Sphaerulina coffaeicola, Sphaerulina coffeicola, Sphaerulina concinna, Sphaerulina conflicta, Sphaerulina coriariae, Sphaerulina cornicola, Sphaerulina corniculata, Sphaerulina coronillae-junceae, Sphaerulina corynephora, Sphaerulina cucumeris, Sphaerulina cucurbitae, Sphaerulina datiscae, Sphaerulina diapensiae, Sphaerulina dioscoreae, Sphaerulina divergens, Sphaerulina dolichotera, Sphaerulina dryadis, Sphaerulina dryophila, Sphaerulina dubiella, Sphaerulina empetri, Sphaerulina endococcoidea, Sphaerulina epigaea, Sphaerulina eucalypti, Sphaerulina ferruginosa, Sphaerulina frondicola, Sphaerulina fuegiana, Sphaerulina gei, Sphaerulina gentianae, Sphaerulina gigantea, Sphaerulina giliae, Sphaerulina hainensis, Sphaerulina halophila, Sphaerulina hamadryadum, Sphaerulina hederae, Sphaerulina helicicola, Sphaerulina hyperici, Sphaerulina inaequalis, Sphaerulina inquinans, Sphaerulina intermedia, Sphaerulina intermixta, Sphaerulina ipomoeae, Sphaerulina islandica, Sphaerulina iwatensis, Sphaerulina juglandis, Sphaerulina leightonii, Sphaerulina lepidiotae, Sphaerulina limnanthemi, Sphaerulina lini, Sphaerulina linicola, Sphaerulina ludwigiae, Sphaerulina mappiae, Sphaerulina marattiae, Sphaerulina marginata, Sphaerulina maroccana, Sphaerulina marsileae, Sphaerulina maydis, Sphaerulina menispermi, Sphaerulina microthyrioides, Sphaerulina mimosae-pigrae, Sphaerulina miyakei, Sphaerulina musae, Sphaerulina muscicola, Sphaerulina muscorum, Sphaerulina musicola, Sphaerulina musiva, Sphaerulina myriadea, Sphaerulina myriadea subsp. myriadea, Sphaerulina myrtillina, Sphaerulina naumovii, Sphaerulina nephromiaria, Sphaerulina oleifolia, Sphaerulina orae-maris, Sphaerulina oryzae, Sphaerulina oryzina, Sphaerulina oxalidis, Sphaerulina oxyacanthae, Sphaerulina pallens, Sphaerulina parvipuncta, Sphaerulina patriniae, Sphaerulina paulistana, Sphaerulina peckii, Sphaerulina pedicellata, Sphaerulina pelargonii, Sphaerulina phalaenopsidis, Sphaerulina phellogena, Sphaerulina phoenicis, Sphaerulina phyllostachydis, Sphaerulina pini, Sphaerulina plantaginea, Sphaerulina pleuropogonis, Sphaerulina polygonorum, Sphaerulina polypodii, Sphaerulina polypodii, Sphaerulina polyspora, Sphaerulina populi, Sphaerulina populicola, Sphaerulina porothelia, Sphaerulina potebniae, Sphaerulina potentillae, Sphaerulina poterii, Sphaerulina primulicola, Sphaerulina pruni, Sphaerulina pseudovirgaureae, Sphaerulina pterocarpi, Sphaerulina pulii, Sphaerulina quercicola, Sphaerulina quercifolia, Sphaerulina quitensis, Sphaerulina rehmiana, Sphaerulina rhabdoclinis, Sphaerulina rhodeae, Sphaerulina rhododendri, Sphaerulina rhododendricola, Sphaerulina rubi, Sphaerulina saccardiana, Sphaerulina saccardoana, Sphaerulina sacchari, Sphaerulina salicina, Sphaerulina sambucina, Sphaerulina sasae, Sphaerulina schaereri, Sphaerulina scirpi, Sphaerulina sepincola, Sphaerulina serograpta, Sphaerulina silacincola, Sphaerulina smilacincola, Sphaerulina socia, Sphaerulina spartii, Sphaerulina staphyleae, Sphaerulina staurochili, Sphaerulina steganostroma, Sphaerulina subgen. Pharcidiella, Sphaerulina subgen, Sphaerulina, Sphaerulina subglacialis, Sphaerulina subtropica, Sphaerulina suchumica, Sphaerulina tabacinae, Sphaerulina tanaceti, Sphaerulina tarda, Sphaerulina taxi, Sphaerulina taxicola, Sphaerulina thujopsidis, Sphaerulina tiliaris, Sphaerulina tirolensis, Sphaerulina todeae, Sphaerulina trapae-bispinosae, Sphaerulina trifolii, Sphaerulina tritici, Sphaerulina umbilicata, Sphaerulina valerianae, Sphaerulina viciae, Sphaerulina vincae, Sphaerulina violae, Sphaerulina vismiae, Sphaerulina vulpina, Sphaerulina westendorpii, Sphaerulina worsdellii, Sphaerulina xerophylli, Sphaerulina yerbae, Sphaerulina ziziphi, Sphaerulina zizyphae, and Sphaerulina zizyphi.

Method for Preventing Cell Division of a Human Cell

It has been found in accordance with this disclosure that PAN domain-containing proteins are involved in regulating the rate of cell division in mammalian cells, and cellular migration in cancer cells. Thus, another aspect of the disclosure is directed to a method for preventing cell division of a human cell and cellular migration in cancer cells comprising inactivating a gene encoding a PAN domain containing protein in the human cell.

In some embodiments, the inactivation is achieved by introducing a non-silent mutation in the gene at a residue encoding a conserved cysteine residue of the PAN domain.

In some embodiments, the PAN domain-containing protein is Hepatocyte Growth Factor (HGF), or a homolog thereof. In some embodiments, the HGF binds to cMET receptor and has an amino acid sequence that is at least 70%, 73% 75%, 78%, 80%, 83%, 85%, 88%, 90%, 93%, 95% or 99%, or more identical to SEQ ID NO: 49.

In some embodiments, the conserved cysteine residue is selected from a residue homologous to a cysteine at position 34, 38, 48, or 60 of SEQ ID NO: 32.

In some embodiments, the non-silent mutation is a non-conservative mutation. In some embodiments, the nonconservative mutation is a cysteine to alanine mutation.

In some embodiments, the inactivating of the selected gene is achieved by introducing an exogenous nucleic acid inhibitor of the gene encoding a PAN domain-containing protein to the cancer cell.

In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the gene encoding a PAN domain containing protein is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the cancer cell a first nucleic acid encoding a Cas9 nuclease, and a second nucleic acid comprising a guide RNA (gRNA), wherein said gRNA is specific to the gene.

In some embodiments, the CRISPR-mediated genome editing comprises introducing into the cancer cell a first nucleic acid encoding a Cas9 nuclease, a second nucleic acid comprising a guide RNA (gRNA), wherein said gRNA is specific to the gene encoding a PAN domain containing protein, and a third nucleic acid comprising a template for homologous recombination.

In some embodiments, the cancer cell is selected from breast cancer, colon cancer, lung cancer, skin cancer, brain cancer, blood cancer, cervical cancer, liver cancer, prostate carcinoma, pancreas carcinoma, gastric carcinoma, ovarian carcinoma, renal cell carcinoma, mesothelioma, and melanoma.

Methods for Improving In Vitro Fertilization (IVF) Efficiency

It has been found in accordance with this disclosure that sperms and oocytes contain PAN domain-containing proteins that play crucial roles in the fertilization process. Without being bound by a particular theory, PAN domain containing proteins are believed to suppress the immune response by the oocyte, or other cells in the uterus, against the sperm (a foreign entity) and the embryo (partially foreign entity). Some cases of infertility can result from mutations in a PAN domain of a PAN domain containing protein expressed in the reproductive system.

Therefore, another aspect of the disclosure is directed to a method for improving in vitro fertilization (IVF) efficiency in a non-human subject suffering from infertility comprising determining the sequence of a gene that encodes a PAN domain-containing protein, and when a mutation is found in a conserved cysteine of the PAN domain of the PAN domain-containing protein obtaining an ovum or a sperm from the subject, correcting the mutation in the PAN domain-containing protein in the ovum or the sperm.

In some embodiments, the PAN domain containing protein gene is a Zona Pellicuda(ZP) protein.

In some embodiments, the conserved cysteine residue is selected from a residue homologous to a cysteine residue in SEQ ID NO: 23.

In some embodiments, the correcting of the PAN domain is achieved by genome editing by a method selected from the group consisting of CRISPR/Cas system, Cre/Lox system, TALEN system, ZFNs system and homologous recombination.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the gene encoding a PAN domain containing protein, and a third nucleic acid comprising a template for homologous recombination that corrects the mutated residue to cysteine.

In some embodiments, wherein the ovum or the sperm are from a domesticated animal. In some embodiments, the domesticated animal is selected from the group consisting of horse, camel, donkey, cat, goat, dog, pig, cow, and sheep.

Methods for Preventing Pregnancy (Immunocontraception)

Another aspect of the disclosure is directed to a method for preventing pregnancy or implantation of a fetus in a non-human subject comprising inactivating a gene encoding a PAN domain-containing protein in an ovum or a sperm.

In some embodiments, the inactivating is achieved by introducing a non-silent mutation in the gene at a residue encoding a conserved cysteine residue of the PAN domain.

In some embodiments, the PAN domain containing protein gene is a Zona Pellicuda protein.

In some embodiments, the conserved cysteine residue is selected from a residue homologous to a cysteine a cysteine residue in SEQ ID NO: 23.

In some embodiments, the non-silent mutation is a non-conservative mutation.

In some embodiments, the nonconservative mutation is a cysteine to alanine mutation.

In some embodiments, the inactivating of the selected gene is achieved by introducing an exogenous nucleic acid inhibitor of the selected gene to the ovum or the sperm.

In some embodiments, the nucleic acid inhibitor is selected from the group consisting of an antisense RNA, a small interfering RNA, an RNAi, a microRNA, an artificial microRNA, and a ribozyme.

In some embodiments, the inactivating of the selected gene is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the selected gene.

In some embodiments, the CRISPR-mediated genome editing comprises introducing into the ovum or the sperm a first nucleic acid encoding a Cas9 nuclease, a second nucleic acid comprising a guide RNA (gRNA), wherein said gRNA is specific to the selected gene, and a third nucleic acid comprising a template for homologous recombination.

In some embodiments, the ovum or the sperm are from a domesticated animal. In some embodiments, the domesticated animal is selected from the group consisting of horse, camel, donkey, cat, goat, dog, pig, cow, and sheep.

Methods for Discovering Oncoproteins

As discussed above, PAN domain-containing proteins have been found to play a role in regulating the rate of cell division. Therefore, another aspect of the disclosure is directed to a method for screening for a novel oncoprotein protein in a mammalian cell comprising assessing the sequence of a candidate protein, and determining that the candidate protein is an oncoprotein when at least one PAN domain is found in the sequence.

In some embodiments, the Plasminogen Apple Nematode (PAN) domain has a consensus sequence as shown in SEQ ID NO: 23.

In some embodiments, the mammalian cell is an animal cell. In some embodiments, the mammalian cell is a human cell.

Method for Inactivating a PAN Domain Containing Protein

PAN domains are involved in protein-protein interactions (as in HGF and cMET). In addition, it has also been found in accordance with this disclosure that introducing a mutation in at least one conserved cysteine of a PAN domain prevents the protein-protein interactions of the PAN domain, thereby inactivating the PAN domain-containing protein and inhibiting its function.

Another aspect of the disclosure is directed to a method for inactivating a PAN domain-containing protein comprising introducing a non-silent mutation in the protein at a conserved cysteine residue of the PAN domain.

In some embodiments, the PAN domain-containing protein gene is selected from the proteins listed in List 1.

In some embodiments, the conserved cysteine residue is selected from a residue equivalent to one of the six cysteine residues in SEQ ID NO: 23.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Cloning, Sequencing and Overexpression of G-RLKs

The coding sequences of SapurV1A.0037s0270.1, SapurV1A.0918s0020 and SapurV1A.1175s0020 were amplified by PCR from cDNA derived from *Salix purpurea* leaves using HiFi polymerase (Clontech). Sequences were determined using Phytozyme using the *Salix purpurea* v.1.0 genome. The pENTR/D-TOPO entry vector was used for the insertion of the PCR products using the pENTR Directional Topo Cloning Kit (Thermo Fisher Scientific). LR Clonase II Enzyme Mix (Thermo Fisher Scientific) was used to transfer the coding sequences into the pGWB402-omega destination vector and transformed into One Shot TOP10 Chemically Competent cells. Vectors were transformed into the *Agrobacterium* strain GV3101 and transformed into Col-0 *Arabidopsis thaliana* using the floral dip method. T1 seeds were selected with Kanamycin and grown in long day growth chambers at 16/8 hours light/dark at 22° C. Three week old leaf tissue was collected for RNA extractions using the Spectrum Plant Total RNA Kit (Sigma) and cDNA synthesized using the Superscript III Reverse Transcriptase with oligo-d(T) primers (Thermo Fisher Scientific). qRT-PCR was performed using the PowerUP SYBR Green Master Mix (Thermo Fisher Scientific) and relative expression for each gene was determined with the 2ΔΔCt method with GAPDH as an internal control.

TABLE 1

Primer sequences

| Primer name | Primer sequence | SEQ ID NO |
|---|---|---|
| 1_0037s0270csF | CACCATGCTTAAGCAGGGCAATTTCT | 1 |
| 2_0037s0270csR | TCATGGTTCCATTGGCCTCT | 2 |
| 5_0918s0020csF | CACCATGGGCGTGACTAGGAATAGAG | 3 |
| 6_0918s0020csR | CTAAGAGGAGTCTACTTCGACCTC | 4 |
| 77_RLK53_GWF | CACCATGGGTACTTTTTCAGTTCTG | 5 |
| 78_RLK53_GWRs | CTACCGGGCCTCTAATGACATC | 6 |
| 23_0037s0270rtF | GGGGTCAAAGCTTTCTACAGAGG | 7 |
| 24_0037s0270rtR | GCCAACCAAACCACAGTTTGC | 8 |
| 27_0918s0020rtF | GCTTTTGTGAAGAGGTTGCCATGG | 9 |
| 28_0918s0020rtR | GACCCCATTTTGAGACACCC | 10 |
| 89_RLK53_RTF | CGTTTCAACCGGAGGAAGC | 11 |
| 90_RLK53_RTR | TTACATTCAGAGCCCCCAAAGC | 12 |
| 177_Arab_WRKY70_RTF | CATGGATTCCGAAGATCACA | 13 |
| 178_Arab_WRKY70_RTR | CTGGCCACACCAATGACAA | 14 |
| 179_Arab_WRKY40_RTF | AAATCAGCCCTCCCAAGAAACG | 15 |
| 180_Arab_WRKY40_RTR | CTTCACGACAGTCTCTTCTCTCTGC | 16 |
| 181_Arab_WRKY33_RTF | AGGCTCATCGATTGTCAGCA | 17 |
| 182_Arab_WRKY33_RTR | CTGCACTACGATTCTCGGCT | 18 |
| 183_Arab_WRKY8_RTF | GTTGTCGGTGATGGTTGTGC | 19 |
| 184_Arab_WRKY8_RTR | CCGGATCTTGCCGGAATCTT | 20 |
| 185_Arab_GAPDH_RTF | AGGCCATCAAGGAGGAATCT | 21 |
| 186_Arab_GAPDH_RTR | GAAAATGCTTGACCTGTTGTCAC | 22 |

TABLE 2

Matching primers to genes and use

| Gene Name | Primer name | Primer use |
|---|---|---|
| SapurV1A.0037s0270 | 1_0037s0270csF | Cloning CDS |
| | 2_0037s0270csR | Cloning CDS |
| SapurV1A.0918s0020 | 5_0918s0020csF | Cloning CDS |
| | 6_0918s0020csR | Cloning CDS |
| SapurV1A.1175s0020 | 77_RLK53_GWF | Cloning CDS |
| | 78_RLK53_GWRs | Cloning CDS |
| SapurV1A.0037s0270 | 23_0037s0270rtF | RT-qPCR |
| | 24_0037s0270rtR | RT-qPCR |
| SapurV1A.0918s0020 | 27_0918s0020rtF | RT-qPCR |
| | 28_0918s0020rtR | RT-qPCR |
| SapurV1A.1175s0020 | 89_RLK53_RTF | RT-qPCR |
| | 90_RLK53_RTR | RT-qPCR |
| WRKY40 (AT1G80840) | 179_Arab_WRKY40_RTF | RT-qPCR |
| | 180_Arab_WRKY40_RTR | RT-qPCR |
| WRKY33 (AT2G38470) | 181_Arab_WRKY33_RTF | RT-qPCR |
| | 182_Arab_WRKY33_RTR | RT-qPCR |
| GAPDH (AT3G26650) | 185_Arab_GAPDH_RTF | RT-qPCR |
| | 186_Arab_GAPDH_RTR | RT-qPCR |

Synteny Analysis Between *Oryza sativa* and *O. punctata*

The CDS sequences and corresponding annotation files for *O. sativa* (IGRSP 1.0) and *O. punctata* (*Oryza_punctata*_v1.2) were downloaded from Ensembl Plants. The CDS files and sequences were then filtered to only retain protein coding genes. The protein coding genes were then annotated with Interproscan 5 (Jones et al., 2014, *Bioinformatics*, 30.9 (2014): 1236-1240). Synteny analysis was then performed via MCScanX and genes containing a PAN domain were searched against resulting synteny blocks. Regions that showed evidence of PAN domain expansion were extracted and visualized with the JCVI utility libraries.

Alignments of G-RLK Sequences

Interproscan 5 was used to identify the PAN domain regions of the 8 G-RLKs in FIG. 1. These regions were then extracted and aligned with MAFFT linsi (Katoh et al., *Molecular biology and evolution*, 30.4 (2013): 772-780) and then visualized with Geneious R11.

Domain Prediction in *Anopheles gambiae* and *Diaphorina citri*

Figure 2:
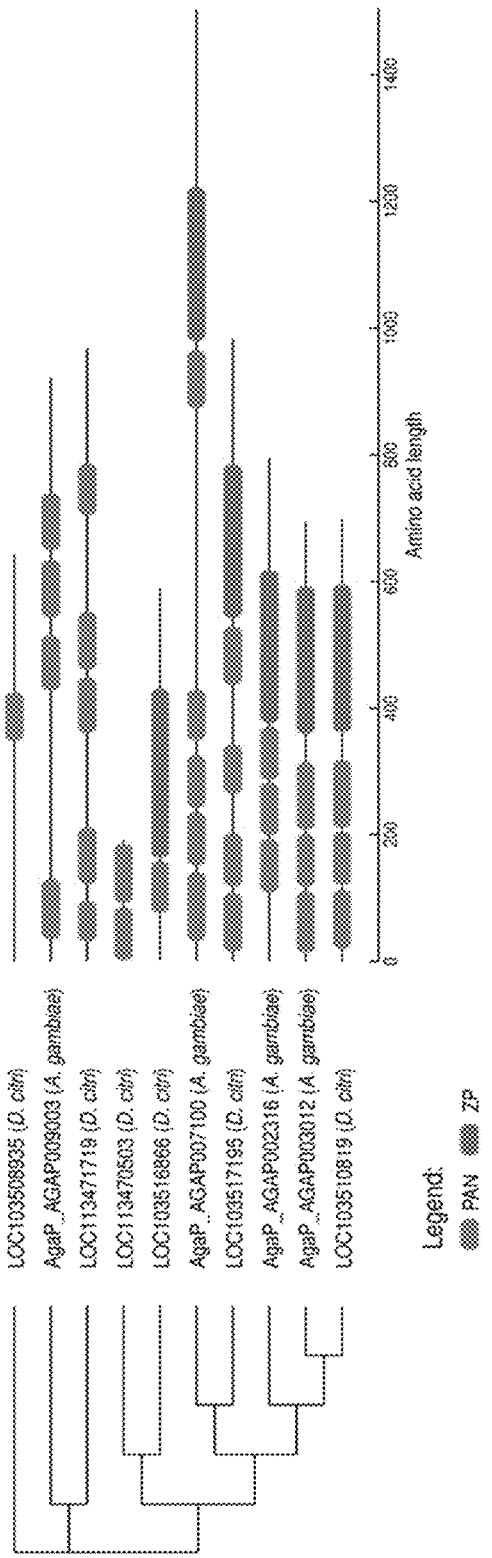

Interproscan 5 was used to identify domains for the 10 proteins in FIG. 2. The proteins were then aligned with MAFFT linsi and a Neighbor-Joining tree was generated with Geneious. The domain structure was then visualized with GSDS 2.0 (Hu et al., *Bioinformatics*, 31.8 (2014): 1296-1297).

Example 2

A protein database survey revealed that the PAN domain is found in >28,000 proteins derived from 2,496 organisms representing 959 genera. These included organisms with a high propensity to recruit symbionts, vector parasites and exhibit parasitic or pathogenic behavior. Additionally, the core conserved cysteine residues of the domain are structurally similar to cysteine-rich peptides that have been implicated in modulation of immune responses. Given the cumulative observations, the inventors propose that the PAN domain is a unifying feature in immunoregulation (e.g., immunosuppression) across divergent organism and propose the existence of an 'immunoregulome' comprised of PAN domain proteins functioning to mediate host-cell invasion.

In revealing a novel role for self-immunosuppression in plants during host-cell invasion by microbes, the PAN domain proteins, D-mannose lectin kinases (G-LecRKs), were shown to function as negative regulators of defense signaling during pathogenesis by the fungal pathogen *Sphaerulina musiva*, parasitism of *Arabidopsis* by nematodes, and conversion of *Arabidopsis* into a host of the fungal symbiont *Laccaria bicolor*. Moreover, PAN domain carrying S-locus kinases, reported to mediate self-incompatibility during pollination, fall under the same class of G-LecRKs.

In *Salix purpurea*, the inventors discovered two G-LecRKs (SapurV1A.0037s0270.1 (RLK5) and SapurV1A.0918s0020 (RLK7)) that, upon overexpression in *Arabidopsis*, triggered defense responses instead of functioning as immunosuppressors. Domain annotation using the PFAM database did not reveal presence of a PAN domain in both proteins, however, upon further analyses, the inventors observed that these two G-LecRKs carried a vestigial PAN domain. Specifically, the inventors compared the PAN domains of the two *Salix* G-LecRKs with ones demonstrated to be immunosuppressive, AT1G61380, Potri.T022200.1 and Potri.005G018000.1 and noted that both had mutations on the conserved asparagine (N) and cysteine (C) amino acids at positions 50 and 51 while SapurV1A.0037s0270 was also missing the cysteine residue at position 1 (FIG. 1).

With this observation, the inventors hypothesized that the PAN domain was essential for immunosuppression.

To test the hypothesis that the PAN domain is necessary for immunosuppression, the inventors sought to evaluate the context in which it is found in other proteins. We scanned protein databases, InterPro and UniProt (https://G-LecRK.uniprot.org), and found >28,000 proteins across eukaryotes, archaea, bacteria and viruses carrying the PAN domain. After classifying 2,496 organisms representing 959 genera, into 13 categories (Alveolata, Archea, Amoebazoa, Bacteria, Cryptophyta, Euglenozoa, Haptophyceae, Opisthokonta, Rhizaria, Rhodophyta, Stramenopilles, Viridplantae, and Viruses), the inventors observed that the domain had high fidelity to co-occurring domains and was found in specific protein families within each category. For example, in bacteria, the PAN domain was almost exclusively found in association with the alpha 2-macroglobulin (A2M) or related domains whereas in euglenozoa, it was found almost exclusively in association with the glycosyl hydrolase protein domain (FIGS. 6A-6K).

To assess the validity of association with immune modulation, the inventors performed a GO-enrichment analysis using the >28,000 protein. This analysis revealed 39 GO-terms that were enriched at $p<0.05$. These included terms like cell recognition (p<1E-30), cell communication (p<1E-30), proteolysis (p<1E-30), pollen-pistil interaction (p<1E-30), reproduction (p<1E-30), response to stimulus (p<1E-30) and response to stress (p<1E-30). These processes are consistent with roles in modulation of immune responses.

Example 3: Role of PAN Domain Proteins in Gamete Fertilization

Since male gametes are essentially foreign invading bodies, immunosuppression is essential during gamete fertilization, failure of which leads to incompatibility and sterility. As the first interface at which male gametes are perceived, the Zona Pellucida (ZP) occurs outside the female gamete as a layer of glycoproteins that has been reported to release species-specific chemoattractants to attract sperms to eggs. Within this glycoprotein matrix, PAN domain-carrying ZP proteins, also regarded as sperm receptors, are found as transmembrane proteins. ZP proteins have been widely implicated in modulating fertility across a wide variety of eukaryotes including mammalian, avian, amphibian, fish, ascidian and molluscan systems. Bertschinger et al. (*Bothalia-African Biodiversity & Conservation,* 48(2), 1-8 (2018)) reported that ZP proteins have been successfully used in immunocontraceptive approaches to manage populations of close to 90 animal species.

In plants, the PAN domain-harboring S-locus, serine-threonine, kinases have been shown to mediate pollen recognition and incompatibility in plants. PAN domain mediates S-locus receptor dimerization in the absence of a ligand and suggested that dimerization primes the receptor for interaction with its ligand to enhance the binding affinity. The S-locus receptor kinase (SRK) protein, located in the epidermal cells of the stigma, binds to its cognate pollen coat localized S-locus cysteine-rich (SCR) protein to initiate a signaling cascade to reject self-pollination. However, a non-self SCR protein will not be able to bind the SRK receptor and cross-pollination will occur unimpeded. This example shows that there is specificity between SRK-SCR interactions that is likely coordinated by the PAN domain as both the SCR and SRK proteins contain cysteine-rich regions capable of forming disulfide bonds.

Example 4: PAN Domain Proteins Implicated in Cell Growth and Proliferation

In animal systems, the PAN domain is found in plasminogen, hepatocyte growth factor (HGF), coagulation factor XI (FXI) and plasma kallikrein (PK), all protein classes implicated in cell growth, proliferation and regulation of immune system responses. Plasminogen and HGF have a similar domain structure with a N-terminal PAN domain, multiple Kringle domains and a serine protease domain. HGF in complex with the MET receptor activates a signaling cascade that initiates cell mobility, tissue regeneration, and angiogenesis. HGF/MET has been shown to have both an immunosuppressive and an immuno-positive role with dysregulation of HGF/MET signaling in tumors leading to invasion and metastasis.

Example 5: Cell Growth and Proliferation Machinery as a Target for Host-Cell Invasion FXI and PK are members of the contact system and consist of 4 N-terminal PAN domains followed by a serine protease domain. The contact system is a group of proteins that are activated by coagulation factor FXII. They bind to surfaces to cause blood coagulation and initiate inflammation responses. The contact system is activated by surface proteins of specific pathogens including, *Streptococcus pyogenes, Salmonella*, and *Escherichia coli*. Previous research by Krem and Di Cera (*Trends in biochemical sciences,* 27(2), 67-74 (2002)), has suggested that the blood coagulation system in vertebrates is an evolutionary by-product of the innate immune system. This is supported by the role of the contact system in initiating a signaling cascade that traps microorganisms in a blood clot to stop their invasion. For example, during *Streptococcus pyogenes* infection, FXII will bind to the surface of the bacteria and activate FXI and PK to trap the bacteria in a fibrin clot and induce a proinflammatory response to clear the infection. Activation of the contact system may also be beneficial to the microbe because the release of bradykinin, a product of contact activation system, will increase vascular permeability and provide a nutrient-rich environment for the bacteria to thrive.

Pathogens have evolved mechanisms to evade this host defense response by targeting another PAN domain-containing protein, plasminogen. In response to the formation of the fibrin clot, *S. pyogenes* secretes streptokinase, a protein that converts plasminogen to its active form of plasmin. Plasmin will degrade the fibrin clot, which allows the bacteria to escape and the infection to spread. *S. pyogenes* is one of multiple organisms that target plasminogen to evade the host defense responses. Additionally, parasitic organisms like *plasmodium* use surface enolase to bind the kringle domain of plasminogen and release plasmin to degrade the extracellular matrix of surrounding tissues and spread the infection.

Example 6: PAN Domain Proteins Involved in Host-Cell Invasion by Parasites

Apicomplexan parasites including, *Plasmodium* spp., *Toxoplasma gondii, Eimeria* spp., and *Cryptosporidium* spp. secrete micronemal proteins that contain the PAN domain. Apical membrane antigen 1 (AMA1), is a micronemal protein with orthologs in *Plasmodium*, the causal agent of malaria in humans, *Toxoplasma* spp., obligate parasites with among the broadest host range in animals, and *Eimeria* spp., which infects poultry and cattle. Numerous studies have demonstrated that AMA1 is essential for erythrocyte invasion where it has been implicated as a key member of the moving junction (MJ) complex. The MJ complex forms at the contact point between the parasite and the host cell where inward invagination of the erythrocyte membrane occurs. Interaction between AMA1 and rhoptry neck protein 2 were shown to be essential for MJ formation. AMA1 has been widely targeted for development of vaccines against multiple parasites and anti-AMA1 antibodies were shown to have efficacy in reducing invasion of the host cell by these parasites. In *T. gondii*, Gong et al. (2012) reported that the PAN domain-containing protein (P104), which carries multiple PAN domains was necessary for optimal invasion efficiency. Similarly, genomes of parasitic worms including *Trichinella* spp., *Ancylostoma* spp., *Pristionchus* spp., which infect humans, carry numerous PAN domain proteins including antiplatelet proteins utilized by Leeches (Haementeria officinalis) to inhibit blood coagulation.

Example 7: PAN Domain Protein Among Insect Vectors of Pathogen and Parasites

Insect vectors of pathogens and parasites pose major disease epidemiological challenges. As such, management of their population using chemicals and, more recently, gene-drives to diminish their populations has been a major focus in efforts to contain transmission of diseases. Given their global economic importance, the inventors compared PAN domain proteins from *Diaphorina citri*, a psyllid vectoring the bacterium *Candidatus liberibacter* which causes citrus greening and *Anopheles gambiae*, a vector of the malaria parasite, plasmodium. Consistent with the inventors' hypothesis and despite major differences in their biology, PAN domains in both organism were found in association with the same ZP domain implicated in immunosuppression during gamete fertilization above (FIG. 2). The inventors propose that these proteins could be targeted by parasites during infection to suppress immune responses, thus enabling persistence of the parasite inside the insect body. This proposition offers the opportunity to target these proteins to lower vector capacity of insects and thus reduce disease transmission.

Figure 7:
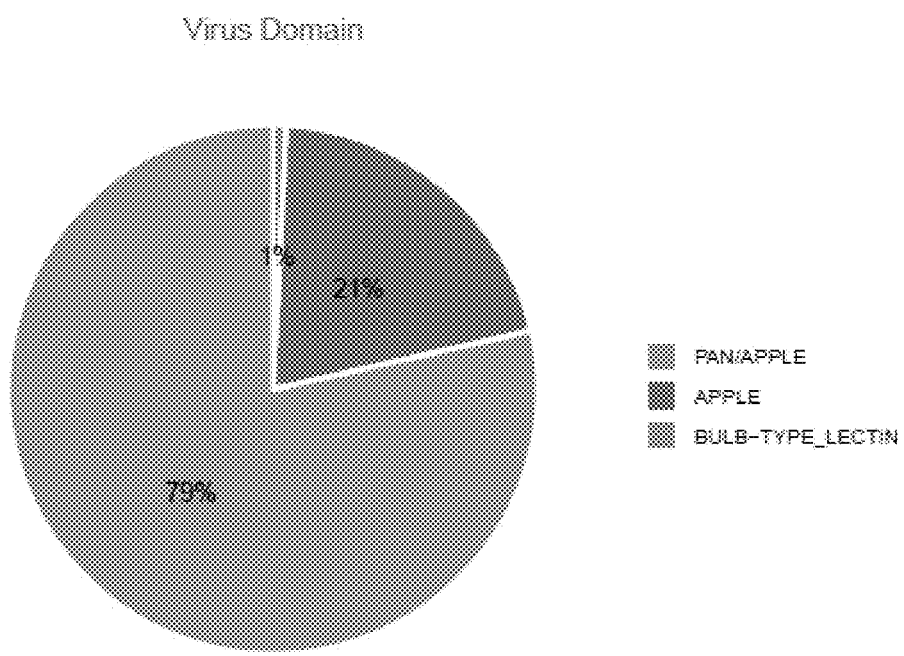

Example 8: Prevalence of PAN Domain Proteins in Infectious Viruses and Pathogens In viruses, long recognized as minimal infectious units, the PAN domain is found in envelope proteins that mostly contain no other recognizable domains except its close relative, the APPLE domain (FIG. 7). This might suggest that, the PAN domain by itself is sufficient for immunosuppression. However, we also found that in Mimiviruses, which include, the African swine virus, *Emiliania huxleyi* virus and Niemeyer virus, the PAN domain is found in association with HGF, TMhelix, transmembrane, non-cytoplasmic and a cytoplasmic domain and signal peptide domains. Mimiviruses, known as giant virus, are recognized for their significantly larger genomes that encode proteins with functions not typically found in common viruses. Consistent with other complex parasites described above, it appears that Mimiviruses require additional manipulation of the host post-immunosuppression to persist in their host cells.

Figure 3:
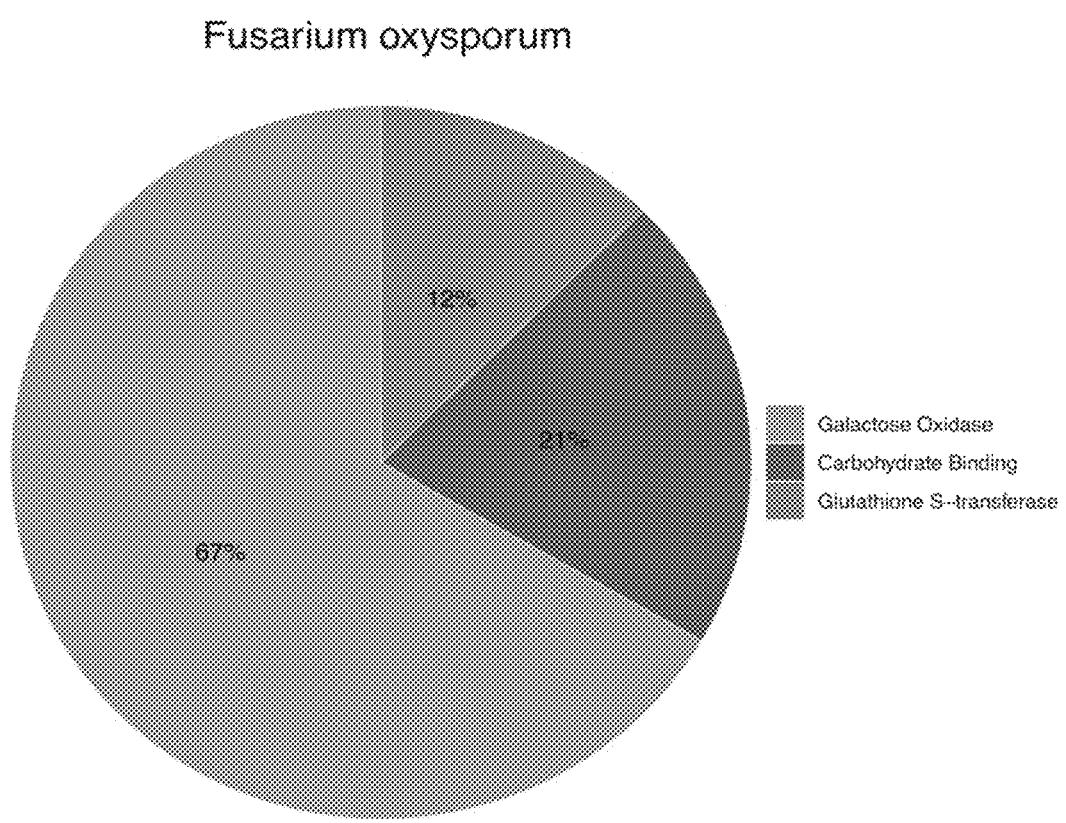
Figure 4A:
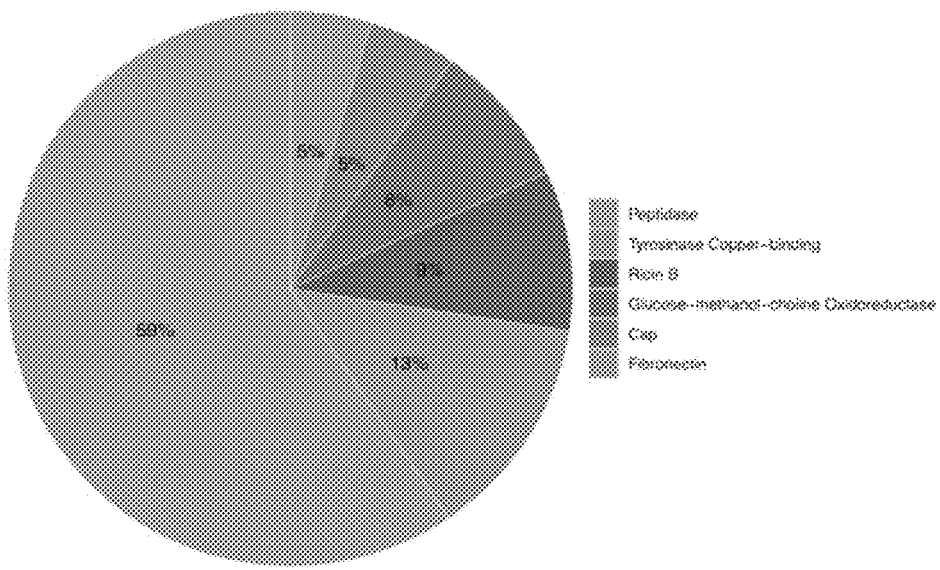
Figure 4B:
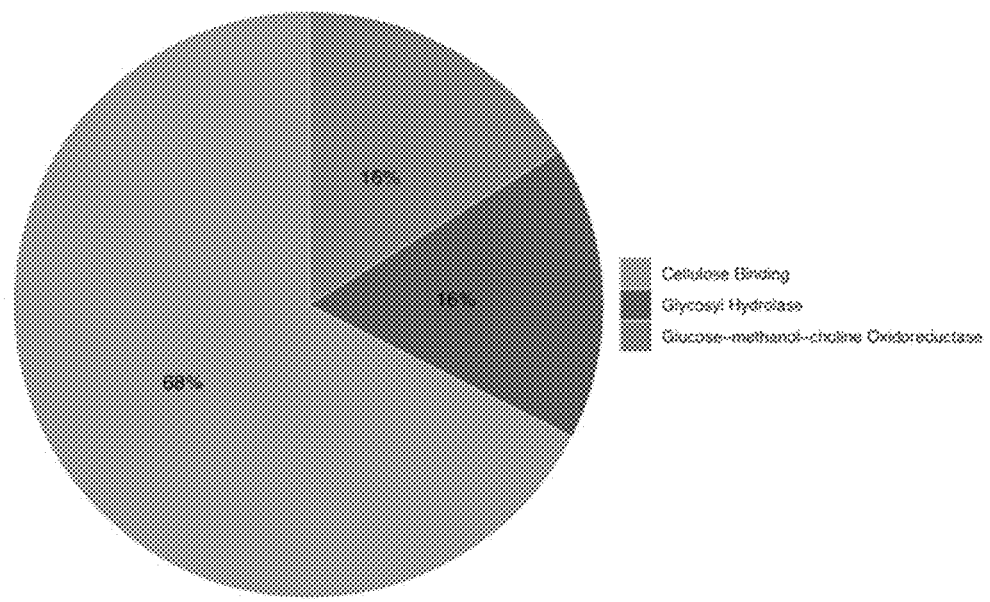

Among fungi, proteins from Ascomycetes represent 97% of PAN domain proteins reported found in our survey. This class of fungi is well recognized for pathogenesis in animals and plants. For example, *Fusarium* spp. are generally considered harmless, but a subset of these fungi are potent pathogens causing severe diseases in both plants and humans. It is noteworthy that based on our survey, five pathogenic *Fusarium* species complexes carried disproportionately higher numbers of proteins with the PAN domain compared to other netriaceaes (List 1). In order of descending-predicted number of PAN domain proteins, these were *F. oxysporum, F. fujikuroi, F. sambucinum, F. solani*, and *Fusarium incarnatum-equiseti*. Galactose oxidase, carbohydrate binding and glutathione S-transferase contributed the largest proportion of co-occurring domains (FIG. 3).

Among heterokonts, proteins of oomycete origin represented 96% of all PAN domain proteins identified in our survey. *Aphanomyces astaci*, the causal agent for crayfish plague and *Phytophthora* spp., one of the most damaging plant pathogens and the causal agent of the sudden oak death epidemic, had disproportionately higher numbers of predicted PAN domain proteins (List 1). Interestingly, the glucose-methanol-choline oxidoreductase (GMC) domain co-occurs with the PAN domain in both organisms. This domain has been implicated in asexual development in *Aspergillus nidulans*, chemical defenses in leaf beetles and cell extension and expansion during metamorphosis in crustaceans. The involvement of these PAN domain proteins in reproduction and cell proliferation is reminiscent of other eukaryotic systems described above. Moreover, GMC family proteins are recognized for their role in sequestration of the plant host-defense metabolite salicin and hence adaptation of beetle larvae to specific host plants. It is noteworthy that infection of oaks by *P. ramorum* is often followed by heavy infestation by beetles, although the exact cause has not been identified. Here, the inventors propose that the sequestration of oak defense-related secondary metabolite by the PAN harboring GMC family proteins in *P. ramorum* could mediate the observed attraction of beetles to infected trees. Similarly, functions performed by GMC proteins in *A. astaci* could mimic metamorphosis-mediated immunosuppression to facilitate infection leading to crayfish plague.

Example 9: PAN Domain Penetrance Among Bacterial Symbionts

Assessment of domain presents in the bacteria kingdom revealed that the PAN domain is found predominantly among alpha proteobacteria, well recognized for their host-cell invasion and symbiosis behavior. Of the 1,783 bacterial proteins carrying the domain, 1,587 (89%) were found in *Rhizobium* sp. and *Rhodobacter* sp. (List 1). These bacteria are specialized in nodulation of land plants and symbiosis with marine danoflagellates, respectively. The PAN domain was almost exclusively found in anti-peptidase proteins and co-occurred with the A2M domain or related macroglobulin domains (FIG. 2). A2M is recognized as a broad-spectrum protease inhibitor that has been widely implicated in immune modulation and is associated with a wide array of diseases. Aside from its anti-protease activity, A2M has binding affinity to a wide variety of molecules. In both *Rhizobium* sp. and *Rhodobacter* sp., heme sequestration is an essential process for the survival of bacteria inside host cells. The exact mechanism underlying this process has remained largely elusive with limited progress in identifying proteins related in to heme sequestration. Here, the inventors note that A2M has been previously reported to function as a Hx:heme receptor, known as the Low-density lipoprotein receptor-related protein-1 (LRP1). LRP1 was shown to play a central role in heme scavenging after intracerebral hemorrhaging in mice. With this observation, the inventors propose that the PAN domain may have been co-opted to act as an immunosuppressant while the A2M domains functions to sequester heme and create the necessary environment for bacterial survival in plant host cells.

Figure 5A:
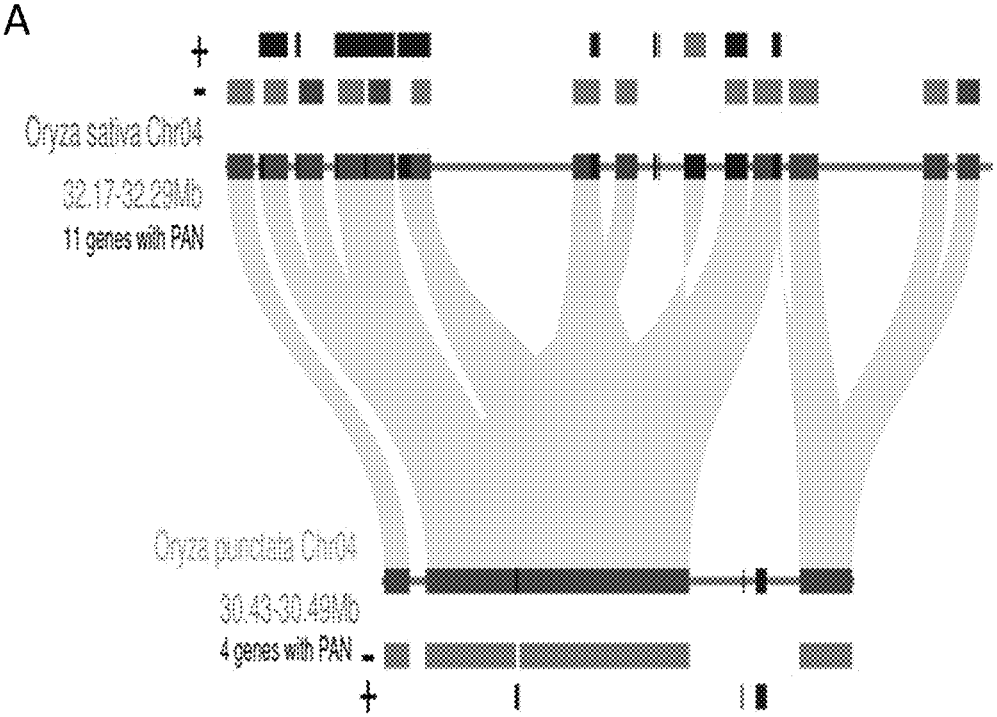
Figure 5B:
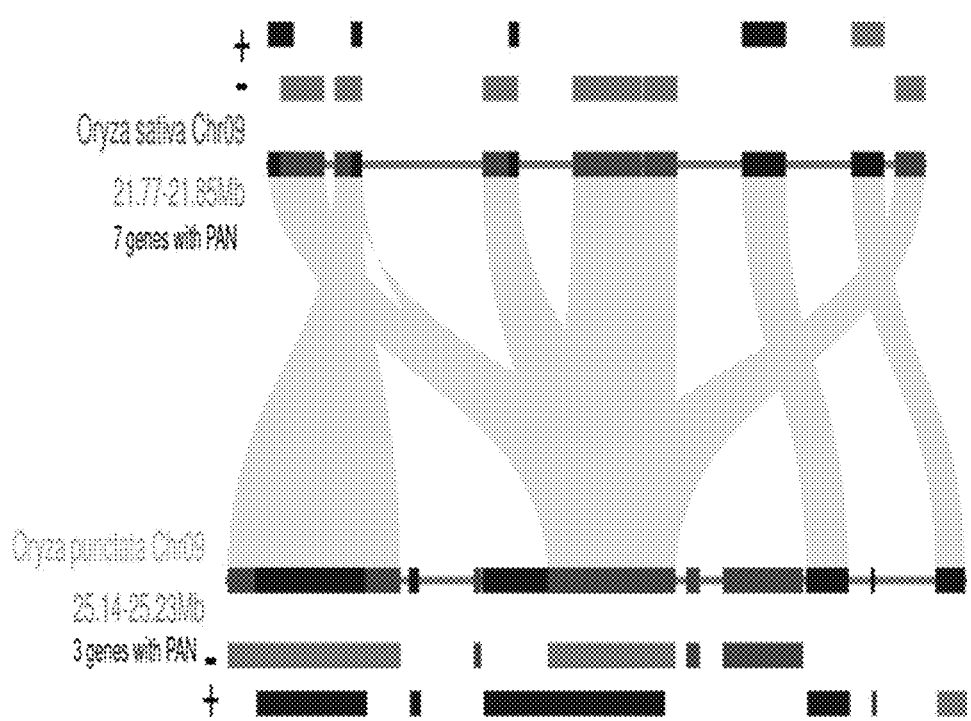
Figure 6A:
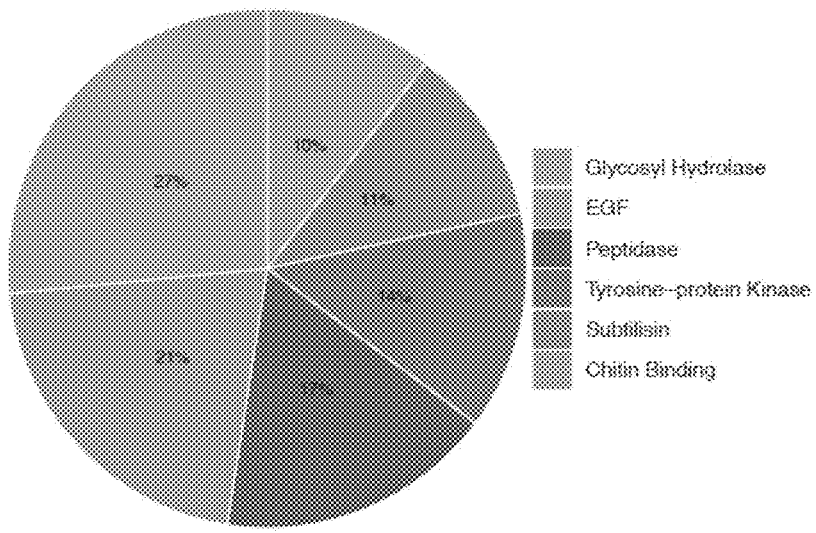
Figure 6B:
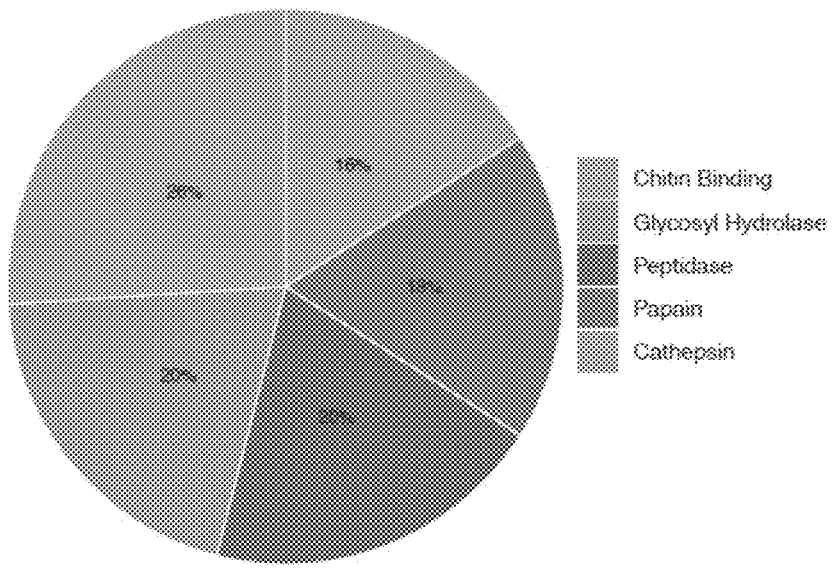
Figure 6C:
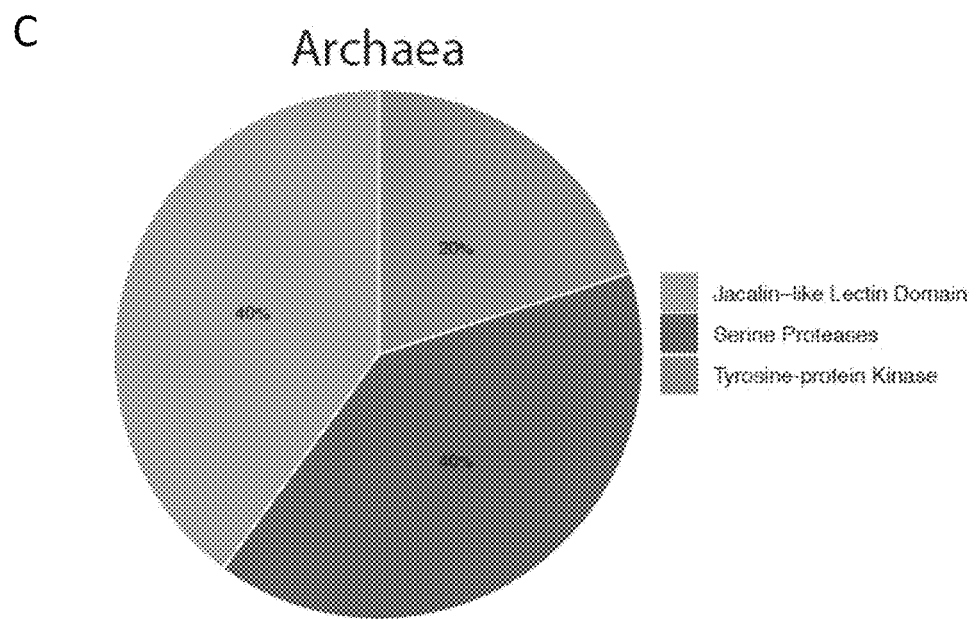
Figure 6D:
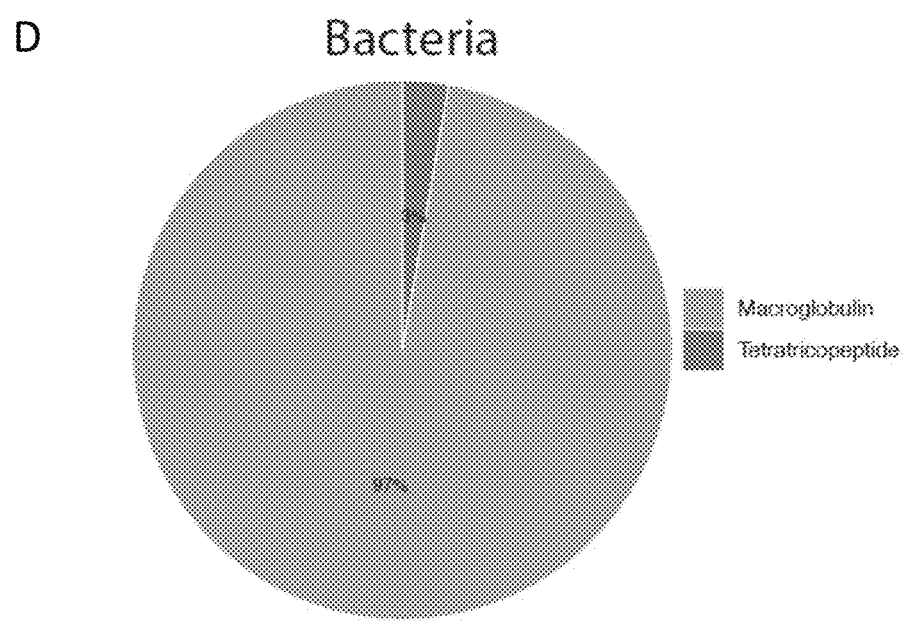
Figure 6E:
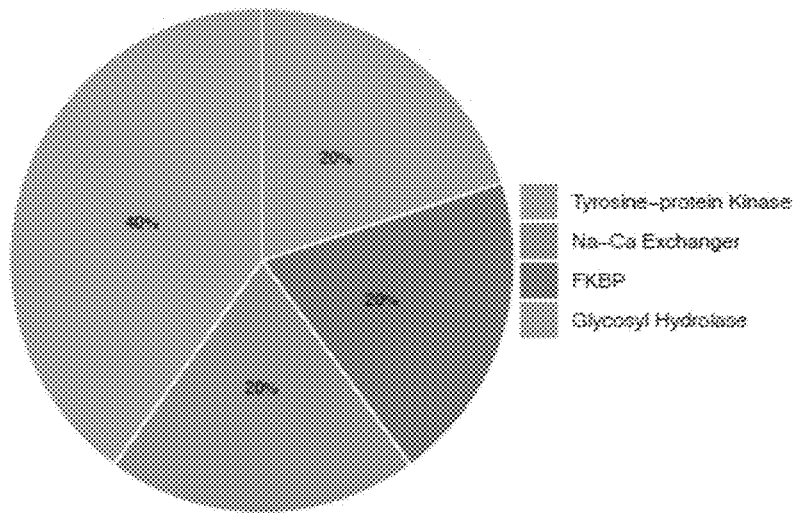
Figure 6F:
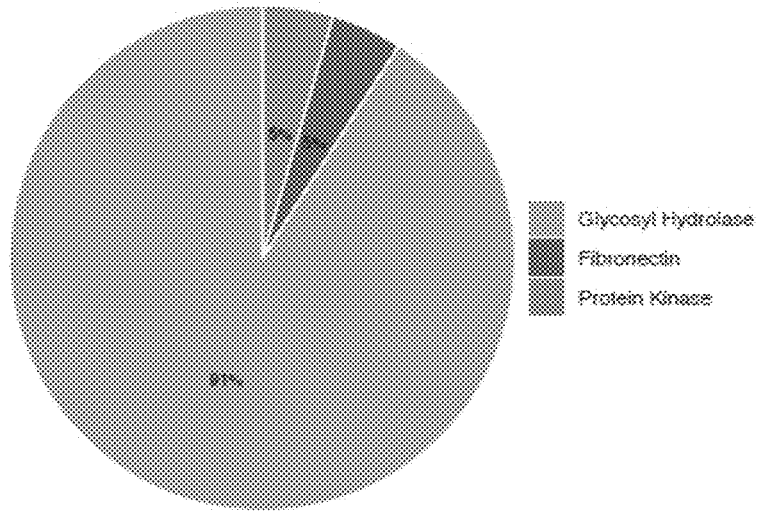
Figure 6G:
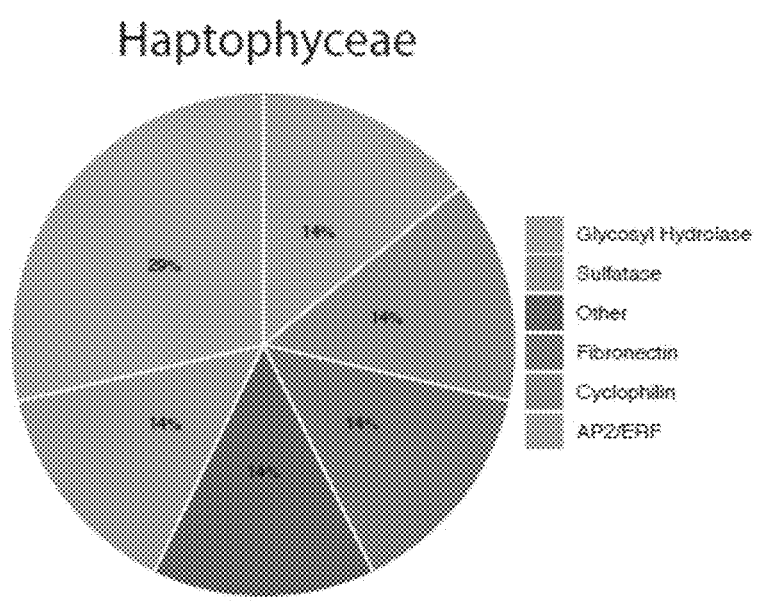
Figure 6H:
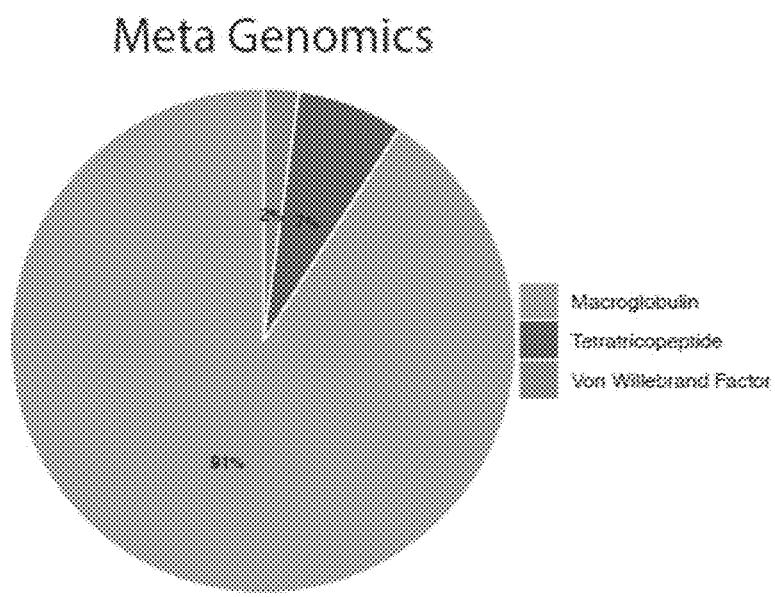
Figure 6I:
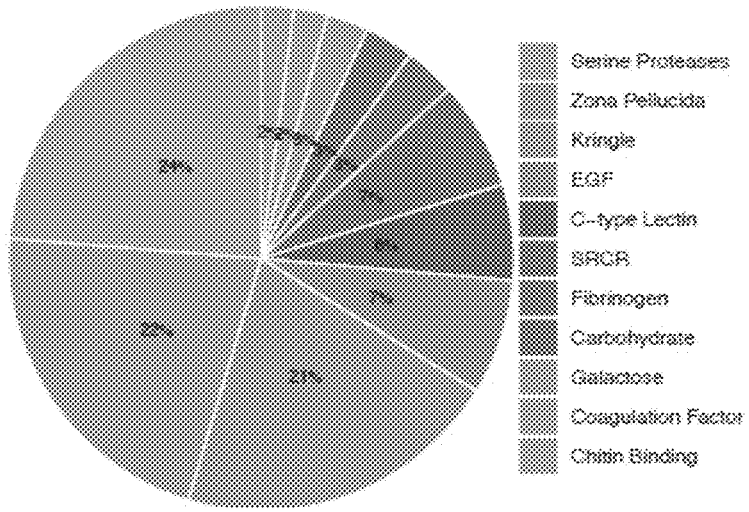
Figure 6J:
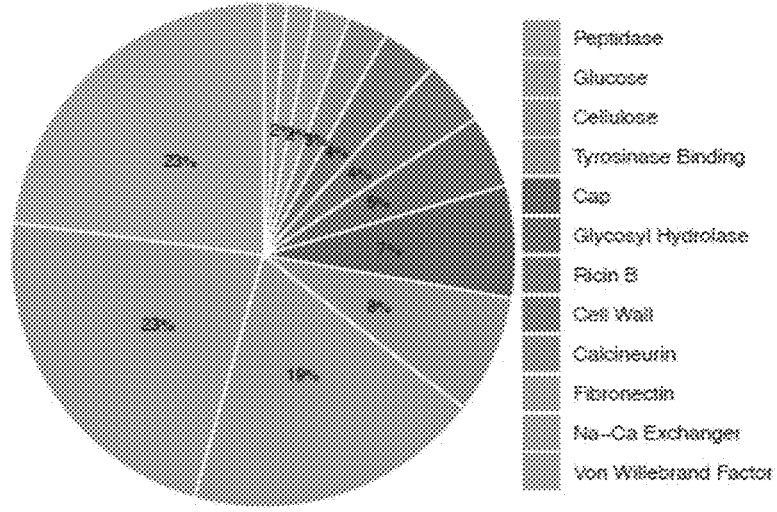
Figure 6K:
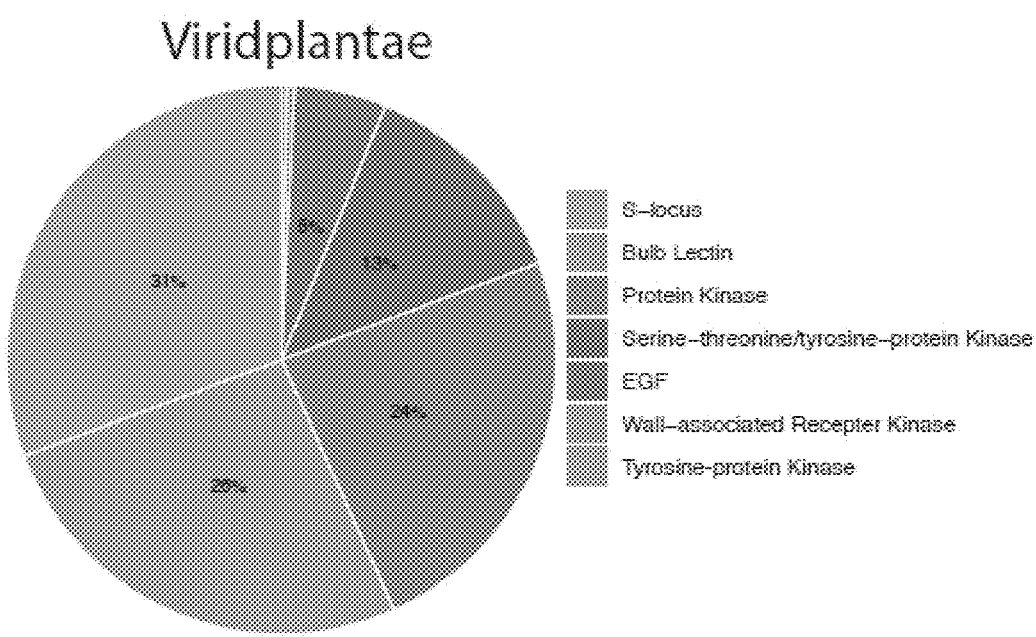

Example 10: Domain Expansion in Organisms Specialized in Symbiont Recruitment Numerous organisms such as corals, planktonic crustaceans and plants depend on symbionts to perform essential functions. In these instances, immunosuppression is a key step in conferring compatibility between hosts and symbionts. For example, *Daphnia magna* is a planktonic crustacean that is considered a model system to study host-parasite interaction since it has highly diverse internal microbiome. Evaluation of PAN domain genes in its genome revealed occurrence of duplicated gene in the protein families such as Brain chitinase, Chorion peroxidase, Class A scavenger receptor (cA-SR) with a serine protease domain, Coagulation factor XI, No mechanoreceptor potential (nomp) A-like, Peroxinectin (PX)-like, putative Transmembrane protease serine, ZP as well as multiple uncharacterized protein. The participation of Chitinase, Coagulation factor XI, proteases and ZP protein in immunosuppression-related proteins was discussed above and cA-SRs have been studied for their function in innate immunity. Akin to *D. magna*, plants also recruit symbionts to perform essential functions including nutrient mobilization. The inventors note that G-LecRKs implicated in immunosuppression during recruitment of fungal symbiont above occur as a large protein family with hundreds of members and exhibit frequent gene-expansion across plant genomes (FIG. 5). The inventors hypothesize that both these organisms coopted immunosuppressive proteins to facilitate their symbiotic lifestyle by allowing rapid expansion of these genes within their genomes.

Example 11: PAN Domain Similarity to Cysteine-Rich Antimicrobial Peptides

Cysteine-rich peptides (CRPs) are produced by multicellular organisms and are known for their use as antimicrobials. While these peptides are not considered PAN domain-containing peptides, they have functional and structural similarities to the PAN domain in that they consist of conserved cysteine residues that form disulfide bonds and are involved in immune modulation. The CRP protein, TAP, was first isolated from bovine tracheal mucosa and were noted to have antimicrobial properties. Defensins are a class of CRPs common to both plants and animals and are involved in host innate immunity. CRPs are secreted by plants and have been shown to be involved in plant defense, symbiotic relationships with bacteria, development, reproduction and pollen-tube guidance. The nodule-specific cysteine-rich (NCR) peptides are a subclass of CRPs in plants that are secreted by the host plant and regulate symbiosis between legumes and *rhizobia* during nodule development and nitrogen fixation. The structure of NCRs resembles plant defensins that are involved in regulating plant innate immunity, but they have a different function in that they regulate symbiosis with *rhizobia* during nitrogen fixation. Given their structural similarity, it is plausible that CRPs function as ligands targeting PAN domain proteins to modulate immunosuppression.

Figure 8:
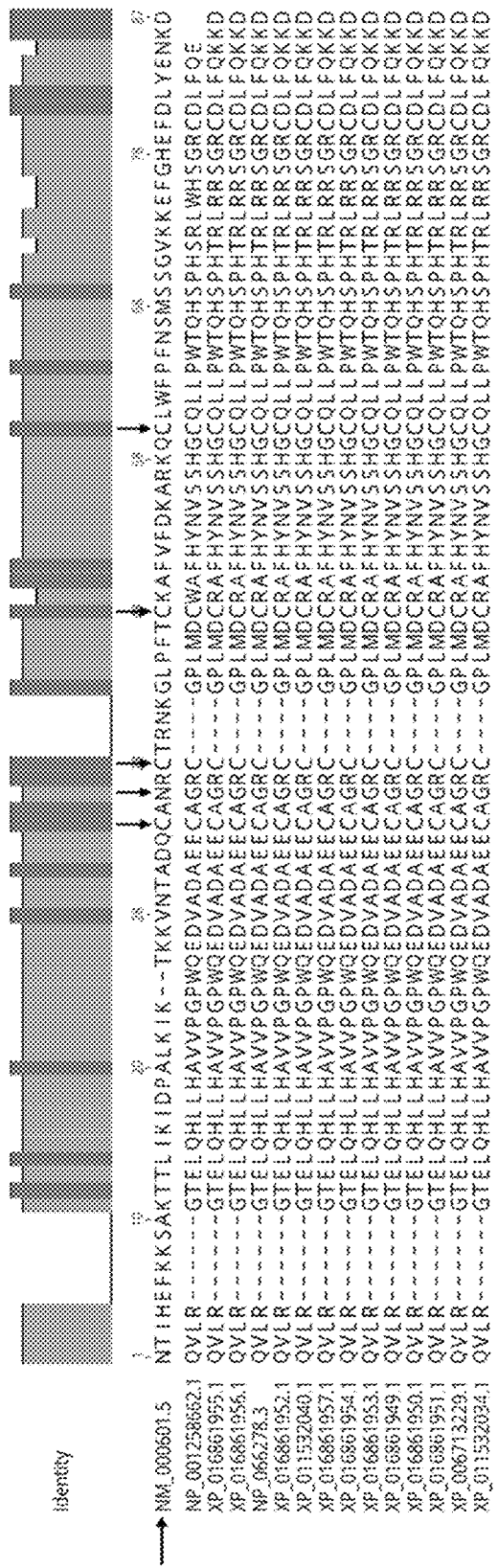

Example 12: Functional Role of the HGF PAN Domain in Human Cell Lines c-MET is a receptor tyrosine kinase which is present on the surface of various epithelial cells. c-MET gets activated by binding with its ligand, HGF. HGF is an important paracrine mediator of growth, invasion and angiogenesis in several cancers. All biological impacts of HGF are triggered by stimulating its cell surface receptor, c-MET with related activation of downstream effector pathway. Upon binding with its ligand, HGF ligand bound c-MET receptor gets internalized via endosomal internalization and undergo lysosomal degradation. HGF possesses a canonical 4 conserved cysteine residues in its PAN domain whose function remains to be determined (FIG. 8).

Example 13: Mutating Cysteine Residues in PAN Domain Results in Enhanced HGF Stability To determine the function of the cysteine residues on the PAN domain, wild type HGF was subjected to mutagenesis and four conserved cysteine (C) residues on PAN domain were mutated to alanine (A) and one conserved asparagine (N) was mutated to aspartic acid (D). HEK293T cells were transfected with Flag tagged wild type and Flag tagged PAN mutants HGF which are HGF 4Cys-4Ala and HGF N-D. Lysates were resolved on a SDS polyacrylamide gel, transferred to PVDF membrane and probed sequentially with antibodies for Flag tagged HGF and endogenous Actin.

Figure 9:
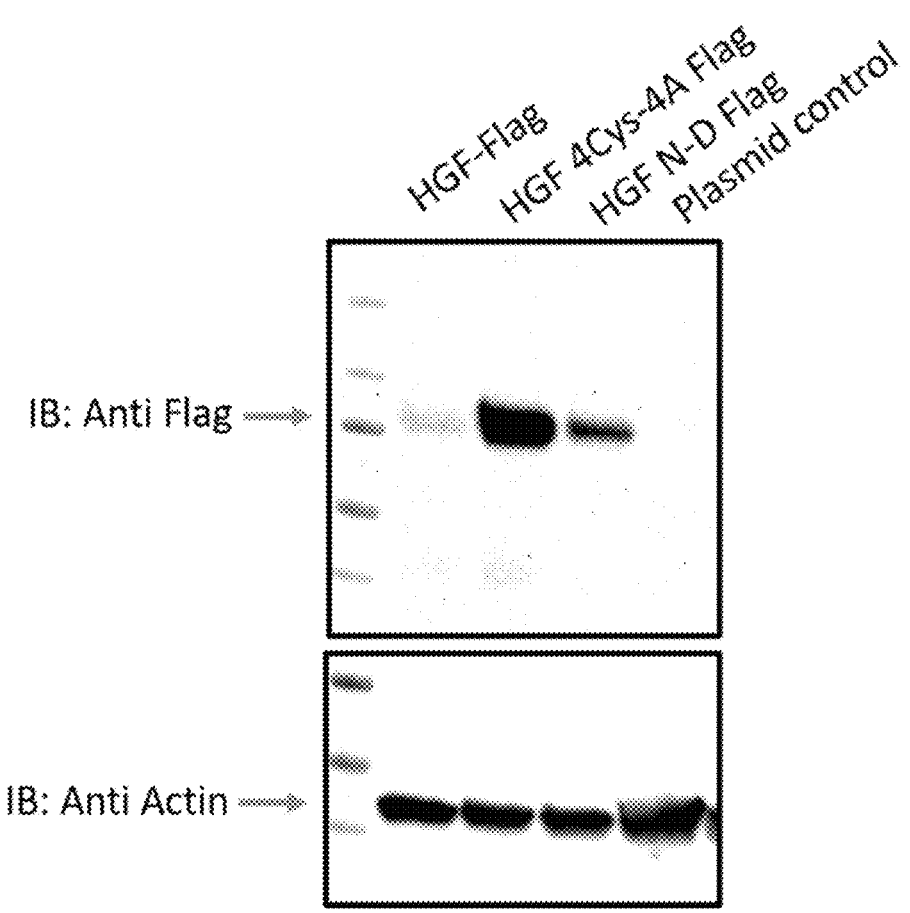
FIG. 9. Conserved cysteine residues in HGF-PAN domain are essential for HGF/c-MET signaling.

Lane 2 of FIG. 9 shows that HGF with four cysteine mutations in PAN domain (HGF 4Cys-4A) had higher stability compared to wild type HGF (Lane 1) when probed against HGF-Flag (FIG. 9). Actin was shown as a loading control. This data suggests that cysteine residues on the PAN domain of HGF mediate proteolysis of the HGF protein.

Figure 10:
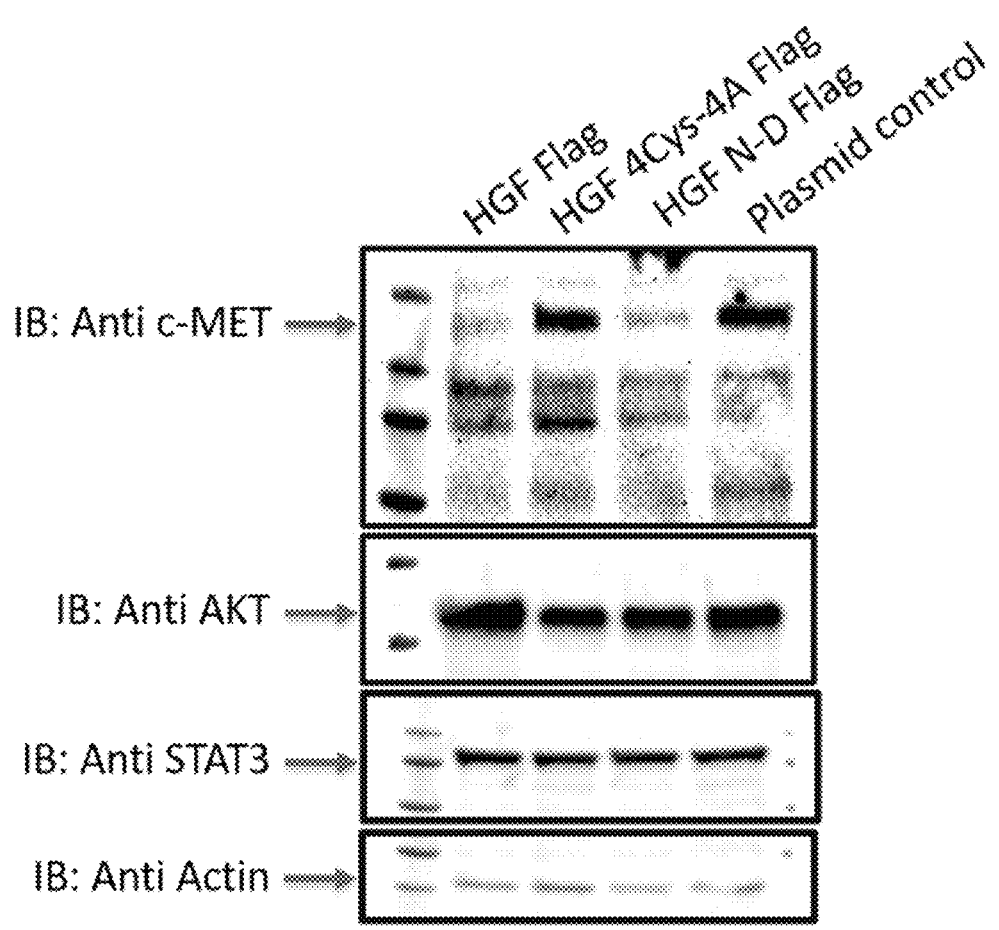
FIG. 10. Mutating cysteine residues in HGF results in enhanced protein stability and attenuation of c-MET signaling.
Figure 11:
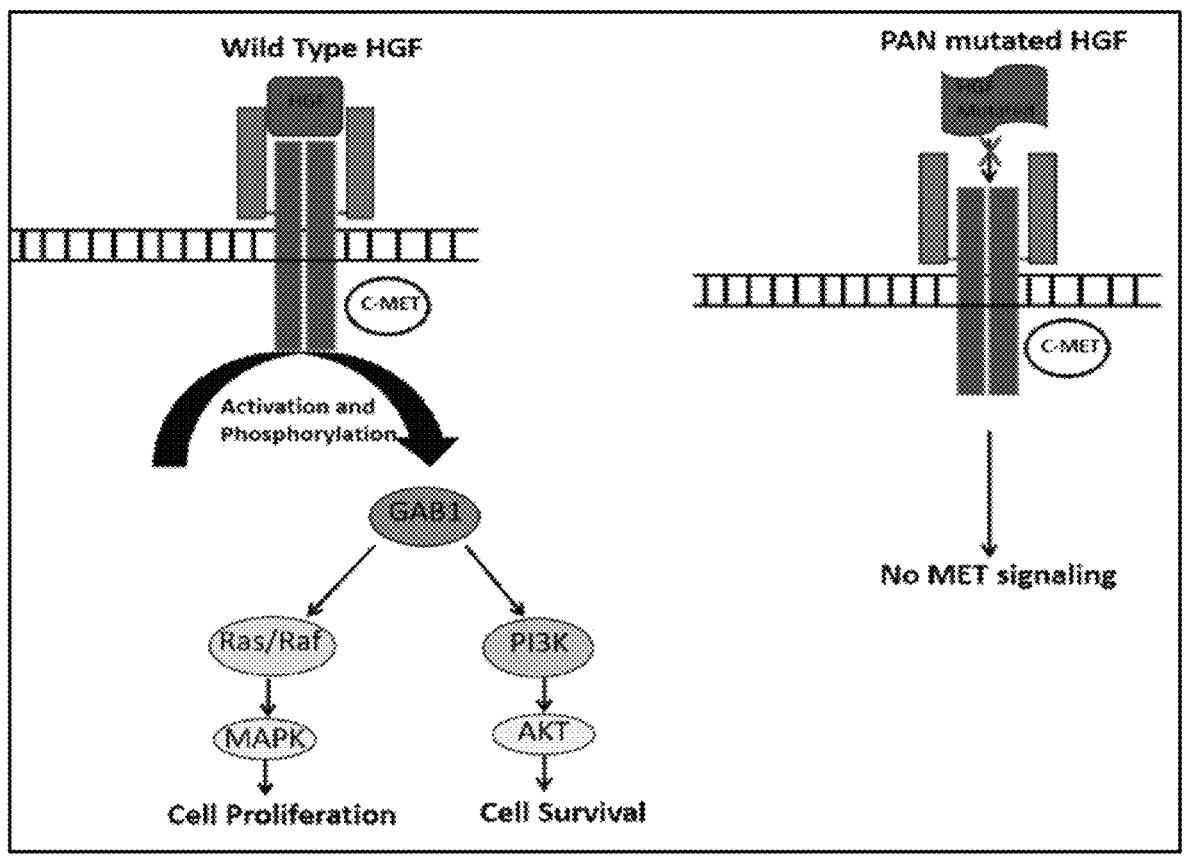
FIG. 11. Schematic representation of the impact of wild type and PAN mutant HGF on c-MET signaling. Wild type HGF can bind with c-MET receptor on the cell membrane and turn on the subsequent signaling cascade whereas the PAN mutant HGF cannot.

Example 14: Activation of MET Signaling is Attenuated by the Cysteine Residues Mutations in HGF PAN Domain Once activated, the HGF/c-MET undergoes a rapid internalization from cell membrane to cytoplasm for degradation/recycling depending on the cellular demand. To address whether the PAN mutant HGF displays more stability as a result of MET binding capability, the inventors studied the endogenous c-MET expression in HEK 293T cells overexpressed with wild type HGF and PAN mutants HGF. FIG. 10 topmost panel shows 4Cys-4Ala HGF was unable to activate HGF-c-MET signaling pathway as evident by stable MET expression. The enhanced stability of the MET receptor indicates that the receptor is retained on the cell surface.

Both wild type HGF and N-D HGF could bind c-MET and activates the cascade results in MET degradation. Signaling downstream from MET receptor is mediated through the recruitment of other adaptor proteins including STAT3 and AKT which are stably expressed in cells even after signaling cascade activation. In FIG. 10, both middle and lower panel showed the presence of both STAT3 and AKT in cells under all circumstances demonstrating the specificity of the HGF PAN for c-MET. This data for the first time, demonstrates a direct link between Cysteine rich PAN domain with HGF function and c-MET signaling.

HEK 293T cells were transfected with Flag tagged wild type HGF and Flag tagged PAN mutants HGF which are HGF 4Cys-4Ala and HGF N-D. Lysates were resolved on SDS-polyacrylamide gel, transferred to PVDF membrane and probed sequentially with antibodies for c-MET, AKT, STAT3 and Actin. FIG. 10, lane 2 in top panel shows significantly higher c-MET stability compared to lane 1 with overexpressed wild type HGF. Lane 4 with overexpressed empty plasmid showed same c-MET stability as lane 2. This confirms HGF 4Cys-4Ala cannot turn on the c-MET signaling and thereby c-MET is not getting degraded. Immunoblot against AKT and STAT3 showed the degradation is c-MET specific as both proteins were stable under all conditions. Actin was used as a loading control.

c-MET is a heterodimer consisting of an extracellular α-chain and a transmembrane β-chain connected through a disulfide bridge. Activation of the MET receptor through HGF binding promotes the autophosphorylation on the tyrosine residues on the intracellular domain of c-MET. This opens a docking site for the recruitment of other signaling protein ultimately establish a downstream signaling cascade and biological response. HGF-cMET signaling cascade triggers the activation of phosphatidylinositol 3-kinase (PI3K) and AKT pathway well defined in cell migration. Besides that, the mitogen activated protein kinase (MAPK) and the extracellular kinases (ERK1/2) are well known downstream mediator of this MET signaling cascade. Abnormal activation of c-MET-HGF cascade has been reported to promote the progress of multiple cancers including glioblastoma, liver, lung, breast, colon to name a few. In all those cancers, activated PI3K/AKT, JAK/STAT and Ras/MAPK pathways have been reported to be elevated. All these have negative impacts on the cancer prognosis.

Figure 19:
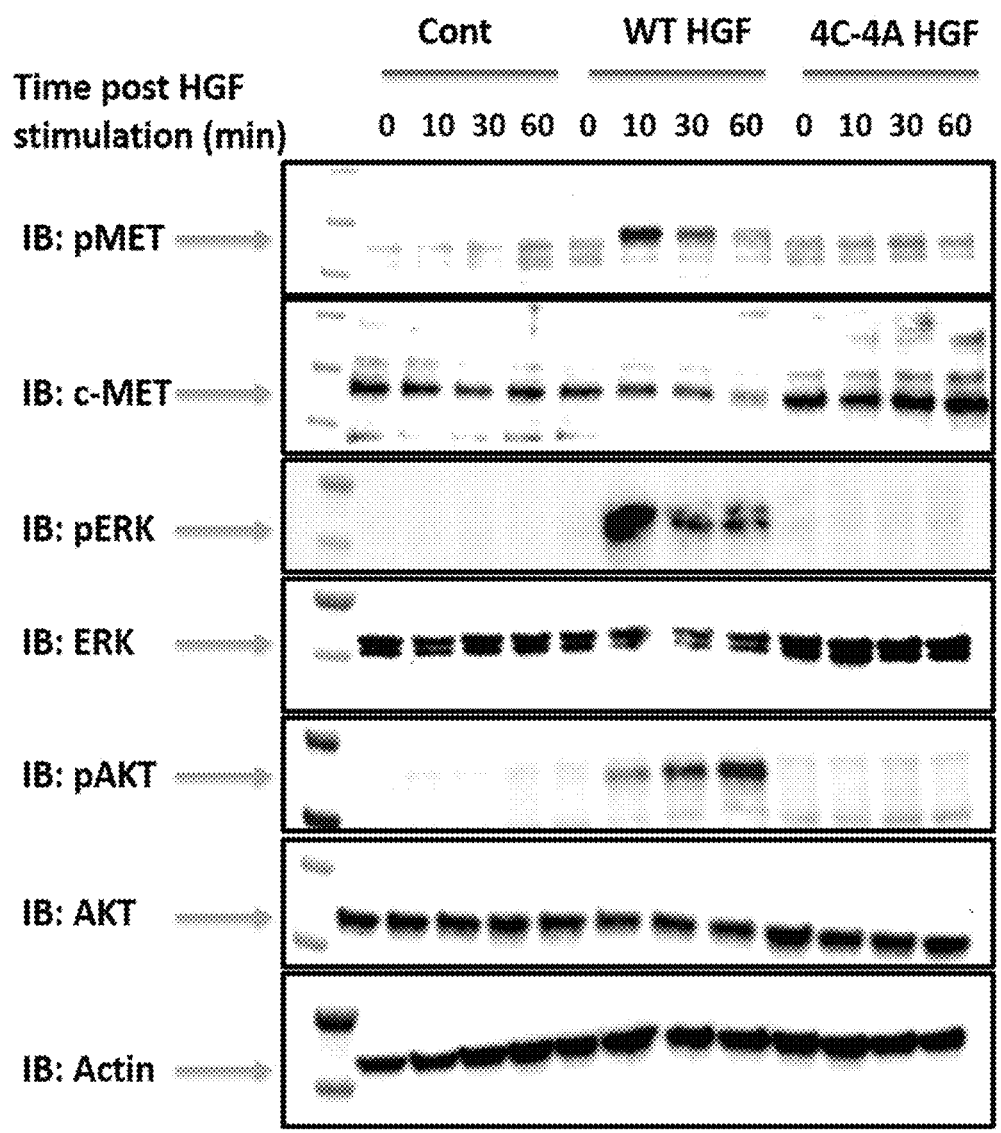

To evaluate the effect of PAN mutations on HGF at a biochemical level, the inventors performed western blotting on the protein lysates derived from HEK293T cells stimulated with wild type HGF and 4Cys-4Ala HGF PAN mutant proteins for the indicated time (FIG. 19). FIG. 19 topmost panel shows, 4Cys-4Ala HGF PAN mutant was unable to activate c-MET as evident by the lack of phosphorylation compared to the wild type (WT) HGF.

However, activation of MET receptor with WT HGF results with WT HGF results the downstream activation of MET signaling cascade as pAKT and pERK levels increased (FIG. 19, panel third and fifth) over time. Mutations on Cysteine residues on PAN were able to completely block the AKT and MAPK pathways.

HEK 293T cells were grown on 6 cm plates and stimulated with both WT HGF and 4Cys-4Ala HGF proteins for the indicated amount of time. Lysates were resolved on SDS-polyacrylamide gel, transferred to PVDF membrane and probed sequentially with antibodies for pMET, c-MET, pAKT, AKT, pERK, ERK and Actin.

Figure 20:
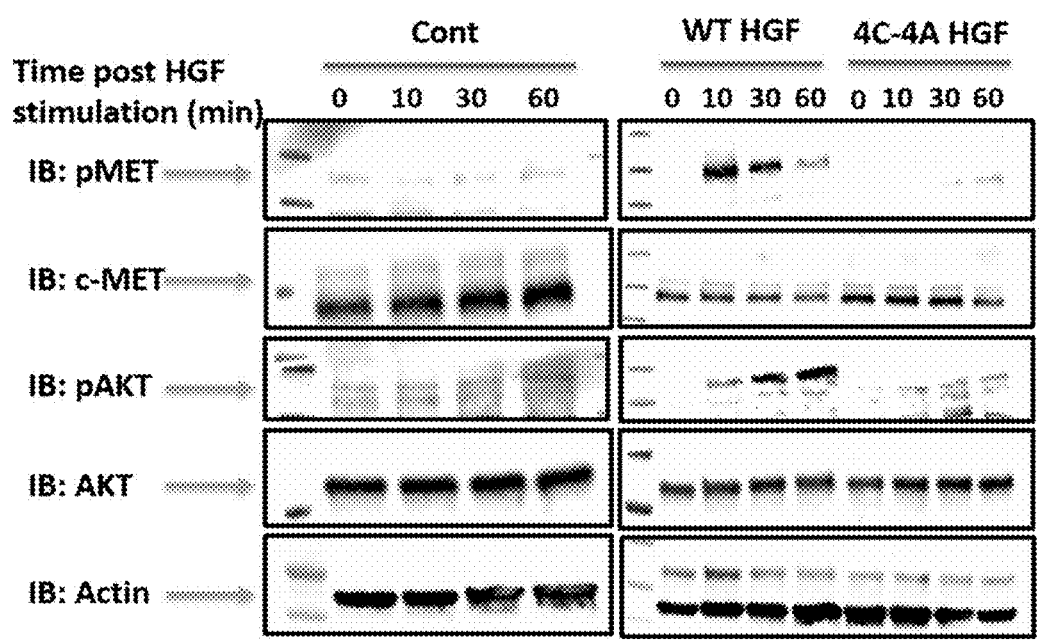

The proto-oncogenic receptor tyrosine kinase c-MET and HGF reported to be deregulated and promote malignancy in cancer and brain tumors. The inventors investigated the impact of PAN mutations on cMET activation in glioblastoma cell lines U87. Human glioblastoma cell line was used and western blotting on cell lysate were performed following the WT and 4Cys-4Ala HGF stimulations for the indicated amount of time (FIG. 20). The results show that PAN mutations on HGF had similar negative impact on cMET signaling cascade activation in glioblastoma cell line.

Analysis of HGF PAN Mutations on cMET Activity in Cells.
Mutations in HGF PAN Domain Alters the Localization of cMET in Cells.

It has been well described before that upon HGF stimulation, cMET gets activated by tyrosine autophosphorylation and is rapidly internalized and translocate to the nucleus. Following the stimulation, c-MET is rapidly internalized to early endosomes and translocate to the nucleus either to initiate calcium signals and or to upregulate PAX5, a transcription factor, in the nuclear compartment. Here we demonstrate that 4Cys-4Ala PAN mutant HGF failed to activate the cMET translocation to nucleus as compared to the WT HGF stimulation. HeLa cells were grown on 24 well plates before stimulated with both WT and 4Cys-4Ala PAN mutant HGF proteins for 30 minutes where indicated. Cells were then fixed, permeabilized and observed against cMET using fluorescence microscope. The fluorescence images confirmed that cMET redistributes to the region of nucleus from cell membrane following WT HGF stimulation but not by the 4Cys-4Ala PAN mutant HGF.

PAN Domain Positively Impacts on Cell Proliferation.

Figure 21:
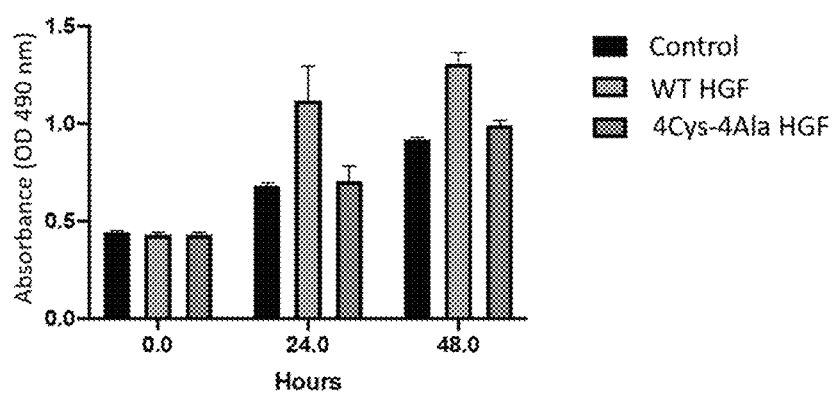

To investigate the role of HGF on cell cycle, HGF WT and 4Cys-4Ala PAN mutant HGF were used as an exogenous factor to determine its impact on cell proliferation. HEK 293T cells were grown in 96 well plates and stimulated with 100 ng/mL WT HGF and 4Cys-4Ala PAN mutant HGF for 0, 24 and 48 hr. MTT, (3-(4,5 dimethylthiazol-2-yl)-2,5-diphenyltetrazolium bromide) reagents were added and absorbance were measured according to manufacturer instructions. There was a significant drop in the absorbance of the cells treated with PAN mutant HGF compared to WT HGF stimulated one (FIG. 21). The absorbance is related to cell proliferation. This observation confirmed a direct evidence of attenuation of cell proliferation over HGF PAN mutations. This also confirmed that targeting four cysteine residues on the PAN domain of HGF can attenuate the cell proliferation which is otherwise elevated in different cancers.

Investigation of Transcriptional Profiles Upon the Stimulation of Cells with PAN Mutant HGF.

Figures 22A, 22B, 22C, 22D, 22E:
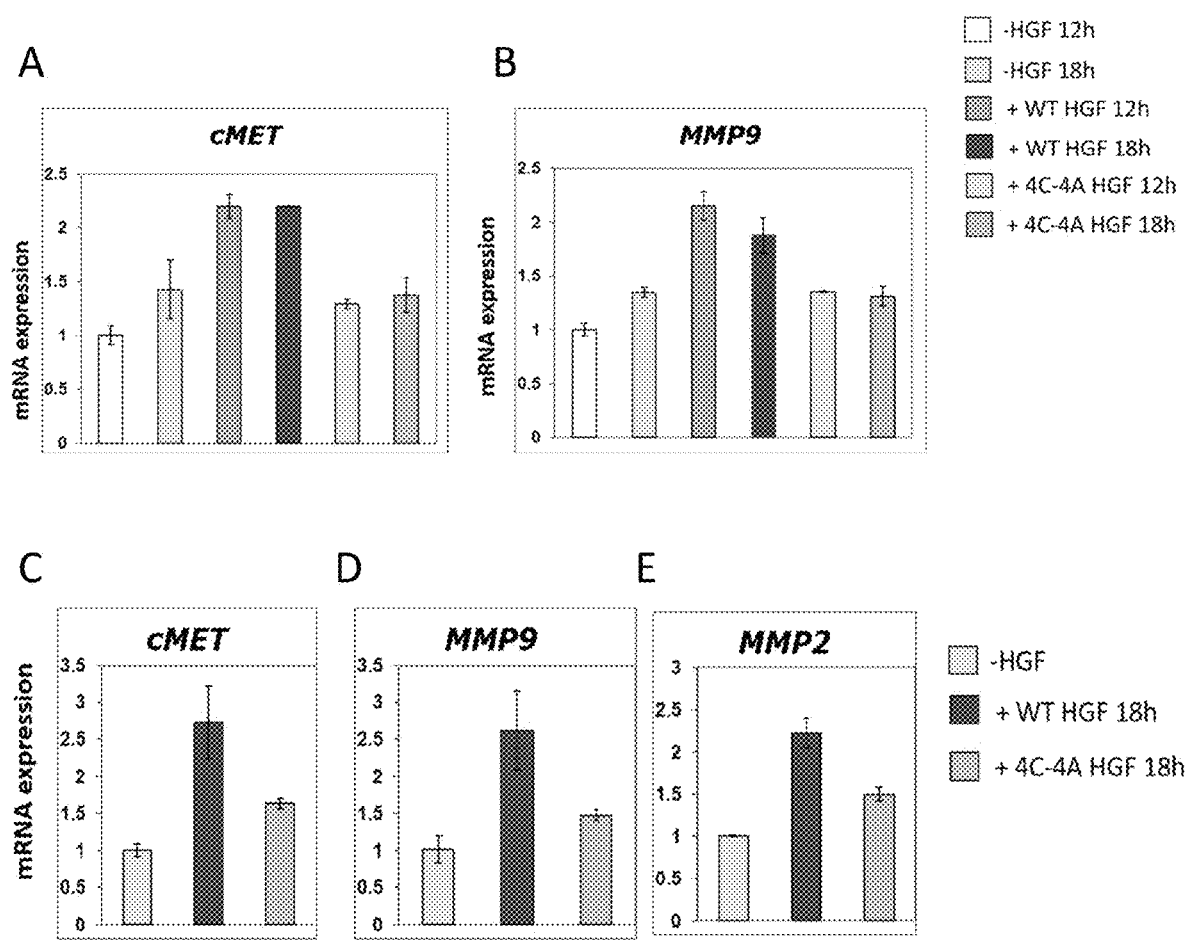

HGF has been demonstrated to stimulate cancer proliferation, migration and metastasis by increasing the migration and expression of matrix metalloproteinases (MMPs) in human. To further address the impacts of PAN mutations on HGF towards cell, the inventors quantified relative mRNA level of cMET, MMP9, and β-actin by real time-PCR according to the protocol following stimulation with WT HGF and PAN mutant HGF. FIGS. 22A-22B show that interaction between HGF-cMET is important for the upregulation of cMET and MMP9 in HEK 293T cells.

Glioblastoma is the most severe brain tumor type with the highest malignancy and lowest prognosis. MMPs can enhance the invasive ability of tumor cells by degrading extracellular matrix proteins (such as collagen, fibronectin and proteoglycan) as well as growth factor binding protein, growth factor precursor, receptor tyrosine kinase, cell adhesion molecule and other proteases. Among the MMPs, the elevated expression level of MMP2 is meticulously related to the progression of glioblastoma malignancy. The inventors further explored the relative mRNA level of MMP9 and MMP2 along with c-MET in glioma cells following HGF stimulation (FIGS. 22C-22E). U87 cells were stimulated with WT HGF and 4Cys-4Ala PAN mutant HGF for 18 hr. Cells were collected and RNA expression level were determined. FIGS. 22D-22E show the relative abundance of MMP9 and MMP2 were low upon PAN mutant HGF treatment as compared to WT HGF stimulation.

Example 15: RLK PAN Domain Mediates G-lecRLK Dimerization

Figures 12A, 12B:
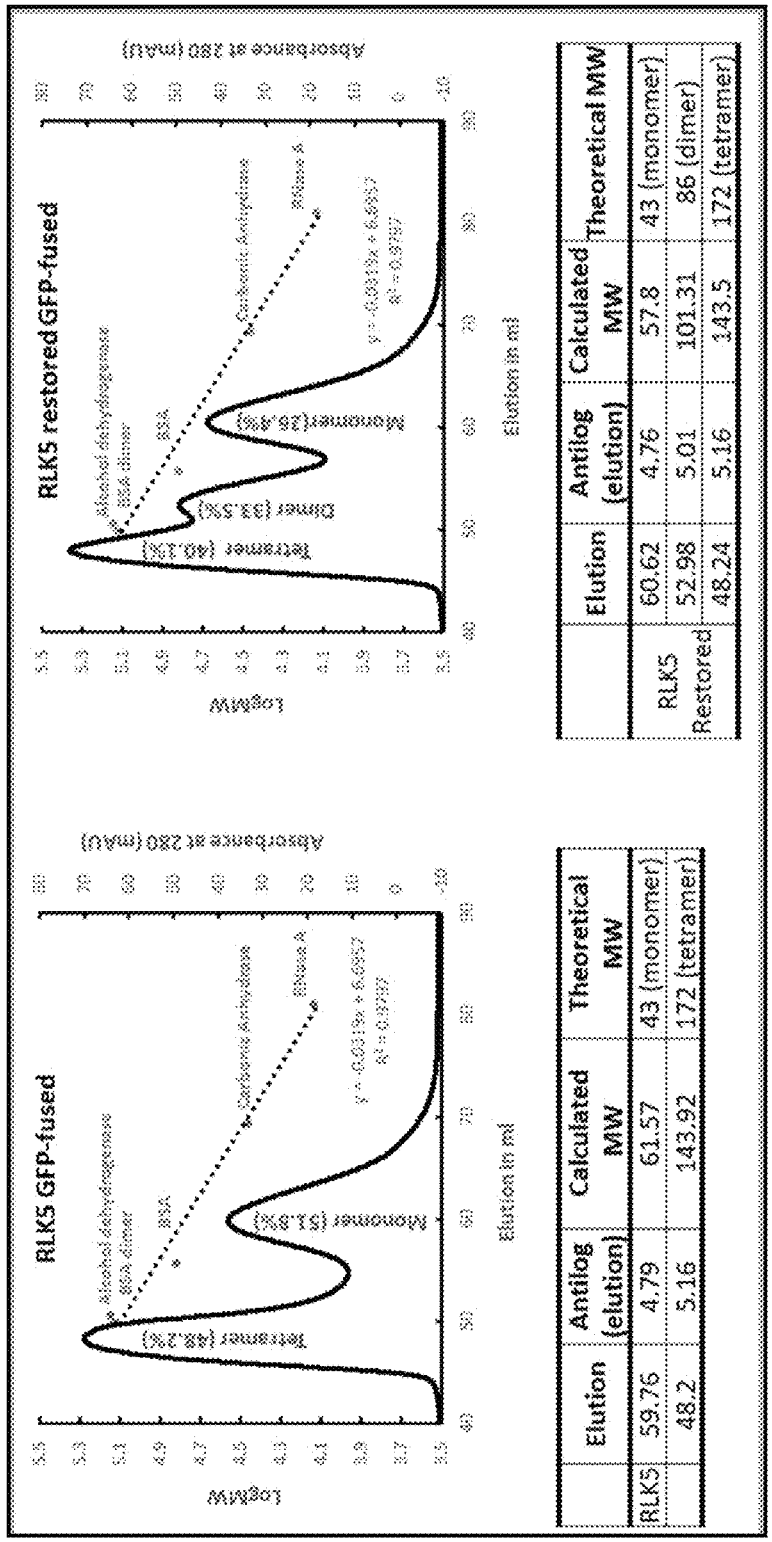
FIGS. 12A-12B. (A) Disruption of homodimerization by minimal mutations in the PAN domain of RLK5 protein. (B) Restoration of PAN amino acids to consensus sequence enhances RLK5R homodimerization.

The PAN domain possesses the characteristic 6-cysteine residues in its core that are highly conserved. These cysteine residues coordinate three disulfide bridges to form a hairpin structure. The inventors hypothesized that cysteine rich PAN domain of G-lecRLKs form disulfide bonds involved in dimerization and subsequent receptor proteolysis to prevent downstream signaling cascades. To address this hypothesis, a GFP tagged PAN domain construct of RLK5 was made. In addition, mutated amino acids in the RLK5 vestigial domain were restored to consensus PAN domain amino acids based on the alignment in FIG. 1, this construct was designated RLK5-restored (RLK5R). Both RLK5 and RLK5R constructs were transfected and overexpressed in HEK293 cells. Proteins were purified on GFP column and loaded into size exclusion column (SEC) to analyze the oligomeric state. Consistent with the inventors' hypothesis, this biochemical assay showed that RLK5R could form dimer in SEC whereas RLK5 could not (FIGS. 12A-12B).

Example 16: RLK PAN Domain Enhances Receptor Degradation Via MAP Kinase Pathway

Pattern recognition receptors recognize invasive microbe-associated signals and confer host immunity by triggering the initial layer of plant defense to prevent pathogen proliferation. Previous studies have shown the importance of MAP kinase (MAPK) in plant innate immunity. This MAPK cascade consists of the MAP kinase kinase kinase, YODA, MAP kinase kinases MKK4 and MKK5, and MAP kinases MPK3 and MPK6. MAP kinases undergo phosphorylation mediated activation. In *Arabidopsis*, prolonged activation of MPK3 and MPK6, two kinases critical for pathogen resistance, results in the inhibition of photosynthesis and accumulation of reactive oxygen species (ROS) in chloroplasts.

Figure 13A:
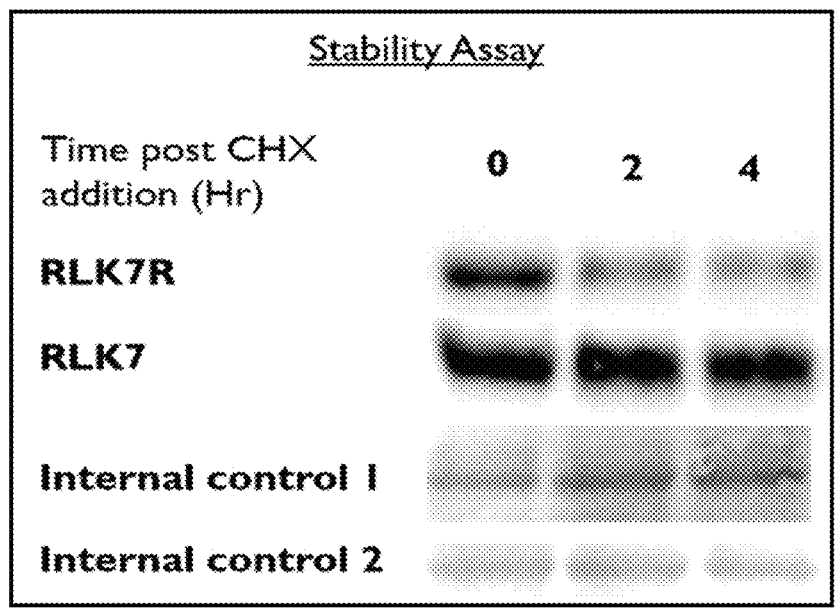
FIGS. 13A-13B. (A) A functional PAN domain enhances receptor proteolysis (RLK7R) whereas minimal mutations in the PAN domain enhance RLK7 stability. (B) Additionally, receptor proteolysis retards MPK3 and 6 expression in RLK7R transgenic lines while the stable RLK7 exhibits induction of both MPK3 and MPK6.
Figure 13B:
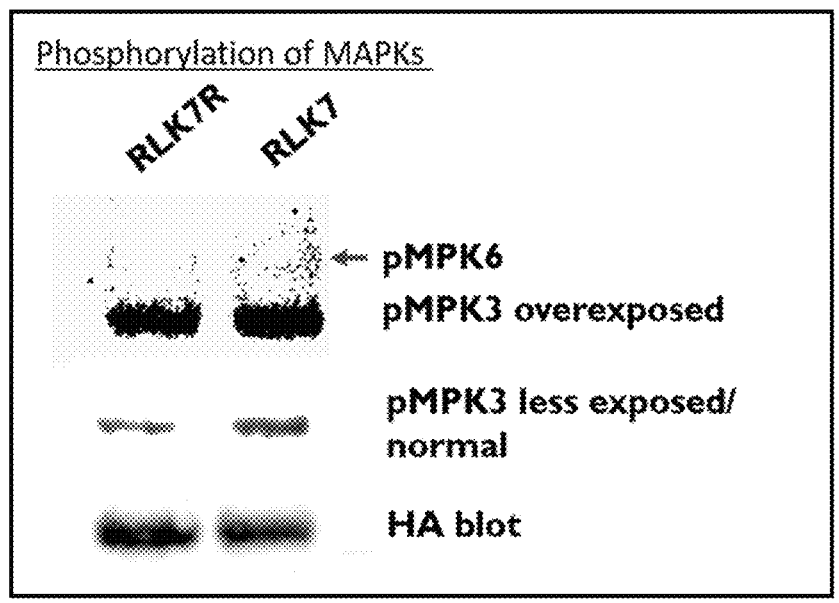

The inventors wanted to test whether PAN domain containing G-lecRLKs undergo dimerization which prevents the phosphorylation mediated activation of downstream signaling cascade. To inventors first performed Cycloheximide (CHX) stability assay. Both RLK7 (PAN mutated variant from *Salix* described above) and RLK7R (PAN domain restored to consensus amino acid sequence) were overexpressed in *Arabidopsis* protoplast followed by CHX treatment at indicated time points, to inhibit the protein turn over. Lysates were resolved with SDS-PAGE gel and documented with chemiluminescence BIO-RAD gel doc system. Resulting data indicated a higher half-life or extended stability for RLK7 over RLK7R following 0-4 hr time points (FIG. 13A). Consistent with expected downstream phosphorylated of MAP kinases, the inventors observed an overall increase in the MPK3 and MPK6 phosphorylation (FIG. 13B).

Since the apparent protein instability of RLK7R resulted in its inability to trigger phosphorylation of MPK3 and 6 as well as subsequent defense response, the inventors hypothesized that RLK5 and RLK7 with mutated PAN domains lost their immunosuppressive roles and thus should trigger defense signaling.

Figures 14A, 14B, 14C:
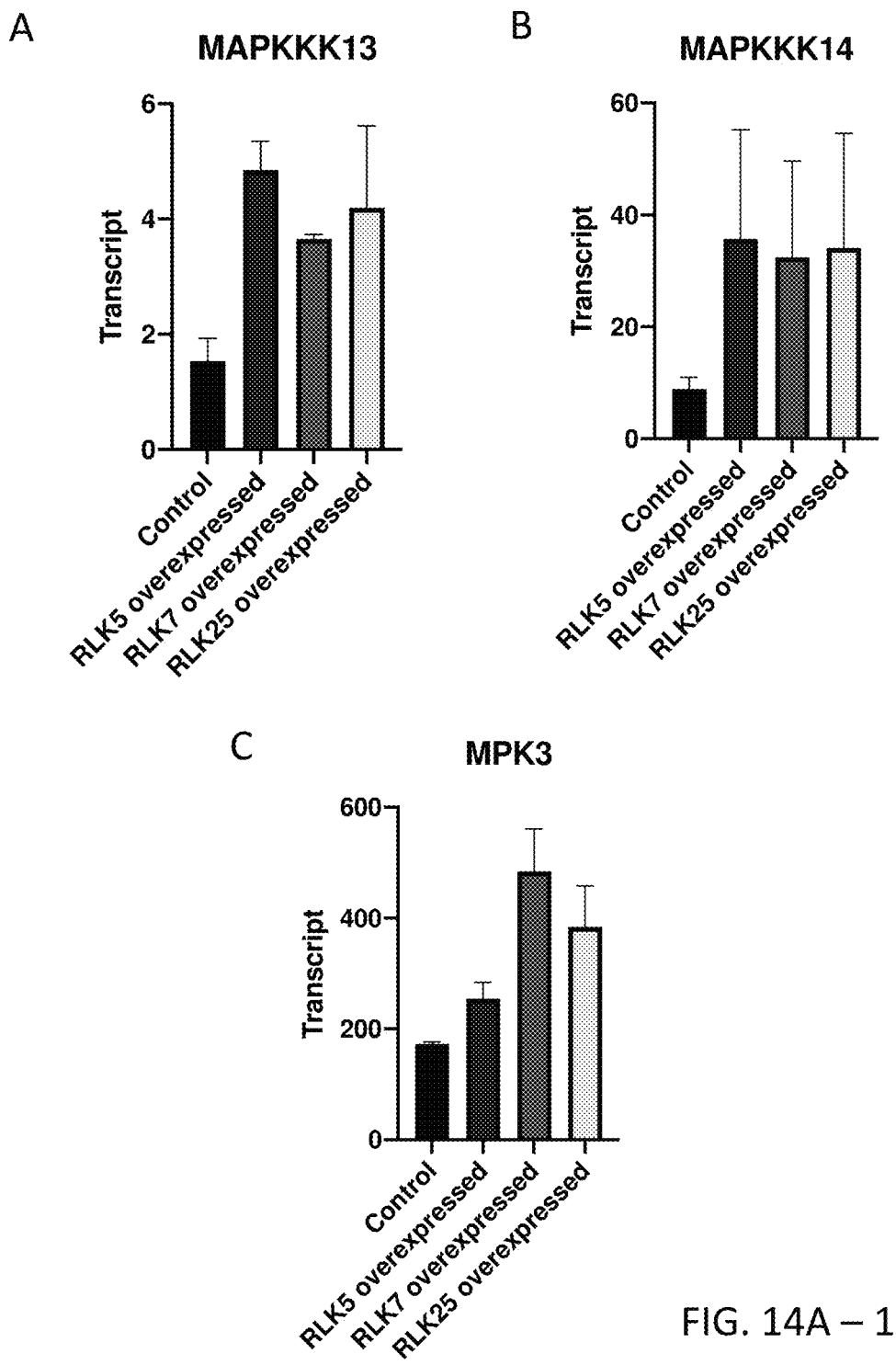
FIGS. 14A-14C. Transcriptional activation of MAP kinases in *Arabidopsis* transgenic lines overexpressing RLK5 and 7. RLK25 is an L-type RLK that functions as positive defense regulator. (A) MAPKKK13; (B) MAPKKK14; (C) MPK3.

Example 17: Central Player of Innate Immune Cascade, MAPKs are Activated in RLK5 and 7 Overexpressed Transgenic Lines Mitogen activated protein kinases (MAPKs) are well conserved protein kinases in eukaryotes where MAPK kinase kinase (MAPKKK) activates MAPK kinase (MAPKK) which ultimately activates MAPKs. Upon the detection of any external stimulus or environmental changes at the cell surface, MAPKs gets upregulated and participates in the classical signal transduction of immune responsive genes. After overexpression of RLK5 and RLK7 in *Arabidopsis*, the inventors were interested to evaluate whether any signature MAPKKK and MAPK were activated. Upstream regulators of this pathway like MAPKKK13 and MAPKKK14 were highly upregulated in transgenic lines (FIGS. 14A-14B). Additionally, the inventors were interested in studying the regulation of downstream MAPKs. MAPK3 is one of the most well-known signature gene of this pathway and showed a significant upregulation in transgenic lines suggesting RLKs with mutated PAN domains could induce immune signaling via MAPK pathway in plants (FIG. 14C).

Example 18: RLK PAN Activates Proteins Involved in JA/ET Pathway

Figures 15A, 15B, 15C, 15D, 15E, 15F:
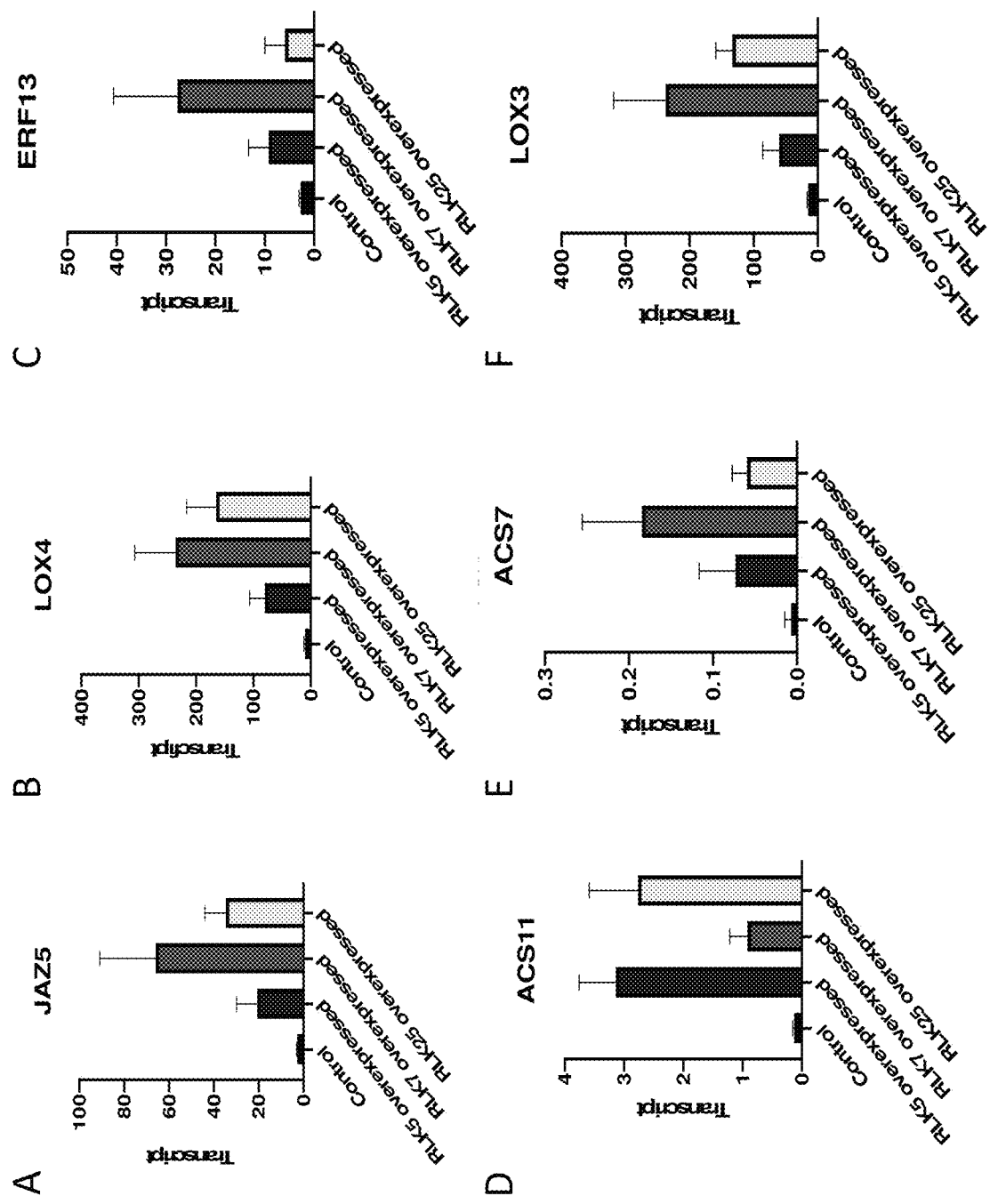
FIGS. 15A-15F. Transcriptional activation of jasmonic acid and ethylene defense marker genes in *Arabidopsis* transgenic lines overexpressing RLK5 and 7. RLK25 is an L-type RLK that functions as positive defense regulator. (A) JAZ5, (B) LOX4, (C) ERF13, (D) ACS11, (E) ACS7, (F) LOX3.

The expression level of the genes related to Jasmonic acid (JA) synthesis were also examined. As shown in FIG. 15B, the inventors were interested to observe the signature genes of the JA and ethylene signal transduction (ET) pathway. LOX3, LOX4 and JAZ5 are the signature genes of JA pathway and are upregulated in transgenic lines compared to wild type. Other signature genes involved in ET and JA pathways are ERF13, ACS11 and ACS7. These mediators are also upregulated in our transgenic lines. This data suggests that constitutive overexpression of RLK5 and RLK7 in *Arabidopsis* activates JA and ET pathway (FIGS. 15A-15F).

Example 19: RLK PAN Attenuates Salicylic Acid Pathway of Plant Innate Immunity

Figures 16A, 16B:
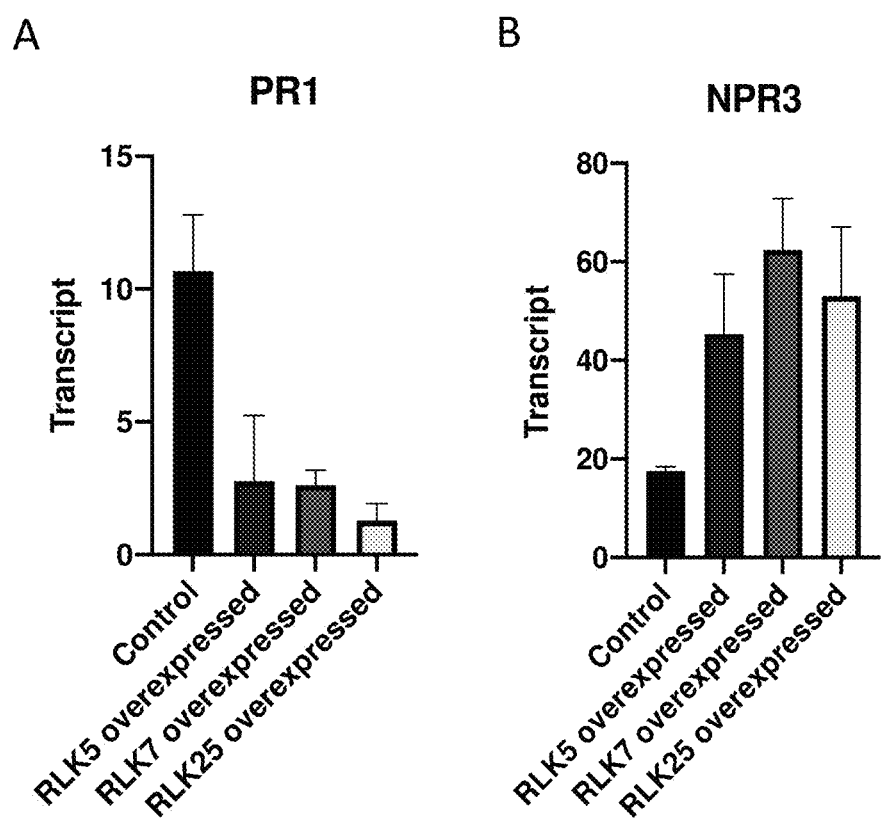
FIGS. 16A-16B. Transcriptional activation of jasmonic acid and ethylene defense marker genes in *Arabidopsis* transgenic lines overexpressing RLK5 and 7. RLK25 is an L-type RLK that functions as positive defense regulator. (A) PR1; (B) NPR3.

Salicylic acid (SA) is an important signal molecule in plant defense response. One essential player in the SA defense response pathway is non-expresser of pathogen related genes 1 (NPR1). NPR1 is a positive regulator of SA pathway. It is well known that *Arabidopsis* npr1 mutant shows increased disease susceptibility and downregulation of genes specifically pathogen related (PR1) gene. PR1 genes were downregulated in transgenic *Arabidopsis* constitutively expressing RLK5 and RLK7 (FIG. 16A). In contrast, NPR3 was significantly overexpressed in transgenic lines compared to wild type (FIG. 16B). From these results, the inventors conclude that constitutive expression of RLK5 and RLK7 contributed to the regulation of SA related genes and appeared to suppress the activation of SA signaling pathway.

Figures 17A, 17B, 17C:
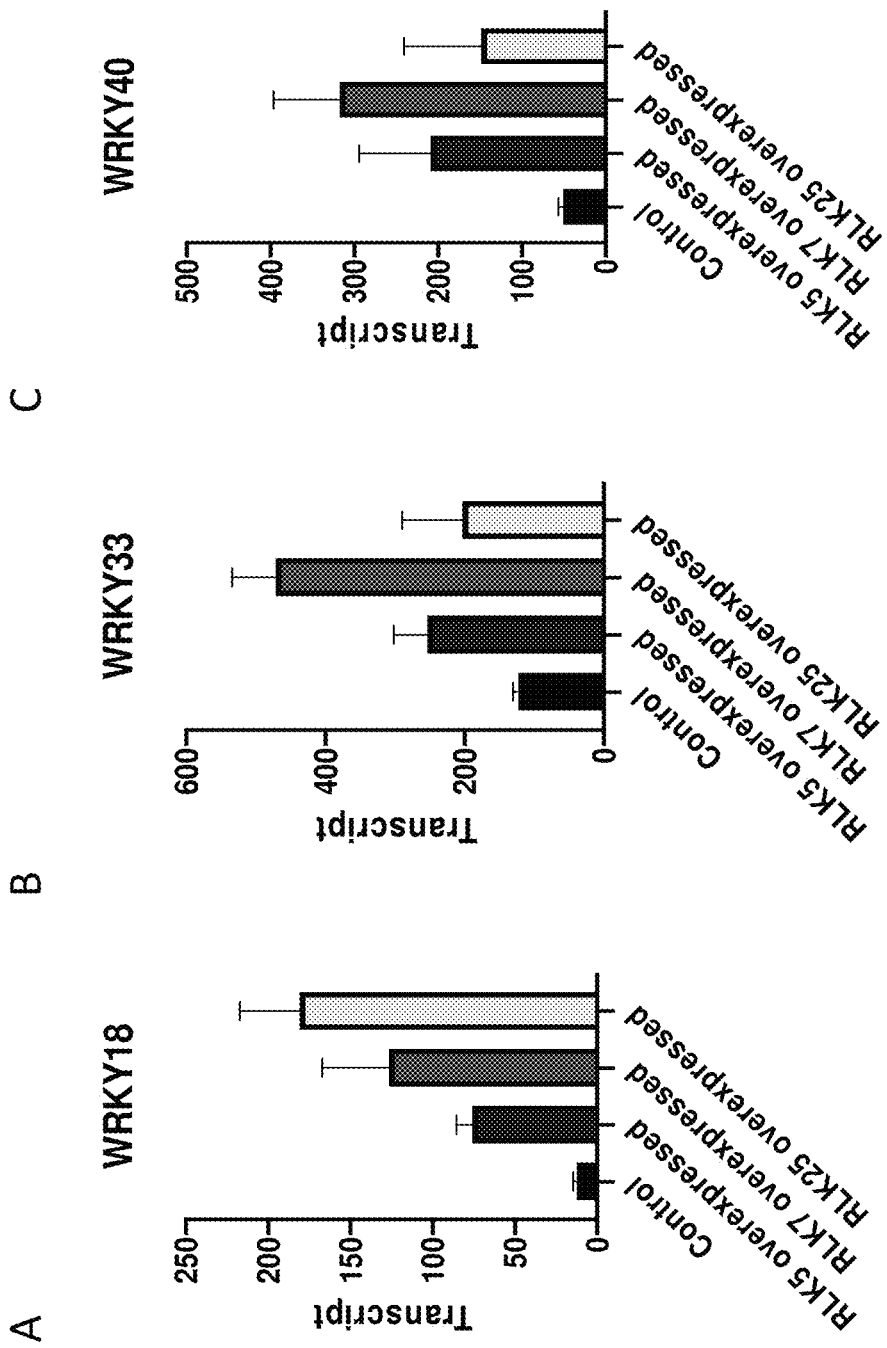
FIGS. 17A-17C. Transcriptional activation of canonical defense-related WRKY transcriptional factors in *Arabidopsis* transgenic lines overexpressing RLK5 and 7. RLK25 is an L-type RLK that functions as positive defense regulator. (A) WRKY18; (B) WRK33; (C) WRKY40.

Example 20: Classical WRKY Genes are Hyperactivated in RLK PAN Transgenic Plants WRKYs are transcription factors involved in various plant processes but notably in fighting against diverse biotic and abiotic stresses. WRKY18, WRKY33 and WRKY40 are the prominent WRKY genes involved in plant immunity and the inventors determined significant upregulation of these transcription factors in transgenic lines as shown in FIGS. 17A-17C.

Figure 18:
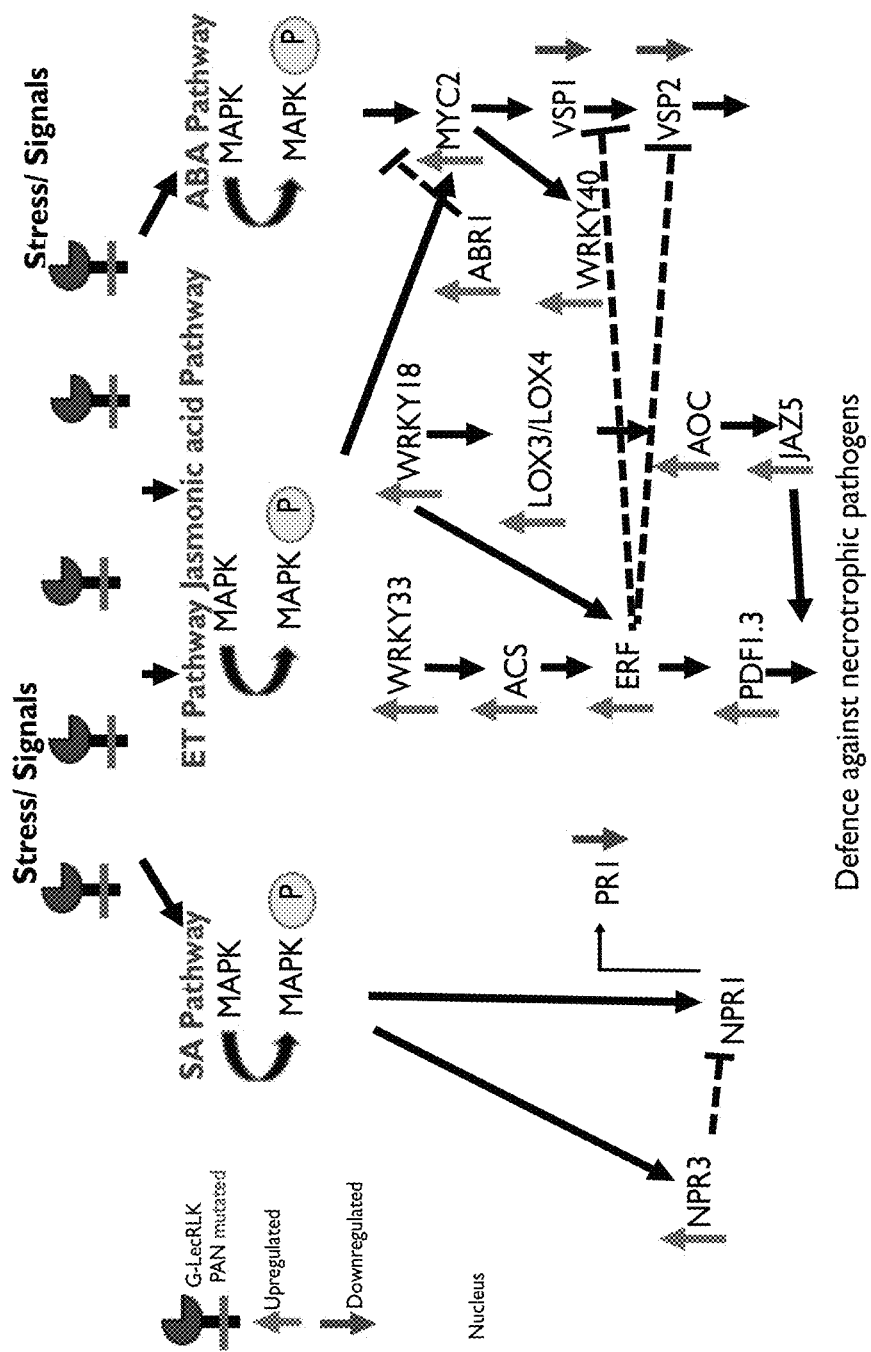
FIG. 18. Proposed model showing RLKs with mutated PAN domains specifically activate ET/JA pathway and attenuates SA and ABA pathway in plant innate immunity. Scheme of activation of JA and ET pathway in RLK PAN overexpressed transgenic pant in *Arabidopsis*. The green arrow indicates upregulation, and the red arrow indicates the downregulation. These results suggest that RLK PAN transgenic plants shows activated ET/JA pathway and attenuated SA and ABA signaling p Targeted Genome Engineering Targeted genome engineering (also known as genome editing) has emerged as an alternative to classical plant breeding and transgenic (Genetically Modified Organism—GMO) methods to improve crop plants. Available methods for introducing site-specific double strand DNA breaks include zinc finger nucleases (ZFNs), TAL effector nucleases (TALENs) and CRISPR/Cas system. ZFNs are reviewed in Carroll, D. (*Genetics,* 188.4 (2011): 773-782), and TALENs are reviewed in Zhang et al. (*Plant Physiology,* 161.1 (2013): 20-27), which are incorporated herein in their entirety.

A proposed model for function of the PAN domain in plant G-lecRLKs is found in FIG. 18.

List 1: List of UniProt IDs for PAN Domain Containing Proteins Across Species.

R4G2C1, R4G7D0, G8EBH2, G8EBN0, G8EDK5, A0A3T1CXD4, A0A3T1CXP1, A0A1E1EXB1, A0A1E1ETK2, A0A1E1EUC2, L8GVM1, L8GRF2, L8GX08, L8GY48, L8H5C9, L8GYA1, J3E810, J2YWZ6, J3IYU5, A0A2L2DLV0, A0A2L2DIZ7, A0A0G2Y717, E3VZX8, E3VYF9, F8V6R0, A0A0G2Y378, A0A0G2Y8U4, A0A2L2DJ09, Q5UPR5, Q5UNW8, Q5UQG0, A0A2L2DM38, A0A0G2Y3S5, A0A0G2YB83, A0A0G2Y7I9, L7RC65, L7RC22, L7RCU4,

A0A091MSS1, A0A091MQE1, A0A3Q1FYN5, A0A452XJW5, A0A453DYR4, A0A453LKH1,
A0A3Q1FW77, A0A3Q1EDF5, A0A3Q1G8B6, A0A453DBP7, A0A453NKT3, A0A453ADR2,
A0A3Q1F1Z0, A0A3Q1I407, A0A316YDH8, A8ZR36, A0A453D3G3, A0A453AAM1, A0A453D3A4,
A0A0A7CPG5, A0A0A7CP60, A0A0A7CN07, A0A453PQK2, A0A453Q1Y2, A0A453LKA1,
A0A0A7CNR8, A0A0A7CN57, A0A0A7CP35, A0A453MGE8, A0A453F7I6, A0A453FPR4,
A0A0A7CMN8, A0A0A7CP65, A0A0A7CP71, A0A453D383, A0A452Z010, A0A453QTP8,
A0A0A7CN98, A0A0A7CP31, A0A1V9ZRA5, A0A453FPN3, A0A453JHT4, A0A453FPT0,
A0A1V9ZDE5, A0A1V9YLY7, A0A1V9Z1A6, A0A453FPK6, A0A453EGB1, A0A453QZE9,
A0A1V9ZKZ6, A0A1V9Z451, A0A0A7CNG8, A0A453BYN4, A0A453KBQ0, A0A452Z4D8,
A0A1V9YJ62, A0A0A7CMR5, A0A0A7CPD7, A0A452ZEX2, A0A453SHI0, A0A453D306,
A0A1V9Z629, A0A0A7CPH5, A0A1V9YJK3, A0A453FPP1, A0A453F7D3, A0A453LN14,
A0A1V9YSE1, A0A1V9YDS4, A0A1V9YHW9, A0A453LK85, A0A453LK71, A0A453H3Z1,
A0A0A7CMJ7, A0A0A7CN31, A0A1V9ZMC6, A0A453DYX5, A0A453FPQ5, A0A453DBC1,
A0A0A7CNG9, A0A1V9YH26, A0A1V9YUS3, A0A452ZGJ2, A0A452ZGK8, A0A452ZEZ6,
A0A1V9ZRD0, A0A0A7CNY9, A0A0A7CM59, A0A453LK88, A0A452YZZ8, A0A453D3A8,
A0A1V9ZKR0, A0A1V9ZUM1, A0A1V9YUE0, A0A453LKC7, A0A453GLW6, A0A453LK95,
A0A1V9YRF9, A0A1V9ZB07, A0A0A7CN88, A0A453LK89, A0A453D358, A0A453QZ76,
A0A1V9YXW4, A0A1V9Z9X3, A0A0A7CLM9, A0A453GMC5, A0A453BYQ7, A0A453T0W6,
A0A1V9Z933, A0A1V9YWJ8, A0A2E4CB18, A0A453DD79, A0A453BBQ0, A0A453Q244,
A0A2E4CBG1, A0A2E4CB13, A0A2E4CBJ3, A0A453DBN0, A0A453GM60, A0A453D325,
A0A2V9ZGI7, A0A150V788, A0A150VFP3, A0A453Q771, A0A453BCU3, A0A452XK72,
A0A3A1WDE8, A0A444V1E0, A0A444V1E2, F4X7R3, A0A453DBI2, A0A453QZN5, A0A453HAH1,
F4X293, F4X6U6, F4X815, F4WMQ5, F4X291, A0A453FPI6, A0A452Z002, A0A453LKB1,
A0A058ZM17, A0A037ZPD6, A0A2R6Q4L0, A0A452XK48, A0A453BBD4, A0A453Q2E7,
A0A2R6RAZ9, A0A2R6Q6W9, A0A2R6QV86, A0A453QZF2, A0A453DBB2, A0A453JEW1,
A0A2R6QWW6, A0A2R6PXQ8, A0A2R6R4I5, A0A453SU32, A0A453FPN4, A0A453DBG7,
A0A2R6PR71, A0A2R6RB30, A0A2R6P2X1, A0A453D337, A0A453LKF9, A0A453F7G5,
A0A2R6R7U2, A0A2R6QA16, A0A2R6PTF8, A0A453SVW0, A0A453BC35, A0A453D3B0,
A0A2R6Q077, A0A2R6QTI6, A0A2R6R4H6, A0A453DA54, A0A453TAB1, A0A453D3G4,
A0A2R6QBV2, A0A2R6PQK3, A0A2R6QCM9, A0A453JHJ1, A0A453SRL9, A0A453ADQ2,
A0A2R6RF49, A0A2R6QDU5, A0A2R6QLP2, A0A453D349, A0A453PFF2, A0A453DA76,
A0A2R6PTF3, A0A2R6PGN0, A0A2R6RRI6, A0A452XH56, A0A453DC09, A0A453QTY7,
A0A2R6RGA0, A0A2R6PWC1, A0A2R6PXW3, A0A453DB70, A0A453DBM7, A0A453FPK2,
A0A2R6Q3G8, A0A2R6Q7Z3, A0A2R6QBX6, A0A453DBH5, A0A453Q2F9, A0A453ADR3,
A0A2R6QLN4, A0A2R6PTE6, A0A2R6QWB9, A0A453DDD0, A0A452Z027, A0A453FPS3,
A0A2R6PJ76, A0A2R6RP34, A0A2R6RB22, A0A453D6J6, A0A453J9S0, A0A453Q2M7,
A0A2R6QXS9, A0A2R6PEE6, A0A2R6NZR5, A0A453LJR3, A0A453D329, A0A453GM00,
A0A2R6RB09, A0A2R6PQU7, A0A2R6QLP8, A0A453BYP5, A0A453BBD9, A0A453BYM4,
A0A2R6QC53, A0A2R6PUZ3, A0A2R6PTE5, A0A453Q291, A0A453QU71, A0A453H3Z4,
A0A2R6QBV5, A0A2R6RB02, A0A2R6QCD9, A0A453SGZ7, A0A453ADQ4, A0A453LKC4,
A0A2R6QBW7, A0A2R6R4H9, A0A2R6QWW7, A0A453LKG3, A0A453DBI3, A0A453DC06,
A0A2R6PK86, A0A2R6NKZ3, A0A2R6PRE4, A0A453SRP6, A0A453SRK1, A0A453ADR9,
A0A2R6PY69, A0A2R6RB03, A0A2R6QDU9, A0A453QZE3, A0A453D3H5, A0A452Z019,
A0A2R6P887, A0A2R6QXB5, A0A2R6QA21, A0A452Y3L8, A0A453DB32, A0A453D353,
A0A2R6PRM8, A0A2R6QMJ8, X1WJB0, J9K2R9, A0A453H9U8, A0A453DBK3, A0A453DBC7,
J9LS79, J9KAI5, J9KPT6, J9JPB7, J9K0U0, J9JMX3, A0A453NLT6, A0A453ILU0, A0A452ZQ21,
B3G4G6, B3G448, B3G4F0, A0A1S4G3R5, Q1HRG8, A0A453DBV6, A0A452Z009, A0A453DDA0,
A0A1S4FK22, Q16Y69, A0A1S4FG50, Q16VE9, Q17JC8, A0A453G5Z3, A0A452ZGN5, A0A453D6L7,
Q171P7, Q17FY1, Q16VE8, A0A182H4K1, A0A453BYQ2, A0A453D2Z9, A0A453DBL2,
A0A182H5Q1, A0A182G6M4, A0A182G9D3, A0A453DBD7, A0A453FPV1, A0A453D352,
A0A182G9D4, A0A452XH92, A0A452ZGN2, A0A453Q591, A0A452ZI59, A0A453Q2L2, A0A453D333,
A0A453BYP1, A0A453LJQ2, A0A452ZGI7, A0A453TA51, A0A453DDL7, A0A453G617,
A0A453HQH7, A0A453AAT9, A0A453DBA5, A0A453D2X4, A0A452XD19, A0A453Q1X4,
A0A453BBE0, A0A453BYQ0, A0A453LK80, A0A453MGQ3, A0A453HRF8, A0A453EGH4,
A0A453ADR6, A0A453Q2G0, A0A452Z039, A0A453HQJ5, A0A453LN67, A0A453DB22,
A0A452ZI33, A0A453D3G9, A0A453DYZ0, A0A453BDB4, A0A453LK93, A0A453DDM1,
A0A453JHI0, A0A453Q2D1, A0A453LKE2, A0A453D369, A0A453DBK6, A0A453SRN7,
A0A453F7F0, A0A453GM45, A0A452Y396, A0A452ZGM5, A0A453D6Q2, A0A453LKB4,
A0A453BYT2, A0A453MEH1, A0A453EGG7, A0A453BYR3, A0A453D3C0, A0A452XD37,
A0A453D372, A0A453SRN1, A0A453FPM7, A0A453DDM6, A0A453ADV9, A0A453FPM3,
A0A453BYQ9, A0A453ADP5, A0A453JI06, A0A453TAE6, A0A453BC47, A0A452XK40,
A0A453DD86, A0A453LKD6, A0A453DYQ0, A0A453F7D6, A0A453NKD5, A0A453DC51,
A0A453ADU5, A0A453XJR0, A0A453JGU6, A0A453DBE4, A0A453T114, A0A453BYS4,
A0A453NKE5, A0A453LKC6, A0A453D3I3, A0A453H3Z7, A0A453ATP0, A0A453G6T0,
A0A453JIH7, A0A453LKE3, A0A453DBY7, A0A452XZ51, A0A453DBW3, A0A452XD28,
A0A453SVX0, A0A453FPN7, A0A453DDB2, A0A453LJR8, A0A453BB79, A0A453D382,
A0A453DB66, A0A453FPT3, A0A453DAW9, A0A453LK83, A0A452ZI63, A0A452XZD5,

A0A452Z4E2, A0A453T139, A0A453DB02, A0A453DB67, A0A452ZGL3, A0A453Q276,
A0A453FPR7, A0A453PFD9, A0A453BBJ6, A0A453QZ80, A0A453MGQ6, A0A453FPJ7,
A0A453LK79, A0A453BBV1, A0A453DBL5, A0A453FPR0, A0A453DBN2, A0A453FPS6,
A0A453FPR9, A0A453D361, A0A452XD46, A0A452XH94, A0A453BBV6, A0A453LN06,
A0A453QZU7, A0A453ATS1, A0A453FPJ1, A0A453DBE9, A0A453ADV4, A0A453DDC4,
A0A452XB26, A0A453QTW5, A0A453BYP4, A0A453EGH0, A0A453D3F8, A0A453IG18,
A0A453D323, A0A453ADR1, A0A452XJS2, A0A453ADQ8, A0A453DBM5, A0A453F7C5,
A0A453FPS0, A0A453FPQ0, A0A453JB99, A0A453LKD9, A0A453DBX3, A0A453D3H9,
A0A453DBF2, A0A453KC08, A0A452XJG0, A0A453D302, A0A453BBC9, A0A452XD12,
A0A453DBT2, A0A453IFX4, A0A452XK35, A0A453DBK1, A0A453SKA3, A0A453HRC9,
A0A453D3B3, A0A453LJU7, A0A453JH21, A0A453DBG1, A0A453DBE1, A0A453D359,
A0A453S9X2, A0A452XJT3, A0A453DBV3, A0A453HAB3, A0A453DDN3, A0A453D6N7,
A0A452Z033, A0A452XH89, A0A453SAP2, A0A452XK26, A0A453T0X8, A0A452ZGM1,
A0A453BBW1, A0A453DC15, A0A453DBY3, A0A453EGH5, A0A453BYM8, A0A453D395,
A0A453DDL1, A0A453D3A1, A0A453D396, A0A453LKC3, A0A453MGP0, A0A453LK53,
A0A453H3Z3, A0A453EGJ2, A0A453DBW8, A0A452XJQ5, A0A453D3A0, A0A453D3C4,
A0A453LKB3, A0A453EGJ7, A0A453G694, A0A452XK20, A0A452XHA4, A0A453JG11,
A0A453Q4I2, A0A453CF81, A0A453FPL3, A0A453DBP9, A0A453DBW4, A0A453JHF1,
A0A453GM65, A0A453GMJ9, A0A452Y3H0, A0A452XHB4, A0A453SRP8, A0A453DBL1,
A0A453D3A3, A0A453DDC2, A0A452ZNP1, A0A453D309, A0A452YZZ3, A0A453DBN5,
A0A452ZGK3, A0A453DBU3, A0A453GQY1, A0A453HAG7, A0A453DBJ1, A0A453DDM2,
A0A453IM88, A0A453D363, A0A453SRL5, A0A452XB20, A0A453D2X9, A0A453SRM5,
A0A453Q2A6, A0A453JHH1, A0A453BBU6, A0A453Q4I8, A0A453DIV2, A0A453BDH9,
A0A453JFZ5, A0A453H3Z2, A0A453XB13, A0A453DDB4, A0A453GMC0,
A0A453DBP2, A0A453LK56, A0A453TAD7, A0A453DBP5, A0A453SRE5, A0A452ZGQ0,
A0A453JH11, A0A453FPS4, A0A452ZGP0, A0A453LKG2, A0A453BDI1, A0A452ZNP3,
A0A453QZV2, A0A453Q1W1, A0A452XH97, A0A453FPR3, A0A453JIE4, A0A453BD61, A0A453D398,
A0A453D2W3, A0A453SVQ7, A0A453DBR6, A0A453FPL9, A0A452ZEW7, M8C3G1, N1QZA4,
A0A453EGJ0, A0A453MGF3, A0A453D3B5, M8BLT1, M8CDU3, M8BQF5, R7W3S1, M8CA09,
A0A453BC42, A0A453Q2K8, A0A453K9H8, M8C8E1, R7W6C2, M8BRL3, M8BNQ4, M8BSU9,
A0A453LJN7, A0A453DBK2, A0A453BBR3, M8B659, M8B657, M8B6T4, R7W524, R7W6Q0,
A0A453AAL0, A0A453SRP1, A0A453FPQ4, M8ARV2, N1R0P4, N1QWT2, M8C3Q0, M8BS71,
A0A453DBE5, A0A453QU60, A0A453SRQ7, M8C8A2, M8CGA2, M8D7P7, M8BGE8, M8AXL9,
A0A453QUA8, A0A453SUC2, A0A453A3H4, N1QQ18, R7W4G4, N1R0J5, M8CMY7, M8BFG4,
A0A453BYQ1, A0A452XD39, A0A453TAB6, M8CQW7, R7W4J2, M8BZH7, R7W0V2, M8BFQ4,
A0A453FPV0, A0A452ZGM7, A0A452ZI86, N1R4A5, M8BVW7, R7W466, N1QUE8, N1QPR6,
A0A453SAJ3, A0A453DBS2, A0A453D394, R7W2M1, M8AQG2, M8D5R8, M8B4Z6, R7WBZ0,
A0A453DB45, A0A452ZGN4, A0A452Z015, N1R267, M8BEL9, M8AXV6, M8BHI2, R7W702,
A0A452ZNQ3, A0A453BBE7, A0A453LK78, N1QZP8, M8BWJ0, M8AR11, R7W5U0, M8BKQ6,
A0A453F7K0, A0A453LKB7, A0A453D375, M8C7I9, R7W886, N1QTT0, R7W6D7, M8AR15,
A0A453DB42, A0A453FPS1, A0A453D385, M8BFJ7, M8B3Y2, M8BW41, M8BV04, M8BSB0,
A0A453LKJ9, A0A453SRH1, A0A453SVF0, M8C2A6, N1QZS0, M8B4G8, M8BIP4, N1QVU3,
A0A453BBF4, A0A453QU28, A0A453SGI2, M8CU22, R7WB01, M8C5G3, M8BSH4, M8BH12,
A0A453DBL7, A0A453AAP4, A0A453KCJ5, M8CC39, N1QZA9, R7W2H2, M8AWU4, R7W5J6,
A0A453D310, A0A453DC24, A0A453D3E6, M8BVP9, M8B6H7, M8CQN8, N1QPF3, N1QVJ3,
A0A453H3Z9, A0A453TA82, A0A453FPU6, M8CV03, M8C2T7, M8BJJ3, M8BBM6, M8C398,
A0A453SGY8, A0A453LK90, A0A452ZQ32, M8C374, M8BRL2, R7W3B4, M8CMA1, M8BMX3,
A0A453EGC1, A0A453D390, A0A452XB18, R7WBP2, M8BAQ4, M8BCF9, M8AI36, M8BZV5,
A0A453LKE6, A0A452ZRM6, A0A453LKA2, N1QRV4, M8AI44, M8CDI5, M8BRQ9, M8BS62,
A0A453EGK8, A0A452Z021, A0A453DDC6, N1QTT3, M8CXN2, R7WAL8, R7W389, M8CS97,
A0A453HR14, A0A453DB15, A0A453GLY9, R7W2A0, M8BMF1, M8CLL1, M8BBG0, N1R416,
A0A453LJT7, A0A453FPS5, A0A453BYR6, A0A453JIE9, M8C0P3, N1QSH2, M8C8P5, M8BC75, R7W9K6,
A0A453FPU5, A0A453T0S7, A0A452Z4F2, M8BZ85, M8AQX6, M8BRA9, M8BV83, N1QUU5,
A0A453Q2M4, A0A453ILU7, A0A452ZGI2, R7W017, M8AWM2, M8C1A2, M8CIT9, M8BR67,
A0A453SFC7, A0A453LJW8, A0A453Q1Y8, N1R3B9, M8BVQ9, M8APF0, R7W5F9, N1QR69,
A0A452ZGM9, A0A452XB15, A0A453MGP2, N1QWL3, R7W6I7, A0A1G5P0D6, K8P0P5,
A0A452ZQ12, A0A453DC10, A0A453LKG5, A0A2M8ZRI2, K8P4L2, A0A090MQ82, A0A380WCA0,
A0A453BBC4, A0A453D2Z4, A0A453Q471, A0A0M3DZ05, D6V6Y8, A0A1M2ZI81, A0A1Q3W3V1,
A0A453H401, A0A453SRN8, A0A453DYZ4, A0A1H0JMN5, W3RJC5, A0A0Q6ZHE5, A0A2D6Z1S1,
A0A453DBH0, A0A453SVS6, A0A453LKB9, P0C9W5, A0A0C5AWG9, A0A1W4XI26,
A0A453ADT9, A0A453SRL4, A0A452XJY3, A0A1W4WER7, A0A1W4WCW5, A0A1W4WMX9,
A0A453EGB6, A0A453DBX4, A0A453D3D9, K2PXK1, A0A0D8KTY2, A0A135P8H9, A0A1S7TYJ4,
A0A453QZF5, A0A452ZEW0, A0A453DBG6, A0A1S7R665, A0A1S7QSC7, Q7CT39, A0A1S7R1K3,
A0A453QZE7, A0A453LJY8, A0A453ADP8, A0A2W5HEG2, A0A3G2D9W1, A0A3G2CW11,
A0A453SRL2, A0A453DDC8, A0A453DC41, A0A1S7N2M1, A0A1S7N2Q8, A0A1S7S8C0,
A0A453D315, A0A453DBP0, A0A453LKE7, A0A1S7MTQ7, A0A1S7N332, A0A1S7R6H0,
A0A453D3A5, A0A453JGZ8, A0A452XHA9, A0A1S7S0T3, B9J7G8, W1KEF2, W1LDB8,

A0A061MPX5, A0A2T7V3G2, A0A2T7VDF4, A0A178H3O1, A0A071HXB3, A0A071HYF2, A0A2S4E9Q9, A0A081CTJ4, A0A1B9TQL4, A0A1S7UAP0, A0A1S9E9P5, A0A1S9E6I0, F0LCJ2, F5J606, A0A3S2U7W8, A0A1R3TJ16, A0A1R3TLG8, A0A427QHU1, A0A0X6ZW52, A0A0X6ZP94, A0A328F968, A0A328ESI4, A0A1S7RVT6, A0A1B3P384, A0A1E3YAW1, A0A0L6K5Z5, A0A349XP92, A0A357X7H8, H0H495, H0HI51, F7UCM7, A0A1S7QYX0, A0A1S7RCW1, A0A1S7T9V4, M8B9N1, A0A1S7RU05, B9JSY8, A0A202F108, A0A1S2DVC4, A7XED0, A0A1S2E625, A0A368NW97, A0A2E0IUI6, A0A2E2RQX8, A0A2E0IF36, A0A2E2RKN7, G1M174, G1LEP0, G1MBX3, G1LET2, G1M194, D2HM20, D2HEU5, G1MDT1, D2H7K2, A0A0A7LYW8, A0A024GUK6, A0A024GTY2, A0A024FUV0, A0A024FUS4, F0WGZ2, F0W170, F0WDJ8, F0WDJ9, F0WGX7, A0A1B9PIN4, A0A151M2C0, A0A151NPI2, A0A151PBF9, A0A151NPX2, A0A151M2C2, A0A151MTI6, A0A151PAG7, A0A1U7S3Q2, A0A1U7R1W7, A0A3Q0GI02, A0A1U8DHU0, D3RPG7, A0A1H3HNT0, A0A0L0S2D3, A0A0L0RXQ9, A0A0U2S302, A0A0U2JFZ1, A0A0U2RH63, A0A1V1PR56, A0A1Q7BNX2, A0A1Q3K2D4, A0A1L9Q6D6, A0A2N3CAF3, A0A2N3CN55, A0A2N3BHU6, A0A2N3BWC8, A0A3M1A8N1, A0A3M1CCK9, A0A3B9YVH5, A0A3B9YUR4, A0A3C0MDP2, A0A177E5Y0, A0A177DMN5, A0A177DB16, A0A177DW37, A0A177D586, A0A177DA37, A0A399GD40, A0A399HQ58, A0A399G9V7, A0A2M9PBP4, A0A0Q3U1E2, A0A0Q3UR44, A0A0Q3MLN8, A0A0Q3MGK6, A0A1E1X339, A0A1E1XND8, W1PSU2, W1NHI6, W1NS07, W1PUY6, U5D4B7, W1PK20, W1NP94, W1PWB1, W1P1F1, W1PJ97, U5CZI6, W1PNM0, W1PYM5, U5D3T0, W1NII4, W1NTK9, W1PI96, W1NKX3, W1PU85, W1PHD9, W1P824, W1P1U3, W1PS15, W1P261, A0A380WPF7, A0A380WLF7, A0A142M5P6, A0A316H1V4, A0A2S0XJL2, A0A0Q6M906, A0A3Q0QWF0, A0A3Q0RP91, A0A3Q0QW88, A0A3Q0QZA4, A0A3Q0QXI1, A0A3Q0QYJ9, A0A3Q0QX28, A0A3Q0RIQ3, A0A3Q0QX05, A0A3Q0RNB8, A0A3Q0QX18, A0A3Q0RNE4, A0A3Q0T1F7, A0A1X7VF86, A0A1X7VJI8, A0A3Q1CUE1, A0A3Q1AZ85, A0A3Q1BNV0, A0A3Q1ASI9, A0A3Q1CEN8, A0A3P8SBR5, A0A3P8U3P7, A0A3P8RV74, A0A3P8SZJ0, A0A3P8T1W7, A0A1W6EWC0, A0A1W6EWB2, A0A2N5IM96, A0A1B7WGH8, A0A3Q1JM01, A0A3Q1JGW1, A0A3Q1HBQ8, A0A3Q1JNC7, A0A3Q1HBU2, A0A3Q1K4Z1, A0A3Q1HBM8, A0A3Q1JWC6, A0A3Q1H376, A0A3Q1JWD0, A0A3Q1H8P6, A0A1F3C361, A0A199VKR8, A0A199W1P5, A0A199VMM6, A0A199V5G5, A0A199V0P4, A0A199VXD4, A0A199UUR3, A0A199UNR1, A0A199UFB6, A0A199V3G9, A0A199UF66, A0A199VMS2, A0A199W3M8, A0A199VXV5, A0A199UW40, A0A199VG00, A0A199VR05, A0A199UW09, A0A199VZH8, A0A199VCY3, A0A199UMA3, A0A199VZ99, A0A199VI10, A0A199UUQ7, A0A199UV66, A0A199UQ24, U3IRP5, U3I6X0, U3II31, R0K1Z7, R0JPB7, R0M4Q0, R0LQI0, A0A368GRP9, A0A368GP95, A0A368GMN0, A0A368H349, A0A368GJB9, A0A368GWF9, A0A368HB09, A0A368G5Y2, A0A368GRQ0, A0A368GVT4, A0A368GWX4, A0A368H7D6, A0A368H3B6, A0A368FPC8, A0A368GP49, A0A368GXY9, A0A368EXZ3, A0A368GJW8, A0A368FA73, A0A368GWI0, A0A368GX96, A0A368GTK6, A0A368H705, A0A368GFH7, A0A368H7B8, A0A368HDM2, A0A368GFI5, A0A368HEE4, A0A368GI28, A0A368GRE3, A0A368FCY8, A0A368FCZ3, A0A368G2Q2, A0A016VKR6, A0A0D6M3P1, A0A016WI38, A0A016V0U2, A0A016S814, A0A016RWJ5, A0A0D6LC48, A0A016WHK2, A0A016SGK6, A0A016T8L1, A0A016SHF1, A0A016WSY7, A0A016S7S9, A0A016S6Y5, A0A0D6LU43, A0A016TUW3, A0A016T0N8, A0A016W3A0, A0A0D6LRJ3, A0A016WIX9, A0A016WRA4, A0A016RV21, A0A016VJZ2, A0A016STN6, A0A0D6LUD3, A0A016SU80, A0A0D6M9L2, A0A016SMB0, A0A016VCU4, A0A016SS42, A0A016W8B6, A0A016V243, A0A016SU41, A0A016V216, A0A016SRZ7, A0A016V3K2, A0A016W7N7, A0A016UI89, A0A016WS77, A0A016UHN2, A0A016TCL6, A0A016T8A6, A0A016WA14, A0A0D6MAD7, A0A016VDI1, A0A016T206, A0A016V2S3, A0A016WI79, A0A016W8D8, A0A0D6M851, A0A016V2R6, A0A016W998, A0A016SR62, A0A016V233, A0A016WTI9, A0A016UJN5, A0A016V3J7, A0A016TTS6, A0A0D6LG45, A0A016VDY5, A0A016WNP3, A0A016STB4, A0A016VIC1, A0A016V2R1, A0A016SS83, A0A016WSZ0, A0A016V1H8, A0A0D6M4L0, A0A016TCJ1, A0A016VFG3, A0A016VEL5, A0A016WGP1, A0A016UG75, A0A0D6LIH3, A0A016TCI8, A0A016VL99, A0A016SU43, A0A016SHA2, A0A016TVN9, A0A016WI62, A0A016T0X6, A0A016WQP5, A0A016SU38, A0A016VJ86, A0A016SL82, A0A016UGP0, A0A016VA51, A0A016WJ45, A0A016WEZ6, A0A016T7T4, A0A016TXR8, A0A0D6LZI8, A0A0D6LVB3, A0A016WN18, A0A016WV69, A0A016RVX3, A0A0D6LXD0, A0A016WHK9, A0A016UHG4, A0A016V2P8, A0A0D6M3G6, A0A016WUK9, A0A0D6M3L0, A0A0D6M584, A0A016RVW0, A0A0C2DVX2, A0A0C2FMV1, A0A0C2G7Y5, A0A0C2CRJ1, A0A0C2GDQ6, A0A0C2H4Q3, A0A0C2GLS5, A0A0C2G2S8, A0A0C2DFM8, A0A0C2DQD8, A0A0C2H0D7, A0A0C2CKU6, A0A0C2C4H3, A0A0C2HCQ8, A0A0C2BR75, A0A0C2FCW8, A0A0C2FEG0, A0A0C2D4J6, A0A0C2F8I9, A0A0C2FGE8, A0A0C2FP16, A0A0C2GFH0, A0A0C2G7Z8, A0A0C2H638, A0A0C2FGY3, A0A0C2CYI0, A0A0C2FI47, A0A0C2F9X1, A0A0C2GVY3, A0A0C2DNE1, A0A0K0DQK0, A0A0K0CXV8, A0A0K0DEV9, A0A158PCD7, A0A0K0D0D1, A0A0K0D3I0, A0A0K0CUG2, A0A0K0DH19, A0A0K0D5J4, A0A0K0D1B4, A0A0K0DJR6, A0A0K0D008, A0A158PB05, A0A158P5X6, A0A158P8Q5, A0A158PAM2, A0A0K0DL22, A0A3P7JT81, A0A158PIZ8, A0A3P7HR75, A0A158PEZ2, A0A3P7J3A0, A0A158PKV1, A0A0R3PDF2, A0A158PGM2, A0A158PE13, A0A158PFJ6, A0A0R3PME5, A0A0R3PZF2, A0A0R3PL23, A0A0R3PMU4, A0A0R3PYM1, A0A158PJ68, A0A158PLM5, A0A0R3PB90, A0A0R3Q188, A0A158PGG5, A0A0R3Q0R2, A0A0E9X3V9, A0A0E9RJH8, A0A3P6NGQ5, A0A0M3JX10, A0A0M3K2F0, A0A3P6SFK2, A0A3P6RLJ8, A0A0M3JD59,

A0A0M3KAT5, A0A0M3KD76, A0A3P6T6E9, A0A3P6RTW8, A0A0M3K8I9, A0A0M3K2Z5, A0A0M3J4P1, A0A0M3J2X5, A0A0M3JVW0, A0A0M3J5I5, A0A0M3KA02, A0A0M3KCU0, A0A0M3JKG2, A0A0M3K200, A0A0M3JKG6, A0A0M3K1Z4, A0A0M3KIH9, A0A0M3K2C6, A0A0M3JY76, A0A158PN22, A0A0M3K2T5, A0A0M3J493, G1KNL2, G1K9G8, G1KBV2, G1KIB0, R4GD12, A0A182F6L9, A0A182F5Z9, A0A182F6L8, A0A182FRE6, A0A182F6M0, A0A182F5Z8, A0A182FDG2, A0A182HU77, B2G0D9, B2G0D5, A0A182HTF9, B2G0D4, A0A182HTG0, B2G0D3, A0A182I7L3, A0A2C9GRZ8, A0A2C9GRP2, A0A182I7L4, A0A182HTF8, A0A182IT52, A0A182ITQ2, A0A182JLI3, A0A182ISL2, A0A182J7H9, A0A2M3Z8D8, A0A182JNP2, A0A182KB58, A0A182JQG9, A0A182KEB4, A0A182KAY0, A0A182JNP1, A0A182LFU3, A0A182LFM7, A0A182KQB0, A0A182LMG3, A0A182LFM6, A0A182M3D4, A0A182MI18, A0A182MAX7, A0A182M333, A0A182M9X2, A0A182LRC3, W5J6L5, W5J5H0, W5JK04, W5JQZ0, A0A182NGA9, A0A2Y9D1G5, A0A182NBM5, A0A182NBM6, A0A2Y9D1N7, A0A182N642, A0A182NGA8, A0A182NGA7, A0A182P472, A0A182PEK4, A0A182NZH6, A0A182NZH5, A0A182PEK5, A0A182PEK6, A0A182P5T7, A0A182QEI7, A0A182QKG0, A0A182QSK0, A0A182QWD4, A0A182QWK0, A0A182Q5P2, A0A182RNR5, A0A182RHD6, A0A182RF54, A0A182R769, A0A182RHD7, A0A182R770, A0A182R771, Q7PTF3, B2G0E1, Q7QBU4, Q7QD96, Q7PWD7, A0A1S4H0L9, A0A1S4GZU1, B2G0F5, B2G0E5, A0A182T9U0, A0A182SV91, A0A182SSP0, A0A182SAF1, A0A182T826, A0A182T015, A0A182TPY7, A0A182TF95, A0A182UCD3, A0A182TQP9, A0A182TPR8, A0A182UC50, A0A182VE60, A0A182VK07, A0A2C9H5R2, A0A182V7G1, A0A182WGE9, A0A182WLF8, A0A182W062, A0A182W2N8, A0A182WGF0, A0A182W2N6, A0A182W2N7, A0A182WWW6, A0A182WXP9, A0A182XM10, A0A182XM08, A0A182WXQ0, A0A182XM09, A0A182WRJ9, A0A084VR87, A0A084VZ46, A0A084W3V7, A0A084W3V8, A0A182XVF9, A0A182Y0J9, A0A182Y0K0, A0A182Y4A5, A0A182YEI6, A0A182XVG0, A0A222E9G5, A0A239JZP1, A0A239G1U7, A0A222E1N3, A0A222E9D9, A0A1D1YV81, A0A1D1YNY0, A0A1D1Z1M7, A0A1D1ZCW2, A0A1D1XWH9, A0A1D1XFS1, A0A1D1ZCH5, A0A1D1YQR8, A0A1D1Y9Q8, A0A1D1Y7P0, A0A1D1YD96, A0A1D1YYX4, A0A1D1YCC3, A0A1D1Z0E3, A0A1D1Z3R3, A0A1D1YIR8, A0A1D1YXD0, A0A1D1ZLQ1, A0A1D1Y6E9, A0A1D1XRS7, A0A1D1XD27, A0A1D1ZCJ4, A0A1D1XNX6, A0A1D1ZGK0, A0A1D1YPM1, A0A1D1XWC5, A0A1D1YK26, A0A1D1XXZ3, A0A1D1YPA4, A0A1D1Y8U2, A0A1D1XS70, A0A1D1ZHQ4, A0A1D1ZBF3, A0A1D1YFK6, A0A1D1Y7K5, A0A1D1YYY6, A0A1D1YYC2, A0A1D1Z4A8, A0A1D1XX47, A0A1D1YX08, A0A1D1YFZ2, A0A1D1ZJN6, A0A1D1XYK2, A0A1D1ZM53, A0A1D1ZFV4, A0A1D1YAP6, A0A1D1L822, A0A/D1XT90, A0A094NGJ6, A0A094L822, A0A094K4U5, A0A2K5DLN0, A0A2K5CCL7, A0A2K5DLM5, A0A2K5DWJ7, A0A2K5DLU9, A0A2K5D8Z0, A0A2K5D8Y5, A0A2K5D923, A0A091N7G4, A0A397C4L9, A0A3R8DBH7, A0A3R6Z9I5, A0A3R6ZA35, A0A397EGH5, A0A418CK86, W4H175, W4FC62, A0A3R7YB83, A0A397C6I0, W4H5C6, W4G226, A0A3R6Y2Z4, A0A397D222, A0A3L6VV49, A0A3L6UWB2, A0A397DZ46, A0A3R7Y206, W4G2B7, A0A397EC98, A0A396ZRW0, A0A397CJH5, A0A397D947, W4F959, A0A3R7B8C5, W4G4H3, A0A3L6V4T6, A0A3R6XZD2, A0A397EMC9, A0A3L6VXF2, A0A3L6VVV3, A0A397FE69, A0A397ER22, A0A3R6ZU09, W4GPE9, A0A3R6Y1Q0, A0A397DAZ4, A0A397FMV1, A0A418C2V2, W4G2D3, A0A425D7X0, A0A3R7BUC6, W4G048, A0A418DV78, A0A418FR37, W4H736, A0A397DY85, A0A3R6Z315, A0A418EI16, A0A397BNB4, A0A396ZQC4, A0A3R7BMT9, A0A397EYS8, A0A396ZVZ8, A0A397ELC4, A0A418FSX8, A0A418BVT6, A0A3R7ABK1, A0A3R7DKS6, W4H234, A0A397B129, A0A425CKN8, A0A418DLV8, A0A418E0M0, W4G2I9, W4FM40, A0A3L6VNC7, A0A418EMF9, W4FJ95, A0A3L6UZY8, A0A418BS39, A0A3R6Y6L2, W4FBD4, A0A397BC55, A0A3R6Z9Q1, W4FAU3, A0A396ZUR5, A0A3R7B511, A0A397CHM2, W4FIU7, A0A397AJZ3, W4FDQ7, A0A3L6V775, A0A397BDL6, A0A3R7CAC59, A0A397A4C7, A0A3R8CZN9, W4FZU6, W4G6A2, W4FEN0, A0A3L6VU69, A0A3L6VUC0, A0A3R8D3V5, A0A397DNW1, A0A397E6J1, A0A3R7AVF3, A0A397CYV4, A0A3R6WWC2, A0A397EBU1, A0A397C7D3, W4GYA7, A0A3L6VPA3, A0A3R7CXJ7, A0A397DAQ9, A0A397B2Z6, A0A397C063, A0A397EVE7, A0A397E7V6, A0A397E2F2, W4GZF9, A0A397EAD8, A0A397AMN7, A0A397FFG6, A0A3R7WJU8, A0A397BRS4, A0A397CFN8, A0A397ATR5, A0A397BCR8, A0A3L6VBL8, A0A397DIQ3, A0A397CN17, A0A3R6WP37, A0A397D709, A0A397FYU7, A0A3R7C4F4, W4GZ73, W4H0H9, A0A397G0U1, A0A3L6VNX6, A0A396ZPP3, W4FES1, A0A418D021, A0A418FQK5, A0A397CWE3, A0A3R6XQ00, A0A418F500, A0A3R7E8Z5, A0A3R6XAD8, A0A3R7EK41, A0A3R7AZA1, A0A397EH51, W4GXF5, A0A3R6Y8H5, A0A3R6ZZZ6, W4GZE8, A0A397DGM4, A0A3R7BA06, A0A397FI29, A0A3R7F475, W4FYV5, A0A397FE42, W4GBI6, A0A397BA52, A0A3L6VUC9, A0A3R6WPT4, A0A397BC03, A0A397D6D7, A0A397BR53, A0A397FF82, W4FKP1, A0A396ZTJ8, A0A397ASG3, A0A418FQ73, W4FWW2, A0A418CSY7, A0A418FU02, A0A397CX05, A0A418CAJ3, A0A3R6XZB8, A0A397EM03, W4FWJ0, A0A425DPY9, A0A418DX93, A0A397DI86, A0A3R7AM78, A0A418CFB1, A0A3R6ZM03, A0A397D336, A0A397D2R9, A0A397C5U1, A0A3R6ZVR7, A0A3R7WGA7, A0A397C1U3, A0A418BP49, A0A397EL04, A0A418DXN6, A0A397B3A6, A0A3R6Y8I4, A0A3R7WIS6, A0A418E5K5, W4FMA4, A0A425DM30, A0A3R6XLJ9, A0A3R7ZIF7, A0A3L6UPJ1, W4FYU2, A0A418FGP0, A0A3R7YVR4, A0A3R6XCY1, A0A397A0Q9, A0A397DYY2, A0A397A3C6, A0A425CZ29, A0A418EHM7, A0A418CJF8, A0A425DJP4, A0A397DYB5, A0A397B9P2, A0A425D1E4, W4G0V0, A0A418CJF6, A0A397B5E3, A0A3L6VJM5, A0A3R7Y395, A0A418CUV0, A0A418BSV9, W4GEU8, W4GHR1, A0A425CPR1, A0A3R7APT9, A0A418FS09, A0A397ES50, A0A425CS30, A0A418E063, A0A397EAV1, A0A3R7WQH8, A0A3L6VZA1, A0A418BJ04, A0A3R6WYY8, A0A397C1F4, A0A397FHZ3, A0A3R6WVI8, A0A397CVV7, A0A3L6VF87,

A0A397C940, A0A397F613, A0A3R7EHY7, A0A397DXJ3, A0A418DCN0, A0A397ER77, A0A418CWS7, A0A3R7AHK3, A0A3R6WXR4, W4H7L0, A0A418BZY3, A0A397D456, W4FRR2, A0A397EV56, W4FGT5, A0A3L6VXT1, A0A397BP25, W4FGX0, W4H101, A0A397FDH7, A0A425DDM5, A0A3R7A4K4, A0A397CJR0, A0A3L6VMY5, A0A418E4P5, A0A418G3N5, A0A397FAR0, A0A3R6XZM3, A0A3R7A7P4, A0A425CZ94, A0A418D8J3, W4GL89, A0A418FA61, A0A397BAP7, A0A396ZQ03, A0A396ZZ96, W4FL12, A0A397ASM2, A0A418C327, A0A397EKX9, A0A3R7AKW5, A0A3R6XRX3, A0A418FLE6, W4FEW7, A0A418E1G2, A0A418DBB7, A0A418CCH5, A0A3R7Z8J7, A0A418FGH1, A0A418FYZ6, A0A397EMD9, A0A3R6XJW2, A0A3R7Z6P2, W4H6A6, A0A418E9V7, W4GDP9, A0A3R7B8T5, A0A397E2H2, A0A418BIJ8, A0A418E419, A0A397EUF6, A0A397D0N4, A0A396ZWI2, A0A425CZR5, A0A397BFX1, A0A3R6WLH3, A0A397F2W6, A0A418FPV6, A0A397CC55, A0A397EVK5, A0A397CFM8, A0A425DEZ5, A0A397CGA6, A0A3L6VYT2, W4FBP1, A0A3R6XF63, A0A3L6VSI2, A0A3L6V4Z0, W4FLQ6, A0A418BUX3, A0A397D6T6, A0A396ZRZ2, A0A418E7S8, A0A396ZT37, A0A397ANE1, A0A3L6VA85, A0A397A932, A0A3L6VJ13, A0A3R6W2X3, A0A3L6V2L6, A0A3R6ZFR3, A0A397A1S1, W4FPQ1, A0A3L6VS68, A0A397BWJ0, A0A397A9C7, A0A3R6YID9, A0A3R7BR36, A0A3L6UUI8, A0A3L6V0T7, A0A3R7AMU4, A0A397C9E7, W4G1X8, A0A3R6X795, A0A397E6K8, A0A3L6UW97, A0A397AFG4, W4FCE8, A0A3R6VM88, A0A3L6VTJ7, A0A3L6V0S4, A0A3L6VQP2, W4F8J2, A0A397BNT6, A0A397BQ30, A0A397AP79, A0A3L6V0R4, A0A397BQC2, W4FI44, A0A397B2U7, A0A397CA05, W4FB83, A0A397ESK0, A0A3R6W590, A0A397BBH9, W4GB84, W4FRB0, A0A397ESI1, A0A397AHE1, A0A397CD13, A0A397ALA4, A0A3R7XTQ9, A0A397E2L9, A0A397AY23, A0A397BNE7, A0A397A1D7, W4G074, W4GF49, A0A3R7WNJ7, A0A3L6V0A9, W4FTM9, A0A397C9P7, W4FC56, A0A397D5B2, A0A3L6UVS9, A0A3R8DIH2, W4G054, A0A397AF63, A0A3R7AA07, A0A3L6VW95, W4G9H4, A0A397DQE0, A0A397CE78, A0A397BWP1, A0A3R7AS62, A0A397BZC2, A0A397F5K6, A0A397CQE7, W4FUT9, A0A397BX76, A0A397EWY4, A0A3L6UTC6, W4FCI5, A0A3R7XUT3, A0A397AF69, A0A397FDL6, A0A3R6W9N8, A0A3R7FC57, A0A3L6V861, A0A397F9B1, A0A397DBN1, W4GGA2, A0A397AHP6, A0A397DW29, A0A397A7S0, A0A3L6VJZ3, A0A397ED42, A0A3R6WAM0, W4GH53, A0A397CR86, A0A397BPQ1, W4GZ49, A0A397EYN3, A0A397DRN3, A0A397DXZ3, A0A397A3K7, W4FCU5, A0A397B480, A0A397C1F3, A0A397EXX4, W4H088, A0A418D470, A0A3R7A612, A0A397ES75, W4GXA1, A0A397AYL9, A0A3R6WDP1, A0A397EYB4, A0A418CY42, A0A397G009, A0A418FZC5, A0A3L6V1Y4, A0A3L6UQC2, W4GFA8, A0A3R6XZQ9, A0A3R6Y2R4, A0A024UHK3, A0A024T9L5, A0A3R7CTQ5, A0A024TVG3, A0A024UH93, A0A3R7A1Q5, A0A418AHC0, A0A024TRP2, A0A024TEL4, A0A418AME6, A0A3R6Y3Y5, A0A3R6WGF2, A0A3R6V2T3, A0A024TPQ1, A0A024UDS5, A0A418AM46, A0A024U7C9, A0A3R6V2B0, A0A024UQH4, A0A024TK95, A0A024UD11, A0A024UDS2, A0A418AND4, A0A024UAK4, A0A418ARH0, A0A024UD26, A0A418AHK8, A0A418AMH7, A0A418AJY7, A0A3R6VR99, A0A024TS56, A0A024TUE0, A0A024TWF3, A0A3R6VF93, A0A3R7A275, A0A024UR54, A0A024TWG0, A0A024T8G1, A0A024TWY4, A0A024TCZ9, A0A024UMA7, A0A024UH78, A0A024TCZ7, A0A024TSD7, A0A024TBE3, A0A3R6Z6F7, A0A024TFF2, A0A024UC37, A0A024U0X8, A0A418B1G9, A0A3R6VQU0, A0A418ASS1, A0A024UP64, A0A3R6WNC5, A0A3R7A440, A0A418AQE9, A0A024UQE9, A0A024UBX1, A0A024UNS3, A0A024TDF0, A0A024U4R8, A0A3R6ZIP0, A0A024U8U9, A0A418AI42, A0A024URA0, A0A024T9U4, A0A418B226, A0A3R6VRZ5, A0A3R7CVB0, A0A3R6VPV8, A0A2A3EFQ3, A0A2A3EQR0, A0A2A3EB22, A0A2A3E6U1, A0A2A3EPT1, A0A2A3EC69, V9IEE8, A0A087ZXY2, A0A088AFH9, A0A088AST6, A0A088AC97, A0A088ANX3, A0A087ZV55, A0A088AG76, A0A2I0ASJ4, A0A2H9ZXD3, A0A2I0B3M2, A0A2I0B5S4, A0A2I0B7B3, A0A2H9ZQW2, A0A2I0ADE7, A0A2I0AA30, A0A2I0B169, A0A2I0ABX1, A0A2I0AA27, A0A2I0B4N6, A0A2I0AQ30, A0A2I0AAT8, A0A2I0B7A3, A0A2I0B7B6, A0A2I0BFH8, A0A2I0A8W9, A0A2I0ACE4, A0A2I0A6S9, A0A2I0AA33, A0A2H9ZQW3, A0A2I0B912, A0A2H9ZYQ7, A0A2H9ZXB8, A0A2I0B2V6, A0A2H9ZX95, A0A2I0A9R7, A0A087QH18, A0A087QYC5, A0A087QH19, A0A087RE68, A0A1I3QH19, A0A1I3RZC0, A0A0H1AF09, A0A2G5DNG3, A0A2G5EQ76, A0A2G5EQJ1, A0A2G5DCP1, A0A2G5C542, A0A2G5E5T2, A0A2G5EYF5, A0A2G5CKR8, A0A2G5D4L1, A0A2G5C571, A0A2G5CRQ3, A0A2G5EDS8, A0A2G5E7L7, A0A2G5E6D6, A0A2G5CRL5, A0A2G5C563, A0A2G5D4L6, A0A2G5E7H8, A0A2G5C847, A0A2G5ESB6, A0A2G5D4N4, A0A2G5CZF9, A0A2G5E7K7, A0A2G5DFA2, A0A2G5DIL6, A0A2G5ET28, A0A2G5D4L8, A0A2G5CH03, A0A2G5CZE7, A0A2G5DF97, A0A2G5CZE9, A0A2G5CRT5, A0A2G5EGS4, A0A2G5D562, A0A2G5EYR8, A0A2G5C581, A0A2G5DEI8, A0A2G5EYJ4, A0A2G5EYQ4, A0A2G5EYD9, A0A2G5D4M2, A0A2G5EYH4, A0A2G5EQJ0, A0A2G5D4M8, A0A2G5CRN7, A0A2G5ES32, A0A2G5CRM7, A0A2G5E7Q3, A0A2G5DFX8, A0A2G5CMW1, A0A2G5CRX1, A0A2G5CRI1, A0A2G5DG44, A0A2G5EYI8, A0A2G5EYI1, A0A2G5EYH5, A0A2G5EYG4, A0A2G5CRL0, A0A2G5D4K8, A0A2G5CGV5, A0A2G5DCI3, A0A2G5DCM8, A0A2G5E5V6, A0A2G5EYI0, A0A2G5D8X1, A0A2G5D4K5, A0A2G5CRR1, A0A2G5CRM4, A0A2G5E7J1, A0A2G5D5G9, A0A2G5E7K3, A0A2G5DE67, A0A2G5EYE0, A0A2G5DCF9, A0A1G6XXE2, V5J679, V5J697, V5J681, V5J6E2, A0A3S9XJJ1, A0A451ES05, A0A451ES06, A0A3S5XGT4, V5J6V5, A0A3S5XGT3, A0A451ES07, V5J691, V5J6A0, V5J6E6, V5J6V1, V5J6X1, A0A3S5XGT1, A0A3Q9JP76, A0A3S5XGT0, V5J698, V5J688, V5J689, A0A3Q9JP70, A0A3Q9JP72, V5J682, V5J699, V5J6E4, A0A3Q9JP73, V5J692, V5J6E9, V5J6F1, V5J6W1, V5J690, V5J683, A0A451ES04, A0A3Q9JP74, A0A451ES08, V5J6W5, A0A3S5XGT2, A0A3Q9JP77, A0A451ES3, V5J680, I7EWH2, I7FWN1, D6NU58, I7FWN4, B2Y4N4, B1P3G7, D0EXX6, I4IY52, D0EXW2, B1P3E5, D0EXX4, B1P3K8, D0EXY1, A7XE46, B1P3H0,

A0A0C5JYN3, D0EXW0, D0EXW6, A7XE66, B1P3I4, A7XE70, A0A068CIR0, A7XE48, A0A068CIP9, A0A0C5K603, A0A0C5K8H5, A0A0C5K8B3, D0EXY8, D0EXX7, A0A068CQG1, Q19MC1, B1P3I7, A0A068CM44, A0A0C5KK99, D0EXY2, B1P3G3, A0A0C5KK72, A7XE76, B1P3I5, Q19MC0, B5TD10, B1P3I6, A0A068CM61, D0EXX0, A7XE72, B1P3G6, A0A0C5K5V8, D0EXY3, A7XE85, D0EXW8, A7XE56, B5TD17, B5TD13, B5TD14, A7XE74, A7XE52, A7XE63, A7XE50, D0EXY7, A7XE68, B1P3K0, A0A068CM37, D0EXY0, D0EXW5, B1P3K4, A7XE58, B1P3H3, A7XE83, A0A0C5K8F4, A7XE60, A7XE64, A0A0C5K5X4, D0EXV9, D0EXY6, A0A0C5K8D6, B5TD16, D0EXX1, A7XE81, A7XE79, D0EXW1, A7XE54, B5TD11, B5TD12, I4IY53, B5TD15, B1P3J6, A0A068CQH3, A0A068CM51, I4IY51, B1P3E8, B1P3F7, D0EXW7, B1P3G8, I7FNZ1, I7FXW5, I7EWH7, I7FWN7, I7FNZ6, I7FXW2, I7EWG7, I7F535, D7KVV7, D7KW17, D7KW16, D7KVK3, D7MEU5, D7KMD6, D7KZN2, D7M0B8, D7MEH3, D7KSZ5, D7KVV6, D7LFY7, D7KV44, D7KW05, D7M4K4, D7KSZ4, D7KW07, D7KVI7, D7KMD5, D7KMC8, D7KW12, D7KW14, D7MWF8, D7MJM6, D7KW03, D7KEK1, D7KVJ8, D7LTX6, D7MUF3, D7KW18, D7KYK2, D7L500, D7KMD4, D7KW15, D7MJN8, D7MEU2, D7KW04, D7MWF7, D7LHZ3, D7M9K1, D7KMD7, D7MEU3, D7M1U9, D7M2R0, D7LIA6, D7KMD1, D7KU49, D7MEH4, D7KME3, D7L1X6, D7LTL2, D7KMC5, D7M5Q3, D7MJG2, V5J6F9, V5J6F7, V5J693, V5J6B0, A0A060D3V0, V5J695, V5J6Y3, V5J6X7, V5J6F3, V5J686, V5J6A1, V5J6F5, V5J6A8, V5J6Z0, V5J6Z6, V5J6A3, V5J696, V5J684, V5J6A6, V5J694, D0EXX3, D0EXZ4, G4WHA0, B5TD25, L7UVM3, Q84XJ6, G4WH68, A0A068CIS1, A0A451ERZ8, A0A451ES00, Q9ATK3, Q19MB7, A0A068CL41, Q19MB2, Q9ATK0, Q9ATK4, G4WH69, Q84XI9, Q84XK2, C3VIF0, Q27JI1, A0A068CQL8, Q9ATK2, A0A3Q9JP26, R9S9V2, Q19MB5, B5TD23, A0A068CIT0, A0A068CIT5, Q19MB6, A0A3Q9JP81, Q84XK1, A0A068CLV9, B5TD21, Q9ATJ7, Q19MB4, Q84XK3, G4WH91, Q19MB0, Q84XJ0, D0EXX2, Q9AVE1, G4WH89, Q19MB8, Q84XJ2, Q84XJ5, G4WH79, Q84XJ4, A0A1J0GTD5, Q9ATJ5, B5TD20, G4WH80, A0A451ERZ9, A0A451ES01, G4WH99, C7FE07, A0A068CLU4, A0A3S9XJG2, A0A068CM84, A0A451ES02, A0A068CL61, Q84XJ9, A0A3Q9JP24, Q84XJ1, A0A3Q9JP42, B5TD24, B5TD18, A0A068CQJ3, B5TD19, A0A3S5XGS9, B5TD27, Q19MB3, G4WH92, A0A3S5XGS8, A8IKA8, Q9ATJ4, G4WHA1, Q9ATJ6, Q9ATK1, Q84XI8, B5TD26, Q84XI4, Q9ATJ9, Q84XI7, Q84XJ3, D0EXV6, Q84XI6, G4WH81, Q84XJ7, B5TD22, Q9ATJ8, C7FE06, R9QT99, Q84XJ8, Q84XI5, D0EXV5, Q9AVE0, Q27JF2, Q27JG5, Q9LPZ9, P0DH86, Q9LW83, Q9S972, O64782, Q39086, O81905, Q39203, O81833, Q39202, Q9ZR08, O64477, Q9LZR8, Q9SXB3, Q9SXB4, O64784, Q9LPZ3, O64778, O64776, O64771, Q9ZVA1, Q9ZVA4, Q9ZVA5, O81906, P0DH87, Q9SXB8, Q9SXB5, O64783, O64774, Q9SY95, O64780, O64770, O64781, Q9SY89, Q9SYA0, O64793, O64777, Q9ZT07, P93756, Q9T058, O81832, A0A1P8AN24, A0A1P8B6N6, A0A1P8AM95, Q9SCT7, A0A1P8B6M9, A0A1P8AS04, A0A1P8AVJ2, Q9LHM1, A0A178VV00, A0A1P8B912, A0A178V611, A0A1P8B838, K9LQT0, A0A178WKT1, A0A178W8X6, A0A1P8AM91, A0A178WAM2, A0A178W4F8, A0A178WMJ8, A0A178WCF7, A0A384KCW1, A0A1P8AN12, K9LQP6, A0A178V4X9, A0A178WEA5, A0A178V3N4, A0A178V2J5, A0A1P8B6N5, A0A178WN39, A0A178UWV5, A0A178WFA7, A0A1P8AU51, F4I7F8, A0A1P8AS39, A0A1P8AVQ7, Q9FVW1, A0A1P8B837, A0A1P8B840, A0A384KEE5, A0A1P8AN14, A0A178UYZ8, A0A1I9LPL1, A0A1P8B600, L7USG8, A0A178V6V9, A0A1P8ATF5, A0A178VFP7, A0A178WA58, A0A1P8AWX0, A0A178WDF4, A0A178WC58, A0A178WA81, A0A178WI76, A0A178VYR4, A0A1P8ARZ8, A0A178WAMD4, A0A1P8B859, A0A1I9LPL5, A0A1P8AMY7, A0A178WJN4, A0A178WJI0, A0A1P8ATC6, A0A1P8ARD8, A0A1P8AU37, A0A178WFP0, A0A178V0J5, A0A178VNJ9, A0A1P8ASG9, A0A1P8ASF1, A0A178WB58, A0A178W2U0, A0A1P8AMT2, A0A178W9H1, A0A1P8AM94, Q41272, A0A178WDZ2, F4I8U6, A0A1P8AVL2, A0A1P8AWT8, A0A1P8ASM5, A0A178UVF9, A0A1P8AN35, A0A178USE7, A0A1P8B5P5, A0A1I9LPL2, A0A1P8AMA7, A0A1P8B844, A0A1P8AM92, A0A1P8AQZ9, A0A1P8AMR1, A0A178WDY1, A0A1P8AMR8, A0A1P8AN06, A0A1P8AQN4, A7Y5W8, A0A1P8AMA0, A0A178W877, A0A178WD43, A0A1P8AN03, A0A1P8AMA3, A0A178UCA7, A0A178WK46, A0A1I9LPL3, A0A1P8B6M8, A0A1P8AVI8, A0A178WL67, A0A1I9LPL6, A0A178WAR7, A0A1P8B6N1, A0A1P8AW73, A0A087GL67, A0A087HF14, A0A087G4N3, A0A087HEZ2, A0A087HEY3, A0A087H0M1, A0A087GH82, A0A087GH84, A0A087G682, A0A087H3L7, A0A087H3L8, A0A087GFR5, A0A087GFR4, A0A087H8W0, A0A087HEZ7, A0A087HJG0, A0A087GDA1, A0A087HEZ3, A0A087GH83, A0A087HEZ6, A0A087GX11, A0A087H0M6, A0A087GPZ0, A0A087H0M5, A0A087GSX0, A0A087HCS1, A0A087GDA2, A0A445BB21, A0A444YSR3, A0A444XXG8, A0A444Y4Z7, A0A445C105, A0A444WXX8, A0A445DZ26, A0A445C101, A0A444XXT2, A0A445BY59, A0A445BY66, A0A444XD73, A0A445CY83, A0A445BYC6, A0A445BY70, A0A445BYB8, A0A445DYY7, A0A445ECY2, A0A445BYJ2, A0A445CQB5, A0A445BS77, A0A445CI63, A0A445BYE2, A0A445CU59, A0A445C0Z1, A0A444Y4V5, A0A445AGS4, A0A444Y4X6, A0A445BYN4, A0A445AFB2, A0A445DZ08, A0A445BP40, A0A445BB53, A0A444Y4Z4, A0A445BB59, A0A445BB22, A0A445C0Z7, A0A445ECU2, A0A444Y554, A0A445BY98, A0A444WNK3, A0A445BB41, A0A444Y534, A0A445DYV4, A0A444YP61, A0A445BX15, A0A444XXD3, A0A445BYB1, A0A444Y584, A0A445DZ14, A0A445BYB2, A0A445A4A8, A0A444WXZ0, A0A445BYA3, A0A444WNL4, A0A445A406, A0A445BX05, A0A445ABG7, A0A444WY41, A0A444Y4V2, A0A444YPC9, A0A445DRJ0, A0A445CHB6, A0A444WY06, A0A444Y6V2, A0A444Z5W0, A0A445DZ35, A0A444XXE0, A0A445DZ07, A0A444WXX4, A0A444Y4Y6, A0A445BB20, A0A444WXY1, A0A445BYA9, A0A445BY84, A0A445C0Z5, A0A445BYW2, A0A445ED07, A0A444WY99, A0A445BB37, A0A444Y4W1, A0A444Y4Y7, A0A445DYT5, A0A445BY88, A0A444Y526, A0A444Y2G7, A0A445DRJ8, A0A445DRJ4, A0A444Y562, A0A445DZ00, A0A444Y519, A0A445BP74, A0A444XBK0, A0A444Y3V7, A0A444Y6P6, A0A445BY81, A0A444WXZ1,

A0A445BYT7, A0A445BY74, A0A445BB43, A0A2U1MK14, A0A2U1KKI3, A0A2U1L628,
A0A444WXZ6, A0A445CI88, A0A445BYA0, A0A2U1LK69, A0A2U1LX06, A0A2U1M3I4,
A0A445ECS9, A0A445BB25, A0A444Y532, A0A2U1LEW8, A0A2U1KKC2, A0A2U1MXT3,
A0A445ECJ8, A0A445BYD0, A0A445CI74, A0A2U1PTA5, A0A2U1KHY4, A0A2U1MUK8,
A0A445BB51, A0A444YRD4, A0A444Y514, A0A2U1L5S7, A0A2U1N8E3, A0A2U1KIY8,
A0A444Y537, A0A444XDC3, A0A445A439, A0A2U1NEM6, A0A2U1P0M6, A0A2U1PDI3,
A0A445EIW0, A0A444Y4Y9, A0A444Y6R2, A0A2U1MSU5, A0A2U1LJ61, A0A2U1PQZ4,
A0A444WY60, A0A445A5E9, A0A445BYB4, A0A2U1PD36, A0A2U1LEY7, A0A2U1MJY2,
A0A444Y6M3, A0A444Y4X4, A0A445C0Z4, A0A2U1KDS1, A0A2U1KXK7, A0A2U1KWP0,
A0A445BYX5, A0A445BYX9, A0A445BB31, A0A2U1LG99, A0A2U1NQJ3, A0A2U1P450,
A0A445BY77, A0A445BYA5, A0A445CI77, A0A2U1N3I9, A0A2U1LNH3, A0A2U1PZ37,
A0A445E8F6, A0A445AII5, A0A445BYX2, A0A2U1MK01, A0A2U1P169, A0A2U1L3H4,
A0A445BYE0, A0A445CBB0, A0A444Y566, A0A2U1NUG1, A0A2U1LPS2, A0A2U1PT69,
A0A445DRJ3, A0A444XD58, A0A445DRQ2, A0A2U1LZ92, A0A2U1LEV4, A0A2U1KQB6,
A0A444WY33, A0A445E825, A0A445BS20, A0A2U1MFI2, A0A2U1MWD6, A0A2U1QDH1,
A0A445C104, A0A445BYZ1, A0A445BB33, A0A2U1PD98, A0A2U1KFT4, A0A2U1PG62,
A0A445BB67, A0A444WUD9, A0A445BP39, A0A2U1M3F8, A0A2U1KBU3, A0A2U1MMK0,
A0A445DG52, A0A445A429, A0A445BB24, A0A2U1KFP7, A0A2U1NQJ1, A0A2U1P8A2,
A0A444Y4T8, A0A445BYM5, A0A444Y4Y5, A0A2U1N8W6, A0A2U1MCQ6, A0A2U1QB20,
A0A445BYV9, A0A444WY17, A0A445BY96, A0A2U1MSB3, A0A2U1MKZ0, A0A2U1MY98,
A0A445DRK7, A0A444Y529, A0A445BB45, A0A2U1PDB5, A0A2U1MGQ2, A0A2U1KLB8,
A0A444Y6M2, A0A444Y6J2, A0A444Y6K9, A0A2U1LNA4, A0A2U1PIG5, A0A2U1PG29, G1XPN8,
A0A445BP47, A0A444WY50, A0A445AZM8, G1XSL9, G1XGI6, G1XG00, G1XSA2, D4ARU1,
A0A445BB36, A0A445C8A4, A0A444WY27, E4UUF0, A0A0A9HRX8, A0A0A9TEG4, A0A0A9DPX1,
A0A445A408, A0A444XXR6, A0A444Y4W8, A0A0A8YWY2, A0A0A9F543, A0A0A9E2Y2,
A0A444WY44, A0A444Y6V9, A0A444Y594, A0A0A9E7P7, A0A0A9QLR5, A0A0A9DFU5,
A0A445BYW3, A0A445BB13, A0A445DRJ9, A0A0A8YEX4, A0A0A9NPY6, A0A0A9GL28,
A0A444WXY2, A0A445A416, A0A445BZ11, A0A0A9DM30, A0A0A9S6Y8, A0A0A9DF09,
A0A445A4D2, A0A290GKF7, A0A445BKE9, A0A0A9BMR2, A0A0A9LN34, A0A0A9TYC3,
A0A444Y540, A0A445BB44, A0A445A4A2, A0A0A9QZ24, A0A0A9DW73, A0A0A9H3W6,
A0A445AIK2, A0A445BY95, A0A445CSW5, A0A0M3IPJ6, A0A0M3HP86, A0A0M3IT96,
A0A445A418, A0A445BB46, A0A444XXR8, A0A0M3IBY8, A0A0M3HND4, A0A0M3HU83,
A0A444Y4Q5, A0A445BB60, A0A444Z8T4, A0A0M3HEY4, A0A0M3IH35, A0A0M3ILR8,
A0A445DJU8, A0A445BB42, A0A444Y6I9, A0A0M3IVC1, A0A0M3IRC3, A0A0M3IAG3,
A0A444WY31, A0A445BZ05, A0A445CIM3, A0A0M3IPG4, A0A0M3HG49, A0A0M3IRJ0,
A0A444Y4Y0, A0A445BYI2, A0A444Y542, A0A0M3HQ47, A0A0M3I750, A0A0M3ITR0, F1L0P3,
A0A444Y535, A0A444WXZ9, A0A445E7X5, F1L0G7, F1LC48, F1KWX7, F1KVZ1, F1KRY6, F1L7L8,
A0A445E0F1, A0A445BB48, A0A444Y4W6, A0A2R8B9F5, A0A3N4IAA5, A0A3N4IAW4,
A0A444Y4Y8, A0A445BB50, A0A445AII6, A0A167YNV3, A0A1R3L6N1, A0A1R3L7T1,
A0A445BY65, A0A445E0N0, A0A445BY56, A0A2G7FEN3, A0A2G7G4M6, A0A1F7ZRV8,
A0A445CBC1, A0A444Y553, A0A445A499, A0A1F8A4B8, A0A1F7ZUM9, A0A0U5FUR8,
A0A445DYX4, A0A444XXS1, A0A445E8D0, A0A0U5GHF6, A0A0U5FUB2, A0A0U5CCI5,
A0A444WY11, A0A445BX01, A0A0D6R0F5, A0A2I1DHJ1, A0A2I1D6S1, A0A2I2FIZ7, A0A2I2EZ59,
A0A0D6QTT4, A0A0D6QT12, A0A0D6QTN1, A1CCE8, A1CBV4, A0A1E3BSI6, A0A319DW04,
A0A0D6R4V4, A0A0D6QT17, A0A0D6QRX4, A0A317WGQ7, B8NFC9, B8NFD0, B8NDN6,
A0A0D6QRZ3, A0A0D6QTH7, A0A0D6QR37, A0A2P2HFU4, A0A2P2HLC7, A0A2P2H4K6,
A0A0D6QRW0, A0A0D6QSZ0, A0A0D6QR91, A0A2P2HM09, A0A2P2HFT0, A0A2P2H9K4,
A0A0D6QR45, A0A1Q3HVR3, A0A2P6M7B1, A0A2P2HPX0, A0A3M7JRD9, A0A3M7JTE8,
A0A091BFC1, A0A0B6XVM2, A0A444SIQ6, A0A3M7K264, A0A364MKB4, A0A364M579,
A0A444TRU3, A0A444SZK2, A0A444SL52, A0A0J5Q2X8, A0A0J5PMA7, A0A1L9VP26,
A0A444SR30, A0A444SMM6, A0A2U1MNQ4, A0A1L9VC48, A0A1L9VP33, A0A1L9VNY3,
A0A2U1MVH2, A0A2U1QG88, A0A2U1KI18, A0A1L9VRE9, A0A317WAR2, A0A395HFU3,
A0A2U1QD59, A0A2U1KPH1, A0A2U1KAR9, A0A395GPB8, G7XTE0, A0A319AAV7, A0A319A7A0,
A0A2U1Q3R8, A0A2U1PGN2, A0A2U1MXM3, A0A0S7DE04, A0A0S7E252, A0A0S7EBW1,
A0A2U1Q692, A0A2U1MYT5, A0A2U1QB37, A0A1M3TFU6, A0A1M3T8Q8, A0A1M3TTZ5,
A0A2U1PC96, A0A2U1MCE3, A0A2U1P9R0, A0A146F4B8, A0A3D8T616, A0A3D8S6I6,
A0A2U1LBZ4, A0A2U1PTC0, A0A2U1NVX8, A0A3D8T3A9, A0A3D8QMJ3, A0A318YC13,
A0A2U1MRL9, A0A2U1MF47, A0A2U1MSA6, A0A318Y1N8, A0A318YAK2, G3XMA4, A2QYV6,
A0A2U1MA90, A0A2U1L2N0, A0A2U1K9W3, A2QTC1, A0A370BU00, A0A370BW53, A0A3F3R4A3,
A0A2U1Q5W4, A0A2U1NCZ8, A0A2U1PHB5, A0A117E3X4, A0A0L1J937, A0A2I1C107, A0A2I1BTK7,
A0A2U1P0Y9, A0A2U1MK05, A0A2U1LB20, A0A2I1CJW4, A0A2I1CCR0, A0A2I1BTA2,
A0A2U1LCW0, A0A2U1P3C5, A0A2U1M6L0, A0A2T5M095, A0A2T5LRQ5, A0A0F8UID4, I8U2J0,
A0A2U1QB05, A0A2U1MFU2, A0A2U1MRH5, I8A614, 18U453, Q2U7K1, Q2UP96, Q2U8A9, Q2U2F0,
A0A2U1L7Y8, A0A2U1Q3Y3, A0A2U1KHM7, A0A1S9DBB6, A0A1S9DIX8, A0A1S9DJT8,
A0A2U1L9K1, A0A2U1PVA8, A0A2U1KTL0, A0A0F0IBG5, A0A0F0ICT4, A0A370PJK5,
A0A2U1PT94, A0A2U1MKG2, A0A2U1MIH0, A0A370PHC2, A0A0F8X4Q4, A0A017SC51,
A0A2U1QHC0, A0A2U1QKQ6, A0A2U1PGR0, A0A017SDA8, A0A318ZXC8, A0A318Z9C0,

A0A318Z979, A0A3A2ZMA4, A0A319EXR3, A0A319EAA1, A0A319ECG3, A0A317VSX8, A0A2I2GSR7, A0A2J5HZ31, A0A2J5HG69, A0A2J5IA66, Q0CRW2, A0A397GTA6, A0A1L9NER7, A0A1L9NHC1, A0A397I0S7, A0A3R7FTI7, A0A421CZV9, A0A397FZA9, A0A397H5H6, A0A397I608, A0A0K8LIL4, A0A319CFJ0, A0A319C2C5, A0A319CGR1, A0A319B527, A0A2V5HBT7, A0A1L9R4F3, A0A1L9RJD3, A0A1L9RI70, A0A3P8R5U0, A0A3P8QWI7, A0A3P8NAK1, A0A3P8NAL8, A0A3P8NKJ4, A0A3P8PUS6, A0A3P8NAX7, A0A3R5SPP4, W5LAJ7, A0A3B1IZ91, W5JZP1, W5LF06, A0A3B1JB59, W5LF07, W5KKK6, A0A158NQ95, A0A158NRJ0, A0A158NUD3, A0A158NCF5, A0A158NFW1, A0A158P387, A0A195BUK4, A0A195B440, A0A151I1P9, A0A195BWB4, A0A195BVH1, A0A195B228, A0A195BU26, A0A195BWF1, A0A1X0T3J5, A0A1M6C5Z3, A0A0B1Q6J5, A0A0B1Q3S9, A0A1H0C5Q6, A0A1I2INE0, A0A1I2J8H4, A0A0S2EVY8, A0A0Q6CLW5, A0A0Q6D7V7, A0A0Q6CNY5, A0A0Q6DNE7, A0A0Q6E7R1, A0A175RVT2, A0A175RB81, A0A175RYG2, A0A074VR01, A0A074W6P0, A0A074VFW8, A0A074VY00, A0A074VWR6, A0A074VMM6, A0A074VQQ6, A0A074W863, A0A074VGQ4, A0A074WSI2, A0A074WT58, A0A074W896, A0A074WDM8, A0A074X5F4, A0A074WD87, A0A074WP99, A0A074WYP5, A0A074X7D6, A0A074X9M1, A0A074XKI4, A0A074XMC5, A0A074XW73, A0A074XUY6, A0A074XV26, A0A1A7MGL9, A0A1A7MIQ4, A0A1A7MHG3, A0A1A7MCT8, A0A1A7MLB2, A0A1A7MP46, A0A1A7MAV7, A0A1A7MR78, A0A1A7MEM4, A0A1A7MN21, A0A1A7MAJ0, A0A1A7MFI3, A0A1A7MS81, A0A1A7MDG6, A0A074Z9D4, A0A074XZQ2, A0A074Y4C9, A0A074YXY8, A0A074Y4Q8, A0A074YRD0, A0A074YLW2, A0A074YDL6, A0A074YCF2, A0A074YUS8, A0A074Y8S5, A0A074YQX7, A0A074YG47, A0A074XZ34, A0A074Z895, F0YIS4, A0A2I4AVX2, A0A2I4CU49, A0A2I4CCC7, A0A2I4D285, A0A2I4D8H5, A0A2I4CKP4, A0A2I4AVX1, A0A2I4BJ83, A0A2I4AVX5, A0A2I4CU47, A0A1D2AC95, A0A1D2ADW2, A0A1D2A527, A0A087SNA2, A0A1D2AA88, A0A3M7KY55, A0A3M7L506, A0A087S9Y1, A0A3M7L688, A0A1D2A2T0, A0A1D1ZN49, A0A1D2AGQ5, A0A087SA78, A0A202DKR6, A0A034V924, A0A034V101, A0A034VV04, A0A034VBU4, A0A034VP05, A0A034V269, A0A034VU87, A0A034VB68, A0A034WDU0, A0A034VQT0, A0A034VAC8, A0A034VA94, A0A0K8WFY5, A0A0K8V187, A0A0K8TYA5, A0A0K8U2Z1, A0A0K8W143, A0A0K8W107, A0A0K8WAG5, A0A0K8UYR3, A0A0K8UC22, A0A0K8W0F9, A0A0K8URT7, A0A0K8W7I2, A0A0K8U7H8, A0A0K8VH83, A0A0K8VDD1, A0A383ZG27, A0A383ZV45, A0A383Z1M8, A0A383ZVD0, A0A384AFX7, A0A384AFQ0, A0A087VQ86, A0A087VHF0, A0A2E9UHU0, A0A2P4SWX5, A0A2P4SJS3, A0A2K9V7N6, A0A2K9V7Z4, A0A2K9V7Z1, A0A1R0FC62, A0A1U9MF28, A0A1Y1WQS1, K8EB66, K8FDI0, K8F4B2, K8EQC3, K8EJ82, K8EAB0, K8F6I2, E5ESL6, F4NSE3, F4NSY5, A0A177WA49, A0A177WAP2, A0AIS8VW60, A0AIS8VHV0, M2LEM6, M2MRY7, M2LJL5, M2N072,

A0A1G6CN88, A0A1G6CP43, A0A2E7GCJ6, A0A2E7G7G0, A0A2E8HW08, J5JQG2, J4WGF4, J4KLZ6, A0A0A2VAI1, A0A0A2VQE8, A0A2N6NCG5, A0A2N6P0V4, A0A2N6NH65, A0A2S7Y029, A0A2S7XWT7, A0A167DY06, A0A162JT95, B2IFP4, A0A2A9MK42, A0A2A9MEK6, A0A2A9MHF7, A0A2A9M2B2, A0A2A9MP64, A0A2A9M947, A0A2A9MH57, A0A2A9MHN4, A0A2A9M1K1, A0A2A9MK31, A0A2A9MLG1, A0A2A9M8Y8, A0A2A9MGA0, A0A2A9M957, A0A2A9M7H0, A0A2A9LZF4, A0A2A9MGC4, A0A2A9MDT6, A0A2A9MEJ6, A0A2A9MEY2, A0A2A9MBU9, A0A2A9MDP9, A0A0J8B6J9, A0A0J8B9T3, A0A0J8DZK2, A0A0J8B8G6, A0A0J8B6H3, A0A0J8B5L4, A0A0J8B9Q2, A0A0J8E0I7, A0A2C9M6E5, A0A2C9M2K3, A0A2C9L085, A0A2C9LUG0, A0A2C9KVY0, A0A2C9JZZ3, A0A2C9LGM4, A0A2C9MAU4, A0A2C9KU12, A0A2C9L1D2, A0A2C9M004, A0A2C9LZ70, A0A2C9L2E0, A0A2C9LWZ3, A0A2C9LD29, A0A2C9KJS2, A0A2C9LP23, A0A2C9KNW3, A0A2C9LTI5, A0A2C9M9Z8, A0A2C9KM74, A0A2C9KKC9, A0A2C9JPS7, A0A2C9M6Q8, A0A2C9KBM1, A0A2C9JPW5, A0A2C9LE46, A0A2C9LTU9, A0A2C9JNC8, A0A2C9LNH2, A0A2C9LXF9, A0A182YU34, A0A2C9JRC5, A0A2C9JBX8, A0A2C9LL38, A0A2C9KHG2, A0A2C9M7I1, A0A2C9KDN6, A0A2C9LWA8, A0A2C9K7K3, A0A2C9KKA8, A0A2C9L3Z3, A0A2C9LBA6, A0A2C9KJ30, A0A2C9M3Q1, A0A2C9M449, A0A2C9KT20, A0A2C9KXA4, W6Z007, W6ZCF9, W6Z4B8, W6ZJU0, W6ZED0, W6ZMD3, W6ZA29, W6Z9A5, W6Z1B7, W7DVV8, W7EBL2, W7ER18, W7EF46, W7EPL2, W7ESE4, W7EV06, W7DVB6, W7E897, W6YTV6, W6Y989, W6YAZ9, W6XJ34, W6Y7X4, W6XU68, W6Y6Y8, W6Y442, W6EIN7, W6EMA3, W6EMA1, W6EIL6, W6EK17, W6EMB1, W6EVT2, W6EVS5, W6EVU1, W6EIM1, W6EIS1, W6EMA7, W6EIT3, W6EVS9, W6EK05, W6EMA5, W6EK24, W6EIM6, W6EK09, W6EK13, W6EIP2, W6EIS9, W6EVT6, W6EIS6, W6EIU2, W6EMA9, A0A352FPY6, A0A2D6H9Y1, A0A1J9RE20, A0A2P8XY43, A0A2P8YQ78, A0A2P8YMN5, A0A2P8YR42, A0A2P8YJK3, A0A2P8YZ76, A0A2P8YR97, A0A2P8Z5Y9, A0A2H4UUU3, A0A2H4UU38, A0A0S4J9J2, A0A0S4J936, A0A0S4JQX2, H9IXB3, H9JA26, H9JJP0, H9JJP1, H9JE81, H9JE80, L8IUV1, L8IA26, L8IEV1, L8IY98, L8IC35, P06868, F1MZD6, A0A1L3G6L5, Q6PZ62, Q6Q0I7, Q2KJB4, E1B726, E1BDW7, A0A3Q1LSS6, A0A3Q1LSX3, A0A3Q1LT55, F1MUT4, Q5NTB3, Q2KJ63, Q24K22, Q76BS1, A7E350, A0A370L6R0, R1GKS9, R1G4N0, A0A384J9B7, A0A384JR75, M7UKG0, M7U138, G2YNK3, G2XPN8, A0A3M7RDQ8, A0A3M7T8X2, A0A3M7RNS1, A0A3M7SMW6, A0A3M7RME1, A0A3M7RDY0, A0A3M7P8R6, A0A3M7PKU0, A0A3M7RGA3, A0A3M7PJ96, A0A3M7SM38, A0A3M7SFE0, A0A3M7RAU7, A0A3M7S8F6, A0A3M7RN83, A0A3M7T9E3, A0A3M7SAU8, A0A3M7RQA8, A0A3M7PUQ9, A0A3M7P3V5, A0A3M7P7Y9, A0A3M7QIW1, A0A3M7REF6, A0A3M7SUT2, A0A3M7S822, A0A3M7QVJ8, A0A3M7P6F2, I1HU53, A0A2K2CXA4, A0A2K2CWA4, A0A0Q3GP11, IJ295, A0A2K2CIR5, I1J2C4, A0A2K2CGC5, I1INT0, I1J2S3, A0A0Q3EAI5, I1GMG6, A0A2K2CIQ8, A0A2K2CIR1, A0A0Q3NIJ9, A0A2K2CIS7, I1IA55, A0A2K2CST1, A0A0Q3EAD2,

A0A0Q3JAA8, A0A2K2CGA7, I1J292, A0A2K2CIR0, I1GYM6, A0A0Q3FVF0, I11349, A0A0Q3ED56, A0A2K2CIS4, A0A0Q3QSF6, I1HJD9, A0A0Q3EYJ6, A0A0Q3IF41, A0A2K2D2Y3, I1HHX6, A0A0Q3GIB6, A0A2K2DI89, I1IXN9, A0A2K2D7E6, A0A0Q3GM35, I1INTI, I1IUS5, I1HW64, A0A0Q3R1L3, I1HSB4, I1HSB6, I1GTM1, A0A0Q3HD16, I1IEU4, A0A2K2CZG2, A0A0Q3HM63, I1HU55, A0A2K2DFH8, A0A2K2CGL7, A0A2K2CIU7, A0A0Q3JCV1, A0A0Q3JHU3, A0A2K2CGB5, I1IU59, A0A2K2CIT3, A0A2K2DFD8, A0A2K2DFF0, I1GTK9, A0A0Q3NYQ7, A0A2K2CIR9, A0A0Q3RAK5, I1GL44, I1HAY1, I1IXN8, A0A0Q3HI45, A0A0Q3INA5, A0A2K2CIS0, A0A0Q3RM98, A0A0Q3KXH5, I1IFY2, I1HSA3, A0A0Q3H363, I1GTM2, A0A2K2CIS1, A0A0Q3LFD5, A0A2K2CIT7, I1HW63, A0A0Q3QIL7, A0A0Q3JZ94, A0A0Q3QBI3, A0A2K2DFD4, I1HDE8, A0A0Q3IWS7, A0A2K2CIP9, A0A2K2DFE9, A0A2K2CIT2, A0A0Q3I905, A0A0Q3EAH6, A0A0Q3EAI4, I1GXK1, A0A0Q3IBU0, A0A0Q3GCR1, I1J2A0, I1HEJ3, A0A0Q3HSS0, A0A0Q3NJG4, A0A2K2CIR6, I1HDE9, A0A0Q3EAE1, A0A0Q3HLT2, A0A2K2CIQ9, A0A2K2DFC3, A0A2K2DFC5, A0A0Q3LK38, A0A2K2DI88, A0A2Z4FIU7, A0A257KNM4, F7QHU6, A0A3S0G3E0, A0A363TXD2, A0A3S0H313, A0A431M7G0, A0A431QX01, A0A3S0EKZ0, A0A1I7FU56, A0A1H1Y2P1, A0A1X3FPA0, A0A1X3GN34, A0A1X3GRS6, Q89V82, A0A2A6N5F9, A0A0E4BN53, A0A0D1MCK2, A0A1E3EC36, A0A1M5KHK6, A0A1N6F532, A0A1M7TM76, A0A1M5HCZ9, A0A1H4ZSB0, A0A410VES2, A0A1B1UPJ0, A0A023XWN2, G7DMB7, A0A1L3FRA1, A0A0A3XV48, A0A1Y2J188, A0A0R3LBX3, A0A1M7AMK6, A0A1M6WVP9, A0A0R3M8G1, A0A2H9V6F8, A0A151FH31, K5CWF7, A0A0R3E5M9, A0A176YZA1, M4Z0Y5, M4ZBW7, A0A2U8P6V6, A0A0R3DMJ3, A0A1B9ZC66, A0A0R3MRW5, A0A1C3WWF3, A5EA89, A4YQL0, A4Z2E2, H0SMB8, H0SCU6, H0SBZ7, A0A2U8PT28, A0A2U8PN93, A0A2U8PT94, A0A2U8Q528, A0A2S6M8B5, A0A1Q5R4X0, A0A150UDS9, A0A176Z2D2, A0A109JGJ9, A0A1V5EYR3, A0A2A6NCZ9, A0A410W142, A0A109QD69, A0A1I3S3F5, A0A113J718, U1H1Q2, A0A150ZHL9, A0A0S6UQ35, A0A160UQP7, A0A1I3V8E7, A0A1I5BXB3, A0A2M8RAB9, A0A0Q6A3Y8, A0A1B9Z3Q7, A0A0D7NXE7, A0A0D7N7J5, A0A0D7Q5V0, A0A430MFG0, A0A2T2QQE6, A0A2T2PZ36, A0A2T2PSY2, A0A2T2Q0F5, A0A2T2PT25, A0A2T2PSY6, A0A2T2Q4P1, A0A1Q5SAH3, A0A1Q5R9S2, A0A1I4H0I3, A0A1H8BXF8, A0A1Y6KJQ2, A0A1Y6KP04, A0A2U3PS34, A0A1G7GWB1, A0A1G8B4K1, A0A1I4URV1, A0A3N6PAA8, I0FZQ2, A0A2K8Y6Q4, H0STR9, H0TBX2, H0TGS9, A0A2M6UE20, A0A1R1QEF7, A0A2A2VLQ2, I2QLW7, H5YCF8, A0A2A6PYD0, J2W3F2, J3I044, A0A160UAV3, A0A0R3KWP9, A0A0R3CA11, A0A385GLI2, A0A385GLJ0, C3YDL6, C3Z071, C3YAZ6, C3ZYT2, C3ZFD3, C3ZHY1, C3YYM3, C3ZAW6, C3XQ58, C3XQ51, C3Y7N4, C3YP82, C3ZLM9, C3Z0V1, C3XPW8, C3Y305, C3ZYG9, C3ZMW2, C3ZMB3, C3Y3P1, C3ZGD7, C3Y566, C3Z0R2, C3ZJ84, C3YU46, C3XY24, C3YC74, C3ZFT9, C3ZHS3, C3Y7E8, C3XW29, C3YDL9, C3ZT44, C3XUJ8, C3YP09, C3ZDY0, C3YS46, C3YDM0, C3ZZJ9, C3YCI7, C3YU47, C3YNF1, C3ZHW8, C3ZG87, C3XY53, C3YWE1, C3XW28, C3YMU3, C3ZK10, Q8LP65, Q84KY8, A0A397YWD8, Q84KX9, A0A3P5Z2T0, Q1XIH3, A8QWH1, A0A398A0U2, A0A1L7NT06, O23856, A0A397YDG2, B5U9A7, A0A397YVY9, A0A397YF45, O23848, A0A3P6C3Y6, A0A3P5ZPK2, A0A3P5XWY0, A0A397YV83, A0A397YFB7, A0A3P5Z9J5, A0A3P6CY69, A0A3P6D969, A0A3P5YJ21, A0A397YBC1, Q2MHJ1, A0A3P6CB57, Q948X2, A0A397Z250, A0A397YV95, A0A397XSU5, A8QZG2, B5U9A8, Q948X1, A0A397YA29, A0A397YPP3, Q9AYP7, O23850, O23855, Q6SVA0, A0A3P6A0C0, Q7DN95, A0A3P6ASY7, A0A398A9P6, A0A3P5ZV33, A0A3P6BWB7, A0A3P5YSC4, A0A397ZSN3, Q2EMZ8, Q6SVA3, A0A3P6A3C2, A8QZC5, A0A397XRI1, A0A3P5Z8N8, Q39279, A0A3P5YE62, A0A3P5XWD4, Q84KX7, A0A398AQ76, O23859, Q84KX6, Q39276, A0A3P5YCU6, A0A398AQ52, Q39280, Q18PE5, Q84KZ0, A0A3P6C0F7, O23851, A0A398A6C5, O23745, Q84KY9, A0A3P6CGF5, O23847, A0A398ARS1, A4UWM4, A0A3P6C098, A0A398AF65, A0A397YVY3, O23860, A0A3P5ZGB7, O23849, Q04034, O23861, Q84KY2, A0A397YCG0, Q84KY4, A8QWH4, A0A3P5Z9S3, A0A398AMH2, Q84KY1, A0A3P6A681, A0A397Y539, Q2MHJ2, E2IV49, A0A3P5Z8U6, Q84KY6, A0A1L7NT17, A0A397Y192, A0A397ZWZ8, A0A1L7NT09, O23852, O23854, A0A397KYV2, A0A398AKR7, Q39277, A0A3P5ZXM2, A0A397XTY3, A0A3P5ZIB6, Q84KY3, Q84KY0, Q41222, A0A3P6A1E3, A8QZG7, A0A3P6BVP4, Q8W407, Q84KY7, G3EXH7, A0A397YV80, Q9AYP5, Q948W9, A0A397Y1U1, A0A397XVY9, Q948X0, A0A398A3C5, A0A397ZLT6, A0A3P5ZRW3, A8QZC9, A0A398ASE3, A0A397KY95, A8QZF8, A0A398ATI7, Q9AYP2, A0A3P6ACK6, A0A3P5YRC2, A0A397YRH6, A0A397KZ86, Q8S9B0, B5U9A6, A0A3P6BCU6, Q6SV99, A0A397YN43, A0A397YFK7, A0A397YPJ3, Q6SV98, A0A1L7NT04, E2IV46, A0A397Z248, Q27IZ4, A0A1L7NT22, A0A397YJM2, A0A1L7NT10, A8QZG5, A0A398A3A1, A0A3P6C7S0, A0A397L944, Q84N09, Q1XIH1, A0A397XUJ7, Q1XHT4, O80430, A0A397XT43, A0A397YZX3, A8QWG5, O80344, A0A397ZXN6, A0A397YGY4, A0A3P5ZWE1, A0A397XUI4, A0A397Y2G3, E2IV47, A0A398AKX8, A0A3P6C0A8, O23857, A0A3P6C053, A0A397Z461, A0A397ZIG8, A0A1L7NT25, Q9ZNW9, A0A1L7NT13, A0A397Y4Y8, Q9SXK6, A0A3P5YMA1, A0A398A4W5, O23853, Q9AYP6, A0A397YQ80, A0A3P5ZPZ5, Q84KX8, A0A3P6CIH1, O23858, A0A3P5YA39, A0A3P5ZWS7, A0A397XQX1, A0A397L1V4, A0A3P6DPZ9, A0A398A9U1, A0A397ZGZ8, A0A397YV89, A0A3P5YQL4, A0A3P5Y7E1, Q1XIH2, A0A397YNB1, A0A3P6BQI0, A8QZD1, A0A3P6A4U7, A0A397YA55, Q84KY5, Q9SAZ7, A0A397XZ92, Q1XHT5, O80343, Q39278, A0A3P6B4Q3, A0A3P6C2F5, A0A397YX37, Q6SVA2, O48512, Q948X3, Q9AYP8, A0A3P5YM72, A0A3P5YDK4, A0A3P5ZQK6, A0A1L7NT14, A0A3P5ZUK5, E2IV48, Q9SXK7, Q18PE6, A0A397ZIB8, A0A397Z263, Q2PML8, Q39282, Q84N10, Q9ZNW6, A0A397ZR25, Q04168, A0A3N6S4L1, A0A3N6QXX1, A0A3N6QKJ3, A0A3N6TM80, A0A3N6QYA9, A0A3N6QM77, A0A3N6R7H2, A0A3N6QNP4, A0A3N6PZG5, A0A3N6QQN7, A0A3N6UQ88, A0A3N6RPS9, A0A3N6T5B6, A0A3N6S057, A0A3N6Q5N7, A0A3N6S1R2, A0A3N6U997, A0A3N6T699, A0A3N6SZL5, A0A3N6RNN4, A0A3N6UJ64, A0A3N6QYV1, A0A3N6UHA9, A0A3N6RZC7, A0A3N6S1W1, A0A3N6QNP5, A0A3N6RFD8, A0A3N6SMY5, A0A3N6R0I4,

A0A3N6R511, A0A3N6QTL5, A0A3N6QXV3, Q8LP64, Q9SBK7, Q8LP62, Q01963, Q9M4E9, Q7FPE1, A0A078FY82, A0A078JHP5, Q43393, A0A078IH30, A0A078JPB3, A0A078GD60, A0A078G3D0, A0A078FY93, A0A078JQF9, A0A078HBI2, Q08700, A0A078I0E8, A0A078HA89, Q6SV95, A0A078HDD4, Q6SV97, A0A078HAC3, A0A078HEK1, A0A078IMG1, A0A078HR13, A0A078IFP5, A0A078HVX7, A0A078IAX0, A0A078HN20, A0A078F3B5, Q6SV92, A0A078GIA3, Q6SV96, Q39356, A0A078GM80, A0A078JYB1, A0A078H8O3, A0A078JCU5, A0A078HR81, A0A078J7X9, A0A078IDY2, A0A078GN24, A0A078HD30, A0A078H8L5, A0A078G7I9, A0A078HAD2, A0A078F337, A0A078I9I0, A0A078ILK5, A0A078H3H5, A0A078JMJ4, A0A078HEM0, A4UWL9, A0A078GS40, A0A078JKE7, A0A078FML4, A0A078FHJ4, A0A078FPN5, Q39363, A0A078J557, A0A078II36, A0A078IIQ7, A0A078HDC2, A0A078JFN3, A0A078FRP9, A0A078FIU1, A6P327, A0A078JBM2, A0A078GVV6, A0A078IDX4, Q39354, A0A078FI59, A0A078HT86, A0A078G2V4, A0A078JE37, A0A078FQ97, A0A078I9I3, A0A078FEU1, A0A078FKQ4, A0A078JIW9, A0A078G2W5, A0A078GU68, A0A078J1N7, A0A078G8J1, A0A078JWL9, A0A078J032, A0A078IYH8, A0A078JVW6, A0A078G3S4, A0A078FWL9, A0A078GJI3, A0A078IFM7, A0A078FQ82, A6P326, A0A078G3D4, A0A078FPH2, A0A078HAQ2, A0A078GYC5, A0A078HCX8, A0A078INX3, Q6SV94, A0A078JB85, A0A078HPD1, A0A078FIU7, A0A078GDP5, A0A078JQK2, A0A078EZE7, Q7DMS5, A0A078G200, A0A078IKU0, A0A078H3H1, A6P328, A0A078FC62, A0A078FE33, A4UWL8, A4UWL4, A4UWM3, A4UWL3, Q39357, A4UWL5, A4UWL6, Q04808, Q8LP61, P22552, P22553, P22551, A0A0D3C9A8, A0A0D3BLV5, A0A0D2ZVD2, A0A0D3AAQ0, A0A0D3E522, A0A0D3DXZ3, A0A0D3A6W5, A0A0D3AAP8, A0A0D3CYG2, A0A0D3E1N6, A0A0D3E528, A0A0D3DA71, A0A0D3DP33, A0A0D2ZU01, A0A0D3AAR4, A0A0D3CJQ9, A0A0D2ZVF6, A0A0D3BVD8, A0A0D3DXZ2, A0A0D3BVD9, A0A0D3CM95, A0A0D3CY96, A0A0D3BFE7, A0A0D3E524, A0A0D3C5Q0, A0A0D3BXW1, A0A0D3BCW1, A0A0D3C227, A0A0D3E3G0, A0A0D3C9A3, A0A0D3DGD4, A0A0D3C9A0, A0A0D3DDG1, A0A0D3BW89, A0A0D3DE12, A0A0D3E3F9, A0A0D3AD84, A0A0D3CY99, A0A0D3DC95, A0A0D3AAR5, A0A0D3DMB4, A0A0D3AAP9, A0A0D3BYM9, A0A0D3EAU1, A0A0D3CY95, A0A0D3D1P0, A0A0D3C9A9, A0A0D2ZVS8, A0A0D3DVG2, A0A0D3BT69, A0A0D3A4U3, A0A0D3DXV5, A0A0D3B6D1, A0A0D2ZWS7, A0A0D3C538, A0A0D3C9C2, A0A0D3DXZ4, A0A0D3BVD6, A0A0D3C9A2, A0A0D3C5D3, A0A0D3DZL7, A0A0D3A4U2, A0A0D3ASG5, A0A0D3ASA4, A0A0D3DP20, A0A0D3D3Q8, A0A0D3CVY3, A0A0D3BAW1, A0A0D3AYW3, A0A0D3E523, A0A0D3BVG5, A0A0D3A6W4, A0A0D3DP40, A0A0D3E5Z4, A0A0D3EI38, A0A0D3DDG2, A0A0D3CEW1, A0A0D3B529, A0A0D3C9B0, A0A0D3C999, A0A0D3DP24, A0A0D3A2M9, A8VP90, Q09092, P17840, P17841, P07761, Q9SXH4, Q93VX9, O23743, Q93VR1, Q93VY7, Q93V96, A0A3P6DR72, O04383, Q9MB87, O23832, Q84KU6, Q8S9B2, A0A3P6EAU3, Q84KV5, Q1ET35, A0A3P6AZG2, A0A3P6DSC9, Q9SXH9, Q84KV2, Q39392, Q84KV1, Q93YJ8, A0A3P6E9L0, Q84KX3, A0A3P6CXY8, A0A3P6DPD4, A0A3P6BST4, A0A3P6CG45, A0A3P6CJK8, Q9ZQU7, B5U9A4, Q9T0M1, A0A3P6G216, Q84KW1, Q84KW3, A0A3P6DQ69, A0A3P6DM94, Q93YK2, A0A3P6H645, A0A3P6DJE8, O23835, A0A3P6EPZ7, O23744, Q9ZQU6, A0A3P6GT52, Q7DLP6, Q84KX5, Q93YJ7, Q84KW2, A0A3P6GDI9, Q39390, A0A3P6CMU3, O23844, A0A3P6FD20, A0A3P6EHB3, A0A3P6DJA8, A0A3P6EN76, A0A3P6G8V9, A0A3P6AM61, Q84KX2, Q93YK0, O23836, O23838, Q84KV7, Q84KW7, A0A3P6DCU3, A0A3P6GW39, A0A3P6FM07, A0A3P6CYJ8, A8QZJ0, O23837, Q84KW0, A0A3P6ECQ4, A0A3P6CA48, Q1ET30, A0A3P6BMB0, Q9MB88, Q84KX4, O23842, O04384, Q9SXH6, Q93VN5, O23841, A0A3P6FB97, A8QZI2, A0A3P6GBD6, A0A3P6G6E7, Q8W408, A0A3P6BHJ6, A0A3P6F1R2, A0A3P6FS98, A0A3P6DWV5, Q1XIG9, O23740, Q9SXH7, O23839, Q84KW4, Q9SXH5, T1Q059, A8QZI1, Q39393, Q84KV0, Q84KV3, O23840, A0A3P6F1Q3, A0A3P6GBB9, Q84KU5, O23863, A0A3P6EDW2, Q84KV4, O23895, Q84KU7, Q43410, A0A3P6GFP0, Q84KV9, A0A3P6CQM2, A0A3P6FF23, A0A3P6EV23, Q1ET32, A0A3P6DR77, A0A3P6AP88, Q84KU9, A0A3P6F267, P93068, A0A3P6F441, Q9SAN1, Q9SXH8, Q9T0M0, Q84KW5, Q84KW8, Q39389, Q84KU8, Q84KV6, O23834, Q8W409, O23833, Q39391, A0A3P6C6P4, A0A3P6E4S9, O23843, A0A3P6FEZ1, Q84KW6, A0A3P6G9V7, O23846, Q03349, T1Q7V5, Q84KW9, A0A3P6GQQ4, A0A3P6EI65, Q93YK1, A0A3P6EAA2, Q43411, A8QZH0, Q84KV8, A0A3P6CK21, O23862, Q9XFW5, Q1ET31, Q41177, A0A3P6FAU8, A0A3P6FN43, A0A3P6FGK6, A8QZH1, O23845, Q84KX1, Q93YJ9, Q84KX0, Q84KU4, A0A3P6B1L3, A0A3P6BNH0, A0A3P6GIA4, Q8LP60, M4DRB6, M4F1X0, M4CIZ8, M4DTL2, M4FBV1, M4EZL4, M4CBQ0, M4D8N1, M4ESL3, M4EE76, M4D938, M4CHF2, M4ERK3, M4F4F3, M4DTM0, M4EE77, M4ECM7, M4DE63, M4FBV0, M4ERK7, M4DK16, M4DTL3, M4F8C2, M4DTM3, M4DK08, M4DTL1, M4D939, M4CIU6, M4EC54, M4ESI7, M4FHG6, M4DAL3, M4DTL9, M4CIZ5, M4DKI6, M4ERK8, M4FC19, M4C7T3, M4D4D3, M4CU98, M4EE78, M4E2N1, M4DTM1, M4DK77, M4DTK0, M4FBW3, M4D3D6, M4DK14, M4CZ69, M4CCH3, M4EEI3, M4FCE8, M4ESI6, M4EXD7, M4CIU7, M4EC53, M4CFP8, M4EAX3, M4EDR6, M4CB53, M4EE74, M4FIP3, M4FHL1, M4DK11, M4CIU5, M4ESI5, M4EE73, M4DTM4, M4DAL2, M4EUB0, Q8LP66, Q8LP59, Q8LP58, A0A2T5VC63, A0A346R2I9, A0A346R164, A0A3P1UMN2, A0A0H5SIF6, A0A0H5S642, A0A0K0J6N5, A0A0J9XW65, A0A0K0J6N4, A0A0H5S3W5, A0A0K0JDL5, A0A0H5S9G2, A0A0H5S1D5, A0A0H5SAY8, A0A0H5SR05, A0A1I9G1H5, A0A158PX07, A0A158PZU7, A0A158PY61, A0A0J9Y7A3, A0A119G322, A0A158PYI4, A0A119G2Y4, A0A0K0JDU5, AA0I9R304, A0A0K0J681, A0A0K0J644, A0A158PX08, A0A0K0JDU6, A0A1I9GCN9, A0A158PY62, A0A0K0JU89, A0A0K0IMD7, A0A0J9XZT0, A0A0J9Y9P8, A0A0K0IQ14, A0A0K0ISE1, A0A0K0JJL0, A0A0J9Y0R4, A0A0J9YCN5, A0A0N4TNB0, A0A158PRG8, A0A0N4TMV2, A0A0N4TSS0, A0A158PSR5, A0A158PQG8, A0A0N4SZC0, A0A0N4T3W4, A0A0N4TFB9, A0A0N4TYT6, A0A0N4T2A3, A0A0N4TLH9, A0A0N4SYT2, A0A0N4TPM2,

A0A0N4TR02, A0A0N4SWY6, A0A0N4TNG8, A0A0N4TVC8, A0A0N4SZ35, A0A3P7TPN6, A0A158PT29, A0A0R3Q302, A0A3P7SG12, A0A0R3QBN5, A0A0R3QQ91, A0A0R3QX15, A0A0R3R813, A0A0R3QCX7, A0A0R3R1C6, A0A0R3R9R2, A0A0R3R309, A0A0R3QNJ6, A0A0R3QRA9, A0A0R3Q4B1, A0A3P7T0Q5, A0A091GKM8, A0A091I300, A0A091HAC8, A0A091HG60, A0A1I7S3Z5, A0A1I7RNK5, A0A1I7RQH8, A0A1I7SVU8, A0A1I7RV17, A0A1I7S9K1, A0A1I7SLP2, A0A1I7RIJ0, A0A1I7SAF2, A0A1I7RLM5, A0A1I7SQH5, A0A1I7S7L5, A0A1I7SX51, A0A1I7RIX3, A0A1I7S4P8, A0A1I7SLS0, A0A1I7SB83, A0A1I7SDI4, A0A1I7SER8, A0A1I7SST9, A0A1I7RHA2, A0A1I7RN79, A0A1I7RHH1, A0A2V1BVR2, A0A2V1BNQ3, A0A2V1B6F2, A0A2V1BD27, A0A2V1BP60, A0A2V1C858, A0A2V1BJ06, A0A2V1B5B9, A0A2V1BWQ8, A0A2V1CUT5, A0A2V1CF77, A0A2V1BSL5, B6VC06, G0NPZ3, G0MVC6, G0N8P6, G0M8F1, G0PGC1, G0M6R7, G0NE96, G0NN92, G0N7Q3, G0MCH5, G0MRH4, G0MHL2, G0PDT9, G0MVD5, G0M8F2, G0NLF9, G0P5N7, G0NU28, G0NII5, G0PEQ2, G0NE92, G0MHP5, G0NGT2, G0P5E1, B0K0A0, A8XM04, A8XU34, A8X9M4, E3CU51, A8WN02, A8XZL8, A8WT52, A8Y2W2, A8X5P5, A8XZR6, A8WPA1, A8XDB5, A8XK91, A8Y0T3, A8X0Q4, A8XQU5, A8WVZ7, A8WRC5, A8X0Q5, A8WXE5, A8Y4J3, Q27394, Q10125, Q09271, Q10952, Q17800, H9G2Z5, H2KZ73, B6EU70, A0A2C9C2X5, A0A2C9C344, Q7YX17, Q22631, C1P662, D0VWP5, Q21782, Q22214, A0A2C9C2R3, O61834, Q9XUE5, Q22815, Q94248, O17347, Q23327, O62201, H8W3Y1, Q18298, G5EBR9, G5ECB3, G5EDB1, Q20167, Q23328, Q22902, O45277, G5ECB4, Q8T3B7, K7GW62, K7HND9, K7GW65, A0A2H2ICP9, A0A2H2I0G9, K7GW61, K7GW66, K7H567, A0A2H2HYS4, K7H566, K7H1H4, A0A2H2I0E1, A0A2H2J0L9, K7GW60, H2WB38, A0A2H2IE65, A0A2H2IWD6, A0A2H2IAG5, A0A2H2IAK0, A0A2H2I6U0, A0A2H2HUZ7, K7GTV4, K7HVV9, A0A2H2I7Z8, K7H652, K7H407, A0A2H2JF03, A0A2H2HU97, A0A2H2IJJ4, K7H1H3, K7H408, K7H6J2, K7HAQ8, A0A2H2I481, K7GTV5, K7H6I4, K7HAQ7, K7HND8, A0A2H2I4H8, K7H6J3, K7HVW0, K7H6I3, A0A261ACA4, A0A261AH64, A0A261CPY0, A0A261CSP6, A0A261AU21, A0A261CNX8, A0A261CR66, A0A261BZ73, A0A261CE90, A0A260ZQN6, A0A261CNC8, A0A261CA21, A0A261CK25, A0A261CGY1, A0A261CP70, A0A261CFW0, A0A261BUT5, A0A261B5J5, A0A261ANV5, A0A260ZQ86, A0A261APP7, A0A261BID9, A0A260ZF97, A0A260ZPE3, A0A2G5T5T2, A0A2G5SYL6, A0A2G5U9C7, A0A2G5U9K5, A0A2G5ULQ0, A0A2G5SZG6, A0A2G5SPU6, A0A2G5UM21, A0A2G5U9C6, A0A2G5V3A7, A0A2G5U4H9, A0A2G5U0G8, A0A2G5T662, A0A2G5SPS0, A0A2G5SIZ1, A0A2G5V2K3, A0A2G5SQ73, A0A2G5U9E1, A0A2G5TVG4, A0A2G5U4R2, A0A2G5VRD3, A0A2G5U9B1, A0A2G5UKX7, A0A2G5TNF2, A0A2G5TY68, A0A2G5UG40, A0A2G5U9E5, A0A2G5U784, A0A2G5V2K1, A0A2G5UH11, A0A2G5SPN6, A0A2G5STL2, A0A2G5UV42, A0A2G5SYP7, A0A2G5THD7, A0A2G5TVG8, A0A2G5SPC7, A0A2G5TNG8, A0A2G5VF01, A0A2G5U9U1, A0A2G5U799, A0A2G5STT6, A0A2G5U4J0, A0A2G5VR02, A0A2G5VEG5, A0A2G5UKS0, A0A2G5STB6, A0A2G5SNI9, A0A2G5U534, A0A2G5U9C2, A0A2G5TI38, A0A2G5U9A0, A0A2G5TNA2, A0A2G5U4J4, A0A2G5TYA1, A0A2G5U787, E3N801, A0A2P4WK92, A0A2P4W3J2, E3M888, E3NWP9, E3M6Q4, E3M5X6, A0A2P4W7N0, A0A261BAQ3, A0A2P4WCC6, A0A261AJI9, A0A260ZJI1, A0A2P4V2Y6, E3M244, A0A2P4WFX4, A0A261AK10, E3NPV1, E3NQB6, E3M5X4, A0A261ATB5, A0A261AI47, A0A2P4VKF5, A0A260Z8D5, A0A261ALS6, A0A2P4WL44, E3M2F3, A0A261B0J8, E3LE81, E3MSS4, A0A2P4V2Z2, A0A2P4W7H8, A0A261BE63, A0A2P4VDA9, A0A2P4VDA1, A0A261AIL2, A0A2P4WLP1, A0A2P4W0U2, A0A2P4VIC1, E3N395, A0A2P4WBE7, E3MUD1, A0A261BE25, E3MQF4, A0A261A2K8, E3LY63, A0A2P4V2Y4, A0A2P4W7D8, E3NF96, E3MSS5, E3NAC3, A0A2P4WMV8, E3NS03, A0A2P4WTN2, A0A260ZUR0, A0A261B7H7, A0A261ASY1, E3LFD4, A0A261BCB7, E3LE82, E3MA09, A0A2P4VZW1, E3MK54, E3NE41, A0A261A2U8, A0A261AY11, E3ND68, A0A261A7H9, A0A2P4WIH5, A0A261AUN6, A0A260Z4Y7, A0A261ADY1, E3M221, E3LFC5, E3LZN5, A0A1I7TRC8, A0A1I7UFP5, A0A1I7TBP9, A0A1I7TB17, A0A1I7U139, A0A1I7UEG5, A0A1I7U2M5, A0A1I7U140, A0A1I7U2M6, A0A1I7T3H6, A0A1I7UDC8, A0A1I7V193, A0A1I7T400, A0A1I7U9T6, A0A1I7UTC6, A0A1I7TB16, A0A1I7V489, A0A1I7U190, A0A1I7TL14, A0A1I7U7E4, A0A1I7ULB1, A0A1I7U7E3, A0A1I7V194, A0A1I7T081, A0A1I7T3Z9, A0A1I7U7E6, A0A1I7U9T5, A0A1I7UTC7, A0A1I7UEG4, A0A1I7TBP8, A0A151SMC5, A0A151SPY9, A0A151UBP4, A0A151SVK7, A0A151S8Z9, A0A151UG46, A0A151TPQ2, A0A151S200, A0A151TU08, A0A151RB11, A0A151RFX6, A0A151TV23, A0A151SVI8, A0A151QZL4, A0A151R1S2, A0A151RF37, A0A151RBF8, A0A151R092, A0A151SY98, A0A151T3Q5, A0A151RFX8, A0A151S5X0, A0A151RKY9, A0A151SMF7, A0A151SVJ6, A0A151S231, A0A151SMD4, A0A151S219, A0A151S5A6, A0A151RBK0, A0A151RQ08, A0A151S2F9, A0A151QYZ7, A0A151RPY9, A0A151TBW7, A0A151SJN1, A0A151UDQ9, A0A151RDZ2, A0A151SH91, A0A151S126, A0A151RPW2, A0A151SMF2, A0A151S5R9, A0A151RKS3, A0A151T1R0, A0A151R0Z5, A0A151RPX4, A0A151RGD5, A0A151RFV9, A0A151RP79, A0A151RFY6, A0A151SJP5, A0A151RPZ1, A0A151S982, A0A151RXG6, A0A151RNK8, A0A151SM99, A0A151QZP1, A0A151RP46, A0A151RQ07, A0A151RGA5, A0A151UH94, A0A151T1Q6, A0A151SVE9, A0A151RPX7, A0A151S658, A0A151RL70, A0A151RE53, A0A151RL12, A0A151RQF6, A0A151TTP7, A0A151RBC2, A0A151RKT0, A0A151SWX4, A0A226MM08, A0A226MNE8, A0A226MN47, F6WH76, F6S5L7, F7EDL5, F6ZZG6, F7I8A8, F6VX63, F7AA32, F6X343, F7GKJ7, V9K997, V9KGH2, V9KIE5, A0A3Q7P3N0, A0A3Q7QI46, A0A3Q7NAT6, A0A3Q7RMW6, A0A3Q7Q6J8, A0A3Q7NFH9, A0A3Q7Q880, A0A3Q7QI91, A0A3Q7PEL9, A0A091HYP2, A0A091HU29, A0A1C9EFM3, T0MC86, S9YNR1, E2AYS0, E2AW54, E2AIC2, E1ZYY0, E2A6H3, E2AEN9, A0A2G6E0Y9, A0A0G0Y802, A0A0T5ZUG2, A0AIF5VTJ5, A0A1F6GNK9, A0A1F6IW58, A0A1F6IW51, A0A2E6AVH4, A0A2E1QA46,

A0A2E8VEV6, A0A081BMC8, A0A3E1D9A6, A0A0H0KSE9, A0A0J9E870, A0A2K8U7S7, A0A0S6WC51, Q867B7, F1PNV5, F1Q421, J9P7N9, U6C2S1, B5LX43, F1PPK8, E2QX19, X1ZK48, X2A7L8, R7T8C6, R7V393, R7U1A9, R7TZY2, R7V723, R7UC69, R7V5X1, R7TYC5, R7UCC3, R7TUV0, R7U099, R7UD86, R7VAV0, R7U4R0, R7V1P5, R7U5C7, R7VIS4, R7UZN9, R7UPR5, R7TN37, R7TTF7, N1PB13, R7T7C0, R7TW97, R7U2J7, R7V1H6, R7TQC9, R7VEV6, R7UHQ9, R7TNK1, R7U9W1, R7UFI6, R7TTM3, R7TL37, R7VDK3, N1PB94, R7UZW7, R7UR22, R7TMW2, R7TC17, R7U7K0, R7T380, R7TB71, R7TTG1, R7TV63, R7TDJ4, R7UDB7, R7TUJ8, R7TA27, R7T436, R7USY4, R7TG23, R7THU4, R7V2I5, R7TW72, R7U6P1, R7V1M6, R7U4L4, R7UEY2, R7TFT8, R7VJV9, R7TX09, R7UIB6, R7U426, R7VEG9, R7TMY6, R7ULX6, R7U7Q9, R7UCW6, R7UUK4, R7U544, R7UUF8, R7TA51, R7UFR7, R7T4S3, R7VFQ5, R7UDP1, R7UH53, R7TBV9, R7VFH4, R7V8L1, R7UGV2, R7VGL6, R7TAP8, R7TYU2, R7V4I7, R7TIG7, R7V0P1, R7T7U1, R7V6R4, R7U6D2, R7V5V9, R7TI76, R7VF14, R7UVT0, R7VG70, A0A452E0U1, A0A452E5W4, A0A452EN11, A0A452E0T2, A0A452E0U8, A0A452FN28, A0A452E7A0, A0A452E0H7, W9YD76, W9YRK9, Q15B70, Q15B72, Q15B73, B9VWJ3, C3USC5, C3USB9, C3USC3, B9VWJ2, A0A330PLR6, A0A330PLQ4, Q159E8, D6PR15, C3US88, Q159E6, D6PR17, Q159E2, B9VWJ4, D6PR14, C3US92, D6PR16, Q159E1, Q15B71, C3US83, A0A330PI91, D6PR65, C3USB8, A5A5D8, A0A330PL92, Q15B68, C3USC0, C3US90, C3USC9, C3USD0, C3US91, C3USC1, A0A330PL82, Q159E5, D6PR13, C3USC8, Q15B69, Q159E7, B9VWJ5, A0A330PKY6, C3USC6, Q159E4, C3USC4, C3US86, C3USC2, C3US84, Q159E3, C3US87, C3US82, D6PR63, D6PR62, C3US81, C3USC7, R0I6W8, R0GTT4, R0H9B0, R0GNE2, R0FI89, R0HTN8, R0GUQ7, R0HUY1, R0H0H3, R0I9M8, G4WHB0, R0IR13, R0GLW7, R0GG20, R0HTH2, R0HWX1, R0HH21, R0F138, R0G349, R0G9X, R0H4Q7, G4WHA9, R0H3X2, R0IQY0, R0HDW3, R0GEJ4, R0I6F3, Q159E9, R0HEM0, R0GB39, R0EV33, R0IB39, R0GFC4, R0GDL4, R0H6A7, R0G917, R0GC32, R0FRL5, R0GGH9, R0GPB0, R0IKR4, R0I6F0, G3LPX2, C3US76, C3US93, G3LPQ9, Q159F0, A0A2G2Z3C2, A0A1U8HJK3, A0A1U8FLD1, A0A1U8G176, A0A1U8FMT3, A0A1U8G0B3, A0A2G2YXS1, A0A2G2Z497, A0A2G2ZR65, A0A2G3A8T5, A0A1U8E006, A0A1U8GC95, A0A1U8FKZ6, A0A1U8EHH7, A0A1U8FWF1, A0A2G2YVW6, A0A1U8HID5, A0A1U8HB94, A0A2G2XXB9, A0A1U8FUE7, A0A1U8FH35, A0A2G2YHC9, A0A2G3A4Y4, A0A1U8DSV0, A0A2G2ZR66, A0A2G3ACA4, A0A1U8GJN2, A0A2G2Z443, A0A1U8GC84, A0A2G2Z3R4, A0A1U8G424, A0A2G3A4P0, A0A2G2XZF1, A0A1U8HJC3, A0A2G2Z3M0, A0A1U8E541, A0A2G2Y426, A0A2G2XXC9, A0A2G2Z5E8, A0A2G2YRI6, A0A1U8FFY8, A0A2G3A8R0, A0A2G3A8S2, A0A2G2Z7W9, A0A1U8F3X5, A0A1U8FMU1, A0A2G2Z4E1, A0A2G2ZGY9, A0A1U8EBB4, A0A1U8GJN8, A0A1U8F5I0, A0A2G2ZR70, A0A1U8FLJ4, A0A2G2Z477, A0A1U8FUF3, A0A1U8H8D5, A0A2G2ZGX9, A0A1U8HCZ6, A0A1U8FGU3, A0A2G2G3AHC7, A0A2G2ZRA6, A0A2G2YBW0, A0A1U8HJK7, A0A2G2ZR53, A0A2G2ZR72, A0A1U8HHR9, A0A1U8EQX3, A0A1U8G097, A0A2G2ZGX6, A0A1U8HFC1, A0A2G2Z069, A0A1U8HJC5, A0A1U8HF58, A0A1U8FWF6, A0A2G2Z4E6, A0A1U8HBY4, A0A1U8GC91, A0A1U8FKF0, A0A2G2ZR54, A0A1U8GLG7, A0A1U8FI52, A0A2G2XZG6, A0A2G2Z588, A0A2G2Z4F9, A0A1U8FMT6, A0A1U8E509, A0A1U8GKK0, A0A1U8GL39, A0A1U8H760, A0A2G3A8W8, A0A2G2Z4D1, A0A1U8HC90, A0A1U8HFP2, A0A2G2Z5A7, A0A2G2XTN5, A0A1U8FCB4, A0A2G2XJB3, A0A1U8HJL6, A0A2G3A3F6, A0A1U8FU12, A0A2G2ZNM4, A0A2G3A8Y5, A0A1U8FUG6, A0A1U8FLF2, A0A2G2YUR9, A0A1U8F5U4, A0A2G2Y412, A0A2G2Y4I0, A0A1U8HHS4, A0A1U8FMU9, A0A1U8FUE2, A0A1U8HD42, A0A1U8FL04, A0A2G2ZR57, A0A2G2ZR87, A0A2G3ZRA9, A0A1U8HD34, A0A2G2Z3A1, A0A2G2Z488, A0A1U8HHK2, A0A2G2YUF5, A0A1U8HD39, A0A2G2ZZ34, A0A1U8GC89, A0A2G3A8R4, A0A1U8H0K4, A0A1U8GCX8, A0A2G2YQD6, A0A1U8FMF8, A0A2G2Z3H8, A0A1U8FQA6, A0A1U8EA38, A0A2G2Z5Q1, A0A1U8HD36, A0A2G2ZR51, A0A2G3A8R3, A0A1U8FLD6, A0A1U8FUF9, A0A2G3A8R3, A0A2G3A8S0, A0A2G2ZR86, A0A1U8FLE0, A0A2G3A8S0, A0A1U8GCY4, A0A2G2ZR97, A0A2G3A8U5, A0A2G2Z5B6, A0A2G2XZG5, A0A2G3A8V8, A0A1U8FGL4, A0A1U8HJB8, A0A2G2ZZZ3, A0A2G3A8A0, A0A2G2YVF7, A0A2G2ZR77, A0A2G2Z5J5, A0A2G2ZR62, A0A2G2Z449, A0A2G2Z595, A0A1U8GJM6, A0A2G2Z4K3, A0A1U8FLD5, A0A1U8FFC8, A0A1U8FEC5, A0A1U8GMK6, A0A2G3AFV5, A0A2G2Z5L0, A0A2G2Z584, A0A2G2ZY67, A0A1U8G841, A0A2G2Z100, A0A2G3A8V4, A0A2G2YUT1, A0A1U8GGN2, A0A2G3A8X5, A0A1U8GK83, A0A1U8E139, A0A1U8HLA8, A0A1U8EB93, A0A2G2Z3E9, A0A2G2WEE9, A0A2G2WVY4, A0A2G2WW96, A0A2G2VY63, A0A2G2VQY9, A0A2G2VAD8, A0A2G2WPR1, A0A2G2WDF9, A0A2G2WEK5, A0A2G2VR35, A0A2G2VQY2, A0A2G2WEJ2, A0A2G2WG78, A0A2G2WZR9, A0A2G2X0B4, A0A2G2WGJ3, A0A2G2VBZ9, A0A2G2XNZ0, A0A2G2VX13, A0A2G2WZV8, A0A2G2WG79, A0A2G2XMD7, A0A2G2VAJ1, A0A2G2XEE7, A0A2G2WEJ3, A0A2G2WDD7, A0A2G2X0L9, A0A2G2VAF3, A0A2G2WEF4, A0A2G2WG85, A0A2G2VBR2, A0A2G2WZY5, A0A2G2XMN2, A0A2G2WG76, A0A2G2VAE7, A0A2G2XBY4, A0A2G2WRP5, A0A2G2VAE4, A0A2G2WEK2, A0A2G2XEX2, A0A2G2WZR1, A0A2G2X0F7, A0A2G2WED8, A0A2G2X1N6, A0A2G2VAK1, A0A2G2WPT7, A0A2G2XMC0, A0A2G2WG69, A0A2G2WG90, A0A2G2WG92, A0A2G2VRB8, A0A2G2WED9, A0A2G2WX08, A0A2G2XCD8, A0A2G2XLJ2, A0A2G2XMA3, A0A2G2XHT8, A0A2G2X346, A0A2G2X0C9, A0A2G2VAE9, A0A2G2WGA3, A0A2G2VAD6, A0A2G2WEI6, A0A2G2VAD0, A0A2G2W6E0, A0A2G2WD99, A0A2G2WEF8, A0A2G2WZR7, A0A2G2VAL5, A0A2G2X3S1, A0A2G2VCQ1, A0A2G2WDF4, A0A2G2VAC5, A0A2G2VKF1, A0A2G2VRK8, A0A2G2WG68, A0A2G2WW24, A0A2G2WG68, A0A2G2VAF6, A0A2G2UYX7, A0A2G2WVX3, A0A2G2X5R0, A0A2G2VPU4, A0A2G2WDS9, A0A2G2WDD3, A0A2G2XFD6, A0A2G2VAF2, A0A2G2X0H2, A0A2G2WGA2, A0A2G3D6E9, A0A2G3C1F1, A0A2G3C1E0,

A0A2G3C1G5, A0A2G3C2Z3, A0A2G3CPI0, A0A2G3DCY1, A0A2G3C316, A0A2G3D2F1, A0A2G3C2Z9, A0A2G3C1E1, A0A2G3D6B8, A0A2G3CPH7, A0A2G3BYB2, A0A2G3CJH8, A0A2G3C300, A0A2G3D9N7, A0A2G3CKE6, A0A2G3C305, A0A2G3C0I4, A0A2G3BJQ2, A0A2G3D6E1, A0A2G3C1I7, A0A2G3C0J7, A0A2G3D6F2, A0A2G3C0I0, A0A2G3C307, A0A2G3CK88, A0A2G3D6G2, A0A2G3D6D1, A0A2G3C0J0, A0A2G3C304, A0A2G3B5S2, A0A2G3CF44, A0A2G3CKB8, A0A2G3C314, A0A2G3CPI6, A0A2G3CPF9, A0A2G3D2F8, A0A2G3BYR9, A0A2G3BIS4, A0A2G3CPH6, A0A2G3BNQ8, A0A2G3D5W0, A0A2G3DEU0, A0A2G3D034, A0A2G3C0M5, A0A2G3D6E2, A0A2G3CPH2, A0A2G3C1F2, A0A2G3D4Y8, A0A2G3CUB9, A0A2G3BNC4, A0A2G3D6F6, A0A2G3C2X9, A0A2G3BKG5, A0A2G3D6D5, A0A2G3C180, A0A2G3C355, A0A2G3D6D6, A0A2G3C0G2, A0A2G3CPJ8, A0A2G3CPG3, A0A2G3C353, A0A2G3CPG9, A0A2G3AYH3, A0A2G3DCW4, A0A2G3C265, A0A2G3CZ75, A0A2G3C313, A0A2G3CPH9, A0A2G3BAY7, A0A2G3D2T3, A0A2G3BSY6, A0A2G3ATR3, A0A2G3CPI5, A0A2G3BXI5, A0A2G3D6G1, A0A2G3CL76, A0A2G3DD18, A0A2G3D5A9, A0A2G3D6C0, A0A2G3CF81, A0A2G3CPV5, A0A2G3BN91, A0A2G3D5Y6, M9RTK5, A0A0U2QU59, A0A091LRX5, A0A091LPV4, A0A147B803, A0A250YCG5, A0A0K2A1W0, A0A1Y2HTZ2, A0A1Y2HS76, A0A091LCZ8, A0A091LCI0, A0A091LH38, A0A091LE22, A0A1V0SBF1, A0A1B1AEB3, H0UU59, H0V4A7, H0VJ51, H0VJK2, H0VMN8, A0A1S6L629, A0A2K5R7R9, A0A2K5S2Q5, A0A2K5S2P6, A0A2K5RX96, A0A2K5S9C9, A0A2K5S2F6, A0A2K5S9D7, A0A2K5S2N2, A0A2R4M5G7, A0A1I3X2Y8, A0A1Q3CUV5, A0A1Q3BH96, A0A1Q3CMR9, A0A1Q3DDN1, A0A1Q3C1X7, A0A1Q3DAG8, A0A1Q3C304, A0A1Q3BHR2, A0A1Q3DDT5, A0A1Q3D9K6, A0A1Q3ATB9, A0A1Q3CIF3, A0A1Q3B9L6, A0A1Q3BTA5, A0A0P1BME7, A0A316VR68, A0A316VS87, A0A316VQI0, W8C6U2, W8C174, W8C1F8, W8ATI6, W8BF27, W8B238, W8BBW0, W8BCC6, A0A2K5MGN8, A0A2K5M9B1, A0A2K5N9N6, A0A2K5NA06, A0A2K5MGR7, A0A2K5N874, A0A2K5N9U0, A0A2K5LD51, A0A2K5N9Z6, A0A2S6CCY8, A0A2S6BQS9, A0A2S6CDU3, A0A2S6BW05, A0A2S6BSE0, A0A2S6CLP9, A0A2S6C3L0, A0A2S6BTN4, A0A2S6C4G5, A0A2S6C470, A0A2S6BY54, A0A2S6C2K4, A0A2G5HUI6, A0A2G5IDK6, A0A2G5IA94, A0A2G5HDH1, A0A2G5HEC5, A0A2G5HCY6, A0A2G5HUJ2, A0A2G5I2T2, A0A2G5HEX4, A0A2G5HP23, A0A2G5HTF1, A0A2G5II N9, A0A2G5HCN3, A0A2G5HGT9, A0A2G5IDY8, A0A2G5HL32, A0A2G5HYX7, A0A2G5I599, A0A2I0RLP9, A0A2I0RUR2, A0A2I0S1B2, A0A2I0RXR6, A0A2I0RX04, A0A2I0RUR7, A0A2I0RNL9, A0A2I0RI80, A0A2I0RRK8, A0A2T4JY52, A0A2W7S7A2, A0A212C8S4, A0A212C7P2, A0A212CKS8, A0A212C307, A0A212C2K8, A0A212C346, G0S7E3, A0A3M7NZG2, A0A3M7NLC0, A0A388K5P6, A0A388K2B3, A0A388LIL5, A0A0A0A1C3, A0A0A0ACH9, A0A0A0A4L1, A0A0A0AEL2, Q11FM9, Q11LR2, A0A2W6Y8B9, M7B6M9, M7B4A9, A0A437B6K6, A0A437BD02, A0A3S2P060, A0A3S2NRB4, A0A3S2TGF1, A0A401S8F4, A0A401SUD6, A0A401T7K4, A0A401S098, A0A250WPW7, A0A250WQA5, A0A250WYW3, A0A2K3DSA5, A0A2K3E6A5, A8HZX7, A0A2K3DB77, A8HQ30, A8IBD2, A0A2K3DBP7, A0A2K3D8X6, A0A2K3E6A3, A0A2K3DB83, A0A2K3CTH7, A0A2K3CSI6, A8IFR1, A8IMR7, A8HQN7, A0A2K3E6U0, A0A2K3DBQ5, A0A2K3DBU7, A8J8N4, A0A2K3D2L0, A0A2K3DS95, A0A2K3DBP8, A0A2K3DMT1, A8J1H4, A0A2K3D8R5, A0A2K3DWJ6, A0A2K3DCU6, A8IKN5, A0A2K3E6C5, A0A2K3D9V3, A8HX99, A0A2K3D9V6, A8JBG8, A8IKN3, A0A091L5H5, A0A091L0G7, A0A091KL34, A0A3L8SH23, A0A3L8S1X4, A0A3L8SV11, A0A3L8S925, A0A2P6TKL9, A0A2P6TF11, A0A2P6U331, A0A2P6TIU0, A0A2P6TGU7, A0A2P6TIQ9, A0A2P6TGF4, A0A2P6TFU2, A0A2P6TLH4, A0A2P6TJF6, A0A2P6U011, A0A2P6TXL2, A0A2P6U051, A0A2P6TCK0, A0A2P6TW22, A0A2P6TZN7, A0A2P6TCJ6, A0A2P6TUR6, A0A2P6THR0, A0A2P6TIQ5, A0A2P6TMR9, A0A2P6TR31, A0A2P6TH81, A0A2P6TP21, A0A2P6TVR3, A0A2P6TES6, A0A2P6TXZ7, A0A2P6TMQ7, A0A2P6TKW1, A0A2P6TQS8, A0A2P6TIZ9, A0A2P6TF15, A0A2P6U012, A0A2P6TMT2, A0A2P6U316, E1ZPG0, E1ZRL2, E1Z6K2, E1ZHG6, E1ZJC2, E1ZUC6, E1ZHR7, E1ZF04, E1ZHR6, E1Z7H7, E1Z291, E1Z6Q1, E1ZJG5, E1ZM59, E1ZG06, E1ZAC6, E1Z965, E1ZBZ7, E1Z7U0, A0A0D9RIP2, A0A0D9S2M3, A0A0D9RHM4, A0A0D9S2M6, A0A0D9RQW6, A0A2E1ZYY8, A0A017T0L6, A0A017T6P0, A0A0G4GGC1, A0A0G4G2T2, A0A0G4HXM5, A0A0G4HH89, A0A0G4GSE8, A0A0G4IBR5, A0A0G4H481, A0A0G4I991, A0A0G4FQB4, A0A0G4GMQ5, A0A0G4GZC4, A0A0G4HGC9, A0A0G4FVU0, A0A0G4F227, A0A0G4FYS2, A0A0G4FGP6, A0A0G4FEZ3, A0A0G4I700, A0A0G4GGB9, A0A0G4F023, A0A0G4FZM7, A0A0G4HZX5, A0A0G4HKE3, A0A0G4HYV2, A0A0N9QJ81, A0A0N9R3K7, A0A0M0JLK2, A0A0M0JFA1, A0A0M0J9M7, A0A0M0J502, A0A0M0JW38, A0A0M0JSY5, A0A0M0JH75, A0A1S2Z201, A0A1S2Y6R3, A0A1S2YVX3, A0A1S2Y702, A0A1S2Z2P8, A0A1S2XCS8, A0A1S2XT54, A0A1S2XFS7, A0A1S2YU61, A0A1S3E0S5, A0A1S2XB68, A0A3Q7YCB7, A0A1S2YU62, A0A1S2XDH3, A0A1S3E9I2, A0A1S3EJ26, A0A1S2ED37, A0A1S2XP43, A0A3Q7XHP2, A0A1S2XCS7, A0A1S2X9K5, A0A1S2XP07, A0A3Q7YC42, A0A3Q7Y1H8, A0A1S3EDN3, A0A1S2XBI0, A0A3Q7YAU0, A0A3Q7Y285, A0A3Q7Y6L8, A0A1S2Z7A8, A0A3Q7XQV7, A0A3Q7YG81, A0A3Q7Y0F7, A0A1S2Z2N4, A0A3Q7XQV2, A0A1S2Y575, A0A1S2Z2N5, A0A3Q7WWB2, A0A1S2Y5U4, A0A1S3E9A9, A0A1S2X9L3, A0A3Q7XBV1, A0A1S2XRR7, A0A1S3E9B2, A0A3Q7XAI7, A0A3Q7YAZ7, A0A3Q7Y008, A0A3Q7YFJ7, A0A1S2Z200, A0A1S3E6X4, A0A1S2YU56, A0A1S2Y443, A0A1S3E803, Q84V84, A0A443PRY7, A0A443NX35, A0A3S3NIB5, A0A443P5K6, A0A443PBN9, A0A443PBP3, A0A443P0S9, A0A443PS04, A0A443PW89, A0A443PS03, A0A3S3MEI8, A0A443PN61, A0A3S3N3K9, A0A443NLN9, A0A3S3MJQ9, A0A3S3NA45, A0A443P5V0, A0A443P2S3, A0A3S3PD76, A0A3S3MXI8,

| | | | | | |
|---|---|---|---|---|---|
| A0A443PCA0, | A0A443P2G4, | A0A443PBN2, | A0A067G6T1, | A0A067G3Y0, | A0A067DXE4, |
| A0A443PS75, | A0A3S3MXL1, | A0A443PBP0, | A0A067GFZ4, | A0A067GG78, | A0A067G404, |
| A0A3S3MR36, | A0A3S3NVL5, | A0A443PBQ1, | A0A067DEU1, | A0A067F642, | A0A067DP44, |
| A0A3S3P012, | A0A3S3NGN2, | A0A443PBP1, | A0A067EP43, | A0A067ECN7, | A0A067EFL5, |
| A0A3S3QL46, | A0A443PBQ8, | A0A3S3MJ71, | A0A067G3Y8, | A0A067ERY8, | A0A067G3Y3, |
| A0A443PBP5, | A0A3S3PSG0, | A0A443PBN3, | A0A067GFX8, | A0A067EMR0, | A0A067GG48, |
| A0A443PDZ2, | A0A3S3N939, | A0A3S3PEW5, | A0A067G7Q9, | A0A067E705, | A0A067G451, |
| A0A3S4PKF1, | A0A3S3NWW4, | A0A3S3MXN2, | A0A067G6R7, | A0A067DMY8, | A0A067ECA5, |
| A0A3S3QIN5, | A0A3S3QJN6, | A0A3S3NA33, | A0A067EVI9, | A0A067DT16, | A0A067DFK5, |
| A0A3S3NPA9, | A0A443NX39, | A0A443N5D8, | A0A067DBK4, | A0A067G3Z3, | A0A067DLD4, |
| A0A3S3N3I2, | A0A443PBQ2, | A0A3S3MLU2, | A0A067EI62, | A0A067EFX3, | A0A067ENV7, |
| A0A3S3MTZ8, | A0A3S3MVZ3, | A0A443PBN5, | A0A067EJB2, | A0A067GG38, | A0A067G3V1, |
| A0A443PS14, | A0A3S3NH01, | A0A3S3MY34, | A0A067GG58, | A0A067DJW6, | A0A067DRX6, |
| A0A3S3QYD7, | A0A3S3NIC6, | A0A443PMN8, | A0A067GFV3, | A0A067G6U4, | A0A067G6W5, |
| A0A3S3N4I9, | A0A443PBM7, | A0A443P2M2, | A0A067G6X4, | A0A067DFT8, | A0A067EP41, |
| A0A3S4PQK3, | A0A3S3QQQ3, | A0A3S3QP22, | A0A067EIF8, | A0A067G6Z0, | A0A067FHX6, |
| A0A443PLP3, | A0A3S3PD65, | A0A443PBN0, | A0A067DIS5, | A0A067DDY5, | A0A067EMP5, |
| A0A443NF22, | A0A443PLH6, | A0A443PS49, | A0A067G6S1, | A0A067GG04, | A0A067GFZ1, |
| A0A3S3NDM0, | A0A3S3PD86, | A0A443PJM2, | A0A067DJF0, | A0A067F0Y8, | A0A067G412, |
| A0A3S3NJS6, | A0A443PLJ7, | A0A443PBQ0, | A0A067G6V2, | A0A067G6U9, | A0A067G3Z1, |
| A0A3S3MXK7, | A0A443P0T7, | Q69HN0, | A0A1W5BT82, | A0A067G3V7, | A0A067GK13, |
| A0A3Q0K068, | A0A3Q0JVM7, | A0A1W2WKK1, | A0A067G7V2, | A0A067GFY1, | A0A067GK25, |
| A0A3Q0JM87, | A0A1W5BJJ9, | A0A3Q0K9Z4, | F6PY33, | A0A2H5PKY8, | A0A2H5PKZ4, | A0A2H5Q9C5, |
| F6UI41, | A0A1W5B4S5, | F6RQT3, | A0A1W5BDQ8, | A0A2H5PSJ2, | A0A2H5PSH0, | A0A2H5QJF9, |
| A0A3Q0JQ58, | H2YF24, | H2ZPV7, | I1ATJ2, | D0D4L1, | A0A2H5PKR2, | A0A2H5PFQ6, | A0A2H5PSI2, |
| A0A355QKE1, | A0A357RS17, | A0A1H3M0F3, | V4UM33, | A0A2H5PSG3, | A0A2H5PSI8, | A0A2H5PSM9, |
| V4S782, | V4WFC0, | V4US31, | V4UM62, | V4W3X3, | A0A2H5PSK6, | A0A2H5PKW4, | A0A2H5PKV3, |
| V4UM47, | V4UGX9, | V4TXJ0, | V4SX72, | V4T0F1, | A0A2H5PKZ1, | A0A2H5PSG8, | A0A2H5PSJ9, |
| V4UGU5, | V4TXM4, | V4UGV0, | V4WFE7, | V4UGU3, | A0A2H5PSH4, | A0A2H5PFR7, | A0A2H5PL00, |
| V4UG60, | V4U8W0, | V4TPH0, | V4TXH2, | V4ULH8, | A0A2H5PLJ0, | A0A2H5PKR5, | A0A2H5P0E0, |
| V4UM07, | V4UAV8, | V4WFD4, | V4UM16, | V4US56, | A0A2H5PYT1, | A0A2H5Q8A5, | A0A2H5PSK1, |
| V4TXI0, | V4WFB7, | V4TXL6, | V4US24, | V4UGR6, | A0A2H5PLK0, | A0A2H5QSC3, | A0A2H5N494, |
| V4RYV2, | V4SQ65, | V4UM23, | V4UR15, | V4WFE2, | A0A2H5NKK7, | A0A2H5PKY5, | A0A2H5MW58, |
| V4TQP7, | V4U0T7, | V4US39, | V4SZW8, | V4UGT3, | A0A2H5PSJ1, | A0A2H5QY31, | A0A2H5PKT9, |
| V4W877, | V4SUW1, | V4UGW8, | V4WFB2, | V4S160, | A0A2H5N543, | A0A2H5PFR2, | A0A2H5QX37, |
| V4WFC6, | V4STW6, | V4T683, | V4UM36, | V4UEI5, | A0A2H5NYH0, | A0A2H5PKT8, | A0A2H5PKS3, |
| V4UM71, | V4USA4, | V4T894, | V4SP31, | V4TXG2, | A0A2H5PSI7, | A0A2H5PKV8, | A0A2H5PKW8, |
| V4W5E2, | V4SHZ9, | V4U0T3, | V4SDM6, | V4UGS3, | A0A2H5QGS6, | A0A2H5PLH7, | A0A2H5PKW9, |
| V4SNM6, | V4TXJ3, | V4TVE6, | V4RYU8, | V4W3W8, | A0A2H5N106, | A0A2H5PSG4, | A0A2H5PBR2, |
| V4US66, | V4W3G2, | V4UCD6, | V4WFN6, | V4TLL6, | A0A2H5PIJ5, | A0A2H5QGL4, | A0A2H5PSL1, |
| V4US48, | V4U017, | V4US05, | V4TXJ7, | V4UM67, | V4US34, | A0A2H5PSF5, | A0A2H5QJI9, | A0A2H5PWC1, |
| V4US51, | V4US13, | V4ULH4, | V4TXK0, | V4UM52, | A0A2H5PLG3, | A0A2H5PSL8, | A0A2H5PKU0, |
| V4SQ60, | V4US61, | V4U986, | V4US73, | V4WFD7, | A0A2H5PKT6, | A0A2H5QX47, | A0A2H5PXG7, |
| V4W873, | V4TXM0, | V4SV65, | V4UM41, | V4U452, | A0A2H5QUK2, | A0A2H5PTF6, | A0A2H5PCI5, |
| V4STW9, | V4STF2, | V4STL9, | V4UGV5, | V4U9H6, | A0A2H5PHZ3, | A0A2H5QGN3, | A0A2H5PKS2, |
| V4W3W6, | V4U5T6, | V4SMY3, | V4SSX8, | V4UGT8, | A0A2H5PHW4, | A0A2H5PSI9, | A0A2H5QTN3, |
| V4S7S5, | V4T687, | V4UGS8, | V4ULH0, | V4UM27, | A0A2H5QDF2, | A0A2H5PKW6, | A0A2H5PKX5, |
| B2CDF6, | A0A067GG52, | A0A067G6T4, | A0A067GFX5, | A0A2H5P8A0, | A0A2H5PKW0, | A0A2H5PKV5, |
| A0A067CZ86, | A0A067GG63, | A0A067GFU2, | A0A2H5PKY2, | A0A2H5PFQ1, | A0A2H5Q8X1, |
| A0A067G437, | A0A067G408, | A0A067GAK8, | A0A2H5PIK0, | A0A2H5PSK7, | A0A2H5PSH7, |
| A0A067GG46, | A0A067ERZ0, | A0A067G3Z5, | A0A2H5PTD6, | A0A2H5PHY6, | A0A2H5MVV6, |
| A0A067G447, | A0A067DNX9, | A0A067ESK3, | A0A2H5PKT3, | A0A2H5N2Y6, | A0A2H5PKW2, |
| A0A067GFW5, | A0A067EC69, | A0A067DC17, | A0A2H5PLM9, | A0A2H5PKW5, | A0A2H5PLK9, |
| A0A067FDW2, | A0A067GFW9, | A0A067DFP7, | A0A2H5MW15, | A0A2H5PKV2, | A0A2H5MXC0, |
| A0A067DJF5, | A0A067G402, | A0A067D6A0, | A0A2H5N221, | A0A2H5QJF2, | A0A2H5N2E3, |
| A0A067DEZ1, | A0A067D709, | A0A067E075, | A0A2H5PTC7, | A0A2H5PSI1, | A0A2H5PSH6, |
| A0A067ESU0, | A0A067ERZ4, | A0A067GG54, | A0A2H5PSF9, | A0A2H5PIL0, | A0A2H5PSJ5, |
| A0A067G3X5, | A0A067GFU7, | A0A067F300, | A0A2H5QDF6, | A0A2H5PYF9, | A0A2H5PFR4, |
| A0A067G6V7, | A0A067G416, | A0A067F0B3, | A0A2H5PSM2, | A0A2H5PLL9, | A0A2H5QGR8, |
| A0A067G7T6, | A0A067GG67, | A0A067FCY6, | A0A2H5QSP4, | A0A2H5PTB7, | A0A2H5MXP2, |
| A0A067GFY6, | A0A067G429, | A0A067EZ26, | A0A2H5QDF7, | A0A2H5PW39, | A0A2H5PKU4, |
| A0A067G407, | A0A067G444, | A0A067DHM7, | A0A2H5PKV9, | A0A2H5PKT1, | A0A2H5PL05, |
| A0A067GG72, | A0A067G7U1, | A0A067DGG9, | A0A2H5MWP9, | A0A2H5PKS5, | A0A2H5PKY1, |
| A0A067G3W6, | A0A067F108, | A0A067GG42, | A0A2H5PKZ0, | A0A2H5PKX3, | A0A2H5PLN9, |
| A0A067EXK6, | A0A067DI35, | A0A067G3X9, | A0A2H5PSN3, | A0A2H5PKY6, | A0A2H5PSI0, |
| A0A067F5Z7, | A0A067G419, | A0A067DP49, | A0A2H5PKU2, | A0A2H5MY89, | A0A2H5PKZ5, |
| A0A067D963, | A0A067ESK4, | A0A067GAK4, | A0A2H5N248, | A0A2H5MVR2, | A0A2H5PC29, |

A0A2H5PSH8, A0A2H5PSJ6, A0A2H5PKZ9, A0A135V7C4, A0A135RXN4, A0A135RR28, A0A2H5PKV0, A0A2H5PKU3, A0A2H5QX61, A0A135T1G0, A0A135T432, A0A135RPI7, A0A2H5PKU8, A0A2H5PXK1, A0A2H5PKS9, A0A066XMA0, A0A066XY08, A0A166RN27, A0A2H5PSK2, A0A2H5PXH5, A0A2H5PKZ7, A0A166S4H7, A0A2K5JR89, A0A2K5JX41, A0A0D2EPW4, A0A0D2H5D0, A0A0D2D5M4, A0A2K5JX37, A0A2K5JX55, A0A2K5JK04, A0A0D1ZW52, A0A0D2D9C0, W9VHA5, A0A1B6E728, A0A2K5HKG1, A0A2K5I747, A0A2K5I7F4, A0A1B6DP44, A0A1B6CQM5, A0A1B6CRN7, A0A2I0MN33, A0A2I0MN31, A0A2I0MV52, A0A1B6D4A1, A0A1B6CPV4, A0A1B6CH46, M1VXP1, A0A2I0MV53, A0A2I0MH63, A0A2I0MN36, A0A1Y1ZIY5, A0A1Y2A3K8, A0A1Y1Y9H3, A0A2I0MN41, A0A3R4B871, A0A407GJQ8, A0A1Y1ZK83, A0A1Y1Z9L6, A0A419PQI0, A0A408KDV5, A0A409SM37, A0A3R2WYC1, A0A3R7EPZ0, A0A419QAI4, A0A419PSE2, G7YA90, A0A3R4Z561, A0A3R1NI64, A0A405Z9C4, G7YBT5, A0A3R7DBB2, A0A3R7CQZ5, A0A419PZ32, A0A3R4NNR5, A0A2T2ZVH0, A0A2T2ZTN0, G7YEU8, G7YWK9, G7Y624, A0A1J1IGE1, A0A2T2ZW89, A0A2T2ZSF1, A0A1J7IVY8, A0A1J1HN04, A0A1J1IXY3, A0A1J1IRI6, A0A1J1I6X9, A0A420Y1M1, A0A420Y084, R7Z4G2, R7YJ26, A0A1J1HMP6, J3K384, J3K388, A0A0J8USD8, R7YYV7, R7Z2B6, R7YKC6, R7YYF5, A0A1T4MT25, A0A0J8S0H2, A0A0J6Y7D1, A0A0J6Y7C8, H8MJT7, A0A1R3IQG2, A0A1R3JAU6, A0A1R3JH31, A0A0J8QTA0, C5P676, C5P674, E9DHQ1, E9DIX1, A0A1R3ICX9, A0A1R3KDQ4, A0A1R3IXI1, E9DIM5, A0A0J6I586, A0A0J6I580, I0YJN3, I0YQC5, A0A1R3I223, A0A1R3I0S0, A0A1R3JCQ7, A0A1R3IHP6, I0YZJ2, I0YQC4, I0Z909, I0YXG6, N4WSB7, N4XA49, A0A1R3I8B4, A0A1R3HWR3, A0A1R3I8E3, N4X4B7, N4WV7, N4XAK1, N4XNR5, N4WIS8, A0A1R3JH09, A0A1R3IIR2, A0A1R3I8B1, N4XE50, N4WKJ0, M2UDR7, M2TCH5, M2UPP8, A0A1R3GUC6, A0A1R3G8B2, A0A1R3IQM1, M2TUB1, M2UZK2, M2UC59, M2TM44, M2SS15, A0A1R3GC79, A0A1R3GXE2, A0A1R3JH02, M2TNS5, M2SEH1, M2TCD4, M2REQ9, M2T729, A0A1R3K5M1, A0A1R3JYE5, A0A1R3IQK9, M2QVU0, M2SRC8, M2SXY7, M2SRR6, A0A068V1N7, A0A1R3IES9, A0A1R3I214, A0A1R3IQG7, A0A068TTW9, A0A068U5I0, A0A068UBR8, A0A1R3IQE6, A0A1R3I248, A0A1R3K9G1, A0A068UMF4, A0A068VIN5, A0A068VAH2, A0A1R3H0C3, A0A1R3GS32, A0A1R3J3W4, A0A068VH78, A0A068U0Z7, A0A068VD61, A0A1R3H636, A0A1R3I8F2, A0A1R3FYR8, A0A068UDX9, A0A068UF61, A0A068UEE7, A0A1R3KLM1, A0A1R3K8S9, A0A1R3KU50, A0A068TT72, A0A068TUQ8, A0A068U920, A0A1R3J5L5, A0A1R3KBY3, A0A1R3JYF5, A0A068UBA7, A0A068UTC4, A0A068TTY9, A0A1R3GIW4, A0A1R3JDE5, A0A1R3KM12, A0A068V6K4, A0A068UCT7, A0A068VAV0, A0A1R3HMG0, A0A1R3I4C7, A0A1R3KA03, A0A068UAW2, A0A068TTU4, A0A068TUK9, A0A1R3H436, A0A1R3HD45, A0A1R3KF17, A0A068UB95, A0A068U7P3, A0A068UAV7, A0A1R3ICZ6, A0A1R3JDF2, A0A1R3FZ78, A0A068U9M3, A0A068TR02, A0A068TUN3, A0A1R3K8S8, A0A1R3J7N3, A0A1R3H3T9, A0A068UC35, A0A068VIA2, A0A068V9X1, A0A1R3GAX3, A0A1R3IDM3, A0A1R3JCH0, A0A068TWF3, A0A068V7U6, A0A068U9A9, A0A1R3H3T1, A0A1R3JZ07, A0A1R3KC06, A0A068V658, A0A068VDF8, A0A068TUN8, A0A1R3HV73, A0A1R3JYS9, A0A1R3KRY3, A0A068URU0, A0A068TWI8, A0A068TPT8, A0A1R3H3Q5, A0A1R3KBU9, A0A1R3H4T5, A0A068UCP1, A0A068UB32, A0A068UU33, A0A1R3KBT7, A0A1R3JYI7, A0A1R3KBW6, A0A068VDL2, A0A068UUD5, A0A068V600, A0A1R3HEM2, A0A1R3KBS9, A0A1R3KBZ0, A0A068U9B6, A0A068U735, A0A068UDJ3, A0A1R3I4A2, A0A1R3H934, A0A1R3K8R8, A0A068VL89, A0A068V636, A0A068TTS6, A0A1R3KBZ3, A0A1R3JYI0, A0A1R3JYB7, A0A068VAU6, A0A068UAW8, A0A068TY94, A0A1R3H3N1, A0A1R3H913, A0A1R3JDG2, A0A068V341, A0A068UDX1, A0A068U7P7, A0A1R3KBV2, A0A1R3H8W0, A0A1R3KU57, A0A068TRE6, A0A068U9C3, A0A068U9L9, A0A1R3I4C0, A0A1R3H3R9, A0A1R3JID2, A0A068UCP7, A0A068V5D0, A0A068U6Z2, A0A1R3KBV6, A0A1R3H3T2, A0A1R3GSE3, A0A068UAL8, A0A068TUH5, A0A068UVZ3, A0A1R3JYJ4, A0A1R3KBX8, A0A1R3KU24, A0A1I0RVR9, A0A285PJ03, A0A1I4ZNL6, A0A1R3HPV5, A0A1R3KGT6, A0A1R3GJ03, A0A285M669, A0A2N5XUY7, A0A3D8Q658, A0A1R3H3P6, A0A1R3K9H9, A0A1R3HSJ9, A0A3D8S2L7, A0A3D8Q9J9, A0A3D8Q983, A0A1R3KYZ9, A0A162K7A9, A0A168IRL7, A0A3D8Q9G4, A0A3D8R5V5, A0A3D8STW8, A0A179IKV7, A0A179IAQ3, A0A167WMS9, G3J8R3, A0A3D8Q6N2, A0A3D8Q4Q0, A0A3D8QNJ8, G3J375, G3JSZ4, G3JUF8, A0A2H4SK15, A0A2H4S7F4, A0A226PF24, A0A226PDM2, A0A226PAM3, A0A2C6AEQ6, A0A2C5ZXP2, A0A091ET11, A0A226NT22, A0A091L82, A0A091KA09, A0A091K6S3, A0A091EJ05, A0A091EWY0, A0A091F8A0, A0A1Q8RWV1, A0A1Q8RVP1, A0A1Q8S2N5, A0A091E9Y9, A0A2T2N6K3, A0A2T2NU07, A0A1Q8S5V0, A0A010QTI5, A0A010SLX6, A0A2T2NYB4, A0A2T2N5T0, A0A2T2NUY0, A0A010RTR1, L2FSS4, L2GE62, L2G3T0, L2FT65, A0A2T2N6K9, Q8LP57, K1QBT9, K1QP59, K1Q5J6, L2FRD2, L2GC03, L2FYL0, T0KBX5, T0KBL3, T0LNX5, K1RL61, K1PV69, K1Q202, K1RCS2, K1R451, K1QEX9, T0K3L5, T0M6Z0, T0K282, T0KJU1, T0KX95, T0KV89, K1RFL1, K1QFL8, K1R782, K1PMX4, K1QE58, E3QKF4, E3Q9X3, E3QHU7, E3R0R1, H1VPP1, H1VE61, K1QC63, K1Q2X3, K1Q0K1, K1RU37, K1QRX2, A0A1B7XYH5, H1VEI3, A0A1B7XYR0, A0A1B7Y121, K1Q0F5, K1PMX3, K1QH76, K1R7M2, K1PKQ8, H1W3P5, A0A162PMT3, A0A166LHG7, A0A1S1W2W6, K1QEU5, K1QEV1, K1Q3J0, K1PJ39, K1R0X1, K1R8Y0, A0A1S1VWS2, A0A162NJN8, A0A162PCP5, K1QI12, K1PUC3, K1PZY8, K1QNX1, K1PEE6, K1PQ16, A0A135SZV4, A0A135UT38, A0A135T629, K1RKN1, K1P151, K1PCZ9, K1P8Q7, K1RDU0, A0A135UX69, N4UZE4, N4UZ75, N4VFT2, N4W403, K1R0V6, K1RNM0, K1QGI9, K1R168, K1QEL7, N4V0X7, A0A1G4B117, A0A1G4BBR1, A0A1G4ATI1, K1RBU1, K1QRJ4, K1R5R6, K1QPK8, K1QPU6, A0A135V7W1, A0A135S139, A0A135URM5, K1QNB3, K1RFB4, K1P8F6, K1QVB6, K1QI33,

K1QDS6, K1QVX2, K1QKJ9, K1QYN7, K1R234, K1Q9S5, K1PXX6, K1QRJ6, K1RGH6, K1PM36, K1R3S9, K1Q4S4, K1R2E6, K1Q9I9, K1Q9I2, K1QQI2, K1P0S6, K1RPI0, K1QP97, K1Q132, K1PMA2, K1P7M9, K1PQG5, K1QIV6, K1PN45, K1R926, K1Q7G5, K1QUA0, K1PUE1, K1PZF9, K1QZS4, K1QYB3, K1QYH7, K1PQV5, A0A1R4H3L7, A0A1H6XYT5, A0A3L7I648, G3HGQ6, A0A3L7IJG9, A0A3L7IG64, A0A061IMW5, A0A3L7HP47, A0A3L7IIX0, A0A061IRF7, G3HPQ5, A0A1J4MK57, A0A1J4MVW0, A0A1J4MU07, A0A1J4MTL5, A0A0S4TCD4, A0A0S4TBC4, A0A0S4TAQ1, A0A0S4TDE6, A0A2P4YWR1, A0A2P4Z358, A0A2P4Z5F0, A0A2P4YWR9, B6AEN1, B6AJC3, B6A964, Q5CSA4, Q5CTT8, Q5CSA0, Q5CV27, Q86PQ7, A0A1J4MKT5, A0A1J4MIN1, A0A1J4MFD1, A0A2J7PDR3, A0A2J7QPV9, A0A2J7Q2V5, A0A2J7R433, A0A2J7R431, A0A2J7PHG6, A0A2J7QD69, A0A2J7R420, A0A2J7PDS5, A0A2J7QD68, A0A2J7QD73, A0A2J7R430, A0A2J7RS16, A0A2J7R424, A0A2J7PWJ5, A0A2J7R441, A0A2J7R451, A0A2J7R454, W8FRI5, A0A091FW85, A0A091GEV6, A0A091GKK8, A0A091GI80, A0A1S4DST8, A0A1S3B409, A0A1S3B3R3, A0A1S4DSQ5, A0A1S4DSX1, A0A1S3B440, A0A1S3B585, A0A1S3B4W7, A0A1S3CSP7, A0A1S3AZX8, A0A1S3AZY6, A0A1S3BZ12, A0A1S4DSR7, A0A1S4DSP8, A0A1S4E4E3, A0A1S3B4H2, A0A1S3B453, A0A1S3B3R8, A0A1S3B5C7, A0A1S4DTJ6, A0A1S4DSS7, A0A1S3B4D0, A0A1S3B536, A0A1S3B5U5, A0A1S3B6L4, A0A1S3B4A8, A0A1S3BTL3, A0A1S4DST5, A0A1S3B4B3, A0A1S3B516, A0A1S3B4F1, A0A1S4DZ25, A0A1S3C0Q9, A0A1S4DSE8, A0A1S3CSN1, A0A1S3BC50, A0A1S4DSS6, A0A1S3B7B8, A0A1S3CF32, A0A1S3C207, A0A1S3B530, A0A1S3BTI5, A0A1S4DSE6, A0A1S4DSS8, A0A1S3CR70, A0A1S3B575, A0A0A0LS73, A0A0A0LS68, A0A0A0LUY8, A0A0A0LX93, A0A0A0LUE6, A0A0A0LRR4, A0A0A0KRF4, A0A0A0K287, A0A0A0LEC1, A0A0A0LUZ3, A0A0A0LDL3, A0A0A0LUF1, A0A0A0LAF2, A0A0A0LRR1, A0A0A0KK10, A0A0A0LBA0, A0A0A0LX89, A0A0A0KC43, A0A0A0L6H7, A0A0A0K3N8, A0A0A0LUZ5, A0A0A0LFV8, A0A0A0LUY4, A0A0A0LII6, A0A0A0LXA0, A0A0A0LD19, A0A0A0LX86, A0A0A0KC37, A0A0A0LRR8, A0A0A0K8W5, A0A0A0L7U1, A0A0A0LRS1, A0A0A0KWZ1, A0A0A0LS76, A0A0A0LUD8, A0A0A0KSR7, A0A0A0LZJ7, A0A0A0K7B0, A0A1B6H4Y5, A0A1B6G4G8, A0A1B6EYW8, A0A1B6FLH2, A0A1B6FYJ9, A0A1B6GHV9, A0A1B6H2T7, A0A1B6FML8, A0A1B6GMC1, A0A1B6FMH3, A0A1B6FYA0, A0A1B6H1R8, B0VZB8, B0WCW6, B0XHR5, B0X861, B0WCW5, B0X859, B0WBN2, B0W214, A0A1S4J279, A0A1S4JBK4, B0WCW7, A0A1Q3FSK0, A0A1Q3FS43, A0A336M006, A0A336LTK1, A0A336LRS2, A0A336N522, A0A336LVN5, A0A336MHF2, A0A336MGD3, A0A336MI32, A0A336MYJ1, A0A336LUN7, A0A336MT58, A0A336MRX6, A0A336LTL3, A0A336LMK2, A0A328DVR3, A0A328D129, A0A328D3T7, A0A328D453, A0A328DBU8, A0A328D973, A0A328DIK3, A0A328DIS6, A0A2S6CT90, A0A2T1F9F0, A0A3B8Y4A2, A0A1D3CT75, A0A1D3D2G3, A0A1D3CZG8, A0A1D3D562, A0A1D3CXV2, A0A1D3CZF4, A0A1D3D4P8, A0A1D3D927, A0A1D3D792, A0A1D3CRX6, A0A1D3CZB5, A0A1D3CRI2, A0A1D3D067, A0A3P6QZS2, A0A3P6QGH9, A0A3P6T344, A0A3P6R246, A0A3P6S9T1, A0A103YIH9, A0A124PXP6, A0A103XS92, A0A103XY72, A0A103Y5E6, A0A103XZ10, A0A103XC99, A0A124S064, A0A103Y815, A0A103XCM9, A0A118JT41, A0A118JSJ8, A0A103XF71, A0A118JU86, A0A124SCT9, A0A124SHJ7, A0A103YJR9, A0A103XQ49, A0A118K316, A0A103XC93, A0A103XYY7, A0A103Y467, A0A118K2V5, A0A124SHS0, A0A103Y6D6, A0A118HIH7, A0A103XU24, A0A103Y212, A0A103Y1Z5, A0A103YD45, A0A103YJV2, A0A103Y7Z6, A0A124SHR9, A0A103XQ54, A0A124SDG2, A0A103XWT3, A0A103YIJ1, A0A124SHK2, A0A103XF58, A0A118GC55, A0A103XQI2, A0A103Y7Z7, A0A103XBG4, A0A103XU62, A0A118JTB4, A0A103XZ33, A0A103MM20, A0A103Y9H4, A0A103Y652, A0A103Y6D3, A0A118JTV8, A0A103YDC6, A0A103Y6C0, A0A103VJ56, A0A103Y9I0, A0A103Y446, A0A103XW W8, A0A103YCS4, A0A103XIZ2, A0A103XDQ3, A0A3P8VG89, A0A3P8UTK9, A0A3P8VDI4, A0A3P8X2L6, A0A3P8X460, A0A3P8V360, A0A3P8VG76, A0A3P8X4M6, W2RU83, A0A195CFB6, A0A151INZ7, A0A195CUA0, A0A195CJ60, A0A151IBX2, A0A195CDF0, A0A3Q2D697, A0A3Q2FWU5, A0A3Q2D220, A0A3Q2FWW5, A0A3Q2E8M8, A0A3Q2D1Q5, A0A3Q2D1Y0, A0A3Q2E737, A0A3Q2D1Q1, A0A3Q2FR25, A0A3Q2DW28, A0A0U2S2V6, A0A250JIW8, A0A2C6KJH5, A0A2C6KQQ7, A0A2C6KGJ2, A0A2C6KJZ8, A0A2C6KRS7, A0A2C6KBF6, A0A2C6KGB3, A0A2C6L9R7, A0A2C6KLD1, A0A2C6LDQ6, A0A2C6KWX7, A0A2C6KJN3, A0A2C6KC22, A0A2C6KHJ6, A0A2C6KXQ4, A0A2C6LH90, A0A2C6KQM3, A0A2C6KV00, A0A2C6KD09, A0A2C6KJE6, A0A2C6KGE6, A0A2C6KQL0, A0A2C6KFU7, A0A2C6KW92, A0A2C6KGC7, A0A2C6KGB5, A0A2C6L6S4, A0A2C6L490, A0A423VS70, A0A423W0P4, A0A423WTP3, A0A423X084, A0A223PK27, S8C318, S8ASF1, S8BMH2, S8A7Q6, S8A4U1, S8BSD4, A0A1Y2XBG1, A0A1Y2WWT8, A0A1Y2XCF1, A0A1Y2WXC0, A0A212F9C1, A0A212FKU3, A0A212FKV4, A0A212F3I1, A0A212EVI3, A0A212FAB7, Q6JAN0, F1REK1, F1Q890, F6PA78, A4IGA7, Q5XFY1, Q90ZN6, E9QGF2, Q5RGG3, Q6PBA6, F1QEZ1, A0A0P5WPN5, A0A0P5HGT8, A0A0P5T1U8, A0A0N8E7S9, A0A0P6AL9, A0A0P5Y462, A0A0P5L4W8, A0A0P5S420, A0A0P5TKN5, A0A0P6A674, A0A0P5YJR7, A0A0P5BMJ7, A0A0P5U7V1, A0A0P6C7R9, A0A0P5M729, A0A0P5DS66, A0A0P5C4X4, A0A0P5D7A2, A0A0P6ATK6, A0A0P5EBG6, A0A0P5XUR1, A0A0P6CTV5, A0A0P5NLP7, A0A0P5E9S4, A0A0P5JUZ4, A0A0P6CI84, A0A0P6C183, A0A0P5TSU1, A0A0P6J986, A0A0P5TJC9, A0A0P5ZKH9, A0A0N8CLP0, A0A0P5BT62, A0A0P6CKZ9, A0A0P5RCJ4, A0A0P6HJG1, A0A0P4XKS6, A0A0P5XUU9, A0A0P5LNA4, A0A0P5NMM3, A0A0P5NBA13, A0A0N8BA13, A0A0P6B472, A0A0N7ZWW0, A0A0N8DMK8, A0A0P5S7M2, A0A0P5CWX9, A0A0P5NCC6, A0A0P6GJS2, A0A0P5PR06, A0A0P6H6H4,

A0A0P6GE29, A0A0N8EJE4, A0A0P5DGB0, A0A0P6H7K9, A0A0P5DXB5, A0A0P5D1S4, A0A0P5XV46, A0A0P5F055, A0A0P6I548, A0A0P6IIP3, A0A0P4Y9G9, A0A164ZHL4, A0A0P6ETE1, A0A0P5T6R7, A0A0P6HQE1, A0A0P4YGM2, A0A0P5ZR54, A0A0P5G8Z5, A0A0P5PKW0, A0A0P5BIZ1, A0A0N8DGI8, A0A0N8CBW6, A0A0P5DCI3, A0A0P6DUY5, A0A0P5LVB4, A0A0P5DBP6, A0A0P5HLY6, A0A0P5T4T8, A0A0P6I8Z3, A0A0P5QEZ7, A0A0P5CK22, A0A0P5TZY1, A0A0P6E4B8, A0A0P6CID3, A0A0P5U9K2, A0A0P5E2Z0, A0A0P4YWG8, A0A0P5REG3, A0A0N8CB13, A0A0N8CAL2, A0A164VXV0, A0A0P5N8V1, A0A0P5YVP4, A0A0P5SEK0, A0A0N8AN73, A0A0P5VJT5, A0A0P4WYW8, A0A0P4Y5I5, A0A164XQP6, A0A0P5H9B6, A0A0P4ZH74, A0A0P5HXM7, A0A0P6HVX9, A0A0P5UDG3, A0A0P6DTI4, A0A0P6FTT5, A0A0P5VB25, A0A0P5Q0M1, A0A0N8AR21, A0A0P5HVL3, A0A0P4ZTX3, A0A0P5PUQ2, A0A0P5Y2H7, A0A0P5CZZ0, A0A0P5NV81, A0A0N8AXC3, A0A0N8BWQ2, A0A0P5BX45, A0A0P5N855, A0A0P5HF26, A0A0P4Y6W6, A0A0P5CI46, A0A0P5GCD4, A0A0P5K8Q2, A0A0N8AQK2, A0A0P5KWZ5, A0A0P5DAL0, A0A0N8DA56, A0A0P6AXE9, A0A0P5TVC1, A0A0P6GSX1, A0A162QLH9, A0A0P5Q6F7, A0A0P5Q4A7, A0A0P5ARZ3, A0A0P5WUS7, A0A0P5ID96, A0A0P5F0V1, A0A0P5IZW7, A0A0P5V3V8, A0A0P5N7S0, A0A0P5TUD8, A0A0P5JTA5, A0A0P5GZR4, A0A0N8A3D1, A0A0P5WMW8, A0A0P5IZ39, A0A0P6G736, A0A0P5RD98, A0A0P5Y4G8, A0A0P5MIM1, A0A0P5RMT5, A0A0P5DZF1, A0A0P6DIA9, A0A0P4Z167, A0A0N8DVY1, A0A0P5LWH8, A0A0P5C3K9, A0A0N8CEH7, A0A0P5ZUY7, A0A0P4XS98, A0A0P5WA39, A0A0P5DSL3, A0A0P6EMY0, A0A0P5YSJ8, A0A0P5LT30, A0A0P5PEL1, A0A0P5YIS8, A0A0P6J1P8, A0A0P5WJZ4, A0A0P5WSP3, A0A0P6F1X9, A0A0P4XVA4, A0A0P5GQ84, A0A0P5VSK6, A0A0N8AZ22, A0A0P6IMA8, A0A0P5E5X7, A0A0N8E8I5, A0A0P5Q8K8, A0A0P4YLV2, A0A0P6EFJ2, A0A0P5UL87, A0A0P4Y7F0, A0A0P5CFI1, A0A0P5FCE1, A0A0P5J8K4, A0A0P5HFI7, A0A0P5DIM6, A0A0P5PZV2, A0A0P5N364, A0A0P5LSH1, A0A0P5JKT7, A0A0N8BZ24, A0A0P6IB26, A0A0N8EFF2, A0A0P5T0H1, A0A0P5YD20, A0A0P4XEQ9, A0A0P5WLD1, A0A0P5U1N0, A0A0P5NZP1, A0A0P5D8R1, A0A0P5HZD6, A0A0P5BFL0, A0A0N8BVC5, A0A0P5LU81, A0A0P4Z4U7, A0A0P5X5U9, A0A0P5NCN9, A0A0P4ZBT1, A0A0P5TAQ3, A0A0P5R736, A0A162RDZ5, A0A0P5C3E7, A0A0P5J8A5, A0A0P5N689, A0A0P5G8N3, A0A0N8B914, A0A0N8CTU0, A0A0N8A5F9, A0A0P5U0B1, A0A0P4XKJ3, A0A0P5W8C4, A0A0P6I7V1, A0A0P5Y7U6, A0A0N8A4V3, A0A0P5XZ51, A0A0P4YXW8, A0A0P6GKX2, A0A0P6CI97, A0A0P6HZU7, A0A0P5AIQ7, A0A0P6GA05, A0A0P6CWH0, A0A0P5YP46, A0A0P5MTF8, A0A0P5W4R4, A0A0P5VVF0, A0A0N8BSP2, A0A0P4XN82, A0A0P6EJL6, A0A0P5WKU1, A0A0P5WJY7, A0A0P5AEQ6, A0A0P4ZZ55, A0A0P5EPQ8, A0A0P5Y923, A0A0P6CL50, A0A0P5YP12, A0A0P4ZPB2, A0A0N8ATY9, A0A0P5TTT7, A0A0P6JTG3, A0A0N8AZB0, A0A0P5RFE3, A0A0P5RHI5, A0A0P5UDV1, A0A0N8EHV2, A0A0P5MR11, A0A0P5T4E7, E9FZF1, E9GUF9, A0A0P6DW53, A0A0P4Y8F4, A0A0P5CPG0, E9HG92, E9H7K0, E9FZT3, E9H7J5, E9GC79, E9HGF3, A0A0P5SGL3, A0A0P4YDX7, A0A0P5C3L8, E9GXM8, E9HXN3, E9HL86, E9HHQ3, E9GB65, A0A0P5HRA4, A0A0P5QFT9, A0A0P6EVG4, E9GDU0, E9FZB7, E9FXU0, E9HD48, E9HD47, A0A0P6AEB8, A0A0P6GFW0, A0A0P5BTL7, E9GMC8, E9GGB7, A0A164VCM7, A0A161YC10, A0A0N8E1L0, A0A0P5YUR1, A0A0P4YWK0, A0A166G9N2, A0A161X5W6, A0A166F2H9, A0A0P5PES0, A0A162RSS1, A0A0N7ZQ97, A0A166IMD7, A0A161ZJQ8, A0A165ZEG6, A0A0P5H5A9, A0A0P5W725, A0A0P5PKS1, A0A164SJH2, A0A162AHQ4, A0A175YMP0, A0A0P6IBH1, A0A0P5KMN8, A0A0P5N3S5, A0A165Z528, A0A166EUZ9, A0A175YJR0, A0A0N8EJ07, A0A0P5MQE4, A0A0P5PNX2, A0A175YJB0, A0A166HZ24, A0A162AF38, A0A0P5RVR9, A0A0P6I9Y3, A0A0P6APJ6, A0A165WAR5, A0A164ZED3, A0A164X3K8, A0A0P6CI42, A0A0P5AX29, A0A0P6BQC9, A0A165ZWM7, A0A164T5C8, A0A166GYV2, A0A0P6E3F3, A0A0P6CUC0, A0A0P5RW36, A0A164ZG59, A0A162ADM0, A0A166IUK9, A0A0N7ZLQ2, A0A0P5TUC3, A0A0P6NEQ9, A0A175YL17, A0A162AE67, A0A164Y320, A0A0P5YU72, A0A0P5MRU3, A0A0P4XHH6, A0A164TNL8, A0A175YLD1, A0A166IME5, A0A0P5SP99, A0A0P5EW58, A0A0P5LF22, A0A166AH33, A0A166I4U3, A0A164TNM5, A0A0P5QI00, A0A165ADR2, A0A0N8BQK6, A0A165Z541, A0A164SJF4, A0A165WAT6, A0A0P5N9W7, A0A0P5CL62, A0A0P5X9Q5, A0A175YLF9, A0A166GYR4, A0A175YLB5, A0A0P5NF07, A0A0P5NQH2, A0A0N8ACN6, A0A175YLR0, A0A166IUK0, A0A175YLW6, A0A0P5UDC3, A0A0P5IA39, A0A0P5YW13, A0A161ZVN8, A0A161ZTW6, A0A166GYN3, A0A0P5D6K9, A0A0P5WU76, A0A0P5ADU9, A0A166GYM4, A0A161ZKU6, A0A175YNJ8, A0A0P5HLP5, A0A0P5PX75, A0A0P5WMQ3, A0A164TNT1, A0A166GV23, A0A164VUU7, A0A0P5WK98, A0A0P6DWY3, A0A0N8CYE6, A0A175YQ77, A0A166G9M3, A0A175YK13, A0A0N8DAF5, A0A0P5U6W6, A0A0P5UHU0, A0A166GBE6, A0A162ADK4, A0A166I4V5, A0A0P5P0S3, A0A164WWC9, A0A0P5TQ92, A0A175YNL1, A0A175YN80, A0A162B3S5, A0A0P5YKC6, A0A0P5ECY0, A0A0N8DNH8, A0A162AD34, A0A175YKE6, A0A165Z6J7, A0A0P6EUA0, A0A0P5RUF3, A0A0P5YP87, A0A164W8A9, A0A175YLN5, A0A166AAK1, A0A0P4XUA1, A0A0P6FIA5, A0A0P5TWW9, A0A164SJM1, A0A164ZI33, A0A165ZED0, A0A0N8BSD6, A0A0P4Z326, A0A0P5B454, A0A166JCX2, A0A166F2G3, A0A175YMV8, A0A164XEY4, A0A0P5WQJ7, A0A0P4YXX0, A0A166AH48, A0A175YM77, A0A166F590, A0A0P5RVL4, A0A0N8AUG9, A0A0P5ZPM0, A0A175YN69, A0A165ZEF7, A0A161ZHE5, A0A0P4YEX3, A0A0P5BTY4, A0A0P6CM30, A0A165Z522, A0A161Y240, A0A166IX90, A0A166CK63, A0A0P4WR04, A0A0P5BT21, A0A0P6GTG9, A0A166AH68, A0A175YM10, A0A164WIW8,

A0A175YMW5, A0A164W8B8, A0A166GYQ3, A0A162ZPJ8, A0A163F3P6, A0A162WAZ1, A0A166AH60, Q6I6Y6, D3P9U3, A0A159Z548, A0A163J5K2, A0A2D8TLG9, A0A443QH82, A0A2R8BKZ6, A0A2S8S490, A0A2W5GAR1, A0A443QVN9, A0A3S4RFD9, A0A443Q9A2, A0A2Y9M5R2, A0A2Y9N707, A0A2Y9N2B0, A0A3S4Q503, A0A443Q760, A0A3S3QB39, A0A2Y9LKQ9, A0A2Y9MXX5, A0A2Y9M328, A0A443RFM8, A0A3S3S9I9, A0A443R8P4, A0A2Y9LK73, A0A2M7PDD6, A0A2M7JKL0, A0A2H3FTD0, A0A2H3F312, A0A1J9S7L6, A0A2H0AN95, A0A0T6AER9, A0A2N2GCD1, A0A1J9R5G2, A0A1J9RDT5, A0A1J9RSV2, A0A1F9CSM5, A0A2E7UQW9, A0A2D5SNG4, A0A1J9R6F7, A0A1J9QKG2, A0A1J9SJL7, A0A2D6MP68, A0A359C885, A0A2I0WMU7, A0A0G2GEA1, A0A0G2E8Z2, A0A0G2DVZ6, A0A2I0XFC1, A0A2I0VZ05, A0A2I0VZ03, A0A0G2GU77, A0A1S8BAS3, A0A2A2JU22, A0A2I0WD68, A0A2I0VCZ8, A0A2I0VY27, A0A2A2L628, A0A2A2JTT9, A0A2A2L657, A0A2I0WAD1, A0A2I0VN57, A0A2I0VZ11, A0A2A2J1X0, A0A2A2K5D7, A0A2A2JJI2, A0A2I0WY89, A0A2I0WQI1, A0A2I0WKE7, A0A2A2JIU6, A0A2A2K5L0, A0A2A2KWG8, A0A2I0VZ09, A0A2I0XCU2, A0A2I0WR68, A0A2A2JS95, A0A2A2LN52, A0A2A2L620, A0A2I0X2L0, A0A2I0VTF8, A0A2I0WD76, A0A2A2J5B9, A0A2A2KVU0, A0A2A2L6B7, A0A2I0WMM2, A0A2I0VDJ3, A0A2I0V982, A0A2A2J211, A0A2A2LYR2, A0A2A2L669, A0A2I0V8Q2, A0A2I0XIC7, A0A2I0VPC9, A0A2A2L5U1, A0A2A2K927, A0A2A2L660, A0A2I0WAG8, A0A2I0WMK7, A0A2I0WUZ0, A0A2A2KCF6, A0A2A2KWT1, A0A2A2JR35, A0A2I0VZ10, A0A2I0V9B4, U4UF05, U4UJ61, U4UHH1, A0A2A2JRM6, A0A2A2K944, A0A2A2L6G5, U4UAS2, U4UHR8, U4U368, U4UMJ6, U4UC62, A0A2A2JTJ2, A0A2A2J269, A0A2A2L631, A0A2A2JJ18, N6TCY6, N6T5M3, U4U5U9, N6TNG4, N6TYW1, A0A2A2JW46, A0A2A2KN03, A0A2A2J7C6, N6SW87, N6SZ63, A0A1J5E4F1, A0A351CCD8, A0A2A2LFJ4, A0A2A2JK27, A0A2A2LSI3, A0A3N5QE56, M1NBW9, A0A117N2V7, A0A0F5QJQ8, A0A2A2K984, A0A2A2J737, A0A2A2JVG0, A0A1E5XPL7, A0A1E5XM33, A0A0F5LGC2, A0A2A2LHE2, A0A2A2J9M8, A0A2A2LZT7, A0A0F5Q359, A0A087M5P3, A0A087M6Z6, A0A2A2LK42, A0A2A2L5A9, A0A2A2L5Z3, A0A0F5L306, A0A087LR20, A0A1M3KU89, A0A2A2K562, A0A2A2JIY3, A0A2A2JB04, A0A1Q3Z4X7, A0A024KDE1, A0A024KC27, A0A2A2JVQ1, A0A2A2M1Y0, A0A2A2L2G3, A0A0K0TS75, A0A2L1S3I6, A0A085EUA2, A0A2A2L2E8, A0A2A2L668, A0A2A2KEI4, Q8LP56, A0A085FE05, A0A0Q4PK00, A0A447I8R2, Q8LP55, A0A1S3FYB6, A0A1S3FZS6, A0A1S3G699, A0A0Q6PUQ7, A0A0Q7E2E7, A0A0Q7I7H2, A0A1S3FYB4, A0A1S3FW29, A0A1S3G403, A0A0T2MN01, A0A0Q8IC41, A0A1H9CCU2, A0A1S3FU82, A0A1S3FX05, A0A1M4MWK1, A0A1H8ZG73, A0A3Q0JEG8, A0A3Q0J9Q0, M1WLK5, M1WM21, M1WJ15, M1WKU1, M1WQZ1, A0A3Q0JCD1, A0A3Q0ISE2, A0A3Q0J8K4, M1WJ16, A0A2Z7CXC8, A0A2Z7D6Z2, A0A2Z7AFH7, A0A1S3D587, A0A0G2HYC6, A0A0G2FQS8, A0A2Z7D8Q9, A0A2Z7CER6, A0A2Z7B0U4, A0A0G2HKP0, A0A0G2FYA3, A0A0G2FNE9, A0A2Z7CJB8, A0A2Z7A354, A0A2Z7BCF0, A0A0G2HTH8, A0A2P5HKQ7, A0A2P5HFP5, A0A2Z6ZZX4, A0A2Z7D973, A0A2Z7AG07, A0A2P5HKH9, A0A2P5HW67, A0A2P5HMQ7, A0A2Z7B1U4, A0A2Z7B0H7, A0A2Z7CYS7, A0A2P5HTN7, A0A2P5HMX3, A0A2P5I8D4, A0A2Z7A3I7, M2YM64, N1PXS3, N1PBL6, M2WMG3, A0A1E5V5N8, A0A1E5WE31, A0A1E5VW96, N1PFX2, A0A3P7PPB3, A0A3P7Q930, A0A0N4U4X9, A0A1E5VZA9, A0A1E5VG01, A0A1E5VSM3, A0A3P7PQ65, A0A0N4UGI5, A0A0N4UGV7, A0A1E5W1E8, A0A1E5VU03, A0A1E5UWE4, A0A0N4UKQ2, A0A0N4U0P8, A0A0N4UIB0, A0A1E5VYJ8, A0A1E5VM23, A0A1E5URK1, A0A0N4UGG1, A0A0N4UDY3, A0A0N4UNZ5, A0A1E5WF62, A0A1E5VK53, A0A1E5UP39, A0A0N4UEW0, A0A0N4U2K8, A0A0N4U723, A0A1E5VK38, A0A1E5V886, A0A1E5W3D1, A0A0N4U3H3, A0A158Q4C2, A0A0N4U9B2, A0A1E5WE45, A0A1E5VDA3, A0A1E5WHY6, A0A0N4ULW1, A0A151GIG1, W7I2Z9, B3MYN7, A0A1E5VK85, A0A1E5UVP0, A0A1E5UR82, B3MF92, B3MFW4, B3LWY2, A0A0P8Y1T9, B3M3A3, A0A1E5ULJ0, A0A1E5VWU8, A0A1E5V9T7, B3M3A4, B3LV56, A0A0M4ESS7, A0A0M4EKR6, A0A1E5V139, A0A1E5ULP8, A0A1E5VY77, A0A0M4EV08, A0A0M5J364, A0A0M4EXF3, A0A1E5WKA8, A0A1E5VIX5, A0A1E5VIW0, A0A0M4EEP6, A0A0M4EME8, A0A0M4ECI2, B3P534, A0A1E5V1A3, A0A1E5VVS7, A0A1E5UY38, B3NSI7, A0A0Q5WP35, A0A0Q5WL19, B3N8M9, A0A1E5VM04, A0A1E5V8G9, A0A1E5VVN3, B3P5C3, B3P535, B3P944, B3P7G9, A0A1W4V338, A0A1E5VKB6, A0A1E5WFT2, A0A1E5W4R6, A0A1W4UYM8, A0A1W4W708, A0A1W4UGH8, A0A1E5WAP0, A0A1E5VM26, A0A1E5WME9, A0A1W4UYB4, A0A1W4U5N1, A0A1W4UGL8, A0A1E5UVF0, A0A1E5VMM0, A0A1E5VU80, A0A1W4U500, A0A1W4V9D3, A0A1W4VW08, A0A1E5VS42, A0A1E5UV74, A0A1E5VIT8, A0A1W4UR70, B4JTG4, B4JSG6, B4J4M5, B4J8W1, A0A1E5VU74, A0A1E5VIF0, A0A1E5VW42, B4JRW8, B4JMU5, B4J4M4, B4JRW7, B4JG50, A0A1E5W8Y3, A0A1E5VS52, A0A1E5WIF4, A0A3B0KC09, A0A3B0KS22, A0A3B0JG58, A0A1E5ULC1, A0A1E5UQP5, A0A1E5VIJ8, A0A3B0JKN7, A0A3B0K9B5, A0A3B0KB54, A0A1E5WCL7, A0A1E5UW57, A0A0D8XPX3, A0A3B0JFB9, A0A3B0K860, A0A3B0JT97, A0A0D8X9K2, A0A0D8XPW4, A0A0D8XME1, A0A3B0JFL0, A0A3B0JKK1, Q9BMD4, Q86P35, A0A0D8X7W5, A0A0D8Y1F7, A0A0D8YBC7, A0A0B4LF37, A0A0B4LEX9, Q9BMD5, Q8IGS2, A0A0D8XDB9, A0A0D8XCM5, A0A0D8XNV8, A1Z7G0, Q1WWD1, B6IDK6, Q9W5Z0, B5X535, A0A0D8XSU8, A0A0D8Y118, A0A0D8Y118, Q32KF1, A1Z7G1, Q8MS37, Q9VCR4, Q9VAG2, A0A0D8XQ45, A0A0D8Y7C0, A0A0D8Y6I0, Q9V9X0, Q9V9X1, A1Z8J3, A1Z8J4, A0A0Q9X7G2, A0A0D8XYW9, A0A0D8Y6A7, A0A0D8XWZ8, B4KR75, A0A0Q9X8J5, B4K8A2, B4KT11, B4K8A0, A0A0D8XEJ7, A0A0D8XTU3, Q54TD6, F0ZKZ0, B4K4N1, B4KT12, B4KMN4, B4L2D3, B4GBV0, A0A163FB68, A0A163C076, A0A162ZDC7, B4GP76, B4GYU7, B4GYU9, B4GGH2, B4GBV1,

B4GNR1, B4H315, B5E0A1, Q29BN3, B5DYT0, B5DYS9, A0A0R3NKK5, Q293D9, B5DKG8, B4HRZ3, B4IM31, B4HNF3, B4HRZ2, B4HZF8, B4IJ01, B4I033, B4HFA6, B4QFU2, A0A0J9TYZ5, A0A0J9TWC5, B4QSN2, B4QB78, B4NSA9, B4QSN1, B4R0T6, A0A0J9R8B2, B4R722, A0A0J9RAB3, B4LMY0, B4MEP6, A0A0Q9WGQ1, B4LZT0, B4LMX9, B4LX01, B4LMZ8, B4MEC9, B4LX02, B4NIE3, B4NMW3, B4NA23, B4MYB6, B4N9U9, B4NMW2, B4NIE6, B4NCY5, B4P7G4, B4PPJ2, A0A0R1E8R0, B4PWJ2, B4P2V3, B4PNE6, B4PNE5, A0A0R1E9F3, B4PN38, A0A0R1DN71, A0A0R1EAK2, A0A0R1E956, A0A093GPD4, A0A093GWQ7, A0A437ACB8, A0A436ZUE2, A0A437A9N2, A0A154NWA8, A0A154PP16, A0A154PDD4, A0A154P8R1, A0A154PGX2, A0A154PF39, A0A2I6QP38, W6UHM1, A0A068WP17, W6UV63, W6UEB0, A0A068WL63, A0A068WDY5, A0A068X3L0, A0A068Y252, A0A068Y2J7, A0A068Y2T5, A0A087VY50, A0A183AP36, D8LQ47, D7FKT5, A0A091JLU0, A0A091JD63, A0A091J4H6, A0A091JSL3, U6GJ11, U6GCD3, U6GPI2, U6GEH8, U6GV22, U6GQW4, U6LNL3, U6M125, U6LQZ6, U6LPX3, U6LG02, U6LEP7, U6M8Q0, G0LEU7, U6M1Y7, U6MAY8, U6LYQ2, U6KE00, U6N3N3, U6N256, U6MUL8, U6MIM2, U6MTA8, U6MUE5, U6MZX5, B0FLX7, U6N5K1, U6H1N4, U6GYZ4, A0A1S6JVG4, U6KPE6, U6L5A4, U6KPH4, A9Q278, U6KZX4, U6KR47, U6L0S8, H9B9Q2, Q9U966, A0A0R3S3W6, A0A0R3RMT7, A0A0R3S175, A0A158Q7L5, A0A0R3S6Y6, A0A0R3RSG8, A0A0R3RQS7, A0A158Q8Q1, A0A0R3RJF9, A0A0R3S0T9, A0A0R3RLA6, A0A158Q7Z5, A0A0R3RNM3, A0A0R3RQF1, A0A0R3RND4, A0A2P7ZU16, A0A2P8A0K2, A0A2P7ZTR3, A0A2P7Z2I6, A0A2P8A4U8, A0A2P8AJH4, A0A2P8A0V9, A0A2P7ZE80, A0A2P7ZEA0, A0A2P7YG32, A0A2P8A7V0, A0A2P7ZAA3, A0A2P7Z3V7, A0A2P8AIG7, A0A2P8A7U5, A0A2P7Z292, A0A2P8ABP9, A0A2P7ZCS8, A0A2P7ZQ48, A0A2P7Z2J1, A0A2P8AE22, A0A2P8A8C3, A0A2P7ZQ26, A0A433T326, A0A3S1BH73, A0A3S0ZKA2, A0A433TIN4, A0A3S0ZE69, A0A3S1BVS8, A0A433SIG5, A0A433U408, A0A433TGA1, A0A433TX18, A0A433U537, A0A433TXC9, A0A3S1HNN2, A0A3S1BNP3, A0A3S1BSL7, A0A3S1BG98, A0A3S1AGJ4, A0A433UC51, A0A3S1CCH7, G8DGE3, R1EI28, R1BAM4, R1B683, R1C548, R1C7G4, R1CY05, R1DNH1, R1F3X8, R1BID0, R1B9P9, R1FUQ2, R1E328, R1BF00, R1D562, A0A0D3I431, R1DXZ7, R1FC05, R1G197, R1F3B4, R1BP77, R1EXU6, R1FN73, R1EEU0, R1C4W0, R1D1K2, U1GDJ7, U1HN00, U1HVD3, A0A2Y9J0Y1, A0A2Y9J0V1, A0A2Y9J9R1, A0A2Y9KTY8, A0A2Y9KI03, A0A2Y9KPG6, A0A2Y9IZ91, A0A2Y9J4D9, A0A444ETX7, A0A444FD73, A0A427BAD6, A0A444E0U3, A0A445MMM3, A0A444DKE0, A0A426Y944, A0A444DNP9, A0A444CQP6, A0A426ZAP5, A0A444DGM2, A0A426XMX6, A0A444DJ88, A0A444FQB9, A0A444EPL5, A0A444DYW9, A0A426Z8Y2, A0A427A7Z6, A0A427ADX1, A0A427A375, A0A426ZAK1, A0A426Y7Y5, A0A444F0S5, A0A426Z0W7, A0A426XTU0, A0A426X112, A0A445MI72, A0A426Y1Q2, A0A426XZ16, A0A444FSB7, A0A444DA88, A0A444CS48, A0A426YR82, A0A444YBE7, A0A444WZY4, A0A444EBR5, A0A444G7H0, A0A444FF33, A0A427BBY0, A0A426YCT9, A0A426X001, A0A426XKV3, A0A426YHE0, A0A444FQX5, A0A444FXT6, A0A444G8Y1, A0A444E0K6, A0A444FSD3, A0A444C1A8, A0A444EZB8, A0A444EYD8, A0A444FT20, A0A426YPX6, A0A444E275, A0A444FI43, A0A426YFG1, A0A427B9L9, A0A445MGF6, A0A426Z6T2, A0A426XGC5, A0A444GI94, A0A444C1E0, A0A444GAN1, A0A444C1T9, A0A444GIB6, A0A444G7E9, W8IAH2, A0A0L8BYH5, A0A2V4WJQ1, A0A285XA72, D1CSF5, A0A1E3VH17, A0A178XXR5, A0A249PID2, A0A2V4ZAK9, A0A2V4ZCS8, A0A1C0SLC3, A0A1C0SWS9, A0A1S1T063, A0A395L2C9, A0A2N8JDI4, A0A2T3DA21, A0A0Q9EJQ9, A0A1G9QSV3, A0A0N4UYF4, A0A0N4VB29, A0A0N4VKQ5, A0A158Q9W4, A0A0N4V3E1, A0A0N4V9C5, A0A0N4VBZ0, A0A0N4V6Q2, A0A0N4V4P5, A0A0N4USF4, A0A0N4UVL6, A0A0N4UTY5, A0A0N4VH10, A0A0N4V8H6, A0A0N4UVC2, A0A158QAV3, A0A158QB01, A0A0N4VNF8, A0A0N4VFH7, A0A0N4UVC1, A0A0N4V445, A0A3P6INW5, A0A1H2U8J0, A0A1Y2LTI9, A0A1Y2M3K0, A0A1Y2LUZ8, A0A1Y2LKS8, A0A1Y2LT57, A0A1Y2M6T7, A0A1Y2M0F2, A0A1Y2LRR1, A0A1Y2M3W5, A0A1Y2LUZ6, A0A1Y2M927, A0A1Y2LUE0, A0A1Y2LJN4, A0A1Y2LMN7, G4WG37, F6USP9, F6ZWI6, F6PR90, F7BK76, A0A3Q2H7K1, A0A3Q2HUE1, F6T3E4, A0A3Q2L7R0, A0A3Q2L1V8, A0A1S3WHJ7, A0A1S2ZDK0, A0A1S3WHE5, A0A1S3A071, A0A1S3W4L1, A0A1S3W4J1, A0A1S2ZMK4, A0A1S3A1S4, A0A1S2ZDJ8, Q29485, Q8LP54, Q8LP53, Q8LP52, Q8LP51, O80355, A0A022QTQ7, A0A022PT68, A0A022R2X9, A0A022QF32, A0A022R014, A0A022RNY5, A0A022QYC6, A0A022QY85, A0A022RTU8, A0A022QN22, A0A022QIR8, A0A022QN16, A0A022R8V5, A0A022Q9S0, A0A022QRE8, A0A022PWI2, A0A022QGP2, A0A022QI21, A0A022R1Z8, A0A022QJW6, A0A022RSP1, A0A022R428, A0A022QNQ9, A0A022QUF4, A0A022R0W8, A0A022QJX3, A0A022QY81, A0A022QT32, A0A022QZT5, A0A022QZQ9, A0A022QW47, A0A022RTP0, A0A022R1U4, A0A022QEX0, A0A022R559, A0A022R2X4, A0A022QPW6, A0A022R1U7, A0A022R4G1, A0A022RYE8, A0A022RS75, A0A022QX25, A0A022QZ29, A0A022QGM9, A0A022QFN7, A0A022R018, A0A022QKT8, A0A022R8M0, A0A074M1L8, A0A0N8GK13, A0A2F0AWT5, A0A3P9A6E8, A0A3P9AKF4, A0A3P8ZCM4, A0A3P8YY57, A0A3P8YIZ1, A0A3P8YIY1, A0A3P8Z4D8, A0A3P8XUT0, A0A3P8X7I2, A0A058ZUL1, A0A059C9G5, A0A059C6C8, A0A058ZUX1, A0A059CAD5, A0A059C8D0, A0A059C8W2, A0A059BMB1, A0A059CF25, A0A059BJE7, A0A059A1V7, A0A059CAF8, A0A059D2A0, A0A058ZTJ3, A0A058ZS00, A0A059BMY5, A0A059C9N1, A0A059CAG3, A0A059BJZ0, A0A059BVD6, A0A059CD96, A0A059D0P0, A0A059CDS6, A0A059C900, A0A059CDJ8, A0A059C9K6, A0A059BCC2, A0A059C904, A0A059C2G3, A0A059C908, A0A059CF20, A0A058ZUY0, A0A059BX54, A0A059BMJ5, A0A059DHG7, A0A059C975, A0A059DG99, A0A059CL14, A0A059CDT6,

A0A059BNH3, A0A059C9N8, A0A058ZSM4, A0A059BVR3, A0A059BUQ9, A0A059BVR0,
A0A059CDK9, A0A059BLH2, A0A059DCZ0, A0A059C7M3, A0A059BB21, A0A059DFD9,
A0A059CZX4, A0A059BAQ1, A0A059CAB5, A0A059BRU7, A0A059C951, A0A059CEQ0,
A0A059CAX2, A0A059BVE0, A0A059A785, A0A059A7T8, A0A059CAX8, A0A058ZQT7,
A0A059C1G2, A0A059A615, A0A059A075, A0A059C0W1, A0A059C9H1, A0A059D1S5,
A0A059C9A3, A0A059C8U8, A0A059B9B7, A0A058ZXR1, A0A059CF34, A0A059BNE6,
A0A059BMI0, A0A059BRV2, A0A059BKX0, A0A059DGE5, A0A059C970, A0A059CDU4,
A0A059BNH7, A0A059A6I8, A0A059C945, A0A058ZVT6, A0A059D0Q2, A0A059C9F8,
A0A059C6U7, A0A059BVV6, A0A059AXJ7, A0A059DG91, A0A059CA18, A0A059BLV9,
A0A059DF87, A0A059C9T6, A0A059DFY6, A0A059CAP5, A0A059A0T8, A0A058ZRN7,
A0A059BN16, A0A059CF13, A0A058ZSA5, A0A059BB75, A0A059CDK1, A0A059BVR4,
A0A059D643, A0A059D1S0, A0A059D249, A0A059CAE0, A0A059BM19, A0A058ZSW3,
A0A059BVR8, A0A058ZTY8, A0A059BTY0, A0A059DG93, A0A059CE63, A0A058ZVN1,
A0A059BVQ8, A0A059CDF2, A0A059BWS9, A0A059D240, A0A059CAE9, A0A059BCB2,
A0A059DGY3, A0A058ZUE3, A0A059BR54, A0A059CE56, A0A059BWP5, A0A059C9H4,
A0A059CDJ4, A0A059CE26, A0A059BLY4, A0A059BRU8, A0A059BAZ9, A0A059CDH8,
A0A059CE51, A0A059BB89, A0A059DGF5, A0A059C9M0, A0A059BC92, A0A059CED7,
A0A059BUD2, A0A059BLZ5, A0A059CUD3, A0A058ZTK4, A0A059CDF8, A0A059BMZ2,
A0A059C982, A0A059C9H8, A0A059C958, A0A059CFL3, A0A059C947, A0A310S483,
A0A059BB94, A0A059CAH7, A0A059CXX9, A0A310SBN6, A0A310SWL1, A0A310SLW1,
A0A059C8V4, A0A059CE41, A0A059BLY9, A0A1Y3B584, A0A1Y3AU99, A0A1Y3AXF6,
A0A059CDR9, A0A059CAB0, A0A059DGX5, A0A1Y3B164, A0A1Y3BLQ2, A0A1Y3AUF8,
A0A059BJD9, A0A059BMJ2, A0A059BNG0, A0A1Y3BLR8, A0A1Y3AZZ7, A0A1Y3AWF6,
A0A059BM31, A0A058ZQZ8, A0A059CPC6, A0A1Y3BKE0, A0A2E4CYV5, A0A093IZQ0, V4MUM3,
A0A059CF29, A0A058ZSW8, A0A059CEE1, V4L7H3, V4KWJ2, V4KQS5, V4KY09, V4MJV0,
A0A059BM22, A0A059CAC4, A0A059A163, V4LNJ7, V4KDR5, V4L028, V4MC52, V4L095, V4L2I0,
A0A059A230, A0A059BVD2, A0A059CEG0, V4KJ04, V4KNB2, V4KHG6, V4M7D2, V4MED4,
A0A059CBT7, A0A059C9B7, A0A059C1I4, V4MBM7, V4LX42, V4LB40, V4MDH2, V4K896,
A0A059BUV4, A0A059D2V1, A0A059D2V0, V4KDS9, V4P511, V4LVA5, V4KWJ7, V4LD36, V4KC43,
A0A059C631, A0A059CD83, A0A059CDT5, V4KHG0, V4L090, V4KDS4, V4L8J2, V4KPI9, V4JV72,
A0A059B8N1, A0A059C5L8, A0A059BMX2, V4MIC9, V4KPJ9, V4JTX9, V4NUT8, V4NAM5,
A0A059A0X2, A0A059BMX6, A0A059AAQ7, V4MH01, V4KFK6, H6C4W5, A0A0D1Y6D0,
A0A059CDH3, A0A059CE67, A0A059BMA5, A0A438NHT6, A0A0D2AIX8, A0A0D2DN60,
A0A059DGF0, A0A059BMG9, A0A059AB79, A0A0D1X4X0, A0A0D1YE49, A0A0D1WNZ7,
A0A059CSN4, A0A059CED3, A0A059C9F2, A0A0D1YQP5, A0A0D1Z1V9, A0A0D2BF00,
A0A059CI09, A0A059BMW7, A0A059BLI8, A0A0D2CZ88, A0A0D2CUE6, A0A0D2D105,
A0A059CE37, A0A059A790, A0A058ZU59, A0A2N9F471, A0A2N9G5U5, A0A2N9ID93,
A0A059BSQ0, A0A059D582, A0A059CEP6, A0A2N9I6Q1, A0A2N9IVV1, A0A2N9F4G1,
A0A059C965, A0A059CB94, A0A059BEM4, A0A2N9F6W7, A0A2N9F3H1, A0A2N9FT24,
A0A059CD78, A0A059CE46, A0A059BLG8, A0A2N9ERT8, A0A2N9G5U0, A0A2N9EZK0,
A0A059DG00, A0A059CF15, A0A059DDF4, A0A2N9I7P8, A0A2N9EYQ2, A0A2N9HI25,
A0A059BJQ8, A0A059B892, A0A059BUD7, A0A2N9I8I7, A0A2N9H741, A0A2N9H8W4,
A0A059BAR2, A0A059BMY1, A0A059AWY3, A0A2N9F7R0, A0A2N9H6F3, A0A2N9H2X2,
A0A059B897, A0A059BJX1, A0A058ZSV0, A0A2N9J533, A0A2N9G8Z2, A0A2N9HS19,
A0A059BNF8, A0A059A0R6, A0A059A823, A0A2N9HL38, A0A2N9IBZ3, A0A2N9G5W6,
A0A059BKW4, A0A059BDD1, A0A059C6B4, A0A2N9HCP4, A0A2N9H5Z2, A0A2N9FDE0,
A0A059DFF0, A0A059DFE3, A0A059BMB6, A0A2N9F3U1, A0A2N9IVM7, A0A2N9FCL3,
A0A059BBN7, A0A059D2I7, A0A059C9R7, A0A2N9HX85, A0A2N9FNS6, A0A2N9FA80,
A0A059BTK0, A0A059BBA1, A0A058ZW23, A0A2N9F6Y2, A0A2N9EZI6, A0A2N9HDA4,
A0A059A1Z3, A0A059BM37, A0A059C9W0, A0A2N9I2U2, A0A2N9IY45, A0A2N9EYP9,
A0A059CF08, A0A059BMH9, A0A059A6J2, A0A2N9HL99, A0A2N9H4B2, A0A2N9HRU4,
A0A059BM34, A0A059BLW8, A0A059AKP5, A0A2N9HI04, A0A2N9FE92, A0A2N9HPG2,
A0A059CAE7, A0A058ZV14, A0A059DFZ6, A0A2N9FX35, A0A2N9H9S5, A0A2N9IUZ4,
A0A059C153, A0A059B9A1, A0A059DFZ4, A0A2N9IV03, A0A2N9I632, A0A2N9J6T9,
A0A059A113, A0A059A235, A0A059C9M3, A0A2N9EYX2, A0A2N9FCP0, A0A2N9F9Y2,
A0A059BMI4, A0A059DGY9, A0A058ZVI2, A0A2N9HTG9, A0A2N9H672, A0A2N9GTW2,
A0A059BMB9, A0A059CB42, A0A059BLZ9, A0A2N9IZ71, A0A2N9HNC1, A0A2N9HE29,
A0A059BUZ3, A0A059C536, A0A059CDU0, A0A2N9FRE3, A0A2N9HZG0, A0A2N9FDT8,
A0A059C8X4, A0A059B232, A0A059AB02, A0A2N9GA03, A0A2N9HIJ0, A0A2N9ICZ8,
A0A058ZZN8, A0A059CBU2, A0A059C1M6, A0A2N9GJI4, A0A2N9IM33, A0A2N9HTB4,
A0A059DGG0, A0A059D5Y0, A0A059CAC9, A0A2N9GJM5, A0A2N9HL23, A0A2N9FCP6,
A0A059C9Q5, A0A059C9M7, A0A059BVV1, A0A2N9G696, A0A2N9IPQ1, A0A2N9GAM8,
A0A058ZZL0, A0A059DG97, A0A059CDS9, A0A2N9J640, A0A2N9FCQ2, A0A2N9EM72,
A0A059BJX7, A0A059CDG7, A0A059CAI8, A0A2N9EE92, A0A2N9ED67, A0A2N9G5P0,
A0A059CDS1, A0A059BLH9, A0A059C8X9, A0A2N9I9D1, A0A2N9HYD5, A0A2N9F021,
A0A059C976, A0A059CEE5, A0A059CAJ3, A0A2N9H5L7, A0A2N9IG02, A0A2N9GLI0,
A0A059BNG6, A0A058ZV47, A0A059BR56, A0A2N9ELE2, A0A2N9ER54, A0A2N9GLH4,

A0A2N9F7N7, A0A2N9HKW5, A0A2N9I6X0, A0A0C9RT62, A0A0C9RVW4, A0A0C9QIV9,
A0A2N9I115, A0A2N9HHV9, A0A2N9I2Z7, A0A0C9RYR6, A0A0C9QF47, A0A0C9RAM8,
A0A2N9EM92, A0A2N9G9P1, A0A2N9EYP4, A0A0C9R7C8, W8PA20, A0A091DZJ9, A0A091DXE1,
A0A2N9H6F1, A0A2N9GWJ5, A0A2N9HS70, A0A091DVM4, A0A091CMD3, A0A093I9I3,
A0A2N9HAB2, A0A2N9FAP6, A0A2N9HI47, A0A093ILG6, A0A093IZP1, A0A1W2EWK8,
A0A2N9EZA0, A0A2N9H5Z0, A0A2N9FCU8, A0A1W2D4E0, Q0G412, A0A2E1H9K8, A0A146MU99,
A0A2N9GXA5, A0A2N9FZ00, A0A2N9ER32, A0A146YM67, A0A146XF35, A0A146SKJ1,
A0A2N9H0J5, A0A2N9IT13, A0A2N9HLN1, A0A146NDC0, A0A146SAR9, A0A3Q2P288,
A0A2N9GJ59, A0A2N9F736, A0A2N9EI38, A0A3Q2U5Q0, A0A146UV90, A0A3Q2PXJ3,
A0A2N9HRI8, A0A2N9FLN9, A0A2N9I3I6, A0A147AF21, A0A146NFQ6, A0A146MVK4,
A0A2N9G737, A0A2N9J704, A0A2N9I596, A0A146NM15, A0A3Q2NV28, A0A146NKH6,
A0A2N9FCQ0, A0A2N9HWH5, A0A2N9GWS3, A0A3Q2QG44, A0A3Q2NUN0, A0A146MX16,
A0A2N9IMS6, A0A2N9I1K9, A0A2N9J9T5, A0A146NV94, A0A146MUA7, A0A3Q2NRI0,
A0A2N9HRW8, A0A2N9HQ34, A0A2N9GA49, A0A146UVF0, A0A146ML14, A0A3Q2P3A5,
A0A2N9GID3, A0A2N9EE63, A0A2N9HNV5, A0A146NEU9, A0A146NDC3, A0A146Y0F0,
A0A2N9IY81, A0A2N9EYQ0, A0A2N9IVN9, A0A146MMW4, A0A146R9E1, A0A146YKS9,
A0A2N9EME6, A0A2N9H6H0, A0A2N9ERJ4, A0A146NEK3, A0A147AX70, A0A3Q2P247,
A0A2N9F311, A0A2N9IBN6, A0A2N9HKN1, A0A146YWT4, A0A146NEL7, A0A3Q2STI2,
A0A2N9EYQ9, A0A2N9IGP9, A0A2N9H563, A0A146YKR1, A0A146ML01, A0A3Q2NUL5,
A0A2N9I8M7, A0A2N9I612, A0A2N9HB53, A0A0S6XK74, A0A0S6X4V7, A0A0C9MAW8,
A0A2N9HHE3, A0A2N9FNV9, A0A2N9GFL6, A0A0S6XHR7, A0A0S6XII5, A0A0S6XQ97,
A0A2N9GUQ4, A0A2N9EYQ8, A0A2N9HFF6, A0A0S6XL07, A0A0C9LMV7, A0A0S6XI06,
A0A2N9GAZ3, A0A2N9GZD3, A0A2N9IE26, A0A0S6XTD5, A0A0S6XM18, A0A0S6XLT8,
A0A2N9HWE4, A0A2N9EZ06, A0A2N9EE70, A0A0S6XMF5, A0A0C9ME04, A0A0S6XI106,
A0A2N9IH59, A0A2N9G6C0, A0A2N9IC01, A0A0S6XNW0, A0A1V1T8U0, A0A1V1T9B7,
A0A2N9HTA6, A0A2N9HEY7, A0A2N9EM85, A0A1V1TBD7, A0A428UEU2, A0A428TVT7,
A0A2N9FTC8, A0A2N9J971, A0A2N9FSD1, A0A428UJD4, A0A428UW00, A0A428U053,
A0A2N9HLB3, A0A2N9HHG3, A0A2N9I338, A0A428U9S6, A0A428TW22, A0A428T8Z1,
A0A2N9FD43, A0A2N9HYX6, A0A2N9HM72, A0A428USM7, A0A428RYB6, A0A428U1S8,
A0A2N9IGI8, A0A2N9IVH2, A0A2N9HDT5, A0A428TDI1, A0A428U0L8, A0A428TDN9,
A0A2N9FXK4, A0A2N9GE58, A0A2N9F4K3, A0A428TDI8, A0A428UAR9, A0A2T4GF04,
A0A2N9G9R4, A0A2N9FW96, A0A2N9GXP3, A0A2T4GEI2, A0A2T4GM20, A0A2T4GQ39,
A0A2N9FYD6, A0A2N9IAR8, A0A2N9F9M6, A0A2T4GZI7, A0A2T4HAV6, A0A2T4H2K6,
A0A2N9GCZ4, A0A2N9G2I6, A0A2N9EYU2, A0A2T4GU55, A0A2T4GS35, A0A2T4GCH5,
A0A2N9G9Q1, A0A2N9IX44, A0A2N9IHR5, A0A2T4GFN6, A0A2T4GL46, A0A2T4GYZ7,
A0A2N9H6L7, A0A2N9HT54, A0A2N9EEA4, A0A2T4GVC4, A0A2T4GS29, A0A2T4GYX5,
A0A2N9I6X5, A0A2N9GG82, A0A2N9FAN8, A0A2T4GET1, A0A2T4H3Y6, A0A2T4GRL8,
A0A2N9G0E5, A0A2N9HDU0, A0A2N9IY90, A0A430M7X9, A0A430KY02, A0A430LYZ3,
A0A2N9JBS8, A0A2N9HW38, A0A2N9HRB8, A0A430L5I8, A0A430LMK1, A0A430LAE0,
A0A2N9GE76, A0A2N9HGR5, A0A2N9HQP2, A0A430M9V2, A0A430LTZ7, A0A430LXM6,
A0A2N9F979, A0A2N9JBR8, A0A2N9I7X6, A0A430LXM7, A0A430L0Q7, A0A430LT59,
A0A2N9IAJ3, A0A2N9EZS8, A0A2N9H640, A0A430L7B2, A0A430LDB8, A0A430LIS3,
A0A2N9G6V6, A0A2N9HI57, A0A2N9H894, A0A430M2H2, A0A430LBT6, A0A430M5A4,
A0A2N9IAS3, A0A2N9F3L2, A0A2N9HEM6, A0A430LG97, A0A3M2RQX3, A0A3M2SJ30,
A0A2N9G7C0, A0A2N9F1Q0, A0A2N9EYP0, A0A3M2S4P6, A0A3M2RRC6, A0A3M2RNA0,
A0A2N9J7F4, A0A2N9H1C2, A0A2N9ERP4, A0A3M2S04, A0A3M2SGY5, A0A3M2RVM1,
A0A2N9HZ89, A0A2N9IA84, A0A2N9IH48, A0A3M2RP84, A0A3M2SAI4, A0A3M2RVN5,
A0A2N9FXU7, A0A2N9H6E0, A0A2N9I4V8, A0A3M2SMU0, A0A3M2SDA7, A0A3M2SDH3,
A0A2N9IER8, A0A2N9IVP2, A0A2N9IHP1, A0A0N0V5S0, A0A0M9EXB1, A0A0N0DCT1,
A0A2N9I4B6, A0A2N9H6F8, A0A2N9IGJ1, A0A0N0V8P4, A0A0M9ETX5, A0A0M9ERF9,
A0A2N9IFD7, A0A2N9J390, A0A2N9HZI8, A0A0M9EKX4, A0A0M9ETU9, A0A0N0DBP2,
A0A2N9IGJ3, A0A2N9FUZ8, A0A2N9G2R4, A0A0M9EQI9, A0A0M9F2P3, A0A395SMB0,
A0A2N9ERG2, A0A2N9GAN0, A0A364JW94, A0A395SU16, A0A395T394, A0A395TAS6,
A0A2H1C6Y1, A0A2H1C2I6, Q9BH09, A0A2I2UAP2, A0A395RLH4, A0A395TAR6, A0A395RR81,
M3WZJ1, M3VWV2, A0A2K5TIV6, M3X3T9, U3K7I1, A0A395T1Z9, A0A395T8X0, A0A395T8W6,
U3K2Y8, U3KBU0, U3KBT4, U3KCE5, A0A238LAN8, A0A395T7Q5, A0A395RWV1, A0A395T6G5,
A0A238LBM3, A0A2A4M1B2, A0A2D5LP88, A0A395SJK3, A0A395T9N8, A0A395TBU9,
A0A0S7BYF0, A0A0K8PA51, A0A226E742, A0A395SWW9, A0A395SJJ1, A0A395T993,
A0A226EIX0, A0A226EJL6, A0A226DUU9, A0A395RYQ6, A0A395TAA6, A0A395RI56,
A0A226ERX6, A0A226EKR3, A0A226EXA3, A0A1L7T250, A0A1L7SNI5, A0A1L7SY16,
A0A226CZ90, A0A226E675, A0A226D8L3, A0A1L7U4Q3, A0A1L7SQ32, A0A1L7TU10,
A0A226DA03, A0A226E8X0, A0A226ES37, A0A1L7UDI1, A0A1L7UAA5, A0A1L7TG43,
A0A226E4B6, A0A226DYP9, A0A226F3C7, A0A1L7TZT8, A0A1L7SRG8, A0A1L7UDC6, A0A1L7
A0A226DMW5, A0A177EZP3, A0A0D2JU71, TI59, A0A1L7TU11, A0A1L7ST20, A0A1L7SY6,
A0A0D2JHM0, A0A178BR81, A0A178BZ24, A0A1L7T2L2, A0A1L7TN71, A0A1L7UJW9,
A0A178BL33, A0A178CTQ1, A0A0D2E424, A0A1L7UHL6, A0A1L7STR4, F9F0W5, F9FQB6,
A0A0C9PLF2, A0A0C9Q7Z9, A0A0C9Q6E7, F9FN55, F9G9P5, F9FRR0, F9FNV4, F9F3M4, F9F4N5,

F9G352, F9G5P5, F9G3D6, F9F676, F9GDQ2, F9FWK6, F9FLK6, F9G1R4, F9G1R3, F9GBZ7, A0A3L6P746, A0A3L6NN57, A0A3L6NQQ4, A0A3L6MW91, A0A3L6NQT5, A0A3L6NPD4, A0A3L6NTI7, A0A3L6NEX4, A0A3L6N5S7, A0A3L6N706, A0A3L6NWN1, A0A3L6NBP9, A0A3L6MWX0, A0A3L6N4Z1, A0A3L6NXP5, A0A3L6N0T9, A0A3L6NTQ6, A0A3L6NQ88, A0A3L6MUU1, X0HDS5, X0IS02, X0HCS8, X0HRY6, X0HVQ1, X0HNT3, X0HXU3, X0HEE6, X0HT53, X0HE86, X0IFF6, X0I6Z5, X0HQT8, X0HZM6, X0HS18, X0HBE0, X0GNF1, X0HVP9, X0HB55, X0H868, X0HRQ2, N4TVA0, N4UWB4, N4UQ87, N4TTM6, N4U5D0, N4U486, N4TXC1, N4TPR8, N4UXC7, N4UER4, N4U8I0, N4V0A9, N4UMR2, N4UFQ1, N4UFD6, N4U504, N4US39, N4TMJ2, N1S2M4, N1RYI2, N1RQ64, N1RQ00, N1S7G0, N1RYM7, N1SAV4, N1SAD8, N1RGZ6, N1S5R5, N1RB09, N1R8K0, N1SB76, N1RPT0, N1RPN7, N1S4B5, N1R9G0, N1RV49, N1RC32, N1S7H6, X0KKH1, X0JD64, X0J7Z6, X0JRR5, X0IXV2, X0K4Y4, X0LFY3, X0IRL6, X0K6S9, X0J8E8, X0J8L0, X0KS72, X0JS17, X0KGE6, X0J5F8, X0KBP3, X0IQZ7, X0LJG6, X0K565, X0K4R2, X0JMF5, A0A0D2XFR8, A0A0D2XY32, A0A0D2Y321, A0A0D2XC3, A0A0D2XY89, A0A0D2X9W2, A0A0D2XKS9, A0A0D2XG03, A0A0D2YBX0, A0A0C4DIY3, A0A0J9W4W2, A0A0D2Y0C7, A0A0J9WPH9, A0A0J9VTQ2, A0A0J9VIA4, A0A0J9UPV1, A0A0J9WAX7, A0A0J9WCE8, A0A0J9UUH4, A0A0D2Y340, A0A0J9W359, A0A0D2Y341, A0A0J9WQB9, A0A0D2YGJ8, A0A0J9VU72, X0AFU5, W9Z4V9, W9ZBD0, X0AIL8, X0ARG8, X0BEV5, X0ATQ4, X0AKC9, X0AP22, W9ZFM9, X0AH58, X0B6E5, X0AJE3, X0AC84, X0B5X6, W9ZBV2, X0A7A2, W9ZGB5, X0A725, W9NLV3, W9PM75, W9NVE9, W9PM48, W9NUL9, W9NXE1, W9NJT9, W9P038, W9PVA4, W9PIK8, W9NWZ0, W9NMU0, W9QB84, W9P2D0, W9PWG0, W9NHW9, W9Q8W3, W9NIE4, W9Q072, W9P3J9, W9PEW3, A0A2H3G3H1, A0A2H3GP16, A0A2H3GPR0, A0A2H3GI26, A0A2H3G3A7, A0A2H3GT41, A0A2H3HFX7, A0A2H3H582, A0A2H3HWB5, A0A2H3G8B5, A0A2H3H7J7, A0A2H3HDQ9, A0A2H3HBA8, A0A2H3HUG8, A0A2H3GTZ9, A0A2H3H1W4, A0A2H3H7B8, A0A2H3GR19, A0A2H3HIX3, X0CBT2, X0CJZ6, X0CA20, X0C0K3, X0BLK2, X0BYZ9, X0BHR3, X0D8W0, X0D9D6, X0BNE2, X0CCJ8, X0D7P5, X0C5I2, X0BWY5, X0BK94, X0C4F8, X0BU43, X0CH27, X0CCJ4, X0BT77, X0BGL4, X0BSM4, X0CBV1, X0KM84, X0KL93, X0LI06, X0LM24, X0L461, X0N5D7, X0MNF5, X0LVS2, X0LLL6, X0KZC8, X0MQ25, X0LJZ4, X0LYG6, X0MWI5, X0MGF6, X0MLD1, X0MQJ9, W9JZF8, W9K3B2, W9K2I6, W9KHK3, W9JKU5, W9KL95, W9KMV3, W9KB71, W9LDU1, W9K179, W9JPG0, W9KU91, W9KWA8, W9K2L5, W9JY72, W9JLD1, W9JH38, W9JK71, A0A420PSH8, A0A420PDU2, A0A2H3SXG2, A0A420PMW4, A0A2H3TNB9, A0A2H3TUT4, A0A2H3TT16, A0A2H3TGN6, A0A420MLC5, A0A420SEB3, A0A2H3TL83, A0A420S1Y6, A0A420QWS3, A0A420PGL0, A0A420NGZ2, A0A420R9X9, A0A420QHW6, A0A420S0P8, A0A420TXI9, A0A420UC75, A0A420MBT8, A0A420PHU3, A0A420QP35, A0A420P6T6, A0A420QIK4, A0A420PYP6, A0A2H3T198, A0A420QQV1, A0A420NBX5, A0A420NZN8, A0A420QQT6, A0A420RGE4, A0A420PWD7, A0A2H3TZQ8, A0A420NEW3, A0A2H3SMM6, A0A420RVH4, A0A420NNM5, A0A2H3T9F1, A0A2H3TSH4, A0A420RN85, A0A420N964, A0A420MDX2, A0A420NZR8, A0A2H3TND6, A0A2H3SPH1, A0A2H3TLK4, A0A420R6D6, A0A420QGY8, A0A420P5A3, A0A420NJK8, A0A2H3TLA9, A0A420MLJ4, A0A2H3U2W3, A0A420R1M2, A0A420UEN2, A0A420SA71, A0A420PG81, A0A420NEU8, A0A2H3T2A7, A0A420U4W6, A0A420PC63, A0A420Q8J1, A0A420U9L0, A0A420N211, A0A2H3T2B5, A0A420SKN9, A0A420RIQ3, A0A2H3T2H0, A0A420MQK5, A0A420S1Y5, A0A2H3SKQ3, A0A420RSV8, A0A420QNM7, A0A420U9X9, A0A420QBG3, A0A1B8AI36, A0A1B8AIV6, A0A1B8AQ51, A0A1B8AHP8, A0A1B8B148, A0A1B8AZG1, A0A1B8AZ43, A0A1B8B687, A0A1B8AHJ0, A0A1B8ARR3, A0A1B8B037, A0A1B8ARV5, A0A1B8AQS5, A0A1B8ADY5, A0A1B8AE77, A0A1B8AH23, A0A1L7VUI1, A0A1L7VQT1, A0A1L7VTN8, A0A1L7VQ64, A0A1L7VRM1, A0A1L7W234, A0A1L7W7F8, A0A1L7W3Q1, A0A1L7VZE6, A0A1L7W7T0, A0A1L7W068, A0A1L7VBG9, A0A1L7VJ89, A0A1L7V6L5, A0A1L7VLJ1, A0A1L7W6T5, A0A1L7W2B6, A0A1L7W3Q7, A0A1L7VAZ6, A0A1L7W9S2, A0A1L7VG50, A0A1L7V558, A0A1L7VE71, A0A1L7VBJ5, K3V6C2, K3VNW8, K3UVA9, K3VI86, K3VD86, K3VSF8, K3VZG0, K3W149, K3UVV0, K3VF03, K3VSH8, K3V8J7, K3W1U8, K3UBY1, K3VV23, K3V722, K3UTP7, K3VPR6, K3VW92, K3VVL6, A0A096PED2, A0A428RK34, A0A428SD27, A0A428RDV5, A0A428RQ68, A0A428SN67, A0A428Q5F5, A0A428SNN1, A0A428S0J4, A0A428RZR3, A0A428RSR8, A0A428RXQ1, A0A428RX08, A0A428RZJ5, A0A428SEZ3, A0A428RPS7, A0A428RNL1, A0A428RDW7, A0A428UIA3, A0A428SWL5, A0A428U3R5, A0A428T156, A0A428U3Z4, A0A428TXX9, A0A428SFD7, A0A428TWR6, A0A428UIJ1, A0A428SQQ5, A0A428U227, A0A428UCR8, A0A428THD3, A0A428S8Z0, A0A428UDE6, A0A428SKX5, A0A428PKQ2, A0A428QUF4, A0A428P7J0, A0A428P7H3, A0A428NDT7, A0A428PH59, A0A428Q7Z0, A0A428QDG1, A0A428RAS8, A0A428NYA2, A0A428NM38, A0A428Q0Y4, A0A428PKP7, A0A428PTI2, A0A428NUP9, A0A428PR63, A0A428P8A4, A0A428R4H3, A0A428NIV0, A0A428NZ95, A0A428PCW5, A0A428Q8W1, A0A428NR66, A0A428NN65, A0A428QD28, A0A428QWP2, A0A428PBY7, A0A428PA97, A0A428QKE9, A0A428P7T0, A0A428NXE6, A0A428P4U5, A0A428QQ80, A0A428PCY9, A0A428NSA9, A0A428PX74, A0A428NS70, A0A395MGQ2, A0A395MGA8, A0A395M7J9, A0A395MAG0, A0A395MLX9, A0A395N4U8, A0A395MHX2, A0A395N159, A0A395M5H5, A0A395MHI4, A0A395MIF4, A0A395MBX0, A0A395N2D5, A0A395N4Y5, A0A395N3C1, A0A395MVX4, A0A395MI62, A0A395MVQ6, A0A395MCF6, A0A395N1D8, A0A395N4X6, A0A395MZD0, A0A366S714, A0A366QWA4, A0A366QY56, A0A366S516, A0A366R509, A0A366S9E0, A0A366S648, A0A366S7J1, A0A366S6E2, A0A366RU34, A0A366SAJ5, A0A366S5H5, A0A366RLX0, A0A366RZB1,

A0A366RSR3, A0A366S6U1, A0A366SA36, A0A366S608, A0A366R259, A0A090N5T3, A0A090MBD1, A0A090N5N0, W9I3C2, W9HY89, W9IHK5, W9HQZ2, W9IYB6, W9I981, W9IXH4, W9IFQ1, W9HPW8, W9HU54, W9HPA2, W9J633, W9IFB4, W9J1V2, W9IC02, W9HM81, A0A395SCF9, A0A395SN15, A0A395SBE5, A0A395S6D9, A0A395SH08, A0A395SBA6, A0A395RVT2, A0A395RRP8, A0A395SJC5, A0A395SIC0, A0A395RMJ7, A0A395RYB3, A0A395RVS6, A0A395SNH5, A0A395SDT1, A0A395S6D1, A0A395SDH6, A0A2L2U374, A0A2L2TJ64, A0A2L2U3G9, A0A2L2TQW0, A0A2L2TFB0, A0A2L2TKB7, A0A2L2TJF0, A0A2L2TLG9, A0A2L2TPW8, A0A2L2U3E5, A0A2L2T6R1, A0A2L2TZ15, A0A2L2TR51, A0A2L2T472, A0A2L2SR66, A0A2L2TU58, A0A2L2T569, A0A2L2U3K6, A0A2L2SSM8, A0A2L2TMX3, A0A2L2TCF7, A0A3G4ZYX2, J3PC95, A0A2M7N8H7, Q90978, Q90865, A0A1D5PAR6, F1NWX6, R4GMH5, E1C8A1, F1NUN5, A0A3Q2U5D1, Q788Q2, A0A315UVV8, A0A315UQL6, A0A315VVX5, A0A315UYF8, A0A315UVQ5, A0A1G0KYN1, A0A2D5I3I9, A0A2D5PM94, A0A2E1JMT7, G3N792, G3NR28, G3Q8D9, G3NR40, G3NX83, G3NR48, G3NX96, G3N8R7, G3PGI4, A0A093F083, A0A1H7ZTR7, A0A2T6B2Z8, A0A3S3UUA3, A0A451GG88, A0A1N7QCJ4, A0A3P3DPT3, A0A398BPI3, A0A398BSF3, A0A358B3Q1, S8CSG8, S8BXM1, S8ECB0, A0A0J9XCZ4, S0E9M1, S0EAW3, S0E050, S0DSB2, S0E1P0, S0DJL6, S0ECM0, S0DSY7, S0E5X7, S0EAP9, S0DSC6, S0EMX3, S0E357, S0E2Q5, S0ECL2, S0E6U9, S0DJP2, S0DZF4, S0EFD2, S0E497, A0A0I9Z138, A0A0I9YAH3, A0A0I9XHA9, A0A0I9Y8Q9, A0A0I9YM17, A0A0I9XFP3, A0A0J0BUY0, A0A2H3RKI8, A0A2H3SN28, A0A0J0CHN8, A0A2H3RR38, A0A2H3SWB6, AA0I9X760, A0A2H3S7W2, A0A0J0CQW4, A0A2H3S359, A0A2H3SM63, A0A2H3RNJ8, A0A2H3RMB7, A0A2H3SWM1, A0A0J0CT57, A0A2H3RRY9, AA0I9Y942, A0A2H3RGR6, A0A0I9XEV3, A0A2H3RUA2, A0A0I9XAZ3, A0A0J0BYF6, A0A2H3RVF2, A0A2H3RW1, A0A0I9XY78, A0A0I9YHM8, A0A2H3RR57, A0A0I9X911, A0A0I9XJR0, A0A0J0C0013, A0A2H3RVE0, A0A2H3SQE6, A0A0I9XAJ6, A0A2H3SHG6, A0A2H3R980, A0A0I9XDN8, A0A420SS68, A0A420TP29, A0A420UB76, A0A365NIV2, A0A365N6M1, A0A365MMV3, A0A365N4F2, A0A365NNN5, A0A365ND98, A0A420T6U9, A0A365NJW8, A0A420SEE3, A0A365N416, A0A365NIH4, A0A420SZ33, A0A365MQF6, A0A420UA77, A0A365MQ14, A0A365MMJ0, A0A420SDB1, A0A365MPJ1, A0A365N099, A0A365NDF6, A0A420SSE2, A0A420T6Q6, A0A420U9Y0, A0A365N1D1, A0A420T9A6, A0A365N275, A0A365MYB1, A0A420TU20, A0A420TTT9, A0A365MRF5, A0A365MKN4, A0A420SGE2, A0A420TM01, A0A420SQ44, A0A365N043, A0A365NGM1, A0A420SEZ4, A0A420SPD6, A0A420SWC9, A0A365MMK9, W7M0V8, W7MQW8, W7LIK3, W7N541, A0A139YBX2, W7MTU5, W7NCD1, W7N6Q6, W7MUN6, W7ME54, W7MSX0, W7MR98, W7MZZ1, W7N269, W7N008, W7LSV5, W7N837, W7LEM9, W7MXJ6, A0A139YBM8, W7M9D1, W7MZW8, A0A366Q8Q7, A0A366Q909, A0A366R737, A0A366S001, A0A366QHY9, A0A366PSC3, A0A366R685, A0A366NS06, A0A366NR83, A0A366RE72, A0A366P026, A0A366P298, A0A366Q4J4, A0A366QZP0, A0A366Q9V0, A0A366PGF9, A0A366RYF1, A0A366RSA3, A0A366QJB0, A0A366RE50, A0A366QC02, A0A366PJS9, A0A366PTB2, A0A366Q4I7, A0A366QQ61, A0A366Q3H7, A0A366Q2F5, A0A366RV94, A0A366RKF4, A0A366PYT4, A0A366PSP3, A0A366R173, A0A366RE58, A0A366QPK3, A0A366PGR0, A0A366R225, A0A2K0W5D0, A0A2K0UTI6, A0A2K0W931, A0A2K0WC09, A0A2K0UTH2, A0A2K0WV95, A0A2K0WIM1, A0A2K0W2B0, A0A2K0W2K6, A0A2K0VVG2, A0A2K0W1N5, A0A2K0UTG7, A0A2K0W8T1, A0A2K0W365, A0A2K0VVT0, A0A2K0WAU9, A0A2K0W3Y3, I1S305, A0A098DHT5, A0A098DJ50, I1RTL3, I1S3P5, A0A098DZ54, I1RLE4, I1S5T9, I1RTD2, I1RV98, I1S3P4, A0A098D7I4, A0A098DJX2, A0A098DZM5, I1RA55, I1RXM0, I1R9J0, I1RKL8, I1S2Z6, A0A1C3YKN6, A0A098E223, A0A1C3YHH6, A0A1C3YKD6, A0A1C3YKB1, A0A2H3HMC5, A0A2H3GRJ6, A0A2H3HSA2, A0A2H3GYF5, A0A2H3FZY4, A0A2H3HDH3, A0A2H3G941, A0A2H3H4N8, A0A2H3GNB0, A0A2H3GIG1, A0A2H3FML8, A0A2H3G768, A0A2H3H9N3, A0A2H3HFP0, A0A2H3GGM8, A0A2H3FHF7, A0A2H3GHH8, A0A397VR36, A0A397W4J7, A0A397VYK2, S3D022, S3CIG6, S3D8B4, S3DNA8, H0EQA9, K3WFA2, K3WFA4, K3WN51, K3WWN0, K3WCW4, K3W5W5, K3WZR8, K3WJD0, K3WPX5, K3WPX2, K3WZD7, K3WD79, K3XBK6, K3WN48, K3WWN3, K3WI68, K3WRX0, K3WI73, K3WCV9, K3WY68, K3WCW1, K3WPX3, K3X667, K3WHY8, K3WGZ7, K3WCW6, K3WI69, K3WI70, K3WRY9, K3XDL0, K3WCV8, K3WP93, K3WPX4, K3WGZ2, K3WCW3, K3WCU2, K3WCU9, K3WK48, K3WFA3, A0A183BI04, A0A183CL17, A0A183BNL9, A0A183CQJ0, A0A183CDV8, A0A183CRD4, A0A183CBM9, A0A183BUJ7, A0A183BWP9, A0A183CDW0, A0A183CBA0, A0A183BWW1, A0A1A9VE33, A0A1A9UM99, A0A1A9UMI6, A0A1A9UK14, A0A1A9UT06, A0A1A9UM92, A0A1A9UV32, A0A1A9WZX2, A0A1A9WYV2, A0A1A9X167, A0A1A9X2J2, A0A1A9WP94, A0A1A9X5N1, A0A1A9X170, A0A1A9W7X4, A0A1A9XI74, A0A1A9XI75, A0A1A9YJ04, A0A1A9XI83, A0A1A9XZJ7, A0A1A9XDF9, A0A1A9XLY9, A0A1A9Y8K0, A0A1B0FQZ0, A0A1B0G5Z0, A0A1B0FMH8, A0A1B0F9A8, A0A1B0FN27, A0A1B0FJ31, A0A1B0FF31, A0A1B0ACN4, A0A1A9ZN42, A0A1B0AFV3, A0A1A9Z7T1, A0A1B0ACN9, A0A1A9Z0F1, A0A1B0ACN0, A0A1B0AAP1, A0A1B0AYB5, A0A1B0B913, A0A1B0BQV5, A0A1B0BRF1, A0A1B0AMM5, A0A1B0B615, A0A1B0BSL7, C6ZRQ3, C6ZS29, K7L2L4, I1L742, A0A0R0EVN8, I1KE73, I1LSR9, I1LSR6, A0A0R0KG24, K7M8Z4, K7KXE1, I1LSX3, I1MIG9, A0A0R0HEP2, K7KXI5, A0A0R0H4D6, I1ME78, K7KXH0, K7LCV5, IM78, K7M2T9, I1LST1, A0A0R0L9K9, K7M1S0, K7K3A5, I1KZA4, K7M1R9, K7KBW2, A0A0R0FWY9, K7LU18, A0A0R0IPR8, I1KE80, A0A0R0JLU1, K7K3A6, I1K7Y3, K7LU19, K7LUX6, I1M2F1, A0A0R0IHT4, K7K9A9, I1KEB9, A0A0R0GW83, A0A0R0JNK4, K7LUW1, K7KXF2, I1LSY1, A0A0R0KJ29, K7KXI4, I1LGT5, K7MZ69, A0A0R0HDR1, I1KEC5, I1KE67, K7M2F6, C6ZRW7,

A0A0R0IRG6, K7M2E9, A0A0R0H8A8, I1KE60, A0A0R0JLS9, K7M8T0, K7MCU5, K7KXH6, A0A0R0HHK1, A0A0R0H240, K7L050, I1M2E7, K7LAQ9, A0A0R0HUZ3, A0A0R0HHN2, A0A0R0H5B6, K7LAS7, I1KEA9, A0A0R0HHS7, A0A0R0KYQ5, A0A0R0JT19, K7LUV4, K7KXC8, A0A0R0HFB3, K7M046, A0A0R0HDU4, I1MKV1, A0A0R0JM62, A0A0R0JM46, K7M1R8, IM79, K7M8Z5, A0A0R0H590, A0A0R0EG65, K7MCU6, A0A0R0J530, A0A0R0HEH1, A0A0R0JRN4, K7LUW3, I1JTI1, K7MCU7, A0A0R0JRK8, K7M2F1, A0A0R0INR7, A0A0R0JLL7, K7K3A1, A0A0R0FWT7, A0A0R0H6A2, K7KXD7, K7LQJ4, I1KZA6, A0A0R0EHM4, K7LCV6, A0A0R0JLQ4, A0A0R0FXR9, I1LSY2, K7KXH7, A0A0R0H7L6, K7LUX4, I1M2F0, A0A0R0H5I9, A0A0R0K7P2, A0A0R0GTK5, K7KBW3, I1KE90, K7KXI2, A0A0R0H043, K7M1R3, I1KF87, K7KDF6, K7KXH2, A0A0R0JLC9, I1M3F1, A0A0R0JVL9, A0A0R0HEE2, A0A0R0HFQ6, A0A0R0G425, K7KXF3, A0A0R0H539, I1KE88, I1KE68, A0A0R0J260, I1LSW7, I1M5U0, K7KI11, I1KE70, I1LAB6, A0A0R0J0N7, K7LAS8, I1KKX7, K7KXE2, A0A0R0KD14, K7MCT9, I1LSX8, K7LAQ6, A0A0R0G5B0, K7KXH9, A0A0R0JLZ5, A0A0R0H884, K7L8G9, A0A0R0FXA7, I1KZ76, K7LUV3, A0A0R0IC73, K7LUY2, K7KXH5, K7LVZ6, I1KZ77, K7M2F0, I1JNE6, A0A0R0EWT5, K7K3A2, I1MNZ4, K7M1R5, A0A0R0JTU4, I1M2E9, K7MYD3, I1JPX6, K7LVZ4, A0A0R0H5T0, I1LSR5, I1KEB0, K7LUW9, K7M1R6, I1KQR8, A0A0R0H5Y2, I1M2E5, K7LVZ3, K7LUS0, I1LLA6, K7KXD3, A0A0R0JLM5, K7KD19, C6ZRU8, K7MG77, I1LSY4, A0A0R0GV60, I1KEB1, A0A0R0H7N3, A0A0R0G5X7, A0A0R0H529, A0A0R0HEQ7, K7LUV6, A0A0R0JRU4, I1KEB7, A0A0R0H5H4, A0A0R0L9J9, A0A0R0H871, A0A0R0FNK4, K7LUV7, A0A0R0HHZ0, A0A0R0JLR9, K7KD21, K7M1R7, A0A0R0GTN5, K7KXI0, K7MCU9, K7M1R2, I1KE64, A0A0R0LIX3, K7KT18, K7LUW8, I1KEA7, A0A0R0H5K4, A0A0R0HFT7, A0A0R0JT32, A0A368UHR2, K7KXH1, A0A445IKH7, A0A445K4J5, A0A445IBB4, A0A445IC32, A0A445IBG5, A0A445KEL5, A0A445I9N1, A0A445IA22, A0A445KEC4, A0A0B2R8A6, A0A0B2RTJ3, A0A0B2R410, A0A0B2RYE8, A0A0B2R3Z9, A0A0B2NQG4, A0A0B2SR89, A0A0B2SHQ9, A0A0B2Q0P0, A0A0B2QFX4, A0A445LDU1, A0A0B2PJD4, A0A0B2PLC0, A0A0B2R8Z3, A0A0B2P2R6, A0A0B2SNF0, A0A0B2QYM0, A0A445KEJ3, A0A0B2SG46, A0A0B2SPZ0, A0A0B2NXR2, A0A0B2S035, A0A0B2S336, A0A0B2SSB0, A0A445GWF0, A0A445IFF3, A0A445HSY4, A0A445IB72, A0A0B2RZB0, A0A445IBT0, A0A0B2SIU2, A0A0B2PEM2, A0A0B2PA07, A0A0B2RQ81, A0A0B2QDD9, A0A0B2NSG5, A0A0B2PTL8, A0A0B2PCY8, A0A0B2QIS7, A0A0B2PHY5, A0A0B2QXQ7, A0A0B2SRB5, A0A0B2QH24, A0A0B2QEU6, A0A0B2SLN0, A0A0B2NSK2, A0A0B2PEM8, A0A0B2PD35, A0A0B2R16, A0A445L056, A0A445IBD0, A0A445KEK2, A0A0B2R2T4, A0A445JAL8, A0A445HQ61, A0A445JPE3, A0A445FGF3, A0A445M1W2, A0A445HN76, A0A445IA45, A0A445HQC5, A0A445HQE3, A0A445JV37, A0A445HPY3, A0A445KEI0, A0A445IB85, A0A445KE92, A0A445HPU3, A0A445HQB7, A0A445KEQ7, A0A445KVH1, A0A445KEH0, A0A0B2RLN3, A0A445KEG9, A0A445KEI1, A0A445L055, A0A445I607, A0A445HPX9, A0A445JAP1, A0A0B2QGK7, A0A445KF02, A0A445GWE9, A0A445JAK5, A0A445KV70, A0A445GGC1, A0A445L8H0, A0A445HSS9, A0A445KZL6, A0A445IZ56, A0A445KF53, A0A0B2PCH0, A0A0B2QFX9, A0A0B2P0P0, A0A0B2RPE1, A0A0B2NX34, A0A0B2P9T3, A0A0B2S2G1, A0A445I3H0, A0A445HXA0, A0A445KEJ2, A0A0B2RKG5, A0A0B2QGL4, A0A0B2P4X3, A0A445IZ50, A0A445IZ45, A0A445HPU8, A0A445IA11, A0A445KED2, A0A445KEI5, A0A445I9L6, A0A445IBA1, A0A445L054, A0A445GQ74, A0A445HQD2, A0A445GQ03, A0A445HQD8, A0A445HQC1, A0A445HQK7, A0A445HST5, A0A445KF01, A0A445HPX5, A0A445JPF3, A0A445KEN4, A0A445KEU4, A0A445IB73, A0A445FIR5, A0A445IBH5, A0A445GWZ7, A0A445I9N6, A0A445JPH7, A0A445HQ82, A0A445KET6, A0A445KVD1, A0A445L5S4, A0A445IBB3, A0A445LQP4, A0A0B2PDS8, A0A0B2QBU1, A0A445KEM0, A0A445HQA5, A0A445K4C6, A0A445I9M8, A0A445HQG0, A0A445JPL0, A0A445JAK4, A0A445KEF7, A0A445JPB5, A0A0B2RX25, A0A0B2SJF3, A0A0B2SL58, A0A0B2QH31, A0A445FNQ5, A0A445HPS5, A0A445KEW3, A0A445I3X8, A0A445FNS9, A0A445LBW9, A0A445L5L3, A0A445HQ49, A0A445HQ40, A0A445HPZ2, A0A445KED1, A0A445HQK9, A0A445HSU7, A0A445IB74, A0A445GQ81, A0A445KEK1, A0A445KEA4, A0A445HSU4, A0A445HN83, A0A0B2R9H1, A0A0B2PX39, A0A0B2PQ09, A0A0B2R9G6, A0A0B2NXL9, A0A0B2RS26, A0A0B2QYI7, A0A0B2QVJ9, A0A0B2NXT7, A0A0B2QCR2, A0A0B2PX80, A0A445KE89, A0A445HQ13, A0A445GQ70, A0A445KES8, A0A445HQG2, A0A0B2SMR2, A0A0B2R2T0, A0A445JAN3, A0A445KED5, A0A0B2RR49, A0A445JPM6, A0A445HQ19, A0A445IC34, A0A445M1S7, A0A445I3D7, A0A445JJ41, A0A0B2PNA6, A0A0B2R151, A0A445HT18, A0A445JPC2, A0A445IC64, A0A445FF01, A0A0B2QCR6, A0A445IB88, A0A445KEM6, A0A445KEJ0, A0A445F251, A0A445GJ58, A0A445HSW1, A0A445HPQ4, A0A445JPA6, A0A445HSU3, A0A445L7J1, A0A0B2PE82, A0A445HPU5, A0A445J754, A0A445HPW8, A0A445KEB3, A0A445GQ56, A0A445HPX8, A0A445HSU0, A0A445I9M0, A0A445HPV7, A0A445HQK5, A0A445HGW0, A0A445HQ03, A0A445K7Z2, A0A445KF30, A0A445I9P9, A0A445HPY4, A0A445JP99, A0A445JYL2, A0A445KEJ4, A0A445I9P3, A0A445L7J0, A0A445JB06, A0A445KEB9, A0A445IB86, A0A445HQF8, A0A445GWL4, A0A445L9S1, A0A445HSV5, A0A445KEE3, A0A445KEX3, A0A445JTF8, A0A445JB16, A0A445KET4, A0A445JXZ8, A0A0B2SV99, A0A0B2PTA3, A0A445GQ60, A0A445HPZ9, A0A445HQE5, A0A445JPB6, A0A445JPB2, A0A445KGH5, A0A445HQD5, A0A445JYL7, A0A445KEK3, A0A0B2RV84, A0A445IZ62, A0A445HQ72, A0A0B2NU47, A0A445M242, A0A0B2PI23, A0A0B2NVK2, A0A0B2NXP7, A0A445JPA5, A0A445KEY2, A0A445GWI7, A0A0B2RRS1, A0A445GWF9, A0A445KEJ8, A0A0B2QVY8, A0A445HPR4, A0A0B2PU27, A0A445M229, A0A0B2SLA2, A0A445GM55, A0A0B2PGJ9, A0A445GMK7,

A0A0B2R815, A0A445GWF8, A0A445IC59, A0A2P5PXQ4, A0A2P5R7A8, A0A2P5RMU3,
A0A445GM53, A0A445KEG8, A0A445HQK6, A0A2P5RU57, A0A2P5RLV9, A0A2P5XRW6,
A0A445I9S8, A0A0B2R405, A0A445KEG0, A0A2P5XRW3, A0A2P5R7B4, A0A2P5WKW0,
A0A139AN84, A0A139AWG3, A0A3P7LQ98, A0A2P5VXE2, A0A2P5VQP7, A0A2P5QAS2,
A0A3P6SB28, A0A183E3M5, A0A183DSQ9, A0A1U8LTN4, A0A1U8IY86, A0A1U8JWT7,
A0A183D9Z8, A0A3P6S9V6, A0A3P7MR12, A0A1U8MSL2, A0A1U8NIT3, A0A1U8JW83,
A0A183D9N7, A0A183CUV3, A0A183CZ86, A0A1U8M088, A0A1U8PII4, A0A1U8MW63,
A0A183CVQ5, A0A183E7Y0, A0A183D9A1, A0A1U8PIK8, A0A1U8PIH7, A0A1U8NKW8,
A0A183CUC2, A0A183DYS1, A0A183D4T0, A0A1U8KUL9, A0A1U8MSI7, A0A1U8MQ96,
A0A183CZ38, A0A183EWR6, A0A183D6N3, A0A1U8MJ01, A0A1U8INS0, A0A1U8J3Z6,
A0A183DDG5, A0A183DJR2, A0A183D2S8, A0A1U8MZ75, A0A1U8J8V8, A0A1U8K7I4,
A0A150G4C6, A0A150G869, A0A150GQC4, A0A1U8HRC6, A0A1U8JD70, A0A1U8K7G9,
A0A150GM43, A0A150GGI9, A0A150FY45, A0A1U8MW53, A0A1U8M3G9, A0A1U8PS02,
A0A150G7V9, A0A150G6Z0, A0A150GXZ1, A0A1U8MWK7, A0A1U8IQI9, A0A1U8IQ79,
A0A150GXR5, A0A150GAR7, A0A150G2N9, A0A1U8J5M7, A0A1U8PL10, A0A1U8PJ03,
A0A150G968, A0A150FX17, A0A150G2Z2, A0A1U8KPI2, A0A1U8KDH7, A0A1U8KPN3,
A0A150GY18, A0A150FX43, A0A150G717, A0A1U8NGI9, A0A1U8MQB6, A0A1U8N4R6,
A0A150GGC8, A0A150GQP5, A0A150GGE4, A0A1U8KIK7, A0A1U8NU95, A0A1U8K568,
A0A150G565, A0A150G8B8, A0A150FU74, A0A1U8JUG2, A0A1U8KP21, A0A1U8HJH7,
A0A452H3F3, A0A452H966, A0A452H952, G3RXF7, A0A1U8MU48, A0A1U8J417, A0A1U8MTB7,
G3R4W6, G3RNU9, G3R2X1, A0A2I2ZIP3, A0A1U8IZ76, A0A1U8MSL8, A0A1U8KFJ8,
A0A2I2YSL6, G3RZ73, A0A2I2ZYB7, G3QLL7, A0A1U8IIC3, A0A1U8PRU7, I0B675, A0A1U8NVM4,
A0A0B0N1R7, A0A0B0PPF2, A0A0B0NU75, A0A1U8N3Z5, A0A1U8J436, A0A1U8MWV1,
A0A0B0MYX5, A0A0B0MTX0, A0A0B0MYU6, A0A1U8L9V7, A0A1U8MU65, A0A1U8K7H3,
A0A0B0MZL4, A0A0B0NP12, A0A0B0N0U6, A0A1U8J5E0, A0A1U8NTW1, A0A1U8J456,
A0A0B0N855, A0A0B0PYF7, A0A0B0N5G9, A0A1U8LQA8, A0A1U8LU33, A0A1U8MJ39,
A0A2P5QME1, A0A2P5WSV9, A0A2P5R530, A0A1U8KJM4, A0A1U8N710, A0A1U8IIU3,
A0A2P5QAQ1, A0A2P5RJB5, A0A2P5PX52, A0A1U8HZZ8, A0A1U8JME3, A0A1U8MSV8,
A0A2P5R799, A0A2P5XQ00, A0A2P5R525, A0A1U8LQ71, A0A1U8KI27, A0A1U8N0I2,
A0A2P5YJR7, A0A2P5WUP4, A0A2P5XQE1, A0A1U8NVW2, A0A1U8JTJ3, A0A1U8MU44,
A0A2P5W537, A0A2P5QYR4, A0A2P5RJD9, A0A1U8HXT9, A0A1U8KN26, A0A1U8NAH6,
A0A2P5SAL6, A0A2P5R4Z5, A0A2P5RMX0, A0A1U8MPV7, A0A1U8NWF2, A0A1U8JA35,
A0A2P5Y4V6, A0A2P5XRT3, A0A2P5RJC7, A0A1U8MWB9, A0A1U8NWR2, A0A1U8MU69,
A0A2P5XLL9, A0A2P5QP15, A0A2P5YQK4, A0A1U8N0D3, A0A1U8MXQ1, A0A1U8KM96,
A0A2P5Q2I3, A0A2P5W0S5, A0A2P5RX37, A0A1U8NTW9, A0A1U8KM40, A0A1U8KUG4,
A0A2P5RFB1, A0A2P5XRP7, A0A2P5YMC7, A0A1U8MSS6, A0A1U8HR08, A0A2P0JA21,
A0A2P5XPY8, A0A2P5W117, A0A2P5Q5R1, A0A1U8N932, A0A1U8LW85, A0A1U8NVG7,
A0A2P5QZB7, A0A2P5Y5I5, A0A2P5SRC9, A0A1U8MT98, A0A1U8L9U6, A0A1U8NWQ7,
A0A2P5RY44, A0A2P5WP31, A0A2P5RWS6, A0A1U8JLD2, A0A1U8NWF7, A0A1U8JPV5,
A0A2P5RMT2, A0A2P5Y6U2, A0A2P5R4X6, A0A1U8PJ85, A0A1U8IIP2, A0A1U8NU86, A0A1U8IJ22,
A0A2P5YX52, A0A2P5XNK6, A0A2P5WUK6, A0A0D2NHR6, A0A0D2S9W7, A0A0D2SHQ6,
A0A2P5XT89, A0A2P5SBC1, A0A2P5SP55, A0A0D2R293, A0A0D2UMW3, A0A0D2U925,
A0A2P5W510, A0A2P5RJE1, A0A2P5QIM8, A0A0D2UF09, A0A0D2R2A3, A0A0D2N3S2,
A0A2P5SJY1, A0A2P5QJX4, A0A2P5SM011, A0A0D2Q7B3, A0A0D2NJM3, A0A0D2Q7C6,
A0A2P5QSI7, A0A2P5WKV8, A0A2P5RN97, A0A0D2U4N2, A0A0D2U7M3, A0A0D2VH44,
A0A2P5RZU3, A0A2P5XM03, A0A2P5S017, A0A0D2R1G8, A0A0D2U3X9, A0A0D2NYP5,
A0A2P5WUK4, A0A2P5QAP8, A0A2P5W0S1, A0A0D2NJL3, A0A0D2S4R5, A0A0D2RIS5,
A0A2P5RMG9, A0A2P5VYB6, A0A2P5Y509, A0A0D2SLX3, A0A0D2W2H3, A0A0D2Q066,
A0A2P5W461, A0A2P5Y5H9, A0A2P5X2H7, A0A0D2R018, A0A0D2VAH9, A0A0D2NJN0,
A0A2P5XQF5, A0A2P5QC40, A0A2P5WKV0, A0A0D2VJL8, A0A0D2T102, A0A0D2Q7A2,
A0A2P5R7M3, A0A2P5WII7, A0A2P5XRR5, A0A0D2U3Z0, A0A0D2VAL8, A0A0D2V8Y9,
A0A2P5S3Y3, A0A2P5PX26, A0A2P5XT09, A0A0D2Q2C4, A0A0D2TKF7, A0A0D2NHP9,
A0A2P5Y4V2, A0A2P5XYY9, A0A2P5YJS7, A0A0D2S2B9, A0A0D2TEH9, A0A0D2ST81,
A0A2P5RWY7, A0A2P5SP77, A0A2P5RWV6, A0A0D2PWM1, A0A0D2SZD9, A0A0D2M695,
A0A2P5R4Z6, A0A2P5R7C6, A0A2P5WUM4, A0A0D2RIT8, A0A0D2Q9G7, A0A0D2QW76,
A0A2P5R7B5, A0A2P5YX45, A0A2P5R500, A0A0D2NG46, A0A0D2RFL5, A0A0D2U430,
A0A2P5W2X4, A0A2P5QPE5, A0A2P5SP93, A0A0D2Q063, A0A0D2R2E2, A0A0D2QHX8,
A0A2P5RMJ4, A0A2P5Q5Q4, A0A2P5Y5L5, A0A0D2V1I8, A0A0D2PWL4, A0A0D2NHQ3,
A0A2P5R4Y1, A0A2P5Y9P7, A0A2P5RZT0, A0A0D2R874, A0A0D2SKU2, A0A0D2NJR3,
A0A2P5XRP9, A0A2P5RUA4, A0A2P5Y109, A0A0D2NHR3, A0A0D2S5T3, A0A0D2ST84,
A0A2P5R7B6, A0A2P5QAB2, A0A2P5QJY8, A0A0D2VA22, A0A0D2T0Z5, A0A0D2R008,
A0A2P5SV42, A0A2P5WSV7, A0A2P5RKW8, A0A0D2Q078, A0A0D2NHS1, A0A0D2TRL9,
A0A2P5WKX2, A0A2P5QJM8, A0A2P5SE83, A0A0D2R2W6, A0A0D2TF92, A0A0D2RIT4,
A0A2P5SP86, A0A2P5R7B3, A0A2P5Q4C5, A0A0D2M871, A0A0D2T212, A0A0D2NTC5,
A0A2P5SE70, A0A2P5RMS7, A0A2P5YQL5, A0A0D2R013, A0A0D2R877, A0A0D2TUH1,
A0A2P5WKU3, A0A2P5R5J1, A0A2P5RN93, A0A0D2TTI3, A0A0D2Q2G3, A0A0D2RSA1,
A0A2P5SP50, A0A2P5XRU3, A0A2P5VNQ9, A0A0D2TQ92, A0A0D2VUT2, A0A0D2M7Q0,

A0A0D2TWT0, A0A0D2RAR6, A0A0D2Q9E3,
A0A0D2U0Y6, A0A0D2M841, A0A0D2UGZ9,
A0A0D2Q059, A0A0D2PQT1, A0A0D2SUB8,
A0A0D2UNZ7, A0A0D2V1J1, A0A0D2Q081,
A0A0D2R033, A0A0D2RQB0, A0A0D2M672,
A0A0D2UF05, A0A0D2UUZ6, A0A0D2W712,
A0A0D2UPR4, A0A0D2UF15, A0A0D2SYV9,
A0A0D2V121, A0A0D2Q2D6, A0A0D2NIU8,
A0A0D2UCR1, A0A0D2QA06, A0A0D2Q2G4,
A0A0D2RIU4, A0A1B6MBH5, A0A1B6MT83,
A0A1B6KHB7, A0A1B6LPX0, A0A1B6MRL1,
A0A1B6KWB9, A0A1B6KTZ0, A0A023AXR7,
A0A023AYU7, A0A023B052, A0A023BAV3,
A0A023B0X7, A0A023B381, A0A023B0X6,
A0A023AXP8, A0A023B1C3, A0A023B0P6, L1JJD2,
L1JJX0, L1JTS3, L1JKL7, L1JCN2, L1IX89, L1K113,
L1IWJ0, L1IIZ2, L1JCP1, A0A3P4KMI5, A0A3P4RU50,
A0A3P4RW44, A0A3P4RAU2, A0A3P4RWP0,
A0A0L7QLL2, A0A0L7R1I8, A0A0L7RF61,
A0A0L7R6V2, A0A0L7R538, A0A0L7RFI2,
A0A212ACR4, A0A086XX93, A0A212AJW7, W6NGT9,
W6NNJ2, A0A158QM82, A0A0N4W5U3, A0A158QK55,
A0A3P7UET5, A0A3P7XBC6, A0A3P7XTV91,
A0A3P7TQB2, A0A0N4WUQ0, A0A0N4W8T5,
A0A158QNJ5, A0A0N4WA48, A0A0N4X5R8,
A0A0N4WPF3, A0A0N4X266, A0A0N4WAZ2,
A0A158QLJ4, A0A158QPL6, A0A158QR36,
A0A158QKJ2, A0A0N4WU40, A0A0N4WJV0,
A0A0N4WKR9, A0A0N4WC06, A0A158QRG0,
A0A0N4W2R6, A0A0N4WAT5, A0A0N4WNL0,
A0A0N4WCR5, A0A0N4WS57, A0A0N4WAG3,
A0A091PRS1, A0A091PH99, A0A091PGF6,
A0A091PJK8, A0A126UY30, A0A1M7I344, W1NCY1,
A0A074SYS7, A0A074SUJ0, A0A074TKE0,
A0A074SSB4, A0A074T9T4, A0A074SY06,
A0A074SSP2, A0A074SRW4, A0A074T002,
A0A074SV30, A0A074SUT3, A0A074SME0,
A0A074T415, A0A074T0Q6, A0A074TPN2,
A0A074SMC6, A0A2G9HBA5, A0A2G9I607,
A0A2G9GS19, A0A2G9HFW2, A0A2G9G3H0,
A0A2G9GBC9, A0A2G9H9N3, A0A2G9FWW5,
A0A2G9G020, A0A2G9H900, A0A2G9G8U4,
A0A2G9H5E2, A0A2G9G0T8, A0A2G9G7H6,
A0A2G9G7F0, A0A2G9HQH7, A0A2G9GLL5,
A0A2G9I602, A0A2G9HMW9, A0A2G9H7Y4,
A0A2G9HVS1, A0A2G9H5H4, A0A2G9FW99,
A0A2G9G9M9, A0A2G9FX93, A0A2G9G0T2,
A0A2G9GFB5, A0A2G9HQJ0, A0A2G9I4A0,
A0A2G9G0G1, A0A2G9HNZ9, A0A2G9GUR0,
A0A2G9H3N1, A0A2G9FY38, A0A2G9G8A6,
A0A2G9GBD2, A0A2G9HQ39, A0A2G9HP33,
A0A2G9G948, A0A2G9G8Y1, A0A2G9GK44,
A0A2G9G7D7, A0A2G9IBJ2, A0A2G9G5U6,
A0A2G9HBA6, A0A2G9G7K3, A0A2G9G7Z8,
A0A2G9G482, A0A2G9GNC7, A0A2G9HBD0,
A0A2G9GA17, A0A2G9GNR7, A0A2G9GGQ5,
A0A2G9I619, A0A2G9G874, A0A2G9GY40,
A0A2G9HZV9, A0A2G9G7A6, A0A2G9GZU4,
A0A2G9GC79, A0A2G9G877, A0A2G9G5N8,
A0A2G9I606, A0A2G9HM51, A0A2G9GUP3,
A0A2G9GEQ2, A0A2G9HNL0, A0A2G9H7Q3,
A0A2G9G4X6, A0A2G9IBI1, A0A2G9GJX1,
A0A2G9I6C9, A0A2G9G5B6, A0A2G9GB96,
A0A2G9HHD9, A0A2G9GFY4, A0A2G9H5D1,
A0A2G9GFA7, A0A2G9GBC7, A0A2G9H719,
A0A2G9H716, A0A2G9IAY0, A0A2G9GX58,
A0A2G9GA47, A0A2G9GKN2, A0A2G9FXC4,
A0A2G9FY42, A0A2G9FXI3, A0A2G9H718,
A0A2G9HP44, A0A2G9GMC6, A0A2G9HMZ3,
A0A2G9I5Y5, A0A2G9G1J5, A0A2G9H762,
A0A2G9GKG3, A0A2G9IBT8, A0A2G9GT09,
A0A2G9G6Z8, A0A2G9I585, A0A2G9HHH7,
A0A2G9HTZ3, A0A2G9HHL8, A0A2G9H5I0,
A0A2G9I2J4, A0A2G9HP00, A0A2G9GSG6,
A0A2G9FYE8, A0A2G9H932, A0A2G9G8L4,
A0A3Q2WKE2, A0A3Q2VWA3, A0A3Q2VMX2,
A0A3Q2W714, A0A3Q2V9X5, A0A3Q3BK39,
A0A3Q3CJW9, E2BZU8, E2BV16, E2C0I8, E2C2K1,
E2B4Q6, E2B676, A0A2C9D802, A0A2S1VNS3,
A0A2S1T9D7, A0A2S1S5U8, A0A2S1RZC7,
A0A2S1URM3, A0A2S1U4N7, A0A2S1SPB8,
A0A2S1U419, A0A2S1TB44, A0A2S1VQC9,
A0A2S1TTA7, A0A2S1T9Z3, A0A2S1T8T6,
A0A2S1S5S5, A0A2S1USV7, A0A2S1V9P5,
A0A2S1SNM0, A0A2S1RSS9, A0A2S1ST77,
A0A2S1U4U7, A0A2S1URK0, A0A2S1V8P7,
A0A2S1V4L5, A0A2S1T8Z6, A0A2S1V3F7,
A0A2S1SGZ7, A0A2S1UQR4, A0A2S1S8P2,
A0A2S1SC29, A0A2S1ULP0, A0A2S1T9K9,
A0A2S1T9M7, A0A2S1TAJ6, A0A2S1T967,
A0A2S1U5M7, A0A2S1UIR2, A0A2S1RT61,
A0A2S1TNE9, A0A2S1T9J2, A0A2S1THT3,
A0A2S1TZ72, A0A2S1U550, A0A2S1U473,
A0A2S1TNN4, A0A2S1UQL0, A0A2S1RSW7,
A0A2S1U760, A0A2S1VDL9, A0A2S1UDJ8,
A0A2S1U3Z2, A0A2S1T939, A0A2S1V5W8,
A0A2S1TDT0, A0A2S1SDU7, A0A2S1T4J5,
A0A2S1SMJ5, A0A2S1TA85, A0A2S1S960,
A0A2S1T8Z8, A0A2S1UJM0, A0A2S1T4T1,
A0A2S1VPZ1, A0A2S1TCA5, A0A2S1TAB3,
A0A2S1SW79, A0A2S1RXK0, A0A2S1S8G7,
A0A2S1TSR7, A0A2S1U418, A0A2S1T909,
A0A2S1TAA8, A0A1Y3BZF9, A0A2S1T8Y8,
A0A2S1RSP8, A0A2S1SSD8, A0A2S1T949,
A0A2S1RMY8, A0A2S1TA21, A0A2S1T2S5,
A0A2S1RN23, A0A2S1T906, A0A2S1UL16,
A0A2S1RV73, A0A2S1RTF5, A0A2S1S990,
A0A2S1STX9, A0A2S1S8Y4, A0A2S1URH5,
A0A2S1S0K1, A0A2S1UEQ1, A0A2S1RNY5,
A0A2S1TL03, A0A2S1SS56, A0A2S1TN10,
A0A2S1THY3, A0A2S1S995, A0A2S1TA25,
A0A2S1T5L3, A0A2S1V227, A0A2S1T959, A0A2S1TL38,
A0A2S1TAD2, A0A2S1SXL9, A0A2S1U5K9,
A0A2S1T266, A0A2S1U403, A0A2S1V611,
A0A2S1THH7, A0A2S1T9X4, A0A2S1TV70,
A0A2S1TAX5, A0A2S1RS35, A0A2S1RS51,
A0A2S1T7B5, A0A2S1T1U1, A0A2S1RNF0,
A0A2S1VBF9, A0A2S1UHX2, A0A2S1U6B1,
A0A2S1ULD7, A0A2S1T3N2, A0A2S1TA13,
A0A2S1T908, A0A2S1U4V0, A0A2S1UAK0,
A0A2S1TAL5, A0A2S1VCQ1, A0A2S1SMN4,
A0A2S1U509, A0A2S1U5G8, A0A2S1SMR2,
A0A2S1UHY6, A0A2S1TY69, A0A2S1TCD7,
A0A2S1U4T1, A0A2S1TJD6, A0A2S1U476,
A0A2S1UPA1, A0A2S1T447, A0A2S1T2R7,
A0A2S1U4S3, A0A2S1VPX0, A0A2S1T8U9,
A0A2S1T1W6, A0A2S1T929, A0A2S1T9Q8,
A0A2S1T2N3, A0A2S1ULK0, A0A2S1TA08,
A0A2S1T9E6, A0A2S1U5H8, A0A2S1T585,
A0A2S1UNM9, A0A2S1SVM1, A0A2S1S0B8,
A0A2S1TAB8, A0A2S1U4T7, A0A2S1VUB1,
A0A2S1U519, A0A2S1UJH6, A0A2S1VLZ7,
A0A2S1SM06, A0A2S1T1Y3, A0A2S1T2F8,
A0A2S1SA55, A0A2S1TAM7, A0A2S1RTF9,

A0A251RTR7, A0A251U5H1, A0A251UTN4, A0A251UTW0, A0A251SU98, A0A251UQN1, A0A251SNN8, A0A251U3Z3, A0A251USS8, A0A251TMP9, A0A251UTL3, A0A251SS58, A0A251S4B6, A0A251SKT0, A0A251T8U8, A0A251U463, A0A251U4V7, A0A251U422, A0A251TAS0, A0A251RMW7, A0A251TAE1, A0A251U8J7, A0A251VPQ8, A0A251U8C6, A0A251SMR8, A0A251TA09, A0A251SS64, A0A251VRM9, A0A251U6A1, A0A251VHM6, A0A251U4T8, A0A251T3G0, A0A2B7WMP5, A0A2B7XNZ2, A0A059LJS3, A0A059LQC7, A0A183GCJ4, A0A183FDS9, A0A183GQL5, A0A183FNG0, A0A183F5N0, A0A183F1S4, A0A183G9U4, A0A183FAM8, A0A183GCA0, A0A183GSN8, A0A183FC10, A0A183FLN4, A0A183GR87, A0A183FV70, A0A183FLD7, A0A183GDB3, A0A183FE94, A0A183FLN5, A0A183GEW6, A0A3P7TAF8, A0A3P7XS44, A0A3P7UBD8, A0A3P7YBC3, A0A3P8CJY4, A0A3P8B899, A0A3P8BPW5, A0A3P7XWA8, A0A3P8FFK8, A0A3P8BG03, A0A3P7Y3L6, A0A3P8AS32, A0A3P8DWK6, A0A3P8CGZ0, A0A3P7YEL9, A0A3P8A3U8, A0A3P7XYB2, A0A3P8C2W2, A0A3P8BGP5, A0A3P8BSP4, A0A3P8E3J7, A0A3P7X235, A0A3P8DNT7, A0A3P7WBJ4, A0A2A4K0R0, A0A2A4J5Y3, A0A2A4J736, A0A2A4IUN6, A0A2A4JF45, A0A2A4JFF2, A0A2A4K3D6, A0A2A4JED9, A0A2A4IXP5, T1FFM4, T1F4T5, T1FEH2, T1F969, T1FKL0, T1FFM5, T1EQR6, T1F4U5, T1F4U0, T1FB09, T1EQR5, T1F1E0, T1FEJ2, T1FUN0, T1F4U7, T1FJS5, T1FFA4, T1F854, T1FVJ6, T1F4U6, T1F4U3, T1FVK2, T1F5M2, T1FEF5, T1FPY2, T1FUT1, T1ETQ4, T1FVK1, T1F970, T1EVQ0, T1F9B8, T1FR64, T1FBN8, T1FCJ6, T1FJA3, T1F4T4, T1FVK0, T1F4T9, T1FDP6, T1EQR7, T1FUN1, T1EP89, T1ET71, T1FFD2, T1FDN8, T1FEJ8, T1F4T6, T1EQP1, T1F4U4, T1FPT1, T1F960, T1FLN5, T1FB69, T1F954, T1EZ95, T1EQP5, T1FV32, T1FKK7, T1F659, T1FLC6, T1FJL9, T1FDA4, T1F4U8, T1F916, T1F973, T1FHL6, T1FJN5, T1FUI3, T1FLN6, T1FJM1, T1EQP4, T1F4T3, T1FBM8, T1FS89, T1EZ93, T1FPY5, T1FF45, T1FEG8, T1FPZ1, T1EQN9, T1FVV8, T1EPB3, T1FLR7, T1F975, T1FFM6, T1FFG1, T1FBA6, T1FDR4, T1FBP2, T1F682, T1FPY3, T1EQP3, T1F4U2, T1FBN9, T1F974, T1FG81, T1F4V1, T1FBM7, T1F4T7, T1FG80, T1FH28, T1FUI8, T1FB01, T1ETA4, T1FB02, T1F4T8, T1EQR0, T1F174, A0A399RHT4, A0A399RLR9, A0A399RSL7, A0A399RMI5, A0A2D8YFK7, A0A0P6JB42, G5BZW9, G5BNV2, G5BNV1, G5B0R1, A0A0P6IYV4, A0A0P6JIW8, A0A0P6J2P0, G5BC53, A0A1I7W716, A0A1I7XH77, A0A1I7WWV5, A0A1I7XSR7, A0A1I7XAF8, A0A1I7XHQ1, A0A1I7X146, A0A1I7XM37, A0A1I7X745, A0A1I7XHZ8, A0A1I7XII8, A0A1I7X5P0, A0A1I7WM55, F2LUA4, A0A3Q2XCJ9, A0A3Q3D5K9, A0A3Q2YZJ7, A0A3Q2YUT9, A0A3Q2YLY3, A0A2P2ICY2, Q9SEB5, Q9SEB2, Q9SEB3, Q9SEB6, Q9SEB4, Q9SEC5, A0A0F7ZU04, V5L2N5, V5L3N5, V5L3U0, A0A3MJH56, A0A3M0KB79, A0A3M0KPT5, A0A286IFF5, A0A317PT30, A9D968, A0A098TDW6, A0A0F2PZU5, A0A0F7PKQ6, A0A2G2DJB6, A0A1B6IND1, A0A1B6JBA6, A0A1B6IQ37, A0A1B6HRP0, P03951, P00747, P03952, P26927, P14210, Q02325, Q15195, Q2TV78, C9WSJ4, G3XAK1, B7Z3P3, A0A0F7G8J1, H0Y596, B4DMX2, C9J075, A8K6K9, C9JS80, B2R7F8, Q59H59, Q9UEG0, C9JCT1, C9JDP4, F8WCD6, Q9UE70, Q53QL7, E9PBC5, B4DPN1, B4DPQ8, A0A2R8YEI1, A6PVI2, B7Z538, A8K9A9, H0YAC1, D6RB32, Q5TEH5, C9WSJ3, B7Z250, Q13208, Q53GN8, A0A2R5GHI4, A0A2R5GZ90, A0A2R5G055, A0A2R5G2W7, A0A2R5GHT1, A0A2R5GPJ4, A0A2R5GQ72, A0A2R5GFH2, A0A2R5GZ49, A0A2R5GMR6, A0A2R5FCZ9, A0A2R5GLX6, A0A2R5GNL7, A0A2R5GI37, A0A2R5GR48, A0A2R5GP36, A0A2R5GCC8, A0A2R5GTZ6, A0A2R5GIQ6, A0A2R5GBG8, A0A2R5GIT4, A0A2R5G3T7, A0A2R5GCH5, A0A2R5GJ87, A0A2R5GGB6, A0A2R5G7Y5, A0A2R5GWX3, A0A2R5GQR5, A0A2R5GUR1, A0A2R5GIX0, A0A2R5GVR7, A0A2R5G8F7, A0A2R5GQH2, A0A2R5GRQ0, A0A2R5GDB9, F2CSY2, M0XR46, A0A287JPN5, F2CQZ9, M0Z8K2, A0A287JKX2, A0A287IUF4, F2CZD5, A0A287KLF9, M0YWF3, M0Y2Z8, A0A287JLH6, A0A287N5Q1, A0A287Q5F5, M0X4U6, A0A287JL69, A0A287LS65, M0XR48, A0A287JKB3, A0A287V5S3, F2E6E0, A0A287VXI1, A0A287KLC6, F2E5G0, A0A287VXR9, A0A287KLB4, A0A287JL74, A0A287JLD4, M0X5T3, A0A287JKR9, M0X4U1, M0WTQ2, A0A287JL26, A0A287S531, M0X4U2, A0A287LSB4, M0XH34, A0A287N5X8, A0A287DZN4, M0UVT7, M0Y3I5, A0A287JKM2, A0A287SWW6, M0Y2Q7, A0A287JKJ1, M0Y9R6, A0A287MK73, M0W648, M0X5T4, F2DE34, A0A287KLB0, A0A287JKS4, A0A287LS98, A0A287S544, M0X4U8, A0A287XZA8, M0VMR6, A0A287JPW4, A0A287KLD9, M0V1J8, A0A287JPJ2, A0A287JPN9, A0A287JKU9, M0YRS9, M0W0I1, A0A287Q137, M0X645, M0VB75, A0A287XIX9, A0A287JVX3, M0VXQ3, M0X4U9, A0A287S793, A0A287KLA1, A0A287HTP8, A0A287JKA6, A0A287XAT4, A0A287LSA0, A0A287HU15, A0A287LS94, A0A287ULQ4, A0A287G0I2, A0A287I9B0, A0A287X4W8, A0A287V603, A0A287JKW2, A0A287VXJ1, A0A287S581, M0USE4, A0A287G0I0, M0YWF2, M0YRS8, A0A287EG31, A0A287G0I1, A0A287JPP7, A0A287X536, A0A287Q497, A0A287JPV5, F2DPF7, A0A287JKP7, A0A287H0I3, F2E9C6, A0A287SY82, A0A287H0K6, A0A287JKX4, A0A287LSB2, A0A287JPY8, A0A287G0J3, A0A287VSN4, A0A287JKP4, F2E736, A0A287E1S1, A0A287JKX3, A0A287JVM6, A0A287IUE8, A0A287NM49, M0WIJ2, F2D8U5, A0A287MNZ7, A0A2R9IZN9, F2CR46, A0A287IUJ8, A0A287S537, A0A287S520, A0A287VS95, A0A287XZG6, A0A287JKV6, A0A287JK91, M0UW74, A0A287H0K5, A0A287XMV2, A0A287ETX1, A0A287EJ56, M0VKE6, A0A287Q400, A0A287IUH9, A0A287H787, A0A287Q1D6, A0A287VSA5, A0A287S509, A0A287H719, A0A287JKP2, F2DZW7, A0A287SK29, A0A287JL87, A0A287LSA4, A0A287IGH2, A0A287EE31, F2DVH7, A0A287XS45, A0A287XIR7, A0A287IGL1, A0A287I9A0, A0A287DZP5, A0A287EG67, M0XKB6, A0A287MK90, A0A287JPN4, A0A287XIJ9, A0A287JKI2, A0A287JKU7, A0A287X8T7, A0A287JKL9, M0US74, A0A287H0Q6, A0A287HTT3, A0A287XAZ9, F2DVP4, A0A287IGC1, A0A287LSA9, A0A287JKZ7, A0A287JDY8, A0A287EXW8, A0A287JPK4, A0A287XJ32, A0A287XS09, A0A287H0I2, A0A287GWW0, A0A287JKA0, A0A287GYF4, A0A287KJ3, A0A287HU10, A0A287JKV4, A0A287JLG8, A0A287JDY3, M0YMH8, A0A287JKH8, A0A287HTI0, M0WAI6, A0A287I9D8, A0A287LSE2, A0A287LSE8, F2DDM1, A0A287Q5G8, A0A287JKQ6,

A0A287LSE1, A0A287LSD9, A0A287S577, A0A287JDM9, A0A287XIY2, M0W0I0, A0A287V653, A0A287JKI8, A0A287EJ83, A0A287JKY5, A0A287JKY7, A0A287HI8, A0A287JL01, A0A287N0H0, M0W0I5, F2DZS5, M0UIL6, A0A287JL57, A0A287EDZ4, M0UVT6, A0A287LSB9, A0A287H0H7, A0A287LS90, A0A287LSA1, A0A287JKZ5, A0A287JKQ5, A0A287IGK1, M0UDY0, M0WBF9, A0A287JL20, A0A287XIT5, A0A287H0J8, A0A287MK96, A0A287GX15, A0A287JKZ9, A0A287L9W8, A0A287G0I8, A0A287LSA5, A0A287Q632, A0A287JKZ4, A0A287KQ24, A0A287M8A3, A0A287LS92, A0A287S515, A0A287JDV3, A0A287HU21, A0A287XS50, A0A287E1N3, A0A287N0G0, A0A287M896, A0A287JKZ2, M0XZ56, A0A287JKM9, A0A287V7H0, A0A287JKR1, A0A287L9U3, A0A287V5K1, A0A287HU00, F2DV22, A0A287S4V9, A0A287JL54, A0A287NLW9, A0A287LS76, A0A287EGH8, A0A287JKU5, A0A287XIJ8, A0A287EG37, A0A287E1N0, F2DZG8, F2DWF4, A0A287JDQ7, A0A287KH06, A0A287VXV7, A0A287GFZ2, A0A287MK60, A0A287H0J7, A0A287H0H8, A0A287E1M5, A0A287EJ40, A0A287GI5, A0A287I9D4, F2D0V2, A0A287HTP3, A0A287XIZ1, F2E792, A0A287H0N6, A0A287JPZ0, A0A287S554, A0A287JLI4, A0A287LS59, A0A287U4M0, A0A287MK62, M0X8T3, F2D0M2, A0A287ETW5, A0A287JKR4, A0A287G0I7, A0A287EG04, A0A287S504, A0A287XAP8, M0UQL7, M0X1P9, A0A287JKQ4, A0A287JKG2, F2DJ24, A0A287JKD6, A0A287T4N7, F2D6A9, A0A287S550, A0A287S507, A0A287JKY8, F2D857, F2E0N1, F2D0S6, A0A287HTS3, A0A287HU22, A0A287N5T2, F2E071, A0A287LSD5, A0A287SWR5, F2DYG0, A0A287E1M9, A0A287TTW0, F2E424, A0A287T1C1, A0A287IGI8, A0A287LSC1, F2DGX1, A0A287N5Y3, A0A287LSD3, A0A287XS04, A0A287HTT9, A0A287S5B0, A0A287LSI8, A0A287JKK0, A0A287TU03, F2DJ90, A0A287S5A2, A0A287JE19, A0A287JKS0, A0A287H785, A0A287G0H8, F2EEQ7, M0X5F1, A0A287LSD4, F2CSL7, A0A287LSF0, A0A287N5T8, A0A287XZF8, M0Y1V6, A0A287G0H7, A0A287JK96, A0A287T4Y6, A0A287G0I6, A0A287XSE7, F2DBV1, A0A287LSC8, A0A287JKV9, A0A287KLG4, A0A287JPP4, A0A287JKI4, A0A287JLH1, A0A287JL30, A0A287LS79, A0A287JKX1, A0A287SWV1, A0A287XMW2, A0A287LS85, A0A287SX07, A0A287VXG8, A0A287V5Z3, A0A287JGN6, A0A287S4X9, A0A287JKT0, A0A287XIU0, A0A287IGE2, A0A287JPV4, A0A287JL84, A0A287H0R0, F2DSN1, A0A287IGB2, A0A287SYA0, A0A287L9W9, A0A287SWS0, A0A287VDJ7, M0V508, A0A287XAQ3, F2ED78, A0A287JLE3, A0A287JKK2, A0A287H0L7, A0A287XIX4, A0A287JKY3, A0A287V5G7, A0A287NLN4, A0A287JVK7, M0UR24, A0A287E1L3, F2D4F6, F2DZY6, A0A287JKH3, M0V5N5, M0XKB5, A0A287H0P5, A0A287S580, A0A287JK95, M0YRS5, A0A287S4W4, A0A287H0I7, M0YDWI, F2E6M1, A0A2R9IZN3, F2CXU1, M0UFX9, A0A287MK66, A0A287KLC4, A0A287FZA9, A0A287H0L1, A0A287L9W2, A0A287N0F8, A0A287M890, A0A287JKR0, A0A287S5E8, A0A287JL81, A0A287JL40, A0A287SY15, A0A287V5G1, A0A287Q1Y2, A0A287I9D7, A0A287JKD0, A0A287JKQ0, A0A287EJ45, A0A287JGA6, A0A287HTT1, M0YMI0, A0A287IGH4, A0A287HTR9, A0A287XIR2, A0A287IUF8, A0A287XS55, A0A287X4U2, A0A287KGI7, A0A287JKN7, A0A287LS81, A0A287V5I8, A0A287Q176, A0A287JKE5, A0A287GG05, A0A287JKL1, A0A287IUE9, A0A287IUL0, M0YMH9, A0A287JL90, A0A287XAW7, A0A287H0P0, A0A287JKK7, F2DQ07, F2DVF8, A0A287EXV5, A0A287EXX5, A0A287EG25, A0A287XZG3, A0A287XBL1, A0A287JKV7, A0A287G0I4, A0A287V5J4, A0A287X4U7, A0A287S5B5, A0A287EG62, A0A287JDT8, A0A287JPY5, A0A287EG71, A0A287JKX7, A0A287JLI6, A0A287N0F4, A0A287HU27, A0A287G0J5, A0A287MK69, F2DP44, A0A287Q173, A0A287I9A6, A0A287ULB9, A0A287XSC3, A0A287JKF5, A0A287XRW5, A0A287N5W5, A0A287HU05, A0A287Q638, F2DDU9, F2EJV9, A0A287UVQ5, A0A287LS87, A0A287LS64, A0A287E1P0, A0A287I9C6, A0A287KLC0, A0A287MUT0, F2DUT1, M0W647, A0A287JGC0, M0X5T2, A0A287KLF4, F2DGU3, M0XSP1, M0W3T9, A0A287I9C1, A0A287JL89, A0A287H0J6, A0A287EFT8, A0A287K4Z4, A0A287FZB8, A0A287XIW0, A0A287KGP2, A0A287NLR1, A0A287SYB4, A0A287H0L5, A0A287HU06, A0A287HTJ9, A0A287KLD6, A0A287V5F6, A0A287LSC4, A0A287EG21, A0A287VST9, A0A287LSA6, A0A287S505, A0A287H0K2, A0A287JKK1, A0A287HU32, A0A287IUK4, A0A287JGI4, M0YSV2, A0A287G0I9, A0A287GY94, A0A287JK87, A0A287JKX9, M0XCH9, A0A287LS99, A0A287S571, A0A1Z5T7T5, A0A1Z5T1G6, A0A1Z5SZU9, A0A1Z5TRS5, A0A1Z5SNU5, A0A1Z5T2F6, A0A1Z5TKS3, A0A1Z5T220, A0A1Z5T860, A0A3M6XEF2, A0A3M6YRP2, A0A3M7B8I9, A0A3M7BD57, A0A3M7EN81, A0A3M7IHZ9, A0A3M7F5J7, A0A3M7CY13, A0A3M7IF39, A0A3M7IKN2, A0A3M7F3Z2, A0A3M7J989, A0A3M7DTD4, A0A3M6X1R5, A0A3M7B9I1, A0A3M7HRW2, A0A3M6ZPM6, A0A3M7A6V9, A0A3M7CW34, A0A3M7FE79, A0A3M6Z7L5, A0A3M6WLT3, A0A3M7IN62, A0A3M7AEZ4, A0A3M7D1M2, A0A3M7GWG3, A0A3M6YTF6, A0A3M7FEQ6, A0A3M7GDI6, A0A3M7GKN4, A0A3M7F5S1, A0A3M7H9H8, A0A3M7E7K4, A0A3M7BMV2, A0A3M6YFN9, A0A3M7HTY7, A0A3M7C6P1, A0A3M6Y8Q0, A0A3M7GBS4, A0A3M7FVY9, A0A3M7AI77, A0A3M7H9D0, A0A3M7F5D2, A0A3M7EZS7, A0A3M6Y2F1, A0A3M7EXQ6, A0A3M7CWK5, A0A3M7FQH4, A0A3M7FKN6, A0A3M7CZJ1, A0A3M7HXS6, A0A3M7ITW6, A0A3M7DCL5, A0A3M7FY57, A0A3M7AY00, A0A3M7HF76, A0A3M6XNG0, A0A3M7IR78, A0A3M7D168, A0A3M7EZ41, A0A3M7E391, A0A3M7GVU9, A0A3M7FYN0, A0A3M7BRN4, A0A3M6X571, A0A3M6XIS4, A0A3M7IC91, A0A3M7F1K5, A0A3M6WR01, A0A3M6WED0, A0A3M7BI24, A0A3M7BYP9, A0A3M7EB66, A0A3M7ETI4, A0A3M7HLN2, A0A3M7DQ18, A0A3M6X7W9, A0A3M7C0U4, A0A3M7AI42, A0A3M7DXT2, A0A3M7CVC3, A0A3M7EYQ9, A0A3M7DQ84, A0A3M7I235, A0A3M7IA13, A0A085W504, M4B6K3, M4B6K2, A0A2J6RSW5, A0A2J6RMZ2, A0A2J6RSV8, A0A2J6RGD2, A0A2J6RVZ8, A0A2J6S4F4, A0A2J6R4R6, A0A2J6RYD0, A0A0R3WZ01, A8S0U4, A0A2M7IBC9, A0A3B0T141, A0A170PTA1, A0A3B0T4U7, A0A3B0S6G0, A0A3B0YDW4, A0A3B0RX13, A0A158QEB2, A0A3P7BEC2, A0A158QBS7, A0A1I7NHV8, A0A2P5KXM8, A0A2P5KRL9,

A0A2S5PBC1, A0A2S5PC10, A0A2S5P4Z9, A0A0F2QD64, A0A1Z9YBG4, A0A2D8ZSJ2, A0A2E3AXJ3, A0A2E4S0J7, A0A2D8ZV35, A0A069E6T4, A0A3B9H2G8, A0A059DX53, A0A3B9KYM9, A0A062U7B1, A0A062UCV7, A0A059FLM4, A0A059G005, A0A059F7I7, A0A059FSS0, Q0BYL9, Q0C462, A0A059G8G7, A0A062VJB5, A0A258BI69, A0A259LR84, A0A0F2RG41, A0A328JPZ2, A0A344WD66, A0A059DSX7, A0A059EES6, A0A062TZP2, A0A2D8W5J1, A0A3D2LBT6, A0A350ZTY8, A0A2D8ER08, A0A2E7B2U2, A0A2E3JXR2, G9P8Z6, G9NQ37, A0A024SGL6, A0A024SLI6, G0RDV7, G0RFA4, G9MYE6, G9NAA5, G9NBF0, G9MT46, A0A1Y2W191, A0A1Y2VQD0, A0A1Y2VLV2, A0A1Y2UVW5, A0A1Y2V838, A0A1Y2V1I2, A0A1Y2TBN0, A0A1Y2U492, A0A1Y2TUW0, A0A1Y2TMZ5, A0A1W0X097, A0A1W0WIH9, A0A1W0WWV0, A0A1W0X6K9, A0A1W0X4X0, A0A1W0WI98, A0A1W0WIM8, A0A1W0WIA3, A0A1W0WQ69, A0A1W0WPS6, A0A1W0WNF7, A0A1W0X6A8, A0A1W0X3K6, A0A1W0WF75, A0A1W0XCI5, A0A1W0WSL7, A0A1W0X0I9, A0A1W0WBY5, A0A1W0X277, A0A1W0X910, A0A1W0WDI1, A0A1W0WXQ4, A0A1W0X8W3, A0A1W0WR27, A0A1W0WFY4, A0A1W0WII5, A0A1W0WII2, A0A1W0WLH6, A0A1W0WG72, A0A1W0WBT5, A0A1A7YAK1, A0A1A7WJK9, A0A2D0S0Y9, W5UJ51, A0A2D0PYF3, A0A2D0PVZ8, A0A2D0PZW9, A0A2D0S0B2, A0A2D0PX86, A0A2D0PN50, A0A2D0PUK1, A0A2D0PXQ6, A0A2D0PYM6, A0A2D0PW18, W5UM75, W5UH86, I3ME70, I3NFV2, I3M1N9, I3MLI1, I3ME62, W9VHP2, A0A177B984, A0A177B686, Q40096, Q40100, Q40099, Q40098, V5HBD1, V5H4U1, V5HJ86, A0A147BGK7, A0A131YAQ2, A0A131XWE4, A0A1C8FEE7, V5HEL7, A0A147BMG4, V5ICT5, B7QCV3, B7Q2N4, B7QM85, B7P1S6, B7P6R1, B7QDU0, B7PWP4, B7PQI9, B7Q7Z0, B7QM84, B7QM83, B7PM04, B7PQI8, A0A316V1R6, A0A1I3UGX8, A0A2Y9B448, Q28VT1, A0A1B6YPR7, A0A1B6Z0H5, A0A067LHY6, A0A067KUJ8, A0A067L0Z2, A0A067L5M7, A0A067JDL7, A0A067L394, A0A067JQ57, A0A067JDL1, A0A067LB03, A0A067KQJ4, A0A067JMW2, A0A067K6D5, A0A067KR73, A0A067JMV5, A0A067KZS2, A0A067KVG4, A0A067KS71, A0A067KMS7, A0A067JLG1, A0A067KWS2, A0A067JLG5, A0A067KVF4, A0A067JMV9, A0A067L3A3, A0A067LB09, A0A067KXT3, A0A067JDL4, A0A067JFW9, A0A067KRX7, A0A067LDD5, A0A067L3A8, A0A067KRY8, A0A067JLG8, A0A067L4G0, A0A067JAL4, A0A067JQM4, A0A067KEY5, A0A067KZQ0, A0A067JQ92, A0A067JII4, A0A067K362, A0A067JAK6, A0A067L4F6, A0A067L4H1, A0A067KVG0, A0A067JAQ2, A0A067L398, A0A067L3B7, A0A067LDW4, A0A067JAQ7, A0A067JWU9, A0A067L392, A0A067K7M8, A0A067KS66, A0A067KRX3, A0A067KVG9, A0A067KB60, A0A067LBK7, A0A067KS82, A0A067K9W6, A0A067KF77, A0A1D9BCC6, A0A2I4GK62, A0A2I4G4M2, A0A2I4H823, A0A2I4FLZ3, A0A2I4FU95, A0A2I4DI82, A0A2I4EPU3, A0A2I4E0M1, A0A2I4HI12, A0A2I4H7B3, A0A2I4GAB4, A0A2I4E0L2, A0A2I4FZE8, A0A2I4HNL1, A0A2I4FFM6, A0A2I4EKA5, A0A2I4ERC6, A0A2I4782, A0A2I4H784, A0A2I4HSV7, A0A2I4EKB9, A0A2I4G4H1, A0A2I4HV68, A0A2I4H7D7, A0A2I4EPT2, A0A2I4DYI9, A0A2I4DYZ0, A0A2I4GFL8, A0A2I4E0L5, A0A2I4GBN2, A0A2I4FA92, A0A2I4DU39, A0A2I4E0L6, A0A2I4FU89, A0A2I4GBS2, A0A2I4HLF8, A0A2I4DYZ5, A0A2I4EGC9, A0A2I4DU26, A0A2I4DGG7, A0A2I4GV20, A0A2I4E0K7, A0A2I4H7H3, A0A2I4HHT8, A0A2I4DYJ2, A0A2I4FLN8, A0A2I4H7E7, A0A2I4GV14, A0A2I4GT05, A0A2I4DGF8, A0A2I4FFQ2, A0A2I4DKP2, A0A2I4GV12, A0A2I4FFG4, A0A2I4FIE0, A0A2I4GGL6, A0A2I4FZE7, A0A2I4ERD8, A0A2I4GT07, A0A2I4DKP0, A0A2I4FJE4, A0A2I4HTL0, A0A2I4HHJ4, A0A2I4GV23, A0A2I4EKK6, A0A2I4HNL3, A0A2I4GA68, A0A2I4HEF2, A0A2I4HLF5, A0A2I4H4Y0, A0A2I4GAY6, A0A2I4ERB9, A0A2I4FU46, A0A2I4HTX2, A0A2I4DQG1, A0A2I4ERD4, A0A2I4H6J2, A0A2I4HP53, A0A2I4GAU2, A0A2I4EGB5, A0A2I4DEN2, A0A2I4ERC8, A0A2I4FIB5, A0A2I4FLY6, A0A2I4G9T9, A0A2I4ERD7, A0A2I4H7C7, A0A2I4FFP8, A0A2I4HHI9, A0A2I4FIE8, A0A2I4H4L2, A0A2I4GG21, A0A2I4G912, A0A2I4GBS9, A0A2I4HPJ3, A0A2I4GAA0, A0A2I4EKJ5, A0A2I4HSV3, A0A2I4HTK6, A0A2I4FIL5, A0A2I4EK97, A0A2I4FFQ0, A0A2I4GV28, A0A2I4HIN1, A0A2I4EMX6, A0A2I4HV91, A0A2I4ERD1, A0A2I4DU21, A0A2I4EKU1, A0A2I4E0L9, A0A2I4GBS6, A0A2I4HP69, A0A2I4GWB0, A0A2I4GAW7, A0A2I4DET7, A0A2I4G4J0, A0A2I4GV30, A0A2I4HV71, A0A2I4FKE4, A0A2I4E7G7, A0A2I4GBT4, A0A2I4DGG1, A0A2I4DU29, A0A2I4FFP3, A0A2I4DN46, A0A2I4HAL5, A0A2I4FLV5, A0A2I4FID4, A0A2I4HV84, A0A2I4GBV7, A0A2I4E8G1, A0A2I4E8H5, A0A2I4E6A6, A0A2I4HNL4, A0A2I4HEG9, A0A2I4E3B8, A0A2I4EWD4, A0A2I4GBR4, A0A2I4EG75, A0A2I4GAA7, A0A2I4EG66, A0A2I4HG78, A0A2I4HSV9, A0A2I4DTA7, A0A2I4HNR2, A0A2I4H926, A0A2I4EG64, A0A2I4DGG9, A0A2I4DEM3, A0A2I4EN07, A0A2I4FU87, A0A2I4FIJ8, A0A2I4GBT2, A0A2I4EGC4, A0A2S5U2E7, A0A1M4XZE6, A0A1E4CVK7, A0A1E4C319, A0A1Y1I6D8, A0A1Y1IA49, A0A1V0SHW7, A0A2W5CL52, A0A3Q2Z9K7, A0A3Q3B1Z9, A0A3Q3B902, A0A3Q3F291, A0A3Q3BH26, A0A3Q3B198, A0A1B9IXV1, A0NVX3, A0NMA0, A0A0M6Y1A7, A0A0M6Y878, A0A0M7AJT2, A0A0M6YXQ5, A0A0M6ZWY2, A0A2S3UK78, A0A2T7H985, U7G8P7, U7GAT6, A0A163UN31, A0A163WYR8, A0A222F1C4, A0A222FCV3, A0A1M7CSY2, A0A3Q3N8L8, A0A3Q3GBJ6, A0A3Q3FDA4, A0A3Q3GEZ8, A0A3Q3GFE0, A0A3Q3N8X5, A0A3Q3GFJ4, A0A3Q3N8N2, A0A3Q3GFZ5, A0A3Q3GB54, A0A3Q3GFB9, A0A2J6K9H8, A0A2J6M9S4, A0A2J6LQZ4, A0A2J6JXN1, A0A2J6KN62, A0A2J6KKT3, A0A2J6KC77, A0A2J6MH90, A0A2J6LXZ5, A0A2J6JZ56, A0A2J6LVI0, A0A2J6K3Q9, A0A2J6L847, A0A2J6L7A5, A0A2J6K925, A0A2J6K8G7, A0A2J6MDS4, A0A2J6M338, A0A2J6LCC7, A0A2J6MGQ2, A0A2J6M6H7, A0A2J6KQ34, A0A2J6MB10, A0A2J6KSB6, A0A2J6M2X5, A0A2J6KQ62, A0A2J6KD61, A0A2J6KDN2, A0A2J6K1B8, A0A2J6K3R7, A0A2J6MI63, A0A2J6MGT2, A0A2J6JXJ5, A0A2J6M5A7, A0A2J6KQC0, A0A2J6JL93, A0A2J6KKU2, A0A2J6JT61, A0A2J6JYI5, A0A2J6KK13, A0A2J6M2T7, A0A2J6KQK0, A0A2J6KS85, A0A2J6LUT0,

A0A2J6KKG9, A0A2J6JXL9, A0A2J6LRN0, A0A2J6M2U7, A0A2J6K992, A0A2J6JM53, A0A2J6KI92, A0A2J6MGS8, A0A2J6MH59, A0A2J6JU53, A0A2J6KQ13, A0A2J6MH39, A0A2J6KDQ7, A0A2J6JXP1, A0A2J6JXM0, A0A2J6K937, A0A2J6JXM4, A0A2J6LRI2, A0A2J6K9T5, A0A2J6JU38, A0A2J6L6J2, A0A2J6LFL5, A0A2J6KI16, A0A2J6KQR3, A0A2J6KQ10, A0A2J6LRK6, A0A2J6M2U5, A0A2J6MFF9, A0A2J6MFK8, A0A2J6LRQ0, A0A2J6JHP7, A0A2J6L1L1, A0A2J6KKP5, A0A2J6LL57, A0A2J6K8G6, A0A2J6L780, A0A2J6K927, A0A2J6JX67, A0A2J6JXK7, A0A2J6JPF2, A0A2J6LV17, A0A2J6LRI5, A0A2J6M2Y3, A0A2J6MGY5, A0A2J6L1K0, A0A2J6LVM5, A0A2J6M6F0, A0A2J6LUM7, A0A2J6MGS4, A0A2J6KZL2, A0A2J6M316, A0A2J6JXN5, A0A2J6JXL3, A0A2J6KFI6, A0A2J6KDB6, A0A2J6LRT0, A0A2J6JM37, A0A2J6KQI6, A0A2J6L1H5, A0A2J6JXA5, A0A2J6JXK1, A0A2J6KJY7, A0A2J6JW82, A0A2J6KQH9, A0A2J6M327, A0A2J6M2S7, A0A2J6K9D7, A0A2J6K917, A0A2J6KQ59, A0A2J6KJX6, A0A2J6KI82, A0A2J6L1I8, A0A2J6L7M7, A0A2J6KJV7, A0A2J6MGS5, A0A2J6M8C4, A0A2J6M2U1, A0A2J6L6Y1, A0A2J6KQ32, A0A2J6L9N2, W0G9U1, W0G5H4, A0A0F8CNM7, A0A0F8ASU5, A0A0J7NTZ9, A0A0J7KV86, A0A0J7KKG3, A0A0J7NL95, A0A0J7NBH3, A0A0J7KUZ9, A0A0J7KRY0, A0A0J7L2K3, M3XJC9, M3XGZ2, H3ACN6, H3AXI3, M3XKU7, E7D1R2, B0ZRK1, B0ZRN7, B0ZRK3, B0ZRK7, B0ZRK0, B0ZRK2, B0ZRJ7, B0ZRM2, B0ZRM5, B0ZRI5, B0ZRP4, B0ZRI9, B0ZRK4, B0ZRP3, B0ZRM6, I1V1S2, B0ZRL1, B0ZRM7, B0ZRL9, A0A2Z4HJD9, B0ZRI6, R9S7T9, B0ZRJ2, B0ZRM8, B0ZRI4, B0ZRK6, B0ZRJ6, B0ZRN9, B0ZRN2, B0ZRJ1, B0ZRM9, B0ZRN6, B0ZRK9, B0ZRM1, B0ZRJ3, B0ZRL7, B0ZRI2, R9S7P5, B0ZRI8, B0ZRL6, B0ZRL5, B0ZRN3, R9S7H9, B0ZRN5, B0ZRL0, R9S9P4, B0ZRJ4, B0ZRI3, B0ZRL8, B0ZRI7, B0ZRN4, B0ZRL4, B0ZRL3, B0ZRJ8, B0ZRM4, B0ZRK8, I3QHF6, B0ZRJ5, B0ZRN0, B0ZRK5, R9SA46, B0ZRM0, B0ZRP0, A0A2Z4HJM8, R9S9V7, B0ZRJ9, B0ZRN1, A0A0D9W6W8, A0A0D9XWL1, A0A0D9W161, A0A0D9WRU9, A0A0D9V8W7, A0A0D9XNS0, A0A0D9WA06, A0A0D9V3Y6, A0A0D9W9Z1, A0A0D9V8T3, A0A0D9V8U6, A0A0D9V8Q3, A0A0D9XGF3, A0A0D9WXV1, A0A0D9W4W1, A0A0D9W9Y8, A0A0D9X052, A0A0D9XGI1, A0A0D9WD80, A0A0D9X057, A0A0D9W9Z0, A0A0D9WTD1, A0A0D9VVN7, A0A0D9V8T2, A0A0D9XB99, A0A0D9W2T7, A0A0D9X065, A0A0D9W9Z8, A0A0D9UY17, A0A0D9XZW4, A0A0D9XGF7, A0A0D9XIR5, A0A0D9WA00, A0A0D9W4V1, A0A0D9WR41, A0A0D9XGF4, A0A0D9W9Y9, A0A0D9V3F7, A0A0D9WA08, A0A0D9VVD3, A0A0D9WRG7, A0A0D9X056, A0A0D9WA07, A0A0D9WA13, A0A0D9V6J6, A0A0D9WIB2, A0A0D9UWX5, A0A0D9XGF8, A0A0D9WGJ8, A0A0D9XWK7, A0A0D9V3Y5, A0A0D9XWK5, A0A0D9W4V4, A0A0D9XGI2, A0A0D9V3F8, A0A0D9XZV4, A0A0D9W1R5, A0A0D9V6K0, A0A0D9W4V9, A0A0D9V6J7, A0A0D9UYF7, A0A0D9VRC5, A0A0D9XGF5, A0A0D9W4V2, A0A0D9XNR9, A0A0D9V6J2, A0A0D9W3Y7, A0A0D9W4V3, A0A0D9W3A9, A0A0D9WA14, A0A0D9W4V7, A0A0D9V7B0, A0A0D9V3Y8, A0A0D9V1T5, A0A0D9WQ05, A0A0D9VAI1, A0A0D9UYF9, A0A0D9V6J9, A0A0D9W3B3, A0A0D9W9Z3, A0A0D9WD66, A0A0D9W2T8, A0A0D9V8T6, A0A0D9WRU8, A0A0D9UYF8, A0A0D9WA03, A0A0D9WAH9, A0A0D9XZV3, A0A0D9XQ93, A0A0D9WA05, A0A0D9WR42, A0A0D9X053, A0A0D9W9Z9, A0A0D9W9Z6, A0A0D9WGJ7, A0A0D9XH63, A0A0D9V6J3, A0A0D9W9Y7, A0A0D9X503, A0A0D9W3B1, A0A0D9W4V6, A0A0D9W4V5, A0A3P3YXB7, A0A3P3YXB3, A4H3V1, A0A3S5H596, A0A1E1INT0, A0A381M993, E9AK14, A0A088RHV5, A0A0P1H8K4, V9VZT4, A0A1H3GY41, A0A0K2TCD8, A0A0K2V009, A0A0K2T1Y7, A0A0K2TPD6, A0A0K2UTX9, A0A0K2TTX1, A0A0K2U3D2, A0A0K2T870, A0A0K2U346, A0A0K2T1X1, A0A0K2SXW0, A0A0K2UNM9, A0A0K2TDI0, A0A0K2TFU3, A0A0K2TBQ4, A0A0K2UUX8, A0A0K2SZ08, A0A0K2U2F7, A0A0K2UVK3, A0A0K2TZM7, A0A0K2UP87, A0A0K2USH8, A0A0K2U0I6, A0A0K2UUV6, A0A0K2UUZ9, A0A0K2UTJ0, A0A0K2TZZ8, A0A0K2UVW1, A0A0K2UU23, A0A0K2UVG2, A0A0K2UWI6, W5NER0, W5M199, W5NEQ8, W5NFF8, W5NAB0, A0A3M9ZBN0, A0A2U3YDU7, A0A2U3X6Q7, A0A2U3YLJ6, A0A2U3YE66, A0A2U3YDS5, A0A2U3YDS8, A0A2U3XSF8, A0A2U3XSB8, A0A2U3X6P8, A0A091PSC7, A0A091PQK1, A0A091Q2P9, E4ZGL2, E5AD62, E5A991, A0A443SF82, A0A443RUF8, A0A443SUS0, A0A443SE45, A0A443RVB4, A0A443SM33, A0A443SQ21, A0A443SF48, A0A443SHP2, A0A443SQI1, A0A443S6A4, A0A443SH42, A0A443SI69, A0A443SN48, A0A2Z5XDQ4, A0A2Z5XDQ7, A0A1Y2FYL8, A0A2I0UCB4, A0A2I0U654, A0A2I0THH2, A0A2I0U125, A0A1S3KCR3, A0A1S3I3B4, A0A2R2MTN1, A0A1S3JBH9, A0A1S3HNX8, A0A1S3HFI9, A0A1S3I1V9, A0A1S3JR18, A0A1S3IEH2, A0A1S3J1T8, A0A1S3H9T3, A0A1S3HBY0, A0A1S3K773, A0A2R2MTZ4, A0A1S3INU8, A0A1S3IE57, A0A1S3JU66, A0A1S3I9N3, A0A1S3JZ08, A0A1S3K775, A0A1S3JZ64, A0A1S3JQD4, A0A1S3J5V4, A0A1S3GZQ5, A0A1S3IAW8, A0A1S3K770, A0A1S3HKV5, A0A1S3I1A6, A0A1S3JFE9, A0A1S3I1Y2, A0A1S3IQU7, A0A1S3KBV0, A0A1S3KC90, A0A1S3INP9, A0A1S3KEU6, A0A1S3H081, A0A1S3K6K4, A0A1S3K0C7, A0A1S3I3C2, A0A1S3KFD1, A0A1S3KEE4, A0A1S3KBC6, A0A1S3H208, A0A2R2MSR5, A0A1S3K4Q7, A0A1S3JEN3, A0A1S3GZU4, A0A1S3I1W2, A0A1S3JBK0, A0A1S3KHB8, A0A1S3INY3, A0A2R2MLU4, A0A1S3H7Z1, A0A1S3HI84, A0A1S3HZL4, A0A1S3KCC7, A0A1S3ISS0, A0A1S3IMR2, A0A1S3HER8, A0A2R2MJK4, A0A1S3KEG7, A0A1S3HEB9, A0A1S3K901, A0A1S3K0Q7, A0A1S3K7Q8, A0A1S3KA03, A0A1S3JR32, A0A1S3H2K1, A0A1S3I4L8, A0A1S3HD07, A0A1S3KAP7, A0A1S3J0J2, A0A1S3J4U5, A0A1S3JX74, A0A1S3K1K5, A0A1S3IC24, A0A1S3JXG0, A0A1S3K6B9, A0A1S3JI63, A0A2R2MRD9, A0A1S3HR32, A0A1S3JYB9, A0A1S3KBX3, A0A1S3JYD2, A0A1S3HYX9, A0A1S3KFK1, A0A1S3I1T9, A0A1S3ILB6, A0A1S3K0U4, A0A1S3JHR9, A0A1S3JBP0, A0A1S3JSJ3, A0A1S3ICN0, A0A1S3JR04, A0A1S3HBM0, A0A1S3J6C4, A0A1S3ID77, A0A1S3JZB8, A0A1S3IZ38, A0A1S3JW52, A0A1S3J693, A0A2R2MIB3, A0A1S3I2T0, A0A1S3K221, A0A1S3KBT6, A0A1S3HVT4, A0A1S3IHR4,

A0A1S3KD35, A0A1S3GZL9, A0A2R2MJM7,
A0A1S3K756, A0A2R2MRG8, A0A1S3IIG5,
A0A1S3JYC8, A0A1S3H9K2, A0A1S3JQN5,
A0A1S3JZA1, A0A2R2MNI0, A0A1S3KB21,
A0A340XF42, A0A340XZU6, A0A340WGH7,
A0A340Y6H1, A0A340Y5U1, A0A340X8C1,
A0A340X7S9, A0A340X8B6, A0A340XEK1,
A0A340XC28, A0A340XC32, A0A3P7K4H3,
A0A3P6TYE8, A0A3P7M9S7, A0A3P7M8L9,
A0A3P6TRE5, A0A3P6V4Q9, A0A3P6S6Z6,
A0A3P6T8W6, A0A3P6USV6, A0A3P6UER0,
A0A3P6U602, A0A3P6U3U8, A0A3P6UAP6,
A0A3P6SQ54, A0A3P6SHG7, A0A3P6V945,
A0A3P6RZY6, A0A1H2WL46, S9QDQ2, A0A1M5BZJ4,
A0A1I6G0Y4, A0A1H9DXX5, A0A420WEA0,
A0A420WFF1, A0A420WKP0, A0A0A7RPZ1,
A0A0A7RPW5, A0A0A7RPU1, A0A1I7VDG7,
A0A1I7VW75, A0A1S0U4V4, A0A1I7VW66,
A0A1I7W211, A0A1I7VX34, A0A1S0U2W5,
A0A1S0U290, A0A1S0TQ84, A0A1S0U4B4,
A0A1I7V595, A0A1S0TXG2, A0A1S0TGL3,
A0A1I7VEP2, A0A1I7W1P7, A0A1I7VM68,
A0A1S0U513, A0A1I7V7Z8, A0A1S0TYRI,
A0A1I7VP24, A0A1I7W1K7, A0A1S0U521,
A0A1I7VEI3, A0A1S0TM76, A0A1S0TVK0,
A0A1I7V913, A0A1S0U7X7, A0A1S0TNT1,
A0A1S0TXD9, A0A1S0U5P5, A0A1I7VER6,
A0A1I7VJ23, A0A1S0TNL5, A0A1S0TP23,
A0A366W4W6, A0A2N3N2R9, A0A218UQI0,
A0A218V7U2, A0A2A8CVC7, B3XXB9, V4ASX7,
V4CNX9, V4AQ34, V4A085, V3ZGG1, V3ZBJ5,
V4AP13, V4A568, V4B215, V3ZQU5, V3ZUA7,
V4AXR6, V4AG04, V4BSL1, V4A7Y1, V4BB69,
V4BDZ0, V4A5J1, V3ZJU6, V4B1H4, V4AGQ9,
V4BAA4, V4BQJ5, V4AWC8, V4CGE2, V4A396,
V3ZYP3, V3ZKE9, V4BQJ9, V4B0J4, V4CE61, V3ZTQ2,
V4AZ96, V4ACW6, V3ZKU5, V4ADH8, V4BC73,
V4A6L5, V3ZFI8, V4ANB3, V3ZGM4, V4C4P7,
V4AFG6, V4AAJ8, V3ZJQ9, V4B893, V4A878, V4AAG6,
V3ZVU7, V4A5C0, V4AF63, V3ZP38, V4ANZ3,
V4BCE9, V4A5K9, V4BEG6, V4ADA5, V4BFS5,
V4ABU2, V4AGS3, V4BI89, V4A0F5, V4BZ59, V4C8K6,
V4ANZ0, V4AAL1, V4BV31, V4AM58, V4BSL7,
V4AJ20, V3ZA19, V4BF63, V4AA83, V3ZC53, V4AZU1,
V4A6E5, V4A9B0, V4AZF9, V3ZRI2, V3ZE05, V4BHI1,
V4CFZ0, V4AAD3, V4BND1, V4A8U5, V4AAP8,
V4A8U0, V4AQF9, V3Z3B9, V3Z9D7, V4BXB3,
V3ZKT4, V4B8Q8, V4A2F6, V4BGT4, V3ZJF4,
V4ATM4, V4BAE3, V4ARJ8, V4BB58, V4AZ26,
V4AJG9, V4B9R7, V3Z371, V4AGU9, V4ALG6, V3Z819,
V4AXG5, V3ZP70, V4A0V8, V4AZ89, V4BDK1,
V3ZNC3, V4A9Q6, V3ZHP8, V4AWY7, V4C4C1,
V4B8W2, V4B493, V4BY76, V3ZM12, V4C7E0,
V4AUH2, V4CL71, V3ZP26, V3ZV91, Q70I28, B0BLA2,
Q70I30, Q8GSP1, B0BLA4, Q70I29, Q8GSP2, I3SEG1,
Q8GSP0, G3TJ67, G3SSI7, G3U701, G3TJ74, G3U7P9,
A0A0L0CF27, A0A0L0BZD3, A0A0L0CF53,
A0A0L0CB36, A0A0L0CRG8, A0A0L0C513,
A0A0L0BPA5, A0A0L0CB71, A0A0L0BLS4, Q8LP50,
A0A1J7H6R4, A0A1J7GA64, A0A1J7HQD3,
A0A394DIC4, A0A1J7I619, A0A1J7H3V7, A0A1J7GFK8,
A0A1J7GZ77, A0A1J7HH30, A0A1J7HEQ0,
A0A1J7GDB9, A0A1J7GNM1, A0A1J7I6S6,
A0A1J7HD03, A0A1J7FWA6, V4RQY9, A0A1H0GW80,
A0A1B0CHS8, A0A1B0CDT4, A0A1B0CQS2,
A0A1B0CJ91, A0A1B0CLB1, A0A146LQ91,
A0A146M6Y4, A0A146KQT6, A0A0K8SEA4,

A0A0A9ZGD8, A0A0A9XMZ2, A0A0A9X4C5,
A0A0A9ZB53, A0A0A9VYR8, A0A0A9YIK1,
A0A0K8T345, A0A0A9VV93, A0A0A9X899,
A0A0A9XR44, A0A0K8SWZ6, A0A0K8SQ51,
A0A146L1N9, A0A146LN03, A0A0A9YAH9,
A0A0S2G5W4, A0A2K5VVK2, G7PKF4, A0A2K5WCZ4,
G7PKF5, A0A2K5WGT6, G7P478, A0A2K5VTJ9,
C9E9X5, A2V9Z1, A0A2K5WGT9, A0A2K5TJJ3,
A0A2K5WH02, A0A2K5VTQ7, C9E9X6, G8F4N5,
A0A2K5TJJ6, F7A5G3, F6PJA8, F6PJA1, G7MSF8,
F7CC91, A0A1D5RGB5, H9FEQ2, G7ML90, G7MSF7,
F6PJ95, F7A5F6, A0A1D5Q7U7, G7MM01, P12545,
A0A2K6DQD1, A0A2K6DDC3, A0A2K6DDA5,
A0A2K6DD94, A0A2K6DCN9, A0A2K6DH51,
A0A2K6E3X7, A0A2K6E3W9, A0A2K6DQE6,
A0A2O0QXH0, A0A2O0RDT1, A0A2O0Q4Y2,
A0A2O0QXM5, A0A2O0Q8X0, A0A2O0QRV5,
A0A2O0QQN4, A0A2O0Q130, A0A2O0QBX7,
A0A2O0R1B1, A0A2O0QTR7, A0A2O0QXK1,
A0A2O0QXI1, A0A2O0QQN7, A0A2O0Q8Y1,
A0A2O0Q8J1, A0A2O0Q0W5, A0A2O0QXH4,
A0A2O0QIT5, A0A2O0Q0X7, A0A2O0QXF5,
A0A2O0QRS4, A0A2O0Q8V5, A0A2O0Q2G3,
A0A2O0Q0W0, A0A2O0QXP0, K2RH51, K2RS30,
K2RCW8, K2RNM7, K2S8A1, K2RUQ8, O18783,
A0A1I8GHF8, A0A1I8FVR7, A0A1I8H365, A0A1I8J167,
A0A267EWK4, A0A1I8IBQ6, A0A1I8JEV8,
A0A1I8FXH1, A0A1I8GNZ2, A0A267GQH1,
A0A267GGW3, A0A1I8GL54, A0A1I8HG15,
A0A1I8IV72, A0A267G2E7, A0A1I8G1P9,
A0A267EA31, A0A267GUN8, A0A1I8IW00,
A0A1I8IVY1, A0A1I8IRT6, A0A1I8H8D5, A0A1I8G8D6,
A0A1I8HC33, A0A1I8IMI9, A0A267FXX8, A0A1I8J0U1,
A0A1I8GHG0, A0A1I8HE61, A0A1I8J1U2, A0A1I8JJX3,
A0A1I8GHR2, A0A1I8JKN1, A0A1I8FX03, A0A1I8J0K0,
A0A1I8GPQ5, A0A267FEP6, A0A1I8GLQ8, A0A1I8J5S5,
A0A1I8GNC3, A0A118GF89, A0A267DMG9,
A0A267H2N9, A0A1I8JF80, A0A1I8GE13,
A0A267DXV5, A0A1I8H2N3, A0A1I8FHG8,
A0A1I8GCM3, A0A1I8FWJ3, A0A1I8GNW6,
A0A1I8IZ00, A0A267F306, A0A267EXC8, A0A267GX64,
A0A1I8GFR2, A0A1I8I316, A0A1I8ID15, A0A1I8G103,
A0A267E9Q2, A0A267DNT5, A0A1I8G9H2,
A0A1I8J5P8, A0A267E0M5, A0A267G2S7, A0A1I8FV01,
A0A1I8HV10, A0A1I8J8F5, A0A1I8GJX9, A0A1I8H4R7,
A0A1I8J9R2, A0A1I8JG79, A0A1I8GZN4, A0A118J542,
A0A1I8JFP1, A0A1I8HVW8, A0A1I8J222, A0A1I8G6K2,
A0A1I8GEP5, A0A1I8G513, A0A1I8I3M0, A0A1I8J5N9,
A0A1I8FTM3, A0A1I8HQT8, A0A118GI38,
A0A1I8GEN9, A0A1I8G9F7, A0A1I8IHH8,
A0A267H9R8, A0A267GB32, A0A267GHE2,
A0A267EFJ6, A0A1I8FYE4, A0A267F4N8,
A0A1I8FY63, A0A1I8FMH1, A0A1I8GYH3,
A0A1I8IU21, A0A1I8GI06, A0A118F694, A0A1I8GHZ2,
A0A1I8GIV2, A0A1I8FT25, A0A267F4Y9, A0A1I8JK67,
A0A1I8GKV5, A0A1I8GC08, A0A1I8GBL5,
A0A1I8GKD7, A0A1I8HSV8, A0A267FJ10, A0A118J628,
A0A1I8HKD5, A0A1I8IZJ9, A0A1I8HM08,
A0A267GBV5, A0A1I8J8D6, A0A267GVU8,
A0A267GP16, A0A1I8JFH6, A0A1I8J7E2, A0A1I8GC74,
A0A1I8H460, A0A267E6R9, A0A1I8FRS9,
A0A267G961, A0A267DRT5, A0A1I8HUT3,
A0A1I8FU86, A0A267EFS8, A0A1I8HYI4, A0A1I8IQU1,
A0A267ETV5, A0A267E615, A0A1I8FYK6,
A0A1I8FWD9, A0A267ETH5, A0A1I8J0A4,
A0A1I8FYP1, A0A1I8GUN9, A0A267FDY5,
A0A1I8IHJ7, A0A175WH97, A0A175W7N1,

A0A175WB07, G4MZI7, Q2KGY0, G4MXA4, G4MZU5, L7J520, L7JDZ1, L7JG00, L7HS16, L7I490, A0A0C4EBJ2, A0A2E6X7J5, A0A2E6X7K3, A0A238JQ45, A0A0B3RUU6, A0A0B3S7C3, A0A2E9I414, A0A2E9I2Q1, A0A2E9I2P9, A0A093QGB8, A0A093Q5H9, A0A2K5ZUK4, A0A2K5Z4M0, A0A2K6AE30, A0A2K5Z4L5, A0A2K5Z4N9, A0A2K6ADW4, A0A2K5YTU2, A0A2K5Y8K1, A0A2K5ZUK1, A0A2K5Z4U2, A0A2C9UZL6, A0A2C9UQY7, A0A2C9U9R2, A0A2C9W6L4, A0A2C9WFX9, A0A2C9VN71, A0A2C9V805, A0A199UBF6, A0A2C9U5I8, A0A2C9U8X9, A0A2C9U847, A0A2C9V7G1, A0A2C9VAX0, A0A2C9VBF0, A0A2C9VNX9, A0A2C9VLQ8, A0A2C9U446, A0A2C9VAL0, A0A2C9U4D2, A0A2C9U801, A0A2C9U4I0, A0A2C9U805, A0A2C9U7Y6, A0A199UAQ8, A0A2C9UYI9, A0A199UBH6, A0A2C9U8Y9, A0A2C9UPX0, A0A2C9UFH3, A0A2C9U3X3, A0A2C9W8T4, A0A2C9U4C4, A0A2C9UF19, A0A2C9W6W4, A0A2C9U642, A0A2C9VNX3, A0A2C9UK30, A0A2C9VP96, A0A2C9W6N6, A0A199U9M8, A0A2C9UUL6, A0A2C9URP0, A0A2C9UZM3, A0A2C9WC49, A0A2C9UX56, A0A2C9U928, A0A2C9UMD6, A0A2C9UFX9, A0A2C9U9Q2, A0A2C9W8S6, A0A199UC06, A0A2C9UF31, A0A2C9U4L0, A0A2C9U5B5, A0A2C9U487, A0A2C9UDV6, A0A199UC16, A0A2C9VLR9, A0A2C9U0H2, A0A2C9VN68, A0A2C9UPX3, A0A2C9UPE4, A0A2C9UY52, A0A199UBJ1, A0A2C9W426, A0A2C9WEY1, A0A2C9W6P6, A0A2C9W2Y5, A0A2C9W6Q6, A0A2C9VLT1, A0A2C9U478, A0A2C9U869, A0A2C9UZ81, A0A2C9WFM5, A0A2C9W6P5, A0A2C9U8V8, A0A2C9U4K0, A0A2C9UFD3, A0A2C9UUW9, A0A2C9VNC9, A0A2C9VF19, A0A2C9UEZ1, A0A2C9UAW2, A0A2C9UYH0, A0A199UBF1, A0A2C9VN80, A0A2C9U9K7, A0A2C9VTQ5, A0A2C9U5A6, A0A2C9UPQ0, A0A2C9U8W8, A0A199UAZ0, A0A2C9VNE5, A0A2C9UPZ5, A0A2C9U839, A0A2C9UFW8, A0A2C9VB28, A0A2C9U816, A0A2C9U5B6, A0A2C9ULZ6, A0A2C9W6L3, A0A2C9VLU2, A0A199UBJ8, A0A2C9U935, A0A2C9VAT4, A0A2C9U7Q9, A0A2C9VLX7, A0A2C9W6M3, A0A2C9U632, A0A2C9VMC6, A0A2C9UEM3, A0A2C9UFH5, A0A2C9U0N6, A0A199UBH1, A0A199UC12, A0A2C9VLU8, A0A2C9VLS2, A0A2C9VP90, A0A2C9WEW1, A0A2C9U537, A0A2C9U4I6, A0A2C9VE98, A0A251IUP5, A0A199UBE6, A0A251JEQ5, A0A176VVC5, A0A176VSU9, A0A2R6WIU0, A0A2R6WIQ4, Q0AR81, A0A1G9Q3S7, A0A1Q8FK24, A0A2E2XTA6, A0A2D7Y7C9, A0A161Q3D4, W0E1A6, A0A3M8NI56, A0A0F9HEY4, A0A225NEP4, A0A2U2BRH1, A0A2U2BSN0, A0A0H4LDC5, A3VM18, A0A1X7NU32, A0A2D9YV70, A0A2D8PDZ1, K1XNZ5, K1WYE2, K1XJ48, A0A218YS99, A0A218Z724, A0A2T0JV19, A0A3Q3MRJ9, A0A3Q3LF07, A0A3Q3MRQ7, A0A3Q3MWE6, A0A3Q3S4P9, A0A3Q3LIA0, A0A3Q3MRT6, A0A3Q3MXL6, A0A3Q3SHD3, A0A3Q3RXI1, A0A3P9CUC6, A0A3P9CVH7, A0A3P9CXJ8, A0A3P9BY20, A0A3P9BCB7, A0A3P9CDB0, A0A3P9CW19, G7ITJ8, G7IK65, A0A072TZ18, A0A072UMY1, A0A072TMX7, G7LFV0, G7IK59, G7LFU9, A0A072UY36, A0A072ULK1, A0A072UP57, G7LFV1, G7JF50, G7JSW6, G7IK51, G7JF44, G7LFU8, G7IK53, G7IVB0, A0A072VB47, G7IRL5, G7IK61, A0A072UA49, A0A072ULW3, A0A072V563, G7LFU6, A0A072UZ61, G7L503, G7K610, G7J0P4, A0A072V398, G7IK50, A0A072TZS6, A0A072UUL6, A0A072UTW4, G7IZ17, G7K613, A0A072UFT0, G7IK52, A0A072U488, A0A072UVG0, A0A072UN27, G7IVA0, A0A072TZ03, G7IZ18, G7IK54, G7J0Q4, A0A072VB61, A0A072VAM1, Q2HTU4, G7JF49, G7J0Q7, A0A072TPH7, G7L990, G7LDQ6, G7LA23, A0A072UA25, A0A072UUL9, A0A072TYW2, A0A072U0S7, G7IYY4, A0A072TZR6, G7L9B9, A0A072THU9, A0A072UA87, A0A072TZY0, G7J708, G7L199, A0A072TQM4, G7IYX7, A0A072TQ44, A0A072TZ15, G7LA28, G7IH64, A0A072UA68, G7IYX3, A0A072UNR6, G7KZ40, G7LA34, G7L986, A0A072UA82, G7IYY1, A0A072TZ68, A0A072UR75, A0A072THC7, A0A072TZY9, G7JZD9, A0A072V9X1, G7J0Q3, A0A072U1F5, A0A072TPK7, A0A072TYZ8, A0A072V4F9, A0A072TQ73, G7LBP9, A0A072TLA3, G7ITK1, A0A072V4F3, A0A072UN78, A0A072VL26, G7IYX6, A0A072U1H2, A0A072V3X0, A0A072U1E3, A0A072TS26, A0A072U0S1, G7KKY8, G7LA08, A0A072TZ74, A0A072U0N7, A0A072UP51, A0A072VBN5, A0A072TTD3, G7J0Q1, A0A072UP20, A0A072TZ09, A0A072TZ31, G7IRK8, A0A072UVG3, A0A072VAL5, G7IK58, A0A072TQ29, G7JXF4, G7IZ14, A0A072UTW1, A0A072TQF1, A0A072UTA1, G7LA16, G7L9C7, A0A072TQ50, G7JXG0, A0A072TZ10, A0A072UTV6, G7JSW4, G7JSV8, A0A072UKC3, A0A072UN82, A0A072V8H5, A0A396GBY0, A0A396IB06, A0A396I8P5, A0A396I8N0, A0A396II14, A0A396GIR1, A0A396IJL1, A0A396IAC3, A0A396GKB0, A0A396GKM1, A0A396GID7, A0A396GXQ7, A0A396IPQ6, A0A396H464, A0A396J1V4, A0A396GHQ0, A0A396IJS7, A0A396GXP2, A0A396IJV7, A0A396IFP3, A0A396GZH7, A0A396J1V8, A0A396GIN5, A0A396IKZ3, A0A396IEA5, A0A396GIL7, A0A396GJK4, A0A396H410, A0A396J0V6, A0A396GXZ2, A0A396H073, A0A396IH94, A0A396IJQ8, A0A396JG02, A0A396ICL0, A0A396H452, A0A396IB36, A0A396J5K8, A0A396H4I4, A0A396GKI2, A0A396GAD8, A0A396JBU6, A0A396I3J8, A0A396GIN1, A0A396IQ10, A0A396I8N1, A0A396GC28, A0A396GHT6, A0A396H0A3, A0A396IJM8, A0A396IDT3, A0A396H2F4, A0A396J9F7, A0A396J198, A0A396IGJ9, A0A396IMY4, A0A396HUI6, A0A396GXR8, A0A396GJX9, A0A396GMB1, A0A396IQZ7, A0A396JBT7, A0A072TFN9, A2Q3L3, G7JSW9, G7JF45, A0A072TZ95, G7L1A0, A0A072TZR2, A0A072TLV0, G7L2A0, A0A072UDX2, G7IXM3, G7L299, G7L994, G7IRM2, A0A072UTA5, G7JZE3, A0A072U7C9, G7IVB2, A0A072TQ06, A0A072UQ11, G7L9B8, A0A072VJ29, G7J0P5, A0A072ULW9, A0A072TR17, A0A072U021, G7J0P6, A0A072USP0, G7JSX3, A0A072UF01, G7L2A2, A0A072U1F1, G7IYX8, G7IK56, G7IZ19, G7IK62, G7ITK2, G7JSX1, G7JSW5, A0A072UM50, A0A072VE90, A0A072TGW7, A0A072VAH2, A0A072VGD0, A0A396HUX6, A0A396GF10, A0A396J9G3, A0A396GLE7, A0A396J1B2, A0A396GK01, A0A396II24, A0A396H0B4, A0A396IAC8, A0A396GKN1, A0A396H9W1, A0A396GKK2, A0A396ICL7, A0A396GQP4, A0A396GIS2, A0A396GZH2, A0A396GZ32, A0A396J4V5, A0A396IIB1, A0A396GY25, A0A396IPU4, T1GV96, T1GCN7, G5CS05, G5CSX9, G5CSY0, K7YVH7, K7Y8W4, K7YGR5, H2EAU8, H2EAV0,

H2EAE1, L7Y445, L7Y5I8, L7XXX5, A0A2P1EIL3, A0A2P1EIK7, A0A2P1EI82, A0A2H8TNX4, A0A2H8TQD0, G1N219, G3UPW8, G3USW9, G1NG08, G1NIF9, G1MVV6, A0A2J6SGV1, A0A2J6SNC2, A0A2J6T0X6, A0A2J6TAR8, A0A0M8ZTA1, A0A0N1IT07, A0A0M9AA61, A0A0N0BEK1, A0A0N0BFS3, A0A0N1IU30, A0A0N0BKD6, A0A250ING7, A0A1I8B4B8, A0A1I8BK90, A0A1I8AXB8, A0A1I8AXZ1, A0A1I8C0R8, A0A1I8BY25, A0A1I8BIP0, A0A1I8B5R6, A0A1I8BYM1, A0A1I8BQ11, A0A1I8B4D5, A0A1I8BG52, A0A1I8AY49, A0A1I8BQG6, A0A1I8BBQ9, A0A1I8BCA3, A0A091QTC3, A0A091QC15, A0A091QSV6, A0A091QSR7, A0A091QUC8, A0A091RMA7, A0A0R3U559, A0A1U7Q8Z9, A0A1U7R772, A0A1U8C9R2, A0A3Q0CLL1, A0A1U7QLW9, A0A3Q0CJX2, A0A1U7R4K2, A0A3Q0CDV3, A0A1U8BGC2, A0A1U8BFL9, A0A1U8BRY1, A0A1I3VIU9, A0A1I4EVC7, H0HTQ8, A0A212DNS9, G6YBH1, A0A2W5AVW2, A0A2W4ZIG5, L0KNN6, A0A1X7PA47, A0A1X7PI50, E8TE24, A0A143NC21, A0A2P9AXN5, A0A2P7SR23, A0A330I171, A0A330H340, A0A2T4IQ86, A0A068DAZ6, A0A068D8X3, Q982A2, Q982A0, Q983Q7, Q98K29, Q982A3, A0A3M9XHZ6, A0A3A5KV12, A0A2W7C7Z2, A0A2W7CT51, A0A271L788, M5F7L2, A0A1G9IZK6, A0A1L3SUG4, F7Y3J3, F7YDM6, A0A090DAC7, A0A090GF48, A0A090GJ86, A0A090EAQ0, A0A0K2VPY4, A0A1R3VHN0, A0A1R3VG59, A0A1G5YRE1, A0A2A6F891, A0A2P7SMF1, A0A1Q3LTY8, A0A1Q4AJJ6, A0A1A5T9T0, A0A395KH22, A0A3R9Y594, A0A2N7SIF6, A6N7X9, A6N7X6, A6N7X7, A6N7X5, A0A330GWG4, A0A3A3HUH9, X6KLP5, X6K883, X6KA10, V7HDL0, X6JHB4, X6JBU3, X6IKL6, X6HND0, V7H8P5, X6FM84, X6GLA2, A0A371XGB0, A0A1S1SGU3, A0A1S1S606, X6EAG6, X6DBJ5, X6DP76, X6EWU4, X6F6P8, X6EVU3, X6CWC0, X6C4J0, X6DDI2, V7G7Z9, X5Y7Z1, A0A0E2NHH7, V7FGS0, X5V9Q4, X5V974, X5UDZ6, X5RA25, X5PRZ7, X5QT36, X5QMX6, X5QIF0, A0A436RRF8, A0A3S2R3M1, A0A437Z7D9, A0A3S2YUX2, A0A3S3C863, A0A3S3YBG7, A0A437YW26, A0A3S3A539, A0A437ZX63, A0A437VVF2, A0A3S2YVR6, A0A437WTZ3, A0A437VGM9, A0A434THQ7, A0A434SHC2, A0A434NS16, A0A434P1D2, A0A434MM88, A0A3S1ILE2, A0A434PMQ0, A0A434L3Y6, A0A3Q8YPJ5, A0A3S9DBX0, A0A3S9DC85, A0A3S9DBY6, A0A3S9D2V1, A0A3S2KY76, A0A437WND3, A0A3S9FK01, A0A3Q9AI45, A0A3S3LC86, A0A443GJA2, A0A3S2I1J4, A0A436SS41, A0A3Q8YI66, A0A3S1KJ31, A0A434SWL3, A0A3S2KH58, A0A3S1NX24, A0A444KCU0, A0A3S3R3Y8, A0A444K8W2, A0A435D6W3, A0A3S1QJG7, A0A3S9BTR5, A0A436QSC2, A0A436SLU0, A0A436SBV8, A0A3S9DJ20, A0A3Q8YYA6, A0A3S9DRS6, A0A434VEP9, A0A3S1E0H8, A0A436Y6Z9, A0A436VBS5, A0A437ZLF5, A0A436P9R0, A0A436PHM8, A0A3S2IWX9, A0A3S2YQZ9, A0A437X9T7, A0A437X6J9, A0A436WL48, A0A436SR86, A0A3S2IF88, A0A3S2KLT7, A0A436SRB7, A0A436YYK0, A0A435B6A1, A0A3S2QL44, A0A434RXG0, A0A436UW61, A0A436WQQ7, A0A3S2LXT0, A0A3S1MLP3, A0A3Q8ZQ16, A0A436R115, A0A3S3QWG9, A0A434MRM8, A0A3S1HQV7, A0A434MG50, A0A434JX21, A0A3S1HYB4, A0A434EHK3, A0A434CMJ8, A0A454WRI7, A0A3S2FRB0, A0A436KR71, A0A436KVN4, A0A3S2F8X3, A0A3S1VTV1, A0A435QXV3, A0A3S1V2H9, A0A435NFG8, A0A435K6G4, A0A3S1V0K8, A0A436HLD5, A0A3S2ERE3, A0A3S2AZW4, A0A3S2LEV5, A0A3S2DZD0, A0A436BIE9, A0A3S2FP85, A0A435P576, A0A3S1U647, A0A3S1TF94, A0A3S1UAZ5, A0A3S2DDW8, A0A436BS52, A0A3S1VGD1, A0A435KA11, A0A3S1VM62, A0A3S1T8V1, A0A3S1TXY0, A0A435UXY3, A0A435U085, A0A3S1X503, A0A435QVB4, A0A436GBI0, A0A436GCM6, A0A436HTL9, A0A3S2HVT7, A0A436KG24, A0A435W6B2, A0A3S1ZTB0, A0A3S1U3E5, A0A435BZ93, A0A3S2DEI1, A0A435APW1, A0A3S1QT55, A0A3S1WAI0, A0A3S1VV68, A0A3S2G7B5, A0A435MSE4, A0A3S2E2D1, A0A3S2FII5, A0A435FX83, A0A3S2I3S2, A0A436GZ56, A0A435RZZ7, A0A3S2PD80, A0A3S2ASJ9, A0A3S2CHW9, A0A435HlJ4, A0A3S2K8R7, A0A434HTC2, A0A434L053, A0A3S2B6C9, A0A435W3M5, A0A3S1RN73, A0A3S1TEX9, A0A435WUH2, A0A3S1YYJ5, A0A3S1Z5H9, A0A3S1P7C5, A0A3S1TWK1, A0A3S1Y0D5, A0A436CQA8, A0A3S2H9U8, A0A435PLS9, A0A434UUY9, A0A3S1LTZ1, A0A3S1NPV1, A0A3S1NFM4, A0A3S1Q0N3, A0A3S1PV14, A0A3T0JEF6, A0A434H439, A0A3S1HEH3, A0A434C2T4, A0A3S1S2I8, A0A3S2A461, A0A3Q8ZK90, A0A3Q8ZHB5, A0A3Q8ZIL9, A0A3S9EAD3, A0A3S1MPI8, A0A434UBI8, A0A434XFT3, A0A436XWS3, A0A3S9F3K3, A0A3S1LKL0, A0A3Q8XZG9, A0A115G550, A0A090DJ28, A0A090DM34, A0A090DBY7, A0A1S1TYY4, A0A3S1DJG9, A0A434DDZ6, A0A0Q6P090, A0A0Q8AAI4, A0A0Q8AHI2, A0A0Q8KRL3, A0A0Q7WFD1, A0A0Q7WHK9, A0A1E2T1C8, A0A090EMI5, M5FEZ9, A0A1C2DYW0, A0A3S1CC63, A0A1W6X7T5, A0A2A3E108, A0A2A3D8Z1, A0A2A3DCN7, A0A2A3CRF1, A0A2A3S3Y9H7, A0A1A5S3H4, A0A2A3C913, A0A2A3BMA6, A0A2A3BJT5, A0A2A3BJX8, A0A2A3BT00, A0A2A3APY2, A0A3F2UDB7, A0A1I7B871, A0A440WS30, A0A441BU16, A0A3S4GRJ1, A0A441KJB7, A0A441X4E6, A0A440BP34, A0A442P447, A0A440DU90, A0A440FRF7, A0A439HIJ1, A0A440UWQ5, A0A440VCK8, A0A3S4JKR1, A0A439H2W3, A0A442F213, A0A3S3MKL6, A0A440LVW5, A0A439LX41, A0A443D0J6, A0A439SGK3, A0A441U7J5, A0A439Y445, A0A3S3FIG9, A0A442J3G7, A0A439J7B3, A0A3S3JNQ5, A0A440S8T8, A0A3S3FVM8, A0A442U2E3, A0A3S4EUE8, A0A439VKN8, A0A439QVQ7, A0A442LAV1, A0A3S3ENK4, A0A440VEQ9, A0A441HPM6, A0A439V159, A0A442JPW1, A0A439P052, A0A442WYU6, A0A3S3DCE8, A0A3S3F5U4, A0A3S3DDR4, A0A3S4EHK5, A0A442ZIC7, A0A442Y373, A0A442Y1R2, A0A440J505, A0A442JQC4, A0A442SPV3, A0A442VU88, A0A439PZL8, A0A440GZD4, A0A442S531, A0A440KF60, A0A442GQ66, A0A442QWA3, A0A441U254, A0A440N3Y3, A0A442MNF5, A0A3S3F8A3, A0A3S4BUS5, A0A3S3FRU0, A0A3S3K08, A0A3S4KZN4, A0A3S3JXW3, A0A443AW77,

A0A439U373, A0A442M396, A0A440I076, A0A443ER01, A0A440CPT0, A0A442G6N0, A0A442JQB2, A0A441T6H6, A0A439IC62, A0A439ZLB8, A0A439FL51, A0A440L807, A0A442XI98, A0A440NAA5, A0A442XL36, A0A442Q031, A0A440T1P1, A0A441CKQ3, A0A439V3E1, A0A441SU59, A0A442YNW8, A0A442HP09, A0A439GTQ9, A0A439Z2H0, A0A440JZN6, A0A442YRX4, A0A442GXF5, A0A439MT07, A0A443G159, A0A442NGT0, A0A442JPV2, A0A439IIB9, A0A443A4B0, A0A439LUJ8, A0A440CVJ3, A0A440GVE4, A0A440JFB0, A0A441TTA0, A0A443EMA7, A0A442IY47, A0A3S3EEL7, A0A443APX6, A0A441V9P3, A0A442J2Z3, A0A442UTB2, A0A440IBK9, A0A440EGN0, A0A439XJM6, A0A443G1J9, A0A442JQC7, A0A442WB73, A0A442ZRR9, A0A440EB87, A0A442I508, A0A442B2D2, A0A439RGV3, A0A442XE59, A0A441XQ43, A0A439KBP8, A0A443FHR0, A0A442V753, A0A439XT51, A0A439KGC3, A0A439FUH3, A0A442VDM9, A0A440FQR3, A0A443CHW7, A0A443CDR9, A0A443E755, A0A442YE60, A0A442QCW7, A0A443E034, A0A443BMA7, A0A440JYY7, A0A442NIN0, A0A3P3G863, A0A271LPN7, A0A3A5KAS4, A0A3A5L844, A0A271KG65, E9DV60, A0A0B2WJX9, A0A0B4GVG0, A0A0B4GKK8, A0A0B4IAF8, A0A0B4G2X5, A0A167AMX9, A0A014N1B6, A0A3N5N557, A0A1V4V301, A0A1V5AGG2, A0A1V5AWY6, Q2FN86, A0A2V2MVB0, A0A3R7NX32, A0A2R4WGM2, A0A1E3GZU6, A0A1E3H0I6, B8EJN0, A0A395CUD5, A0A177P9W2, A0A2U1SNI8, A0A2D2CXA0, A0A2P6V6K0, A0A2P6VA87, A0A2P6VCG7, A0A2P6V942, A0A2P6VI36, A0A2P6VHH0, A0A2P6VA39, A0A2P6V3M9, A0A2P6V2A4, A0A2P6VB87, A0A2P6VES9, A0A2P6VPE2, A0A2P6VH52, A0A2P6VES2, A0A2P6VML2, A0A2P6V2M3, A0A2P6VH58, A0A2P6VK95, A0A2P6VMI8, A0A2P6VBH1, A0A2P6V9Q5, A0A2P6VI19, A0A2P6VGM6, A0A238FKR1, A0A349JEI0, A0A136J612, A0A136IJV1, A0A136J606, A0A136J3L2, A0A136ITG3, C1EAS9, C1E8G6, C1E8N1, C1FJX3, C1E192, C1MHF5, C1MZS3, C1MT37, A0A086MKH3, A0A159ZQX3, A0A159ZSK6, A0A165XJE2, A0A3S8UXA9, A0A3Q8U814, A0A3S8UYS9, A0A1L6LTM2, A0A246H318, A0A2G9CDV5, A0A1I6IYG6, A0A210Q014, A0A210Q865, A0A210QCM8, A0A210QRE0, A0A210PFV8, A0A210Q3Z0, A0A210QIL1, A0A210QAM1, A0A210R204, A0A210Q475, A0A210PED4, A0A210Q439, A0A210QTF2, A0A210R6V4, A0A210PET2, A0A210QAL4, A0A210QH12, A0A210PTJ6, A0A210QDU9, A0A210PKW3, A0A210PYD7, A0A210PEI4, A0A210Q2X6, A0A210QH27, A0A210Q9G7, A0A210QMZ3, A0A210PNY2, A0A210PKZ8, A0A210QAL2, A0A210QQF1, A0A210Q9Y6, A0A3Q3W1J6, A0A3Q3WBY9, A0A3Q3W970, A0A3Q4B8Q9, A0A3Q3WI21, A0A3Q3XDI1, A0A3Q3VSX4, A0A395J3G5, A0A395J2C4, E2L5Y0, V2YJ73, A0A0W0G933, F7G1K1, F7F243, F7FKH6, F6Y0F0, F7FL16, A0A3Q3IFF7, A0A3Q3Q2I1, A0A3Q3Q2G6, A0A3Q3QBW9, A0A3Q3JMK3, A0A3Q3ILB0, A0A3Q3IFK2, A0A3Q3KJG2, A0A0D2MPA4, A0A0D2LGW3, A0A0D2N2N7, A0A0D2J9H2, A0A0D2M8B4, A9V705, A9V3K4, A9V0V7, A9VCQ3, A9VCI2, A9VUY0, A9VDX2, A9UWN2, A9VAX1, A9UWV1, A9UTM0, A9V068, A9V646, A9V0Z5, A9UNM7, A9UTM0, A9UVN3, Q8LP49, W9S1W6, W9SC56, W9S2J3, W9RMV6, W9R2F2, W9SEU6, W9RS41, W9RZT6, W9RGD7, W9SVD8, W9S9U6, W9SAT2, W9SGF4, W9SFY6, W9R8I4, W9QN88, W9RRQ7, W9S089, W9QYJ9, W9SJF4, W9R8B3, W9RV46, W9SEU1, W9SHC4, W9QI76, W9RLJ1, W9RUW2, W9S558, W9S6F9, W9QMK7, W9S5M0, W9S6T4, W9RG28, W9SB99, W9RS35, W9SIC7, W9S774, W9R087, W9S4J8, W9QCV1, W9QMB2, W9QMB6, W9RTS6, W9QJS9, W9RP60, W9S6W6, W9R543, A0A2P1EL58, A0A2P1ELG5, A0A2P1ELE8, M1NNC1, M1PN76, M1PXF7, H2EEU0, H2EF15, H2EET9, A0A371HKR4, A0A371E8L2, A0A371HQJ5, A0A371F8L2, A0A371HH60, A0A371E8Q5, A0A371GAP6, A0A371I1M6, A0A371HCN9, A0A371HKR5, A0A371GHE4, A0A371FRB0, A0A371H143, A0A371IEP8, A0A371HMC9, A0A371G0L4, A0A371H7G4, A0A371F5G3, A0A371EQX7, A0A371HK74, A0A371HCI3, A0A371F802, A0A371GT85, A0A371E352, A0A371H7E8, A0A371EKZ3, A0A371EVC7, A0A371HGU5, A0A371GDQ1, A0A371H1M0, A0A371G1Y0, A0A371EKI3, A0A371HKT8, A0A371HDB0, A0A371GTF3, A0A371G807, A0A371G1X9, A0A371F145, A0A371GCZ5, A0A371HJ92, A0A371HMD7, A0A371GXN7, A0A371FRU0, A0A371HB49, A0A371HDD5, A0A371HKS1, A0A371IER3, A0A371EZ33, A0A371HH99, A0A371F945, A0A371IEM8, A0A371E4N2, A0A371EL02, A0A371HBI0, A0A371F936, A0A371HME2, A0A371FJ78, A0A371GQ72, A0A371HCE8, A0A371EN60, A0A371GC08, A0A371E6H1, A0A371HKB0, A0A371FWJ5, A0A371HMF4, A0A371GXU7, A0A371HMY2, A0A371HME4, A0A371ECI5, A0A371EGW9, A0A371HMM7, A0A371HK49, A0A371H7E5, A0A371EBC1, A0A371EB07, A0A371ECG7, A0A371FNR9, A0A371HAZ0, A0A371EUQ1, A0A371E529, A0A371HCF5, A0A371EGY1, A0A371ET34, A0A371FNL4, A0A371E3B1, A0A371EG56, A0A371HB25, A0A371HB07, A0A371I1M7, A0A371ER06, P20918, Q08048, P26928, P26262, Q3V1T9, Q6TCI0, Q8C4E2, E0CXN0, H9H9R5, Q3UZ05, Q91XG8, Q8C9G5, Q91Y47, M0SRJ9, M0SUC6, M0U4G9, M0RY71, M0SRJ7, M0TM00, M0S383, M0RH24, M0TF78, M0TDY2, M0U372, M0TB77, M0T6Z8, M0SRJ8, M0RVH0, M0TDY4, M0T1W0, M0S810, M0U587, M0TCZ2, M0RY70, M0TNE6, M0UAY4, M0SP19, M0TVR6, M0S240, M0S243, M0TZM0, M0T308, M0U8W4, M0TLZ6, A0A1I8MY63, A0A1I8M6T0, A0A1I8M8N5, A0A1I8N6V2, A0A1I8NAG5, A0A1I8MV57, A0A1I8NEV1, G9K488, M3YFX5, M3Z3L5, M3YFW6, M3YQ99, M3XZU6, G2QGY9, A0A2T5B5R9, A0A2T5BAW0, S7PRA1, S7QDN3, S7MS05, S7NFT0, L5LR27, L5LGA9, L5M976, G1PGD5, G1PSR3, G1Q6A3, A0A409V789, A0A3L5TVE3, A0A3L5TQ46, A0A3R5Q2Z7, A0A2E8RW71, A0A2D5EZ81, A0A0F7E4G9, A0A1I0BCH0, L7U0L6, Q68BK5, K7J454, K7IRC8, K7J148, K7J2B0, K7J4P8, W2TTT0, W2TUD4, W2TVZ2, W2TY26, W2SM98, W2TYP1, W2U1I9, W2TDU4, W2TCG9, W2T3P4, W2TVN9, W2TK17, W2SPF8, W2TZT5, W2SJP5, W2T4Y4, W2TP33, W2TVL3, W2TNE7, W2T4H9, W2T7H4, W2T2S3,

W2TRM4, C7YKV9, C7ZLU7, C7YHL5, C7ZII7, C7ZNF6, C7Z7I1, C7YTH9, C7ZD94, C7ZLD5, C7ZBG8, C7YSG4, C7ZEX1, C7Z173, C7ZLD0, C7YXE5, A0A1U8Q9H4, A0A1U7ZHR0, A0A1U8AZI5, A0A1U8QBE6, A0A1U7ZR51, A0A1U7ZR95, A0A1U7YTF2, A0A1U8PYZ2, A0A1U7ZWW8, A0A1U8A5W5, A0A1U8B247, A0A1U8A090, A0A1U8AYK2, A0A1U8Q8H4, A0A1U8B4B8, A0A1U8A4R2, A0A1U7Z5Y2, A0A1U7Z9J8, A0A1U7ZJI1, A0A1U8A7C2, A0A1U8B095, A0A1U7ZYN8, A0A1U8QBD9, A0A1U7ZYY7, A0A1U8Q7Y9, A0A1U7ZSA9, A0A1U8ARE9, A0A1U8Q7X5, A0A1U8BCK6, A0A1U7ZLL7, A0A1U7Z475, A0A1U8QCS1, A0A1U7ZID0, A0A1U8B0A1, A0A1U7YTS6, A0A1U8AM32, A0A1U8AN45, A0A1U8B9J8, A0A1U8AIZ5, A0A1U8Q0W3, A0A1U7ZY78, A0A1U8AZI0, A0A1U8BI59, A0A1U8ABD3, A0A1U8AY95, A0A1U7ZHQ5, A0A1U8QAY8, A0A1U7ZFF0, A0A1U7ZRU9, A0A1U7Z1L5, A0A1U8A603, A0A1U7Z5Y7, A0A1U8ARI0, A0A1U8Q9G1, A0A1U8ALH3, A0A1U7Z9W7, A0A1U8Q6V5, A0A1U8BCG2, A0A1U7Z2V6, A0A1U7Z4C3, A0A1U7Z3J0, A0A1U8A7U0, A0A1U8AN31, A0A1U8Q7F4, A0A1U8Q349, A0A1U8BA38, A0A1U8BGB5, A0A1U8AM80, A0A1U7ZY31, A7SZH1, A7SIZ3, A7SRX6, A7SBL4, A7RSM4, A7RNE4, A7RMZ7, A7S8E8, A7RX77, A7RFP1, A7RRU0, A7SBM9, A7RQ47, A7SHY9, A7S6R4, A8DUZ5, A7RU88, A7T3J8, A7SHH8, A7S968, A7SRE8, A7RPS0, A7SM86, A7SEE3, A7S366, A7T6F6, A7RWW1, A7S6Y4, A7S6U4, A7SAJ9, A7S7H3, A7SFL5, A7S6T9, A7RNV4, A7SDI1, A7S941, A7RKH7, A7S6Y5, A7T2L8, A7SEM5, A7SGJ1, A7SRX5, A7RU08, A7S942, A7SRE3, A7T7G4, A7SCA6, A7RIK4, A7RWB2, A7T1F4, A7RQ57, A7SI46, A7SBD5, A7RHX3, A7RQH4, A7T3Q6, A7SFU7, A7RSX6, A7RWB4, A7RUJ4, A7SVL2, A7RVC4, A7SXQ3, A7SIB1, A7SCH3, A7S3Q4, A7RWZ4, A7S293, A7SX86, A7SSU6, A7S547, A7SR11, A7S6D1, A7SDG5, A7RJD0, A7RQE2, A7RP92, A7S3L4, A7T9M2, A7T780, A7T8U0, A7SE24, A7RYZ8, A7SD38, A7SC13, A7S6L2, A7SJ07, A7SN79, A7TCJ6, A7RTC0, A7T1Z2, A7RWV8, A7S6U0, A7SL04, A7RJN3, A7SNB6, A7RM74, A7SK70, A7S6Y3, A0A1Y2A5T7, A0A3Q4MLG0, A0A3Q4I4H3, A0A1Y2BK59, A0A3Q4H1X3, A0A3Q4HU08, A0A3Q4I627, A0A3Q4GWT9, A0A3Q4IEG5, A0A1U7LM76, A0A2Y9H1Q2, A0A2Y9HDN4, A0A2Y9HJV5, A0A2Y9HGI1, A0A2Y9HK72, A0A2Y9HH66, A0A2Y9GTJ0, A0A2Y9HJV1, A0A2Y9H6M8, A0A0P7B6P7, A0A0P7BBW4, A0A0P7BTD6, A0A0N8H811, A0A0P7BG58, A0A0P7BD71, A0A0P7ALI4, A0A0P7BIY5, A0A0P7B5T9, A0A0P7B6I9, A0A0P7BLF3, A0A0P7AUR2, A0A0P7AKI4, A0A0P7BL89, A0A0P7BSA0, A0A341BPU6, A0A341BNE4, A0A341C1A0, A0A341BM03, A0A341ATW5, A0A341C3X0, A0A341BNF2, A0A341CM99, A0A341BLW0, A0A068TC39, A0A0T7H3C9, A0A0T7FB36, A0A0T7FXT8, A0A068SW47, A0A0T7HIV6, A0A386E2E6, A0A346YQL0, A1DN01, Q4WBJ3, B0YAB7, B0XSS6, A0A229XX59, A0A229X3Y5, F0V833, F0V892, F0VKE6, F0VBW4, F0V9H8, F0JAV0, F0VJW9, F0VDC1, F0V7W6, F0VJW8, F0VI90, F0VKF4, A0A0F7UGU6, A0A0F7UM27, F0VKE8, A0A0F7UH55, F0VQW3, F0V8T4, A0A0F7UIB5, A0A0F7U8D9, A0A0F7U4M4, F0V8K8, F0VKE7, A0A0F7UQW1, F0VCD3, F0VJW7,

A0A0H4LVB4, A0A0H4LYS9, A0A0H4MAT4, Q2KHJ3, A0A1A6FUU5, A0A1A6FTR8, A0A1A6GY88, A0A1A6HIS2, A0A1A6FW21, U6CR68, A0A2P6L9E4, A0A2P6L9F6, A0A2P6LI56, A0A2P6L9G3, A0A2P6KM95, A0A2P6K685, A0A2P6L9F0, A0A2P6K678, A0A2P6KT77, A0A2P6K695, D6PR18, D6PR67, A0A091S6P5, A0A091SBL5, A0A091T5V5, A0A091S1J9, A7UVW4, Q7S109, V5ILM8, Q7SFE8, V5ILY1, A0A0B0DW84, Q96U11, A0A0B0E396, A0A0B0E9R9, A0A0B0E9P7, F8N82, F8N4S9, F8MEC8, F8MC30, G4U7X4, G4UFH6, G4UD81, G4U9Q3, A0A1J6HWP7, A0A314L2N5, A0A314KMT1, A0A1J6IQT9, A0A314KMZ2, A0A314KWS7, A0A314LDT0, A0A1J6J3K8, A0A1J6KDN9, A0A1J6ISD8, A0A1J6I486, A0A1J6ICK1, A0A1J6KII4, A0A1J6JDG5, A0A314KM80, A0A1J6IQM4, A0A314L5L5, A0A314KNT5, A0A314L814, A0A1J6I9A0, A0A314L5W9, A0A1J6INQ4, A0A1J6IB07, A0A1J6IG63, A0A1J6JYU0, A0A1J6KUR6, A0A314L5M3, A0A1J6I9G8, A0A1J6KXS8, A0A1J6L9X1, A0A1J6IAJ9, A0A314KLH0, A0A314KHP6, A0A1J6K8T5, A0A1J6K0Y6, A0A1J6KY06, A0A1J6I3J3, A0A1J6I7I0, A0A1J6J380, A0A314L474, A0A1J6HU55, A0A1J6KMP9, A0A1J6JV58, A0A314L438, A0A1J6IJN2, A0A314L6V5, G4XXY5, A0A1J6J9K7, A0A1J6KSS8, A0A1J6IF17, A0A1J6ID41, A0A314L7K3, A0A1J6L0B3, A0A1J6IWL3, A0A1J6IGU9, B9A9C5, B6EB06, A0A1U7VDG6, A0A1U7VUJ3, A0A1U7X9V3, A0A1U7WCZ7, A0A1U7XDD8, A0A1U7VEB0, A0A1U7Y2A8, A0A1U7XQK4, A0A1U7WXX2, A0A1U7WDB0, A0A1U7YLM9, A0A1U7WKL4, A0A1U7WLL2, A0A1U7XQZ3, A0A1U7W2G6, A0A1U7WAK5, A0A1U7W505, A0A1U7WKF6, A0A1U7VZG2, A0A1U7WH46, A0A1U7Y9T1, A0A1U7WED3, A0A1U7WV83, A0A1U7VL33, A0A1U7XGW4, A0A1U7VQE3, A0A1U7YRY2, A0A1U7W1W1, A0A1U7XXL7, A0A1U7Z1C5, A0A1U7YL89, A0A1U7WMH9, A0A1U7VPX9, A0A1U7X9V8, A0A1U7V5P9, A0A1U7XLP8, A0A1U7WT92, A0A1U7V2M1, A0A1U7WD36, A0A1U7VZ90, A0A1U7XDE3, A0A1U7V541, A0A1U7VJP5, A0A1U7W2Y1, A0A1U7VKV2, A0A1U7W5R6, A0A1U7WW15, A0A1U7W09, A0A1U7Y7Q9, A0A1U7VN54, A0A1U7VUC4, A0A1U7WBT7, A0A1U7XL68, A0A1U7W973, A0A1U7X5P3, A0A1U7YK15, A0A1U7XTF4, A0A1U7WPB7, A0A1U7UUN4, A0A1U7WCX4, A0A1U7XPV3, A0A1U7Y3E7, A0A1U7XGV9, A0A1U7Y6J9, A0A1U7VQF3, A0A1U7XPM9, A0A1U7WVB8, A0A1U7W731, A0A1U7XYW4, A0A1U7VPS9, A0A1U7WLD5, A0A1U7XC49, A0A1U7XLK4, A0A1U7W910, A0A1U7WKM8, A0A1U7Y8N9, A0A1U7VET8, A0A1U7WMI3, A0A1U7VC33, A0A1U7XCN9, A0A1U7W9Z4, A0A1U7X4E1, A0A1U7VW07, A0A1U7W8N5, A0A1U7VNJ5, A0A1U7VUJ7, A0A1U7XS99, A0A1S4A8G6, A0A1S3Z9W1, A0A1S3ZKW9, A0A1S3YVQ2, A0A1S3ZKG6, A0A1S3ZPQ4, A0A1S3XZW1, A0A1S4AIL3, A0A1S4AMR9, A0A1S4DLY3, A0A1S4AQV3, A0A1S4A3C8, A0A1S4BVH7, A0A1S3YT81, A0A1S4DJR1, A0A1S4BG39, A0A1S4AAV5, A0A1S3YCL1, A0A1S3YGV9, A0A1S4AS71, A0A1S4CBP5, A0A1S4AIV1, A0A1S3YGK9, A0A1S4C8A5, A0A1S3ZLY6, A0A1S3XKI4, A0A1S4BVI6, A0A1S3YS52, A0A1S3XGG9, A0A1S4C2V4, A0A1S4C7V6,

A0A1S3YX32, A0A1S3X9D4, A0A1S4D768, A0A1J3E7G3, A0A1J3F3A5, A0A1J3JPT9, A0A1J3DU93,
A0A1S4CCG0, A0A1S4C7R5, A0A1S4AAW3, A0A1J3DTR9, A0A1J3CXR2, A0A1J3JBY9,
A0A1S3ZFI4, A0A1S4C0I7, A0A1S3Z379, A0A1S4CT07, A0A1J3E9F3, A0A1J3FSR4, A0A1J3JJ88, A0A1J3H7F2,
A0A1S4BZ07, A0A1S4CBP9, A0A1S4YCE1, A0A1J3JTS5, A0A1J3FCK6, A0A1J3FKJ0, A0A1J3DSR5,
A0A1S3Y0A5, A0A1S4DI92, A0A1S4ASV5, A0A1J3GCV7, A0A1J3FI92, A0A1J3G1G3,
A0A1S3XFC6, A0A1S3X1W3, A0A1S4D7F2, A0A1J3HR35, A0A1J3DHA0, A0A1J3E845,
A0A1S4D8R5, A0A1S4C899, A0A1S4AB13, A0A1J3FS72, A0A1J3G1T7, A0A1J3H5P9, A0A1J3CQE8,
A0A1S3YI37, A0A1S4BCW1, A0A1S3ZBM9, A0A1J3IWX7, A0A1J3G0P7, A0A1J3IM74,
A0A1S3ZWG5, A0A1S3YH70, A0A1S4DEP7, A0A1J3DTR0, A0A1J3JQL3, A0A1J3E7J0, A0A1J3DTZ1,
A0A1S3YCZ3, A0A1S4BQF7, A0A1S3Z2M2, A0A1J3J3Q6, A0A1J3CCB9, A0A1J3FIV7,
A0A1S4DM05, A0A1S4DN45, A0A1S4BD11, A0A1J3EAN5, A0A1J3IVU3, A0A1J3GZI8,
A0A1S3Z7R3, A0A1S3ZF88, A0A1S3ZBH4, A0A1J3HK52, A0A1J3HAN9, A0A1J3JM42,
A0A1S3ZK91, A0A1S3XKN5, A0A1S4DEY0, A0A1J3DI79, A0A1J3DSA9, A0A1J3DX70,
A0A1S4DPZ0, A0A1S3YCZ7, A0A1S4BJE9, A0A1J3HPH3, A0A1J3DW17, A0A1J3DSG0,
A0A1S4B6P0, A0A1S4DER9, A0A1S4A3U1, A0A1J3FWI3, A0A1J3IK70, A0A1J3IIK4, A0A1J3JKH6,
A0A1S3ZG58, A0A1S4BX98, A0A1S3YZW8, A0A1J3CFM4, A0A1J3EV57, A0A1J3IX87, A0A1J3I886,
A0A1S4AAQ4, A0A1S3Y6Q2, A0A1S3Y621, A0A1J3J875, A0A1J3EEU1, A0A1J3ES29, A0A1J3JTY3,
A0A1S4BVJ0, A0A1S4DI53, A0A1S4AGM7, A0A1J3I7Z8, A0A1J3EFY5, A0A1J3CL94, A0A1J3I0U3,
A0A1S3ZWE8, A0A1S4C7S1, A0A1S4C2N1, A0A1J3IVB8, A0A1J3D311, A0A1J3EEH9, A0A1J3DS04,
A0A1S4BVM4, A0A1S4AHG2, A0A1S4BIZ9, A0A1J3D5T0, A0A1J3DME5, A0A1J3IH96, A0A1J3F2S3,
A0A1S3Z1I1, A0A1S4BD90, A0A1S3ZKX2, A0A1J3JRD9, A0A1J3GZM1, A0A1J3FB28,
A0A1S4B4B4, A0A1S3Z7T1, A0A1S3ZXB1, A0A1J3EN22, A0A1J3HDE8, A0A1J3CMT3,
A0A1S3YHU7, B9A9C4, A0A1S4BF74, A0A1S4A7H4, A0A1J3EEN0, A0A1J3FFP7, A0A1J3JUT5, A0A1J3D2I7,
A0A1S3YH89, A0A1S3ZFQ4, A0A1S3XJQ9, A0A1J3H709, A0A1J3DF21, A0A1J3J0E4, A0A1J3H499,
A0A1S4AV00, A0A1S3ZWC2, A0A1S4AJE1, A0A1J3GMB9, A0A1J3GVE5, A0A1J3DWJ7,
A0A1S4C3P0, A0A1S3Z2H5, A0A1S3Z761, A0A1J3JHE1, A0A1J3DMM0, A0A1J3JS61, A0A1J3IP86,
A0A1S3ZGF4, A0A1S4ARU2, A0A1S4AAC7, A0A1J3FSR0, A0A1J3J1W0, A0A1J3GG27,
A0A1S3ZBB3, A0A1S3ZWF8, A0A1S3ZIS3, A0A1J3EMF4, A0A1J3G4X8, A0A1J3ELH1,
A0A1S4BU26, A0A1S3ZIZ8, A0A1S4CTL2, A0A1J3EPX9, A0A1J3GZP2, A0A1J3F8K9, A0A2I3GPI4,
A0A1S3Y6I1, A0A1S4BXG7, A0A1S3WZV5, G1RKX8, M3ZBA9, G1RLC0, A0A2I3G9T1, G1RXL8,
A0A1S4BFA7, A0A1S3YUE5, A0A1S3ZFP6, A0A2I3HH53, G1RLE8, G1R5A0, A0A2R5FFP8,
A0A1S4BBN7, A0A1S4AAQ8, A0A1S4A7H2, A0A2D0H9I4, A0A318AZE0, A0A1A8UHT3,
A0A1S3YHW7, A0A1S4BF06, A0A1S4B7P0, A0A1A8U2N8, A0A1A8UGE6, A0A1A8AMP3,
A0A1S4A3X6, A0A1S4BF18, A0A1S4DQJ7, A0A1A8UYV9, A0A1A8DKN8, A0A1A8CX61,
A0A1S4C7S6, A0A1S4DI64, A0A1S3YNY7, A0A1A8F858, A0A1A8KU64, A0A1A8J1X1,
A0A1S3YZ96, E5D7E5, A0A1S4BTQ9, A0A1S4AAV8, A0A1A8HP15, A0A1A8Q0T0, A0A1A8M3J2,
A0A1S4BVJ1, A0A1S4CI20, A0A1S3YL50, A0A1A8N5R8, A0A1A8S3A7, A0A3D1P0S1,
A0A1S4AHU4, A0A1S4AGG2, A0A1S4C7S0, A0A3D1P0P9, A0A2T4ZM68, A0A2D9MLX3,
A0A1S4AGE4, A0A1S4C7G1, A0A1S4C1I5, A0A2E5UVY4, Q2CK54, A0A1N6H695, A0A254R8C3,
A0A1S4C7F1, A0A1S4DEL0, A0A1S4C4Q3, K2I7J2, A6X4J9, A0A011UJA9, A0A137XJ12,
A0A1S4BTX0, A0A1S4CUC0, A0A0U2UIV4, A0A3R8ZDT7, A0A1J6HPX3, A0A256FNR5,
A0A0U2TUD0, A0A0U2K3G9, A0A091VZY0, A0A397M124, A0A2P9HHH8, U4V6A2, C4WPE7,
A0A091W0K6, A0A091UP08, A0A091ULT1, M5JM46, A0A256GVM1, A0A2S7J3N1, A0A256G407,
A0A0N4XE48, A0A3P7CNB1, A0A0N4YIX3, A0A1A9FPL5, A0A256F053, A0A2M9SAC5,
A0A3P7A1Y9, A0A3P7AQW4, A0A0N4Y5X9, A0A2M9RTW1, A0A2M9RPN7, A0A248UL68,
A0A158R0D4, A0A0N4XTQ9, A0A3P7B0Z6, A0A248UDK1, A0A421BXV1, U1XL45, A0A3N0BIY1,
A0A0N4YDL0, A0A0N4Y521, A0A0N4XTZ4, A0A2S8YAJ0, A0A2S8Y7R3, A0A2S8TZD4,
A0A0N4YX44, A0A158QWT4, A0A158R0F4, A0A1V3YWR0, A0A317LE59, A0A292GL07,
A0A0N4YRN0, A0A0N4XCL2, A0A158R0A2, A0A256FB23, A0A0L8HR65, A0A0L8G008,
A0A0N4XP57, A0A0N4YJU3, A0A158QZV0, A0A0L8GIC5, A0A0L8G5H6, A0A0L8HWE5,
A0A0N4XMB6, A0A158R2Z3, A0A0N4YT44, A0A0L8HQP4, A0A0L8HYY9, A0A0L8G081,
A0A0N4XW83, A0A158R099, A0A0N4XDZ8, A0A0L8HPA3, A0A0L8HXI7, A0A0L8HS26,
A0A0N4XLC5, A0A0N4YJQ3, A0A0N4YT73, A0A0L8FY82, A0A0L8HWF0, A0A0L8HQ38,
A0A0N4XKU9, A0A158QZH2, A0A158QX22, A0A0L8G444, A0A0L8IDR0, A0A0L8G3A8,
A0A0N4YVS7, A0A0N4XWH8, A0A0N4XTR1, A0A0L8HMG8, A0A0L8HW99, A0A0L8HWE2,
A0A0N4YUM8, A0A0N4YSD3, K2PNL4, K2P3G0, A0A0L8H6T5, A0A0L8HQN8, A0A0L8HP85,
K2LLY9, A0A1H4K6F6, A0A2P8ND91, A0A2E0JHX2, A0A0L8HDL0, A0A0L8FNP5, A0A0L8FJ32,
Q1QRJ6, A0A1Q3JTV4, A0A1M3C7Q1, A3WSN9, A0A0L8HW19, A0A0L8GXG5, A0A0L8GT95,
A0A1V4I335, Q3SMU6, A0A1H8BAS7, A0A1I0D0D5, A0A0L8GXD9, A0A0L8HWB9, A0A0L8GSV1,
A0A1H9S965, A0A358JLT2, A0A2N6HD53, A0A0L8GYH4, A0A0L8FUE7, A0A0L8HNN0,
A0A1J3FP03, A0A1J3HMF5, A0A1J3HW34, A0A0L8H7N3, A0A0L8GWJ9, A0A0L8G1Z8,
A0A1J3GB39, A0A1J3JNB8, A0A1J3ZS2, A0A1J3ISG7, A0A0L8HP77, A0A0L8G183, A0A0L8FRC1,
A0A1J3DXH5, A0A1J3E580, A0A1J3GBL6, A0A0L8I283, A0A0L8HWA4, A0A0L8I485,
A0A1J3K818, A0A1J3H057, A0A1J3GQN5, A0A0L8GWC4, A0A0L8H6J5, A0A0L8HZ03,
A0A1J3HRL3, A0A1J3DRG8, A0A1J3GNA1, A0A0L8HPE9, A0A0L8FRF9, A0A0L8HWA4,
A0A1J3J3Z7, A0A1J3JRE5, A0A1J3FL37, A0A1J3JQL6, A0A2U3VGE7, A0A2U3VVF2, A0A2U3X506,
A0A1J3GRF7, A0A1J3JX24, A0A1J3GGC1, A0A2U3W015, A0A2U3VZS1, A0A2U3ZHH0,

A0A2U3X5D6, A0A2U3X502, A0A2U3X508,
A0A0B1SMS5, A0A0B1SZF3, A0A0B1T7G4,
A0A0B1TNZ7, A0A0B1SVQ8, A0A0B1TSF3,
A0A0B1THL2, A0A0B1RPJ3, A0A0B1TVI4,
A0A0B1T7X3, A0A0B1TLL5, A0A0B1SJV9,
A0A0B1SZQ3, A0A0B1TJJ8, A0A0B1TQU4,
A0A0B1SPE9, A0A0B1TRM5, A0A0B1TM49,
A0A0B1TP05, A0A0B1TLV5, A0A0B1SLD5,
A0A0B1T699, A0A0B1TQQ2, A0A0B1SIU2,
A0A0C3GVM9, A0A0C3GHZ3, A0A0C3GYJ2,
A0A0C3C6A0, A0A0C3GWZ0, E4YAT7, E4X175,
E4Z726, E4XPL0, E4YKT2, E4WX62, E4WXA9, E4X236,
E4XM60, E4X025, E4YGB1, E4YEZ4, E4Y3D2,
A0A3N6PYR2, D7RJY6, D7RJY4, B6JDB0,
A0A238BQ40, A0A183HYH0, A0A183HKI7,
A0A183H9Q1, A0A183HZR7, A0A183HM98,
A0A183I5Y8, A0A183H621, A0A183HW79,
A0A183HZQ7, A0A183HBN7, A0A183HGE2,
A0A183I2D1, A0A183I087, A0A183GZD3, A0A238C1L1,
A0A238C0I5, A0A238BZT1, A0A238C1R8,
A0A3P7VC50, A0A183HF33, A0A238BHJ2,
A0A238C1C5, A0A238BUI0, A0A238BPJ5,
A0A3P7KGB4, A0A182ERB1, A0A3P7JTR2,
A0A182EUC0, A0A182E9R2, A0A182E294,
A0A3P6SEL8, A0A3P6STP6, A0A182EK23,
A0A182EGU8, A0A182EBS9, A0A182ELR8,
A0A182E8N8, A0A182E853, A0A182E148,
A0A182E7K9, A0A182DWJ9, A0A182E5V3,
A0A044TXH1, A0A044TB24, A0A044V6J3,
A0A044SAK8, A0A044T6C9, A0A044TQE7,
A0A044VG28, A0A044TXN9, A0A044QW86,
A0A044TQV4, A0A044TS10, A0A044VIE3,
A0A044SXT1, A0A2K6W0F3, A0A2K6VJT9,
A0A2R7VUY6, A0A2R7WMN5, A0A2R7X3S8,
A0A2R7VTV5, A0A2R7WIU5, A0A2R7WIV9,
A0A2R7WJA5, A0A060X7U1, A0A060XRA8,
A0A060XME5, A0A060XFN8, A0A060W8B1,
A0A060WHF0, Q5DVP8, A0A060XU84, A0A026W7N3,
A0A3L8E197, A0A026VZ91, A0A026WBB7,
A0A3L8DVC2, A0A3L8DB52, A0A026W4C2,
A0A3L8DPD8, A0A026X1V9, A0A3L8E1U8,
A0A3L8DP99, A0A026W2Z5, A0A3L8DFM8,
A0A0L7LTQ8, A0A0L7L2P1, A0A0L7LM72,
A0A0L7L0G5, A0A0L7L335, A0A0L7L2H0,
A0A0L7LA69, T5ADX7, T5AAZ9, A0A2A9PMS4,
A0A2A9PLL3, V8NK09, V8PHB4, S3D177, S3C2I7,
A0A091WHX0, A0A091XY89, A0A091WJ34,
A0A091WK45, A0A1S8WUG3, A0A074ZV38,
A0A075A3I4, A0A1S8X8S4, A0A1S8WQZ1,
A0A074Z2H8, A0A074Z9I0, A0A1S8WPP4,
A0A074ZMS3, A0A2E9RXB9, A0A1D2NBH8,
A0A1D2MZY1, A0A1D2NJJ1, A0A1D2MYU3,
A0A1D2ND60, I3K037, I3KFD6, I3K036, I3KFB8,
I3KCE9, I3JAQ5, I3JAR3, I3KCF0, I3KFB7, I3J849,
I3J1D2, A0A0P6YFR3, A0A293M3U3, A0A293LHY5,
F7CM56, F7BQ99, F7FSH7, F7CM40, F7FSI1, O80354,
A0A0T6BGW1, A0A0T6B7H3, A0A0T6B598, Q95ME7,
D0PTV6, G1U9Q9, G1SSQ6, G1T127, G1SMZ3, G1SFS6,
D0PPI8, C9E9X4, E0CW66, E0CW57, B9V0G8,
A0A0D3HR23, A0A0D3HAE3, A0A0D3EL74,
A0A0D3G020, A0A0D3HR22, A0A0D3EX91,
A0A0D3H9S4, A0A0D3GD84, A0A0D3ESA3,
A0A0D3EUU8, A0A0D3FJY4, A0A0D3GS78,
A0A0D3EUU6, A0A0D3G016, A0A0D3EUU9,
A0A0D3GS89, A0A0D3FKE2, A0A0D3ESB1,
A0A0D3H9S5, A0A0D3FU00, A0A0D3EUU5,
A0A0D3GD82, A0A0D3EUU4, A0A0D3EUV0,
A0A0D3FU04, A0A0D3ESA2, A0A0D3EWT3,
A0A0D3GI36, A0A0D3HI98, A0A0D3EQN3,
A0A0D3FR49, A0A0D3EL79, A0A0D3FXQ4,
A0A0D3G018, A0A0D3H9R8, A0A0D3FTZ3,
A0A0D3G022, A0A0D3GHQ2, A0A0D3EX86,
A0A0D3EWT4, A0A0D3FVT7, A0A0D3HHT7,
A0A0D3GS79, A0A0D3G017, A0A0D3G132,
A0A0D3EL82, A0A0D3FVU0, A0A0D3H9S1,
A0A0D3FVT5, A0A0D3HCH4, A0A0D3EL84,
A0A0D3FU01, A0A0D3EUU3, A0A0D3HS10,
A0A0D3HV71, A0A0D3G021, A0A0D3H9R9,
A0A0D3EUV2, A0A0D3ESB4, A0A0D3FFK8,
A0A0D3EX49, A0A0D3HSZ8, A0A0D3HX90,
A0A0D3H9S2, A0A0D3GIF2, A0A0D3G9H3,
A0A0D3HJF3, A0A0D3G019, A0A0D3FVT4,
A0A0D3G3N6, A0A0D3FUK4, A0A0D3HHT5,
A0A0D3G011, A0A0D3GS82, A0A0D3GS90,
A0A0D3GI35, A0A0D3G012, A0A0D3G7P0,
A0A0D3G013, A0A0D3G550, A0A0D3G024,
A0A0D3FVS9, A0A0D3EL80, A0A0D3HCH7,
A0A0D3EX87, A0A0D3FVT0, A0A0D3GI32,
A0A0D3HHT9, A0A0D3G3N8, A0A0D3FRT4,
A0A0D3ESB0, A0A0D3FT93, A0A0D3HHU2,
A0A0D3G023, A0A0D3FUM6, A0A0D3ESA7,
A0A0D3GS81, A0A0D3FVS8, A0A0D3HJF4,
A0A0D3G3N7, A0A0D3G3P0, A0A0D3EJR8,
A0A0D3G131, A0A0D3EL81, A0A0D3ERR0,
A0A0D3G9G2, A0A0D3FAT2, A0A0D3EUU7,
A0A0D3HV70, A0A0D3EL83, A0A0D3FU02, J3L4R2,
J3L0V7, J3MLV8, J3LUL2, J3L5D6, J3LLH5, B9V0I5,
J3MZX1, J3LPV8, J3L2Q4, J3NBU7, A0A0U1WXR2,
J3M4A9, G2XM38, J3L2R2, J3MFK0, J3N1W7, J3L2A1,
J3LX34, J3KXU0, J3M263, J3MZW5, J3M1Q6, J3MLV6,
J3LQ96, J3MZW8, J3NB41, J3KXT4, J3L6M2, J3MQB8,
J3KWJ2, J3LXT3, J3M4A7, J3MID2, J3M1Q3, J3L4R1,
J3KXU3, J3L2Q7, J3MEX9, J3MLV9, J3M4A8, J3MF85,
G2XM40, J3LVJ9, J3LXT4, J3L6J2, J3LWL4, J3MQW0,
J3KUK1, J3M1Q9, J3M265, J3M1Q4, J3MEX8, J3LXT1,
J3KW69, J3L2Q8, J3L809, J3M264, J3NFE2, J3MF84,
J3L4Q9, J3LXT5, J3LW49, J3KXU2, J3LWL5, J3L2Q3,
J3MLW9, J3L2Q5, J3M780, J3M7G4, J3MGY9, J3LXT6,
J3N0F9, I1NQI2, I1NQI4, I1PZU2, I1NKC7, I1PL71,
I1QTK2, I1NU21, I1P904, I1R3R0, I1NTS1, I1NQI7,
I1PL76, I1NQI3, I1R3R2, I1R4I3, I1PCQ7, I1QS23,
G2XMM6, I1PL69, I1Q381, I1PJJ4, G2XMM7, G2XMM5,
I1PPM3, I1QR22, I1PTT5, I1R3R1, G2XMM4, I1PPM4,
I1PIJ8, I1QR27, I1PL68, I1QR20, I1PQE8, I1PL73,
I1PST0, I1NU52, I1PL72, I1QR24, I1PX09, I1PZT8,
I1PPM7, I1NQI6, G2XMV1, I1PST2, I1PMV0, I1QR21,
I1R8A7, I1R3Q9, I1PL77, I1NTS0, I1QYI5, I1NLF0,
I1QR28, I1PPM6, I1NS91, I1PK04, I1QXD1, I1PL79,
I1P0W9, I1PCD1, I1P4I6, I1PPL9, I1NU57, I1PK06,
I1Q383, I1R5B8, I1NQI9, I1NLF3, I1QXD4, I1PK03,
I1QBG0, I1QBF9, I1QR19, I1PPM5, I1QBG7, I1PH64,
I1QBF7, I1QYI6, I1NQI5, G2XLC0, I1PPM0, I1Q380,
I1PQE7, I1PJ7, I1PSR4, I1PL75, I1NLE2, I1PPM2,
I1PL74, I1PSS6, I1PSS8, I1NTS2, I1QTK4, I1Q3F8,
I1NLF2, I1NS88, A0A0D9YK84, A0A0D9YCX9,
A0A0D9ZG94, A0A0D9ZKN7, A0A0D9ZJI1,
A0A0D9YIH2, A0A0D9ZKN8, A0A0D9ZR94,
A0A0E0B677, A0A0D9YFW0, A0A0D9Y5E5,
A0A0E0AL88, A0A0D9YI07, A0A0E0ARK9,
A0A0D9Y5D1, A0A0D9ZMW8, A0A0D9Y5E7,
A0A0D9Z436, A0A0D9ZR74, A0A0E0AL85,
A0A0D9ZIM8, A0A0D9YFW3, A0A0E0A5I8,
A0A0D9Y5C8, A0A0D9ZUP3, A0A0E0BEX9,
A0A0E0AL72, A0A0E0AL76, A0A0D9ZR97,

A0A0E0BFC3, A0A0E0B678, A0A0D9ZIN0, A0A0E0HSU5, A0A0E0FQ49, A0A0E0H0P1,
A0A0D9ZFJ1, A0A0D9ZRA5, A0A0D9YFW4, A0A0E0GX02, A0A0E0HJW4, A0A0E0HS89,
A0A0D9ZRA4, A0A0D9ZR98, A0A0D9ZRA7, A0A0E0GKI7, A0A0E0I7U3, A0A0E0H0P8,
A0A0D9ZR81, A0A0E0AIR6, A0A0D9YA73, A0A0E0FGF6, A0A0E0J8N8, A0A0E0INB5,
A0A0E0BNH0, A0A0D9YIC5, A0A0E0BNG7, A0A0E0HUM6, A0A0E0H0N9, A0A0E0FWA9,
A0A0D9ZG93, A0A0D9ZZ82, A0A0D9ZJF8, A0A0E0GDA8, B9V0Q1, A0A0E0H2X3, A0A0E0HY24,
A0A0E0A5J0, A0A0D9Z9I2, A0A0D9ZRS7, A0A0E0G7M5, A0A0E0FIM7, A0A0E0FQR3,
A0A0D9Y5C9, A0A0D9ZIM7, A0A0E0AL74, A0A0E0H6W8, A0A0E0GXL4, A0A0E0IXT2,
A0A0D9YC92, A0A0D9Y4Z1, A0A0D9YCY7, A0A0E0FWU1, A0A0E0FQR6, A0A0E0H0P7,
A0A0D9ZRA6, A0A0D9ZR95, A0A0D9Y5E4, A0A0E0JB34, A0A0E0GW59, A0A0E0HGH5,
A0A0D9Y5E6, A0A0D9ZR83, A0A0D9Y3F4, A0A0E0IZH0, A0A0E0H0P6, A0A0E0INB6,
A0A0E0BGJ9, A0A0E0BR07, A0A0D9YFX1, A0A0E0FIN2, A0A0E0HR40, A0A0E0GKJ1,
A0A0D9ZR90, A0A0D9YCY3, A0A0D9YI02, A0A0E0FIP9, A0A0E0INC5, A0A0E0H0N5,
A0A0D9ZIN2, A0A0E0B670, A0A0E0B668, A0A0E0HY06, A0A0E0FQR7, A0A0E0GKJ2,
A0A0D9ZR80, A0A0E0BNG4, A0A0D9YYI7, A0A0E0GKH3, A0A0E0I273, A0A0E0INB4,
A0A0E0A5J1, A0A0E0BR04, A0A0E0B667, A0A0E0IZH1, A0A0E0FIN0, A0A0E0HGG1,
A0A0E0B671, A0A0D9YI05, A0A0D9YCY4, A0A0E0HS95, A0A0E0GKI5, A0A0E0H0P0,
A0A0D9ZUP5, A0A0D9Y5D0, A0A0D9ZR79, A0A0E0J2D2, A0A0E0GXK3, A0A0E0J696,
A0A0D9YIG5, A0A0E0ARL0, A0A0E0ABJ9, A0A0E0I250, A0A0E0GKI3, A0A0E0FQS1,
A0A0D9ZKP7, A0A0E0BPR9, A0A0D9Z920, A0A0E0HLM1, A0A0E0GXR3, A0A0E0FWQ0,
A0A0D9YIH3, A0A0D9Y5E8, A0A0E0B705, A0A0E0J8N4, A0A0E0HS91, A0A0E0HLM4,
A0A0D9Y5D3, A0A0D9YFW1, A0A0E0ARL1, A0A0E0IZG9, A0A0E0I254, A0A0E0INC4,
A0A0E0BVT0, A0A0E0A194, A0A0D9ZRA3, A0A0E0FU79, A0A0E0GYT0, A0A0E0J9E6,
A0A0D9YFW2, A0A0D9ZUP4, A0A0D9ZR96, A0A0E0FLY3, A0A0E0FIP7, A0A0E0GPL9,
A0A0D9Y5D2, A0A0E0B985, A0A0E0B664, A0A0E0HST7, A0A0E0J7G5, A0A0E0FI93,
A0A0D9ZRS6, A0A0D9ZKN9, A0A0E0B982, A0A0E0FWT5, A0A0E0I249, A0A0E0I0E2,
A0A0D9YT30, A0A0D9YCY1, A0A0D9YFX0, A0A0E0H0N6, A0A0E0GP69, A0A0E0H0N7,
A0A0D9YIG8, A0A0D9ZG92, A0A0D9ZR82, A0A0E0IGG9, A0A0E0IXT5, A0A0E0IXT1,
A0A0D9YFW8, A0A0E0ARK8, A0A0D9ZR78, A0A0E0I252, A0A0E0FU81, A0A0E0GKJ0,
A0A0E0AIE6, A0A0D9ZIM6, A0A0D9YFW7, A0A0E0JCW6, A0A0E0JB33, A0A0E0GP70,
A0A0D9ZKP8, A0A0D9YI03, A0A0E0BTG8, A0A0E0GKI9, A0A0E0HSU3, A0A0E0FIN9,
A0A0D9ZRA2, A0A0E0DCW6, A0A0E0C8L4, A0A0E0J698, A0A0E0H6W7, A0A0E0FNQ7,
A0A0E0DFW2, A0A0E0EUL2, A0A0E0DE62, A0A0E0GKJ3, A0A0E0FWT8, A0A0E0J2D0,
A0A0E0CAW3, A0A0E0DNX0, A0A0E0EUM2, A0A0E0HT73, A0A0E0HS88, A0A0E0FIN8,
A0A0E0CLE9, A0A0E0EUK8, A0A0E0BXB3, A0A0E0INB8, A0A0E0FU76, A0A0E0FIN7, B9V0Q0,
A0A0E0DE59, A0A0E0DC72, A0A0E0EUK7, A0A0E0FIN4, A0A0E0KQI0, A0A0E0KF64,
A0A0E0DIT6, A0A0E0C5U5, A0A0E0ECX2, A0A0E0KVP1, A0A0E0MCH2, A0A0E0M481,
A0A0E0DXL5, A0A0E0DIT9, A0A0E0DSY1, A0A0E0KM14, A0A0E0LRX0, A0A0E0JS11,
A0A0E0EWS8, A0A0E0EUL1, A0A0E0FCQ8, A0A0E0JFS6, A0A0E0KQJ0, A0A0E0KVP4,
A0A0E0FA77, A0A0E0EUL0, A0A0E0EUM1, A0A0E0M493, B9V0S7, A0A0E0KNA2, A0A0E0LM11,
A0A0E0C5U3, A0A0E0CBD2, A0A0E0DE49, A0A0E0KVP5, A0A0E0LRW9, A0A0E0JPL8,
A0A0E0DE58, A0A0E0CBC9, A0A0E0E351, A0A0E0KYW2, A0A0E0JFS5, A0A0E0MC44,
A0A0E0CL32, A0A0E0F268, A0A0E0CAW4, A0A0E0JPM2, A0A0E0LCW7, A0A0E0JQG4,
A0A0E0DC71, A0A0E0C599, A0A0E0DIU3, A0A0E0LDK4, A0A0E0MJ94, A0A0E0KVP2,
A0A0E0E354, A0A0E0DC70, A0A0E0ECX0, A0A0E0JPL6, A0A0E0LHZ7, A0A0E0LBV1,
A0A0E0BZ76, A0A0E0FAG5, A0A0E0F2L6, A0A0E0L4C9, A0A0E0JPM1, A0A0E0KQI6,
A0A0E0DE64, A0A0E0C5U8, A0A0E0DXL9, A0A0E0M482, A0A0E0M4V9, A0A0E0LZP4,
A0A0E0F269, A0A0E0CB81, A0A0E0E2S8, A0A0E0JFQ8, A0A0E0LYC7, A0A0E0MJ93,
A0A0E0EWS6, A0A0E0C5U2, A0A0E0C5U7, A0A0E0MQ50, A0A0E0M487, A0A0E0LRW7,
A0A0E0DML9, A0A0E0DC67, A0A0E0DCZ3, A0A0E0KML7, A0A0E0LM19, A0A0E0KW47,
A0A0E0E3L6, A0A0E0DE54, A0A0E0FA73, A0A0E0KVN9, A0A0E0M6P1, A0A0E0M6P2,
A0A0E0D9W7, A0A0E0BZ80, A0A0E0DIS8, A0A0U1WXQ2, A0A0E0LZM8, A0A0E0KSK1,
A0A0E0FA68, A0A0E0BZ68, A0A0E0DC68, A0A0E0KQI4, A0A0E0JE78, A0A0E0K0K1,
A0A0E0C3C6, A0A0E0D9B1, A0A0E0DBN8, A0A0E0KAM8, A0A0E0MKA3, A0A0E0KQI5,
A0A0E0ECW5, A0A0E0EUK6, A0A0E0D2Q4, A0A0E0L2K7, A0A0E0JFS2, A0A0E0JRX9,
A0A0E0F3G5, A0A0E0FAZ3, A0A0E0DIU0, A0A0E0KFK8, A0A0E0KVN4, A0A0E0KQI8,
A0A0E0DIS6, A0A0E0DE56, A0A0E0FA37, A0A0E0JM75, A0A0E0LCW4, A0A0E0KQI3,
A0A0E0DJC4, A0A0E0FA69, A0A0E0ECX4, A0A0E0LD93, A0A0E0LCX3, A0A0E0M492,
A0A0E0EIN0, A0A0E0DIS7, A0A0E0DE65, A0A0E0KNT6, A0A0E0K5I5, A0A0E0JLN9,
A0A0E0DML8, A0A0E0EA66, A0A0E0BZ79, A0A0E0KVP3, A0A0E0KRU6, A0A0E0JM78,
A0A0E0FDQ6, A0A0E0DIS5, A0A0E0C8L7, A0A0E0KYV9, A0A0E0KLA8, A0A0E0JS10,
A0A0E0ECW7, A0A0E0E264, A0A0E0FDQ5, B9V0L1, A0A0E0LM06, A0A0E0MC39, A0A0E0KNA3,
E0CW78, A0A0E0GKI4, A0A0E0FIN1, A0A0E0FIP8, A0A0E0JRK2, A0A0E0KYY4, A0A0E0LM08,
A0A0U1WYS9, A0A0E0HGH4, A0A0E0J8N9, A0A0E0JRK4, A0A0E0KJLN5, A0A0E0L8B2,
A0A0E0INR6, A0A0E0H0N8, A0A0E0FQS6, A0A0E0MDQ4, A0A0E0KVN6, A0A0E0JM73,
A0A0E0GKI6, A0A0E0GKI2, A0A0E0HXK8, A0A0E0KQI2, A0A0E0JPL9, A0A0E0JM82,
A0A0E0J697, A0A0E0GX03, A0A0E0FQR8, A0A0E0LYG7, A0A0E0KNT9, A0A0E0LET8,

A0A0E0JS09, A0A0E0LZM7, A0A0E0KNU2, A0A0E0JS12, A0A0E0LRW8, A0A0E0JM79, A0A0E0JRX7, A0A0E0KYY5, A0A0E0LZM9, A0A0E0JTU7, E0CWC2, A0A0E0P929, A0A0E0QUS7, A0A0E0Q9Q2, A0A0E0R5M3, A0A0E0R5M2, A0A0E0N0I2, A0A0E0PPL5, A0A0E0N0I7, A0A0E0N0I1, A0A0E0PEJ2, A0A0E0QUS6, A0A0E0PEJ4, A0A0E0PY75, A0A0E0R492, A0A0E0N0I4, A0A0E0PI15, A0A0E0NWN9, A0A0E0QF46, A0A0E0R5M4, A0A0E0PTZ3, A0A0E0MRI6, A0A0E0PEI3, A0A0E0PYZ1, A0A0E0R5M1, A0A0E0PEJ6, A0A0E0P930, A0A0E0R3S3, A0A0E0RKL1, A0A0E0Q9N8, A0A0E0MYM4, A0A0E0RI41, A0A0E0N0H4, A0A0E0Q9P1, A0A0E0PZV4, A0A0E0PEJ5, A0A0E0PZG7, A0A0E0QF44, A0A0E0P3N3, A0A0E0P717, A0A0E0PZ15, A0A0E0Q9Q1, A0A0E0P724, A0A0E0P936, A0A0E0REI6, A0A0E0N628, A0A0E0NRR4, A0A0E0QUS8, A0A0E0MS90, A0A0E0QVH0, A0A0E0RDA8, A0A0E0P672, A0A0E0N0H5, A0A0E0PEI8, A0A0E0PEJ3, A0A0E0N633, A0A0E0MT99, A0A0E0QF47, A0A0E0QF43, A0A0E0PZG2, A0A0E0P571, A0A0E0PF17, A0A0E0MT98, A0A0E0PEI6, A0A0E0NL99, A0A0E0QXV0, A0A0E0MTA1, A0A0E0N631, A0A0E0N5M2, A0A0E0N3D9, A0A0E0Q505, A0A0E0PI17, A0A0E0P556, A0A0E0P7R6, A0A0E0Q6Z5, A0A0E0P4C6, A0A0E0PF18, A0A0E0QUT5, A0A0E0N3E2, A0A0E0P934, A0A0E0P723, A0A0E0MSU8, A0A0E0RDA9, A0A0E0N0J0, A0A0E0N5M3, A0A0E0QUT6, A0A0E0P935, A0A0E0NFS2, A0A0E0QXU8, A0A0E0MT87, A0A0E0P933, A0A0E0N5Z2, A0A0E0RFL8, A0A0E0PZG5, A0A0E0PEJ1, A0A0E0P726, A0A0E0PBB3, A0A0E0NX59, A0A0E0PTY5, A0A0E0Q9N9, A0A0E0N3D6, A2YMH7, B8AP81, B8A9Q7, B8B3W2, A2YDY8, A2XYE9, B8AUV8, B8BFX5, A2XPF2, B8B7X0, B8AUV4, B8AAG4, A2XRP3, B8B3K4, B8AAN9, B8A6L2, B8BIX3, B8B784, B8A6Z2, B8BE63, A2X9W0, B8BBD1, B8AYF8, A2Z666, A2Y9R2, B8A7D5, B8ASQ4, B8A779, A2ZIL9, A2XRP6, B8AUV7, A2YEC0, B8AAP0, A2WVT4, B8BM83, A2XTD8, B8B2E5, A2ZBG9, B8AUV2, B8AS67, B8BEE8, A2YMH8, A2Y2G0, A2YMG6, B8ASF5, A2ZCH9, A2XTE2, B8ATQ3, B8BE64, A2XTD2, B8ATQ2, B8AS68, B8ATQ5, B8A780, A2WM87, B8BLW7, B8AK50, A2YMG7, A2XTE5, B8AUZ5, A2WTM1, B8AUV3, A2Z664, A2Z3T6, A2WXE7, B8AB24, A2YER5, B8AAN5, A2WXT2, B8AUW7, B8BE67, A2WVT7, A2XVC1, A2YTP0, B8BLW6, B8A783, A2XTD1, A2XTD0, B9V0N4, B8ATQ4, A2ZB52, B8BEE9, A5JS87, A2ZB38, A2WTM3, A2Y9Q7, B8AZQ7, B8A782, B8AUW5, A2XE17, A2ZN71, A2WRY3, A2WKV0, A2XTD4, B8A7B9, A2Y0R8, B8AUV5, B8ATY7, A2XII0, A2XTE4, A2X5J7, A2Y0Q5, B8BE62, B8AVL9, A2ZB35, A2WT48, A2XTE3, B8AUV6, A2XNU0, A2XXZ2, B8AUW6, B8BE66, B8AUV1, B8B3W0, B8BP34, A2ZHT0, A2ZCI0, Q0JDY0, Q69MP3, B9FEC4, B9FBW5, B9EYI9, Q0JD96, B9FZD1, B9FCW6, B9GBP9, Q5N835, A0A0P0Y6H8, B9G4Y0, B9FMN5, A0A0P0WFW5, B9ETD6, Q60D67, A3CFG6, A0A0P0UZX5, A0A0P0XQJ7, Q0J9S4, A0A0P0WIC4, Q5Z607, Q0J9S9, A0A0P0WSZ1, Q2R920, A0A0N7KR84, A0A0P0XQY3, A0A0P0V6A7, Q5NB60, Q0J9S8, Q5QNL1, Q69MN9, A0A0N7KJ20, A3C195, Q7X6C7, Q0JEB3, A0A0P0Y0I8, B9FCQ2, Q2QY66, B9FMM3, B9FEC2, B9FCW7, A0A0P0XQ09, A0A0P0XQ04, A0A0P0WXZ2, B9FCQ0, C7J132, A0A0P0XRC3, Q7XQT3, Q0JH14, A3BL04, C7J1M6, Q2RAY8, Q5QLM8, A3AVE3, A3BCZ7, A0A0P0Y6V4, A3AXR8, Q5JQW1, A0A0P0WF90, A0A0P0WF87, B9F816, B9FCQ5, A0A0P0XYU6, C7J3E6, B9FXT7, Q0IZT3, A0A0P0Y7N1, A0A0P0X5S1, A0A0P0VAV4, A0A0P0WG14, A0A0P0XQ32, A0A0P0WIA4, A0A0P0WAJ2, A2ZYH9, Q0J9T9, Q0JEB, Q2QWY4, Q7XL24, B9FEC1, B9GE14, A3AS58, A0A0P0VBI4, B9G4X2, A0A0P0V6F2, A0A0P0W6Q5, Q0J9T4, B9FCP9, A0A0P0XYD6, B9EUW0, Q0J9S6, Q8H353, A0A0P0V6E9, B9FCP8, Q7XQU2, A0A0P0VBE8, B9EU56, A0A0N7KHG5, Q7XMH7, B9F999, Q0J9T3, Q0ITY0, B9G985, Q0E0R8, Q7XL27, B9FCQ4, B9EU61, A3A0E3, B9EUW2, B9EVA3, A0A0P0Y700, A0A0P0XPZ9, A0A0P0W9H2, A0A0P0WF77, A0A0P0WF71, A0A0N7KDE3, A0A0N7KJS0, Q0JEPI, Q7XQU6, B9FKZ6, A0A0P0X7Q1, A0A0P0WAE2, A0A0P0XRC1, B9EYJ0, B9FCQ1, B9ETD5, B9GCM6, A3B8R2, Q6ATL4, Q7XQU0, A3C9L3, B9FD08, B9G4X9, A3A014, B9FCQ3, B9FMN4, B9G4X5, A3CEN4, B9FF59, A0A0P0WFH6, Q7XJ40, A0A0P0W6K3, A0A0P0WAN9, B9FXT6, B9FF58, A0A0P0WF66, Q7XNW1, A0A0P0WF95, A3A0E0, Q7XQT7, Q8W054, Q69MN2, Q7XI25, Q5NAQ9, Q8LMB0, Q2QPI9, Q7XHV3, Q2R917, Q5QLR7, Q5QLN0, Q9LE23, Q5ZAL3, Q0JH38, Q53PX8, Q0IUV4, Q8W3C9, Q5N9Y5, Q7XMR2, Q0JKJ3, Q7XXJ5, Q5ZAK8, Q7XQU3, Q2QLI8, Q851M7, Q60D69, Q7EZ32, Q60EJ2, Q5ZBQ1, Q8H821, Q6ZF83, Q8S0R2, Q7XQT8, Q5Z604, Q7XTD6, Q7X6I1, Q2RAY6, Q5VRR9, Q84MF7, Q6Z6H3, Q5Z601, Q7XTD7, Q9LDT8, Q2RAY2, Q7XMH4, Q5Z932, Q69XK0, Q2QUP5, Q0J9T7, Q69MM4, Q0JD95, Q2QY70, Q5SMQ2, Q2QY68, Q7XMG8, Q7XMG6, Q2RAY4, Q2R918, Q0D733, Q10JE9, Q5NB61, Q6H6Q2, Q8LMB2, Q7XQT9, B7F353, Q7XMH8, Q7XMG5, Q7XMC0, Q5QLM9, Q0J9T2, Q7EZ33, A2ZWE1, Q8LQN6, Q8W059, Q8LQH1, B9FEC3, Q60D78, Q60D68, Q0JIQI, Q5ZAV5, B9FJP0, Q7Y1P1, Q2QY71, Q943Q1, Q7XMH0, Q7XUM4, Q7XQX5, Q69MM9, Q0JPG7, Q7XSF1, Q7XMH5, Q7XMH1, Q25A54, Q0I1KU2, Q0I1J05, Q25A55, Q8LLI2, Q25A21, Q0I1MD3, Q8LLI3, Q0I1K00, Q25AB4, Q0I1KM2, Q0I1MD6, Q25A60, Q8LLI4, Q0I1K01, Q0I1K07, Q9LLN5, Q0I1MD7, Q0I1LZ8, Q0I1N33, Q0I1K06, Q0I1N32, Q25A58, Q25A57, Q0I1MD8, Q0I1K02, K0JBC6, Q25AB6, Q0I1M86, Q8LLI1, Q25A00, Q0I1M00, Q259Z7, Q25A01, A0A437CU31, A0A3S2U5L5, A0A3S2MCZ5, A0A437DAI2, A0A3S2MFY0, A0A437DEQ2, A0A3P9ICR8, Q50LG6, A0A3B3I1H2, A0A3P9MP48, A0A3P9K011, A0A3P9I2I7, H2LF02, A0A3P9JAV4, A0A3P9LI60, A0A3P9J614, H2MEZ4, A0A3P9MAE3, A0A3P9LHP9, H2MEU2, H2M0V9, A0A3P9HMN6, A0A3P9K000, A0A3P9JJS7, A0A3P9LIA1, A0A3B3D7P0, I1SRG1, A0A3B3D5Q6, A0A3B3BZR1, A0A3B3CM08, I1SRH8, A0A3B3DHX8, C1BLZ6, A4S6G3, A0A1Y5IBM2, A0A096P7Z7, A0A090N4R5, A0A1Y5I2L6, A0A1Y5IDE4, A0A1Y5I7I8, A0A090LXV4, A0A096P9I0, A0A1Y5I593, A0A096P7B4, A0A090MCI5, H0XRY6, H0WTA2, H0WJV6, H0X5J0, H0WJV3, W5PEM0, W5P3R3, W5PEI4, W5PUG1, W5Q5H9, A0A1X6WFX5, A0A1X6WF83, A0A086XR69, A0A2R9CEQ2, A0A2R9B5R5, A0A2R9CAN4, A0A2R9B8J6, A0A2R9B1Y7, A0A2R9CER0, A0A2R9CES0, A0A2R9CL99, A0A2R9BBJ0, A0A2J8L7X0, A0A2J8JZZ2, A0A2J8L7Y1, A0A2J8L7X6, A0A2J8L807, A0A2I3RJ89, A0A2I3S7A8, A0A2J8L7W7,

A0A2J8L7X2, A0A2J8LGB0, A0A2I3S7L0, A0A2I3SM29, A0A2J8JZY8, H2QIA7, A0A2J8K5V2, A0A2J8LGB6, A0A2J8LGB4, A0A2I3S5X5, K7CWX4, A0A2J8L7V9, H2QUU8, A0A2J8K020, H2QU06, A0A2I3TJS6, A0A2I3T423, A0A2I3REN2, H2QQJ4, A0A2I3TKS5, A0A2I3SRY8, K7BAC9, K7AMD5, A0A2J8K5U6, H2R8A3, A0A409YP06, A0A409YU19, A0A2T7D0I5, A0A2T7EVK0, A0A2T7EDS2, A0A2T7E6P0, A0A2T7DT33, A0A2T7CS41, A0A2T7CTI1, A0A2T7E553, A0A2T7E643, A0A2T7ET21, A0A2T7ER75, A0A2T7DIN6, A0A2T7DDD3, A0A2T7CBD2, A0A2T7EVJ0, A0A2T7D0G2, A0A2T7CT36, A0A2T7E6C1, A0A2T7C4S3, A0A2T7DFU5, A0A2T7DFU8, A0A2T7CMR2, A0A2T7EF41, A0A2T7EWK1, A0A2T7BYK9, A0A2T7DLQ8, A0A2T7DJ77, A0A2T7D0E9, A0A2T7C3A3, A0A2T7DDF0, A0A2T7EW50, A0A2T7CBC7, A0A2T7CL36, A0A2T7EX72, A0A2T7EIN3, A0A2T7D0E7, A0A2T7D509, A0A2T7CFW6, A0A2T7DT37, A0A2T7CUW6, A0A2T7D0D5, A0A2T7DLD3, A0A2T7F513, A0A2T7E7E6, A0A2T7F551, A0A2T7F5F3, A0A2T7D0D9, A0A2T7F5F1, A0A2T7CUW0, A0A2T7D494, A0A2T7EBW9, A0A2T7D0E0, A0A2T7E7B7, A0A2T7DFW0, A0A2T7F436, A0A2T7EVJ2, A0A2T7CUW5, A0A2T7CUZ3, A0A2T7CMN6, A0A2T7E7C7, A0A2T7CB30, A0A2T7EX73, A0A2T7EX64, A0A2T7ER93, A0A2T7D0F4, A0A2T7EVJ5, A0A2T7ERX6, A0A2T7EX66, A0A2T7DDD0, A0A2T7D0E4, A0A2T7CBK9, A0A2T7E0A7, A0A2T7D0F3, A0A2T7D0D8, A0A2T7DV28, A0A2T7DT28, A0A2T7DIM9, A0A2T7DX83, A0A2T7DIM2, A0A2T7F574, A0A2T7F5H7, A0A2T7D0J0, A0A2T7DFV2, A0A2T7EVK4, A0A2T7CUW4, A0A2T7DX94, A0A2T7D0Q9, A0A2T7EVI9, A0A2T7EJU9, A0A2T7EBW4, A0A2T7CB26, A0A2T7EBW3, A0A2T7EVI4, A0A2T7DFU4, A0A2T7C4G3, A0A2T7DJ67, A0A2T7D0F2, A0A2T7DFW9, A0A2T7E6H9, A0A2T7DLC8, A0A2T7BYV2, A0A2T7ENB4, A0A2T7CUV7, A0A2T7D0Y3, A0A2T7DLE0, A0A2T7CUW3, A0A2T7DRA7, A0A2T7DDA9, A0A2T7D0K1, A0A2T7DLD0, A0A2T7D0Q0, A0A2T7EBV8, A0A2T7D0H3, A0A2T7E7B6, A0A270R6Y3, A0A2S3HXW3, A0A2T8IPC6, A0A2T8KJ78, A0A2T8ICA6, A0A2S3HTA8, A0A2S3IAP2, A0A2T8I4D3, A0A2T8KV97, A0A2S3H0F9, A0A2S3IAP8, A0A2S3H1N8, A0A2S3HIG5, A0A2S3IAR5, A0A2T8KQB7, A0A2S3I5P1, A0A2T8IE12, A0A2T8KRJ5, A0A2S3H2E7, A0A2S3HGY6, A0A2S3IKM6, A0A2S3IAM3, A0A2S3H186, A0A2S3I0N4, A0A2T8I4D7, A0A2S3H205, A0A2S3H7F5, A0A2T8IJZ0, A0A2S3H1U7, A0A2T8KUQ8, A0A2T8IC99, A0A2T8I0T0, A0A270R6C5, A0A2T8IE65, A0A2S3HTE7, A0A2T8KRK0, A0A2T8IE16, A0A2S3HAQ3, A0A2S3IGG3, A0A2S3HPQ6, A0A2S3HR11, A0A2T8IDZ9, A0A2S3ID39, A0A2T8IE34, A0A2S3H3A8, A0A2S3GXJ4, A0A2S3H396, A0A2T8KM77, A0A2S3HUX0, A0A2S3IAS7, A0A2S3H762, A0A2T8IE17, A0A2T8IE14, A0A2S3IAP0, A0A2T8KS60, A0A2S3IS50, A0A2S3HP70, A0A2S3HK05, A0A2S3IQN4, A0A2S3IPM5, A0A2S3HAQ6, A0A2S3HR06, A0A2T8KNP2, A0A2T8KRH6, A0A2S3IGI2, A0A2S3HR12, A0A2S3HD01, A0A2S3H5Z0, A0A2S3IE86, A0A2S3HT43, A0A2S3IQM7, A0A2T8IJ38, A0A2S3II5, A0A2S3IB91, A0A2T8JCF9, A0A2S3IAQ3, A0A2T8IE28, A0A2S3I6M3, A0A2T8KV35, A0A2S3IBD2, A0A2S3IPQ8, A0A2T8KHH4, A0A2S3H6Z9, A0A2S3IAP1, A0A2S3HV18, A0A2S3HBZ4, A0A2S3HRI0, A0A2S3I6M7, A0A2S3GP95, A0A2S3HUW3, A0A2T8KRL1, A0A2S3HJZ4, A0A2S3HP69, A0A2T8II B4, A0A2S3IAN4, A0A2T8IAS4, A0A2T8II1S3, A0A2T8IDZ2, A0A2S3H370, A0A2S3HW47, A0A2S3IAP4, A0A2T8IE05, A0A2T8KRJ0, A0A2S3HGB8, A0A2S3HZ22, A0A2S3GNM4, A0A2S3HFW8, A0A2S3H7E9, A0A2S3HIN5, A0A2T8KLZ9, A0A2S3I6H4, A0A2S3IAN6, A0A2T8I8I3, A0A2T8IBV6, A0A2S3I506, A0A2T8IJW5, A0A2S3IAP7, A0A2S3HAP8, A0A2T8KHP9, A0A2S3I6I3, A0A2S3GTT4, A0A2T8II1Q5, A0A2S3IST7, A0A2T8KVD3, A0A2T8IE22, A0A2T8IJV0, A0A2T8IE03, A0A2S3GYI1, A0A2S3IAT7, A0A2S3HZR6, A0A2S3IAN7, A0A2T8IKX9, A0A3L6TCR6, A0A3L6PZS7, A0A3L6S5J8, A0A3L6PDC5, A0A3L6QHJ2, A0A3L6PX19, A0A3L6PCT4, A0A3L6PL39, A0A3L6PX91, A0A3L6S5N0, A0A3L6QA61, A0A3L6PG20, A0A3L6SUD9, A0A3L6RDD5, A0A3L6Q4M6, A0A3L6PCG6, A0A3L6SC35, A0A3L6QNE5, A0A3L6PWM5, A0A3L6SS66, A0A3L6S1T6, A0A3L6SHN4, A0A3L6PTZ7, A0A3L6TP99, A0A3L6SU86, A0A3L6R9E9, A0A3L6SL66, A0A3L6QSF1, A0A3L6Q3C3, A0A3L6TLT5, A0A3L6PTZ2, A0A3L6Q8B0, A0A3L6QWW8, A0A3L6RTV3, A0A3L6SY93, A0A3L6THN0, A0A3L6S034, A0A3L6SRC3, A0A3L6QXJ3, A0A3L6T0D2, A0A3L6T329, A0A3L6R3K6, A0A3L6RCL0, A0A3L6T8M5, A0A3L6QUJ7, A0A3L6SPW4, A0A3L6T7S6, A0A3L6QCA5, A0A3L6RXE5, A0A3L6T8Z5, A0A3L6RSY0, A0A3L6SVG3, A0A3L6R496, A0A3L6RL96, A0A3L6PWI7, A0A3L6T589, A0A3L6T3C1, A0A3L6R910, A0A3L6QPB7, A0A3L6SAN9, A0A3L6Q7C9, A0A3L6T2B5, A0A3L6SZ69, A0A3L6R808, A0A3L6PV23, A0A3L6R2W0, A0A3L6TPL9, A0A3L6S8F1, A0A3L6QW70, A0A3L6PE95, A0A3L6R0F3, A0A3L6RH98, A0A3L6SDA3, A0A3L6P9T3, A0A3L6PX52, A0A3L6RQD8, A0A3L6S172, A0A3L6TFE8, A0A3L6SSN5, A0A3L6S7G8, A0A3L6SBX7, A0A3L6QI59, A0A3L6SGX8, A0A3L6PSV3, A0A3L6PB20, A0A3L6SW57, A0A3L6PS89, A0A3L6T996, A0A3L6QZB1, A0A3L6Q8B5, A0A3L6RFQ9, A0A3L6R701, A0A3L6QDT6, A0A3L6SN21, A0A3L6T804, A0A3L6QYH1, A0A3L6SXL6, A0A3L6TUW6, A0A3L6STY3, A0A3L6TQD8, A0A3L6QWJ0, A0A3L6T346, A0A0K6HYJ7, A0A378ZUH8, A0A0U3PCH3, A0A224XG17, A0A224XJC5, A0A224XLL6, A0A224XI83, A0A194RNJ8, A0A194R138, A0A0N1PJM0, A0A194RDJ8, A0A194R2I6, I4DM08, A0A0N1I4I2, A0A194PVK1, A0A194PQ35, I4DIJ2, A0A194QJF1, A0A194PTA1, A0A194PXM5, A0A2I3MER4, A0A096NQZ2, A0A2I3MEH4, A0A096MT27, A0A096NZY9, A0A2I3LKX1, A0A096MR85, A0A2I3M8D7, A0A096NC95, A0A1H6MTW0, S5XSK4, A0A3D9XH37, A0A1G9LDL1, A0A1W6CWQ5, A1B4L0, A0A2W5A1K7, A0A099F544, A0A368YRU1, A0A1K1YUK1, A0A454NRD8, A0A1I5KJ26, A0A2A2GLC7, A0A1N7M497,

A0A099GIU4, A0A1H2UIH5, A0A418SQD8, A0A3R7P0E8, A0A3R7PNR3, A0A3R7PF83, A0A2K9F7T9, A0A3N7HKP6, A0A1X7K5P3, A0A1L9S4X6, A0A1L9SBG1, A0A1V6PCL2, A0A3S4DYQ8, A0A0V0Q0U8, A0A1N6QLJ3, A0A1F5LG55, A0A1F5LFH2, A0A1F5LBV1, A0A3E0CAT2, A0A369U330, A0A386UNW4, A0A1F5L7N0, A0A1F5LFH7, A0A1F5L4M3, A0A2D2C4W0, A0A1V0GXG8, A0A2H5F0H5, D1M702, A0A0G4PQR1, A0A1V6UT76, A0A1V6URX4, A0A135HYP7, A0A3B3T1V7, A0A3B3T2D5, A0A1V6USL6, A0A1V6PHF0, A0A0A2ITH3, A0A3B3QTI7, A0A3B3T216, A0A3B3R816, A0A1V6SGC7, A0A0A2KKT0, A0A1V6WU75, A0A3B3T3Q0, A0A3B3QMB5, A0A3B3T389, A0A1V6Z413, S8B8Z7, S7ZRP3, S7ZGN1, S7ZMP6, A0A3B3T3H8, A0A3B3T3U8, A0A177CZE2, A0A135LCH0, A0A135LCH3, A0A135LCQ1, W6Q172, A0A177CRA0, A0A177CUG9, A0A177C382, B6HSU8, A0A1V6QSF1, A0A1V6QSE8, A0A2H3III4, A0A177C6N6, A0A177CID1, A0A1C7P136, A0A2H3IC68, A0A1V6SRD0, A0A1Q5T8E6, A0A2P5BJA4, A0A2P5BW50, A0A2P5B4R0, A0A1Q5TYZ6, A0A1V6RF18, A0A1V6RE75, A0A2P5BW53, A0A2P5BW51, A0A2P5BM82, A0A1V6RG25, A0A1V6S597, A0A1V6RFI7, F1C726, A0A2P5A6J9, A0A2P5BW67, A0A2P5E4M6, F1C7D0, A0A2V1DWV5, A0A2V1D2D5, A0A2V1DIZ4, A0A2P5D441, A0A2P5BW21, A0A2P5BKD8, A0A2V1DJW4, A0A2V1DLD9, A0A2V1D8T0, A0A2P5E4L5, A0A2P5BMA8, A0A2P5BKI9, A0A3B3ZPQ5, A0A3B3ZY43, A0A3B3ZXI2, A0A2P5AA39, A0A2P5BMB4, A0A2P5B4Q4, A0A3B3ZP74, A0A3B3ZYU4, A0A3B4AGU9, A0A2P5BM80, A0A2P5DYR7, A0A2P5AHJ9, A0A3B3ZP80, A0A3B3ZYS8, A0A0L1L095, A0A2P5E4N0, A0A2P5D258, A0A2P5BW45, A0A3M6VL27, A0A3M6VAW8, A0A425CJM8, A0A2P5BKH5, A0A2P5E4Q5, A0A2P5A6G1, A0A3R7Y325, A0A3M6V6Z7, W3XET2, W3X3J5, A0A2P5BM96, A0A2P5B4Q6, A0A2P5BW66, W3XMF5, W3XPT6, W3XC43, W3WRT1, W3XNX9, A0A2P5BM92, A0A2P5BN11, A0A2P5BMD0, A0A2J6QKC3, A0A366X020, A0A1B0ZTK3, A0A2P5CS31, A0A2P5BMA5, A0A2P5E4N1, A0A0P1GVW2, A0A0P1IHK9, B7G5U0, A0A0G2E5S8, A0A2P5B4P1, A0A2P5CSJ2, A0A2P5BM72, Q0UMP0, Q0U636, Q0V168, Q0V5G3, Q0V4N1, A0A2P5E4Q3, A0A2P5BH32, A0A2P5B4S4, Q0TZX6, Q0UPL0, Q0UWY3, Q0UP20, A0A091ULD3, A0A2P5CFJ1, A0A2P5E4M4, A0A2P5DP24, A0A091T5G0, A0A091TAK8, A0A091TBV2, A0A2P5BIW1, A0A2P5CC51, A0A2P5BM84, A0A093QYY4, A0A093TDY9, A0A093QPS2, A0A2P5BM71, A0A2P5BJC8, A0A2P5B4T3, A0A093QSI2, A0A0L9TKR2, A0A0L9VGP0, A0A2P5BKJ2, A0A2P5AA49, A0A2P5BW30, A0A0L9UFV5, A0A0L9ULD5, A0A0L9TCV5, A0A2P5BW41, A0A2P5BW35, A0A2P5B1T6, A0A0L9V3Z2, A0A0L9UKZ9, A0A0L9U8P2, A0A2P5E4R8, A0A2P5B1R8, A0A2P5DGX2, A0A0L9U553, A0A0L9TLV1, A0A0L9U6Q9, A0A2P5B4R2, A0A2P5B4Q1, A0A2P5B4S3, A0A0L9UIH5, A0A0L9ULI3, A0A0L9UM53, A0A2P5BJA2, A0A2P5BW77, A0A2P5BW40, A0A0L9U552, A0A0L9V319, A0A0L9UN60, A0A2P5B4Q8, A0A2P5DYQ3, A0A2P5CA29, A0A0L9TLV8, A0A0L9ULD1, A0A0L9V362, A0A2P5AIJ3, A0A2P5BM74, A0A2P5E4J2, A0A0L9V8X3, A0A0L9V600, A0A0L9ULS9, A0A2P5BJC9, A0A2P5BM50, A0A2P5A6F1, A0A0L9T851, A0A0L9VUB8, A0A0L9TGQ7, A0A2P5BW89, A0A2P5BW37, A0A2P5BW20, A0A0L9U4V0, A0A0L9THP8, A0A0L9VUS9, A0A2P5E4P8, A0A2P5BW58, A0A2P5E4M9, A0A0L9V9B9, A0A0L9UIP6, A0A0L9UPU8, A0A2P5E4P4, A0A2P5E4N5, A0A2P5B4R9, A0A0L9TKM5, A0A0L9V913, A0A0L9VTA1, A0A2P5A6G8, A0A2P5DYT0, A0A2P5BW31, A0A0L9V3F3, A0A0L9V376, A0A0L9UN55, A0A2P5AEM1, A0A2P5D7Y5, A0A2P5BW71, A0A0L9V4V3, A0A0L9V1W9, A0A0L9V3H0, A0A2P5BMA2, A0A2P5AH20, A0A2P5B4S8, A0A0L9VFN3, A0A0L9UTN1, A0A0L9TGU5, A0A2P5BMC0, A0A2P5BXQ1, A0A2P5BVZ5, A0A0L9V3V3, A0A0L9UPN2, A0A0L9TGG9, A0A2P5BKL3, A0A2L2YD42, A0A2L2Z1W7, A0A0L9V486, A0A0L9UMB7, A0A0L9VGI7, A0A2L2Z8H1, A0A2L2ZA53, A0A2L2Z530, A0A0L9UJE5, A0A0L9TUI5, A0A0L9V464, A0A2L2YWS1, A0A0N4ZHI4, A0A0N5A0H4, A0A0L9VFU0, A0A0L9U5F8, A0A0L9U882, A0A0N4ZPS9, A0A0N5A3M1, A0A0N4ZRF2, A0A0L9UJ28, A0A0L9VSL2, A0A0L9UMD9, A0A0N4Z938, A0A0N4Z4J1, A0A0N4ZE42, A0A0L9UM48, A0A0L9VFN1, A0A0L9V5Z3, V7BQJ3, A0A0N4Z1R8, A0A0N4Z6U2, A0A0N4ZP70, V7CQM2, V7AIN2, V7BX92, V7B6U7, V7AIF8, A0A0N5A5G9, A0A0N4ZHI3, A0A0N4ZNC4, V7BXZ6, V7ALS3, V7B4W4, V7AHY7, V7AGA5, A0A0N4ZKC3, A0A0N4ZPV9, A0A0N4Z312, V7AIM9, V7AIL8, V7CPR4, V7BXT0, V7AIF2, A0A0N4ZIU0, A0A0N4Z5S0, A0A0N4ZS52, V7AHM7, V7BUN3, V7ALT3, V7AMQ9, V7AIH2, A0A402ESB7, A0A402FAU3, A0A402FMT0, V7AJU3, V7APL9, V7B7X1, V7ALI5, V7AHN7, A0A402EEM0, A0A2D8XC50, A0A1V4K051, V7BVD1, V7AHQ4, V7AMQ6, V7AJR9, V7BRW9, A0A1V4JKY3, A0A1V4JG98, A0A1V4JKX2, V7AE52, V7ALQ7, V7BV89, V7AJK3, V7D2F6, V7BZ49, A0A1V4K8H7, A0A1V4K1P3, A0A1V4K8P3, V7AHK3, V7CPG4, V7B5J8, V7AID3, V7AIM3, A0A1E1WSI0, A0A1E1WED2, E0VCL9, E0VHE3, V7BYK2, V7B3V1, V7AH65, V7BXM2, V7AJP5, E0VC84, E0VX62, E0VX61, E0VJE4, A0A1P8UUY1, V7BYJ9, V7BQM9, V7BZ42, V7B3X6, V7AJE9, V7AJS5, Q0FI61, A0A2D6BAV5, A0A1E4DW35, A0A1E4FC43, V7ATU1, V7CPG0, V7CM72, V7AST9, V7ALL6, A0A1E4GBY0, A0A1E4GLE6, A0A1Y5RQR3, V7CZ14, V7BTA1, V7AKL3, V7BXZ1, V7AHE0, A0A2U2CX27, A0A238KIZ4, A0A2T7G6G5, V7ALR2, V7ALS5, V7AKL1, V7AVN9, V7C143, A0A091SM44, A0A091TMT4, A0A091TWU6, V7C7H2, V7CA41, V7ALS8, V7B451, V7D003, V7ANE1, A0A091STZ2, E5RLR1, K7GFR6, K7GGY8, K7FLF2, V7AVN4, V7BUI7, V7AMN5, V7AHR0, V7BTA2, A0A347ZT03, A0A3R7LS22, A0A423SJ34, A0A423TTP3, V7AMM7, V7AHK9, V7AMO9, V7ALF8, V7BUL6, A0A3R7M4Q0, A0A423SF89, A0A3R7MK76, V7AGA9, V7AHL4, V7BWF6, A0A194X242, A0A3R7P3K5, A0A423U6F6, A0A423TME0, A0A194XBS6, A0A132BBB6, A0A194WTN9, A0A423TTP4, A0A3R7M498, A0A3R7MRL0, A0A132B592, A0A194X7W7, A0A194X856,

A0A194XR54, A0A194WSB8, A0A194WSX5, A0A194WTK6, A0A194XX66, A0A132BCG7, A0A132B964, A0A1L7XLE9, A0A1L7X859, A0A1L7WF44, A0A1L7XLL5, A0A1L7XTN8, A0A1L7X9R0, A0A1L7WMU3, A0A0N0NQR5, A0A0N1HGJ5, A0A0N0NQ51, A0A0N1GX61, A0A0N1H4B9, A0A0N1NZ06, A0A0N1HG31, A0A370TCU2, A0A370TYQ2, A0A370TJW0, A0A370TQF0, A0A1B0GNH6, A0A1B0D9P3, A0A1B0DGU9, A0A1B0DI86, A0A1B0GP61, A0A091U239, A0A091UAN5, A0A3Q0HVZ9, A0A3Q0HMY7, A0A3Q0I1K4, A0A2H3ZIZ6, A0A2H3ZAB6, A0A3Q0I914, A0A2H3X918, A0A3Q0HT42, A0A2H3ZS58, A0A3Q0IFF5, A0A3Q0HQF8, A0A3Q0HSM9, A0A3Q0HVI7, A0A3Q0HTF0, A0A2H3XGF9, A0A2H3X9J5, A0A2H3X0Q6, A0A2H3X3J0, A0A2H3YZ59, A0A2H3Y805, A0A2H3X8K1, A0A2H3XA64, A0A2H3WXV9, A0A2H3X7L6, A0A2H3ZCS3, A0A2H3ZIK9, A0A3Q0HR72, A0A2H3XQV7, A0A2H4A1V3, A0A2H3ZJF3, A0A3Q0HQX3, A0A3Q0HSL1, A0A2H3X0N3, A0A2H3YKV9, A0A2H3Z3E8, A0A3Q0HVZ4, A0A3Q0HTK9, A0A2H3XJR1, A0A3Q0I0R7, A0A2H3YI52, A0A2H3X0N6, A0A3Q0I4E3, A0A2H3Y849, A0A2H3ZQ89, A0A2H3Y8E0, A0A2H3ZT49, A0A3Q0IGU8, A0A3Q0HRL0, A0A2H3YUK0, A0A2H3X6E4, A0A3Q0IBE3, A0A3Q0I4N2, A0A2H3Z4R9, A0A2H3Y059, A0A2H3WYX2, A0A3Q0HQU7, A0A2H3ZI64, A0A2H3XQR6, A0A2H3ZW91, A0A1Y1KHG4, A0A1Y1MWD5, A0A1Y1N456, A0A1Y1LYJ5, A0A1Y1K6Q9, A0A1Y1KVK9, A0A1Y1NDL0, A0A1Y1MWC5, A0A1Y1KDA6, A0A1Y1N145, A0A1Y1N670, A0A1Y1MXX0, A0A2E1XX07, A0A368ZAV4, A0A368Z5S6, A0A2P7BX27, A0A2P7B2B9, A0A2P7B199, A0A318STX6, A0A2S9JB27, A0A368K297, A0A2P7BBS7, A0A2S9IZ33, A0A1H0QMP3, J3CCV4, A0A1H0UPJ4, A0A2N9VRL8, A9SNW9, A0A2K1K665, A0A2K1KEJ6, A0A2K1K664, A0A2K1IS53, A9T7Y0, A0A2K1JCS2, A0A2K1ISB0, A9TEC1, A9SP81, A0A2Y9FNN2, A0A2Y9FMM8, A0A2Y9S5B0, A0A2Y9FL53, A0A2Y9FNH7, A0A2Y9FVN1, A0A2Y9RZG7, A0A329R7W9, A0A329R9F3, A0A329RYD9, A0A329SSU7, A0A329RKN5, A0A329S4Z6, A0A329T4J1, A0A329SHI1, A0A329S9V0, A0A329SRY9, A0A329RNK1, A0A329SNY9, A0A329S7M0, A0A329S1Z2, A0A329SRE1, A0A329S1D7, A0A329SWT6, A0A329S4B3, A0A329SPJ8, A0A329RIU8, A0A329SPU9, A0A329RT73, D0MY50, D0NX36, D0NX35, D0NTA4, D0MY47, D0P0I6, D0NEY9, D0NYL6, D0NTB0, D0P1E8, D0N2D7, D0N7R8, D0MT29, D0NRT7, D0MRR0, D0MY49, D0P0T9, D0NUN5, D0NQ00, D0NZF4, D0N386, D0P028, Q2M441, B9VUU8, A0A421GDD8, A0A3R7K3Z6, A0A3F2RDE5, A0A421FHH8, A0A3R7K0A4, A0A3R7HDZ2, A0A421ETD0, A0A421FA97, A0A3F2RJX1, A0A3F2RE35, A0A3F2RF52, A0A3R7IQA6, A0A3F2RY02, A0A3F2RER3, A0A3F2RZC8, A0A3F2RR68, A0A3R7KUW5, A0A3R7JT10, A0A3R7J7R7, A0A3F2RF49, A0A3R7G004, A0A3R7HP88, A0A225WAC9, A0A225WNV7, A0A225VPW0, A0A225VX31, A0A225V0S2, A0A225WNJ4, A0A225VUT8, A0A225V861, A0A225VY03, A0A225VWU9, A0A225WU58, A0A225UTR0, A0A225US74, A0A225VHE2, A0A225WUN7, A0A225VTE7, A0A225WIB3, A0A225WKQ4, A0A0W8C7T1, A0A0W8CDF7, A0A0W8DMY0, A0A0W8DQS0, A0A0W8C6H3, A0A0W8DC43, A0A0W8CY53, A0A0W8C244, A0A0W8DC46, A0A0W8BQT9, A0A0W8BN24, A0A0W8C8H2, A0A0W8CP70, A0A0W8C0L1, A0A0W8CT29, A0A0W8DME7, A0A0W8D9R0, A0A0W8C2P6, A0A0W8CY27, A0A0W8CIP5, A0A0W8B357, A0A0W8AZV8, A0A2P4YEQ1, A0A2P4YER5, A0A2P4Y0Y6, A0A2P4XL73, A0A2P4XH46, A0A2P4XJK4, A0A2P4XVK1, A0A2P4Y6J7, A0A2P4X3D0, A0A2P4XLE8, A0A2P4X3F5, A0A2P4YFR7, A0A2P4Y2R6, A0A2P4YH90, A0A2P4XUW4, W2Q467, W2RHF8, W2QVF4, W2Q4M7, W2PJM9, W2PLH6, W2Q1I5, W2PKG5, W2QD00, W2QZF4, W2QTN8, W2Q634, W2Q9Y7, W2PJB5, W2R209, W2PFP4, W2PU68, W2QCZ4, W2REW3, W2PEG7, W2Q870, W2WEV6, W2X913, W2X1M9, W2X5D1, W2VX79, W2WUZ2, W2X348, W2XWF0, W2VZ24, W2WSU4, W2W607, W2W0N8, W2VXA4, W2XT69, W2WTF3, W2W2G5, W2XAA7, W2WHH5, W2VUZ5, W2XAB2, W3A0G8, W2Y5P0, W2ZM34, W3A6G4, W2ZDS8, W2ZHI4, W2YS73, W2Z3U6, W2YNN5, W2Y9I4, W2Z3S0, W2ZBQ5, W2YBW1, W2ZD75, W2ZHQ3, W2YGM9, W2Y8A6, W2YD26, W2Z356, W2YBY5, V9EY76, V9E3H4, V9DZZ5, V9FZZ4, V9FE93, V9E8N5, V9EY37, V9EX27, V9F9H0, V9E3Y2, V9ENS5, V9F7A9, V9F7C6, V9E3S0, V9FXZ9, V9FC98, V9EKG8, V9EI96, V9FDK5, V9EC42, V9E1H4, A0A081AYV0, A0A081A0S9, A0A081A8Z3, A0A080ZLK1, A0A081AB04, A0A081B3V1, A0A080Z747, A0A081A0T1, A0A080Z748, A0A080Z738, A0A080ZP81, A0A081AYU8, A0A080Z4Y8, A0A081AYU4, A0A081A1R2, A0A080Z2Z3, A0A081AB01, A0A081AH92, A0A080ZDR9, A0A080ZAI3, W2LFS8, W2HKN0, W2L0R5, W2P1G7, W2FR98, W2K4B4, W2J7J1, W2KMQ1, W2FPQ8, W2K6H5, W2K5X3, W2P694, W2L728, W2K2G5, W2MHW4, W2NET7, W2GUQ1, W2J9V7, W2GNC4, W2H193, O42830, W2HY18, W2K697, W2MTG5, W2MC44, W2KBB4, W2G7E9, W2IG72, W2J2Z4, W2J2Z6, W2MA47, W2FRI0, W2M865, W2GWC8, W2GWD7, W2L8Q2, W2I021, W2M2S0, W2N786, W2N694, W2G037, W2G9R5, W2JQ56, W2I5H9, W2HZQ8, W2MA56, W2ISN0, W2H2J5, W2NEV2, W2HNT1, W2JB43, W2I254, W2MW48, W2NEU1, H3G593, H3H1Z2, H3GT31, H3HDS4, H3H1Y9, H3H2Y9, H3H2Y8, H3G5T4, H3H1Y8, B2ZU37, B2ZU68, B2ZU62, H3GQA8, B2ZU49, H3H1Y6, H3H1U8, H3GLB2, H3G5P9, H3H1Z1, B2ZU72, H3GQA7, B2ZU45, H3H2Z0, H3GT32, H3G5B0, H3H2Y7, H3GDG9, B2ZU71, H3H1Z0, B2ZU70, B2ZU32, A0A088CB98, B2ZU23, H3GVW9, B2ZU31, A0A2L0WUS4, A1EAQ0, G4Z5J6, G4ZN72, G4ZGF9, G4YIR5, G5ABJ2, G4Z8P9, G5AEI8, G4ZGF6, G4YRJ3, G4Z802, G5A0U5, G4YU93, G4YIR6, G4YTG2, G5AEI6, G4Z8P8, G4ZRE5, G4YIR7, G4YXF1, G4Z8Q8, G4Z5J7, G4YRE7, G4ZT51, G4Z5J8, G4Z8Q0, G5AEI5, G4YW39, G4ZTF9, B8LRA5, B8LRG3, A0A194ANQ8, L0N3W3, A0A1Y1VF86, A0A1Y1V4N4, A0A1Y3NGF1, A0A2D9 PRI4, A0A2P6NN51, A0A2P6NBD6, A0A2P6NS16, A0A2P6NFX0, A0A2P6NBF7, A0A2P6NM78, A0A2P6NZX6, A0A2P6NQW3, A0A2P6NJ93, A0A2P6NKK7, A0A2P6NXQ1, A0A2P6N0O4, A0A2P6N8A1, A0A2P6MQS5, A0A2P6NWD1, A0A2P6N6L8, A0A2P6NUU8, A0A2P6NYV0, A0A2P6MVG3,

A0A2P6N8R1, A0A2P6N8J2, A0A2P6NNF7, A0A3M6UUS4, A0A3M6U1B0, A0A3M6U9H5,
A0A2P6NJU3, A0A2P6NZG2, A0A2P6NJU9, A0A3M6U252, A0A3M6T542, A0A3M6UJV7,
A0A2P6NU31, A0A2P6NNX6, A0A2P6MNV7, A0A3M6TA55, A0A3M6T9T7, A0A3M6TWX2,
A0A2P6N4J7, A0A2P6P052, A0A2P6NPL0, A0A3M6V721, A0A3M6U9I9, A0A3M6U1G7,
A0A2P6N398, A0A2P6NVG2, A0A2P6MWF9, A0A3M6U527, A0A3M6U1R3, A0A3M6V1Z1,
A0A2P6NLH5, A0A2P6N891, A0A2P6NKS8, A0A3M6UQ36, A0A3M6TI45, A0A3M6UIZ7,
A0A2P6NRU2, A0A2P6NI63, A0A2P6NPR4, A0A3M6UMS9, A0A3M6UY19, A0A3M6UPE3,
A0A2P6NBF0, A0A2P6NL20, A0A2P6NRH4, A0A3M6TNQ1, A0A3M6UMU0, A0A3M6TGA7,
A0A2P6NWM6, A0A2P6MUC2, A0A2P6MQR6, A0A3M6TX72, A0A3M6V494, A0A3M6UG64,
A0A2P6NL12, A0A2P6NVA7, A0A2P6NKZ3, A0A3M6UK86, A0A3M6UYI3, A0A3M6V0I9,
A0A2P6MZC6, A0A2P6NII8, A0A2P6P0D1, A0A3M6T8D1, A0A3M6TZS0, A0A3M6TCK3,
A0A2P6NUJ5, A0A2P6NMA2, A0A2P6NGP7, A0A3M6UF72, A0A3M6URU5, A0A3M6U5L9,
A0A2P6MT35, A0A2P6MSH3, A0A2P6NK96, A0A3M6UQ23, A0A3M6U9G1, A0A3M6UGB6,
A0A2P6NR97, A0A0P1B1W3, A0A0P1A668, A0A3M6UUP1, A0A3M6TGX0, A0A3M6UKV3,
A0A0P1B457, A0A0P1ALX1, D0VX36, D0VX37, A0A3M6U1N8, A0A3M6V463, A0A3M6UKM5,
A0A411F668, A0A2G9WWN9, A0A114U8D5, A0A3M6TYF4, A0A3M6U0N0, A0A3M6UMN0,
A0A2Z6HIWP3, A0A2Z6I0M2, A0A179F4S7, A0A3M6U2G5, A0A3M6T9Q3, A0A3M6TY60,
A0A179F441, A0A3M6TS79, A0A3M6USF2, A0A3M6UCM1, A0A3M6TVJ0, A0A3M6U3I0,
A0A3M6U8L5, A0A3M6T8B8, A0A3M6UTQ7, A0A3M6VBM0, A0A3M6TTN4, A0A3M6TST7,
A0A3M6V1M2, A0A3M6TMM1, A0A3M6T9H4, A0A3M6V143, A0A3M6TTD9, A0A3M6U218,
A0A3M6UUH4, A0A3M6UCX4, A0A3M6TR63, A0A3M6U1Q8, A0A3M6T410, A0A3M6UKS4,
A0A3M6TQV1, A0A3M6UUS3, A0A3M6T9L3, A0A3M6T9Q5, A0A3M6US86, A0A3M6TYB9,
A0A3M6UH21, A0A3M6UFJ0, A0A3M6TLA8, A0A3M6TTW0, A0A3M6TCD6, A0A3M6UMC9,
A0A3M6TXJ3, A0A3M6UNB9, A0A3M6TV38, A0A3M6USH7, A0A3M6TD69, A0A3M6UK11,
A0A3M6UY98, A0A3M6UGR8, A0A3M6UHN8, A0A3M6UVR5, A0A3M6U2Q5, A0A3M6V3V5,
A0A3M6TQC2, A0A3M6UZT4, A0A3M6TG14, A0A3M6UBX9, A0A3M6UK88, A0A3M6UUI1,
A0A3M6UAH9, A0A3M6U389, A0A3M6T9B4, A0A3M6TKL2, A0A3M6V0I0, A0A3M6TK69,
A0A3M6TK43, A0A3M6TKR9, A0A3M6UW14, A0A3M6TDY5, A0A3M6TIX2, A0A3M6TYN3,
A0A3M6USD4, A0A3M6TZG9, A0A3M6UIH2, A0A094L7R4, A0A094NEK3, A0A094KG51,
A0A3M6UHX1, A0A3M6TJU1, A0A3M6TLI2, A0A094LT96, B2B3F1, B2AEW5, B2ASY6, B2B631,
A0A3M6UQ55, A0A3M6UM67, A0A3M6T7C9, A0A090CJ60, A0A447CBI5, A0A447CFK1,
A0A3M6T879, A0A3M6TMQ8, A0A3M6U799, A0A447C1B4, A0A447CHJ2, A0A087YC08,
A0A3M6UYP3, A0A3M6UY17, A0A3M6V3Y0, A0A087YDJ9, A0A096M9X7, A0A096MHY9,
A0A3M6UUQ2, A0A3M6TKU3, A0A3M6UYG1, A0A096LUY1, A0A087XAX0, A0A087YK42,
A0A3M6TTJ5, A0A3M6TY63, A0A3M6TFR8, A0A096M7R2, A0A087YBW9, A0A3B3V3Z1,
A0A3M6U3C3, A0A3M6U1C9, A0A3M6U041, A0A3B3TJZ9, A0A3B3V421, A0A3B3V1M0,
A0A3M6U1S3, A0A3M6TKF4, A0A3M6TTS0, A0A3B3UUE6, A0A3B3W2N5, A0A3B3VXR8,
A0A3M6U9P4, A0A3M6TU17, A0A3M6V0G4, A0A3B3TK34, A0A3B3USD0, A0A3B3TX33,
A0A3M6UKJ5, A0A3M6U9D2, A0A3M6UMI0, A0A3B3VD97, A0A3B3V427, A0A3B3TZ12,
A0A3M6V1P4, A0A3M6TZE9, A0A3M6U9C4, A0A3B3XYA2, A0A3B3YGN7, A0A3B3YU59,
A0A3M6UK43, A0A3M6TDQ0, A0A3M6UQ00, A0A3B3YUM0, A0A3B3XXC4, A0A3B3XJP2,
A0A3M6T9N0, A0A3M6TL38, A0A3M6UGQ2, A0A3B3XXG3, A0A3B3X0F3, A0A3B3XY03,
A0A3M6T5E6, A0A3M6TYN4, A0A3M6UZA1, A0A3B3YUR5, A0A3B3XRS1, A0A3B3Z3V6,
A0A3M6V499, A0A3M6TZ45, A0A3M6T7Z7, A0A3B3WRD1, A0A3B3YVC7, A0A3P9Q3Q9,
A0A3M6UQN2, A0A3M6V0A1, A0A3M6UAD8, A0A3P9Q2T6, A0A3P9NA69, A0A3P9Q2U6,
A0A3M6TA22, A0A3M6UL69, A0A3M6V562, A0A3P9Q2Z7, A0A3P9Q320, A0A3P9Q335,
A0A3M6UHQ1, A0A3M6V6G0, A0A3M6U1J0, A0A3P9Q431, A0A3P9Q3Q0, A0A3P9Q4J8,
A0A3M6ULX9, A0A3M6TX33, A0A3M6V3R3, A0A3P9Q3N5, A0A3P9PH03, A0A3P9Q356,
A0A3M6UG70, A0A3M6TFV1, A0A3M6TCE3, A0A0S7K5B4, A0A0S7J5R7, A0A0S7K6Q0,
A0A3M6U1L3, A0A3M6USJ5, A0A3M6UV09, A0A0S7KT15, A0A0S7K5P7, A0A0S7M8P1,
A0A3M6THX6, A0A3M6TSD4, A0A3M6UHD5, A0A0S7L542, A0A0S7ELW6, A0A0S7K6K9,
A0A3M6TIM9, A0A3M6V609, A0A3M6UMN1, A0A0S7K5V9, A0A0S7M7Y8, A0A0S7EN80,
A0A3M6T7T9, A0A3M6TRU4, A0A3M6UPF6, A0A0S7EV87, A0A125SL75, A0A125SL77, Q9Y1V3,
A0A3M6TA00, A0A3M6TTM9, A0A3M6T9S3, F2IW28, A0A2B7YVT1, A0A2B7Y09, A0A2B7XRG7,
A0A3M6V4P3, A0A3M6URI8, A0A3M6T6W2, A0A2T7PUF8, A0A2T7P4A6, A0A2T7P2C2,
A0A3M6TGI7, A0A3M6U3G3, A0A3M6UL17, A0A2T7NW21, A0A2T7NVT2, A0A2T7P293,
A0A3M6UCE1, A0A3M6USZ6, A0A3M6UMF9, A0A2T7NRV8, A0A2T7P283, A0A2T7NUX7,
A0A3M6TET4, A0A3M6TG44, A0A3M6U3J1, A0A2T7NZW8, A0A2T7P282, A0A2T7NPR7,
A0A3M6UXV8, A0A3M6TWK8, A0A3M6UV46, A0A2T7NP19, A0A2T7PDK6, A0A2T7PBM0,
A0A3M6UL16, A0A3M6ULU8, A0A3M6T6A8, A0A2T7NH27, A0A2T7NGZ5, A0A2T7PVC4,
A0A3M6U377, A0A3M6TAL1, A0A3M6T5X9, A0A2T7P296, A0A2T7NPP6, A0A2T7PIV1,
A0A3M6V0S5, A0A3M6UZX3, A0A3M6V292, A0A2T7NT09, A0A2T7P290, A0A2T7P2A0,
A0A3M6USE0, A0A3M6V1C4, A0A3M6TRT6, A0A2T7NT13, A0A2T7PXQ6, A0A2T7P2A4,
A0A3M6TGP2, A0A3M6TNZ6, A0A3M6U6B3, A0A2T7P9Q0, A0A2T7NDL4, A0A2T7NMC9,
A0A3M6TYI9, A0A3M6U5N1, A0A3M6TZH8, A0A2T7PII0, A0A2T7Q143, A0A2T7P231,
A0A3M6TZB0, A0A3M6U1T5, A0A3M6UTP6, A0A2T7NAQ2, A0A2T7NUW9, A0A2T7PVQ3,
A0A3M6V3G9, A0A3M6UAU9, A0A3M6UVP6, A0A2T7PQ77, A0A2J8T957, K7EVW6, A0A2J8VLI2,

A0A2J8VLJ4, A0A2J8T3S9, A0A2J8VLH8, A0A2J8T3R6, H2PKT3, A0A2J8T3Q1, A0A2J8VLJ0, A0A2J8TGX6, A0A2J8T3Q9, H2PAR3, A0A2J8T3Q0, A0A2J8VLK6, A0A2J8VLJ5, A0A2J8TGY3, H2PEX4, A0A2J8VLK7, A0A2J8T3Q5, A0A2J8T3T1, Q5R976, A0A2J8T3R5, Q5R502, H2PEX7, H2PN16, A0A2J8T950, Q5R8X6, A0A1R3WSM0, A0A2D9RCA7, A0A2D6GQ64, A0A2D7IW65, A0A2D9RE05, A0A0W7WIT4, A0A0W7WNN3, A0A0W7WKJ9, A0A0W7WED2, A0A385JHS5, A0A3S9LX70, A0A385JID9, A0A385JIC9, A0A385JIW5, A0A3S9LX83, A0A3S9LX72, A0A385JIF5, A0A3S9LX97, A0A1L6K4F6, A0A3S9LX71, A0A3S9LX61, A0A3S9LXA8, A0A3S9LX98, A0A3S9LXB3, A0A3S9LX57, A0A3S9LXA3, A9PJX6, A0A3N7FJX8, B9HYR9, A0A3N7FA41, A0A2K1Y5Z8, U5FEZ9, U7E2S0, A0A3N7FPW1, A0A2K2CBM7, A0A3N7H0W6, A0A3N7FQG9, B9I033, A0A2K1YMT8, A0A2K2CD15, A0A2K1YMD4, A0A2K1YF78, A0A2K1YF67, B9HYQ3, A0A2K2AP05, A0A2K2CBR0, A0A3N7G2Z5, U5GW32, A0A2K1YMF9, A0A2K1YMF8, A0A2K2CBV8, U7DXY3, A0A2K1YLY5, A0A3N7H7G1, B9HYS3, A0A2K1YJB9, U7E151, A0A2K1R9J9, A0A2K2CBS5, A0A2K1XDN9, A0A3N7FS13, U5G9S9, A0A2K1YF84, B9I035, B9NGV9, A0A3N7EEZ9, A0A3N7ETB6, A0A3N7GAS2, U7DV48, A0A3N7EEW7, A0A3N7G946, A0A2K1YMS1, A0A2K2AP11, A0A3N7GLP6, A0A3N7FPY6, A0A3N7FJT6, U7DVW0, A0A2K2BAE9, A0A3N7FRW4, A0A3N7GIT0, A0A2K1YF54, A9PFH0, A0A3N7FPB6, A0A2K2CBN3, A0A2K1YMF6, A0A2K1YF72, A0A2K1YF37, A0A3N7FK42, A0A2K1YJI6, A0A2K2CBU0, A0A3N7FQ27, A0A2K1YMF7, A0A2K1YMK1, A0A2K1R9K1, U7DZT8, A0A2K2CBV2, A0A2K1YRU7, U5FQT0, A0A2K1R435, A0A2K2CBU5, A0A3N7FKB6, A0A3N7EYY1, A0A3N7F931, A0A2K1R9M9, A0A3N7HDJ2, A0A3N7H721, A0A2K2CBR5, A0A2K1YMD5, U7DWR5, U7E0R0, A0A3N7G378, A0A3N7G0M4, A0A2K2CBS7, U5GSZ3, A0A2K1YF20, A0A2K1YCZ6, A0A2K2AP00, A0A2K2CBS4, A0A2K1R9L1, A0A2K1R9K8, A0A2K1YF88, A0A2K2CBR3, A0A3N7EYL9, A0A3N7FPG8, U7DYK7, A0A3N7EJM8, A0A2K1YMF0, B9IFY4, A0A2K1R9K3, A0A2K1R9L4, U7E198, A0A3N7FBU8, A0A3N7HE18, U7E213, A0A3N7FRQ4, A0A2K1R7A4, U7DZU3, A0A3N7FTM4, A0A2K1YJJ2, A0A2K2CAQ6, A0A3N7F920, A0A3N7FQE7, A0A2K2AAA5, B9HAE5, A0A2K1XB50, A0A2K1YMH4, A0A2K1YJA7, A0A2K1YMF3, U5FZN7, A0A2K1WRN2, A0A3N7EEZ8, A0A2K1R9I9, B9I048, A0A2K1R9K2, A0A2K2CBW8, A0A3N7FBT5, A0A2K1YF32, U5FP35, A0A3N7H774, A0A3N7FUN1, A9PF61, A0A2K1YJJ1, A0A2K2AQM5, A0A2K1YF42, A0A2K1R9J8, A0A3N7ERB7, A0A2K1ZA48, A0A3N7FRY4, A0A2K2AAA9, A0A3N7G2Z7, A0A2K1YF57, A0A3N7EBP4, A0A2K1R5I9, A0A3N7EXE8, B9INT4, B9MU91, A0A3N7EII0, A0A3N7HDF5, A0A2K1YF71, A0A2K2AAC8, A0A2K2CBV0, A0A2K1R9L6, A0A2K1YF62, A0A3N7EMG0, A0A3N7GEG5, A0A3N7FKU0, A0A2K2CC26, A0A2K1R9K7, A0A2K1R9L9, A0A3N7FQE2, A0A3N7FE30, B9IQL6, B9HYQ6, A0A2K2CBS0, A0A2K1Y5X3, A0A2K2CBN5, A0A3N7I1Z5, A0A2K1R9K4, U7E275, A0A2K2CBV3, A0A3N7GT81, A0A3N7FK00, A0A2K1YJT6, A0A3N7GCP1, A0A3N7FXT6, A0A3N7FWX1, A0A2K2CBR2, U7E2B5, A0A2K1YJJ4, A0A2K2CBQ6, A0A2K1Y5Y0, U7DTV7, A0A2K1R9J0, A0A2K1YJC0, A0A3N7EN77, A0A3N7HDH1, A0A2K2CBV5, A0A2K1YMS3, A0A3N7H760, A0A2K2CBU2, A0A3N7FMC7, A0A3N7FFN1, A0A2K1YII9, A0A2K1YFA5, A0A2K1YMG3, Q0ZCC5, A0A3N7F1A3, A0A2K1YMC5, A0A2K1R9L8, A0A2K2CBS9, A0A2K1YF89, A0A2K1YJB0, A0A3N7G5C0, B9I819, A0A3N7EZT8, B9H1V2, A0A2K1YF22, A0A2K1YKS5, A0A3N7FQ08, A0A2K2CBS8, A0A2K2AC56, A0A2K1YF85, A0A2K2AA68, A0A2K2CBS3, A0A2K1YF29, A0A2K1YF09, U7DZK5, A0A2K2AA71, A0A2K2CBQ2, A0A3N7F8U4, B9INU0, A0A2K2CD09, A0A2K2BQD8, A0A2K2CBR1, A0A2K1YME5, A0A3N7FHR5, A0A2K1YIJ7, U7DSM0, B9MUS9, B9H1U4, A0A3N7FQ25, A0A2K1YF75, A0A2K1YME2, A0A2K1YF38, A0A3N7G9D1, B9H9X2, B9I050, A0A2K1R9I3, A0A3N7F8V7, A0A2K1WUY0, A0A2K2AP04, A0A3N7FUP4, A0A2K2AP06, A0A3N7FF46, A0A3N7FTN5, A0A2K1YF58, A0A1X6NVT8, A0A1X6NQM4, A0A1X6PFD2, A0A1X6P8C6, A0A1X6NNT9, A0A1X6P5P1, A0A0N0JQI8, A0A167RBV0, A0A167R7I2, A0A167RBU3, A0A2R8AUK0, H3FLN2, H3FU64, A0A2A6CLV0, H3G269, H3DYL1, A0A2A6BKN6, A0A2A6CL96, H3F912, A0A2A6CKS7, H3DXL2, H3EPT2, A0A2A6BKX0, A0A2A6BRD4, H3EMR6, H3F239, H3FWN3, H3EMS5, H3E6Q3, A0A2A6CW20, H3G484, A0A2A6CWJ1, A0A2A6BQE5, H3G483, A0A2A6C8D4, A0A2A6CWL7, H3F6C9, A0A2A6BXL8, A0A2A6BTB7, H3E9C6, H3F0T6, A0A2A6CRJ5, H3FU41, A0A2A6CC90, A0A2A6CXB5, H3EUD8, H3EUB5, A0A2A6CVS9, A0A2A6C5D7, H3EYA4, A0A2A6CNU0, A0A2A6CPM8, H3FXU2, H3FXP1, H3FH55, H3FDU0, H3DRR5, H3F6D1, A0A2A6C0F3, A0A2A6CJP0, H3FUP4, H3EC28, A0A2A6C3M2, H3E6Q4, A0A2A6BWE1, A0A2A6CV10, A0A2A6C2I9, A0A2A6BTN5, H3FDT3, A0A2A6BRT5, H3EUB4, A0A2A6BRY8, H3EIL7, A0A2A6B687, H3F237, A0A2A6B8K1, A0A2A6CBV8, A0A2A6BIV2, A0A2A6BTB0, H3EA22, A0A2A6CPA6, A0A2A6D2U8, A0A2A6CLQ3, H3G4B7, A0A2A6BP16, H3FP67, A0A2A6B6P2, A0A454XRJ9, A0A2A6CS22, A0A2A6BMJ9, A0A2A6CVF2, A0A2A6C5B7, H3FKW8, H3E9C4, H3FLR8, A0A2A6CL26, A0A2A6CAV6, A0A2A6C0V0, H3DT54, A0A2A6C9M6, H3F624, A0A2A6CIU4, H3G421, H3EKC8, A0A2A6CYT9, A0A2A6CJH0, A0A2A6CTB6, H3FFI6, A0A2A6BY19, A0A2A6BF62, A0A2A6C2U7, A0A2A6C8U6, A0A2A6CM39, A0A2A6BTW0, A0A2A6B724, H3EWG7, A0A2A6CGU1, A0A2A6C3N2, A0A2A6BRI6, A0A2K6FYF0, A0A2K6FWB1, A0A2K6FWE4, A0A2K6GMV5, A0A2K6FWC7, A0A2K6GU92, A0A2K6FYE7, A0A2K6EIZ2, A0A0P6W8Z7, A0A1W9IFG2, A0A1W9I8T4, A0A2W4P8I4, A0A2W4P3J5, A0A3A0F8E5, A0A317HTN1, A0A448WDT9, A0A3S5A576, E6YCZ6, E6YCZ1, M5WXQ1, A0A251PZP6, A0A251Q7E1, A0A251PF29, A0A251PTU7, M5WCL9, A0A251Q445, M5VZY3, A0A251PKI1, A0A251Q478, A0A251P735, A0A251PF35, M5WJ95, A0A251Q7C8, A0A251PKC2, M5WMF2, Q6DU55, M5X5D7, M5WWL5, M5VUG0, A0A251PN29, A0A251PMZ2, A0A251RBW4, M5WM53, M5WZG6, A0A251Q443, M5XEL7, M5X9Q1, A0A251PMZ1, A0A251PN38, A0A251REA2, A0A251Q484, A0A251RGM7, M5X9P7, A0A251PF27, M5VTG3, M5WZA7, M5WZT3, A0A251PF21, M5WK87, A0A251PZD2, A0A251PLL1, A0A251NRG7, A0A251PID0, M5WZ40, A0A251NHZ5, A0A251PWJ2,

M5WPH8, M5VZT1, A0A251PKJ4, A0A251Q4B5, A0A251PLJ6, A0A251PGK7, M5X1J1, M5WG45, M5WD24, A0A251PF18, A0A251PN12, A0A251PLY0, A0A251PMY4, A0A251Q434, M5X8S1, M5X455, A0A251PYL5, M5XQT3, M5X887, M5X3N3, M5Y1R6, M5W6E4, A0A251P734, M5WH13, M5Y3U1, M5X159, M5WK95, A0A251PF34, A0A251Q485, M5WPP2, A0A251NRF5, A0A251PF25, M5WLB2, A0A251Q454, M5XAQ5, A0A251PN32, M5WPS0, M5X3A2, A0A251PN76, A0A251PKI0, A0A251PQ97, M5WXJ1, A0A251PN13, A0A251PF23, M5WKA3, M5WM79, A0A251Q5C4, A0A251Q4D5, A0A251RGX7, M5X9S4, A0A251NRE5, M5WXU6, A0A251REE6, A0A251PN41, M5XL06, A0A251Q458, M5X216, M5WH09, A0A251Q463, M5X8Y5, A0A251Q479, M5XMQ7, M5XHF0, M5WQ28, M5X7U6, M5WVR7, M5WSH4, A0A251NDA6, A0A251PN25, A0A251PN53, A0A251Q7F0, A0A251Q464, A0A251NT57, M5X6Z5, A0A251PRA6, A0A251PLN9, M5WPY5, M5WPV3, A0A251NIW0, M5WJJ1, M5X3N0, A0A251Q190, M5X3I1, A0A251N2H7, A0A251PK13, M5WNI3, A0A251PN15, A0A251PPI2, A0A251PWI5, A0A251PEY5, A0A251NFQ2, A0A251Q5B2, A0A251PF13, A0A251PN44, A0A251Q406, A0A251PEZ5, M5WVG0, A0A251PN23, A0A251PF11, M5WPG0, A0A251PPF4, A0A251PWI0, A0A251Q435, M5WN54, M5WDJ6, M5X2T2, A0A251REB1, A0A251PPD9, M5X9G3, A0A251NKN9, A0A251PWL4, A0A251Q4A4, M5WZT2, M5W812, M5WX54, A0A251PKK4, M5X978, M5WZV5, M5WPY0, A0A251PF28, A0A251PN85, M5WWQ5, A0A251PN40, A0A251PWJ6, M5XIJ4, A0A251QKG7, M5WNK5, M5WM02, A0A251Q470, A0A251Q456, M5VVP2, A0A251PF31, A0A251PEZ9, A0A251PN33, M5WWU8, A0A251PEC6, A0A251PKE3, M5WPH5, A0A314U9M1, A0A314Y373, A0A314Z0A8, A0A314ZKH3, A0A314XG48, A0A314YPW4, A0A314XMH1, A0A314YT22, A0A314XP08, A0A314XQJ9, A0A314Y542, A0A314UQL0, A0A314YBU3, A0A314YQ99, A0A314UY39, A0A314YQW7, A0A314YYP7, A0A314YVF9, A0A314XGA1, A0A314UX31, A0A314Z5K6, A0A314Z001, A0A314YRN2, A0A314YT57, A0A314YBR0, A0A314XP39, A0A314Z720, A0A314Y5X9, A0A314UHG7, A0A314Z8Q0, A0A314Y699, A0A314YB32, A0A314UTP8, A0A314UPQ4, A0A314V0I2, A0A314ZFK4, A0A314YL52, A0A315AX60, A0A314YAA4, A0A314Z0M5, A0A314Z3J4, A0A314Y7M3, A0A314V0X4, A0A314YXT4, A0A314YUF3, A0A314UJA2, A0A315AGJ7, A0A314ZPW0, A0A314Y1L0, A0A314XZH9, A0A314ZSU2, A0A314UXP5, A0A314Y0Z2, A0A314YAA6, A0A314Y818, A0A314Y3J8, A0A314ZB68, A0A314ZP76, A0A314YUG3, A0A314Z802, A0A314UEM7, A0A314YRH3, A0A314Y8A2, A0A314UWI0, A0A315ARL6, A0A315A6R0, A0A314UJ27, A0A314YAF3, A0A314UEA8, A0A314Y3B8, A0A314ZHU3, A0A314YJP3, A0A314XSE1, A0A314YFP3, A0A314Y3T4, A0A314Y829, A0A314Z9C8, A0A314ZVV1, A0A314YLI7, A0A314ZJ97, A0A314YUI6, A0A314YBY2, A0A314XVQ6, A0A314XIP0, A0A314XP62, A0A314UP42, A0A314UV53, A0A314XIQ0, A0A314Z5Z0, A0A314YBQ1, A0A314YSN1, A0A314YKD5, A0A314UCK4, A0A314YAE2, A0A314YCB1, A0A314XVQ9, A0A314UXN9,

A0A0L1JPX5, A0A1V8RTC8, A0A1V8RVS0, A0A316C775, A0A432VCJ6, A0A432UZB1, K9SMW0, A0A448Z8L7, A0A167HEY0, A0A0F6AB37, A0A161Z1S3, A0A1C0TWN0, A0A1Y6CLA4, A0A1Y6C4J4, A0A1Y6CJZ7, A0A139HR58, A0A139H9G6, A0A139HU89, A0A139HUE9, A0A139H0C0, A0A139HE34, A0A139HF24, M3AJY5, M3ABI7, N1QAP8, M3AM66, A0A1391DZ4, A0A139ISD7, A0A139IAH9, A0A139I9V6, A0A139IQ32, A0A139HLG1, A0A139I5S0, A0A139IE78, A0A139IRW9, A0A139I5G1, A0A139I8T4, A0A366DTY3, A0A0V0Q930, L8FX08, A0A177A5U9, A0A177AEB2, A0A1B8FQ74, A0A1B8FAM6, A0A1B8FAB7, A0A1B8EVM3, A0A1B8DV39, A0A1B8EGD8, A0A1B8DP42, A0A1B8DS74, A0A1B8E4V2, A0A1B8DQT9, A0A1B8D360, A0A1B8DGK9, A0A094EGR9, A0A094DWV3, A0A094E8W1, A0A094ECR8, A0A094F5X7, A0A093X015, A0A093Y9E1, A0A093ZSP4, A0A093XA42, A0A094AHX5, A0A093YEN8, A0A093YI19, A0A093ZRK7, A0A093ZUL1, A0A093YA26, A0A093Y8L0, A0A093XLF2, A0A093XX47, A0A093XB82, A0A093ZC45, A0A093ZL44, A0A093Z902, A0A094BF38, A0A094B572, A0A094B804, A0A094AQ42, A0A094AF07, A0A094CGQ0, A0A094AJK3, A0A094C0V4, A0A094AXJ9, A0A094C5H2, A0A094CCB3, A0A094DRK2, A0A094D2R0, A0A094DJC7, A0A094D600, A0A094CUY7, A0A094D6Z9, A0A094CLP7, A0A094FL50, A0A094DH72, A0A094FUT8, A0A094GG55, A0A094FUK7, A0A094G2V6, A0A094G2T3, A0A094F380, A0A094HAD8, A0A094FXE5, A0A094F3W2, A0A094IUK4, A0A094FUX7, A0A094GE65, A0A094IFS5, A0A094FC36, A0A094HXC7, A0A094HR56, A0A094JG43, A0A094HUW8, A0A094H2I0, A0A094GL04, A0A094IWA8, A0A094HPW1, A0A094I5T1, A0A094K6B1, A0A094H1N9, A0A094KPW5, A0A094HXM1, A0A094IA09, A0A094I941, A0A094HH70, A0A094H7Z8, A0A094HW58, A0A1B8CEM6, A0A1B8C167, A0A1B8BVH8, A0A1B8BVN1, A0A1B8CLH8, A0A1B8GFJ5, A0A1B8GIK4, A0A1B8G6U4, A0A1B8G8P5, A0A1B8GXU4, A0A371BDI6, A0A0Q7TDU5, A0A345ZXK6, A0A1Y2DW08, A0A1Y2D6M0, A0A1Y2E0V4, A0A1Y2DSV9, A0A1Y2D8N4, A0A1Y2E3R2, A0A1Y2E4X6, A0A1Y2E8Q9, A0A2V4SND8, A0A2T5HEC1, A0A0A0EH55, A3U263, A0A1X6ZN84, A0A1I1NTG6, A0A399J8R4, A0A2E3H3U4, A0A2E2PAW3, A0A1M6RS66, A0A081MMN6, A0A1H8C883, A0A433S634, A0A2M8MZT2, A0A257GRH4, A0A1W6ZZH9, A0A2T0RJD8, A0A1G8QA31, A0A1M7Z7T5, A0A081CEQ5, A0A093DR50, L5JNS7, L5KBX5, L5KUG3, A0A3B4GGZ1, A0A3B4ER40, A0A3B4EPW7, A0A3B4EUN9, A0A3B4G794, A0A3B4GLL4, A0A3B4F895, A0A218X271, A0A2I0HMY7, A0A2I0J4H2, A0A218X161, A0A2I0IJU8, A0A2I0J4I9, A0A218Y2C4, A0A2I0HIQ9, A0A2I0J9K2, A0A218Y341, A0A2I0IQT3, A0A2I0KMH9, A0A2I0IJ58, A0A2I0KZ71, A0A218X0P0, A0A218WZC1, A0A218WYH1, A0A218WXK1, A0A2I0JQJ0, A0A218WZ09, A0A2I0HYS2, A0A218WXG4, A0A218WUD1, A0A2I0HAP0, A0A218XP01, A0A218WER6, A0A2I0IQZ3, A0A2I0HSV7, A0A218Y426, A0A2I0HST7, A0A218Y3D0, A0A2I0HPH7, A0A218Y2B4, A0A218WC26,

A0A218VVJ2, A0A2I0KRY6, A0A218Y294, A0A2I0I1Y2, A0A218WXR5, A0A218WY26, A0A2I0HEN9, A0A2I0KGT9, A0A218X1M6, A0A218X8E1, A0A2I0I1U5, A0A2I0K6N7, A0A218X1Y4, A0A218Y0Y4, A0A2I0HHU4, A0A2I0KWU4, A0A2I0IB26, A0A2I0KD33, A0A2I0JRD0, A0A218Y212, A0A218VZL6, A0A218X0N1, A0A218Y398, A0A218X6V7, A0A218W3Q4, A0A218X0A3, A0A2I0IHT5, A0A218VUN0, A0A218Y175, A0A218WY07, A0A2I0I1X9, A0A218Y1X1, A0A218X956, A0A218Y478, A0A218XUG7, A0A2I0I3E5, A0A218WYF1, A0A2I0I1U6, A0A2I0KZ81, A0A218Y494, A0A218W9L6, A0A218XS02, A0A218Y227, A0A218X264, A0A218WXQ6, A0A2I0L0F4, A0A2I0J4I3, A0A2I0HKJ3, A0A2I0KZ88, A0A2I0KZ67, A0A2I0KYL9, A0A218X7K9, A0A218WXT2, A0A2I0KZ70, A0A218WY64, A0A2I0KW29, A0A2I0KZA1, A0A2I0J932, A0A2I0IJ71, A0A2I0KG46, A0A2I0I6U2, A0A2I0HSU7, A0A218WXY7, A0A218XFG8, A0A218XFR5, A0A2I0KN21, A0A2I0HKH6, A0A2I0I2C3, A0A218X1C5, A0A218Y271, A0A2I0KET6, A0A218X305, A0A218Y234, A0A218Y351, A0A2I0KX43, A0A218X2P8, A0A218Y2C0, A0A2I0IHV8, A0A2I0IPE4, A0A218WYC8, A0A2I0KFP7, A0A2I0IHT9, A0A218XW17, A0A218XFS5, A0A218Y0Y2, A0A2I0IQG0, A0A2I0KAW6, A0A2I0KC11, A0A2I0JYX5, A0A218W566, A0A218WF52, A0A218WZS3, A0A218Y3E1, A0A2I0HIE5, A0A2I0KWT0, A0A2I0HT88, A0A218X7K7, A0A218WXZ7, A0A2I0L4U1, A0A218WY16, A0A218WYD8, A0A218XUR4, A0A218WY96, A0A2I0KZ61, A0A218X3M6, A0A218XAX6, A0A218XDE2, A0A2G8RAW8, A0A238VTL4, A0A0J5QAI6, A0A179GCR8, A0A2U3DTP8, A0A2U3DSM1, A0A179G1G3, A0A2U3ECC8, A0A179HQR1, A0A179GK49, A0A3B4BXA6, A0A3B4DRA6, A0A3B4BXD6, A0A3B4D157, A0A3B4BXJ5, A0A3B4C326, A0A3B4C1E6, A0A3B4C446, A0A3B4DN28, A0A093P1B8, A0A093RLN1, A0A093QRK6, A0A093N8L5, A0A178E6Z5, A0A178EA49, A0A178EEX5, A0A178DK72, A0A178DY86, A0A3M7M5G6, A0A3M7MFK4, A0A3M7MG51, A0A3M7M128, A0A3M7MCE0, E3S6M1, E3S7C0, E3RU61, E3RPP7, B2WLR3, B2VUM0, B2WMT4, B2WBS3, A0A2W1GRF2, A0A2W1HFA3, A0A2W1HWY2, A0A2W1EGN9, A0A2W1ELB0, A0A2D4C6Q4, A0A2D4BUE8, A0A2D4CGH4, A0A2D4C0E0, A0A2D4C4K6, A0A2D4C7F2, A0A2D4BJS7, A0A2D4BHR4, A0A2D4BT34, A0A2D4BXK6, A0A2D4BRG2, A0A2D4BI32, A0A2D4C690, A0A2D4BGL9, A0A2D4C6A5, A0A2D4C3B2, A0A2D4C8R4, A0A2D4C6I3, A0A1V8SZ61, A0A1V8TRB4, A0A1V8T5T1, A0A1V8TF18, A0A1V8TEM5, A0A1V8SMS7, A0A1V8TN34, A0A1V8SPQ2, A0A1V8TVE0, A0A1V8ST60, A0A1V8TZH6, A0A1V8UTC1, A0A1V8V8Q1, A0A1V8UBK3, A0A1V8UW76, A0A1V8U0N8, A0A1V8U6W6, A0A1V8TZA8, A0A1V8U585, A0A1D1VG42, A0A1D1UP37, A0A1D1UTW6, A0A1D1VPW1, A0A1D1UMW3, A0A1D1I436, A0A1D1W957, A0A1D1UIH8, A0A1D1UU11, A0A1D1W7T4, A0A1D1VJV1, A0A1D1VJT6, A0A1D1VAI5, A0A2D3V2X9, A0A2D3ULC3, A0A2D3UWU9, A0A2D3V3D6, A0A2D3V0K0, A0A2D3UT01, A0A2D3V4J3, Q9SBP5, Q9SBP1, Q9SBP4, Q9SBP3, Q9SBP2, Q9SBP0, A0A0D5XMK2, A0A0D5XNG1, Q8LP63, A0A0D5XNJ2, A0A387IHF6, O80347, O80351, Q6L8R0, A0A2D1CRR0, A0A3B1EZU5, O80350, A0A387IHI8, O80346, Q5QHE9, A0A387IHE2, D2I902, A0A387IHI2, A0A387IHE1, O80349, A0A3B1EZV1, Q6L8R6, Q5QHE7, Q940W8, A0A387IHI7, Q001P7, Q6L8R1, G4XN45, G4XN49, A0A387IHI6, Q6L8R4, A0A387IHH3, G4XN46, Q6L8Q9, Q6L8R2, A0A3B1EZU3, Q6L8R3, O80356, A0A387IHI4, Q940W6, A0A387IHH9, O80352, Q940X0, Q5QHE8, G4XN47, Q5QHE6, Q6L8R7, Q5QH04, A0A387IHF0, O80353, A0A2D1CRR9, O80348, G4XN48, Q6Q2Z5, A0FLG6, A0A387IHE8, A0A3B1EZU4, Q6L8R5, Q940W9, P93511, Q940W7, A0A2V0NKU4, A0A2V0PBY3, A0A2V0PFW8, A0A2V0P2D6, A0A2V0PQQ0, A0A2V0NRX2, A0A2V0NLP1, A0A2V0NLF4, Q01177, P17945, P14272, A0A0G2K4I9, F7FMS0, P70521, Q5FVS2, Q6TUF8, A0A1V1FYM3, A0A1V1FQA1, A0A1I8CMM6, A0A1I8C8R0, A0A1I8CK66, A0A1I8CA14, A0A1I8C8S3, A0A1I8D6L7, A0A1I8CRQ9, A0A1I8C3E9, A0A1I8CQ74, A0A1I8CUY7, A0A1I8CVM8, A0A1I8D1P2, A0A1I8CH38, A0A1I8CBE6, A0A1I8CKM7, A0A118CF77, A0A1I8CLA6, A0A1I8CV32, A0A2K6L170, A0A2K6MRU0, A0A2K6MWT8, A0A2K6N2E4, A0A2K6MN57, A0A2K6MWU2, A0A2K6MWT4, A0A2K6N2J7, A0A2K6L173, A0A2K6PRN4, A0A2K6NWB1, A0A2K6N799, A0A2K6RCW8, A0A2K6NTA1, A0A2K6N7A2, A0A2K6N796, A0A2K6NWB3, A0A2K6NWB7, A0A2K6PRM9, A0A2K6NTA8, Q8I6X5, A0A2D8K1E4, A0A1Q4C6M3, A0A1Q4DD97, A0A1M2Z0A0, A0A1Q3KY06, A0A2E4Z0V6, A0A2E2MCQ3, A0A2E2M8M6, A0A2N6AXD7, A0A2N6B0J3, A0A2A5G4Z8, A0A2N6B7F0, A0A2A4P7M7, A0A3A0EE51, A0A2A4R9T6, A0A349QK41, A0A2A4NQQ8, A0A0N1DQF6, A0A0N0LCX8, A0A1C3Y3G1, A0A2U2DQR8, A0A109K3K2, A0A3S0SF88, A0A246DZ15, Q2K005, B3Q100, B3PUG4, A0A1L5PF86, S5S373, A0A0A8GIJ8, F2AFE1, A0A327YDD0, W6RLA5, G9AGQ7, A0A2L0H058, A0A2A6LWB4, A0A2L0HFL1, A0A2A6LVY4, N6V882, A0A0B4XEY4, A0A1L5NUL5, S3H7T7, A0A370KJW2, A0A1C3WED0, A0A2A6KF27, A0A387FJY0, A0A1S9GBZ1, A0A1S9GD17, A0A072BW40, C6B7V3, C6B6X0, B6A442, W0IT72, J0KL73, J0L6R4, I9N4J7, I9NL44, A0A1C9HR08, A0A1C9HXI1, A0A3E1B354, A0A3E1AZA5, A0A3E1BI76, Q1M687, Q1M724, J0K300, J0VE20, A0A1Q8H6V5, A0A2L1CRP2, A0A1Q8HGY6, A0A222U8G4, A0A222U658, A0A444NFR8, A0A179BUW9, A0A1B1CLA0, A0A154IRG5, A0A1L3ZLB7, A0A3S4Z848, A0A154IPB2, A0A444HN98, A0A444IGJ5, A0A444NC52, A0A3S3WH50, A0A2K9ZEW6, A0A2K9ZE91, A0A2Z4YEZ8, A0A3S4ZBC5, A0A2Z4YX29, A0A1G4TJ35, A0A1B4YZE1, A0A1B4YZG6, A0A1B4YZE6, A0A2N5AWF1, A0A1B4YGK0, A0A316CJ14, A0A117N3F6, A0A101KVC7, A0A1B4YE29, A0A1A5HXY1, A0A1A5QH69, A0A1A5R3P7, A0A1C3W6S0, Q92VA6, A0A2J0Z7E8, A0A437F0L4, A0A222GTF2, A0A437G4H5, A0A222K2F7, A0A3S2TJR4, A0A437E078, K0Q667, K0PTJ5, A0A1C3U1J6, A0A1C3WEX5, A0A376ASS4, A0A376AR20, A0A0D8KAH4, A0A1X7CLE5, A0A1Q9AYC7, A0A1Q8ZX36, A0A1W6GK72,

A0A1W6GQX6, A0A0M3GJ47, A0A0M3GFH7,
A0A192TDW1, A0A192TJG2, A0A2U3CMZ0,
A0A3R9AP92, A0A1L9CN61, A0A1S9ESQ4,
A0A176XJZ8, A0A0X8IY53, A0A0D0J656,
A0A176X4G7, A0A1B9SXL8, A0A0D0KZ04,
A0A1V2AH49, A0A1B9UR06, A0A2T7W9Z1,
A0A2L2LHE9, A0A083ZGC6, A0A2C5Z3N8,
A0A109VT16, A0A3G2DPM2, A0A420FYH9,
A0A024IWY1, A0A3B8F8H3, A0A2T7W547,
A0A1Q9ALQ8, A0A1Q9AGL9, A0A376ABJ2,
A0A3R9CXJ4, A0A2A5KUS5, A0A248W2A8,
A0A444LBM9, A0A1L8PLX4, A0A1M3P8H7,
A0A1M2YPN5, A0A143ZFH2, A0A0N1AWY9,
A0A0N1A5V6, A0A1B9RQK2, A0A1B9S8M0,
A0A292ECM0, A0A292EB32, A0A420CH60,
A0A420CND4, A0A285Y1D3, J2DBP0, J2WMP8,
A0A432P6G8, A0A432NWE3, A0A3S0Q0E5,
A0A2A6JF54, J5QAT9, A0A387GV30, W6WJL6, J2IQH9,
J1T8K3, A0A1W6KW30, A0A2A6R2N3, A0A098RMU8,
A0A060I507, U4Q372, A0A2A6K1I0, A0A2T3EJJ0,
A0A2S6BBW7, A0A2A6ICH9, A0A2A6I5L3,
A0A2A6HV73, A0A2A6HMS6, A0A2A6I066,
A0A2A6KX61, A0A0M3B778, A0A0M3B5N6,
A0A1S1T9A9, A0A1S1TD64, A0A0Q4WAW7,
A0A0Q5D0H9, A0A0Q5E1T4, A0A0Q5W5J8,
A0A0Q5WYK9, A0A0Q6H5F7, A0A2A6LEH7,
A0A192M5Y9, A0A235AY41, A0A235AJ79,
A0A235AZH9, A0A1G5HB02, A0A1H9WX89,
A0A1I0ZNA8, A0A1H6GJQ1, A0A329AJB1, L0NJT2,
A0A1W6PV42, A0A1W6PZX1, A0A2L0W608,
A0A2L0W9E8, A0A1G8WJR3, H4EZX2, K0VNQ6,
A0A2V4UN27, A0A2V4VIK9, A0A2V4UL45,
A0A246SBW7, A0A246T4R1, A0A246T354,
A0A246TWX7, A0A437NBS0, A0A0Q6QM12,
A0A0Q6RH95, A0A0Q6S6H3, A0A0Q6VUN6,
A0A0Q6UVB6, A0A0Q6ZH68, A0A0Q7XTZ6,
A0A0T1WTZ2, A0A0Q7NJK2, A0A0Q7PCQ9,
A0A0Q8C8S6, A0A0Q8BTC4, A0A0Q8GJX7,
A0A0Q8NRH2, A0A1S1PS94, A0A1N6XKQ2,
A0A1N6UY85, A0A1W2DVC3, A0A2T3GU97,
A0A2N4XYT7, A0A2V5CDS1, A0A198YKG9,
A0A198YI97, A0A2K0ZQK3, A0A2K0ZP10,
A0A1E4YFI2, A0A095UEN9, A0A3D3BI31,
A0A2W6XJX2, A0A2M8U1J2, A0A353G6F7,
A0A285U5F1, A0A2N0DBB1, A0A1Q9A5B5,
A0A1H8WJ94, A0A1H8IHA7, L0LF24, A0A329Y7X4,
A0A2T0P999, A0A2W4CTD1, A0A2W4B084,
A0A432PRA9, A0A1Y2CKU5, A0A1Y2CE17,
A0A1Y2B783, A0A1Y2AMS3, A0A1Y2C375,
A0A1Y2C103, A0A1Y2CFU8, A0A1Y2BGJ3,
A0A1Y2CP39, A0A1Y2BQK0, A0A1Y2CED3,
A0A1Y2AE69, A0A1Y2CJV3, A0A1Y2CDM5,
A0A1Y2C0V7, A0A1Y2BFL8, A0A1Y2CJS8,
A0A1Y2AQ77, A0A1Y2BHM1, A0A1Y2CL98,
A0A2P2IMF7, A0A2P2IIC6, A0A2P2JRF0, A0A2P2II72,
A0A2P2MSG9, A0A2P2MSG6, A0A2P2MQG3,
A0A2P2MSF5, A0A2P2K922, A0A1V3P122, T1HW46,
T1HKB1, T1HVY5, T1H815, T1I1K7, T1HB28,
A0A1N7LNA9, A0A2T5JUG7, A0A2T4JF26, D5AST4,
A0A0E2PIW9, A0A1G7E3U5, A0A330HGS9,
A0A285SYE0, A0A239GLZ7, A0A285CQ45,
A0A366K6J3, A0A1H4S7Q6, A0A421BL93, C8RWS1,
A0A3D6CUW1, Q3IY48, A4WNG2, A3PFM8, B9KQL4,
A0A370XYR7, A0A2W5U3H5, A0A3G6W6P9,
A0A2T4J571, A0A2T4JJD8, A0A1N7KZF5,
A0A318U1P8, A0A2G1CH11, A0A372EZL6,
A0A327M0R4, A0A3N2R174, A0A347UC92,

A0A3S3T2P1, A0A2M7EPC2, A0A1B6YLV4,
A0A0P7W120, B6ATT1, A3JM87, A0A418SAV9,
A0A3L9Y7X3, A0A257F196, A0A0B4E3A1,
A0A372IHY4, A0A3D4DUJ2, A0A3D5PSG7,
A0A2V5FZ51, A0A2D4V2U9, A0A2A4NME6,
A0A2E3PJV4, A0A2E3FHN5, A0A356V427,
A0A2E3PH72, A0A350AHD8, A0A2E3PP51,
A0A2A4ZFU9, A0A2D5J967, A0A2V5G5E0,
A0A2D5IXH4, A0A259DA28, A0A259LR21,
A0A1Q4CVQ4, A0A1G3GSI9, B6B7T2, A0A2G6ISQ3,
A0A2G6CFH3, A0A2G6I8H1, A0A2G6II81,
A0A2G6IV12, A0A2A4S6F2, A0A355T6E9,
A0A2Z4UG21, A0A2E5BRN7, A0A2A5EMY3,
A0A327JMD5, A0A327KJ78, A0A327K3R9,
A0A3S4B6R7, A0A327L3N5, A0A127F2Y1,
A0A318TNH4, Q6NBK5, Q07TU8, Q212S6, Q21BD4,
Q13CZ0, E6VBP2, Q2IR81, B3QEG9, A0A0D7EX63,
A0A0D7F517, A0A323UFY3, A0A2R4GPL3,
A0A418UYX9, A0A336JVI2, A0A1H8TZ49,
A0A0N1C8P1, A0A365U4P5, A0A2E7W3G6,
A0A2T5U026, A0A428K1H3, A0A366C229,
A0A1V0I275, J5PI78, A0A2E2JWZ9, A0A1Q9QUC6,
A0A1E1KPQ4, A0A1E1LMW4, A0A1E1KU29,
A0A1E1KM25, A0A1E1JTK9, A0A1E1LGC2,
A0A1E1K9E7, A0A1E1KXI0, A0A1E1KAU5,
A0A1E1LP64, A0A1E1MDX2, A0A1E1M5W1,
A0A1E1MFU2, A0A1E1M9F8, A0A1E1MTL8,
A0A1E1MD61, A0A1E1M215, B9SSB2, B9STG0,
B9SEN3, B9RXY2, B9SXC2, B9RQP9, B9RFM4,
B9SIG2, B9SSB7, B9TAY3, B9R758, B9RHL2, B9SJQ1,
B9T444, B9SV42, B9S7P6, B9SIQ7, B9SSB5, B9T7U7,
B9RLS4, B9SIR0, B9R757, B9R755, B9SSA1, B9RXX5,
B9R760, B9SNG5, B9RQP5, B9SSC0, B9R761, B9S0R9,
B9SRH2, B9SFF3, B9RI65, B9S9P6, B9SFF2, B9SFX3,
B9RXY0, B9RXY1, B9RVX8, B9SW97, B9SFX5,
B9SFF5, B9SIR1, B9SZ96, B9RXX9, B9SFF1, B9RFM6,
B9S858, B9SSB8, B9RV63, B9RLS2, B9T7U8,
A0A2G2GCP5, A0A2G2R0P0, A0A2G1YWK1,
A0A2G2HQX6, A0A2G2GH02, A0A2P6Q8G4,
A0A2P6SHN7, A0A2P6SCY4, A0A2P6Q365,
A0A2P6QUU6, A0A2P6Q342, A0A2P6S2Q9,
A0A2P6QU66, A0A2P6PXU3, A0A2P6Q3D1,
A0A2P6S898, A0A2P6SAU9, A0A2P6RJH7,
A0A2P6Q908, A0A2P6QQ00, A0A2P6QVT9,
A0A2P6QJ32, A0A2P6Q399, A0A2P6S8C4,
A0A2P6Q341, A0A2P6RSA0, A0A2P6PFN5,
A0A2P6Q3C0, A0A2P6RCT1, A0A2P6QB94,
A0A2P6Q3C5, A0A2P6Q391, A0A2P6QHF8,
A0A2P6Q8G0, A0A2P6S2T7, A0A2P6S756,
A0A2P6RTY8, A0A2P6Q351, A0A2P6QBC3,
A0A2P6QBG0, A0A2P6PXY7, A0A2P6QBF8,
A0A2P6RCR1, A0A2P6QAY4, A0A2P6Q3C2,
A0A2P6Q3E7, A0A2P6R3M6, A0A2P6Q0T1,
A0A2P6RX36, A0A2P6SAB0, A0A2P6Q3A9,
A0A2P6Q390, A0A2P6QB71, A0A2P6S6W6,
A0A2P6S765, A0A2P6Q3D5, A0A2P6Q8T0,
A0A2P6QBH7, A0A2P6Q3A8, A0A2P6Q3C6,
A0A2P6Q8Z8, A0A2P6Q367, A0A2P6RX44,
A0A2P6QU56, A0A2P6QE17, A0A2P6QE07,
A0A2P6QVC9, A0A2P6QAX3, A0A2P6Q355,
A0A2P6Q396, A0A2P6RRU2, A0A2P6Q2N8,
A0A2P6RUA2, A0A2P6Q3A7, A0A2P6RRQ5,
A0A2P6SCB0, A0A2P6RU56, A0A2P6RS89,
A0A2P6Q372, A0A2P6QM19, A0A2P6PX37,
A0A2P6Q374, A0A2P6Q0Q2, A0A2P6SGJ1,
A0A2P6QR39, A0A2P6Q381, A0A2P6Q362,
A0A2P6QBG3, A0A2P6S2K8, A0A2P6S2R0,

A0A2P6Q3B2, A0A2P6QBH3, A0A2P6RBI2, A0A1S3SIB8, A0A1S3SIC4, A0A1S3KP78, A0A2P6S6X4, A0A2P6PD71, A0A2P6SD05, A0A1S3SH12, A0A1S3LE48, A0A1S3P228, F2TWZ6, A0A2P6S6W4, A0A2P6RST1, A0A2P6QBL5, F2UF68, F2TWR8, F2UG85, F2UPS4, F2USW3, F2U618, A0A2P6PXZ1, A0A2P6Q348, A0A2P6RVC0, F2UA60, F2UFK9, F2U2Y5, F2UGI4, F2U386, F2UIR6, A0A2P6RRR7, A0A2P6S2Q6, A0A2P6S2L9, F2UHB7, F2TVR9, F2UJ78, F2UIC5, F2UDJ0, F2U6I3, A0A2P6Q397, A0A2P6Q8F1, A0A2P6S2P5, A0A140E138, W6GGU3, A0A140E0U4, A0A2E0TIG6, A0A2P6QBJ8, A0A2P6QVN2, A0A2P6Q8K4, T0RAA8, T0RYA1, T0QTS1, T0Q639, T0RYL1, T0PVB7, A0A2P6QBA5, A0A2P6RU59, A0A2P6Q8F3, T0RQN3, T0R976, T0RRW1, T0QUWI, T0QNZ2, A0A2P6QR92, A0A2P6P691, A0A2P6Q8G5, T0RMV6, T0PNV2, T0RAF6, T0QYA6, T0S243, T0RG82, A0A2P6PDR1, A0A2P6QB88, A0A2P6RRU7, T0QXL6, T0RI62, T0RPR9, T0R5M4, T0RIQI, T0RBY8, A0A2P6Q394, A0A2P6SAD4, A0A2P6SAC0, T0QL36, T0PWZ1, T0QQ07, T0RBY3, T0RH69, T0QGJ1, A0A2P6Q3A3, A0A2P6Q8H0, A0A2P6S8D3, T0RJM1, T0PH14, T0R5A9, T0Q529, T0PVB2, T0RYU4, A0A2P6Q8G3, A0A2P6PDQ4, A0A2P6QM80, T0PU14, T0RJM4, T0QZF9, T0R762, T0S1C6, T0R8A8, A0A2P6RCQ5, A0A2P6Q8U1, A0A2P6Q0P6, T0Q4I6, T0QAA3, T0Q2C6, T0QMW7, T0QN46, T0RIN6, A0A2P6RVC4, A0A2P6Q3B1, A0A2P6SAY2, T0QI45, T0QJB1, T0QUH0, T0RQM9, T0Q4C3, A0A2P6RUW8, A0A2P6Q8U4, A0A2P6QW50, A0A067BU55, A0A067BYE3, A0A067BYA7, A0A2P6R760, A0A2P6RCX2, A0A2P6RRU6, A0A067BJE2, A0A067C8S2, A0A067CBB6, A0A2P6REX4, A0A2P6PDQ7, A0A2P6SLZ0, A0A067C0P6, A0A067BSE2, A0A067BIR1, A0A2P6Q385, A0A2P6S6Y9, A0A2P6Q8L4, A0A067C156, A0A067BJJ2, A0A067CR05, A0A2P6QQ26, A0A2P6RCS7, A0A2P6SD19, A0A067CK80, A0A067C126, A0A067CKM6, A0A2P6RU70, A0A2P6R9I7, A0A2P6S2N8, A0A067C128, A0A067BMR9, A0A067CL67, A0A2P6Q8V1, A0A2P6PXZ2, A0A2P6S8C8, A0A067BJT0, A0A067CFL9, A0A067BLZ4, A0A2P6QM44, A0A2P6QBI9, A0A2P6PAH1, A0A067BU12, A0A067BRT0, A0A067CCE3, A0A2P6QBF9, A0A2P6QBI2, A0A2P6QBK6, A0A067CGD2, A0A067BEG5, A0A067CYL5, A0A2P6Q387, A0A2P6Q392, A0A2P6QBI6, A0A067CF87, A0A067C4Y2, A0A067C8W4, A0A2P6REY3, A0A2P6Q8I8, A0A2P6QVT7, A0A067BUH1, A0A067D5R2, A0A067CQB6, A0A2P6QA23, A0A2P6S790, A0A2P6QL63, A0A067CG93, A0A067CKH3, A0A067C9Y0, A0A2P6RW66, A0A2P6S8G7, A0A2P6QR51, A0A067BWR1, A0A067BRT6, A0A067CC90, A0A2P6Q3C7, A0A2P6PXY8, A0A2P6Q3C3, A0A067BYB2, A0A067C8G3, A0A067C2R2, A0A2P6Q3D6, A0A2P6Q398, A0A2P6QB80, A0A067D5R8, A0A067CDQ0, A0A067BZY9, A0A2P6S2F9, A0A2P6S2M5, A0A2P6PEP6, A0A067C9M8, A0A067C9D7, A0A067C6I2, A0A2P6QBC9, A0A2P6RS63, A0A2P6RRT9, A0A067CHH5, A0A067BRS1, A0A067BXJ9, A0A2P6QBC1, A0A2P6Q388, A0A2P6S745, A0A067CJ02, J5KAB5, A0A368BEY8, Q08668, P81860, A0A2P6PXY5, A0A2P6RS64, A0A2P6Q8Y2, Q26539, G3WZ37, G3VTC0, G3WZ36, G3VQX8, A0A2P6QP61, A0A2P6PD75, A0A2P6S2K2, G3VAC2, G3VAC3, G3WT27, G3VQX9, A0A131ZZD7, A0A2P6QBA3, A0A2P6R9L9, A0A2P6RWS3, A0A132A4Q6, A0A132A395, A0A132A5Y6, A0A2P6S2N2, A0A2P6S729, A0A2P6Q8F7, A0A132A5S6, A0A131ZTE1, A0A131ZSZ0, A0A2P6QBK3, A0A2P6S742, A0A2P6RS56, A0A1S5V1F4, A0A1S5V1F6, A0A1S5V127, A0A2P6PDH3, A0A2P6Q393, A0A2P6QBH0, A0A084G238, A0A084G6H4, A0A084G8P5, A0A2P6Q8Y0, A0A2P6Q378, A0A2P6PY16, A0A0X3PVM5, A0A430QM43, A0A430QQG0, A0A2P6S8D1, A0A2P6S8F6, A0A2P6Q8U6, A0A183JN66, A0A183JYW3, A0A095C245, A0A2P6Q3J3, A0A2P6PXZ6, A0A2P6R9M2, A0A094ZN30, Q5DBB4, A0A3Q0KQV0, A0A183MF64, A0A2P6SB38, A0A2P6QBK4, A0A2P6QBN7, A0A183NRF4, A0A3P8BBP8, A0A183R1Q6, A0A2P6QBL2, A0A2P6SCZ3, A0A2P6QUV7, A0A2S2N7W5, A0A2S2NT68, A0A2S2P2Z5, A0A2P6QWZ3, A0A2P6Q389, A0A2P6QA32, A0A2S2NBX7, A0A2S2NWJ0, A0A2S2PP89, A0A0P7W3J3, A0A3B0MGU5, W8RZV3, E2CPR9, A0A2S2NVK1, A0A2S2NBX8, A0A2S2NQG9, A0A316GM60, A0A1Y5S619, X7F4L9, A0A1N7JUR1, A0A2S2NP55, A0A1W5APA3, A0A0P7VVQ1, A0A2T6B3V4, A0A1I1U481, A0A1W2TSD6, A0A1W5APF2, A0A0P7XEA4, A0A0P7ZBC4, A0A1W2TQM6, B7RMG1, A3X6K1, A4ET50, A0A0P7UFY3, A0A1W4Y2F3, A0A0P7ULB2, A0A1X7BTA5, A0A1X6YTQ2, A0A0T5NYW0, A0A1W4YBZ6, A0A1W4YNQ9, A0A1W5A615, A0A0T5PEA0, A0A114YX20, A0A1N7E9E7, A3SKX6, A0A0P7UJJ9, A0A1W4ZAZ3, W9CB98, W9C6T6, A0A348WF88, A0A176F0X4, A0A176FFA7, A0A1D9Q902, A0A1D9PTT0, A0A1D9PV26, A7E7Z9, A0A3A8B3W9, A0A365TZC0, A0A2E2S3M6, A7E800, A7F252, A0A2U9B2H8, A0A2U9BYQ0, A0A2D9CQ95, A0A1H8EWM5, A0A017HNB8, A0A2U9CUU6, A0A2U9CZF4, A0A2U9BGH2, A0A1Y5RCZ8, A0A1G7AEP1, A0A0X3TTM9, A0A2U9CZ16, A0A2U9CYT4, A0A2U9D1N9, A0A2R8C330, Q5LWT4, A0A346SKI6, A0A2V3VSP3, A0A2U9CUM9, A0A2U9CYZ6, A0A401NHP4, A0A1E3D7V4, A0A1E3DCB0, A0A2S7PS49, A0A401NSN8, A0A401NY63, A0A401PJU3, A0A2S7PDR4, A0A2S7Q765, A0A2R4QNS3, A0A401P1Q0, A0A2Z5XDQ5, A0A0P4WNK8, A0A2K8WAW8, A3K2N2, A0A2K6UT93, A0A2K6SSN8, A0A0P4WFH3, A0A0P4WR24, A0A0N7ZDF3, A0A2K6S9K0, A0A2K6S9I8, A0A2K6UT83, A0A0P4WF65, A0A0P4WMW9, A0A3E2GVD1, A0A2K6SSN3, A0A2K6SSP3, A0A2K6UTP6, A0A116XD87, A0A3T0N402, A0A3T0N638, D8R4F7, A0A2K6UYV6, A0A2K6UYX4, A0A0E9NMM4, D8SC04, D8QZ24, D8TB11, D8T7A8, D8TF62, D8S1J3, A0A1H8QTL5, A0A327Y1D3, A0A1G8I7T9, S9QTS7, D8SDZ7, D8QTB9, D8RST4, D8S4Y9, D8QZK2, A0A1U7D1X3, A0A1G7KG72, A0A1S3LE46, D8T4B9, D8SRG6, D8RA35, D8RHS8, D8S2E7, D8TG77, A0A1S3S8H0, A0A1S3SH05, A0A1S3MAB2, D8RWA6, D8SX02, D8SNE6, D8SC01, D8QTB8, A0A1S3SH07, A0A1S3SH04, A0A1S3MLI3, D8S6U2, D8R007, D8R008, D8RVP2, Q5NJB1, R4G2C9, A0A1S3SH06, A0A1S3N1I0, A0A1S3SH08, R4G7D8, A0A3B4TE38, A0A3B4T255, A0A3B4THQ6,

A0A3B4TCE1, A0A3B4UM85, A0A3B4X7F7, A0A3B4WXD7, A0A3B4WCE8, A0A3B4WX70, A0A3B4X514, A0A3B4Y8L3, K4A2F5, K3Z304, A0A368R0J1, A0A368REB7, K3XQN4, A0A368RTU8, A0A368RZT1, A0A368RZL0, A0A368PG49, A0A368SB62, A0A368RZH4, K3XPE2, K3XSM1, K3Z530, A0A368R959, A0A368R9A6, K3ZF16, A0A368QBK5, A0A368QCH9, A0A368Q4U7, A0A368Q482, K3ZPX7, A0A368RTX5, A0A368RTT9, K3XPE3, K3YDB8, A0A368RS21, K3YDQ0, A0A368RU04, A0A368QK95, A0A368RIC1, A0A368QBY1, A0A368R0I2, A0A368QB50, A0A368R8H3, K4A740, A0A368RSJ9, A0A368QB49, A0A368QCI5, A0A368R1M3, A0A368Q1T4, A0A368RZS3, K3YDS3, K3Y1Y9, A0A368Q4R1, K3ZCG7, K3XFB5, A0A368RZL6, A0A368RZL1, A0A368RZK1, K4A6H6, A0A368RZK0, K3YPU6, K3YEW1, K3YGJ6, K3XSH2, A0A368Q490, A0A368SI17, A0A368RZG9, A0A368RZG3, K3XEF3, K3YD20, A0A368RBT8, K3ZQI9, K3Y585, A0A368Q289, A0A368R1M5, A0A368R0L6, K3Y129, A0A368SAN2, A0A368Q6K5, A0A368Q6G7, A0A368Q569, K3Y505, K3ZZR5, K3ZRF9, A0A368RZI0, A0A368RZJ2, A0A368Q4J9, A0A368QR38, A0A368QXB9, A0A368Q621, A0A368PRU5, A0A368S195, A0A368RZM3, K3YD40, A0A368RZK9, A0A368R030, A0A368PK67, A0A368Q4N4, A0A368RU08, A0A368RZE2, A0A368RBV9, A0A368RZK6, K3XVB7, K3XIC1, A0A368R502, K3XEI2, K4A357, A0A368R9C0, A0A368QYB1, A0A368Q4M4, A0A368QBF6, K3Y2F6, A0A368S2P0, A0A368R035, A0A368RVM9, A0A368RZF9, K3XEM4, K3Y572, A0A368SR44, A0A368QMF4, K3YCM4, K4ALT0, K4A323, A0A368QPX0, A0A368RZI2, A0A368Q570, K4A115, K4AMY1, A0A368R970, K3Y5N0, A0A368RBZ6, A0A368RE63, A0A368SH77, A0A368RZR9, A0A368Q474, K3YEX8, A0A368R046, K4A086, A0A368RZF3, A0A368RH05, K3ZLB6, A0A368RRV9, K3Y545, K3Y5K2, A0A368Q6F6, K3YDM6, K4A5Z2, A0A368QBG1, K3XVB8, A0A368QJJ5, A0A368RZN4, K3YCU3, K3Z37, A0A0Q3PQD3, A0A368RFZ5, A0A368SP74, A0A368R3U7, A0A368RZU1, A0A368SII8, A0A368QW32, A0A368S227, A0A368RG75, A0A368RAQ1, A0A368Q480, A0A368RZI6, A0A368QC37, K3Z3T5, A0A368STV8, A0A368RZM9, A0A368QCP0, A0A368SC73, A0A368R950, K4A5S5, K3XQB1, A0A368SB67, K3ZQM2, K3YDM0, A0A368RZM0, A0A368R4P0, A0A368SBE7, K3YDB1, K4A1K7, K3ZQP3, K3Y559, A0A368SP77, K3XEG7, A0A368R690, K3Z3U1, K3XEE4, K3Y247, K3YC50, K4A5Y3, A0A368R8Y6, K3Y179, K3ZQP4, K4A5Y7, R0IH14, R0JVZ7, R0K2V0, A0A2P8FBJ9, A0A114K541, A0A114DH54, A0A0P1FE41, A0A0N0V3A4, A0A021XGD0, A0A1A9FVP4, A0A372NA60, A0A372NIR6, A0A2W6YNN0, A0A2W6XTN2, A0A2W6TGS4, C9D0Y9, U3M974, Q8LP48, Q8LP47, Q9SEC7, Q8LP46, Q9SEB7, Q9SEC6, A0A443L654, A0A443KHG8, A0A443IWD5, A0A443LU18, A0A443KBX3, A0A443JST8, A0A3N2DQJ3, A0A1L3LEX8, A0A1L3KYZ3, A0A2S3YKP1, A0A2S3YS27, A0A1L3LHN3, A0A1L3LX24, D1CSK6, C3KRM2, A0A2Z3G701, A0A2U8GC90, A0A249Q4C1, A0A0T6ZYX4, I3X127, I3XBU9, A0A0E0UPB7, F7XGE8, H0G729, A0A178Y5H3, A0A178YA01, A0A1V3R0M3, A0A2A6PA40, A0A249P2H9, A0A249NZ41, A0A0T6ZY03, A0A0T6YWU1, A0A226CRW2, A0A2N8JWB1, A0A1G5WW04,

A0A2A6MGF3, A0A2A6MEJ3, A0A1B3MF54, A0A1B3MIS4, A0A0T6XVR8, A0A0T6Z662, A0A2S2R1U8, A0A2S2R590, A0A2S2PZK0, A0A2S2PXW4, A0A2S2R5W8, A0A2S2PY34, A0A2S2PWP9, A0A2S2Q0X7, R9S9Z3, R9SAI4, R9S9I9, A0A183IUB1, A0A183IUA7, A0A183IL94, A0A183J2V0, A0A183IH80, A0A183IL56, A0A183ISK1, A0A183J3L0, A0A183IHX2, A0A183IAW3, A0A183IZI2, A0A183IV49, A0A183IMR6, A0A183IBD8, A0A183IAM1, A0A183IN87, A0A183IPU9, A0A183IMI5, A0A183J9K8, A0A183ITM5, A0A3P7ZKR8, A0A183IID0, Q17U57, A0A0V0GU91, A0A0V0IAL3, A0A0V0IL88, A0A0V0IT75, A0A0V0H401, A0A0V0GP59, A0A0V0IZC1, A0A0V0ITT0, A0A0V0ISB1, A0A0V0HK80, A0A0V0HB28, A0A0V0IWF8, A0A0V0I7O0, A0A0V0GWH3, A0A0V0HTT1, A0A0V0IQW6, A0A0V0ISZ6, A0A0V0HEP1, A0A0V0IW22, A0A0V0IQJ4, A0A0V0ITB2, A0A3Q7FRL4, A0A3Q7JRJ5, A0A3Q7IBI2, A0A3Q7GDZ4, A0A3Q7F4P0, K4CH55, K4B9J0, A0A3Q7FY38, A0A3Q7HF37, A0A3Q7HDB6, A0A3Q7G892, A0A3Q7G5Y6, A0A3Q7F4L9, A0A3Q7F595, A0A3Q7G6E0, A0A3Q7IAB2, A0A3Q7G8E1, A0A3Q7FWM1, A0A3Q7EL09, A0A3Q7J270, A0A3Q7F4Q9, A0A3Q7HBS1, A0A3Q7HEV3, A0A3Q7EWM9, A0A3Q7F4N0, A0A3Q7IAP8, A0A3Q7F4K4, A0A3Q7HYY7, A0A3Q7G5X9, A0A3Q7HTG3, A0A3Q7FFS6, A0A3Q7G8V9, A0A3Q7HF02, A0A3Q7GP81, A0A3Q7F2Q7, A0A3Q7HHX3, A0A3Q7FRL0, A0A3Q7HHD3, A0A3Q7FRP6, A0A3Q7F582, A0A3Q7G5Z5, A0A3Q7I091, K4BE95, A0A3Q7I1N1, A0A3Q7IBL7, A0A3Q7HQY4, A0A3Q7INM2, A0A3Q7G218, A0A3Q7F3P0, A0A3Q7I8J1, A0A3Q7IBE5, A0A3Q7I8I7, A0A0D4BTD1, A0A0D4BT35, A0A0D4BTY2, M1C323, M1BNV7, M1A4E2, M1A1M0, M1C8X1, M0ZGV4, M1CGZ5, M1B352, M1C1G6, M1DW58, M1BYZ9, M1BIT6, M1D080, M1B369, M1CJN9, M1BGH7, M0ZKJ6, M1A1J1, M1BZ01, M1BGB2, M1B373, M1BNW8, M1CVL9, M1BP27, M1BGH6, M1BP21, M1DRI9, M0ZGV5, M1A1J0, M1AFX4, A0A0M3STW8, M1BIU3, M1CRP0, M1CVM0, M1CGZ4, M1BNV6, M1AFZ1, M1D081, M1CH47, M0ZUR7, M1A1I5, M1BGH3, M1CVL4, M1C1G5, M1ASH7, M1BGG2, M1BNW9, M1A1M2, M1A1I7, M1C1G7, M1BP20, M1BNV8, M1BZ00, M1BNX0, M1A1I8, M1BGB0, M1DRP4, M1CGZ2, M1A226, M1CGZ3, M1A1I9, M1AJH1, M1B367, M1B363, M1B357, M1BIU2, M1BGA3, M1CVM1, M1AJH2, M1BNV5, M1BIU4, M1B356, M1AFY9, M1BGA2, M1C322, M1CGZ7, M1AFZ0, M1B366, M1DZ63, M1BGA7, M1BGA4, M1BGG5, M1C8X2, M1CC72, M1BNV4, M1BNW1, M1CJP1, M1BIT7, M1CVL6, M1A4E5, M1CH44, M1B371, E9J8M2, E9IHS5, E9IN88, E9J669, E9J909, E9J910, E9IHS6, E9IN89, A0A150STA1, F7VYZ6, F7VR72, F7W2U3, A0A1Z5R405, A0A1W0W663, A0A1Z5RKG3, A0A1Z5R8K9, C5YTR3, A0A1B6Q1T4, A0A1B6P7F5, A0A1W0W011, C5XIK1, C5X8J9, A0A1W0W6A4, A0A1B6QDZ9, A0A1Z5R8L3, C5XNJ5, A0A1B6PQ00, A0A1B6Q6I4, A0A1W0W4G9, C5YRQ1, A0A1Z5RF80, C5XKC4, A0A1B6QBX0, C5XG13, A0A1B6QJV5, A0A194YPP4, C5YI80, A0A1Z5S8X7, A0A1B6PN86, A0A1B6Q0T3, A0A1Z5RF61, A0A1B6P674, A0A1W0VTK0, A0A194YKI9, A0A1B6QP87, A0A1B6QBJ7, A0A1B6PNF9, A0A194YKJ5, C5Z879, A0A1Z5RCU0, A0A1B6QDZ0, A0A1W0W4H9, C5YFX5,

A0A1B6QEU8, C5YZF4, A0A1B6QE05, C5XAW9, A0A1B6QPL1, C5YGN7, A0A1Z5RCV0, C5YGM5, A0A1Z5R1H2, A0A1Z5RGB4, C5XAX0, A0A1W0VYV0, A0A1B6P8A7, A0A1Z5RF79, C5XNJ6, C5XL73, A0A1Z5RF74, C5X9Y1, A0A1B6Q255, A0A1Z5RFW8, A0A1B6Q7G8, A0A1Z5RIL9, C5WQK6, A0A1Z5RKG6, A0A1W0W6M4, A0A194YHF9, A0A1B6P5Y4, A0A1B6PNE9, A0A1W0VTM8, A0A1W0VTM2, C5XLS4, A0A1Z5RFC4, A0A1Z5R535, C5YT42, A0A1B6PNG4, C5Y4M3, C5X494, C5YV85, C5WV97, A0A1Z5RF78, C5XSW0, C5X2A2, C5YGP6, A0A1B6QE00, A0A1W0W6E0, A0A1B6QBX3, A0A1B6PNF5, A0A1Z5S3X9, A0A1W0W6U5, A0A1W0W672, A0A1B6Q6J1, C5YGP5, A0A1W0VSW8, A0A1B6QBW8, A0A1B6QBW6, C5YI84, Q8LJZ0, A0A2K1QVG0, A0A2K1QHN6, A0A2K1QKQ3, A0A2K1QK63, A0A2K1QSX4, A0A2K1QFH6, A0A2K1QKW0, A0A2K1QK44, A0A2K1QZH3, A0A2K1QY48, A0A2K1QX05, A0A2K1QSH2, A0A2K1R2J1, A0A2K1QRG3, A0A2K1QKB9, A0A2K1QGJ2, A0A2K1R3T9, M3AV53, M3BZM1, A0A349QUZ7, A0A354KFP2, A0A2T7WNY4, A0A2T7WSG0, A0A1L3JC18, A0A1L3JC23, A0A1L3JC30, A0A371B272, A0A371BHY4, A0A371BHT8, A0A0K9RR85, A0A0K9RDP3, A0A0K9QHY2, A0A0K9QR37, A0A0K9R7Z2, A0A0K9Q8S7, A0A0K9S0X2, A0A0K9QPL4, A0A0K9RF56, A0A0K9S213, A0A0K9RH17, A0A0K9RT23, A0A0K9RB42, A0A0K9QZ62, A0A0K9RVT8, A0A0K9R8M3, A0A0K9Q888, A0A0K9RMQ3, A0A0K9QW25, A0A0K9S082, A0A0K9R4K7, A0A0K9QRC1, A0A0L0HA63, A0A0L0H8G6, A0A2H1WV32, A0A2H1VNI1, A0A2H1VQJ4, A0A2H1WDX9, A0A2H1W4L3, A0A0H5QFI6, A0A0H5QHL0, A0A0C2ER25, A0A162MRJ9, A0A167PWC0, U7Q5P1, A0A0F2LUQ6, A0A084B8D0, A0A084AUC4, A0A084AH70, A0A084AW91, A0A084R5E6, A0A084R699, A0A084RSS0, A0A084R0N3, A0A084QS85, A0A084QWE9, A0A084QR64, A0A178AM66, A0A178B4D4, A0A178B8B6, A0A178AC45, A0A178AYG8, A0A178B8W6, A0A178AV13, A0A178B2D4, A0A285S9J4, A0A1Y1SPA5, A0A420AAV3, A0A1H2FDZ7, A0A2E6Y7I2, A0A3B4ZKK7, A0A3B5B6X3, A0A3B4ZPZ3, A0A3B4ZIA4, A0A3B5ADV9, A0A3B4ZH28, A0A3B4ZII7, A0A087T2K8, A0A087U8M8, A0A087UVI0, A0A087UVI1, A0A087UVH9, A0A087T2K7, A0A087TCV3, A0A087SWB4, A0A087UKG6, A0A087SVJ4, A0A087UKG5, A0A087UBD7, A0A087UAP8, A0A087TMG3, A0A087T9G3, A0A087T7G6, A0A087T2C9, A0A087T0G3, A0A087TEI6, A0A087UVX7, A0A087THX0, A0A1I8AEG0, A0A1I7Y5R0, A0A1I8AKS5, A0A1I8AL78, A0A1I7Y544, A0A1I8A6X3, A0A1I8ATW3, A0A1I8AU60, A0A1I7YBL2, A0A1I8A4V1, A0A1I7Z6J2, A0A1I8A5G4, A0A1I7YSK9, A0A1I7YBL9, A0A1I7Y0N0, A0A1I7ZHS2, A0A1I7Y6B7, A0A1I7YB77, A0A1I7ZQD0, A0A1I7ZLK9, A0A1I7ZW10, A0A1I7Y539, A0A1I7Z2T9, A0A1I7YQG9, A0A1I7ZVA4, A0A1I7YYH6, A0A1I8AAT9, A0A1I8AAI7, A0A1I7Z483, A0A1I8ARD3, A0A364NG07, A0A364N8Y3, A0A364NBE1, A0A2G8KGD5, A0A2G8KPK3, A0A2G8KY26, A0A2G8JWF4, A0A2G8KY13, A0A2G8KMR0, A0A2G8K0N1, A0A2G8LND1, A0A2G8LNU1, A0A2G8JX12, A0A2G8KPX2, A0A2G8KPE7, A0A2G8K4I4, A0A2G8K4G4, A0A2G8JWF7, A0A2G8L1A0, A0A2G8KPD9, A0A2G8KPE6, A0A2G8L837, A0A2G8LH26, E3FLQ8, Q098U7, A0A1I8PQ32, A0A1I8QFD3, A0A1I8PLI1, A0A1I8NR90, A0A1I8QDM2, A0A1I8PQE0, A0A1I8QFE6, A0A1I8QFB9, A0A1I8NPE1, T1JBA9, T1ILR6, T1IZB1, T1IYR6, T1J1D9, T1J1D8, T1J1E1, T1J2Z9, T1IYR5, T1IUF2, T1IWK2, W4YFT8, W4XEH1, W4Y9R3, W4Y7C8, W4Y7X2, W4ZAY8, W4YX16, W4ZEP3, W4Z4Q9, W4Y1M2, W4Z490, W4XV31, W4XT52, W4Y4J9, W4YJJ7, W4Y4H6, W4XV55, W4XRN9, W4YFP9, W4ZK20, W4YB28, W4ZB03, W4YM62, W4ZIR0, W4YUE3, W4Z6A9, W4Y9R4, W4Z5T2, W4ZD80, W4XET4, W4XV33, W4Y748, W4YH25, W4YVK8, W4Y2F2, W4YXL4, W4Z1A9, W4YQ09, W4XPT9, W4ZG23, W4Y9H1, W4XN66, W4Z197, W4ZKJ1, W4YMZ9, W4Z0S4, W4YI87, W4Y1N4, W4Z525, W4XT71, W4XAZ6, W4Y432, W4Z5T3, W4XGA6, W4Z430, W4XDS2, W4YJJ8, W4Y9R5, W4XX39, W4Z280, A0A0N5BIA2, A0A0N5CCT3, A0A0N5CGC3, A0A0N5BMA1, A0A0N5B5D0, A0A0N5CGC2, A0A0N5BQ06, A0A0N5B5E6, A0A0N5BCK0, A0A0N5B3M3, A0A0N5C548, A0A0N5C796, A0A0N5BRL1, A0A0N5BF41, A0A0N5C8M1, A0A0N5C2G3, A0A0N5C549, A0A0N5C5W7, A0A0N5BTC5, A0A090MZF3, A0A090LAM2, A0A090KSC6, A0A090KTL6, A0A090MTX8, A0A090L5S9, A0A090KXK0, A0A090KWR4, A0A090KR38, A0A090LBK0, A0A090KZM2, A0A090LMM7, A0A090LMB5, A0A090L0U9, A0A090L8Q0, A0A090LEE0, A0A090KR99, A0A090LS81, A0A090LH59, A0A090L2B1, A0A090KZU3, A0A0K0EQ10, A0A0K0EN25, A0A0K0ENZ3, A0A0K0EPC1, A0A0K0E3P4, A0A0K0E4B4, A0A0K0EFB6, A0A0K0ES05, A0A0K0EEE0, A0A0K0ESE2, A0A0K0E6Z7, A0A0K0DU24, A0A0K0E1P0, A0A0K0EGC5, A0A0K0EE54, A0A0K0DX88, A0A0K0DTQ3, A0A0K0EGC4, A0A0K0E8Q0, A0A0K0EJ96, A0A0K0E4B5, A0A0K0FAY7, A0A0K0FYJ7, A0A0K0F449, A0A0K0F450, A0A0K0F9B8, A0A0K0FA09, A0A0K0F2N2, A0A0K0G164, A0A0K0FJN2, A0A0K0FCQ4, A0A0K0G4U8, A0A0K0EWF5, A0A0K0F5J9, A0A0K0F3F0, A0A0K0EUB2, A0A0K0F008, A0A0K0FCQ5, A0A0K0EZ99, A0A0K0F0L9, A0A0K0FEV0, A0A3P7ILC4, A0A3P7I9T4, A0A3P7JE85, A0A3P7IEU2, A0A3P7KH13, A0A3P7IJW3, A0A3P7IZH6, A0A3P7I491, A0A3P7LAH1, A0A3P7J5F1, A0A3P7IRM1, A0A3P7JJX8, A0A3P7J7H7, A0A3P7IN45, A0A3P7JMN8, A0A3P7INY8, A0A3P7LGM1, A0A3P7J2L6, A0A3P7JB01, A0A3P7JA70, A0A3P7L1J1, A0A093KD36, A0A093HHU1, A0A093HGM9, A0A2B4SM39, A0A2B4RRZ6, A0A2B4SJV0, A0A2B4SAG5, A0A2B4SES4, A0A2B4RBI1, A0A2B4S2H8, A0A2B4S3A5, A0A2B4SNH9, A0A2B4S207, A0A2B4S6F9, A0A2B4R7J5, A0A2B4SFG4, A0A2B4S741, A0A2B4SJX2, A0A2B4RAJ9, A0A2B4SUX3, A0A2B4SH64, A0A2B4SU12, A0A2B4R4B9, A0A2B4S3B6, A0A2B4R832, A0A2B4SXX8, A0A2B4SUD0, A0A2B4R2R9, A0A2B4RFK9, A0A2B4RMT1, A0A2B4R623, A0A2B4R7E0, A0A2B4RD03, A0A2B4S9T7, A0A2B4RFP1, A0A2B4RPK6, A0A2B4R401, A0A2B4RAC0, A0A2B4RS71,

A0A2B4RXZ8, A0A2B4T1E8, A0A2B4RAX9, A0A0N5AVN4, A0A0N5AWJ9, A0A0N5AKP3,
A0A2B4R5W3, A0A2B4REV2, A0A2B4RBF8, A0A0N5ASE0, A0A0N5AQE8, A0A0N5AV92,
A0A2B4SUP0, A0A2B4RLC2, A0A2B4T0K3, A0A0N5ABP9, A0A0N5AMT9, A0A158R5G1,
A0A2B4RYT3, A0A2B4RW39, A0A2B4R37, A0A0N5AYU3, A0A0N5AT40, A0A0N5A8Y8,
A0A2B4RK16, A0A2B4SDB6, A0A2B4SD97, A0A0N5AUH4, A0A158R6C4, A0A158R5U4,
A0A2B4R0H8, A0A2B4SY37, A0A2B4RMM4, A0A0N5AX21, A0A0N5AAC3, A0A0N5AES2,
A0A2B4R9P6, A0A2B4SAP0, A0A2B4S7C1, A0A0N5AR84, A0A0N5AWX5, A0A411Z4S3,
A0A2B4T076, A0A2B4RQ27, A0A2B4RZ31, A0A3S8U2P2, A0A2N4YG23, A0A0R3VTQ5,
A0A2B4SW57, A0A2B4RQZ6, A0A2B4SW29, A0A3P6NAE9, A0A158R765, H0ZG36, H0YWJ9,
A0A2B4SXJ7, A0A2B4R394, A0A2B4REL3, H0ZY21, H0ZML2, H0Z9B7, H0Z415, A0A3B5KNQ7,
A0A2B4SKC3, A0A2B4RCQ4, A0A2B4RCF9, A0A0S3P5S3, A0A3B5JVN8, H2U253, A0A3B5K7U1,
A0A2B4SGL1, A0A2B4SKU4, A0A2B4S352, H2UIX2, A0A3B5K478, H2U252, A0A3B5K8C0,
A0A2B4RR27, A0A2B4R5T8, A0A2B4RIF0, H2UB48, A0A3B5KSI5, H2UB51, A0A364L110,
A0A2B4SI30, A0A2B4RF56, A0A2B4S048, A0A1Q5QBL9, A0A0U1LQB1, B6QAW5, B6Q7P1,
A0A2B4S8S0, A0A2B4RCW0, A0A2B4S421, B6QVR0, B8M4W0, B8MRL4, R4X8Q8, A0A163ZG59,
A0A2B4S3Y9, A0A2B4SWB5, A0A2B4RNZ9, A0A370QWB2, A0A1H6PBW2, A0A239NTK9,
A0A2B4RKY5, A0A2B4SYK2, A0A2B4RCU9, A0A2U0TH97, A0A420ATD9, A0A3Q0DMW9,
A0A2B4RG52, A0A2B4SQ47, A0A2B4SFY8, A0A1U7SYT3, A0A1U7U5V8, A0A1U7U7M3,
A0A2B4SEZ0, A0A2B4RQ71, A0A2B4RI82, A0A1U7TY18, A0A3Q0DKG9, A0A1U7SMG8,
A0A2B4RXE4, A0A2B4R8V7, A0A2B4SNN3, A0A1U7UC10, A0A3Q0DG51, A0A3Q0DM20,
A0A2B4S8F7, A0A2B4R5T1, A0A2B4RA51, A0A1P8MZ84, A0A0B4C503, A0A093CH68,
A0A2B4RNS9, A0A2B4RAH7, A0A2B4RTJ2, A0A093CND7, A0A093CVC3, A0A093CQR8,
A0A2B4SKD6, A0A2B4RCL9, A0A2B4S0E1, A0A2G9TXP9, A0A2G9U3X5, A0A2G9UGS1,
A0A2B4S0Y6, A0A2B4RJW9, A0A2B4SZU0, A0A2G9UVF5, A0A2G9UD74, A0A2G9TB90,
A0A2B4SRH6, A0A2B4T229, A0A2B4S0G9, A0A2G9UAM5, A0A2G9T9Y6, A0A2G9U041,
A0A2B4S040, A0A2B4RDG4, A0A2B4R9R0, A0A2G9UK14, A0A2G9U3J8, A0A2G9U5G6,
A0A2B4R5S5, A0A2B4SPN4, A0A2B4S8L9, A0A2G9U6U5, A0A2G9UCE1, A0A2G9V4H0,
A0A2B4SBF7, A0A2B4R907, A0A2B4RDE8, A0A2G9UF90, A0A2G9U0T0, A0A2G9UAE0,
A0A2B4RFA7, A0A2B4S2N4, A0A2B4SVB4, A0A2G9U9D4, A0A2G9UTY8, A0A2G9UH07,
A0A2B4SXM9, A0A2B4RIY2, A0A2B4RLZ3, A0A3C1S3E6, A0A3C1S4B8, A0A081BAR4, C5BI67,
A0A2B4S0I5, A0A2B4S7S6, A0A2B4RYB4, A0A3G4ZLM1, A0A2J7ZPE6, A0A2J7ZJB7,
A0A2B4SE06, A0A2B4S470, A0A2B4R8S2, A0A2J8AH70, A0A2J8AIZ8, A0A2J8A820,
A0A2B4SYR5, A0A2B4RI65, A0A2B4RE37, A0A2J8A4H3, A0A2J8AFD0, A0A2J7ZQC3,
A0A2B4RJT3, A0A2B4RHB2, A0A2B4S982, A0A2J8AFF5, A0A2J7ZX95, A0A2J8A7Q4,
A0A2B4SI73, A0A2B4RI05, A0A2B4RX94, A0A2J7ZFF2, A0A383W609, A0A383W2V6,
A0A2B4SNE8, A0A2B4RJP3, A0A2B4SBI8, A0A383VA02, A0A383VTL8, A0A383VEC8,
A0A2B4R7I8, A0A2B4RED5, A0A2B4R819, A0A383W0C6, A0A383VRV3, A0A383VVE2,
A0A2B4RAT8, A0A2B4RDB8, A0A2B4RM65, A0A383VV90, A0A383WH61, A0A383VIT8,
A0A2B4SMY1, A0A2B4RXN2, A0A2B4SDQ3, A0A383VX83, A0A383V476, A0A383WKH6,
A0A2B4S5V1, A0A1I1VVN6, A0A073ILQ0, A0A383VAP4, A0A383VSI6, Q236L9, Q2I2L4,
A0A196QUR2, A0A420DSB1, A0A061SV07, A0A3G5ANY0, T1L2L9, T1JTQ3, T1JZ41, T1JZ38,
A0A2T6CEN1, A0A221K513, A0A1J0WMJ3, T1KP84, T1L6E3, T1KXB8, T1KLX8, T1K1X0, T1KJV3,
A0A196P088, A0A345Q6D2, P06867, F1SPS6, F1SB93, T1JQK0, T1K882, T1KJA7, T1L2F0, T1JY66, T1KEM9,
F1RZN7, A0A286ZVK1, O97506, A0A286ZR66, F1SB81, T1L0H5, T1KY75, T1KVC5, T1KP75, T1L6B7, T1L4K2,
A0A1Q9ESG7, A0A1Q9CQI2, A0A1Q9C6C8, T1L0U8, T1K0C2, T1JY60, T1KXD7, T1K0A5, T1KP31,
A0A1Q9CCQ0, A0A1Q9EEK4, A0A1Q9D1E5, T1KNH0, T1L2M1, T1KVC7, T1K0C1, AA158P574,
A0A1Q9DKU8, A0A1Q9DRV2, A0A1Q9F029, T1L0H6, T1K0C0, T1K6H1, T1K0A4, T1L1K0, T1JXS1,
A0A1Q9ESU8, A0A1Q9EQ68, A0A1Q9D2R1, T1K414, A0A158P575, T1KVB7, T1K276, T1K0A1,
A0A1Q9E4J1, A0A1Q9CW84, A0A1Q9CMK9, T1KW32, T1L1J9, T1KP56, T1L4K1, T1KP60, T1K0A3,
A0A1Q9CF00, A0A1Q9C5U3, A0A1Q9E8L2, T1K411, T1L2E5, T1KVC8, T1K0A9, T1KF99, T1KP59,
A0A1Q9D4N5, A0A1Q9EKZ9, A0A1Q9C5H9, T1JXR7, T1JXS5, T1K0A7, T1K0E3, T1JV21, T1KP64,
A0A1Q9E9H4, A0A1Q9C600, A0A1Q9CGB9, T1K7E7, Q4RF08, H3CM48, Q4RX91, H3CWI4,
A0A1Q9BXP7, A0A1Q9CQY3, A0A1Q9CR00, H3DBA6, H3D0B7, Q4RF09, Q4SIS6, Q4SBT4, H3C6P0,
A0A1Q9CAA1, A0A1Q9EMW5, A0A1Q9DB15, H3DPE4, H3CV10, H3CWH8, A0A061RM82,
A0A1Q9CW09, A0A1Q9CR59, A0A1Q9ED26, A0A061QU17, A0A061SFA1, A0A061S0K3,
A0A1Q9ERZ2, A0A1Q9CQZ9, A0A1Q9CZK1, A0A061R340, A0A061S6B9, A0A061RKH4,
A0A1Q9DNS4, A0A1Q9F1U4, A0A1Q9CT81, A0A061SLP2, A0A061QSN4, A0A061S9I3,
A0A1Q9D3Z6, A0A1Q9CQ66, A0A1Q9CSN6, A0A061R7K6, A0A061QSD4, A0A061R2B1,
A0A1Q9ERZ8, A0A1Q9D1P7, A0A1Q9ES05, A0A061R0X8, A0A061QSK8, A0A061SA98,
A0A1Q9CUS2, A0A1Q9DZF4, A0A1Q9CAP7, A0A2P0VNG3, A0A2P0VNJ5, K0R003, K0T569,
A0A1Q9DAV4, A0A1Q9DVU6, A0A1Q9BZ14, K0R8M5, K0R4V6, K0TI40, K0S3W9, K0R053, K0RJ23,
A0A1Q9DA38, A0A1Q9EUE8, A0A1Q9DT95, K0R2N3, A0A0P1FYC3, A0A0P1FXN8, A0A369TVA4,
A0A1Q9EUA8, A0A1Q9DLH6, A0A1Q9D262, A0A369TQK7, A0A0D8D6E0, J4C7F0, A0A2T7I917,
A0A1Q9D697, A0A1Q9DPD5, A0A1Q9EBY1, A0A2T7IN49, A0A0N5D4A3, A0A0N5DAH6,
A0A1Q9D3F0, A0A1Q9CMG7, A0A1Q9EUA6, A0A0N5D0V9, A0A0N5CNH4, A0A0N5D8L1,
A0A1Q9F599, A0A1Z9KW32, A0A1Z9L6H2, A0A0N5CN06, A0A0N5D5Z9, A0A158RB75,
A0A2M7BBY6, A0A1V4Y3U4, A0A0N5AQ74, A0A158RB18, A0A158RCJ6, A0A0N5CL57,

A0A0N5CMM8, A0A0N5D941, A0A0N5CU49, A0A0B2VKX7, A0A0B2VCC1, A0A0B2VBP0,
A0A0N5CLL0, A0A0N5D6J3, A0A0N5CU48, A0A0B2VDF6, A0A0B2VTH8, A0A0B2VE70,
A0A0N5D3M6, A0A0N5D0H3, A0A0N5CU50, A0A183V0Y4, A0A183TW29, A0A3P7IEE1,
A0A0C2N594, A0A061FES3, A0A061F6M2, A0A0B2V8X8, A0A0B2V3M1, A0A183U4G9,
A0A061F6Q9, A0A061F858, A0A061F7U2, A0A061E4J3, A0A3P7EW77, A0A0B2VCY3, A0A0B2VUZ8,
A0A061F7S0, A0A061DSY4, A0A061F7R6, A0A0B2VRS5, A0A0B2VS27, A0A0B2V756,
A0A061F5X2, A0A061F5W4, A0A061DK79, A0A0B2V7G5, A0A0B2VLY9, A0A0B2V1Y2,
A0A061GFZ4, A0A061FE28, A0A061FDY8, A0A0B2UVF7, A0A0B2UUB7, A0A3P7F9F7,
A0A061GMY9, A0A061DT57, A0A061FE35, A0A0B2VJJ4, A0A183UFM8, A0A0B2UVS9,
A0A061F6S4, A0A061ESM6, A0A061F7P5, A0A0B2W5N5, A0A125YNB1, S8EWI3, A0A125YP11,
A0A061FE32, A0A061GN00, A0A061DJB7, S8EXK9, S8FBN1, S8GJR8, S8GTW7, S8GU33,
A0A061F829, A0A061FAS2, A0A061GJY1, A0A061GJ76, A0A125YN33, S8GE96, S8EWJ0, S8G8W7, S8EUX1,
A0A061E2S8, A0A061FXH6, A0A061FQL2, S8F2N4, S8EVK9, S8GIC9, S8FBK4, S8F0R5, S8EZX1,
A0A061GGE3, A0A061GSK0, A0A061F5V9, S7UGM9, S7UVS3, S7W921, S7VS18, S7ULA3,
A0A061GGC0, A0A061F6T1, A0A061FEW2, S7W1D2, A0A125YUY4, S7VZR7, S7V4Y3, S7VNS6,
A0A061GMZ5, A0A061FA86, A0A061E2J3, S7VUK4, S7UNU6, S7URJ3, S7WIY4, S7UL27, S7UID9,
A0A061GF26, A0A061F5X6, A0A061F6R7, A0A061FII3, S7UMV2, S7UFC4, A0A125YP10, S7V4X6,
A0A061GA93, A0A061GGC6, A0A061FBL4, A0A125YMJ2, B6KPA5, B9QJ65, V5BN10, B9PXJ3,
A0A061ETG0, A0A061F7N9, A0A061EAF9, A0A0F7UY76, A0A0F7V6F0, A0A0F7UZC2, V4ZN28,
A0A061GG11, A0A061F862, A0A061GF19, V5B2C7, B9QHA2, A0A125YYV2, V4ZE44, V4ZEU8,
A0A061F9V0, A0A061F5Y4, A0A061GS10, V4Z8E3, V4Z683, A0A0F7UY36, A0A0F7VB90,
A0A061F798, A0A061DLF5, A0A061GH37, A0A0F7V4E0, V4YRM6, B9QHI1, A0A0F7USH6,
A0A061FEJ0, A0A061F7L9, A0A061ERV1, A0A0F7UP20, A0A0F7UTL5, A0A0F7V2Y2,
A0A061GGD8, A0A061GFZ9, A0A061F6A9, A0A125YH93, V4ZAX9, V4ZEU3, V4ZQP4,
A0A061F7T9, A0A061F463, S1RWJ4, A0A061F7A3, A0A0F7V7R9, V4Z2B5, A0A0F7V2N5, V4ZSH6,
A0A061E4H9, A0A061F772, A0A061F7R1, A0A061F7T8, A0A139Y8B9, A0A139XR75, A0A139XT94,
A0A061E2S4, A0A061F771, A0A061FDW5, A0A139XR22, A0A139XUT5, A0A139XV46,
A0A061FE49, A0A061E2U3, A0A061F6S1, A0A061F7S7, A0A139Y523, A0A139XII1, A0A139XUW2,
A0A061E4H6, A0A061E3P7, A0A061F784, A0A139XRH6, A0A139XI69, A0A139XIG5,
A0A061F5W9, A0A061F6J2, A0A061FFC7, A0A139XQZ9, A0A139XIW7, A0A139XYI0,
A0A061E9M0, A0A061GG05, A0A061F6R3, A0A139XIH6, A0A139YAJ0, A0A139XI83,
A0A061GF31, A0A061EQQ6, A0A061E3Q5, A0A139XUB1, A0A139XIA3, A0A425HTR7,
A0A061FDY1, A0A061FGI5, A0A061GH52, A0A425HLG8, A0A3R8FZK1, A0A3R7YPK8,
A0A061G8B1, A0A061FE26, A0A061EZN1, A0A3R8BM20, A0A3R8AJM0, A0A425HTJ6,
A0A061ERB8, A0A061EAF4, A0A061E3Q2, A0A3R7Z551, A0A3R7ZDF1, A0A3R7ZER8,
A0A061GN44, A0A061ETH9, A0A061GGD2, A0A3R8GAD6, A0A425HLE6, A0A425HRD9,
A0A061FC33, A0A061GBN6, A0A177E7S8, A0A425HTP5, A0A425HNT2, A0A425II A5,
A0A0S3QUQ3, A0A179D652, G2QZQ3, A0A3S4ATD0, A0A425HTB8, A0A425HNI2, A0A3R8AFY2,
F9UF48, A0A1H2T5K1, A0A074JZA8, I3YA25, L0H1B6, A0A2G8XSQ7, A0A2G8XUD9, A0A2G8Y8M6,
G2DZW1, A0A1H6F9F4, A0A0A7CLS4, A0A0A7CM27, A0A2G8XUK9, A0A2G8XV07, A0A2G8XU33,
A0A0A7CMA6, A0A1V9ZCI3, A0A0A7CLY0, A0A2G8XVA9, A0A2G8XLM8, A0A2G8XM15,
A0A1V9Y7R8, A0A1V9ZQ59, A0A1V9ZX23, A0A2G8Y7C4, A0A2G8XYW5, A0A2G8XU35,
A0A0A7CM73, A0A1V9ZWR3, A0A0A7CLP3, A0A2G8YB46, A0A2G8XVB5, A0A2G8XLP9,
A0A1V9ZWD5, A0A1W0A8G8, A0A1V9Z6L2, A0A2G8XM02, A0A2G8XWV2, A0A086KZL5,
A0A0A7CMR6, A0A1W0A9L7, A0A1V9Y3Z2, A0A086L8S1, A0A086KXX3, A0A086JKK2,
A0A0A7CMJ9, A0A0A7CLZ4, A0A0A7CLK9, A0A086LDQ0, A0A086JHJ8, A0A086K039,
A0A1V9Y7V8, A0A0A7CLD0, A0A0A7CM37, A0A086K045, A0A086JSN5, A0A086LF74,
A0A1V9YW96, A0A0A7CMD3, A0A1V9ZV18, A0A086KUA3, A0A086LGR4, A0A086KUA2,
A0A1V9ZQU5, A0A1W0A6N9, A0A0A7CM15, A0A086LC13, A0A086KT20, A0A086KZ32,
A0A1V9ZX55, A0A1V9YS19, A0A1W0A3D9, A0A086KBL4, A0A086KJB6, A0A086KPR8,
A0A1W0A1E0, A0A0A7CLV9, A0A1V9YHU4, A0A086JRW4, A0A086JAN6, A0A086JTG7,
A0A1V9Y7T4, A0A1V9YS21, A0A1W0A6T9, A0A086JAS2, A0A086JRJ6, A0A086KBL3,
A0A1W0A2R4, A0A1V9ZRW9, A0A0A7CMA3, A0A086KAV4, A0A086J9Y0, A0A086K6N1,
A0A0A7CM84, A0A0A7CM21, A0A0A7CM83, A0A086JBU3, A0A086KWD4, A0A086JSD4,
A0A177U9L0, A0A177VNW5, A0A066V6E8, A0A086KNW2, A0A086JH56, A0A086QPX5,
A0A099ZKM4, A0A099YWG8, A0A099ZHV8, A0A086QPX6, A0A086QS28, A0A086QR16,
A0A099ZGB5, R8BMT1, R8BT17, A0A2S4KXQ7, A0A086QSB4, A0A086QZQ0, A0A086QXJ7,
A0A2S4KU31, A0A0A1T7V7, A0A183V6M5, A0A086PMI4, A0A086PJV3, A0A086QPJ5,
A0A183UMU0, A0A183V0Y5, A0A183VH40, A0A086Q7X9, A0A086QSK0, A0A086QDJ1,
A0A183URQ0, A0A183UCS5, A0A183UGS8, A0A086Q5C2, A0A086PJS5, A0A086PJV4, A0A086PP13,
A0A183VGT9, A0A183UGB4, A0A183UJW2, A0A086JYT0, A0A086JYV7, A0A086KQT7,
A0A183VFR8, A0A183V6I3, A0A183V8F0, A0A086JUX0, A0A086JEK0, A0A086K9B0,
A0A183UKJ7, A0A183UZI3, A0A183UCS4, A0A086J6M2, A0A086L3H4, A0A086JYV2,
A0A183TZ03, A0A183UXD4, A0A183UPE8, A0A086J6A5, A0A086JAT8, A0A086JW34,
A0A183VHD0, A0A183V3X8, A0A183UN76, A0A086KKD3, A0A086J6E7, A0A086KW68,
A0A183V0R7, A0A183UZ80, A0A0B2V222, A0A086JUW9, A0A086JYW7, A0A086LN03,
A0A0B2W1F4, A0A0B2VYQ4, A0A0B2VKQ9, A0A086LVF2, A0A086LIM6, A0A086LJ27,

A0A086LIY4, A0A086LWU1, A0A086MAA6, A0A139WEU2, A0A139WF13, A0A2Y9D6R9,
A0A086LX43, A0A086LX44, A0A086LTJ4, A0A2Y9RN69, A0A2Y9D6V5, A0A2Y9DUI6,
A0A086M0U2, A0A086M4H2, A0A086LIS3, A0A2Y9REY6, A0A2Y9DUP3, A0A2Y9RJN7,
A0A086M306, A0A086LUX9, A0A086LV63, A0A2Y9QP02, A0A2Y9D6R6, A0A2Y9R8V0,
A0A086M612, A0A086M0U7, A0A086LJF7, A0A0V1CBM7, A0A0V1CL20, A0A0V1CF23,
A0A086LJF6, A0A2T6IZJ0, A0A2T6II53, A0A2T6IQ36, A0A0V1D321, A0A0V1DE70, A0A0V1CNZ7,
A0A2T6IQ28, A0A2T6IUI9, A0A2T6IIA3, A0A2T6II49, A0A0V1DDL1, A0A0V1CYA0, A0A0V1D3X8,
A0A2T6ID59, A0A2T6II52, A0A2T6IRS2, A0A2T6J4Y3, A0A0V1D312, A0A0V1D2Z4, A0A0V1DGI6,
A0A2T6IDB2, A0A2T6ISI1, A0A2T6J2S6, A0A2T6IS88, A0A0V1DIR9, A0A0V1DGQ0, A0A0V1D9K9,
A0A2T6IQD1, A0A151GZ57, A0A151HHT1, A0A0V1DCG4, A0A0V1D9Q7, A0A0V1CAI1,
A0A151HQ98, A0A151GZ62, A0A151HIC2, A0A0V1CF35, A0A0V1DGL4, A0A0VCBT7,
A0A151HH74, A0A151HFL2, A0A151H2M3, A0A0V1CQV4, A0A0V1CL47, A0A0V1D4Y2,
A0A151H4P4, A0A151HDF6, A0A151GYR0, A0A0V1CL07, A0A0V1CJ57, A0A0V1CQS1,
A0A151HIU0, A0A151HH38, A0A151HIP1, A0A0V1CPE6, A0A0V1D2G1, A0A0V1DCQ6,
A0A151HGR3, A0A151HL78, A0A151HGN6, A0A0V1CGZ2, A0A0V1CKH2, A0A0V1C8F4,
A0A086PTH3, A0A086PPL1, A0A086PIW8, A0A0V1D5M4, A0A0V1D5G8, A0A0V1CY65,
A0A086PGB6, A0A086QHG9, A0A086PYL8, A0A0V1CIY6, A0A0V1CS09, A0A0V1DDG4,
A0A086PIX2, A0A086PGB7, A0A086PG37, A0A0V1D628, A0A0V1CL51, A0A0V1D3L4,
A0A086PFY3, A0A086PSX1, A0A086PFS3, A0A0V1D9P6, A0A0V1CF47, A0A0V1CEP1,
A0A086Q6Y4, A0A086PYK3, A0A086PZC2, A0A0V1CR67, A0A0V1D2S7, A0A0V1CCF9,
A0A086PIX4, A0A086Q258, A0A086PSX2, A0A0V1CI86, A0A0V1D4Z1, A0A0V1D8K4,
A0A086PYV6, A0A086QF78, Q1JSE8, D8L561, D8L553, A0A0V1CY85, A0A0V1CIZ3, A0A0V1CLE7,
D8L555, D8L551, D8L554, D8L556, D8L552, D8L559, A0A0V1D8Y2, A0A0V1CIU3, A0A0V1CLV0,
Q1JSK6, D8L558, D8L550, Q9XZH7, D8L557, W8VX31, A0A0V1D4H1, A0A0V1D4T5, A0A0VCLT4,
A0A195E6P4, A0A195DN17, A0A195DN14, A0A0V1CC34, A0A0V1CQM7, A0A0V1CIG0,
A0A151JQX2, A0A151J1A2, A0A195DID1, A0A151J003, A0A0V1C615, A0A0V1CYG1, A0A0V1CL59,
A0A151J024, A0A195F9C1, A0A195FXK7, A0A0V1D176, A0A0V1CLC2, A0A0V1DDF7,
A0A195FSC2, A0A195F1L6, A0A195EZ81, A0A195FP32, A0A0V1CJ14, A0A0V0U668, A0A0V0TU85,
A0A151WZ08, A0A151X5L2, A0A151XCA5, A0A0V0U6A2, A0A0V0UGN9, A0A0V0T888,
A0A151WZC1, A0A151WMX4, A0A151WFX6, A0A0V0T7J2, A0A0V0TGR2, A0A0V0TE11,
A0A438AHQ8, A0A2P5EEL5, A0A2P5E9P3, A0A0V0TLQ5, A0A0V0TLA0, A0A0V0UAM2,
A0A2P5E9P1, A0A2P5D0W9, A0A2P5D0Z2, A0A0V0UI40, A0A0V0TLP7, A0A0V0TBB8,
A0A2P5D0Y8, A0A2P5F2U6, A0A2P5F1R2, A0A0V0U7B1, A0A0V0TSM0, A0A0V0TU80,
A0A2P5EHK8, A0A2P5D0X0, A0A2P5F9V6, A0A0V0UAP6, A0A0V0TWW5, A0A0V0UI96,
A0A2P5FFA8, A0A2P5BR45, A0A2P5E9N6, A0A0V0T000, A0A0V0TLE6, A0A0V0U6B0,
A0A2P5BDV9, A0A2P5E9S9, A0A2P5E300, A0A0V0UIZ5, A0A0V0TKS4, A0A0V0U6A5,
A0A2P5BB99, A0A2P5D0W8, A0A2P5AU86, A0A0V0TUK2, A0A0V0U664, A0A0V0TGD8,
A0A2P5ELI9, A0A2P5BDW2, A0A2P5BXZ5, A0A0V0U6L1, A0A0V0TW68, A0A0V0TZG6,
A0A2P5CM83, A0A2P5BDX9, A0A2P5EJU3, A0A0V0TZB3, A0A0V0U3H5, A0A0V0TR48,
A0A2P5E5Q8, A0A2P5EJY0, A0A2P5E9N1, A0A0V0UAV4, A0A0V0TSU0, A0A0V0U6J8,
A0A2P5E7C6, A0A2P5DNM0, A0A2P5D1I1, A0A0V0TQX3, A0A0V0TCV2, A0A0V0T869,
A0A2P5CM53, A0A2P5EJU9, A0A2P5EGL2, A0A0V0T5X4, A0A0V0T304, A0A0V0UOF0,
A0A2P5D0X3, A0A2P5DNJ7, A0A2P5E9Q9, A0A0V0T3U0, A0A0V0TSV2, A0A0V0T8Y2,
A0A2P5BR70, A0A2P5E7F0, A0A2P5EM89, A0A0V0TLJ2, A0A0V0TTX4, A0A0V0THH3,
A0A2P5CM78, A0A2P5E7F7, A0A2P5EM81, A0A0V0TCQ5, A0A0V0UGL3, A0A0V0T7W1,
A0A2P5EM56, A0A2P5E7E7, A0A2P5E7E4, A0A0V0TGF1, A0A0V0TT12, A0A0V0TV07,
A0A2P5BDZ8, A0A2P5D0Y7, A0A2P5E7F8, A0A0V0UJZ1, A0A0V0T591, A0A0V0TFQ9,
A0A2P5D0W7, A0A2P5AU55, A0A2P5E7E0, A0A0V0TW29, A0A0V0U516, A0A0V0TPM2,
A0A2P5E9N7, A0A2P5EGQ1, A0A2P5E7C3, A0A0V1KNK0, A0A0V1KLF7, A0A0V1KYR3,
A0A2P5AVW6, A0A2P5E7E1, A0A2P5D0X7, A0A0V1KYC8, A0A0V1LNJ6, A0A0V1LAI7,
A0A2P5E7E9, A0A2P5CM65, A0A2P5D0Y2, A0A0V1KPV0, A0A0V1KPB9, A0A0V1KKU9,
A0A2P5E9K7, A0A2P5EK01, A0A2P5E796, A0A0V1L1F4, A0A1Y3EXK1, A0A0V1LJJ4,
A0A2P5CM46, A0A2P5AU80, A0A2P5DKI1, A0A0V1LAS4, A0A0V1KMH3, A0A1Y3E8Z7,
A0A2P5EEU6, A0A2P5AW26, A0A2P5E7I1, A0A1Y3E6K9, A0A1Y3EHJ6, A0A0V1LIU2,
A0A2P5AU99, A0A2P5E7K1, A0A2P5E9P7, A0A1Y3E6I2, A0A1Y3EHG2, A0A1Y3EE55,
A0A2P5EMF7, A0A2P5CM64, A0A2P5E7F2, A0A0V1KPJ6, A0A0V1L0L9, A0A0V1LEN4,
A0A2P5DUH7, A0A2P5EGL5, A0A2P5EJX1, A0A0V1LMK8, A0A1Y3EMP1, A0A0V1KMD9,
A0A2P5E329, A0A2P5E7G0, A0A2P5EMG7, A0A1Y3E8I5, A0A0V1L1M0, A0A1Y3E9F8,
A0A2P5E305, A0A2P5ARA6, A0A2P5C4S2, A0A0V1LIH7, A0A0V1L1N0, A0A1Y3EK45,
A0A2P5EJT3, A0A2P5D0X8, A0A2P5E322, A0A0V1L5K7, A0A0V1LAY9, A0A0V1L1G4,
A0A2P5EM74, A0A2P5BDW0, A0A2P5B3V3, A0A1Y3E3J3, A0A0V1KM43, A0A0V1LBC3,
A0A2P5BCJ5, A0A2P5EJU7, A0A2P5BCJ8, A0A1Y3E9Q0, A0A0V1KYR0, A0A0V1L1E8,
A0A2P5B9F2, A0A2P5E7C7, A0A2P5E9R8, A0A0V1KP52, A0A0V1L0I9, A0A0V1LEV0,
A0A2P5EGP2, A0A2P5B3Y1, A0A2P5FB9, A0A0V1LAP5, A0A0V1L1M7, A0A0V1LE33,
A0A2P5EJU0, A0A2P5E9R2, A0A2P5EGN4, A0A1Y3EH27, A0A1Y3E603, A0A0V1LJH2,
A0A161M4M9, A0A023EZN7, A0A023F552, D6X332, A0A0V1LMI4, A0A0V1KYB0, A0A1Y3ET15,
D6WSE9, D2A5T8, D6WCQ0, D6WEC2, A0A139WM22, A0A0V1L1E6, A0A0V1KR57, A0A0V1L136,

| | | | | | |
|---|---|---|---|---|---|
| A0A0V1LT84, | A0A0V1KLJ0, | A0A1Y3EP57, | A0A0V0ZMW0, | A0A0V0ZPP6, | A0A0V0ZJ05, |
| A0A1Y3EUE7, | A0A0V1KXX6, | A0A1Y3EF82, | A0A0V1A350, | A0A0V0Z9K2, | A0A0V0ZQB1, |
| A0A1Y3EZI1, | A0A0V1KXY2, | A0A1Y3E7T0, | A0A0V1A5H0, | A0A0V0ZQQ6, | A0A0V1A5B9, |
| A0A0V1KPL5, | A0A1Y3E8Z4, | A0A0V1KX10, | A0A0V0ZCY3, | A0A0V1ACU1, | A0A0V0ZID7, |
| A0A0V1LFN7, | A0A1Y3ENN2, | A0A1Y3EJ87, | A0A0V0ZJE6, | A0A0V0ZA86, | A0A0V1AEG0, |
| A0A1Y3F0N2, | A0A1Y3EDK3, | A0A1Y3E9V6, | A0A0V0ZHM8, | A0A0V0ZU82, | A0A0V0ZXE1, |
| A0A0V1KPY5, | A0A1Y3EJ46, | A0A0V1LE29, | A0A0V1A735, | A0A0V0ZBC9, | A0A0V1A2Y6, |
| A0A0V1LED3, | A0A0V1LLN6, | A0A1Y3EUS4, | A0A0V1ADC4, | A0A0V1A315, | A0A0V0ZG93, |
| A0A0V1L2N9, | A0A0V1L3H8, | A0A0V1KR45, | A0A0V0ZG08, | A0A0V0ZBZ0, | A0A0V0ZC36, |
| A0A0V1LAL0, | A0A0V1KS99, | A0A1Y3EGT9, | A0A0V0ZBF0, | A0A0V1A3P0, | A0A0V0ZBK7, |
| A0A0V1LCN5, | A0A1Y3ETI7, | A0A1Y3EAN3, | A0A0V1ACP2, | A0A0V0ZUN7, | A0A0V1ACR5, |
| A0A1Y3EH07, | A0A0V1LU40, | A0A1Y3E7K6, | A0A0V1A6I5, | A0A0V0ZRK6, | A0A0V0ZDM2, |
| A0A0V1KSI2, | A0A0V1LES1, | A0A1Y3E7U1, | A0A0V0ZC11, | A0A0V0ZSY6, | A0A0V0ZAI4, |
| A0A1Y3E9F9, | A0A0V1LB56, | A0A0V1LNE5, | A0A0V1AGP3, | A0A0V0ZK36, | A0A0V1ABN4, |
| A0A0V1L7E6, | A0A0V1L6Z9, | A0A0V0RYN5, | A0A0V0ZK58, | A0A0V0Z425, | A0A0V1K9D8, |
| A0A0V0SCW7, | A0A0V0RIU1, | A0A0V0RN79, | A0A0V1JL75, | A0A0V1KA64, | A0A0V1IA74, |
| A0A0V0SH81, | A0A0V0SCZ0, | A0A0V0RV95, | A0A0V1ECJ0, | A0A0V1ERM8, | A0A0V1EJT7, |
| A0A0V0S538, | A0A0V0RM32, | A0A0V0SCM0, | A0A0V1E276, | A0A0V1K9L3, | A0A0V1IPI2, |
| A0A0V0RFG5, | A0A0V0RRH9, | A0A0V0RRB5, | A0A0V1IKD9, | A0A0V1IKA3, | A0A0V1IPX2, |
| A0A0V0RG56, | A0A0V0S806, | A0A0V0RZJ1, | A0A0V1KD92, | A0A0V1JZQ7, | A0A0V0YKR7, |
| A0A0V0RDH2, | A0A0V0RGM5, | A0A0V0SNF7, | A0A0V1JCJ6, | A0A0V1JE87, | A0A0V1J8T7, | A0A0V1JS72, |
| A0A0V0S2V9, | A0A0V0RYH3, | A0A0V0RGW1, | A0A0V1IJ16, | A0A0V0YL79, | A0A0V1K592, |
| A0A0V0SCX3, | A0A0V0REU3, | A0A0V0RZP8, | A0A0V1IE69, | A0A0V1K9L2, | A0A0V0XEJ1, |
| A0A0V0RT14, | A0A0V0S6I1, | A0A0V0RJS2, | A0A0V1JC56, | A0A0V1I359, | A0A0V1K7S5, |
| A0A0V0SEE5, | A0A0V0RZB8, | A0A0V0RK34, | A0A0V1IQ50, | A0A0V1J492, | A0A0V0YE74, |
| A0A0V0S5T4, | A0A0V0RZM6, | A0A0V0SMX2, | A0A0V0Y8V0, | A0A0V1EVN0, | A0A0V1K9K9, |
| A0A0V0RX40, | A0A0V0S9B4, | A0A0V0RFF5, | A0A0V1KD78, | A0A0V1G4T5, | A0A0V1IAL1, |
| A0A0V0RYQ4, | A0A0V0S5G1, | A0A0V0REL5, | A0A0V1FH81, | A0A0V1IDD8, | A0A0V1JC58, |
| A0A0V0RSM5, | A0A0V0RYQ1, | A0A0V0SCP1, | A0A0V1J0K8, | A0A0V0Y705, | A0A0V1EVL8, |
| A0A0V0SCK5, | A0A0V0RF35, | A0A0V0RFT3, | A0A0V1K9B4, | A0A0V0XNP3, | A0A0V1FRY9, |
| A0A0V0RPN2, | A0A0V0RQB5, | A0A0V0RHM2, | A0A0V1IAQ7, | A0A0V0XX86, | A0A0V1IQJ7, |
| A0A0V0RZD1, | A0A0V0REM5, | A0A0V0S4Z2, | A0A0V1JE40, | A0A0V1FHE6, | A0A0V1K4X2, |
| A0A0V0RZT2, | A0A0V0RS35, | A0A0V0S652, | A0A0V1H366, | A0A0V1FQ76, | A0A0V1EVA7, |
| A0A0V0RG20, | A0A0V0RM92, | A0A0V0S584, | A0A0V0XW16, | A0A0V1K5I2, | A0A0V1EUZ6, |
| A0A0V0S4X7, | A0A0V0RDD2, | A0A0V0S541, | A0A0V0YGT7, | A0A0V1IAS5, | A0A0V1E2U6, |
| A0A0V0REJ1, | A0A0V0S0D1, | A0A0V0RK03, | A0A0V1E1V7, | A0A0V1G2W2, | A0A0V1JI52, |
| A0A0V0S3G7, | A0A0V0RX96, | A0A0V0RHC1, | A0A0V1G298, | A0A0V1EV41, | A0A0V1EMN5, |
| A0A0V0RSZ9, | A0A0V0RIE7, | A0A0V0S9G5, | A0A0V1JHF0, | A0A0V1KDC2, | A0A0V1K5A6, |
| A0A0V0RTR4, | A0A0V0RIE5, | A0A0V0RYP8, | A0A0V1JJD4, | A0A0V1K9V2, | A0A0V1FLB8, |
| A0A0V0RSK8, | A0A0V0RFI6, | A0A0V0S2H6, | A0A0V0XY64, | A0A0V1FYN9, | A0A0V1J0M9, |
| A0A0V0S5G8, | A0A0V0S0F9, | A0A0V0S5R1, | A0A0V1J4L5, | A0A0V0YMV1, | A0A0V1FQM2, |
| A0A0V1MVW8, | A0A0V1MAI7, | A0A0V1MYP5, | A0A0V1GQ57, | A0A0V1KEH4, | A0A0V0YGT1, |
| A0A0V1N2V7, | A0A0V1MUG7, | A0A0V1MUG4, | A0A0V0XY09, | A0A0V1EUS6, | A0A0V1K589, |
| A0A0V1MYQ2, | A0A0V1MGC0, | A0A0V1N6W8, | A0A0V1XTS1, | A0A0V1ETL0, | A0A0V1FFS0, |
| A0A0V1N6W7, | A0A0V1MF20, | A0A0V1MNC5, | A0A0V1JL92, | A0A0V1ED64, | A0A0V1ETL9, |
| A0A0V1MJU5, | A0A0V1MYR0, | A0A0V1MZ66, | A0A0V1EV55, | A0A0V1J0J8, | A0A0V1G235, |
| A0A0V1MAV6, | A0A0V1MYQ0, | A0A0V1N2Z9, | A0A0V1KDB0, | A0A0V1K3Q7, | A0A0V1EEX1, |
| A0A0V1MH28, | A0A0V1MVV2, | A0A0V1N167, | A0A0V0XTR8, | A0A0V1FEX1, | A0A0V0Y6W9, |
| A0A0V1MYJ7, | A0A0V1MT15, | A0A0V1MH70, | A0A0V0XKW1, | A0A0V0XKX5, | A0A0V1K9J3, |
| A0A0V1M2G6, | A0A0V1MUW3, | A0A0V1M9J0, | A0A0V0XKY0, | A0A0V1EMK3, | A0A0V1FRL6, |
| A0A0V1MHZ6, | A0A0V1MTF5, | A0A0V1MGN0, | A0A0V1F4T6, | A0A0V1KDD7, | A0A0V1FBJ2, |
| A0A0V1MZ68, | A0A0V1N6Q2, | A0A0V1MGD7, | A0A0V1K421, | A0A0V1FBW8, | A0A0V1EVA1, |
| A0A0V1MIW0, | A0A0V1N5S4, | A0A0V1MYM3, | A0A0V0XU04, | A0A0V1IRZ9, | A0A0V1EV45, |
| A0A0V1MI03, | A0A0V1MYL8, | A0A0V1MSA4, | A0A0V0XNW4, | A0A0V1EVN2, | A0A0V0YMZ8, |
| A0A0V1MZA7, | A0A0V1MZ29, | A0A0V1MUK2, | A0A0V0XJ62, | A0A0V0YFK6, | A0A0V1JPJ3, |
| A0A0V1MZ89, | A0A0V1MUM5, | A0A0V1MIL5, | A0A0V1J0J3, | A0A0V0Y715, | A0A0V1FMV7, |
| A0A0V1MZ88, | A0A0V1MTC8, | A0A0V1M8W6, | A0A0V1JCP9, | A0A0V1E9M7, | A0A0V1KDC1, |
| A0A0V1M0N9, | A0A0V1N9C6, | A0A0V1MN65, | A0A0V1FEU7, | A0A0V1K0T0, | A0A0V1DST8, |
| A0A0V1MNB1, | A0A0V1MWG2, | A0A0V1N8S1, | A0A0V1IHH3, | A0A0V1J0I8, | A0A0V1G0P4, |
| A0A0V1MYJ6, | A0A0V1N750, | A0A0V1MH06, | A0A0V0XL17, | A0A0V1ESY5, | A0A0V1K9H0, |
| A0A0V1MYI7, | A0A0V1MYQ1, | A0A0V0ZT98, | A0A0V0XUM5, | A0A0V1EVN4, | A0A0V1EU35, |
| A0A0V1AAJ2, | A0A0V0ZDL2, | A0A0V1AFC5, | A0A0V1DXH2, | A0A0V1JCS1, | A0A0V0XNL7, |
| A0A0V0ZMA2, | A0A0V0ZI13, | A0A0V1ADL5, | A0A0V1E5G0, | A0A0V1G1X6, | A0A0V1EWX6, |
| A0A0V0ZA63, | A0A0V0ZJI5, | A0A0V1AGR2, | A0A0V1K6H8, | A0A0V1FAF9, | A0A0V0YNX4, |
| A0A0V0ZEN6, | A0A0V0ZJY6, | A0A0V0ZI71, | A0A0V1K3Q0, | A0A0V1JE80, | A0A0V1HB36, |
| A0A0V0ZJV3, | A0A0V1A9E4, | A0A0V0ZKA1, | A0A0V1IYZ4, | A0A0V1KEG0, | A0A0V0XUB1, |
| A0A0V1A5G3, | A0A0V1AH40, | A0A0V0Z9W9, | A0A0V0YN83, | A0A0V1IIS1, | A0A0V1K9N4, |

A0A0V1EV51, A0A0V1K5S7, A0A0V0XS62, A0A0V1P5T0, A0A0V1P8Q0, A0A0V1NE86,
A0A0V1IVQ1, A0A0V1FQU3, A0A0V1K9E0, A0A0V1P280, A0A0V1NS27, A0A0V1P770,
A0A0V1JPK7, A0A0V1ETF5, A0A0V1FAR0, A0A0V1PI77, A0A0V1P7C0, A0A0V1PFJ0,
A0A0V1ENV6, A0A0V1FMQ4, A0A0V1JPN2, A0A0V1P721, A0A0V1NYC7, A0A0V1P6T8,
A0A0V1J380, A0A0V0XJI2, A0A0V1KDE3, A0A0V1NLN2, A0A0V1NLK1, A0A0V1PAZ0,
A0A0V1DXF5, A0A0V0YE73, A0A0V1F7L0, A0A0V1P2H3, A0A0V1NXE2, A0A0V1P6D6,
A0A0V1JEB3, A0A0V1F5X2, A0A0V0YMM2, A0A0V1NVS2, A0A0V1NVB0, A0A0V1P6Q0,
A0A0V1FBB6, A0A0V1ESS6, A0A0V1G0K7, A0A0V1PF39, A0A0V1PEY2, A0A0V1P7H3,
A0A0V1EVU6, A0A0V1JBG7, A0A0V1G4S3, A0A0V1P9E1, A0A0V1NX80, A0A0V1NTT6,
A0A0V0YMZ0, A0A0V1KDD9, A0A0V1IVW1, A0A0V1NYS7, A0A0V1P6M8, A0A0V1NGF7,
A0A0V0YGE0, A0A0V1JZL9, A0A0V0XXD7, A0A0V1P4Z0, A0A0V0VJK1, A0A0V0VR93,
A0A0V0XEA7, A0A0V1JE69, A0A0V1J0L5, A0A0V0UTV5, A0A0V0UQR6, A0A0V0UM00,
A0A0V0XFS5, A0A0V1K9R0, A0A0V1G5W1, A0A0V0V174, A0A0V0V426, A0A0V0UTZ7,
A0A0V1JCL5, A0A0V0XUK2, A0A0V1DX07, A0A0V0VRE1, A0A0V0VRI1, A0A0V0UNQ3,
A0A0V0XZB1, A0A0V1IZ01, A0A0V1ET77, A0A0V0VRC8, A0A0V0VE39, A0A0V0VFJ5,
A0A0V1F060, A0A0V1JEA8, A0A0V1FY33, A0A0V0UQ81, A0A0V0VFQ4, A0A0V0VFH2,
A0A0V1FQA4, A0A0V1JHS7, A0A0V1ED73, A0A0V0VPC7, A0A0V0UUY9, A0A0V0VRE0,
A0A0V1K5M6, A0A0V0Y1Z1, A0A0V1JCM7, A0A0V0VP79, A0A0V0V552, A0A0V0VFW1,
A0A0V1IHF8, A0A0V1J0Q3, A0A0V1IVX3, A0A0V0VS73, A0A0V0VWE9, A0A0V0V155,
A0A0V1ETT3, A0A0V1EU49, A0A0V1E0G2, A0A0V0VCB7, A0A0V0VMC3, A0A0V0V7D6,
A0A0V1KD83, A0A0V1FAL4, A0A0V1ET37, A0A0V0UPR0, A0A0V0UUV8, A0A0V0V210,
A0A0V0XNN7, A0A0V1K5K3, A0A0V0XRQ1, A0A0V0VE27, A0A0V0VRQ3, A0A0V0VEC8,
A0A0V1EKP8, A0A0V1G1T4, A0A0V1JJ61, A0A0V0UQH4, A0A0V0VFX1, A0A0V0VSL6,
A0A0V1IHH9, A0A0V1EVH0, A0A0V1ETP5, A0A0V0VRE9, A0A0V0V6V2, A0A0V0VP70,
A0A0V0XUH1, A0A0V0XLI9, A0A0V1J0K0, A0A0V0VSK7, A0A0V0UUX7, A0A0V0VED2,
A0A0V1IYY2, A0A0V1JPL8, A0A0V0XNN5, A0A0V0VFN7, A0A0V0V499, A0A0V0V3J5,
A0A0V0Y6W4, A0A0V1G0P5, A0A0V0WI90, A0A0V0V587, A0A0V0VW86, A0A0V0VQ95,
A0A0V0WS36, A0A0V0X5U7, A0A0V0WZP8, A0A0V0VCJ2, A0A0V0VSS5, A0A0V0UJV4,
A0A0V0WF21, A0A0V0WMF7, A0A0V0WJN0, A0A0V0UPU4, A0A0V0VGC0, A0A0V0U3P2,
A0A0V0X647, A0A0V0WMC0, A0A0V0X8U0, A0A0V0VE47, A0A0V0UTV0, A0A0V0UMK8,
A0A0V0WGF2, A0A0V0WGK4, A0A0V0WEM4, A0A0V0T3U1, A0A0V0VPC1, A0A0V0V159,
A0A0V0X8Q3, A0A0V0WH09, A0A0V0WML0, A0A0V0VRW7, A0A0V0VTE1, A0A0V0VJ88,
A0A0V0X6B4, A0A0V0WZT2, A0A0V0WS86, A0A0V0UVL3, A0A0V0UUP5, A0A0V0VE17,
A0A0V0X7G3, A0A0V0WYZ7, A0A0V0W8L3, A0A0V0V119, A0A0V0UNR0, A0A0V0VFK5,
A0A0V0W0I6, A0A0V0WGI7, A0A0V0WYQ7, A0A0V0VLU4, A0A0V0VDL9, A0A0V0VW85,
A0A0V0WX01, A0A0V0WF38, A0A0V0W1G0, A0A0V0VRG0, A0A0V0UQQ3, A0A0V0VEJ2,
A0A0V0W776, A0A0V0WXK0, A0A0V0WA24, A0A0V0VDY8, A0A0V1BV44, A0A0V1ASI9,
A0A0V0X335, A0A0V0WS82, A0A0V0W1K5, A0A0V1AWR7, A0A0V1C327, A0A0V1ARX7,
A0A0V0W1Z3, A0A0V0W1S4, A0A0V0WAI4, A0A0V1ASM2, A0A0V1BM31, A0A0V1ASM0,
A0A0V0WHC9, A0A0V0V0P6, A0A0V0WHA1, A0A0V1BY88, A0A0V1BSS1, A0A0V1BU64,
A0A0V0WM77, A0A0V0WJ02, A0A0V0X0M5, A0A0V1BYB4, A0A0V1B1M0, A0A0V1BFH0,
A0A0V0X5Y4, A0A0V0WF91, A0A0V0X004, A0A0V1BTA4, A0A0V1BU83, A0A0V1BYZ5,
A0A0V0X092, A0A0V0WZR3, A0A0V0X0N1, A0A0V1BYW3, A0A0V1ASI6, A0A0V1B1C8,
A0A0V0X081, A0A0V0WDP4, A0A0V0WD03, A0A0V1BUM6, A0A0V1BY31, A0A0V1AWB4,
A0A0V0WHG0, A0A0V0W0M1, A0A0V0ULH6, A0A0V1AUR8, A0A0V1BTZ8, A0A0V1AZ75,
A0A0V0WX65, A0A0V0WJM1, A0A0V0V1L2, A0A0V1BF39, A0A0V0Z9Z1, A0A0V1B1K9,
A0A0V0WKK3, A0A0V0WJS6, A0A0V0WIF0, A0A0V1BF98, A0A0V1AUN2, A0A0V1BG87,
A0A0V0WET2, A0A0V0W1R2, A0A0V0WK58, A0A0V1AQK3, A0A0V1BXK5, A0A0V1BGU0,
A0A0V0W771, A0A0V0WAQ3, A0A0V0WJZ4, A0A0V1BV17, A0A0V1BY17, A1DYF2, A0A0V1C087,
A0A0V0V151, A0A0V0WWY8, A0A0V0VUH1, A0A0V1AW82, A0A0V1ARD6, A0A0V1BYW4,
A0A0V0X4G5, A0A0V0WXW5, A0A0V0WHJ7, A0A0V1AQ90, A0A0V1ARB8, A0A0V1BHN0,
A0A0V0WJM5, A0A0V0WF23, A0A0V0UYA2, A0A0V1AQK5, A0A0V1BSR9, A0A0V1AV98, E5S9D6,
A0A0V0W7A7, A0A0V0VH07, A0A0V0W798, A0A0V1ASN4, A0A0V1BZS3, A0A0V1BYF9,
A0A0V0WXH6, A0A0V0W6U1, A0A0V0X369, A0A0V1BY68, A0A0V1AWE1, A0A0V1C324,
A0A0V0W1Y2, A0A0V0W1I5, A0A0V0WJZ8, A0A0V1BV78, A0A0V1BIN6, A0A0V1BV40,
A0A0V0W0F4, A0A0V0W1K6, A0A0V0VYK2, A0A0V1BZG3, A0A0V1AT94, A0A0V1AZ10,
A0A0V0WAX9, A0A0V0X4A4, A0A0V0WY03, A0A0V1AUX5, A0A0V1AU60, A0A0V1AQI4,
A0A0V0WHZ9, A0A0V0W4Y7, A0A0V0WM81, A0A0V1BG93, A0A0V1BGM2, A0A0V1BT93,
A0A0V1P5U0, A0A0V1NES3, A0A0V1P2I1, A0A0V1BYD9, A0A0V1C2F3, A0A0V1ALY2,
A0A0V1PI68, A0A0V1P853, A0A0V1NF35, A0A0V1BY24, A0A0V1BY86, A0A0V1BUE7, E5SVP5,
A0A0V1PCG3, A0A0V1NXA6, A0A0V1NL85, A0A0V1ARU4, A0A0V1BMR3, A0A0V1ARE7,
A0A0V1NGD5, A0A0V1PF26, A0A0V1PK08, A0A0V1HCU6, A0A0V1HT58, A0A0V1HB44,
A0A0V1NHJ3, A0A0V1NLL0, A0A0V1PLE3, A0A0V1HUT8, A0A0V1I1I8, A0A0V1HNV1,
A0A0V1P795, A0A0V1PJS4, A0A0V1NY22, A0A0V1GP67, A0A0V1H9N6, A0A0V1HMQ6,
A0A0V1P7K0, A0A0V1P5F5, A0A0V1NLV9, A0A0V1H7J5, A0A0V1I1W3, A0A0V1HAB7,
A0A0V1NG13, A0A0V1P9L4, A0A0V1P7L8, A0A0V1HXL0, A0A0V1HW85, A0A0V1H4C6,
A0A0V1NEN6, A0A0V1P771, A0A0V1NM54, A0A0V1I5B5, A0A0V1HR65, A0A0V1HBV3,

A0A0V1I259, A0A0V1I3Y0, A0A0V1HLA0, A0A2K3PCX5, A0A2K3MTX0, A0A2K3P0N9,
A0A0V1HW02, A0A0V1HLD1, A0A0V1HVP2, A0A2K3K2X8, A0A2K3K1G0, A0A2K3P4N6,
A0A0V1HLM5, A0A0V1I5C9, A0A0V1I289, A0A2K3MMY0, A0A2K3N390, A0A2K3PRU0,
A0A0V1HBL5, A0A0V1H4G7, A0A0V1H7I9, A0A2K3NHE9, A0A2K3MP42, A0A2K3L7A3,
A0A0V1HYK5, A0A0V1I3Y7, A0A0V1GSV2, A0A2K3KDT6, A0A2K3L793, A0A2K3NJM8,
A0A0V1HE40, A0A0V1H7R5, A0A0V1I5B7, A0A2K3NHS7, A0A2K3M7W6, A0A2K3P4W6,
A0A0V1HAK7, A0A0V1HBJ8, A0A0V1HX30, A0A2K3NNI7, A0A2K3L7X0, A0A2K3LKJ0,
A0A0V1HDT3, A0A0V1I4J6, A0A0V1H559, A0A2K3MQU1, A0A2K3JN77, A0A2K3PRC7,
A0A0V1HQU5, A0A0V1HAU6, A0A0V1HAX6, A0A2K3LSP2, A0A2K3LQR6, A0A2K3NAV2,
A0A0V1HCF7, A0A0V1HEP2, A0A0V1HCA8, A0A2K3N5F0, A0A2K3P2Q7, A0A2K3NIV7,
A0A0V1HEI2, A0A0V1HTQ9, A0A0V1H6F1, A0A2K3MTU5, A0A2K3MZS0, A0A2K3JM43,
A0A183VXQ2, A0A183VLN0, A0A3P8HFW6, A0A2K3LPU5, A0A2K3N4M8, A0A2K3PJS0,
A0A395NMG6, A0A395NGU7, A0A395NHQ3, A0A2K3NB85, A0A2K3M7I7, A0A2K3NDE7,
A0A2T3ZPF6, A0A2T3ZAJ6, A0A2T3YU56, A0A2K3KSU5, A0A2K3PLE0, A0A2K3M3U1,
A0A2T3YQC3, A0A2T3YQB8, A0A2T3ZA54, A0A2K3L147, A0A2K3P033, A0A2K3LVH3,
A0A2T3YQC0, A0A2T4B6T4, A0A2T4B5A6, A0A2K3N391, A0A2K3NHE1, A0A2K3NPS4,
A0A2K0TAN5, A0A1T3CP57, A0A1T3CIF4, A0A2K3L0P8, A0A2K3MRR9, A0A2K3P8M4,
A0A2T3ZRT3, A0A2T3ZXU3, A0A2T4ANA8, A0A2K3M9G4, A0A2K3JVE5, A0A2K3LWR5,
A0A2T3ZX63, A0A2K0TYA4, A0A2N1LZN2, A0A2K3KZ94, A0A2K3KSU6, A0A2K3LB77,
A0A0F9ZNQ8, A0A2N1L2X0, A0A2N1LKG2, A0A2K3NP95, A0A2K3N177, A0A2K3P0P9,
A0A2K0U895, A0A2N1LM61, A0A0F9X8N3, A0A2K3LRR4, A0A2K3PL10, A0A2K3PJV4,
A0A2T4CJY3, A0A2T4CIH3, A0A2H2Z6Q9, A0A2K3NSR0, A0A2K3KLD8, A0A2K3LCR5,
A0A2H2Z2T5, A0A232F3J2, A0A232FIF8, A0A232F941, A0A2K3NTH2, A0A2K3PKC0, A0A2K3MMJ1,
A0A232F4N8, A0A232F7T9, F2SMU2, A0A022W2V9, A0A2Z6LMC9, A0A2Z6MW96, A0A2Z6M7P9,
A0A178F2Y8, A0A022XTQ1, A0A178FP64, A0A2Z6NDV6, A0A2Z6MC05, A0A2Z6MAQ7,
A0A369RWP4, A0A0N5E1P0, A0A0N5DL77, A0A2Z6N0I3, A0A2Z6LQ21, A0A2Z6MXN7,
A0A0N5DPD5, A0A0N5DH91, A0A0N5DXR0, A0A2Z6M5F5, A0A2Z6MXE3, A0A2Z6P679,
A0A0N5DPD6, A0A0N5DRN3, A0A0N5DYA9, A0A2Z6LR55, A0A2Z6MQ73, A0A2Z6MDJ9,
A0A0N5DYK6, A0A0N5DUR4, A0A0N5DEG2, A0A2Z6NUW8, A0A2Z6MKZ5, A0A2Z6NWU0,
A0A0N5DVP1, A0A0N5DR95, A0A0N5DR76, A0A2Z6ME77, A0A2Z6MPN7, A0A2Z6NJ42,
A0A0N5E6W2, A0A0N5DHF1, A0A0N5DRT2, A0A2Z6LL70, A0A2Z6LM12, A0A2Z6P1H7,
A0A0N5DD95, A0A0N5DM82, A0A085NT68, A0A2Z6LMM9, A0A2Z6MPK7, A0A2Z6N5W6,
A0A085N873, A0A085MF87, A0A085MJD4, A0A2Z6MAP8, A0A2Z6N1K5, A0A2Z6NTN7,
A0A0B1PQG5, A0A085M562, A0A085LN72, A0A2Z6LQG0, A0A2Z6LQW7, A0A2Z6LPI7,
A0A085N482, A0A0B1PME0, A0A0B1PKA9, A0A2Z6MQ16, A0A2Z6MDD8, A0A2Z6P268,
A0A085MJ81, A0A085LWZ9, A0A085NTB9, A0A2Z6LPS2, A0A2Z6P3R5, A0A2Z6MYS4,
A0A0B1PI26, A0A0B1PIN9, A0A085MPH9, A0A2Z6LPQ7, A0A2Z6NJK2, A0A2Z6P441,
A0A085LXR5, A0A085NL76, A0A085NGB0, A0A2Z6NAG1, A0A2Z6MMM3, A0A2Z6M4K0,
A0A085M826, A0A0B1PP49, A0A085MVC4, A0A2Z6MVN2, A0A2Z6LPR4, A0A2Z6LTH3,
A0A085M330, A0A085LIA0, A0A085N5V9, A0A2Z6PUS7, A0A2Z6MQE3, A0A2Z6NF42,
A0A085MK20, A0A0B1PRQ3, A0A085NN81, A0A2Z6MF49, A0A2Z6MQ83, A0A2Z6MRQ0,
A0A085LIK5, A0A085M8H3, A0A085MX09, A0A2Z6MFP6, A0A2Z6NXT5, A0A2Z6N7M7,
A0A085N8R6, A0A085M2H7, A0A085NKE8, A0A2Z6P962, A0A2Z6LPY4, A0A2Z6NL64,
A0A085LQT6, A0A077YW89, A0A077YZL9, A0A2Z6M8M8, A0A2Z6P518, A0A2Z6P2F4,
A0A077Z1E9, A0A077ZBA3, A0A077Z7J7, A0A2Z6MYB5, A0A2Z6LTQ0, A0A2Z6LV78,
A0A077Z0B4, A0A077ZF09, A0A077Z0L9, A0A2Z6MVE1, A0A2Z6LKE4, A0A2Z6PDH2,
A0A077Z8C3, A0A077Z0L5, A0A077YVM8, A0A2Z6M528, A0A2Z6MVF6, A0A3B6NPP9,
A0A077ZAR2, A0A077ZB27, A0A077Z4C4, A0A3B6IPA0, A0A3B6GXA5, A0A3B6CFN8,
A0A077ZFL2, A0A077YY03, A0A077ZGT3, A0A3B6GVI4, A0A3B6AVA7, A0A3B6ITK6,
A0A077Z244, A0A077ZE86, A0A392PT57, A0A3B6DM60, A0A3B6AVU8, A0A3B6EJV5,
A0A392M1H5, A0A392TWG0, A0A392PBX8, A0A3B6DAX4, A0A3B6I2Q0, A0A3B6FV60,
A0A392N1T7, A0A392Q1K1, A0A392NG93, A0A077RVZ3, A0A3B6GWT1, A0A3B6FV65,
A0A392NDB2, A0A392RWA2, A0A392NAQ6, A0A3B5Y188, A0A3B6FQR7, A0A3B5Y1P0,
A0A392NVW7, A0A392PE82, A0A392PGQ4, A0A3B6CIE0, A0A3B5YYY7, A0A3B6GVI9,
A0A392N2X5, A0A392PG95, A0A392N4E7, A0A3B6DAD8, A0A3B6C3X4, A0A3B6MW88,
A0A392PA83, A0A392NWT8, A0A392NQL4, A0A3B6IKZ5, A0A3B6B802, A0A3B6C476,
A0A392MBY4, A0A392Q8A5, A0A392PMK5, A0A3B5XTG1, A0A3B6CDR2, A0A3B6CFN2,
A0A392MI51, A0A392NQF2, A0A392Q3T9, A0A3B6DQD8, A0A3B6ML17, A0A3B6D535,
A0A392NX73, A0A392N067, A0A392P4S9, A0A3B6TPW9, A0A3B6DN59, A0A3B6HWP0,
A0A392NR91, A0A392MH64, A0A392NFX7, A0A3B5Z3I2, A0A3B6KT61, A0A3B6FWV1,
A0A2K3N545, A0A2K3NIL3, A0A2K3NQL2, A0A3B5ZXT0, A0A3B6SIG2, A0A3B6CFN4,
A0A2K3PPK5, A0A2K3PAC8, A0A2K3N5G0, A0A3B6DQC5, A0A2X0SW72, A0A3B6FER1,
A0A2K3PGR8, A0A2K3PAJ7, A0A2K3PNI7, A0A3B6CFL5, A0A3B6DW1, A0A3B6QD29,
A0A2K3L2K4, A0A2K3NKF3, A0A2K3MWB2, A0A3B6U554, A0A3B6MWW1, A0A3B6Z0,
A0A2K3MNA4, A0A2K3PFA1, A0A2K3LYQ1, A0A3B6IXZ8, A0A3B6C118, A0A3B6MWI7,
A0A2K3NPR5, A0A2K3PKJ0, A0A2K3KY21, A0A3B6RA84, A0A3B6DM95, A0A3B6KNX5,
A0A2K3P821, A0A2K3N0U2, A0A2K3NIX8, A0A3B5XTI8, A0A3B6RP60, A0A0R8CAF3,

| | | | | | |
|---|---|---|---|---|---|
| A0A3B6B844, | A0A3B5YZH3, | A0A3B5ZZY7, | A0A3B5Z1E9, | A0A3B6CFP7, | A0A3B6HT43, |
| A0A3B5ZYM3, | A0A3B6DM69, | A0A3B6D841, | A0A3B6RSP0, | A0A3B5YT59, | A0A3B6CFN5, |
| A0A3B6IWH6, | A0A3B6NXU2, | A0A3B6D593, | A0A3B6KNX0, | A0A3B6TK76, | A0A3B6SIF3, |
| A0A3B6C633, | A0A3B6UAV8, | A0A3B6CDW2, | A0A3B6PST4, | A0A3B6CC02, | A0A3B6TUP1, |
| A0A3B6RDT9, | A0A3B6CDV2, | A0A3B6LUF7, | A0A3B6B0K5, | A0A3B6CHY5, | A0A3B6B7R1, |
| A0A3B6DQ92, | A0A3B6SL80, | A0A3B6N0N1, | A0A3B6B826, | A0A1D5UGG3, | A0A3B5ZZV1, |
| A0A3B6DLD6, | A0A2X0SND0, | A0A3B5ZZF6, | A0A3B6B022, | A0A3B6KD22, | A0A3B6KRL2, |
| A0A3B6B2F3, | A0A3B6MYX9, | A0A3B5Z1X9, | A0A3B6U115, | A0A3B6GNZ2, | A0A3B6JDU7, |
| A0A3B6DMT7, | A0A3B6KN82, | A0A3B6NWS4, | A0A3B5Y527, | A0A2X0SBL5, | A0A3B6CDT0, |
| A0A3B5XT21, | A0A3B6C8K8, | A0A3B6DMB1, | A0A3B6C3Z6, | A0A3B5Y3Q9, | A0A3B6QL00, |
| A0A3B6JIP6, | A0A3B6G0F8, | A0A3B6CFH5, | A0A3B6SJY6, | A0A3B6ESF4, | A0A3B6DJP0, |
| A0A3B6C728, | A0A3B6QP32, | A0A3B6RMY0, | A0A3B6ER67, | A0A3B6RJV3, | A0A3B6CFJ4, |
| A0A3B6DML0, | A0A3B6RPD1, | A0A3B6SA65, | A0A3B5Y5D0, | A0A3B6CDT5, | A0A3B6JF83, |
| A0A3B6DQD5, | A0A3B6MP47, | A0A3B6DL71, | A0A3B6SDH4, | A0A3B6DL99, | A0A3B6AQB5, |
| A0A3B6IV36, | A0A3B6DJM6, | A0A3B6MWH8, | A0A3B6H388, | A0A3B6PSS9, | A0A3B6FRH5, |
| A0A3B6B8U6, | A0A3B6TNK8, | A0A3B6MWJ6, | A0A3B6NSZ0, | A0A3B6CFN7, | A0A3B6C3W9, |
| A0A3B6CFR7, | A0A3B6GPP5, | A0A2X0TGT9, | A0A3B6ENW4, | A0A3B6B7N8, | A0A3B6DGA7, |
| A0A2X0S0A4, | A0A3B6B6Z5, | A0A3B6AR12, | A0A3B6D4L4, | A0A3B6MXW0, | A0A2X0SNE0, |
| A0A3B6DDD0, | A0A3B6TFJ0, | A0A3B6CI24, | A0A3B6DNS5, | A0A3B6B820, | A0A3B6DL80, |
| A0A3B6TPC6, | A0A3B6B568, | A0A3B6IWJ1, | A0A3B6LS69, | A0A3B6CI19, | A0A3B6TNR8, |
| A0A3B6SEP2, | A0A3B6KLI6, | A0A3B6EKY9, | A0A3B5ZVB3, | A0A3B6R9Q9, | A0A3B6CG09, |
| A0A3B6CG16, | A0A3B6B8T6, | A0A3B6RPA4, | A0A3B5ZME6, | A0A3B6IMW8, | A0A3B6SLK7, |
| A0A3B6TT98, | A0A3B6H304, | A0A3B6EH46, | A0A3B6H2G6, | A0A3B6KNM0, | A0A3B6DAE3, |
| A0A3B6FUN9, | A0A3B6CFS0, | A0A3B6KRY5, | A0A3B6SLZ3, | A0A3B6IR46, | A0A3B6CDX8, |
| A0A3B6B571, | A0A3B6TQ03, | A0A3B6GVH4, | A0A3B6RMR3, | A0A3B6JK14, | A0A3B6LP53, |
| A0A3B6CDR7, | A0A3B6I3N0, | A0A3B6B7D6, | A0A3B6SQQ3, | A0A3B6LSC8, R9UC29, | A0A2X0SUV4, |
| A0A3B6CFM9, | A0A3B6LRY8, | A0A3B6DJM2, | A0A3B6B733, | A0A3B6GZL0, | A0A2X0SCV8, |
| A0A3B6MV81, | A0A3B5ZNL3, | A0A3B6A183, | A0A3B6BXQ7, | A0A3B6RPT7, Q56DH9, | A0A3B6TE76, |
| A0A3B6QP21, | A0A3B6BZH0, | A0A3B6J0A9, | A0A3B6SNL4, | A0A3B6B7Z9, | A0A3B6IZM9, |
| A0A3B6B640, | A0A3B6DL82, | A0A3B6QNH4, | A0A3B6CG90, | A0A3B6TPR0, | A0A3B6AWA3, |
| A0A3B6U4W3, | A0A3B5Z2P0, | A0A3B6CDX1, | A0A3B6B7V1, | I0JTU1, A0A3B6GWS6, | A0A3B5Z166, |
| A0A3B6JP90, | A0A3B6S8I2, | A0A3B6MV89, | A0A3B6EEA5, | D8L9S5, A0A3B6AYR6, | A0A3B6CFM6, |
| A0A3B6LXS1, | A0A3B6QP12, | A0A3B6B6T4, | A0A3B6SHS1, | A0A3B6KSI0, | A0A3B6CFN3, |
| A0A3B5XT90, | A0A3B6DQE1, | A0A3B6CH00, | A0A3B6NLJ3, | A0A3B6CFN9, | A0A3B5Z2J0, |
| A0A3B6KN77, | A0A077RVZ1, | A0A3B5Z285, | A0A2X0SBH9, | A0A2X0U0Z3, | A0A3B6MXW5, |
| A0A3B6AZK9, | A0A3B6B840, | A0A3B6CFZ6, | A0A3B6LQP0, | A0A3B6JI87, | A0A3B6REN4, |
| A0A3B6SBZ7, | A0A3B6PVE3, | A0A3B6LDI3, | A0A3B6RMR6, | A0A3B6BZR8, | A0A3B6B5R5, |
| A0A3B6N2M7, | A0A3B6C6J6, | A0A3B6DN39, | A0A3B6CI12, | A0A3B6DHA3, | A0A3B6KAL1, |
| A0A3B6DLB0, | A0A3B6B710, | A0A3B6DN68, | A0A3B6B715, | A0A2X0SPL7, | A0A3B5ZMU9, |
| A0A3B6LQP4, | A0A3B5XVZ4, | A0A3B6TQM2, | A0A3B6H6M7, | A0A3B6AWQ0, | A0A3B6TF32, |
| A0A3B6I168, | A0A3B6CFM3, | A0A3B6LXQ4, | A0A3B6HPJ6, | A0A3B6RTD5, | A0A3B6DKA3, |
| A0A3B6CDS2, | A0A3B5Z158, | A0A3B6TXD5, | A0A3B6LJM9, | A0A3B6ESW5, | A0A3B6DM74, |
| A0A3B6UAM6, | A0A2X0SCN5, | A0A3B6UC57, | A0A3B6TW12, | A0A3B6B6D0, | A0A3B6LRZ0, |
| A0A3B6SRM5, | A0A3B6TW06, | A0A2X0SNF0, | A0A3B6MXV5, | A0A3B6RB18, | A0A3B6NWL7, |
| A0A3B6MII3, | A0A3B6CEN4, | A0A3B6DJN6, | A0A3B6AVX3, | A0A3B6C9J4, | A0A3B6SQF7, |
| A0A3B6B7S8, | A0A3B6KNC2, | A0A3B6CDU3, | A0A2X0U1E9, | A0A3B6B7V7, | A0A3B6RPG4, |
| A0A3B6C714, | A0A3B6MXU5, | A0A3B6QKM8, | A0A3B6CF85, | A0A3B6D812, | A0A3B6LM48, |
| A0A3B6FN69, | A0A3B5ZME3, | A0A3B6N370, | A0A3B6TLB6, | A0A3B6AVW3, | A0A3B6EHS5, |
| A0A3B6B8R0, | A0A3B6LRZ5, | A0A3B6LY19, | A0A3B6IK35, | A0A3B6B8F8, | A0A2X0SCT9, |
| A0A3B6B6X0, | A0A3B6GTI5, | A0A3B6HX59, | A0A3B6U7R0, | A0A3B5ZP26, | A0A3B5XTI4, |
| A0A3B6LR65, | A0A3B6KLI0, | A0A3B6B7J7, | A0A3B6U6Q9, | A0A3B5ZRQ8, | A0A3B6DPF6, |
| A0A3B5Y5C6, | A0A3B6SDH9, | A0A3B6SPZ5, | A0A3B6RR09, | R9UFG9, A0A3B6QL55, | A0A3B6EM35, |
| A0A3B6D4X4, | A0A3B6DQM1, | A0A3B6DDV3, | A0A3B6DAS8, | A0A3B6EM42, | A0A3B6EJL4, |
| A0A3B6TAX9, | A0A3B6KKP1, | A0A3B6AVA1, | A0A3B6B738, | A0A3B6FRT0, | A0A3B6GQZ4, |
| A0A3B6DLC1, | A0A3B6EKT7, | A0A3B6SQQ6, | A0A3B6NVE3, | A0A3B5Y4W4, | A0A3B6HT50, |
| A0A3B6C001, | A0A3B6H0E6, | A0A3B6LEV2, | A0A3B6RQ82, | A0A3B6JK06, | A0A2X0SCX3, |
| A0A3B6LS79, | A0A3B6B644, | A0A3B6DE47, | A0A3B6DAS6, | A0A3B6B0L1, | A0A3B6U6W6, |
| A0A3B6DL94, | A0A2X0SNW6, | A0A3B6AX84, | A0A3B6PSW1, | A0A3B6MI22, | A0A3B6EM39, |
| A0A3B6BXA3, | A0A3B6TT93, | A0A3B5XUG7, | A0A3B6FUK0, | A0A3B6EJW4, | A0A3B6C439, |
| A0A3B6PV04, | A0A3B6CDW7, | A0A3B6ARF6, | A0A3B5ZYD7, | A0A3B6FUJ5, | A0A3B6C3V9, |
| A0A3B6B7Q6, | A0A3B6A030, | A0A3B6JCZ0, | A0A3B6DAW9, | A0A3B6C3Y1, | A0A3B6H012, |
| A0A3B6KKN0, | A0A3B5Y464, | A0A3B6B7H2, | A0A3B6NIA4, | A0A2X0RZC4, | A0A3B6DE52, |
| A0A3B6CDT7, | A0A3B5Z410, | A0A3B6BZG5, | A0A3B5ZYE5, | A0A2X0U219, | A0A3B6EH34, |
| A0A3B6CFP5, | A0A3B6SKQ8, | A0A3B6G1T3, | A0A3B6AVB1, | A0A3B6GXA9, | A0A3B6EJV9, |
| A0A3B6LP90, | A0A3B6MPM0, | A0A3B5ZQN2, | A0A3B6DN34, | A0A3B6KN67, | A0A3B6C6J2, |
| A0A3B6MWW7, | A0A3B6FI27, | A0A3B6GSI9, | A0A3B6AX65, | A0A3B6AX70, | A0A3B6A137, |
| A0A3B5Z165, | A0A3B6CEJ7, | A0A3B6H694, | A0A3B6CFK5, | A0A3B6FRS5, | A0A3B6NX53, |

A0A3B6DKK6, A0A3B6QCT9, A0A3B6LXE2, A0A446MWF9, A0A446K644, A0A446VWF4,
A0A3B6GXB4, A0A3B6C471, A0A3B6AWQ3, A0A446MWD8, A0A446M560, A0A446W8K1,
A0A3B6DNI2, A0A3B6A1F9, A0A3B6AVW8, A0A446YTG2, A0A446LLE9, A0A446LLA9,
A0A3B6EJK8, A0A3B6FUK5, A0A3B6JE30, A0A446MV52, A0A446MRN3, A0A446LHW9,
A0A3B6GWT6, A0A3B6CDY1, A0A3B6DKS5, A0A446NRW8, A0A446RQK6, A0A446RQM9,
A0A3B6AWA8, A0A3B6C434, A0A3B6GVH9, A0A446M588, A0A446UJ35, A0A446UJ06,
A0A3B6B5S4, A0A3B6DLD1, A0A3B5XW78, A0A446VSN4, A0A446UJB3, A0A446LMD3,
A0A3B6H0F8, A0A3B6N1N1, A0A3B6AZ76, A0A446S8Q2, A0A446LI11, A0A446LHV2,
A0A3B6MWV6, A0A3B5ZZF3, A0A3B6CG64, A0A446REN0, A0A446YTE0, A0A446MRL7,
A0A3B6H5X7, A0A2X0SDG7, A0A3B6TPX5, A0A446LHV8, A0A446MRL2, A0A446UJ76,
A0A3B6BXA2, A0A3B5XTC5, A0A3B6CFT5, A0A446TC94, A0A446IP34, A0A446NRW5,
A0A3B6DM84, A0A3B6BWH3, A0A3B6HTC9, A0A446XSM0, A0A446TCA5, A0A446KA03,
A0A3B6PUX9, A0A3B5YQ73, A0A3B6DBG8, A0A446YTD1, A0A446MW57, A0A446M577,
A0A3B6SK28, A0A3B6MWX7, A0A3B6CDU5, A0A446UJ96, A0A446K654, A0A446LLJ7, A0A446K022,
A0A3B6DMH8, A0A3B6LUS0, A0A3B6DM89, A0A446WQH4, A0A446KP30, A0A446MUV2,
A0A3B6LRZ3, A0A3B6DJM9, A0A3B5Z2V7, A0A446X5A7, A0A446NRU9, A0A446MVY3,
A0A3B6B883, A0A3B6B6C5, A0A3B5Z2G7, A0A446MUV4, A0A446X576, A0A446NRV0,
A0A3B6B8V7, A0A3B6DMH3, A0A3B6EF95, A0A446L422, A0A446LLB4, A0A446L9C3,
A0A3B5YQF7, A0A3B6CHZ0, A0A3B5XWA5, A0A446YVN7, A0A446NRW9, A0A446XZM9,
A0A3B5XTJ9, A0A3B6LRZ4, A0A3B6HYQ9, A0A446MV59, A0A446Y2M9, A0A446LL76,
A0A3B6RP18, A0A3B6GZZ9, A0A3B6AQC9, A0A446MV73, A0A446UJ87, A0A446L975,
A0A3B6B980, A0A3B6LRX9, A0A3B6DLC6, A0A446Y3N5, A0A446KV41, A0A446K617,
A0A3B6NXN1, A0A3B6SLK3, A0A3B6B7T6, A0A446QGE1, A0A446MV32, A0A446PK69,
A0A2X0SCN7, A0A3B6CDX6, A0A3B6DMA2, A0A446SK23, A0A446YZ67, A0A446MI06, A0A446LI16,
A0A3B6B036, A0A3B6B576, A0A3B6C3Z0, A0A446XY56, A0A446YP66, A0A446LL77,
A0A3B6ASJ6, A0A3B6HW93, A0A2X0RZB1, A0A446REX2, A0A446NK72, A0A446UJA1,
A0A3B6CFS5, A0A3B6DBG3, A0A3B6KSQ6, A0A446YLI9, A0A446K601, A0A446UJ43,
A0A3B6C6A4, A0A2X0TS56, A0A3B6PLI1, A0A446NK74, A0A446LL83, A0A446XPQ6,
A0A3B6B719, A0A3B6CFR6, A0A3B6H004, A0A446VUA3, A0A446NRU8, A0A446KUV2,
A0A3B6C787, A0A2X0TYQ5, A0A3B5ZXN5, A0A446Q9Q4, A0A446K5J4, A0A446WSK7,
A0A3B6CG60, A0A3B6DLA4, A0A3B6DQ26, A0A446NRZ1, A0A446M568, A0A446JML1,
A0A3B6SF92, A0A2X0SBJ0, A0A3B6DLN1, A0A446SLJ0, A0A446R9Q0, A0A446UK57,
A0A3B6E8J0, A0A3B6GLR2, A0A3B6KUH0, A0A446LI26, A0A446M587, A0A446XU41,
A0A3B5YQG9, A0A3B6CFK3, A0A3B6B8P2, A0A446UJ71, A0A446T6X8, A0A446KV32,
A0A3B6DMG8, A0A2X0SBA4, A0A3B6TUB4, A0A446LM41, A0A446L404, A0A446MV88,
A0A3B6EDF4, A0A3B6RPB1, A0A3B6DMF8, A0A446NRW1, A0A446J771, A0A446M551,
A0A3B6UCL0, A0A3B6PUV2, A0A3B6H0E9, A0A446KUW7, A0A446KUU3, A0A446MV70,
A0A3B5Y7C0, A0A3B6GN82, A0A3B6AX75, A0A446LHW7, A0A446MV74, A0A446M5B2,
A0A3B6LQN7, A0A3B6DLB6, A0A3B6DKS9, A0A446LL46, A0A446MV68, A0A446PK92,
A0A3B6LRY4, A0A3B6DKI6, A0A3B6GX38, A0A446MVS2, A0A446XVJ2, A0A446LHU2,
A0A3B5ZMG1, A0A3B5Z1I1, A0A2X0SCS8, A0A446UKD3, A0A446M590, A0A446K035,
A0A3B6TI56, A0A3B6CFI4, A0A3B6AQU8, A0A446SLG8, A0A446LKQ3, A0A446QEY0,
A0A3B6C782, A0A3B5ZZT3, A0A3B6KL84, A0A446MUR6, A0A446IP50, A0A446P3S7,
A0A3B6RL94, A0A3B6TQ21, A0A3B6LRY9, A0A446QNL4, A0A446R7C5, A0A446JML0,
A0A3B6QN56, A0A3B5YRB3, A0A3B6UAH4, A0A446NRW7, A0A446MRN0, A0A446MRN9,
A0A3B6AR71, A0A3B6KED9, A0A3B6TWJ5, A0A446MUS6, A0A446R1Y3, A0A446LJB5,
A0A3B6ERL9, A0A3B6B6E3, A0A3B6H1E1, A0A446KHJ9, A0A446YPI4, A0A446XPR5,
A0A3B6DN47, A0A3B6FXS0, A0A3B6MX31, A0A446LHT9, A0A446KUZ6, A0A446MVB0,
A0A3B6FMU4, A0A3B6APH5, A0A2X0RZY7, A0A446K6J7, A0A446LHY6, A0A446Q9Y2,
A0A3B6DNR6, A0A3B6RL87, A0A3B6TMT8, A0A446TBU5, A0A446L175, A0A446MRK5,
A0A3B6RQ86, A0A3B6EJJ5, A0A3B6B232, A0A446Q9T2, A0A446UJ22, A0A446M562,
A0A3B6RQ77, A0A2X0TMP3, A0A1D6RPH0, A0A446MRI6, A0A446P3S9, A0A446SK01,
A0A2X0SCP5, A0A1D5UXF1, A0A077S3W5, W5D450, A0A446YS27, A0A446MI08, A0A446MCY9,
A0A1D5UN73, W5C0L4, A0A1D5UXD7, A0A077RQ16, A0A446MRR0, A0A446MRK8, A0A446KV16,
A0A1D5UVZ2, A0A077RZC2, A0A077RQQ4, A0A446M570, A0A446L164, A0A446M582,
A0A077RFI1, A0A341ZF31, A0A1D5UKP6, A0A446REF2, A0A446JA06, A0A446MRP1,
A0A077S2M2, A0A1D5UK73, A0A1D5UY85, A0A446M580, A0A446M565, A0A446SLJ2,
A0A077S0P5, A0A1D5MVQ3, A0A446LHZ4, A0A446J9N6, A0A446MDG6, A0A446UJC2,
A0A446REL1, A0A446MUR9, A0A446UJ83, A0A446UJ81, A0A446SLP8, A0A446LL86, A0A446Y563,
A0A446YSZ1, A0A446TC95, A0A446SLK3, A0A446MZY1, A0A446K620, A0A446MVV2,
A0A446LI13, A0A446MV11, A0A446UJ84, A0A446NB74, A0A446LLA2, A0A446MUS4,
A0A446NKA8, A0A446Q0W6, A0A446VU93, A0A446TT86, A0A446LRA6, A0A446L9G2,
A0A446Y561, A0A446NRX1, A0A446SJZ5, A0A446LI414, A0A446K5H4, A0A446SXH2,
A0A446L3Y0, A0A446KV21, A0A446PDR2, A0A446MV89, A0A446MRJ7, A0A446QNN2,
A0A446LHU9, A0A446MRR5, A0A446PDR2, A0A446MRS6, A0A446L9B9, A0A446NRU1,
A0A446Q0X4, A0A446TCN2, A0A446LI10, A0A446MWC8, A0A446MVB4, A0A446UJ63,
A0A446MVF3, A0A446LHZ0, A0A446PK86, A0A446NRY5, A0A446K9J8, A0A446MW84,

A0A446USM4, A0A446K5G2, A0A446MRT0, A0A446MRM4, A0A446LHS8, A0A446UJA5,
A0A446UQJ9, A0A446JML2, A0A446UJ99, A0A446XNN9, A0A446NRV9, A0A446NRY6,
A0A446MSW5, A0A446MUV5, A0A446L406, A0A446LHY1, A0A446X3F2, A0A446NRX3,
A0A446RS14, A0A446SAY9, A0A446YNY1, A0A446WT80, A0A446NRV2, A0A446TBX2,
A0A446NS01, A0A446KV78, A0A446LL87, A0A446MRI3, A0A446NS43, A0A446MWZ7,
A0A446K036, A0A446L9A2, A0A446NRY3, A0A446WSF8, A0A446JGF3, A0A446X5C0,
A0A446MUH3, A0A446NRV5, A0A446L3X8, A0A446NYC9, A0A446WSC2, A0A446X5E5,
A0A446LL80, A0A446QLZ4, A0A446UJ94, A0A446MRJ3, A0A446MDA4, A0A446MRG9,
A0A446MUY4, A0A446NAL7, A0A446VV46, A0A446Y558, A0A446UJ53, A0A446NRY0,
A0A446MVA2, A0A446LM62, A0A446UJ59, A0A446KUV4, A0A446MV57, A0A446KUW8,
A0A446MRJ9, A0A446MV20, A0A446LHR2, A0A446LL74, A0A446LHW1, A0A446SWQ4,
A0A446LL97, A0A446MRG0, A0A446LHX1, A0A446YTB1, A0A446YP03, R9UD00, A0A446M557,
A0A446U9T5, A0A446XVM3, A0A446M558, A0A446MRP0, A0A446NA00, A0A446L155,
A0A446R9M6, A0A446JGG2, A0A446UJ85, A0A446MVK1, A0A446MV76, A0A446LHY3,
A0A446TQK5, A0A446KVB1, A0A446YTB0, A0A446XU55, A0A446WTD2, A0A446WSD5,
A0A446MY43, A0A446K667, A0A446MVJ1, A0A446XS86, A0A446LI36, A0A446J7A5, A0A446LI37,
A0A446LL78, A0A446TR27, A0A446TQK4, A0A446YPB5, A0A446TQL2, A0A446NAE6,
A0A446REI4, A0A446JA28, A0A446Q0X1, A0A446IP93, A0A446MD40, A0A446NRW2,
A0A446K647, A0A446RLD6, A0A446RM11, A0A446MUS9, A0A446MV97, A0A446P468,
A0A446LSA0, A0A446MUX5, A0A446MVA1, A0A446USI9, A0A446MVI9, A0A446UJ90, A0A446J796,
A0A446K6G4, A0A446UJ65, A0A446KGH3, A0A446R1M6, A0A446KHK3, A0A446RQL8,
A0A446KV82, A0A446KV63, A0A446MV50, A0A446VUB8, A0A446RQK5, A0A446IP14,
A0A446NK01, A0A446IHX8, A0A446MRT7, A0A446KV31, A0A446LLA5, A0A446Y304,
A0A446K639, A0A446MRH0, A0A446MV40, A0A446MUN3, A0A446MV33, A0A446KV62,
A0A446R1L1, A0A446RQM3, A0A446K5K0, A0A446KVC1, A0A446LL47, A0A446NRX4,
A0A446MD27, A0A446MW47, A0A446LHX2, A0A446L993, A0A446M585, A0A446IP36,
A0A446TQK1, A0A446L9F6, A0A446RDR5, A0A446UQG9, A0A446M527, A0A446VAR7,
A0A446XSM3, A0A446KV34, A0A446MV21, A0A446MUY8, A0A446L401, A0A446U9S4,
A0A446M526, A0A446R9J1, A0A446QA33, A0A446Y557, A0A446M553, A0A446MV07,
A0A446NS73, A0A446Q9P9, A0A446TT87, A0A446UWT0, A0A446NBI9, A0A446M528,
A0A446SMN3, A0A446P4B8, A0A446K5Z2, A0A446LLF8, A0A446Q0V8, A0A446LI24,
A0A446MV84, A0A446LHW3, A0A446UIZ6, A0A446MUU3, A0A446YLJ5, A0A446MV00,
A0A446XTI5, A0A446RZS7, A0A446LJA8, A0A446MRJ2, A0A446TBW0, A0A446KUQ8,
A0A446KUZ3, A0A446MRI0, A0A446QA44, A0A446R9L4, A0A446MUL5, A0A446TBX1,
A0A446MUT9, A0A446LLE5, A0A446VUA1, A0A446IHX1, A0A446KV07, A0A446N0X4,
A0A446M5A4, A0A446LHT8, A0A446KGV8, A0A446K677, A0A446RZ10, A0A446MI12,
A0A446J7A1, A0A446M579, A0A446RQK2, A0A446V4H5, A0A446MV35, A0A446VQ63,
A0A446LR36, A0A446NRY7, A0A446NK41, A0A446MUM6, A0A446LLB3, A0A446QEZ2,
A0A446NRV3, A0A446XPD9, A0A446K031, A0A446PK75, A0A446XNN5, A0A446K6I0,
A0A446N0X5, A0A446P3S3, A0A446Q9R0, A0A446TC97, A0A446M5A2, A0A446KV22,
A0A446UJ70, A0A446TBW3, A0A446UJC6, A0A446TRY9, A0A446NRW4, A0A446SK08,
A0A446S8Q6, A0A446X3F4, A0A446MVC2, A0A446UWU1, A0A446MVP0, A0A446MUY6,
A0A446WSC8, A0A446RZ79, A0A446Y556, A0A446L973, A0A446MW55, A0A446K6L6,
A0A446SJZ8, A0A446Q9P3, A0A446Y367, A0A446II08, A0A446XPB9, A0A446LHU8, A0A446J9R0,
A0A446WMX9, A0A446Q9Q0, A0A446L3Z8, A0A446MD20, A0A446LI00, A0A446UZM1,
A0A446LJJ7, A0A446J765, A0A446UJ32, A0A446K938, A0A446MRL6, A0A446YRY6, A0A446MRN5,
A0A446NRY8, A0A446UJ23, A0A446N128, A0A446LHV3, A0A446R1U8, A0A446MW53,
A0A446UJ69, A0A446LL91, A0A446JP82, A0A446MVW1, A0A446N457, A0A446Q0X7,
A0A446MRL0, A0A446Q9P6, A0A446SLQ8, A0A446KUW1, A0A446LL55, A0A446L487,
A0A446LHT2, A0A446LR56, A0A446MVD0, A0A446JGM8, A0A446QQX8, A0A446YZ82,
A0A446NRX7, A0A446K9M4, A0A446MVX3, A0A446Y148, A0A446WQF2, A0A446MIA1,
A0A446K1Q8, A0A446NAD8, A0A446N9Y9, A0A446NRU7, A0A446UJ72, A0A446XU56,
A0A446UJ82, A0A446NK52, A0A446YTG9, A0A446L9A0, A0A446PV58, A0A446WSH4,
A0A446MRM3, A0A446UJ89, A0A446NS53, A0A446SAW2, A0A446NS67, A0A446MRL5,
A0A446KFS7, A0A446Q8P2, A0A446TIF8, A0A446MRK7, A0A446YTC2, A0A446RT60,
A0A446PVA8, A0A446WSF5, A0A446K631, A0A446YT98, A0A446WU68, A0A446UJ54,
A0A446NAK8, A0A446TBV6, A0A446L425, A0A446J7B3, A0A446VLN6, A0A446VUB4,
A0A446MW67, A0A446XZR0, A0A446NK46, A0A446Q9P0, A0A446LHV1, A0A446UJ60,
A0A446U2C0, A0A446JGI5, A0A446P474, A0A446K605, A0A446MV39, A0A446MVB2, A0A446KV26,
A0A446YZ88, A0A446M589, A0A446PV83, A0A446LHV4, A0A446KUW4, A0A446KV73,
A0A446YAM4, A0A446LMA9, A0A446MWH4, A0A446Q0W0, A0A446MV61, A0A446Y562,
A0A446QNY6, A0A446QH58, A0A446LHY0, A0A446MV98, A0A446R7D5, A0A446MV30,
A0A446PV42, A0A446M569, A0A446Q0X5, A0A446KV89, A0A446IHW9, A0A446PV86,
A0A446KV52, A0A446MVE3, A0A446MAN9, A0A446WVE1, A0A446MT54, A0A446L3Y7,
A0A446MUR3, A0A446M561, A0A446MVD1, A0A446MRL9, A0A446LLB2, A0A446MV41,
A0A446X556, A0A446M5B3, A0A446R1T8, A0A446RZ83, A0A446X395, A0A446U371,
A0A446KUY6, A0A446LHX4, A0A446P114, A0A446UW14, A0A446MUU4, A0A446QA53,

A0A446SLI6, A0A446LM93, A0A446NRZ4, A0A3Q7XNM7, A0A384BVT0, A0A384DPH5,
A0A446KVA1, A0A446PV26, A0A446L9A8, A0A384BP91, A0A384D4U8, A0A384BPA7,
A0A446QLB6, A0A446MRN4, A0A446L4A2, A0A384DNT9, A0A452VCB3, A0A452U7G2,
A0A446UJ74, A0A446UW15, A0A446UJ12, A0A452VCC2, A0A452U7G7, A0A194V1F2,
A0A446WUB2, A0A446MRL4, A0A446MVE2, A0A194UVJ5, A0A194ULX3, A0A194VCV2,
A0A446KUU1, A0A446SLN0, A0A446Y3A1, A0A194W0K5, A0A194W6W9, A0A194VR95,
A0A446L430, A0A446Q8F8, A0A446SK49, A0A194W4H9, A0A423VPM3, A0A423VSL1,
A0A446KUU5, A0A446RQP4, A0A446Y2R3, A0A423WD94, A0A423W9F7, A0A423WZH0,
A0A446LHV9, A0A446UJA0, A0A446NRV7, A0A423WV28, A0A423WIT3, A0A423WH16,
A0A446NRW6, A0A446UEC6, A0A446MRI7, A0A423VR78, A0A423VA80, A0A0S3PPN4,
A0A446MRJ5, A0A446SXG6, A0A446MRQ6, A0A1E7U9P5, A0A250DK61, E6V8Z5, A0A0P9AFP2,
A0A446MZY9, A0A446P423, A0A446M576, A0A2G6X860, A0A115PZ82, A0A2N4SJ19,
A0A446Q9N8, A0A446LZ06, A0A446IP45, A0A2E9C131, A0A370IXJ3, A0A370JCW3,
A0A446M592, A0A446X394, A0A446KUU6, A0A2V5TIP4, A0A2D5MT73, A0A0D1XT13,
A0A446LNU4, A0A446KUX7, A0A446M574, A0A0D1YG70, C9SWV4, G2XFJ0, A0A2J8BUS4,
A0A446UJB1, A0A446MVG4, A0A446MVM9, A0A444SAT6, A0A366Q651, A0A0G4M299,
A0A446LSA5, A0A446WSC9, A0A446YSZ5, A0A0G4MAI0, A0A0G4MID9, A0A0G4MA18,
A0A446VU91, A0A446MVE4, A0A446KV50, A0A3M9Y2Y5, A0A0S3SI41, A0A0S3S9L1,
A0A446MUZ5, A0A446UJA3, A0A446N116, A0A0S3SVK9, A0A0S3RUP5, A0A0S3RDA5,
A0A446RDR4, A0A446L474, A0A446LLE4, A0A0S3S2D1, A0A0S3SFB8, A0A0S3SI12, A0A0S3S983,
A0A446MT19, A0A446UJA4, A0A446MRI4, A0A0S3SHB1, A0A0S3S2C4, A0A0S3RAQ9,
A0A446LHS2, A0A446MVL2, A0A446Q9R4, A0A0S3SI52, A0A0S3SBH8, A0A0S3SHD6,
A0A446YS15, A0A446MUR2, A0A446MRQ2, A0A0S3RUY5, A0A0S3RV54, A0A0S3SWB4,
A0A446RS78, A0A446KUZ2, A0A446RS84, A0A0S3SI31, A0A0S3SIJ7, A0A0S3S2E3, A0A0S3T100,
A0A446QR39, A0A446UJ79, A0A446LHU0, A0A0S3SAD2, A0A0S3SFJ3, A0A0S3S9H7,
A0A446MVA5, A0A446NRV8, A0A446R7D1, A0A0S3QZQ6, A0A0S3SKU3, A0A0S3SHG6,
A0A446KUY2, A0A446LLE1, A0A446M599, A0A0S3S9C6, A0A0S3RUP4, A0A0S3SYJ7,
A0A446UZL9, A0A446MV19, A0A446II24, A0A0S3RUT8, A0A0S3SII5, A0A0S3RTM0,
A0A446MV85, M7YPH8, M7ZVA3, M7ZF50, M7YWV4, A0A0S3QZS6, A0A0S3RQC6, A0A0S3SBP8,
M7Z5B8, M7YN61, M8AE45, M7ZNB1, M7YXB0, A0A0S3SKN8, A0A0S3S9A9, A0A0S3S9H4,
M8AST1, M7YR24, M7ZA47, M7YT26, M7YJ40, A0A0S3S2C1, A0A0S3S9B5, A0A0S3RV98,
M8ADD0, M7ZJA7, M7YQ54, M8AUM9, M8ANE0, A0A0S3RBJ5, A0A0S3QZN0, A0A0S3SHY7,
M7ZXQ8, M8AUZ7, M7ZHG8, M7ZXN9, M7ZBE9, A0A0S3SA88, A0A0S3SU71, A0A0S3SVC8,
M7YEQ0, M7ZCG6, M8AAR3, M8A1P2, T1NTJ1, A0A0S3RUR6, A0A0S3SHH7, A0A0S3RUS8,
T1N2R3, T1LF75, T1N4J2, T1MJA6, T1M819, T1LC35, A0A0S3SB63, A0A0S3T043, A0A0S3RZL4,
T1MQA5, T1LSX1, T1MIZ5, T1LNZ0, T1N671, A0A0S3S969, A0A0S3RZ03, A0A0S3SB96,
T1MUZ3, T1NI12, T1NKJ6, T1NR99, T1LEM3, A0A0S3QZV8, A0A0S3SHB5, A0A0S3S9G1,
T1M0W0, T1NAZ0, T1MFP5, T1LZ01, T1NPH7, A0A0S3QZX3, A0A0S3S2F1, A0A3Q0FG34,
T1NHL1, T1MDZ0, T1NS03, T1M9E3, T1LM18, A0A1S3UY68, A0A1S3URP2, A0A1S3URH0,
T1LAC9, T1LBZ0, T1MXQ5, T1MQD4, T1MPW5, A0A3Q0ET99, A0A3Q0EYW5, A0A1S3TL02,
T1LM09, T1NPT5, T1LM19, T1LU09, T1NK32, T1LUD5, A0A1S3W0Y9, A0A1S3U2W6, A0A1S3W0T2,
T1NF00, T1NC78, T1NN82, T1MA35, T1L9J1, T1MBB1, A0A1S3W0T7, A0A1S3W144, A0A1S3U4J5,
T1LXJ4, T1LKE2, T1LGV7, T1MAS0, T1MPD3, A0A1S3TNA8, A0A1S3T9S3, A0A1S3VJI6,
T1MSD0, T1LRP0, T1MF28, T1L9J3, T1M1J0, T1NWB7, A0A1S3TMS8, A0A3Q0ESJ5, A0A1S3TLG9,
T1M5P2, T1NBE0, T1LGV4, T1LSN9, T1NGW2, A0A1S3VUM7, A0A1S3TUL8, A0A1S3TSI3,
T1LNY8, T1MDI5, T1NVC5, T1NHJ6, T1LSX0, T1L8X2, A0A1S3U0N3, A0A3Q0EZS4, A0A1S3VLI3,
T1MZ83, T1LD28, T1LAN4, T1LAN5, T1NM62, T1LF74, A0A1S3U6F1, A0A3Q0EVU4, A0A3Q0ET57,
T1LGV3, T1LF77, T1MQD3, T1LI56, T1NW29, T1N4G6, A0A1S3VJJ8, A0A1S3T8I0, A0A1S3W0Y5,
T1M6J5, T1LC36, T1M1I9, T1LHM4, T1MAK7, T1ME31, A0A3Q0F2X9, A0A1S3TGW0, A0A1S3VEP0,
T1MKF8, T1LI57, T1LM22, T1LBJ3, T1LAN6, M7YNN7, A0A1S3VT28, A0A1S3U039, A0A3Q0FL44,
M7Z646, M8A2P4, A0A0P1GFE6, A0A0P1GTJ8, A0A1S3W0L1, A0A1S3VU23, A0A3Q0EIT8,
A0A238J853, A0A239KUI1, A0A1V9XN76, A0A3Q0EQK2, A0A1S3TYK8, A0A1S3U5X8,
A0A1V9XRJ6, A0A1V9XWL9, A0A1V9XIR5, A0A1S3TUD5, A0A3Q0F6W5, A0A1S3U6A4,
A0A1V9X1B6, A0A1V9Y2Z8, A0A1V9X236, A0A1S3TSG7, A0A3Q0ERZ1, A0A3Q0FGU0,
A0A1V9X4X2, A0A144ZKR4, L9J9W1, L9J9Q4, A0A3Q0EP47, A0A3Q0ELC1, A0A1S3U943,
L8Y0B6, A0A2K9L9B3, A0A2K9L3H7, A0A2K9L521, A0A3Q0EVT5, A0A3Q0F3I1, A0A1S3VE13,
A0A2K9L700, A0A2K9L519, A0A2K9L1A9, A0A1S3VKA1, A0A1S3TI08, A0A3Q0FK37,
A0A2K9L2G0, A0A2K9L0F4, A0A2K9L648, A0A1S3VLA4, A0A3Q0F5J2, A0A1S3U186,
A0A2K9L6M7, A0A2U4CNJ2, A0A2U3V1A2, A0A3Q0FKN7, A0A3Q0FHK9, A0A1S3TXM9,
A0A2U4CNJ3, A0A2U4A725, A0A2U4CNU7, A0A1S3U6A9, A0A1S3TLE5, A0A1S3W149,
A0A2U4CNK8, A0A2U4BS66, A0A2U4A724, A0A1S3U6B7, A0A1S3VCH7, A0A1S3TU21,
A0A093FWK3, A0A093FQ32, A0A1W5CXS0, A0A1S3U951, A0A3Q0F0J3, A0A3Q0EUC6,
A0A1W5CXL4, K2AG36, A0A212KZK8, A0A452RK74, A0A3Q0EX51, A0A1S3USU6, A0A1S3VJQ9,
A0A452RW34, A0A452QNT0, A0A452RK69, A0A1S3VSU2, A0A3Q0FH19, A0A3Q0EQ28,
A0A3Q7VTE7, A0A3Q7W7U3, A0A3Q7WRV2, A0A1S3Q0EWF0, A0A3Q0F0F3, A0A3Q0FGP8,
A0A3Q7XCY5, A0A3Q7WHD8, A0A3Q7V5V4, A0A1S3VBZ6, A5C4W8, A0A438HK40, F6GZ95,
A0A3Q7X1Z0, A0A3Q7WRV6, A0A3Q7XCZ2, A0A438HSA8, A0A438K4K8, F6H2A3, F6H2N4,

A0A438HPG9, F6GXQ1, F6GYD8, F6HRT0, A5BHL6, A5B7V9, A0A438IDB7, A0A438JV19, A0A438J4D4, A0A438J4P8, F6H2B3, F6HL29, A5BJG8, A5AH51, A5BYN3, F6H549, F6HD38, F6HD40, F6HL32, A5BFJ9, A5ALH9, F6I0H1, F6GZ96, F6H296, D7U4I0, F6I7L4, A5ACT5, F6H5E3, A5BH08, F6H5E2, A5BRV2, A5AD43, F6HW07, F6HL33, F6GYE5, A0A438G9R9, A0A438GDM0, A0A438H0P0, A5ASQ2, F6GXQ3, F6HJX6, F6GZ98, A5BY61, A5B986, D7T5C7, A5C5N7, E0CSX4, F6H7Z9, D7TJ25, A5BIS9, F6H543, F6GZX7, A5BXA4, F6H1X1, A5BQP9, F6H2A5, A5BH06, D7TRQ9, A0A438HNC4, A5BKS7, D7UAZ5, D7U6R5, A5ALK0, F6HL31, F6H2G3, A5AQY5, F6HYF4, F6H2B6, F6I2E8, E0CSZ7, F6H2G5, F6HL30, F6I1Y7, A5BRU4, A5BQQ0, F6H298, F6H2C0, A5C1U2, F6GZ97, F6HH96, F6H2A9, F6HW06, A5BXZ3, A0A438EUR3, A0A438DP60, A0A438IDB3, F6GYG6, A0A438G921, A0A438BSL5, A0A438G9P6, A0A438HN97, A0A438GDR0, A5AG42, A0A438GF75, A0A438HLK8, A0A438G9V2, A0A438G9Q8, A0A438H0K0, A0A438ID79, A0A438HSB1, A0A438HK35, A0A438G270, A0A438G9S5, A0A438HAT9, A5BHL5, A5AUE6, A0A438BPR1, F6H559, A0A438BSE3, A0A438DBA0, A0A438CR06, A0A438BPQ2, A0A438G973, A0A438JAW2, A0A438FCT8, A0A438HSB6, A0A438JS26, A0A438EA03, A0A438GV90, A0A438CSM6, A0A438HS93, A0A438BPP3, A0A438GVE3, A0A438CK55, A0A438G8Z3, A0A438BSB7, A0A438ITA4, A0A438K4I2, A0A438BSD0, A0A438FQF7, A0A438C0M0, A0A438GDR3, A0A438BSF9, A0A438G3D9, A0A438KNQ7, A0A438G911, A5BHL9, A0A438EGN8, F6H2A8, A0A438J4V0, A0A438K4L8, A0A438GDM4, A0A438DY93, A0A438HN88, A0A438HN57, A0A438GVF0, A0A438GDM2, A0A438GVA2, A0A438BS99, A0A438DBE8, A0A438JAQ1, A0A438DP71, A0A438BS80, F6H2A0, A0A438G9S9, A0A438HU56, A0A438BPN8, A0A438HS63, F6GXQ9, A0A438GVC3, A0A438FWU9, A0A438GDN5, A0A438GDN4, A0A438GDQ3, A0A438EUS9, A0A438E5D3, A0A438I408, A0A438G271, A0A438DE69, F6GYD9, A0A438HPI4, A0A438BPY9, A0A438BSI7, A0A438I405, A0A438BS96, A0A438K4H2, A0A438GDQ0, A0A438C054, A0A438H4L4, A0A438G257, A0A438BSC6, A0A438G9Q4, A0A438BPQ7, A0A438HSC6, A0A438GVB8, A0A438IDD7, A0A438HPK3, A0A438G9Q3, A0A438BSC1, A0A438G5Q0, A0A438BSM6, A0A438BSC0, A0A438DP46, A0A438DGJ9, F6GYE3, A0A438JLB1, A0A438IDA7, A0A438GVD0, A0A438GDQ6, A0A438DF00, A0A438DP50, A0A438G9P1, A0A438GBQ1, A0A438JKA7, A0A438KF31, A0A438IDB0, A0A438G907, A0A438H6B4, A0A438GV93, A0A438G943, A0A438CYC5, A0A438BSE2, A0A438BSD9, A0A438DB91, A0A438G9Q7, A0A438BSA2, A0A438GVA1, A0A438GDN6, A0A438FCS0, A5AQ78, A0A438C802, A0A438HLD8, A0A438HZ10, A0A438GVD3, A0A438G908, A0A438GVB4, A5BLU0, A0A438HPJ7, A0A438G5P6, A0A438DE77, A0A438C111, A0A438HCT6, D7SRN6, F6GXQ6, A5BKZ4, A0A438BSD1, F6H2G7, F6GZX9, F6GZD2, F6H294, F6I0I1, A5ACT7, A5BRU5, A5BVG8, F6H542, F6HL34, F6I2A7, F6I291, E0CT00, A5AQI0, A5C9P3, F6HFB8, F6GXQ0, A5BGQ9, E0CSJ3, F6HRS4, A5C0J8, F6HD39, F6H801, F6I1Y9, F6H2B7, F6GZX6, F6H2G6, F6GYE4, A5BEU8, E0CT03, F6H295, F6I2E9, A0A438GVB5, A0A438DPA7, A0A438DP66, A0A438HAT4, A0A438CQW8, A0A438HLG1, A5C437, F6GZX1, A0A438DBZ7, A5BEK3, D7TK53, F6HYF3, F6H329, A5BIW6, A0A438D3S7, A5APY4, F6HL08, F6H2A2, A5BHL4, A0A438EA11, A0A438CFB9, A0A438G8X0, A0A438EAE1, A0A438GDP7, A0A438BPQ9, A0A438JP69, A0A438HLN0, A0A438G975, A0A438HPK0, A0A438BSA0, A0A438FHJ0, A0A438G906, F6GXR2, A0A438G919, A0A438F254, A0A438EGP7, A0A438BS88, A0A438HS95, A0A438GVD6, A0A438E9X1, A5AWE1, A0A438GVB1, A0A438G952, A0A438IDD5, A0A438G9P4, A0A438BSF2, A0A438G5Q1, A0A438HS43, A0A438JK94, A0A438JAS5, A0A438ID88, A0A438ITJ2, A0A438HLS7, A0A438DP63, A0A438HPH4, A0A438BPR7, A0A438G918, A0A438JAY5, A0A438G9T4, A5BFK0, A0A438BSE1, A5C187, F6H290, F6I1Y8, A5AS83, A5C1Y4, F6H292, A5AST3, F6HCT4, A0A438HS08, A0A438IT97, A0A0G4H1K6, A0A0G4FPW0, A0A0G4EVW8, A0A0G4G2P6, A0A0G4EX32, A0A0G4EK41, A0A0G4GV94, A0A0G4FK32, A0A0G4FSG0, A0A0G4GBE1, A0A0G4FEA5, A0A0G4G667, A0A0G4G5L3, A0A0G4GUX0, A0A0G4H7X7, A0A0G4FED4, A0A0G4GC70, A0A0G4EL21, A0A0G4EFA5, A0A0G4FS69, A0A0G4G6X5, A0A0G4GSW5, A0A0G4FB70, A0A0G4FJV3, A0A0G4ELW9, A0A0G4F302, A0A0G4H591, A0A0G4GFR4, A0A0G4FNT8, A0A0G4H797, A0A0G4FKH8, A0A0G4GBQ5, A0A0G4G8Z9, A0A0G4FBG5, A0A0G4FUC6, A0A0G4EES0, A0A0G4GY87, A0A0G4FN79, A0A0G4FG97, A0A0G4GU04, A0A0G4GAX4, A0A0G4EKA7, A0A0G4E9C4, A0A0G4GA99, A0A0G4GC21, A0A0G4F4H5, A0A0G4GTL7, A0A0G4EC69, A0A0G4EDQ0, A0A0G4F1H0, A0A0G4GX24, A0A0G4GSZ4, A0A0G4GQI0, A0A0G4FAD2, A0A0G4EYY7, A0A0G4ECR3, A0A0G4FRN1, A0A0G4F3I1, A0A0G4GJ27, A0A0G4FWK0, A0A0G4FT88, A0A0G4ER04, A0A0G4FH06, A0A0G4GJ92, A0A0G4EN10, A0A0G4FC64, A0A0G4G604, A0A0G4H617, A0A0G4EE30, A0A0G4EMH2, A0A0G4EXD3, A0A0G4F467, A0A0G4ESG9, A0A0G4H5A7, A0A0G4H147, A0A0G4ELP5, A0A0G4EW80, A0A0G4EYN3, A0A0G4EVX9, A0A0G4G194, A0A0G4FYF0, A0A0G4ENT8, A0A0G4E913, A0A0G4EZ90, A0A0G4GDZ1, A0A0G4EV77, A0A0G4F2L7, A0A0G4FW07, A0A0G4END2, A0A0G4G025, A0A0G4EJ16, A0A0G4G3W1, A0A0G4ED81, A0A0G4EA18, A0A0G4GZE5, A0A0G4FZK6, A0A0G4F356, A0A0G4GY92, A0A0G4EP61, A0A0G4ERN6, A0A0G4F257, A0A0G4FG25, A0A0G4GJ87, A0A0G4GFW8, A0A0G4GN70, A0A0G4EGD8, A0A0G4GV35, A0A0G4EDK7, A0A0G4FDV3, A0A0G4EN36, A0A0G4FU39, A0A0G4G6I2, A0A0G4FAX9, Q948Y6, D8U662, D8UDJ2, D8UHS7, D8UHS1, D8U663, D8TZF2, D8TWV3, D8TZP2, D8ULZ4, D8U0L1, D8THZ2, D8U661, D8U9Q0, D8TUD4, D8TWS3, D8U5V3, D8TWS6, D8U656, D8UHS6, D8U0K8, D8TWV6, D8U3S1, A0A3Q7TWA6, A0A3Q7T0P7, A0A3Q7SNP7, A0A3Q7V334, A0A3Q7TKS7, A0A3Q7TAD2, A0A3Q7TW96, A0A3Q7UEY3, A0A0D0QEL7, A0A0D0PB00, A0A1M6EL45, A0A0C9S462, A0A0C9QPG3, A0A0C9RV88, A0A0C9RSU0, A0A0C9QPV3, A0A0C9RSN7, A0A0C9S6M8,

A0A118E9A3, J9DND2, A0A3P7DL77, A0A1I8ELN8, A0A3P7EWD2, A0A1I8EZC2, J9ETT3, A0A118EY91, A0A118EL26, A0A1I8EZH7, A0A3P7GM02, J9DZA9, A0A3P7FT60, A0A3P7GCY4, J9E1R8, A0A1I8EFL2, A0A118EF35, A0A3P7EEQ9, A0A3P7FCC9, A0A3P7DVJ1, A0A3P7DV86, A0A1I8ET18, A0A3P7DDB0, A0A3P7DLR8, A0A1I8F0Y1, J9F728, J9F5K7, A0A1I8ELS4, A0A3P7EE66, A0A1I8EA12, J9ELM2, J9EVZ5, J9E6Y8, J9ESJ0, J9AHN9, A0A3P7GJ34, A0A1I8ESS3, J9E0L8, J9EHN5, A0A1I8ECU1, J9FCK3, A0A3P7FKH0, A0A3P7EG90, J9F005, J9FHZ7, J9F0L7, J9EDU4, A0A1I8EPI5, A0A1I8ENJ3, A0A1I8EHS2, A0A3P7E3Y0, A0A1I8ER89, J9AZF1, J9B8V2, A0A1L8G2F6, Q91691, A0A1L8GHB0, A0A1L8G2M6, A0A1L8GP52, Q7ZTN9, A0A1L8GTY1, A0A1L8GZD1, Q6GP14, Q6AZS7, P70006, F7EDW8, F6YRB8, F7AR31, Q91402, A0A3P5XFD2, A0A3B5KRY2, A0A3B5KXI9, A0A3B5KR76, A0A3B5MPU6, A0A3B5M999, A0A3B5KPF4, A0A3B5KR79, A0A3B5KQW4, A0A3B5MUP9, A0A3B5M3B3, A0A3B5MDS7, A0A3B5KJF0, A0A3B5MW25, M4ASA0, A0A3B5R264, M4AQQ5, A0A3B5R3X9, M4AAJ3, M3ZXK8, M3ZTS0, M3ZXL1, M3ZXJ9, M3ZQC7, A0A3B5PQ81, A0A439DFT7, A0A439CN67, A0A439CTF6, A0A2E1D5Y3, A0A2T6KMQ7, A0A116G2U0, A0A3L6D9L1, A0A3L6E7F7, A0A317YAC8, A0A3L6DRV9, A0A3L6E476, A0A317YET9, A0A3L6E218, A0A317YKF8, B6TY46, A0A317Y521, P17801, A0A1D6KQI4, C0P6F5, A0A1D6KH09, A0A096T7Z1, A0A1D6M0L4, A0A1D6LBB2, A0A1D6DXI3, A0A1D6F8W0, A0A1D6N9S7, A0A1D6DXH8, A0A1D6H9Q0, A0A1D6GN29, K7UZN2, A0A1D6IEQ3, A0A1D6P507, A0A1D6DXM7, A0A1D6J6V6, K7VD35, A0A1D6IAX9, C0P9N1, A0A1D6JF78, A0A1D6GA13, A0A1D6FGJ5, K7VRP4, A0A1D6DXM5, A0A1D6ML66, A0A1D6GA09, A0A1D6N9S3, A0A1D6HLB4, A0A1D6IER4, A0A1D6N9Q9, C0HFM8, A0A1D6KIF9, A0A1D6IEQ5, A0A1D6GA12, A0A1D6KAQ9, A0A1D6IEI3, A0A1D6FSS8, A0A1D6IEI1, A0A1D6N9R8, A0A1D6MFC2, A0A1D6M2E6, A0A1D6J6V7, A0A3L6E4L3, A0A1D6DXH6, A0A1D6J6V1, A0A1D6J6V2, A0A1D6M0N6, A0A1D6EWT3, B4G1J2, A0A1D6ITQ0, A0A1D6KQI3, A0A1D6KL97, A0A1D6N9R3, K7UIF8, A0A1D6M0N7, A0A1D6EB48, A0A1D6QAA8, A0A1D6P2B1, A0A1D6M0N8, A0A3L6DU79, A0A3L6EU45, A0A317Y2S5, B7ZXB0, A0A3L6FU88, A0A3L6DL74, B6U2B7, A0A3L6FAJ7, A0A3L6DY96, A0A1Q1B749, A0A3L6ET80, B6SWL2, A0A3L6GBB9, A0A3L6G7X6, A0A3L6E4K1, A0A3L6D8A7, A0A3L6DCB9, A0A3L6DDA9, B4F952, A0A3L6G155, O24571, A0A3L6G2G8, B6ST43, A0A3L6FWI8, A0A3L6EU60, B4FYC6, A0A1V0E7H4, B4F8X7, A0A1D6M0M0, A0A1D6KIH3, A0A1D6N9S8, A0A1D6G7A2, A0A1D6KNU3, A0A1D6P015, K7TKD2, C0P3V1, A0A3L6G196, A0A1D6DXM6, A0A1D6HWK7, A0A1D6DXF1, A0A1D6IEQ4, A0A1D6KII4, B4FB05, A0A1D6IBG7, A0A1D6DXI2, A0A1D6N9R2, K7UC64, A0A1D6G136, A0A1D6LHG9, A0A1D6Q5J8, A0A1D6DXH9, A0A1D6FSS9, A0A1D6DXI7, A0A1D6G137, A0A1D6IEI2, A0A1D6JTK4, A0A1D6JF77, K7U3E7, A0A1D6QHL5, A0A1D6HLB7, A0A1D6I5R1, A0A1D6GA10, A0A1D6LGF6, A0A1D6DXM4, A0A1D6EUL5, A0A317YAM4, A0A3L6ETW0, A0A3L6E3M3, O49974, A0A3L6FYL3, A0A3L6EW75, A0A317Y7G4, A0A317Y3N4, A0A3L6FI05, A0A3L6DN41, C0PE10, A0A3L6G6F6, A0A3L6G1E6, A0A3L6DU70, C0HEN9, A0A3L6G8Y0, A0A3L6FT98, A0A3L6EX22, A0A3L6EHP0, O82103, A0A3L6DLS3, B7ZXT8, A0A3L6F189, A0A3L6FL65, A0A3L6E7I6, B7ZWT1, A0A3L6G679, A0A3L6DII2, A0A3L6FF64, A0A3L6DKE6, A0A3L6FXI5, A0A3L6GCE3, A0A3L6FWN1, A0A3L6FGU1, A0A3L6GBY8, A0A3L6EFC7, A0A3L6FT74, A0A3L6EBY7, A0A317Y6J9, C0P3U3, A0AA1XIZ1, A0A0A1XS55, A0A0A1X650, A0A0A1XQ87, A0A0A1X1C0, A0A0A1XB00, A0A0A1X8W7, A0A0A1WII0, A0A0A1XIF3, A0A0A1WSF6, A0A2G1QQ59, A0A067RG78, A0A067RN91, A0A067R6A7, A0A067RBZ2, A0A067RIJ5, A0A0K9NV78, A0A0K9Q5Q1, A0A0K9PK14, A0A0K9P5Q8, A0A0K9NYD2, A0A0K9PEI3, A0A0K9PPY6, A0A0K9PXR7, A0A0K9PLY7, A0A0K9NWC4, A0A0K9PKC6, A0A0K9NQT5, A0A0K9P3S2, A0A0K9PQY0, A0A0K9PLW0, A0A0K9P3C4, A0A0K9PPJ9, A0A0K9P0C4, A0A0K9PY30, A0A0K9PNK6, A0A0K9PP88, A0A0K9P1W2, A0A0K9NS31, A0A0K9NWR2, A0A0K9NMN3, A0A0K9NJ97, A0A0K9PD87, A0A0K9NTS5, A0A0K9Q4R1, A0A0K9NIZ5, A0A0K9NQH7, A0A0K9PG70, A0A0K9NRX4, A0A0K9NV14, A0A0K9NLX9, A0A0K9P5H7, A0A0K9NPE2, A0A0K9P819, A0A0K9PRP8, A0A0K9P5Q0, A0A0K9PM56, A0A0F4GX70, A0A0F4GNN3, A0A0F4GDY3, A0A0F4G7R0, A0A0F4GJL4, A0A0F4G525, A0A0F4GKZ5, A0A0F4GK64, A0A0F4GK12, A0A0F4GVA7, A0A0F4GTQ5, A0A0F4GJJ0, A0A0F4GPQ0, A0A0F4GLI2, F9X4T1, F9XHT4, F9XH72, F9XJG6, F9XDZ3, F9X146, F9XK84, F9XCF6, F9XP87, F9X6W1, F9XFV9, F9XM39, F9XAK9, F9XNE3, A0A1Y6LP08, A0A1Y6LZ79, A0A1Y6LY30, A0A1Y6LT89, A0A1Y6L814, A0A1Y6LQH5, A0A1Y6LQU6, A0A1Y6L5Q9, A0A1Y6LXG6, A0A1Y6LN68, A0A1Y6LFZ2, A0A1Y6LBN0, A0A1Y6LDV9, A0A1Y6L8C9, A0A1Y6LRA7, A0A2H1FJ88, A0A2H1GP22, A0A2H1H488, A0A2H1FZK2, A0A2H1H533, A0A2H1FLY6, A0A2H1H4S8, A0A2H1GT42, A0A2H1GHG1, A0A2H1H5M8, A0A2H1GTE8, A0A2H1FQ02, A0A2H1G5G9, A0A2H1GXW6, A0A2H1GZK0, A0A2H1GNU0, A0A2H1GST3, A0A2H1H7P5, A0A1X7RYL6, A0A1X7RF14, A0A1X7RL97, A0A1X7RUL5, A0A1X7S239, A0A1X7RV33, A0A1X7RNL6, A0A1X7RY43, A0A1X7S9D0, A0A1X7S2M2, A0A1X7S7L9, A0A1X7RBY3, A0A1X7S0P9, and A0A1X7RID6.

What is claimed is:

1. A method for screening for a therapeutic compound targeting a PAN domain in a protein, comprising:
   contacting the protein comprising the PAN domain with a candidate therapeutic compound, and assessing whether the compound binds specifically to the PAN domain;
   wherein the protein is selected from the group consisting of a plant protein, an animal protein, a bacterial protein, a viral protein and a fungal protein; and
   wherein the PAN domain has a consensus sequence as shown in SEQ ID NO: 23.

2. The method of claim 1, wherein the PAN domain-containing protein is selected from the group consisting of hepatocyte growth factor (HGF), natriuretic peptide receptor 3 (NPR3), natriuretic peptide receptor 1 (NPR1), WRKY transcription factors, receptor-like kinase 5 (RLK5), receptor-like kinases 7 (RLK7), and S-locus receptor kinase (SRK) polypeptides.

* * * * *

SEQUENCE LISTING

<160> NUMBER OF SEQ ID NOS: 52

<210> SEQ ID NO 1

```
<211> LENGTH: 26
<212> TYPE: DNA
<213> ORGANISM: Artificial Sequence
<220> FEATURE:
<223> OTHER INFORMATION: Oligonucleotides

<400> SEQUENCE: 1
caccatgctt aagcagggca atttct                                          26

<210> SEQ ID NO 2
<211> LENGTH: 20
<212> TYPE: DNA
<213> ORGANISM: Artificial Sequence
<220> FEATURE:
<223> OTHER INFORMATION: Oligonucleotides

<400> SEQUENCE: 2
tcatggttcc attggcctct                                                 20

<210> SEQ ID NO 3
<211> LENGTH: 26
<212> TYPE: DNA
<213> ORGANISM: Artificial Sequence
<220> FEATURE:
<223> OTHER INFORMATION: Oligonucleotides

<400> SEQUENCE: 3
caccatgggc gtgactagga atagag                                          26

<210> SEQ ID NO 4
<211> LENGTH: 24
<212> TYPE: DNA
<213> ORGANISM: Artificial Sequence
<220> FEATURE:
<223> OTHER INFORMATION: Oligonucleotides

<400> SEQUENCE: 4
ctaagaggag tctacttcga cctc                                            24

<210> SEQ ID NO 5
<211> LENGTH: 25
<212> TYPE: DNA
<213> ORGANISM: Artificial Sequence
<220> FEATURE:
<223> OTHER INFORMATION: Oligonucleotides

<400> SEQUENCE: 5
caccatgggt acttttcag ttctg                                            25

<210> SEQ ID NO 6
<211> LENGTH: 22
<212> TYPE: DNA
<213> ORGANISM: Artificial Sequence
<220> FEATURE:
<223> OTHER INFORMATION: Oligonucleotides

<400> SEQUENCE: 6
ctaccgggcc tctaatgaca tc                                              22

<210> SEQ ID NO 7
<211> LENGTH: 23
<212> TYPE: DNA
<213> ORGANISM: Artificial Sequence
<220> FEATURE:
<223> OTHER INFORMATION: Oligonucleotides
```

-continued

<400> SEQUENCE: 7
ggggtcaaag ctttctacag agg                                    23

<210> SEQ ID NO 8
<211> LENGTH: 21
<212> TYPE: DNA
<213> ORGANISM: Artificial Sequence
<220> FEATURE:
<223> OTHER INFORMATION: Oligonucleotides

<400> SEQUENCE: 8
gccaaccaaa ccacagtttg c                                      21

<210> SEQ ID NO 9
<211> LENGTH: 24
<212> TYPE: DNA
<213> ORGANISM: Artificial Sequence
<220> FEATURE:
<223> OTHER INFORMATION: Oligonucleotides

<400> SEQUENCE: 9
gcttttgtga agaggttgcc atgg                                   24

<210> SEQ ID NO 10
<211> LENGTH: 20
<212> TYPE: DNA
<213> ORGANISM: Artificial Sequence
<220> FEATURE:
<223> OTHER INFORMATION: Oligonucleotides

<400> SEQUENCE: 10
gaccccattt tgagacaccc                                        20

<210> SEQ ID NO 11
<211> LENGTH: 19
<212> TYPE: DNA
<213> ORGANISM: Artificial Sequence
<220> FEATURE:
<223> OTHER INFORMATION: Oligonucleotides

<400> SEQUENCE: 11
cgtttcaacc ggaggaagc                                         19

<210> SEQ ID NO 12
<211> LENGTH: 22
<212> TYPE: DNA
<213> ORGANISM: Artificial Sequence
<220> FEATURE:
<223> OTHER INFORMATION: Oligonucleotides

<400> SEQUENCE: 12
ttacattcag agcccccaaa gc                                     22

<210> SEQ ID NO 13
<211> LENGTH: 20
<212> TYPE: DNA
<213> ORGANISM: Artificial Sequence
<220> FEATURE:
<223> OTHER INFORMATION: Oligonucleotides

<400> SEQUENCE: 13
catggattcc gaagatcaca                                        20

<210> SEQ ID NO 14

```
<211> LENGTH: 19
<212> TYPE: DNA
<213> ORGANISM: Artificial Sequence
<220> FEATURE:
<223> OTHER INFORMATION: Oligonucleotides

<400> SEQUENCE: 14
ctggccacac caatgacaa                                                  19

<210> SEQ ID NO 15
<211> LENGTH: 22
<212> TYPE: DNA
<213> ORGANISM: Artificial Sequence
<220> FEATURE:
<223> OTHER INFORMATION: Oligonucleotides

<400> SEQUENCE: 15
aaatcagccc tcccaagaaa cg                                              22

<210> SEQ ID NO 16
<211> LENGTH: 25
<212> TYPE: DNA
<213> ORGANISM: Artificial Sequence
<220> FEATURE:
<223> OTHER INFORMATION: Oligonucleotides

<400> SEQUENCE: 16
cttcacgaca gtctcttctc tctgc                                           25

<210> SEQ ID NO 17
<211> LENGTH: 20
<212> TYPE: DNA
<213> ORGANISM: Artificial Sequence
<220> FEATURE:
<223> OTHER INFORMATION: Oligonucleotides

<400> SEQUENCE: 17
aggctcatcg attgtcagca                                                 20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotides

<400> SEQUENCE: 18
ctgcactacg attctcggct                                                 20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotides

<400> SEQUENCE: 19
gttgtcggtg atggttgtgc                                                 20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotides
```

<400> SEQUENCE: 20
ccggatcttg ccggaatctt                                          20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotides

<400> SEQUENCE: 21
aggccatcaa ggaggaatct                                          20

<210> SEQ ID NO 22
<211> LENGTH: 23
<212> TYPE: DNA
<213> ORGANISM: Artificial Sequence
<220> FEATURE:
<223> OTHER INFORMATION: Oligonucleotides

<400> SEQUENCE: 22
gaaaatgctt gacctgttgt cac                                      23

<210> SEQ ID NO 23
<211> LENGTH: 120
<212> TYPE: PRT
<213> ORGANISM: Artificial Sequence
<220> FEATURE:
<223> OTHER INFORMATION: polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (35)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (51)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (90)..(90)

```
<223> OTHER INFORMATION: Xaa can be any naturally occurring amino acid
<220> FEATURE:
<221> NAME/KEY: misc_feature
<222> LOCATION: (93)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (118)..(119)
<223> OTHER INFORMATION: Xaa can be any naturally occurring amino acid

<400> SEQUENCE: 23

Cys Xaa Xaa Xaa Leu Ile Val Met Phe Tyr Xaa Xaa Xaa Xaa Leu
 1               5                  10                  15

Ile Val Met Phe Tyr Xaa Xaa Xaa Asp Glu Asn Gln Leu Ile Val Met
             20                  25                  30

Phe Tyr Xaa Xaa Xaa Xaa Xaa Xaa Xaa Xaa Cys Xaa Xaa Xaa
         35                  40                  45

Cys Thr Xaa Xaa Xaa Cys Xaa Leu Ile Val Met Phe Tyr Phe Xaa
 50                  55                  60

Phe Tyr Xaa Xaa Xaa Xaa Xaa Xaa Xaa Xaa Xaa Xaa Cys
65                  70                  75              80

Xaa Leu Ile Val Met Phe Tyr Arg Lys Xaa Ser Thr Xaa Xaa Xaa Xaa
                 85                  90                  95

Xaa Xaa Xaa Xaa Xaa Xaa Xaa Xaa Ser Gly Xaa Ser Thr Leu
            100                 105                 110

Ile Val Met Phe Tyr Xaa Xaa Cys
            115                 120

<210> SEQ ID NO 24
<211> LENGTH: 85
<212> TYPE: PRT
<213> ORGANISM: Salix purpurea

<400> SEQUENCE: 24

Cys Glu Arg Thr Gln Asn Asp Gly Gln Val Pro Lys Glu Asp Gly Phe
 1               5                  10                  15

Ser Lys Leu Glu Arg Val Lys Val Pro Asp Phe Ala Glu Trp Ser Ser
             20                  25                  30

Ser Ile Thr Glu Gln Lys Cys Arg Asp Asp Cys Leu Asn Asn Cys Ser
         35                  40                  45

Cys Ile Ala Tyr Ala Tyr Tyr Ser Gly Ile Tyr Cys Met Leu Trp Arg
 50                  55                  60

Gly Asn Leu Thr Asp Ile Lys Lys Phe Ser Ser Gly Ala Asp Leu
65                  70                  75              80

Tyr Ile Arg Leu Ala
                 85

<210> SEQ ID NO 25
<211> LENGTH: 82
<212> TYPE: PRT
<213> ORGANISM: Salix purpurea

<400> SEQUENCE: 25

Cys Ser Asp Lys Val Gly Phe Leu Lys Tyr Thr Gly Met Lys Leu Pro
 1               5                  10                  15

Asp Thr Ser Ser Ser Trp Tyr Asp Lys Ser Ile Ser Leu Lys Glu Cys
             20                  25                  30
```

```
Glu Gly Leu Cys Leu Lys Asn Cys Ser Cys Thr Ala Tyr Ala Asn Leu
        35                  40                  45

Asp Ile Arg Asn Gly Gly Ser Gly Cys Leu Ile Trp Phe Gly Asp Leu
 50                  55                  60

Ile Asp Thr Arg Arg Ser Ala Gly Asp Gly Gln Asp Leu Tyr Val Arg
 65                  70                  75                  80

Met Asn

<210> SEQ ID NO 26
<211> LENGTH: 79
<212> TYPE: PRT
<213> ORGANISM: Salix purpurea

<400> SEQUENCE: 26

Asp Ser Asp Tyr Asn Met Asp Thr Tyr Glu His Thr Phe Leu Tyr Gly
 1               5                  10                  15

Ile Tyr Pro Pro Asn Glu Ala Ile Ile Ala Ser Leu Gln Gln Cys
            20                  25                  30

Arg Glu Val Cys Met Gln Asp Pro Gly Cys Thr Ala Ala Thr Phe Thr
        35                  40                  45

Asn Asp Gly Thr Ser Gln Cys Arg Met Lys Thr Ser Pro Tyr Phe Ser
 50                  55                  60

Gly His Gln Asn Pro Ser Leu Ser Ser Ile Ser Phe Val Lys Thr
 65                  70                  75

<210> SEQ ID NO 27
<211> LENGTH: 83
<212> TYPE: PRT
<213> ORGANISM: Salix purpurea

<400> SEQUENCE: 27

Cys Asp His Gly Glu Gly Phe Val Lys Ile Glu Asn Tyr Cys Leu Pro
 1               5                  10                  15

Asp Thr Ser Ser Ala Ala Trp Val Asp Lys Lys Ser Arg Ala Asp
            20                  25                  30

Cys Glu Leu Glu Cys Lys Arg Asn Cys Ser Cys Ser Ala Phe Ser Ile
        35                  40                  45

Ile Arg Ile Pro Gly Lys Gly Glu Gly Cys Leu Ala Trp Tyr Arg Glu
 50                  55                  60

Leu Val Asp Ile Arg Tyr Gly Arg Ser Glu Ser Asp Glu Leu Tyr Val
 65                  70                  75                  80

Arg Val Asp

<210> SEQ ID NO 28
<211> LENGTH: 81
<212> TYPE: PRT
<213> ORGANISM: Salix purpurea

<400> SEQUENCE: 28

Cys Lys Met Asn Thr Ser Met Met Val Met Arg Gln Thr Phe Leu Tyr
 1               5                  10                  15

Gly Leu Tyr Pro Pro Gln Asp Val Asp Ile Met Leu Ser Glu Lys Ala
            20                  25                  30

Cys Lys Glu Tyr Cys Ser Asn Asp Thr Asn Cys Ile Ala Ala Thr Ser
        35                  40                  45

Lys Asn Asp Gly Ser Gly Ile Cys Thr Ile Lys Arg Thr Ser Phe Ile
 50                  55                  60
```

```
Thr Gly Tyr Gly Asn Pro Ser Val Ser Ala Thr Ser Phe Leu Lys Val
 65                  70                  75                  80

Cys

<210> SEQ ID NO 29
<211> LENGTH: 87
<212> TYPE: PRT
<213> ORGANISM: Arabidopsis thaliana

<400> SEQUENCE: 29

Cys Gln Ala Lys Ser Ser Met Lys Thr Gln Gly Lys Asp Thr Asp Ile
  1               5                  10                  15

Phe Tyr Arg Met Thr Asp Val Lys Thr Pro Asp Leu His Gln Phe Ala
             20                  25                  30

Ser Phe Leu Asn Ala Glu Gln Cys Tyr Gln Gly Cys Leu Gly Asn Cys
         35                  40                  45

Ser Cys Thr Ala Phe Ala Tyr Ile Ser Gly Ile Gly Cys Leu Val Trp
     50                  55                  60

Asn Gly Glu Leu Ala Asp Thr Val Gln Phe Leu Ser Ser Gly Glu Phe
 65                  70                  75                  80

Leu Phe Ile Arg Leu Ala Ser
                 85

<210> SEQ ID NO 30
<211> LENGTH: 85
<212> TYPE: PRT
<213> ORGANISM: Populus balsamifera subsp. trichocarpa

<400> SEQUENCE: 30

Cys Gln Asn Lys Lys Ser Thr Gly Lys Lys Asp Gly Phe Leu Lys Met
  1               5                  10                  15

Ser Ile Leu Thr Leu Pro Glu Asn Ser Lys Ala Tyr Gln Lys Val Ser
             20                  25                  30

Val Ala Arg Cys Arg Leu Tyr Cys Met Lys Asn Cys Tyr Cys Val Ala
         35                  40                  45

Tyr Ala Tyr Asn Ser Ser Gly Cys Phe Leu Trp Glu Gly Asp Leu Ile
     50                  55                  60

Asn Leu Lys Gln Ser Glu Ile Ala Ala Gly Arg Ala Gly Ala Glu Ile
 65                  70                  75                  80

Tyr Ile Arg Leu Ala
                 85

<210> SEQ ID NO 31
<211> LENGTH: 81
<212> TYPE: PRT
<213> ORGANISM: Populus balsamifera subsp. trichocarpa

<400> SEQUENCE: 31

Cys Ser Gly Asp Gly Phe Gln Lys Leu Ser Gly Leu Lys Leu Pro Glu
  1               5                  10                  15

Thr Lys Thr Ser Trp Phe Asn Thr Ser Met Asn Leu Glu Glu Cys Lys
             20                  25                  30

Lys Lys Cys Ile Lys Asn Cys Ser Cys Thr Ala Tyr Ser Asn Leu Asp
         35                  40                  45

Ile Arg Asn Gly Gly Ser Gly Cys Leu Leu Trp Phe Gly Asp Leu Ile
     50                  55                  60
```

```
Asp Ile Arg Val Ile Ala Val Asn Glu Gln Asp Val Tyr Ile Arg Met
 65                  70                  75                  80

Ala

<210> SEQ ID NO 32
<211> LENGTH: 89
<212> TYPE: PRT
<213> ORGANISM: Homo sapiens

<400> SEQUENCE: 32

Asn Thr Ile His Glu Phe Lys Lys Ser Ala Lys Thr Thr Leu Ile Lys
  1               5                  10                  15

Ile Asp Pro Ala Leu Lys Ile Lys Thr Lys Lys Val Asn Thr Ala Asp
                 20                  25                  30

Gln Cys Ala Asn Arg Cys Thr Arg Asn Lys Gly Leu Pro Phe Thr Cys
             35                  40                  45

Lys Ala Phe Val Phe Asp Lys Ala Arg Lys Gln Cys Leu Trp Phe Pro
         50                  55                  60

Phe Asn Ser Met Ser Ser Gly Val Lys Lys Glu Phe Gly His Glu Phe
 65                  70                  75                  80

Asp Leu Tyr Glu Asn Lys Asp Tyr Ile
                 85

<210> SEQ ID NO 33
<211> LENGTH: 77
<212> TYPE: PRT
<213> ORGANISM: Homo sapiens

<400> SEQUENCE: 33

Gln Val Leu Arg Gly Thr Glu Leu Gln His Leu Leu His Ala Val Val
  1               5                  10                  15

Pro Gly Pro Trp Gln Glu Asp Val Ala Asp Ala Glu Glu Cys Ala Gly
                 20                  25                  30

Arg Cys Gly Pro Leu Met Asp Cys Trp Ala Phe His Tyr Asn Val Ser
             35                  40                  45

Ser His Gly Cys Gln Leu Leu Pro Trp Thr Gln His Ser Pro His Ser
         50                  55                  60

Arg Leu Trp His Ser Gly Arg Cys Asp Leu Phe Gln Glu
 65                  70                  75

<210> SEQ ID NO 34
<211> LENGTH: 77
<212> TYPE: PRT
<213> ORGANISM: Homo sapiens

<400> SEQUENCE: 34

Gln Val Leu Arg Gly Thr Glu Leu Gln His Leu Leu His Ala Val Val
  1               5                  10                  15

Pro Gly Pro Trp Gln Glu Asp Val Ala Asp Ala Glu Glu Cys Ala Gly
                 20                  25                  30

Arg Cys Gly Pro Leu Met Asp Cys Trp Ala Phe His Tyr Asn Val Ser
             35                  40                  45

Ser His Gly Cys Gln Leu Leu Pro Trp Thr Gln His Ser Pro His Ser
         50                  55                  60

Arg Leu Trp His Ser Gly Arg Cys Asp Leu Phe Gln Glu
 65                  70                  75
```

```
<210> SEQ ID NO 35
<211> LENGTH: 77
<212> TYPE: PRT
<213> ORGANISM: Homo sapiens

<400> SEQUENCE: 35

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
                20                  25                  30

Arg Cys Gly Pro Leu Met Asp Cys Trp Ala Phe His Tyr Asn Val Ser
            35                  40                  45

Ser His Gly Cys Gln Leu Leu Pro Trp Thr Gln His Ser Pro His Ser
        50                  55                  60

Arg Leu Trp His Ser Gly Arg Cys Asp Leu Phe Gln Glu
65                  70                  75

<210> SEQ ID NO 36
<211> LENGTH: 77
<212> TYPE: PRT
<213> ORGANISM: Homo sapiens

<400> SEQUENCE: 36

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
                20                  25                  30

Arg Cys Gly Pro Leu Met Asp Cys Trp Ala Phe His Tyr Asn Val Ser
            35                  40                  45

Ser His Gly Cys Gln Leu Leu Pro Trp Thr Gln His Ser Pro His Ser
        50                  55                  60

Arg Leu Trp His Ser Gly Arg Cys Asp Leu Phe Gln Glu
65                  70                  75

<210> SEQ ID NO 37
<211> LENGTH: 77
<212> TYPE: PRT
<213> ORGANISM: Homo sapiens

<400> SEQUENCE: 37

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
                20                  25                  30

Arg Cys Gly Pro Leu Met Asp Cys Trp Ala Phe His Tyr Asn Val Ser
            35                  40                  45

Ser His Gly Cys Gln Leu Leu Pro Trp Thr Gln His Ser Pro His Ser
        50                  55                  60

Arg Leu Trp His Ser Gly Arg Cys Asp Leu Phe Gln Glu
65                  70                  75

<210> SEQ ID NO 38
<211> LENGTH: 77
<212> TYPE: PRT
<213> ORGANISM: Homo sapiens

<400> SEQUENCE: 38

Gln Val Leu Arg Gly Thr Glu Leu Gln His Leu Leu His Ala Val Val
1               5                   10                  15
```

```
Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 39
<211> LENGTH: 77
<212> TYPE: PRT
<213> ORGANISM: Homo sapiens

<400> SEQUENCE: 39

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 40
<211> LENGTH: 77
<212> TYPE: PRT
<213> ORGANISM: Homo sapiens

<400> SEQUENCE: 40

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 41
<211> LENGTH: 77
<212> TYPE: PRT
<213> ORGANISM: Homo sapiens

<400> SEQUENCE: 41

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60
```

Arg Leu Trp His Ser Gly Arg Cys Asp Leu Phe Gln Glu
65                  70                  75

<210> SEQ ID NO 42
<211> LENGTH: 77
<212> TYPE: PRT
<213> ORGANISM: Homo sapiens

<400> SEQUENCE: 42

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 43
<211> LENGTH: 77
<212> TYPE: PRT
<213> ORGANISM: Homo sapiens

<400> SEQUENCE: 43

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 44
<211> LENGTH: 77
<212> TYPE: PRT
<213> ORGANISM: Homo sapiens

<400> SEQUENCE: 44

Gln Val Leu Arg Gly Thr Glu Leu Gln His Leu Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 45
<211> LENGTH: 77
<212> TYPE: PRT
<213> ORGANISM: Homo sapiens

<400> SEQUENCE: 45

Gln Val Leu Arg Gly Thr Glu Leu Gln His Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 46
<211> LENGTH: 77
<212> TYPE: PRT
<213> ORGANISM: Homo sapiens

<400> SEQUENCE: 46

Gln Val Leu Arg Gly Thr Glu Leu Gln His Leu His Ala Val Val
1               5                   10                  15

Pro Gly Pro Trp Gln Glu Asp Val Ala Asp Ala Glu Glu Cys Ala Gly
            20                  25                  30

Arg Cys Gly Pro Leu Met Asp Cys Trp Ala Phe His Tyr Asn Val Ser
        35                  40                  45

Ser His Gly Cys Gln Leu Leu Pro Trp Thr Gln His Ser Pro His Ser
    50                  55                  60

Arg Leu Trp His Ser Gly Arg Cys Asp Leu Phe Gln Glu
65                  70                  75

<210> SEQ ID NO 47
<211> LENGTH: 4023
<212> TYPE: DNA
<213> ORGANISM: Populus trichocarpa

<400> SEQUENCE: 47
atgtgtgtta ttacaaagcc aagtttctgg ttctttgtgc tgttgttgct attcgtttcc      60
cactggaatt gcttctccat tgaaggtgat acccttttga ttggccagtc tctctctgca     120
agccagacac tgtatctca  aaatggcatt tttgaactcg gtttcttcaa gccaggcgct     180
tctttaaaca tttaccttgg aatttggtat aagaactccg cagataagat gattgtttgg     240
gtggcaaaca gggagagccc tttaaacaac cctgcttcat cgaagcttga attatcaccg     300
gatggcattc ttgtcctact gacaaatttc accaaaacag tttggtcaac agctcttgca     360
tcttcagtgc cgaataacag tacagcacaa gcagcacttc ttgataatgg aaactttgtc     420
attaaagatg gctcaaaccc atccgctatt tactggcaga gttttgacaa tccaactgat     480
acattgctac tggtggaaa  gcttggaatc aacaagcaca ctgggaaagt gcagaagctt     540
atttcctgga aaacccaga  agatcctgca ccaggtatgt tctcgattac gatggacccc     600
aatggcagta gtcagatttt tatagagtgg aacaaggtca cacatgtatt ggagcagtgg     660
ggtttggaat ggacaaagat tttccatggt tcctgagatg aatttgaact attatttcaa     720
ttatagttat atatcgaatg aaaatgaaag ctatttcacc ttttctgtgt acaatgctga     780
aatgctctca agatacgtga ttgatgtttc aggacaaatc aaacaattaa attggttagc     840
aggtgttagg aattggtcag aattctgggc ccagcccagt gaccaagctg gtgtttatgg     900
tttatgcggg gttttggag  tctttcatgg aaactcatcg agctcttgtg aatgcttgaa     960

```
aggttttgaa ccattagtac aaaatgattg gtcaagcggt tgtgttagga aatctccttt    1020
gcagtgtcaa aataagaaaa gtactgggaa aaaagatggg ttcctgaaga tgtcgattct    1080
gacattacca gaaaattcaa aagcatatca aaaagtgagt gttgcaagat gtagattgta    1140
ttgcatgaaa aattgttatt gcgtggctta tgcctataat agcagtgggt gttttttatg    1200
ggaaggagat cttataaact taaaacagtc agagattgct gctgggaggg ctggagcaga    1260
aatttacatc agacttgctg cttctgagct tgaacctcag attggtagtg gcagtatccg    1320
aacaggtaag gtagaaaggt tttatatata tagttataaa tgatccaata gatgttgagc    1380
aatgatttct tacaaaataa cagcatagtc tttccagata aaatggtgga tgaaatgttt    1440
cctgtagaga agtgtggaag acataaccta acttcccata tctttctatc aaaataaaaa    1500
catcttaatt cgttaaaagt aaatttcttg gtttatgatt tggttaatgt ttgatctatg    1560
cttacaagta ggcaaatatc aaatggaaaa tacggacaac cttggctgtg gctgttccag    1620
taactctgat tacctaggc ctcttcatat acttcagctg tctgcgcaag gaaaagctca    1680
tacacaaagg tacatcctgt tcttgcttta atttctgctg tctcctggta ggctttaatt    1740
aaccctcaag ttactggtga ctagaaaaaa ccctcctttg taattgatta tgtcttaggt    1800
atgcagatgg taaggttcat tttgatggag atagagggac agaaatgttt tgttttgcat    1860
aaaatatttt accgaaataa gttttttattt tttatttatt tatatatgtt tgtttcttgt    1920
aaaatatctg acaagaagag tgatcaatat aaattatttt atagttaacc ttcatattag    1980
ttcatttatt aaaatatttt ctcatctctt aaaattttat aaaatatttt atgaaaaata    2040
aaacaatcac aatatcttac aacaaattta tccatataaa atgtttagga ggtaaaatat    2100
tttatgtcaa acaaacacca aagtttctta tttatgaaaa aaactgacat ttagaatacc    2160
ttttaacgtc cgaattgtgg ttatgctaac ctgaagttgt taccttttt gcttgatatt    2220 atcagaatag ctggatattg ttcaacaaag tgaatgtgtt caatcatttt tattttata    2280 tttttcttga aacagcgaag gaacgtgcaa gtcacaattt attgcgtttt aatttcgatg    2340
ccgatcctaa ctcaactacc aatgaatcta gctctgttga caatcggaag aaaagatgga    2400
gtaaaaatat agaatttcca ttattcagtt atgagagcgt atcagtggca actggacagt    2460
tctcagataa gcttggagag ggaggattcg gacctgttta taaggtaaat ttacgttcaa    2520
atgagaaatg ctgattttcc taagaaaaat gttaaaatag ttcgaatgaa ctttcagaat    2580
gacttttggt tcatttaaca gggcaaatta cccacgggac tggaaatagc agtgaagagg    2640
ctttcagaaa gatctgggca ggggcttgag gagttcagaa atgagacaac tctaatcgcc    2700
aaactccagc accggaatct tgtcaggcta ctgggttcct gtattgaatg ggatgagaaa    2760
atgctaatct atgagtacat gccaaataaa agcttggatt tctttctcta tggtcagcat    2820
ttagttcttt tctaatttca ttaacttttc aaatgcttca agaaatttat aacagatttg    2880
tgtataaaat ataaacagat gcaaacagag gacaaatctt agattggggt gcacggattc    2940
ggataatcga aggaattgct caaggccttc tgtatctaca tagatactcg cggttacgaa    3000
tcattcacag ggatttaaag cctagcaaca ttctattaga cagtgagatg aatccaaaaa    3060
tatccgattt cgggatggct cgaattttcg gaggcaacga aactcaagca cacaccaaca    3120
ggatcgttgg aacatagtaa gtttcttaaa ttctgttttc caggacatgc tacttaacat    3180
gatctgcgct gaccttttca aatgttagtg gctatatgtc ccctgaatat gctatggagg    3240
gtctcttctc aataaaatct gatgtgttta gcttcggggt gctggtactt gagattgtca    3300
```

```
gcggcaagaa gaacactagt ttctaccaca gcgacaccct ccatcttctt ggacatgtgg    3360
ggagctttca tacaccctct tttctttta ttcctccttg aattgtattt gaatactttc    3420
ctagtctcca cactaatggt gcagcatttg cgttgttata caatagacat ggaagttatg    3480
gaattctaat aaagctttgg acttgatgga tccaatcctg ggagatcctc cttcaactgc    3540
tacgctgttg agatacataa acatagggct tctttgtgtc caggaaagtc ctgctgatcg    3600
gcctacaatg tctgatgtta tatccatgat tgcaaacgaa cacgtagctc tcccagaacc    3660
aaagcaacct gcttttgttg catgcagaaa catggcagaa caaggaccat tgatgagctc    3720
ttctggggta ccttccgcga ataatgtgac aataacagcg atagatggga gatagttttt    3780
tcatcaagag gtctaaagga catgaagcta cttcaatatc agagcgagga agctatgagt    3840
atggagctta gatcaagctt atttgtataa gttctccgat ttgaatcgta caatagtttg    3900
tttcagtttt tcctattatt ctcgttgtat tgaaacatga acaaaatcaa atcaagtatt    3960
cataaaacac atttaattca gatcttaaat atattaaaaa ctcattttcc ttttagtaca    4020
aat                                                                  4023
```

<210> SEQ ID NO 48
<211> LENGTH: 724
<212> TYPE: PRT
<213> ORGANISM: Populus trichocarpa

<400> SEQUENCE: 48

```
Met Cys Val Ile Thr Lys Pro Ser Phe Trp Phe Phe Val Leu Leu Leu
1               5                   10                  15

Leu Phe Val Ser His Trp Asn Cys Phe Ser Ile Glu Gly Asp Thr Leu
            20                  25                  30

Leu Ile Gly Gln Ser Leu Ser Ala Ser Gln Thr Leu Ile Ser Gln Asn
        35                  40                  45

Gly Ile Phe Glu Leu Gly Phe Phe Lys Pro Gly Ala Ser Leu Asn Ile
    50                  55                  60

Tyr Leu Gly Ile Trp Tyr Lys Asn Ser Ala Asp Lys Met Ile Val Trp
65                  70                  75                  80

Val Ala Asn Arg Glu Ser Pro Leu Asn Asn Pro Ala Ser Ser Lys Leu
                85                  90                  95

Glu Leu Ser Pro Asp Gly Ile Leu Val Leu Leu Thr Asn Phe Thr Lys
            100                 105                 110

Thr Val Trp Ser Thr Ala Leu Ala Ser Ser Val Pro Asn Asn Ser Thr
        115                 120                 125

Ala Gln Ala Ala Leu Leu Asp Asn Gly Asn Phe Val Ile Lys Asp Gly
    130                 135                 140

Ser Asn Pro Ser Ala Ile Tyr Trp Gln Ser Phe Asp Asn Pro Thr Asp
145                 150                 155                 160

Thr Leu Leu Pro Gly Gly Lys Leu Gly Ile Asn Lys His Thr Gly Lys
                165                 170                 175

Val Gln Lys Leu Ile Ser Trp Lys Asn Pro Glu Asp Pro Ala Pro Gly
            180                 185                 190

Met Phe Ser Ile Thr Met Asp Pro Asn Gly Ser Ser Gln Ile Phe Ile
        195                 200                 205

Glu Trp Asn Lys Met Asn Leu Asn Tyr Tyr Phe Asn Tyr Ser Tyr Ile
    210                 215                 220

Ser Asn Glu Asn Glu Ser Tyr Phe Thr Phe Ser Val Tyr Asn Ala Glu
225                 230                 235                 240
```

```
Met Leu Ser Arg Tyr Val Ile Asp Val Ser Gly Gln Ile Lys Gln Leu
                245                 250                 255

Asn Trp Leu Ala Gly Val Arg Asn Trp Ser Glu Phe Trp Ala Gln Pro
            260                 265                 270

Ser Asp Gln Ala Gly Val Tyr Gly Leu Cys Gly Val Phe Gly Val Phe
            275                 280                 285

His Gly Asn Ser Ser Ser Cys Glu Cys Leu Lys Gly Phe Glu Pro
            290                 295                 300

Leu Val Gln Asn Asp Trp Ser Ser Gly Cys Val Arg Lys Ser Pro Leu
305                 310                 315                 320

Gln Cys Gln Asn Lys Lys Ser Thr Gly Lys Lys Asp Gly Phe Leu Lys
                325                 330                 335

Met Ser Ile Leu Thr Leu Pro Glu Asn Ser Lys Ala Tyr Gln Lys Val
                340                 345                 350

Ser Val Ala Arg Cys Arg Leu Tyr Cys Met Lys Asn Cys Tyr Cys Val
                355                 360                 365

Ala Tyr Ala Tyr Asn Ser Ser Gly Cys Phe Leu Trp Glu Gly Asp Leu
            370                 375                 380

Ile Asn Leu Lys Gln Ser Glu Ile Ala Ala Gly Arg Ala Gly Ala Glu
385                 390                 395                 400

Ile Tyr Ile Arg Leu Ala Ala Ser Glu Leu Glu Pro Gln Ile Gly Ser
                405                 410                 415

Gly Ser Ile Arg Thr Gly Lys Gly Lys Leu Pro Thr Gly Leu Glu Ile
                420                 425                 430

Ala Val Lys Arg Leu Ser Glu Arg Ser Gly Gln Gly Leu Glu Glu Phe
                435                 440                 445

Arg Asn Glu Thr Thr Leu Ile Ala Lys Leu Gln His Arg Asn Leu Val
450                 455                 460

Arg Leu Leu Gly Ser Cys Ile Glu Trp Asp Glu Lys Met Leu Ile Tyr
465                 470                 475                 480

Glu Tyr Met Pro Asn Lys Ser Leu Asp Phe Phe Leu Tyr Asp Ala Asn
                485                 490                 495

Arg Gly Gln Ile Leu Asp Trp Gly Ala Arg Ile Arg Ile Ile Glu Gly
                500                 505                 510

Ile Ala Gln Gly Leu Leu Tyr Leu His Arg Tyr Ser Arg Leu Arg Ile
                515                 520                 525

Ile His Arg Asp Leu Lys Pro Ser Asn Ile Leu Leu Asp Ser Glu Met
                530                 535                 540

Asn Pro Lys Ile Ser Asp Phe Gly Met Ala Arg Ile Phe Gly Gly Asn
545                 550                 555                 560

Glu Thr Gln Ala His Thr Asn Arg Ile Val Gly Thr Tyr Gly Tyr Met
                565                 570                 575

Ser Pro Glu Tyr Ala Met Glu Gly Leu Phe Ser Ile Lys Ser Asp Val
            580                 585                 590

Phe Ser Phe Gly Val Leu Val Leu Glu Ile Val Ser Gly Lys Lys Asn
            595                 600                 605

Thr Ser Phe Tyr His Ser Asp Thr Leu His Leu Gly His Thr Trp
            610                 615                 620

Lys Leu Trp Asn Ser Asn Lys Ala Leu Asp Leu Met Asp Pro Ile Leu
625                 630                 635                 640

Gly Asp Pro Pro Ser Thr Ala Thr Leu Leu Arg Tyr Ile Asn Ile Gly
                645                 650                 655
```

```
Leu Leu Cys Val Gln Glu Ser Pro Ala Asp Arg Pro Thr Met Ser Asp
            660                 665                 670

Val Ile Ser Met Ile Ala Asn Glu His Val Ala Leu Pro Glu Pro Lys
        675                 680                 685

Gln Pro Ala Phe Val Ala Cys Arg Asn Met Ala Glu Gln Gly Pro Leu
    690                 695                 700

Met Ser Ser Ser Gly Val Pro Ser Ala Asn Asn Val Thr Ile Thr Ala
705                 710                 715                 720

Ile Asp Gly Arg

<210> SEQ ID NO 49
<211> LENGTH: 728
<212> TYPE: PRT
<213> ORGANISM: Homo sapiens

<400> SEQUENCE: 49

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300
```

```
Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720
```

Leu Thr Tyr Lys Val Pro Gln Ser
            725

<210> SEQ ID NO 50
<211> LENGTH: 121
<212> TYPE: PRT
<213> ORGANISM: Artificial Sequence
<220> FEATURE:
<223> OTHER INFORMATION: polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (35)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (51)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (93)..(107)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (119)..(120)
<223> OTHER INFORMATION: Xaa can be any naturally occurring amino acid

<400> SEQUENCE: 50

Cys Xaa Xaa Xaa Leu Ile Val Met Phe Tyr Xaa Xaa Xaa Xaa Xaa Leu
1               5                   10                  15

Ile Val Met Phe Tyr Xaa Xaa Xaa Asp Glu Asn Gln Leu Ile Val Met
            20                  25                  30

Phe Tyr Xaa Xaa Xaa Xaa Xaa Xaa Xaa Xaa Xaa Xaa Cys Xaa Xaa Xaa
        35                  40                  45

```
Cys Thr Xaa Xaa Xaa Xaa Cys Xaa Leu Ile Val Met Phe Tyr Phe Xaa
    50                  55                  60

Phe Tyr Xaa Xaa Xaa Xaa Xaa Xaa Xaa Xaa Xaa Xaa Xaa Xaa Xaa Cys
 65                  70                  75                  80

Xaa Leu Ile Val Met Phe Tyr Arg Lys Xaa Ser Thr Xaa Xaa Xaa Xaa
                85                  90                  95

Xaa Xaa Xaa Xaa Xaa Xaa Xaa Xaa Xaa Xaa Ser Gly Xaa Ser Thr
            100                 105                 110

Leu Ile Val Met Phe Tyr Xaa Xaa Cys
            115                 120

<210> SEQ ID NO 51
<211> LENGTH: 121
<212> TYPE: PRT
<213> ORGANISM: Artificial Sequence
<220> FEATURE:
<223> OTHER INFORMATION: polypeptide
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (35)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (51)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (94)..(107)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (119)..(120)
<223> OTHER INFORMATION: Xaa can be any naturally occurring amino acid
```

<400> SEQUENCE: 51

Cys Xaa Xaa Xaa Leu Ile Val Met Phe Tyr Xaa Xaa Xaa Xaa Xaa Leu
1               5

```
<221> NAME/KEY: misc_feature
<222> LOCATION: (94)..(108)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid

<400> SEQUENCE: 52

Cys Xaa Xaa Xaa Leu Ile Val Met Phe Tyr Xaa Xaa Xaa Xaa Xaa Leu
1               5                   10                  15

Ile Val Met Phe Tyr Xaa Xaa Xaa Asp Glu Asn Gln Leu Ile Val Met
            20                  25                  30

Phe Tyr Xaa Xaa Xaa Xaa Xaa Xaa Xaa Xaa Xaa Cys Xaa Xaa Xaa
        35                  40                  45

Cys Thr Xaa Xaa Xaa Xaa Cys Xaa Leu Ile Val Met Phe Tyr Phe Xaa
        50                  55                  60

Phe Tyr Xaa Xaa Xaa Xaa Xaa Xaa Xaa Xaa Xaa Xaa Xaa Xaa Xaa
65                  70                  75                  80

Cys Xaa Leu Ile Val Met Phe Tyr Arg Lys Xaa Ser Thr Xaa Xaa Xaa
            85                  90                  95

Xaa Xaa Xaa Xaa Xaa Xaa Xaa Xaa Xaa Xaa Xaa Xaa Ser Gly Xaa Ser
            100                 105                 110

Thr Leu Ile Val Met Phe Tyr Xaa Xaa Cys
        115                 120
```